(12) United States Patent
Gonzalez Lopez de Turiso et al.

(10) Patent No.: US 11,168,095 B2
(45) Date of Patent: Nov. 9, 2021

(54) ASK1 INHIBITING AGENTS

(71) Applicant: BIOGEN MA INC., Cambridge, MA (US)

(72) Inventors: Felix Gonzalez Lopez de Turiso, Cambridge, MA (US); Martin Himmelbauer, Cambridge, MA (US); Michael J. Luzzio, Groton, CT (US)

(73) Assignee: BIOGEN MA INC., Cambridge, MA (US)

( * ) Notice: Subject to any disclaimer, the term of this patent is extended or adjusted under 35 U.S.C. 154(b) by 0 days.

(21) Appl. No.: 16/483,790

(22) PCT Filed: Feb. 6, 2018

(86) PCT No.: PCT/US2018/017061
§ 371 (c)(1),
(2) Date: Aug. 6, 2019

(87) PCT Pub. No.: WO2018/148204
PCT Pub. Date: Aug. 16, 2018

(65) Prior Publication Data
US 2019/0359634 A1   Nov. 28, 2019

Related U.S. Application Data

(60) Provisional application No. 62/470,533, filed on Mar. 13, 2017, provisional application No. 62/456,011, filed on Feb. 7, 2017.

(51) Int. Cl.
*C07D 498/14* (2006.01)

(52) U.S. Cl.
CPC .................................. *C07D 498/14* (2013.01)

(58) Field of Classification Search
CPC ..................................................... C07D 498/14
See application file for complete search history.

(56) References Cited

U.S. PATENT DOCUMENTS

2020/0283404 A1* 9/2020 Jin ....................... C07D 498/18

FOREIGN PATENT DOCUMENTS

WO   2011/008709 A1   1/2011

OTHER PUBLICATIONS

International Search Report and Written Opinion for Application No. PCT/US2018/017061, dated Apr. 26, 2018, 8 pages.

* cited by examiner

*Primary Examiner* — Sun Jae Yoo
(74) *Attorney, Agent, or Firm* — McCarter & English, LLP; Steven G. Davis; Xin Zhang

(57) ABSTRACT

Provided are compounds of Formulas (I'), (I), (II') and (II), or pharmaceutically acceptable salts thereof, and methods for their use and production.

16 Claims, No Drawings

ASK1 INHIBITING AGENTS

RELATED APPLICATIONS

This application is a 35 U.S.C. § 371 national stage filing of International Application No. PCT/US2018/017061, filed on Feb. 6, 2018, which claims the benefit of the filing date, under 35 U.S.C. § 119(e), of U.S. Provisional Application No. 62/456,011, filed on Feb. 7, 2017, and U.S. Provisional Application No. 62/470,533, filed on Mar. 13, 2017. The entire contents of each of the above-referenced applications are incorporated herein by reference.

TECHNICAL FIELD

Provided are certain agents that inhibit apoptosis signal-regulating kinase 1 (ASK1), and methods of making and using such agents.

BACKGROUND

Apoptosis Signal-regulating Kinase 1 (ASK1), also known as MAP3K5, is a member of the mitogen-activated protein kinase kinase kinase ("MAP3K") family that activates the c-Jun N-terminal protein kinase ("JNK") and p38 MAP kinase (Ichijo, H. et al., Science 1997, 275, 90-94). ASK1 is an evolutionary conserved and stress-responsive mitogen-activated protein kinase (MAPK). In mouse, ASK1 has been found to be expressed in heart, brain, lung, liver and kidney, as well as in developing skin, cartilage and bone (Tobiume et al., Biochem Biophys Res Commun. 1997, 239(3), 905-10). ASK1 is a central regulator of cell death and participates in several stress-induced and receptor-mediated cell death pathways triggered by various forms of cellular stress, including oxidative stress, reactive oxygen species (ROS), endoplasmic reticulum (ER) stress and unfolded protein response (UPR), mitochondrial stress, bacterial infection, increased calcium influx, DNA damage, UV radiation, viral infection, heat shock, osmotic shock, endotoxic lipopolysaccharide (LPS), FasL, and activation by pro-inflammatory cytokines such as tumor necrosis factor (TNF) and interleukin-1 (Nishitoh et al., Genes Dev. 2002, 16, 1345-1355; Matsukawa et al., Nat. Immunol., 2005, 6, 587-592; Tobiume et al., EMBO Rep. 2001, 2, 222-228; Hayakawa R. et al., Proc. Jpn. Acad. Ser B Phys. Biol. Sci. 2012, 88(8), 434-53; Takeda et al. Cell Struct. Funct. 2003, 28(1), 23-29; Tibbles et al., Cell Mol Life Sci. 1999, 55(10), 1230-1254; Hattori et al., Cell Comm. Signal. 2009, 7, 1-10; Takeda et al., Annu. Rev. Pharmacol. Toxicol. 2007, 48, 1-8.27; Nagai et al. J. Biochem. Mol. Biol. 2007, 40, 1-6).

ASK1 undergoes activation via autophosphorylation at Thr838 in response to these signals and in turn phosphorylates MAP2Ks, such as MKK3/6 and MKK4/7, which then phosphorylate and activate p38 and JNK MAPKs, respectively. Activation of the JNK and p38 pathways induces stress responses related to cell death, differentiation and the production of inflammatory cytokines. In non-stressed conditions, ASK1 is kept in an inactive state through binding to its repressor Thioredoxin (Trx) (Saitoh, M. et al., Embo J. 1998, 17, 2596-2606), and through association with AKT (Zhang, L., et al. Proc. Natl. Acad. Sci. U.S.A. 1999, 96, 8511-8515).

ASK1 plays an essential role not only in cell death pathways, but also in inflammatory and innate immune responses including cytokine responses, and cell differentiation.

Phosphorylation of ASK1 protein can lead to apoptosis or other cellular responses depending on the cell type. ASK1 activation and signaling have been reported to play an important role in a broad range of diseases including neurodegenerative, cardiovascular, inflammatory, autoimmunity, and metabolic disorders. In addition, ASK1 has been implicated in mediating organ damage following ischemia and reperfusion of the heart, brain, and kidney (Watanabe et al. BBRC 2005, 333, 562-567; Zhang et al., Life Sci 2003, 74-37-43; Terada et al. BBRC 2007, 364: 1043-49).

Therefore, there is a need for new compounds that can function as ASK1 inhibitors.

SUMMARY

A first embodiment of the invention is a compound of Formula (I'):

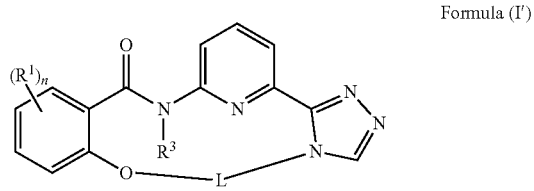

Formula (I')

or a pharmaceutically acceptable salt thereof, wherein:

n is selected from 0, 1 and 2;

L is selected from $C_{3-5}$alkylene and $C_{3-5}$alkenylene, wherein said $C_{3-5}$alkylene and $C_{3-5}$alkenylene are optionally substituted with one or two $R^2$;

$R^1$ in each occurrence is independently selected from $C_{1-6}$alkyl, $C_{2-6}$alkenyl, $C_{2-6}$alkynyl, carbocyclyl, heterocyclyl, halo, —CN, —C(O)$R^{1a}$, —C(O)$_2R^{1a}$, —C(O)N($R^{1a}$)$_2$, —N($R^{1a}$)$_2$, —N($R^{1a}$)C(O)$R^{1a}$, —N($R^{1a}$)C(O)$_2R^{1a}$, —N($R^{1a}$)C(O)N($R^{1a}$)$_2$, —N($R^{1a}$)S(O)$_2R^{1a}$, —O$R^{1a}$, —OC(O)$R^{1a}$, —OC(O)N($R^{1a}$)$_2$, —S$R^{1a}$, —S(O)$R^{1a}$, —S(O)$_2R^{1a}$, —S(O)N($R^{1a}$)$_2$, and —S(O)$_2$N($R^{1a}$)$_2$, wherein said $C_{1-6}$alkyl, $C_{2-6}$alkenyl, $C_{2-6}$alkynyl, carbocyclyl, and heterocyclyl, are optionally substituted with one or more $R^{10}$;

$R^{1a}$ in each occurrence is independently selected from H, $C_{1-6}$alkyl, $C_{2-6}$alkenyl, $C_{2-6}$alkynyl, carbocyclyl, and heterocyclyl, wherein said $C_{1-6}$alkyl, $C_{2-6}$alkenyl, $C_{2-6}$alkynyl, carbocyclyl, and heterocyclyl in each occurrence are optionally and independently substituted with one or more $R^{10}$;

$R^{10}$ in each occurrence is independently selected from $C_{1-6}$alkyl, $C_{2-6}$alkenyl, $C_{2-6}$alkynyl, carbocyclyl, heterocyclyl, halo, —CN, —C(O)$R^{10a}$, —C(O)$_2R^{10a}$, —C(O)N($R^{10a}$)$_2$, —N($R^{10a}$)$_2$, —N($R^{10a}$)C(O)$R^{10a}$, —N($R^{10a}$)C(O)$_2R^{10a}$, —N($R^{10a}$)C(O)N($R^{10a}$)$_2$, —N($R^{10a}$)S(O)$_2R^{10a}$, —O$R^{10a}$, —OC(O)$R^{10a}$, —OC(O)N($R^{10a}$)$_2$, —S$R^{10a}$, —S(O)$R^{10a}$, —S(O)$_2R^{10a}$, —S(O)N($R^{10a}$)$_2$, and —S(O)$_2$N($R^{10a}$)$_2$, wherein said $C_{1-6}$alkyl, $C_{2-6}$alkenyl, $C_{2-6}$alkynyl, carbocyclyl, and heterocyclyl in each occurrence are optionally and independently substituted with one or more halo, —CN, —C(O)$R^{10a}$, —C(O)$_2R^{10a}$, —C(O)N($R^{10a}$)$_2$, —N($R^{10a}$)$_2$, —N($R^{10a}$)C(O)$R^{10a}$, —N($R^{10a}$)C(O)$_2R^{10a}$, —N($R^{10a}$)C(O)N($R^{10a}$)$_2$, —N($R^{10a}$)S(O)$_2R^{10a}$, —O$R^{10a}$, —OC(O)$R^{10a}$, —OC(O)N($R^{10a}$)$_2$, —S$R^{10a}$, —S(O)$R^{10a}$, —S(O)$_2R^{10a}$, —S(O)N($R^{10a}$)$_2$, and —S(O)$_2$N($R^{10a}$)$_2$;

$R^{10a}$ in each occurrence is independently selected from H, $C_{1-6}$alkyl, $C_{2-6}$alkenyl, $C_{2-6}$alkynyl, carbocyclyl, and heterocyclyl;

$R^2$ in each occurrence is independently selected from $C_{1-6}$alkyl, —CN, —C(O)$R^{2a}$, —C(O)$_2R^{2a}$, —C(O)N($R^{2a}$)$_2$, —NO$_2$, —N(R$^{2a}$)$_2$, —N(R$^{2a}$)C(O)R$^{2a}$, —N(R$^{2a}$)C(O)$_2$R$^{2a}$, —N(R$^{2a}$)C(O)N(R$^{2a}$)$_2$, —N(R$^{2a}$)S(O)$_2$R$^{2a}$, —OR$^{2a}$, —OC(O)R$^{2a}$, —OC(O)N(R$^{2a}$)$_2$, —SR$^{2a}$, —S(O)R$^{2a}$, —S(O)$_2$R$^{2a}$, —S(O)N(R$^{2a}$)$_2$, and —S(O)$_2$N(R$^{1a}$)$_2$, wherein said C$_{1-6}$alkyl is optionally substituted with one or more R$^{20}$;

R$^{2a}$ in each occurrence is independently selected from H, C$_{1-6}$alkyl, C$_{2-6}$alkenyl, C$_{2-6}$alkynyl, carbocyclyl, and heterocyclyl wherein said C$_{1-6}$alkyl, C$_{2-6}$alkenyl, C$_{2-6}$alkynyl, carbocyclyl, and heterocyclyl in each occurrence are optionally and independently substituted with one or more R$^{20}$; and R$^{20}$ is independently selected from C$_{1-6}$alkyl, halo and —OR$^{20a}$;

R$^{20a}$ in each occurrence is independently selected from H, C$_{1-6}$alkyl, C$_{2-6}$alkenyl, C$_{2-6}$alkynyl, carbocyclyl, and heterocyclyl; and R$^3$ is H or C$_{1-4}$alkyl.

In one embodiment, the compound of the present invention is a compound of Formula (I):

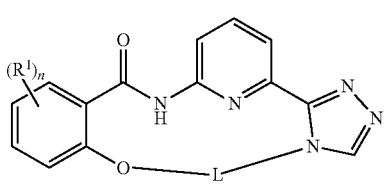

(I)

or a pharmaceutically acceptable salt thereof, wherein:

n is selected from 0, 1 and 2;

L is selected from C$_{3-5}$alkylene and C$_{3-5}$alkenylene, wherein said C$_{3-5}$alkylene and C$_{3-5}$alkenylene are optionally substituted with one or two R$^2$;

R$^1$ in each occurrence is independently selected from C$_{1-6}$alkyl, C$_{2-6}$alkenyl, C$_{2-6}$alkynyl, carbocyclyl, heterocyclyl, halo, —CN, —C(O)R$^{1a}$, —C(O)$_2$R$^{1a}$, —C(O)N(R$^{1a}$)$_2$, —N(R$^{1a}$)$_2$, —N(R$^{1a}$)C(O)R$^{1a}$, —N(R$^{1a}$)C(O)$_2$R$^{1a}$, —N(R$^{1a}$)C(O)N(R$^{1a}$)$_2$, —N(R$^{1a}$)S(O)$_2$R$^{1a}$, —OR$^{1a}$, —OC(O)R$^{1a}$, —OC(O)N(R$^{1a}$)$_2$, —SR$^{1a}$, —S(O)R$^{1a}$, —S(O)$_2$R$^{1a}$, —S(O)N(R$^{1a}$)$_2$, and —S(O)$_2$N(R$^{1a}$)$_2$, wherein said C$_{1-6}$alkyl, C$_{2-6}$alkenyl, C$_{2-6}$alkynyl, carbocyclyl, and heterocyclyl are optionally substituted with one or more R$^{10}$;

R$^{1a}$ in each occurrence is independently selected from H, C$_{1-6}$alkyl, C$_{2-6}$alkenyl, C$_{2-6}$alkynyl, carbocyclyl, and heterocyclyl, wherein said C$_{1-6}$alkyl, C$_{2-6}$alkenyl, C$_{2-6}$alkynyl, carbocyclyl, and heterocyclyl in each occurrence are optionally and independently substituted with one or more R$^{10}$;

R$^{10}$ in each occurrence is independently selected from C$_{1-6}$alkyl, C$_{2-6}$alkenyl, C$_{2-6}$alkynyl, carbocyclyl, heterocyclyl, halo, —CN, —C(O)R$^{10a}$, —C(O)$_2$R$^{10a}$, —C(O)N(R$^{10a}$)$_2$, —N(R$^{10a}$)$_2$, —N(R$^{10a}$)C(O)R$^{10a}$, —N(R$^{10a}$)C(O)$_2$R$^{10a}$, —N(R$^{10a}$)C(O)N(R$^{10a}$)$_2$, —N(R$^{10a}$)S(O)$_2$R$^{10a}$, —OR$^{10a}$, —OC(O)R$^{10a}$, —OC(O)N(R$^{10a}$)$_2$, —SR$^{10a}$, —S(O)R$^{10a}$, —S(O)$_2$R$^{10a}$, —S(O)N(R$^{10a}$)$_2$, and —S(O)$_2$N(R$^{10a}$)$_2$;

R$^{10a}$ in each occurrence is independently selected from H, C$_{1-6}$alkyl, C$_{2-6}$alkenyl, C$_{2-6}$alkynyl, carbocyclyl, and heterocyclyl;

R$^2$ in each occurrence is independently selected from C$_{1-6}$alkyl, —CN, —C(O)R$^{2a}$, —C(O)$_2$R$^{2a}$, —C(O)N(R$^{2a}$)$_2$, —NO$_2$, —N(R$^{2a}$)$_2$, —N(R$^{2a}$)C(O)R$^{2a}$, —N(R$^{2a}$)C(O)$_2$R$^{2a}$, —N(R$^{2a}$)C(O)N(R$^{2a}$)$_2$, —N(R$^{2a}$)S(O)$_2$R$^{2a}$, —OR$^{2a}$, —OC(O)R$^{2a}$, —OC(O)N(R$^{2a}$)$_2$, —SR$^{2a}$, —S(O)R$^{2a}$, —S(O)$_2$R$^{2a}$, —S(O)N(R$^{2a}$)$_2$, and —S(O)$_2$N(R$^{1a}$)$_2$, wherein said C$_{1-6}$alkyl is optionally substituted with one or more R$^{20}$;

R$^{2a}$ in each occurrence is independently selected from H, C$_{1-6}$alkyl, C$_{2-6}$alkenyl, C$_{2-6}$alkynyl, carbocyclyl, and heterocyclyl wherein said C$_{1-6}$alkyl, C$_{2-6}$alkenyl, C$_{2-6}$alkynyl, carbocyclyl, and heterocyclyl in each occurrence are optionally and independently substituted with one or more R$^{20}$; and R$^{20}$ is independently selected from C$_{1-6}$alkyl, halo and —OR$^{20a}$; and R$^{20a}$ in each occurrence is independently selected from H, C$_{1-6}$alkyl, C$_{2-6}$alkenyl, C$_{2-6}$alkynyl, carbocyclyl, and heterocyclyl.

The present invention also provides a pharmaceutical composition comprising at least one compound described herein, or a pharmaceutically acceptable salt thereof, and at least one pharmaceutically acceptable excipient.

In one embodiment, the invention is a method of treating a disorder responsive to inhibition of ASK1 in a subject comprising administering to said subject an effective amount of at least one compound described herein, or a pharmaceutically acceptable salt thereof.

The present invention also includes the use of at least one compound described herein, or a pharmaceutically acceptable salt thereof, for the manufacture of a medicament for the treatment of a disorder responsive to inhibition of ASK1. Also provided is a compound described herein, or a pharmaceutically acceptable salt thereof for use in treating a disorder responsive to inhibition of ASK1.

Other features or advantages will be apparent from the following detailed description of several embodiments, and also from the appended claims.

DETAILED DESCRIPTION

The compounds or pharmaceutically acceptable salts thereof as described herein, can have activity as ASK1 modulators. In particular, compounds or pharmaceutically acceptable salts thereof as described herein, can be ASK1 inhibitors.

In a second embodiment of the invention, the compound is represented by formula (I') or (I), or a pharmaceutically acceptable salt thereof, wherein L is C$_{3-5}$alkylene optionally substituted with one or two R$^2$ and the definitions for the other variables are as defined in the first embodiment.

In a third embodiment of the invention, the compound is represented by formula (I') or (I), or a pharmaceutically acceptable salt thereof, wherein L is C$_4$alkylene optionally substituted with one or two R$^2$, and the values of the other variables are as defined in the first embodiment.

In a fourth embodiment of the invention, the compound is represented by formula (I') or (I), or a pharmaceutically acceptable salt thereof, wherein L is C$_4$alkenylene optionally substituted with one or two R$^2$, and the values of the other variables are as defined in the first embodiment.

In a fifth embodiment of the invention, the compound is represented by formula (I') or (I), or a pharmaceutically acceptable salt thereof, wherein:

R$^2$ in each occurrence is independently selected from C$_{1-6}$alkyl, —CN, —C(O)R$^{2a}$, —C(O)$_2$R$^{2a}$, —C(O)N(R$^{2a}$)$_2$, —NO$_2$, —N(R$^{2a}$)$_2$, —N(R$^{2a}$)C(O)R$^{2a}$, —N(R$^{2a}$)C(O)$_2$R$^{2a}$, —OR$^{2a}$, —OC(O)R$^{2a}$, and —OC(O)N(R$^{2a}$)$_2$, wherein said C$_{1-6}$alkyl is optionally substituted with one to four R$^{20}$;

R$^{2a}$ in each occurrence is independently selected from H or C$_{1-6}$alkyl, wherein said C$_{1-6}$alkyl in each occurrence is optionally and independently substituted with one to three $R^{20}$; and $R^{20}$ is independently halo or —$OR^{20a}$;

$R^{20a}$ in each occurrence is independently H or $C_{1-6}$alkyl, and the values of the other variables are as defined in the first, second, third, or fourth embodiments.

In a sixth embodiment of the invention, the compound is represented by formula (I') or (I), or pharmaceutically acceptable salt thereof, wherein $R^2$ is $C_{1-4}$alkyl, and the values of the other variables are as defined in the fifth embodiment.

In a seventh embodiment of the invention, the compound is represented by formula (I') or (I), or pharmaceutically acceptable salt thereof, wherein $R^2$ is methyl, and the values of the other variables are as defined in the fifth embodiment.

In an eighth embodiment of the invention, the compound is represented by formula (I') or (I), or pharmaceutically acceptable salt thereof, wherein L is —$(CH_2)_3$—, —$(CH_2)_4$—, —$CH(CH_3)$—$CH_2$—$CH_2$—$CH_2$—, —$CH_2$—$CH(CH_3)$—$CH_2$—$CH_2$—, —$CH_2$—$CH_2$—$CH(CH_3)$—$CH_2$—, —$CH_2$—$CH_2$—$CH_2$—$CH(CH_3)$—, —$(CH_2)_5$—, —$CH_2$—$CH$=$CH$—$CH_2$—, or —$CH_2$—$CH_2$—$CH$=$CH$—$CH_2$—, and the values of the other variables are as defined in the first embodiment. In one embodiment, L is —$(CH_2)_4$—, —$CH_2$—$CH(CH_3)$—$CH_2$—$CH_2$—, —$CH_2$—$CH_2$—$CH_2$—$CH(CH_3)$—, —$(CH_2)_5$—, —$(CH_2)_3$—, or —$CH_2$—$CH$=$CH$—$CH_2$—, and the values of the other variables are as defined in the first embodiment.

In a ninth embodiment of the invention, the compound is represented by formula (I') or (I), or pharmaceutically acceptable salt thereof, wherein n is 0, and the values of the other variables are as defined in the first, second, third, fourth, fifth, sixth, seventh, or eighth embodiment.

In a tenth embodiment of the invention, the compound is represented by formula (I') or (I), or pharmaceutically acceptable salt thereof, wherein:

$R^1$ in each occurrence is independently selected from $C_{1-6}$alkyl, $C_{2-6}$alkenyl, $C_{2-6}$alkynyl, 4- to 7-membered monocyclic non-aromatic heterocyclyl, 5- to 6-membered N-containing heteroaryl, 6- to 8-membered spiro or bridged bicyclic heterocyclyl, halo, —CN, —$C(O)R^{1a}$, —$C(O)_2R^{1a}$, —$C(O)N(R^{1a})_2$, —$N(R^{1a})_2$, —$OR^{1a}$, —$S(O)_2R^{1a}$, and —$S(O)_2N(R^{1a})_2$, wherein said $C_{1-6}$alkyl, $C_{2-6}$alkenyl, 4- to 7-membered monocyclic non-aromatic heterocyclyl, 5- to 6-membered N-containing heteroaryl, and 6- to 8-membered spiro or bridged bicyclic heterocyclyl, are optionally substituted with one to four $R^{10}$;

$R^{1a}$ in each occurrence is independently selected from H, $C_{1-6}$alkyl, and 4- to 7-membered monocyclic N-containing non-aromatic heterocyclyl, wherein said $C_{1-6}$alkyl, and 4- to 7-membered monocyclic N-containing non-aromatic heterocyclyl in each occurrence are optionally and independently substituted with one or three $R^{10}$; and $R^{10}$ in each occurrence is independently selected from $C_{1-6}$alkyl, halo, —$N(R^{10a})_2$, —$OR^{10a}$, —CN, $C_{3-6}$cycloalkyl, 4- to 7-membered monocyclic non-aromatic heterocyclyl, wherein said $C_{1-6}$alkyl, $C_{3-6}$cyloalkyl, and 4- to 7-membered monocyclic non-aromatic heterocyclyl are optionally substituted with one or more halo, —CN, —$C(O)R^{10a}$, —$C(O)_2R^{10a}$, —$C(O)N(R^{10a})_2$, —$N(R^{10a})_2$, —$N(R^{10a})C(O)R^{10a}$, —$N(R^{10a})C(O)_2R^{10a}$, —$N(R^{10a})C(O)N(R^{10a})_2$, —$N(R^{10a})S(O)_2R^{10a}$, —$OR^{10a}$, —$OC(O)R^{10a}$, —$OC(O)N(R^{10a})_2$, —$SR^{10a}$, —$S(O)R^{10a}$, —$S(O)_2R^{10a}$, —$S(O)N(R^{10a})_2$, and —$S(O)_2N(R^{10a})_2$;

$R^{10a}$ in each occurrence is independently H or $C_{1-4}$alkyl, and the values of the other variables are as defined for the first, second, third, fourth, fifth, sixth, seventh, or eighth embodiment.

In one embodiment, for compounds of formula (I') or (I) or pharmaceutically acceptable salt thereof, $R^1$ in each occurrence is independently selected from $C_{1-6}$alkyl, $C_{2-6}$alkenyl, 4- to 7-membered monocyclic non-aromatic heterocyclyl, 5- to 6-membered N-containing heteroaryl, 6- to 8-membered spiro or bridged bicyclic heterocyclyl, halo, —CN, —$C(O)R^{1a}$, —$C(O)_2R^{1a}$, —$C(O)N(R^{1a})_2$, —$S(O)_2R^{1a}$, and —$S(O)_2N(R^{1a})_2$, wherein said $C_{1-6}$alkyl, $C_{2-6}$alkenyl, 4- to 7-membered monocyclic non-aromatic heterocyclyl, 5- to 6-membered N-containing heteroaryl, and 6- to 8-membered spiro or bridged bicyclic heterocyclyl, are optionally substituted with one to four $R^{10}$;

$R^{1a}$ in each occurrence is independently selected from H, $C_{1-6}$alkyl, and 4- to 7-membered monocyclic N-containing non-aromatic heterocyclyl, wherein said $C_{1-6}$alkyl, and 4- to 7-membered monocyclic N-containing non-aromatic heterocyclyl in each occurrence are optionally and independently substituted with one or three $R^{10}$; and $R^{10}$ in each occurrence is independently selected from $C_{1-6}$alkyl, halo, and $C_{3-6}$cyloalkyl, and the values of the other variables are as defined in the first, second, third, fourth, fifth, sixth, seventh, or eighth embodiment.

In an eleventh embodiment of the invention, the compound is represented by formula (I') or (I), or a pharmaceutically acceptable salt thereof, wherein:

$R^1$ in each occurrence is independently selected from $C_{1-6}$alkyl, $C_{2-6}$alkenyl, $C_{2-6}$alkynyl, $C_{3-6}$cycloalkyl selected from cyclopropyl, cyclobutyl, cyclopentyl, and cyclohexyl, 4- to 7-membered monocyclic heterocyclyl selected from azetidinyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, dihydrofuranyl, imidazolinyl, dihydropyranyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, tetrahydropyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, azepinyl, oxepinyl, thiepinyl, diazepinyl, and thiazepinyl, 6- to 8-membered spiro or bridged bicyclic heterocyclyl selected from 3-azabicyclo[3.1.0]hexanyl, 3-azabicyclo[3.1.1]heptanyl, 2-azaspiro[3.3]heptanyl, 2-oxa-6-azaspiro[3.3]heptanyl, 3-oxa-8-azabicyclo[3.2.1]octanyl, 6-oxa-3-azabicyclo[3.1.1]heptanyl, 8-oxa-3-azabicyclo[3.2.1]octanyl, 3-oxa-6-azabicyclo[3.1.1]heptanyl, and 5-azaspiro[2.3]hexanyl, 4,5,6,7-tetrahydropyrazolo[1,5-a]pyrazinyl, halo, —CN, —$OR^{1a}$, —$NHR^{1a}$, —$C(O)R^{1a}$, and —$S(O)_2R^{1a}$, wherein said $C_{1-6}$alkyl, $C_{2-6}$alkenyl, $C_{3-6}$cycloalkyl, 4- to 7-membered monocyclic heterocyclyl, and 6- to 8-membered spiro or bridged bicyclic heterocyclyl are optionally substituted with one to four $R^{10}$;

$R^{1a}$ in each occurrence is H, $C_{1-6}$alkyl or 4- to 7-membered monocyclic heterocyclyl selected from azetidinyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, and azepinyl, wherein said $C_{1-6}$alkyl or 4- to 7-membered monocyclic heterocyclyl is independently optionally substituted with one to three $R^{10}$; and $R^{10}$ in each occurrence is independently selected from $C_{1-6}$alkyl, $C_{3-6}$cycloalkyl selected from cyclopropyl, cyclobutyl, cyclopentyl, and cyclohexyl, oxatanyl, —$OR^{10a}$, —$N(R^{10a})_2$ and halo;

$R^{10a}$ is H or $C_{1-4}$alkyl; and the values of the other variables are as defined for the first, second, third, fourth, fifth, sixth, seventh, or eighth embodiment.

In one embodiment, for compounds of formula (I') or (I) or pharmaceutically acceptable salt thereof, $R^1$ in each occurrence is independently selected from $C_{1-6}$alkyl, $C_{2-6}$alkenyl, $C_{3-6}$cycloalkyl selected from cyclopropyl, cyclobutyl, cyclopentyl, and cyclohexyl, 4- to 7-membered monocyclic heterocyclyl selected from azetidinyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, dihydrofuranyl, imidazolinyl, dihydropyranyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, azepinyl, oxepinyl, thiepinyl, diazepinyl, and thiazepinyl, 6- to 8-membered spiro or bridged bicyclic heterocyclyl selected from 3-azabicyclo[3.1.0]hexanyl, 3-azabicyclo[3.1.1]heptanyl, 2-azaspiro[3.3]heptanyl, 2-oxa-6-azaspiro[3.3]heptanyl, 3-oxa-8-azabicyclo[3.2.1]octanyl, 6-oxa-3-azabicyclo[3.1.1]heptanyl, 8-oxa-3-azabicyclo[3.2.1]octanyl, 3-oxa-6-azabicyclo[3.1.1]heptanyl, and 5-azaspiro[2.3]hexanyl, halo, —CN, —$C(O)R^{1a}$, and —$S(O)_2R^{1a}$, wherein said $C_{1-6}$alkyl, $C_{2-6}$alkenyl, $C_{3-6}$cycloalkyl, 4- to 7-membered monocyclic heterocyclyl, and 6- to 8-membered spiro or bridged bicyclic heterocyclyl are optionally substituted with one to four $R^{10}$;

$R^{1a}$ in each occurrence is H, $C_{1-6}$alkyl or 4- to 7-membered monocyclic heterocyclyl selected from azetidinyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, and azepanyl; and $R^{10}$ in each occurrence is independently selected from $C_{1-6}$alkyl, $C_{3-6}$cycloalkyl selected from cyclopropyl, cyclobutyl, cyclopentyl, and cyclohexyl, and halo, wherein the values of the other variables are as defined for the first, second, third, fourth, fifth, sixth, seventh, or eighth embodiment.

In a twelfth embodiment of the invention, the compound is represented by formula (I') or (I), or pharmaceutically acceptable salt thereof, wherein:

n is 1;

$R^1$ in each occurrence is independently selected from —$CH_3$, —$CF_3$, —C≡CH, —$CH_2NH_2$, —$CH_2N(CH_3)_2$, —$C(CH_3)_2OH$, —$C(CH_3)_2OCH_3$, —$C(CH_3)_2CN$, —CH=$CH_2$, heterocyclyl selected from azetidinyl, pyrrolidinyl, tetrahydrofuranyl, piperidinyl, tetrahydropyranyl, piperazinyl, morpholinyl, dihydrofuranyl, dihydropyranyl, imidazolyl, pyrazolyl, triazolyl, tetrahydropyridinyl, pyridinyl, pyrimidinyl, pyridazinyl, 2-oxa-6-azaspiro[3.3]heptanyl, 3-oxa-8-azabicyclo[3.2.1]octanyl, 6-oxa-3-azabicyclo[3.1.1]heptanyl, 8-oxa-3-azabicyclo[3.2.1]octanyl, and 3-oxa-6-azabicyclo[3.1.1]heptanyl, 4,5,6,7-tetrahydropyrazolo[1,5-a]pyrazinyl, —Br, —F, —CN, —$OR^{1a}$, —$NHR^{1a}$, —$C(O)R^{1a}$, and —$S(O)_2R^{1a}$, wherein said heterocyclyl is optionally substituted with one to three $R^{10}$ and said —C≡CH is optionally substituted one $R^{10}$;

$R^{1a}$ in each occurrence is H, —$CH_3$, —$CH_2CH_2OCH_3$, —$CH_2CH_2N(CH_3)_2$, or pyrrolidinyl; and $R^{10}$ in each occurrence is independently selected from —$CH_3$, —$CH_2CH_3$, —$CH(CH_3)_2$, —$CF_3$, cyclopropyl, cyclobutyl, oxatanyl, 3-methyloxetan-3-yl, —$CH_2CH_2N(CH_3)_2$, and —F; and the values of the other variables are as defined for the first, second, third, fourth, fifth, sixth, seventh, or eighth embodiment.

In one embodiment, for compounds of formula (I') or (I) or pharmaceutically acceptable salt thereof, n is 1;

$R^1$ in each occurrence is independently selected from —$CH_3$, —$CF_3$, —CH=$CH_2$, heterocyclyl selected from azetidinyl, pyrrolidinyl, tetrahydrofuranyl, piperidinyl, tetrahydropyranyl, piperazinyl, morpholinyl, dihydrofuranyl, dihydropyranyl, imidazolyl, pyrazolyl, triazolyl, pyridinyl, 2-oxa-6-azaspiro[3.3]heptanyl, 3-oxa-8-azabicyclo[3.2.1]octanyl, 6-oxa-3-azabicyclo[3.1.1]heptanyl, 8-oxa-3-azabicyclo[3.2.1]octanyl, and 3-oxa-6-azabicyclo[3.1.1]heptanyl, —Br, —F, —CN, —$C(O)R^{1a}$, and —$S(O)_2R^{1a}$, wherein said heterocyclyl is optionally substituted with one to two $R^{10}$;

$R^{1a}$ in each occurrence is H, —$CH_3$ or pyrrolidinyl;

$R^{10}$ in each occurrence is independently selected from —$CH_3$, —$CH_2CH_3$, cyclopropyl, and —F, wherein the values of the other variables are as defined for the first, second, third, fourth, fifth, sixth, seventh, or eighth embodiment.

In a thirteenth embodiment of the invention, the compound is represented by Formula (II') or (II):

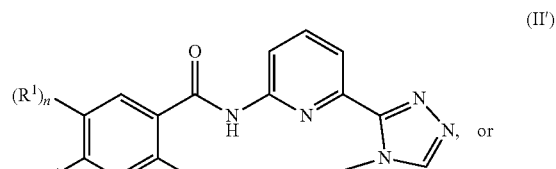

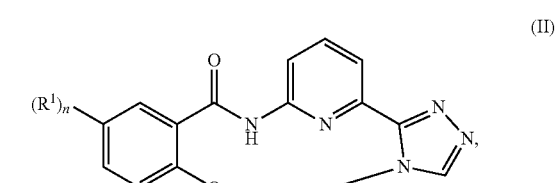

or a pharmaceutically acceptable salt thereof, wherein:

L is —$(CH_2)_4$—, —$CH_2$—$CH_2$—$CH_2$—$CH(CH_3)$— or —$CH(CH_3)$—$CH_2$—$CH_2$—$CH_2$—;

n is 0 or 1;

$R^1$ is —CN, halo, heterocyclyl selected from imidazolyl, pyrazolyl, pyridine, piperazine, 1,2,3,6-tetrahydropyridine, piperidine, pyrimidine, and 6-oxa-3-azabicyclo[3.1.1]heptanyl, wherein said heterocyclyl is optionally substituted with one $R^{10}$;

$R^{1'}$ is halo, $R^{10}$ is $C_{1-4}$alkyl or $C_{3-6}$cycloalkyl, wherein said $C_{1-4}$alkyl is optionally substituted with one —$N(R^{10a})_2$; and $R^{10a}$ is H or $C_{1-4}$alkyl.

In a fourteenth embodiment of the invention, the compound is represented by the Formula (II):

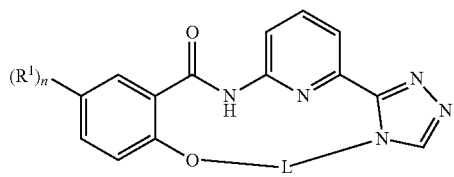

(II)

or a pharmaceutically acceptable salt thereof, wherein:

L is —(CH$_2$)$_4$— or —CH$_2$—CH$_2$—CH$_2$—CH(CH$_3$)—;

n is 0 or 1;

R$^1$ is heterocyclyl selected from imidazolyl, pyrazolyl, and 6-oxa-3-azabicyclo[3.1.1]heptanyl, wherein said heterocyclyl is optionally substituted with one R$^{10}$; and R$^{10}$ is C$_{1-4}$alkyl or C$_{3-6}$cycloalkyl, and the values of the other variables are as defined in the first embodiment.

In a fifteenth embodiment of the invention, the compound is represented by formula (II') or (II), or pharmaceutically acceptable salt thereof, wherein R$^1$ is —CN, —F, or a heterocyclyl selected from the following:

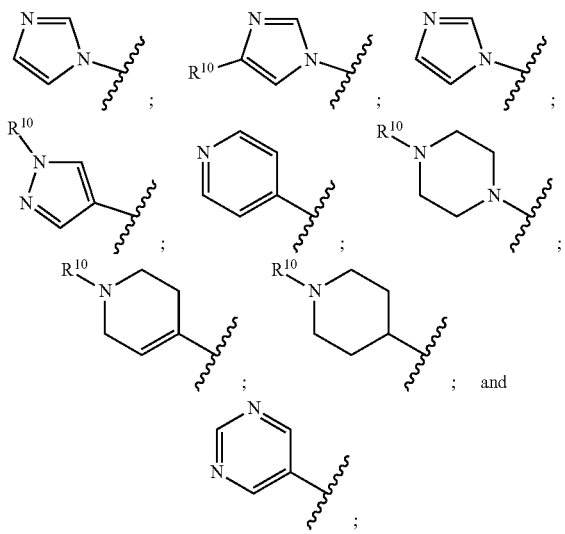

R$^{1'}$ when present is —F; and the values of the other variables are as defined for the thirteenth or fourteenth embodiment.

In a sixteenth embodiment of the invention, the compound is represented by formula (II), or pharmaceutically acceptable salt thereof, wherein R$^1$ is a heterocyclyl selected from the following:

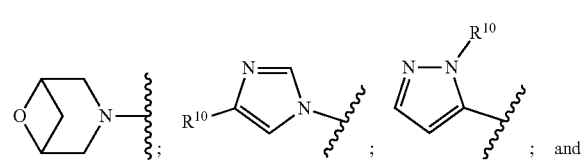

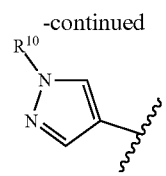

and the values of the other variables are as defined for the thirteenth or fourteenth embodiment.

In a seventeenth embodiment of the invention, the compound is represented by formula (II') or (II), or pharmaceutically acceptable salt thereof, wherein R$^{10}$ is —CH$_3$, —CH$_2$CH$_2$N(CH$_3$)$_2$ or cyclopropyl, and the values of the other variables are as defined for the thirteenth, fourteenth, fifteenth or sixteenth embodiment.

In a eighteenth embodiment of the invention, the compound is selected from:

5$^5$-Bromo-1$^4$H-6-oxa-3-aza-2(2,6)-pyridina-1(3,4)-triazola-5(1,2)-benzenacyclodecaphan-4-one;

1$^4$H-6-Oxa-3-aza-2(2,6)-pyridina-1(3,4)-triazola-5(1,2)-benzenacyclodecaphan-4-one;

5$^5$-Morpholino-1$^4$H-6-oxa-3-aza-2(2,6)-pyridina-1(3,4)-triazola-5(1,2)-benzenacyclodecaphan-4-one;

5$^5$-(2-Oxa-6-azaspiro[3.3]heptan-6-yl)-1$^4$H-6-oxa-3-aza-2(2,6)-pyridina-1(3,4)-triazola-5(1,2)-benzenacyclodecaphan-4-one;

5$^5$-(3-Oxa-8-azabicyclo[3.2.1]octan-8-yl)-1$^4$H-6-oxa-3-aza-2(2,6)-pyridina-1(3,4)-triazola-5(1,2)-benzenacyclodecaphan-4-one;

5$^5$-(6-Oxa-3-azabicyclo[3.1.1]heptan-3-yl)-1$^4$H-6-oxa-3-aza-2(2,6)-pyridina-1(3,4)-triazola-5(1,2)-benzenacyclodecaphan-4-one;

5$^5$-(8-Oxa-3-azabicyclo[3.2.1]octan-3-yl)-1$^4$H-6-oxa-3-aza-2(2,6)-pyridina-1(3,4)-triazola-5(1,2)-benzenacyclodecaphan-4-one;

5$^5$-(3-Oxa-6-azabicyclo[3.1.1]heptan-6-yl)-1$^4$H-6-oxa-3-aza-2(2,6)-pyridina-1(3,4)-triazola-5(1,2)-benzenacyclodecaphan-4-one;

5$^5$-(3,3-Difluoroazetidin-1-yl)-1$^4$H-6-oxa-3-aza-2(2,6)-pyridina-1(3,4)-triazola-5(1,2)-benzenacyclodecaphan-4-one;

5$^5$-(3,3-Difluoropyrrolidin-1-yl)-1$^4$H-6-oxa-3-aza-2(2,6)-pyridina-1(3,4)-triazola-5(1,2)-benzenacyclodecaphan-4-one;

5$^5$-(3,3-Difluoropiperidin-1-yl)-1$^4$H-6-oxa-3-aza-2(2,6)-pyridina-1(3,4)-triazola-5(1,2)-benzenacyclodecaphan-4-one;

5$^5$-(4,4-Difluoropiperidin-1-yl)-1$^4$H-6-oxa-3-aza-2(2,6)-pyridina-1(3,4)-triazola-5(1,2)-benzenacyclodecaphan-4-one;

5$^5$-(4-Ethylpiperazin-1-yl)-1$^4$H-6-oxa-3-aza-2(2,6)-pyridina-1(3,4)-triazola-5(1,2)-benzenacyclodecaphan-4-one;

5$^5$-(2,5-Dihydrofuran-3-yl)-1$^4$H-6-oxa-3-aza-2(2,6)-pyridina-1(3,4)-triazola-5(1,2)-benzenacyclodecaphan-4-one;

rac-5$^5$-(Tetrahydrofuran-3-yl)-1$^4$H-6-oxa-3-aza-2(2,6)-pyridina-1(3,4)-triazola-5(1,2)-benzenacyclodecaphan-4-one;

5$^5$-(3,6-Dihydro-2H-pyran-4-yl)-1$^4$H-6-oxa-3-aza-2(2,6)-pyridina-1(3,4)-triazola-5(1,2)-benzenacyclodecaphan-4-one;

5$^5$-(Tetrahydro-2H-pyran-4-yl)-1$^4$H-6-oxa-3-aza-2(2,6)-pyridina-1(3,4)-triazola-5(1,2)-benzenacyclodecaphan-4-one;

5⁵-Methyl-1⁴H-6-oxa-3-aza-2(2,6)-pyridina-1(3,4)-triazola-5(1,2)-benzenacyclodecaphan-4-one;
5⁵-Vinyl-1⁴H-6-oxa-3-aza-2(2,6)-pyridina-1(3,4)-triazola-5(1,2)-benzenacyclodecaphan-4-one;
4-Oxo-1⁴H-6-oxa-3-aza-2(2,6)-pyridina-1(3,4)-triazola-5(1,2)-benzenacyclodecaphane-5⁵-carbonitrile;
5⁵-(4-Methyl-1H-imidazol-1-yl)-1⁴H-6-oxa-3-aza-2(2,6)-pyridina-1(3,4)-triazola-5(1,2)-benzenacyclodecaphan-4-one;
5⁵-(4-Cyclopropyl-1H-imidazol-1-yl)-1⁴H-6-oxa-3-aza-2(2,6)-pyridina-1(3,4)-triazola-5(1,2)-benzenacyclodecaphan-4-one;
5⁵-(1-Methyl-1H-pyrazol-5-yl)-1⁴H-6-oxa-3-aza-2(2,6)-pyridina-1(3,4)-triazola-5(1,2)-benzenacyclodecaphan-4-one;
5⁵-(1-Methyl-1H-pyrazol-4-yl)-1⁴H-6-oxa-3-aza-2(2,6)-pyridina-1(3,4)-triazola-5(1,2)-benzenacyclodecaphan-4-one;
5⁵-(Pyridin-2-yl)-1⁴H-6-oxa-3-aza-2(2,6)-pyridina-1(3,4)-triazola-5(1,2)-benzenacyclodecaphan-4-one;
5⁵-(Pyridin-3-yl)-1⁴H-6-oxa-3-aza-2(2,6)-pyridina-1(3,4)-triazola-5(1,2)-benzenacyclodecaphan-4-one;
5⁵-(Pyridin-4-yl)-1⁴H-6-oxa-3-aza-2(2,6)-pyridina-1(3,4)-triazola-5(1,2)-benzenacyclodecaphan-4-one;
5⁵-(Methylsulfonyl)-1⁴H-6-oxa-3-aza-2(2,6)-pyridina-1(3,4)-triazola-5(1,2)-benzenacyclodecaphan-4-one;
5⁵-(1-Methyl-1H-imidazol-5-yl)-1⁴H-6-oxa-3-aza-2(2,6)-pyridina-1(3,4)-triazola-5(1,2)-benzenacyclodecaphan-4-one;
5⁵-(1-Methyl-1H-1,2,3-triazol-4-yl)-1⁴H-6-oxa-3-aza-2(2,6)-pyridina-1(3,4)-triazola-5(1,2)-benzenacyclodecaphan-4-one;
5⁵-(Pyrrolidine-1-carbonyl)-1⁴H-6-oxa-3-aza-2(2,6)-pyridina-1(3,4)-triazola-5(1,2)-benzenacyclodecaphan-4-one;
5⁵-(1,3-Dimethyl-1H-pyrazol-4-yl)-1⁴H-6-oxa-3-aza-2(2,6)-pyridina-1(3,4)-triazola-5(1,2)-benzenacyclodecaphan-4-one;
5⁵-(1,3,5-Trimethyl-1H-pyrazol-4-yl)-1⁴H-6-oxa-3-aza-2(2,6)-pyridina-1(3,4)-triazola-5(1,2)-benzenacyclodecaphan-4-one;
5⁵-(1,3-Dimethyl-1H-pyrazol-5-yl)-1⁴H-6-oxa-3-aza-2(2,6)-pyridina-1(3,4)-triazola-5(1,2)-benzenacyclodecaphan-4-one;
5⁵-(1-Cyclobutyl-1H-pyrazol-4-yl)-1⁴H-6-oxa-3-aza-2(2,6)-pyridina-1(3,4)-triazola-5(1,2)-benzenacyclodecaphan-4-one;
5⁵-(1-Isopropyl-1H-pyrazol-4-yl)-1⁴H-6-oxa-3-aza-2(2,6)-pyridina-1(3,4)-triazola-5(1,2)-benzenacyclodecaphan-4-one;
5⁵-(1,5-Dimethyl-1H-pyrazol-4-yl)-1⁴H-6-oxa-3-aza-2(2,6)-pyridina-1(3,4)-triazola-5(1,2)-benzenacyclodecaphan-4-one;
5⁵-(1-(Oxetan-3-yl)-1H-pyrazol-4-yl)-1⁴H-6-oxa-3-aza-2(2,6)-pyridina-1(3,4)-triazola-5(1,2)-benzenacyclodecaphan-4-one;
5⁵-(1-(2-(Dimethylamino)ethyl)-1H-pyrazol-4-yl)-1⁴H-6-oxa-3-aza-2(2,6)-pyridina-1(3,4)-triazola-5(1,2)-benzenacyclodecaphan-4-one;
5⁵-(5-Methyl-4,5,6,7-tetrahydropyrazolo[1,5-a]pyrazin-3-yl)-1⁴H-6-oxa-3-aza-2(2,6)-pyridina-1(3,4)-triazola-5(1,2)-benzenacyclodecaphan-4-one;
5⁵-(1H-Imidazol-1-yl)-1⁴H-6-oxa-3-aza-2(2,6)-pyridina-1(3,4)-triazola-5(1,2)-benzenacyclodecaphan-4-one;
5⁵-(4,5-Dimethyl-1H-imidazol-1-yl)-1⁴H-6-oxa-3-aza-2(2,6)-pyridina-1(3,4)-triazola-5(1,2)-benzenacyclodecaphan-4-one;
5⁵-(2-Methyl-1H-imidazol-1-yl)-1⁴H-6-oxa-3-aza-2(2,6)-pyridina-1(3,4)-triazola-5(1,2)-benzenacyclodecaphan-4-one;
5⁵-(1H-Pyrazol-1-yl)-1⁴H-6-oxa-3-aza-2(2,6)-pyridina-1(3,4)-triazola-5(1,2)-benzenacyclodecaphan-4-one;
5⁵-(3-Methyl-1H-pyrazol-1-yl)-1⁴H-6-oxa-3-aza-2(2,6)-pyridina-1(3,4)-triazola-5(1,2)-benzenacyclodecaphan-4-one;
5⁵-(5-Methyl-1H-pyrazol-1-yl)-1⁴H-6-oxa-3-aza-2(2,6)-pyridina-1(3,4)-triazola-5(1,2)-benzenacyclodecaphan-4-one
5⁵-(3,5-Dimethyl-1H-pyrazol-1-yl)-1⁴H-6-oxa-3-aza-2(2,6)-pyridina-1(3,4)-triazola-5(1,2)-benzenacyclodecaphan-4-one;
5⁵-(Aminomethyl)-1⁴H-6-oxa-3-aza-2(2,6)-pyridina-1(3,4)-triazola-5(1,2)-benzenacyclodecaphan-4-one;
5⁵-((Dimethylamino)methyl)-1⁴H-6-oxa-3-aza-2(2,6)-pyridina-1(3,4)-triazola-5(1,2)-benzenacyclodecaphan-4-one;
5⁵-(2-Hydroxypropan-2-yl)-1⁴H-6-oxa-3-aza-2(2,6)-pyridina-1(3,4)-triazola-5(1,2)-benzenacyclodecaphan-4-one;
5⁵-(2-Methoxypropan-2-yl)-1⁴H-6-oxa-3-aza-2(2,6)-pyridina-1(3,4)-triazola-5(1,2)-benzenacyclodecaphan-4-one;
2-Methyl-2-(4-oxo-1⁴H-6-oxa-3-aza-2(2,6)-pyridina-1(3,4)-triazola-5(1,2)-benzenacyclodecaphane-5⁵-yl)propanenitrile;
5⁴-Fluoro-5⁵-(pyridin-4-yl)-1⁴H-6-oxa-3-aza-2(2,6)-pyridina-1(3,4)-triazola-5(1,2)-benzenacyclodecaphan-4-one;
5⁴-Fluoro-5⁵-(2-(trifluoromethyl)pyridin-4-yl)-1⁴H-6-oxa-3-aza-2(2,6)-pyridina-1(3,4)-triazola-5(1,2)-benzenacyclodecaphan-4-one;
5⁴-Fluoro-5⁵-(2-methylpyridin-4-yl)-1⁴H-6-oxa-3-aza-2(2,6)-pyridina-1(3,4)-triazola-5(1,2)-benzenacyclodecaphan-4-one;
5⁴-Fluoro-5⁵-(2-fluoropyridin-4-yl)-1⁴H-6-oxa-3-aza-2(2,6)-pyridina-1(3,4)-triazola-5(1,2)-benzenacyclodecaphan-4-one;
5⁵-(2-Cyclopropylpyridin-4-yl)-5⁴-fluoro-1⁴H-6-oxa-3-aza-2(2,6)-pyridina-1(3,4)-triazola-5(1,2)-benzenacyclodecaphan-4-one;
5⁴-Fluoro-5⁵-(6-methylpyridin-3-yl)-1⁴H-6-oxa-3-aza-2(2,6)-pyridina-1(3,4)-triazola-5(1,2)-benzenacyclodecaphan-4-one;
5⁴-Fluoro-5⁵-(5-(trifluoromethyl)pyridin-3-yl)-1⁴H-6-oxa-3-aza-2(2,6)-pyridina-1(3,4)-triazola-5(1,2)-benzenacyclodecaphan-4-one;
5⁵-(6-Cyclopropylpyridin-3-yl)-5⁴-fluoro-1⁴H-6-oxa-3-aza-2(2,6)-pyridina-1(3,4)-triazola-5(1,2)-benzenacyclodecaphan-4-one;
5⁴-Fluoro-5⁵-(pyrimidin-5-yl)-1⁴H-6-oxa-3-aza-2(2,6)-pyridina-1(3,4)-triazola-5(1,2)-benzenacyclodecaphan-4-one;
5⁴-Fluoro-5⁵-(pyridazin-4-yl)-1⁴H-6-oxa-3-aza-2(2,6)-pyridina-1(3,4)-triazola-5(1,2)-benzenacyclodecaphan-4-one;
5⁵-(1,5-Dimethyl-1H-pyrazol-4-yl)-5⁴-fluoro-1⁴H-6-oxa-3-aza-2(2,6)-pyridina-1(3,4)-triazola-5(1,2)-benzenacyclodecaphan-4-one;
5⁴-Fluoro-5⁵-(1-methyl-1H-pyrazol-4-yl)-1⁴H-6-oxa-3-aza-2(2,6)-pyridina-1(3,4)-triazola-5(1,2)-benzenacyclodecaphan-4-one;
5⁵-(1-(2-(Dimethylamino)ethyl)-1H-pyrazol-4-yl)-5⁴-fluoro-1⁴H-6-oxa-3-aza-2(2,6)-pyridina-1(3,4)-triazola-5(1,2)-benzenacyclodecaphan-4-one;

5⁴-Fluoro-5⁵-(5-methyl-4,5,6,7-tetrahydropyrazolo[1,5-a]pyrazin-3-yl)-1⁴H-6-oxa-3-aza-2(2,6)-pyridina-1(3,4)-triazola-5(1,2)-benzenacyclodecaphan-4-one;

5⁴-Fluoro-5⁵-(4-methyl-1H-imidazol-1-yl)-1⁴H-6-oxa-3-aza-2(2,6)-pyridina-1(3,4)-triazola-5(1,2)-benzenacyclodecaphan-4-one;

5⁵-(3,6-Dihydro-2H-pyran-4-yl)-5⁴-fluoro-1⁴H-6-oxa-3-aza-2(2,6)-pyridina-1(3,4)-triazola-5(1,2)-benzenacyclodecaphan-4-one;

5⁴-Fluoro-5⁵-(tetrahydro-2H-pyran-4-yl)-1⁴H-6-oxa-3-aza-2(2,6)-pyridina-1(3,4)-triazola-5(1,2)-benzenacyclodecaphan-4-one;

5⁴-Fluoro-5⁵-(1-methyl-1,2,3,6-tetrahydropyridin-4-yl)-1⁴H-6-oxa-3-aza-2(2,6)-pyridina-1(3,4)-triazola-5(1,2)-benzenacyclodecaphan-4-one;

5⁴-Fluoro-5⁵-(1-methylpiperidin-4-yl)-1⁴H-6-oxa-3-aza-2(2,6)-pyridina-1(3,4)-triazola-5(1,2)-benzenacyclodecaphan-4-one;

5⁴-Fluoro-5⁵-morpholino-1⁴H-6-oxa-3-aza-2(2,6)-pyridina-1(3,4)-triazola-5(1,2)-benzenacyclodecaphan-4-one;

5⁵-(6-Oxa-3-azabicyclo[3.1.1]heptan-3-yl)-5⁴-fluoro-1⁴H-6-oxa-3-aza-2(2,6)-pyridina-1(3,4)-triazola-5(1,2)-benzenacyclodecaphan-4-one;

5⁴-Fluoro-5⁵-(4-methylpiperazin-1-yl)-1⁴H-6-oxa-3-aza-2(2,6)-pyridina-1(3,4)-triazola-5(1,2)-benzenacyclodecaphan-4-one;

5⁴-Fluoro-4-oxo-1⁴H-6-oxa-3-aza-2(2,6)-pyridina-1(3,4)-triazola-5(1,2)-benzenacyclodecaphane-5⁵-carbonitrile;

5⁴-Fluoro-5⁵-(2-methoxyethoxy)-1⁴H-6-oxa-3-aza-2(2,6)-pyridina-1(3,4)-triazola-5(1,2)-benzenacyclodecaphan-4-one;

5⁵-(2-(Dimethylamino)ethoxy)-5⁴-fluoro-1⁴H-6-oxa-3-aza-2(2,6)-pyridina-1(3,4)-triazola-5(1,2)-benzenacyclodecaphan-4-one;

5⁵-(1-(2-(Dimethylamino)ethyl)-1H-pyrazol-4-yl)-5⁴-(trifluoromethyl)-1⁴H-6-oxa-3-aza-2(2,6)-pyridina-1(3,4)-triazola-5(1,2)-benzenacyclodecaphan-4-one;

5⁴-(1-Methyl-1,2,3,6-tetrahydropyridin-4-yl)-1⁴H-6-oxa-3-aza-2(2,6)-pyridina-1(3,4)-triazola-5(1,2)-benzenacyclodecaphan-4-one;

5⁴-(1-Methylpiperidin-4-yl)-1⁴H-6-oxa-3-aza-2(2,6)-pyridina-1(3,4)-triazola-5(1,2)-benzenacyclodecaphan-4-one;

5⁴-Morpholino-1⁴H-6-oxa-3-aza-2(2,6)-pyridina-1(3,4)-triazola-5(1,2)-benzenacyclodecaphan-4-one;

5⁴-(4-Methylpiperazin-1-yl)-1⁴H-6-oxa-3-aza-2(2,6)-pyridina-1(3,4)-triazola-5(1,2)-benzenacyclodecaphan-4-one;

(S)-5⁴-(2,4-Dimethylpiperazin-1-yl)-1⁴H-6-oxa-3-aza-2(2,6)-pyridina-1(3,4)-triazola-5(1,2)-benzenacyclodecaphan-4-one;

(R)-5⁴-(2,4-Dimethylpiperazin-1-yl)-1⁴H-6-oxa-3-aza-2(2,6)-pyridina-1(3,4)-triazola-5(1,2)-benzenacyclodecaphan-4-one;

5⁴-(1-Methyl-1H-pyrazol-4-yl)-1⁴H-6-oxa-3-aza-2(2,6)-pyridina-1(3,4)-triazola-5(1,2)-benzenacyclodecaphan-4-one;

5⁵-Fluoro-5⁴-(1-methyl-1,2,3,6-tetrahydropyridin-4-yl)-1⁴H-6-oxa-3-aza-2(2,6)-pyridina-1(3,4)-triazola-5(1,2)-benzenacyclodecaphan-4-one;

5⁵-Fluoro-5⁴-(1-methylpiperidin-4-yl)-1⁴H-6-oxa-3-aza-2(2,6)-pyridina-1(3,4)-triazola-5(1,2)-benzenacyclodecaphan-4-one;

5⁵-Fluoro-5⁴-morpholino-1⁴H-6-oxa-3-aza-2(2,6)-pyridina-1(3,4)-triazola-5(1,2)-benzenacyclodecaphan-4-one;

5⁵-Fluoro-5⁴-((2-methoxyethyl)amino)-1⁴H-6-oxa-3-aza-2(2,6)-pyridina-1(3,4)-triazola-5(1,2)-benzenacyclodecaphan-4-one;

(R)-8-Methyl-1⁴H-6-oxa-3-aza-2(2,6)-pyridina-1(3,4)-triazola-5(1,2)-benzenacyclodecaphan-4-one;

(S)-8-Methyl-1⁴H-6-oxa-3-aza-2(2,6)-pyridina-1(3,4)-triazola-5(1,2)-benzenacyclodecaphan-4-one;

(S)-10-Methyl-1⁴H-6-oxa-3-aza-2(2,6)-pyridina-1(3,4)-triazola-5(1,2)-benzenacyclodecaphan-4-one;

(R)-10-Methyl-1⁴H-6-oxa-3-aza-2(2,6)-pyridina-1(3,4)-triazola-5(1,2)-benzenacyclodecaphan-4-one;

(S)-10-Methyl-5⁵-(4-methyl-1H-imidazol-1-yl)-1⁴H-6-oxa-3-aza-2(2,6)-pyridina-1(3,4)-triazola-5(1,2)-benzenacyclodecaphan-4-one;

(R)-10-Methyl-5⁵-(4-methyl-1H-imidazol-1-yl)-1⁴H-6-oxa-3-aza-2(2,6)-pyridina-1(3,4)-triazola-5(1,2)-benzenacyclodecaphan-4-one;

(S)-10-Methyl-5⁵-(1-methyl-1H-pyrazol-4-yl)-1⁴H-6-oxa-3-aza-2(2,6)-pyridina-1(3,4)-triazola-5(1,2)-benzenacyclodecaphan-4-one;

(R)-10-Methyl-5⁵-(1-methyl-1H-pyrazol-4-yl)-1⁴H-6-oxa-3-aza-2(2,6)-pyridina-1(3,4)-triazola-5(1,2)-benzenacyclodecaphan-4-one;

(S)-5⁴-Fluoro-10-methyl-1⁴H-6-oxa-3-aza-2(2,6)-pyridina-1(3,4)-triazola-5(1,2)-benzenacyclodecaphan-4-one;

(R)-5⁴-Fluoro-10-methyl-1⁴H-6-oxa-3-aza-2(2,6)-pyridina-1(3,4)-triazola-5(1,2)-benzenacyclodecaphan-4-one;

(S)-5⁵-Fluoro-10-methyl-1⁴H-6-oxa-3-aza-2(2,6)-pyridina-1(3,4)-triazola-5(1,2)-benzenacyclodecaphan-4-one;

(R)-5⁵-Fluoro-10-methyl-1⁴H-6-oxa-3-aza-2(2,6)-pyridina-1(3,4)-triazola-5(1,2)-benzenacyclodecaphan-4-one;

(S)-5⁵-Bromo-5⁴-fluoro-10-methyl-1⁴H-6-oxa-3-aza-2(2,6)-pyridina-1(3,4)-triazola-5(1,2)-benzenacyclodecaphan-4-one;

(R)-5⁵-Bromo-5⁴-fluoro-10-methyl-1⁴H-6-oxa-3-aza-2(2,6)-pyridina-1(3,4)-triazola-5(1,2)-benzenacyclodecaphan-4-one;

(S)-5⁴-Fluoro-10-methyl-5⁵-morpholino-1⁴H-6-oxa-3-aza-2(2,6)-pyridina-1(3,4)-triazola-5(1,2)-benzenacyclodecaphan-4-one;

(10S)-5⁵-(6-Oxa-3-azabicyclo[3.1.1]heptan-3-yl)-5⁴-fluoro-10-methyl-1⁴H-6-oxa-3-aza-2(2,6)-pyridina-1(3,4)-triazola-5(1,2)-benzenacyclodecaphan-4-one;

(S)-5⁴-Fluoro-10-methyl-5⁵-(4-methylpiperazin-1-yl)-1⁴H-6-oxa-3-aza-2(2,6)-pyridina-1(3,4)-triazola-5(1,2)-benzenacyclodecaphan-4-one;

(S)-5⁴-Fluoro-10-methyl-5⁵-(1-methyl-1,2,3,6-tetrahydropyridin-4-yl)-1⁴H-6-oxa-3-aza-2(2,6)-pyridina-1(3,4)-triazola-5(1,2)-benzenacyclodecaphan-4-one;

(S)-5⁴-Fluoro-10-methyl-5⁵-(1-methylpiperidin-4-yl)-1⁴H-6-oxa-3-aza-2(2,6)-pyridina-1(3,4)-triazola-5(1,2)-benzenacyclodecaphan-4-one;

(S)-5⁵-(3,6-Dihydro-2H-pyran-4-yl)-5⁴-fluoro-10-methyl-1⁴H-6-oxa-3-aza-2(2,6)-pyridina-1(3,4)-triazola-5(1,2)-benzenacyclodecaphan-4-one;

(S)-5⁴-Fluoro-5⁵-(3-fluoropyridin-4-yl)-10-methyl-1⁴H-6-oxa-3-aza-2(2,6)-pyridina-1(3,4)-triazola-5(1,2)-benzenacyclodecaphan-4-one;

(S)-5⁴-Fluoro-10-methyl-5⁵-(pyrimidin-5-yl)-1⁴H-6-oxa-3-aza-2(2,6)-pyridina-1(3,4)-triazola-5(1,2)-benzenacyclodecaphan-4-one;

(S)-5⁴-Fluoro-10-methyl-5⁵-(5-(trifluoromethyl)pyridin-3-yl)-1⁴H-6-oxa-3-aza-2(2,6)-pyridina-1(3,4)-triazola-5(1,2)-benzenacyclodecaphan-4-one;

(S)-5⁴-Fluoro-10-methyl-5⁵-(pyridin-4-yl)-1⁴H-6-oxa-3-aza-2(2,6)-pyridina-1(3,4)-triazola-5(1,2)-benzenacyclodecaphan-4-one;

(S)-5⁴-Fluoro-10-methyl-5⁵-(4-methyl-1H-imidazol-1-yl)-1⁴H-6-oxa-3-aza-2(2,6)-pyridina-1(3,4)-triazola-5(1,2)-benzenacyclodecaphan-4-one;

(S)-5⁴-Fluoro-10-methyl-5⁵-(1-methyl-1H-pyrazol-4-yl)-1⁴H-6-oxa-3-aza-2(2,6)-pyridina-1(3,4)-triazola-5(1,2)-benzenacyclodecaphan-4-one;

(S)-5⁵-(1-(2-(Dimethylamino)ethyl)-1H-pyrazol-4-yl)-5⁴-fluoro-10-methyl-1⁴H-6-oxa-3-aza-2(2,6)-pyridina-1(3,4)-triazola-5(1,2)-benzenacyclodecaphan-4-one;

(S)-5⁴-Fluoro-5⁵-(2-methoxyethoxy)-10-methyl-1⁴H-6-oxa-3-aza-2(2,6)-pyridina-1(3,4)-triazola-5(1,2)-benzenacyclodecaphan-4-one;

(S)-5⁵-(2-(Dimethylamino)ethoxy)-5⁴-fluoro-10-methyl-1⁴H-6-oxa-3-aza-2(2,6)-pyridina-1(3,4)-triazola-5(1,2)-benzenacyclodecaphan-4-one;

(S)-5⁴-Fluoro-10-methyl-4-oxo-1⁴H-6-oxa-3-aza-2(2,6)-pyridina-1(3,4)-triazola-5(1,2)-benzenacyclodecaphane-5⁵-carbonitrile;

(S)-5⁵-Bromo-10-methyl-5⁴-(methylsulfonyl)-1⁴H-6-oxa-3-aza-2(2,6)-pyridina-1(3,4)-triazola-5(1,2)-benzenacyclodecaphan-4-one;

(S)-5⁴-Bromo-10-methyl-1⁴H-6-oxa-3-aza-2(2,6)-pyridina-1(3,4)-triazola-5(1,2)-benzenacyclodecaphan-4-one;

(R)-5⁴-Bromo-10-methyl-1⁴H-6-oxa-3-aza-2(2,6)-pyridina-1(3,4)-triazola-5(1,2)-benzenacyclodecaphan-4-one;

(S)-10-Methyl-5⁴-(4-methylpiperazin-1-yl)-1⁴H-6-oxa-3-aza-2(2,6)-pyridina-1(3,4)-triazola-5(1,2)-benzenacyclodecaphan-4-one;

(R)-10-Methyl-5⁴-(4-methylpiperazin-1-yl)-1⁴H-6-oxa-3-aza-2(2,6)-pyridina-1(3,4)-triazola-5(1,2)-benzenacyclodecaphan-4-one;

(S)-5⁵-Bromo-5⁴-fluoro-9-methyl-1⁴H-6-oxa-3-aza-2(2,6)-pyridina-1(3,4)-triazola-5(1,2)-benzenacyclodecaphan-4-one;

(R)-5⁵-Bromo-5⁴-fluoro-9-methyl-1⁴H-6-oxa-3-aza-2(2,6)-pyridina-1(3,4)-triazola-5(1,2)-benzenacyclodecaphan-4-one;

(S)-5⁴-Fluoro-9-methyl-5⁵-morpholino-1⁴H-6-oxa-3-aza-2(2,6)-pyridina-1(3,4)-triazola-5(1,2)-benzenacyclodecaphan-4-one;

(S)-5⁴-Fluoro-9-methyl-5⁵-(1-methylpiperidin-4-yl)-1⁴H-6-oxa-3-aza-2(2,6)-pyridina-1(3,4)-triazola-5(1,2)-benzenacyclodecaphan-4-one;

(S)-5⁴-Fluoro-5⁵-(2-fluoropyridin-3-yl)-9-methyl-1⁴H-6-oxa-3-aza-2(2,6)-pyridina-1(3,4)-triazola-5(1,2)-benzenacyclodecaphan-4-one;

(S)-5⁴-Fluoro-5⁵-(6-fluoropyridin-3-yl)-9-methyl-1⁴H-6-oxa-3-aza-2(2,6)-pyridina-1(3,4)-triazola-5(1,2)-benzenacyclodecaphan-4-one;

(S)-5⁵-(1-(2-(Dimethylamino)ethyl)-1H-pyrazol-4-yl)-5⁴-fluoro-9-methyl-1⁴H-6-oxa-3-aza-2(2,6)-pyridina-1(3,4)-triazola-5(1,2)-benzenacyclodecaphan-4-one;

(S)-5⁴-Fluoro-9-methyl-5⁵-(5-methyl-4,5,6,7-tetrahydropyrazolo[1,5-a]pyrazin-3-yl)-1⁴H-6-oxa-3-aza-2(2,6)-pyridina-1(3,4)-triazola-5(1,2)-benzenacyclodecaphan-4-one;

(R)-5⁴-Fluoro-9-methyl-5⁵-(5-methyl-4,5,6,7-tetrahydropyrazolo[1,5-a]pyrazin-3-yl)-1⁴H-6-oxa-3-aza-2(2,6)-pyridina-1(3,4)-triazola-5(1,2)-benzenacyclodecaphan-4-one;

(S)-5⁴-Fluoro-9-methyl-5⁵-(4-methyl-1H-imidazol-1-yl)-1⁴H-6-oxa-3-aza-2(2,6)-pyridina-1(3,4)-triazola-5(1,2)-benzenacyclodecaphan-4-one;

(S)-5⁴-Fluoro-9-methyl-5⁵-((3-methyloxetan-3-yl)ethynyl)-1⁴H-6-oxa-3-aza-2(2,6)-pyridina-1(3,4)-triazola-5(1,2)-benzenacyclodecaphan-4-one;

(S)-5⁴-Fluoro-5⁵-(2-methoxyethoxy)-9-methyl-1⁴H-6-oxa-3-aza-2(2,6)-pyridina-1(3,4)-triazola-5(1,2)-benzenacyclodecaphan-4-one;

(S)-5⁵-Bromo-7-methyl-1⁴H-6-oxa-3-aza-2(2,6)-pyridina-1(3,4)-triazola-5(1,2)-benzenacyclodecaphan-4-one;

(R)-5⁵-Bromo-7-methyl-1⁴H-6-oxa-3-aza-2(2,6)-pyridina-1(3,4)-triazola-5(1,2)-benzenacyclodecaphan-4-one;

(S)-7-Methyl-1⁴H-6-oxa-3-aza-2(2,6)-pyridina-1(3,4)-triazola-5(1,2)-benzenacyclodecaphan-4-one;

(R)-7-Methyl-1⁴H-6-oxa-3-aza-2(2,6)-pyridina-1(3,4)-triazola-5(1,2)-benzenacyclodecaphan-4-one;

(S)-7-Methyl-5⁵-(4-methylpiperazin-1-yl)-1⁴H-6-oxa-3-aza-2(2,6)-pyridina-1(3,4)-triazola-5(1,2)-benzenacyclodecaphan-4-one;

(R)-7-Methyl-5⁵-(4-methylpiperazin-1-yl)-1⁴H-6-oxa-3-aza-2(2,6)-pyridina-1(3,4)-triazola-5(1,2)-benzenacyclodecaphan-4-one;

(S)-7-Methyl-5⁵-morpholino-1⁴H-6-oxa-3-aza-2(2,6)-pyridina-1(3,4)-triazola-5(1,2)-benzenacyclodecaphan-4-one;

(R)-7-Methyl-5⁵-morpholino-1⁴H-6-oxa-3-aza-2(2,6)-pyridina-1(3,4)-triazola-5(1,2)-benzenacyclodecaphan-4-one;

(S)-7-Methyl-5⁵-(pyridin-4-yl)-1⁴H-6-oxa-3-aza-2(2,6)-pyridina-1(3,4)-triazola-5(1,2)-benzenacyclodecaphan-4-one;

(R)-7-Methyl-5⁵-(pyridin-4-yl)-1⁴H-6-oxa-3-aza-2(2,6)-pyridina-1(3,4)-triazola-5(1,2)-benzenacyclodecaphan-4-one;

(S)-5⁵-(1-(2-(Dimethylamino)ethyl)-1H-pyrazol-4-yl)-7-methyl-1⁴H-6-oxa-3-aza-2(2,6)-pyridina-1(3,4)-triazola-5(1,2)-benzenacyclodecaphan-4-one;

(R)-5⁵-(1-(2-(Dimethylamino)ethyl)-1H-pyrazol-4-yl)-7-methyl-1⁴H-6-oxa-3-aza-2(2,6)-pyridina-1(3,4)-triazola-5(1,2)-benzenacyclodecaphan-4-one;

(S)-7-Methyl-5⁵-(4-methyl-1H-imidazol-1-yl)-1⁴H-6-oxa-3-aza-2(2,6)-pyridina-1(3,4)-triazola-5(1,2)-benzenacyclodecaphan-4-one;

(R)-7-Methyl-5⁵-(4-methyl-1H-imidazol-1-yl)-1⁴H-6-oxa-3-aza-2(2,6)-pyridina-1(3,4)-triazola-5(1,2)-benzenacyclodecaphan-4-one;

(S)-7-Methyl-4-oxo-1⁴H-6-oxa-3-aza-2(2,6)-pyridina-1(3,4)-triazola-5(1,2)-benzenacyclodecaphane-5⁵-carbonitrile;

(R)-7-Methyl-4-oxo-1⁴H-6-oxa-3-aza-2(2,6)-pyridina-1(3,4)-triazola-5(1,2)-benzenacyclodecaphane-5⁵-carbonitrile;

5⁵-Bromo-3-methyl-1⁴H-6-oxa-3-aza-2(2,6)-pyridina-1(3,4)-triazola-5(1,2)-benzenacyclodecaphan-4-one;

5⁴-(Trifluoromethyl)-1⁴H-6-oxa-3-aza-2(2,6)-pyridina-1(3,4)-triazola-5(1,2)-benzenacyclodecaphan-4-one;

(E)-5⁴-(Trifluoromethyl)-1⁴H-6-oxa-3-aza-2(2,6)-pyridina-1(3,4)-triazola-5(1,2)-benzenacyclodecaphan-8-en-4-one;

(Z)-5⁴-(Trifluoromethyl)-1⁴H-6-oxa-3-aza-2(2,6)-pyridina-1(3,4)-triazola-5(1,2)-benzenacyclodecaphan-8-en-4-one;

5⁴-Fluoro-1⁴H-6-oxa-3-aza-2(2,6)-pyridina-1(3,4)-triazola-5(1,2)-benzenacyclodecaphan-4-one;

(E)-5⁴-Fluoro-1⁴H-6-oxa-3-aza-2(2,6)-pyridina-1(3,4)-triazola-5(1,2)-benzenacyclodecaphan-8-en-4-one;

(E)-5⁵-Fluoro-1⁴H-6-oxa-3-aza-2(2,6)-pyridina-1(3,4)-triazola-5(1,2)-benzenacyclodecaphan-8-en-4-one;

(Z)-5⁵-Fluoro-1⁴H-6-oxa-3-aza-2(2,6)-pyridina-1(3,4)triazola-5(1,2)-benzenacyclodecaphan-8-en-4-one;

5⁵-Fluoro-1⁴H-6-oxa-3-aza-2(2,6)-pyridina-1(3,4)-triazola-5(1,2)-benzenacyclodecaphan-4-one;

(Z)-5⁵-Bromo-1⁴H-6-oxa-3-aza-2(2,6)-pyridina-1(3,4)tri-azola-5(1,2)-benzenacyclodecaphan-8-en-4-one;
(E)-5⁵-Bromo-1⁴H-6-oxa-3-aza-2(2,6)-pyridina-1(3,4)-tri-azola-5(1,2)-benzenacyclodecaphan-8-en-4-one;
(E)-5³-Bromo-1⁴H-6-oxa-3-aza-2(2,6)-pyridina-1(3,4)-tri-azola-5(1,2)-benzenacyclodecaphan-8-en-4-one;
(Z)-5³-Bromo-1⁴H-6-oxa-3-aza-2(2,6)-pyridina-1(3,4)tri-azola-5(1,2)-benzenacyclodecaphan-8-en-4-one;
5³-Bromo-1⁴H-6-oxa-3-aza-2(2,6)-pyridina-1(3,4)-triazola-5(1,2)-benzenacyclodecaphan-4-one;
(E)-5³-(Trifluoromethyl)-1⁴H-6-oxa-3-aza-2(2,6)-pyridina-1(3,4)-triazola-5(1,2)-benzenacyclodecaphan-8-en-4-one;
(Z)-5³-(Trifluoromethyl)-1⁴H-6-oxa-3-aza-2(2,6)-pyridina-1(3,4)-triazola-5(1,2)-benzenacyclodecaphan-8-en-4-one;
(E)-5⁵-Morpholino-1⁴H-6-oxa-3-aza-2(2,6)-pyridina-1(3,4)-triazola-5(1,2)-benzenacyclodecaphan-8-en-4-one;
(Z)-5⁵-morpholino-1⁴H-6-oxa-3-aza-2(2,6)-pyridina-1(3,4)-triazola-5(1,2)-benzenacyclodecaphan-8-en-4-one;
5⁵-Bromo-1⁴H-6-oxa-3-aza-2(2,6)-pyridina-1(3,4)-triazola-5(1,2)-benzenacycloundecaphan-4-one;
1⁴H-6-oxa-3-aza-2(2,6)-pyridina-1(3,4)-triazola-5(1,2)-benzenacycloundecaphan-4-one;
5⁵-Morpholino-1⁴H-6-oxa-3-aza-2(2,6)-pyridina-1(3,4)-triazola-5(1,2)-benzenacycloundecaphan-4-one;
5⁵-(2-Oxa-6-azaspiro[3.3]heptan-6-yl)-1⁴H-6-oxa-3-aza-2(2,6)-pyridina-1(3,4)-triazola-5(1,2)-benzenacycloundecaphan-4-one;
(E)-1⁴H-6-Oxa-3-aza-2(2,6)-pyridina-1(3,4)-triazola-5(1,2)-benzenacycloundecaphan-9-en-4-one;
(Z)-1⁴H-6-oxa-3-aza-2(2,6)-pyridina-1(3,4)-triazola-5(1,2)-benzenacycloundecaphan-9-en-4-one;
(E)-5⁵-Bromo-5⁴-fluoro-1⁴H-6-oxa-3-aza-2(2,6)-pyridina-1(3,4)-triazola-5(1,2)-benzenacycloundecaphan-9-en-4-one;
(Z)-5⁵-Bromo-5⁴-fluoro-1⁴H-6-oxa-3-aza-2(2,6)-pyridina-1(3,4)-triazola-5(1,2)-benzenacycloundecaphan-9-en-4-one;
(E)-5⁵-(1-(2-(Dimethylamino)ethyl)-1H-pyrazol-4-yl)-5⁴-fluoro-1⁴H-6-oxa-3-aza-2(2,6)-pyridina-1(3,4)-triazola-5(1,2)-benzenacycloundecaphan-9-en-4-one;
(Z)-5⁵-(1-(2-(Dimethylamino)ethyl)-1H-pyrazol-4-yl)-5⁴-fluoro-1⁴H-6-oxa-3-aza-2(2,6)-pyridina-1(3,4)-triazola-5(1,2)-benzenacycloundecaphan-9-en-4-one;
(Z)-5⁴-Fluoro-5⁵-(pyridin-4-yl)-1⁴H-6-oxa-3-aza-2(2,6)-pyridina-1(3,4)-triazola-5(1,2)-benzenacycloundecaphan-9-en-4-one;
(Z)-5⁴-Fluoro-5⁵-(pyridin-4-yl)-1⁴H-6-oxa-3-aza-2(2,6)-pyridina-1-(3,4)triazola-5(1,2)-benzenacycloundecaphan-9-en-4-one;
(Z)-5⁴-Fluoro-5⁵-(5-methyl-4,5,6,7-tetrahydropyrazolo[1,5-a]pyrazin-3-yl)-1⁴H-6-oxa-3-aza-2(2,6)-pyridina-1(3,4)-triazola-5(1,2)-benzenacycloundecaphan-9-en-4-one;
5⁵-Bromo-1⁴H-6-oxa-3-aza-2(2,6)-pyridina-1(3,4)-triazola-5(1,2)-benzenacyclononaphan-4-one; and
5⁵-Morpholino-1⁴H-6-oxa-3-aza-2(2,6)-pyridina-1(3,4)-triazola-5(1,2)-benzenacyclononaphan-4-one;
or a pharmaceutically acceptable salt thereof.

In a nineteenth embodiment of the invention, the invention is any one of the compounds disclosed in the Exemplification section as a neutral compound or a pharmaceutically acceptable salt thereof.

As used herein, when L is defined as a specific $C_{3-5}$alkylene or $C_{3-5}$alkenylene group, the radical on the left side of L is connected to the —O— group of formula (I) or (II) and the radical on the right side of L is connected to the triazole group of formula (I) or (II). For example when L is —CH$_2$—CH$_2$—CH$_2$—CH(CH$_3$)—, the —CH$_2$— on the left side is connected the —O— group and the —CH(CH$_3$)— on the right side is connected to the triazole group.

As used herein, the term "alkyl" refers to a fully saturated branched or unbranched hydrocarbon moiety. Preferably the alkyl comprises 1 to 6 carbon atoms, or 1 to 4 carbon atoms. In some embodiments, an alkyl comprises from 6 to 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, or n-hexyl.

"Alkenyl" refers to an unsaturated hydrocarbon group which may be linear or branched and has at least one carbon-carbon double bond. Alkenyl groups with 2-6 carbon atoms can be preferred. The alkenyl group may contain 1, 2 or 3 carbon-carbon double bonds, or more. Examples of alkenyl groups include ethenyl, n-propenyl, isopropenyl, n-but-2-enyl, n-hex-3-enyl and the like.

"Alkynyl" refers to an unsaturated hydrocarbon group which may be linear or branched and has at least one carbon-carbon triple bond. Alkynyl groups with 2-6 carbon atoms can be preferred. The alkynyl group may contain 1, 2 or 3 carbon-carbon triple bonds, or more. Examples of alkynyl groups include ethynyl, n-propynyl, n-but-2-ynyl, n-hex-3-ynyl and the like.

The number of carbon atoms in a group is specified herein by the prefix "$C_{x-xx}$", wherein x and xx are integers. For example, "$C_{1-4}$alkyl" is an alkyl group which has from 1 to 4 carbon atoms.

"Halogen" or "halo" may be fluoro, chloro, bromo or iodo.

As used herein, the term "heterocyclyl" refers to a saturated or unsaturated, monocyclic or bicyclic (e.g., bridged or spiro ring systems) ring system which has from 3- to 10-ring members, or in particular 3- to 8-ring members, 3- to 7-ring members, 3- to 6-ring members or 5- to 7-ring members or 4- to 7-ring members, at least one of which is a heteroatom, and up to 4 (e.g., 1, 2, 3, or 4) of which may be heteroatoms, wherein the heteroatoms are independently selected from O, S and N, and wherein C can be oxidized (e.g., C(O)), N can be oxidized (e.g., N(O)) or quaternized, and S can be optionally oxidized to sulfoxide and sulfone. Unsaturated heterocyclic rings include heteroaryl rings. As used herein, the term "heteroaryl" refers to an aromatic 5- or 6-membered monocyclic ring system, having 1 to 4 heteroatoms independently selected from O, S and N, and wherein N can be oxidized (e.g., N(O)) or quaternized, and S can be optionally oxidized to sulfoxide and sulfone. In one embodiment, a heterocyclyl is a 3- to 7-membered saturated monocyclic or a 3- to 6-membered saturated monocyclic or a 5- to 7-membered saturated monocyclic ring or a 4- to 7-membered saturated monocyclic ring. In one embodiment, a heterocyclyl is a 3- to 7-membered monocyclic or a 3- to 6-membered monocyclic or a 5- to 7-membered monocyclic ring. In another embodiment, a heterocyclyl is a 6 or -7-membered bicyclic ring. In yet another embodiment, a heterocyclyl is a 4- to 7-membered monocyclic non-aromatic ring. In another embodiment, a heterocyclyl is 6- to 8-membered spiro or bridged bicyclic ring. The heterocyclyl group can be attached at a heteroatom or a carbon atom. Examples of heterocyclyls include, but are not limited to, aziridinyl, oxiranyl, thiiranyl, oxaziridinyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, dihydrofuranyl, imidazolinyl, dihydropyranyl, and heteroaryl rings including azetyl, thietyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, azepinyl, oxepinyl, thiepinyl, diazepinyl, and thiazepinyl and the like.

In one embodiment, a heterocyclyl is a 4- to 7-membered monocyclic heterocyclyl. Examples of 4- to 7-membered monocyclic heterocyclic ring systems include, but are not limited to azetidinyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, azepanyl, oxepanyl, thiepanyl, dihydrofuranyl, imidazolinyl, dihydropyranyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, azepinyl, oxepinyl, thiepinyl, diazepinyl, and thiazepinyl.

As used herein, a "4- to 7-membered monocyclic non-aromatic heterocyclyl" is a monocyclic heterocyclyl having 4- to 7-ring members and is saturated or partially unsaturated (i.e., non-aromatic). Examples of 4- to 7-membered monocyclic non-aromatic heterocylyls include, but are not limited to, azetidinyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, azepanyl, oxepanyl, thiepanyl, dihydrofuranyl, imidazolinyl, and dihydropyranyl.

As used herein, "6- to 8-membered spiro or bridged bicyclic heterocyclyl" refers to a bicyclic heterocyclyl ring that is a bridged or spiro ring system having total of 6- to 8-ring members. Examples of 6- to 8-membered spiro or bridged bicyclic heterocyclic ring systems include, but are not limited to, 3-azabicyclo[3.1.0]hexanyl, 3-azabicyclo[3.1.1]heptanyl, 2-azaspiro[3.3]heptanyl, 2-oxa-6-azaspiro[3.3]heptanyl, 3-oxa-8-azabicyclo[3.2.1]octanyl, 6-oxa-3-azabicyclo[3.1.1]heptanyl, 8-oxa-3-azabicyclo[3.2.1]octanyl, 3-oxa-6-azabicyclo[3.1.1]heptanyl, and 5-azaspiro[2.3]hexanyl.

The term "bridged ring system", as used herein, is a ring system that has a carbocyclyl or heterocyclyl ring wherein two non-adjacent atoms of the ring are connected (bridged) by one or more (preferably from one to three) atoms selected from C, N, O, or S. A bridged ring system may have from 6 to 8 ring members.

The term "spiro ring system," as used herein, is a ring system that has two rings each of which are independently selected from a carbocyclyl or a heterocyclyl, wherein the two ring structures having one ring atom in common. Spiro ring systems have from 5 to 8 ring members.

As used herein, the term "N-containing heterocyclyl" or "N-containing heteroaryl" refers to a heterocyclyl or a heteroaryl containing at least one N as ring atom. The N-containing heterocyclyl group or the N-containing heteroaryl group can be attached at a N or a carbon atom. A "4- to 7-membered monocyclic non-aromatic heterocyclyl" is a saturated or partially unsaturated N-containing heterocyclyl that is monocyclic. Examples of 4- to 7-membered monocyclic non-aromatic heterocyclyl include azetidinyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, thiomorpholinyl, azepanyl, and imidazolinyl. A "5- to 6-membered N-containing heteroaryl" is a N-containing heteroaryl containing 5- or 6-ring members. Examples of 5- to 6-membered N-containing heteroaryl include imidazolyl, pyrazolyl, oxazolyl, isoxazolyl, thiazolyl, isothiazolyl, oxadiazolyl, thiadiazolyl, triazolyl, tetrazolyl, pyridinyl, pyrazinyl, pyrimidinyl, pyridazinyl, triazinyl, tetrazinyl and the like.

As used herein, the term "carbocyclyl" refers to saturated or unsaturated monocyclic or bicyclic hydrocarbon groups of 3-7 carbon atoms, 3-6, or 5-7 carbon atoms. The term "carbocyclyl" encompasses cycloalkyl groups and aromatic groups. The term "cycloalkyl" refers to completely saturated monocyclic or bicyclic or spiro hydrocarbon groups of 3-7 carbon atoms, 3-6 carbon atoms, or 5-7 carbon atoms. Exemplary monocyclic carbocyclyl groups include, but are not limited to, cyclopropyl, cyclobutyl, cyclopentyl, cyclohexyl, cycloheptyl, cyclopropenyl, cyclobutenyl, cyclopentenyl, cyclohexenyl, cycloheptenyl, cyclobutadienyl, cyclopentadienyl, cyclohexadienyl, cycloheptadienyl, phenyl and cycloheptatrienyl. Exemplary bicyclic carbocyclyl groups include bicyclo[2.1.1]hexyl, bicyclo[2.2.1]heptyl, bicyclo[2.2.1]heptenyl, tricyclo[2.2.1.0$^{2,6}$]heptanyl, 6,6-dimethylbicyclo[3.1.1]heptyl, or 2,6,6-trimethylbicyclo[3.1.1] heptyl, spiro[2.2]pentanyl, and spiro[3.3]heptanyl.

In cases where a compound provided herein is sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, or α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, can include but are not limited to, sodium, potassium, lithium, ammonium, calcium or magnesium salts. Salts derived from organic bases can include, but are not limited to, salts of primary, secondary or tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocycloalkyl amines, diheterocycloalkyl amines, triheterocycloalkyl amines, or mixed di- and tri-amines where at least two of the substituents on the amine can be different and can be alkyl, substituted alkyl, alkenyl, substituted alkenyl, cycloalkyl, substituted cycloalkyl, cycloalkenyl, substituted cycloalkenyl, aryl, heteroaryl, or heterocycloalkyl and the like. Also included are amines where the two or three substituents, together with the amino nitrogen, form a heterocycloalkyl or heteroaryl group. Non-limiting examples of amines can include, isopropylamine, trimethyl amine, diethyl amine, tri(iso-propyl) amine, tri(n-propyl) amine, ethanolamine, 2-dimethylaminoethanol, trimethamine, lysine, arginine, histidine, caffeine, procaine, hydrabamine, choline, betaine, ethylenediamine, glucosamine, N-alkylglucamines, theobromine, purines, piperazine, piperidine, morpholine, or N-ethylpiperidine, and the like. Other carboxylic acid derivatives can be useful, for example, carboxylic acid amides, including carboxamides, lower alkyl carboxamides, or dialkyl carboxamides, and the like.

The compounds or pharmaceutically acceptable salts thereof as described herein, can contain one or more asymmetric centers in the molecule. In accordance with the present disclosure any structure that does not designate the stereochemistry is to be understood as embracing all the various stereoisomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis, or chromatographic separation using a chiral stationary phase). When a particular enantiomer of a compound used in the disclosed methods is depicted by name or structure, the stereochemical purity of the compounds is at least 20%, 30%, 40%, 50%, 60%, 70%, 80%, 90%, 95%, 97%, 99%, 99.5% or 99.9%. "Stereochemical purity" means the weight percent of the desired stereoisomer relative to the combined weight of all stereoisomers.

The disclosed compounds may exist in tautomeric forms and mixtures and separate individual tautomers are contemplated. In addition, some compounds may exhibit polymorphism.

In one embodiment, the compounds of the invention or a pharmaceutically acceptable salt thereof include deuterium.

Another embodiment is a pharmaceutical composition comprising at least one compound described herein, or a pharmaceutically acceptable salt thereof, and at least one pharmaceutically acceptable carrier.

The compounds, or pharmaceutically acceptable salts thereof described herein may be used to decrease the activity of ASK1, or to otherwise affect the properties and/or behavior of ASK1, e.g., stability, phosphorylation, kinase activity, interactions with other proteins, etc.

One embodiment of the invention includes a method of treating a disorder responsive to inhibition of ASK1 in a subject comprising administering to said subject an effective amount of at least one compound described herein, or a pharmaceutically acceptable salt thereof.

Studies have demonstrated that ASK1 is involved in ROS- or ER stress-related disease mechanisms, suggesting its therapeutic role in various human diseases. The accumulation of misfolded proteins in the endoplasmic reticulum induces ER stress, leading to the disturbance of ER function. Unfolded-protein response (UPR) is the ER quality control system to restore function. Apoptosis signaling is induced with prolonged ER stress or malfunction of the UPR. The role for ASK1 activation in neurodegenerative disease involves both ER and oxidative stress mechanisms.

In one embodiment, the disorders responsive to inhibition of ASK1 include, but are not limited to, neurodegenerative disorders, cardiovascular diseases, metabolic (e.g. diabetes) disorders, inflammatory diseases, damage following ischemia, autoimmune disorders, destructive bone disorders, polyglutamine diseases, glutamate neurotoxicity, pain, traumatic brain injury, hemorrhagic stroke, ischemia, acute hypoxia, kidney fibrosis (renal fibrosis), kidney injury (Terada et al., Biochem Biophys Res Commun. 2007, 364 (4), 1043-92007), diabetic kidney disease/diabetic nephropathy, non-alcoholic steatohepatitis (NASH), pulmonary arterial hypertension (PAH), optic neuritis, liver diseases, respiratory diseases (chronic obstructive pulmonary disease COPD, lung injury), heart reperfusion injury (Gerczuk P Z et al., J Cardiovasc Pharmacol. 2012, 60(3), 276-82.), cardiac hypertrophy, cardiac fibrosis (Yamaguchi et al., J Clin Invest. 2004, 114(7), 937-43.), energy metabolic disorders, cancers (such as liver cancer, gastric cancer (Hayakawa et al., Proc Natl Acad Sci USA. 2011, 108(2), 780-5), and infection (e.g. sepsis).

In one embodiment, the invention provides a method for treating a neurodegenerative disease. In one embodiment, the neurodegenerative diseases include, but are not limited to, Alzheimer disease, hippocampal sclerosis, frontotemporal dementia (FTD), frontotemporal lobar degeneration (FTLD), Huntington's disease, corticobasal degeneration, amyotrophic lateral sclerosis, spinal muscular atrophy, motor neuron disease, inclusion body myositis, Parkinson's disease, dementia with Lewy bodies, Lewy body disease, multiple system atrophy, progressive supranuclear palsy, Pick's disease, prion diseases, traumatic brain injury, ischemic and hemorrhagic stroke, cerebral ischemia, hypoxia, and glutamate neurotoxicity. In particular, the neurodegenerative disease is selected from Alzheimer's disease (AD), Parkinson's disease, Huntington's disease, and Amyotrophic lateral sclerosis (ALS).

ALS is a progressive neurodegenerative disease that affects nerve cells in the brain and spinal cord. The progressive degeneration of motor neurons in ALS eventually leads to their death. When motor neurons die, the ability of the brain to initiate and control muscle movement is lost. With voluntary muscle action progressively affected, people may lose the ability to speak, eat, move, and breathe. Patients in the later stages of the disease may become totally paralyzed.

In vitro studies show that ASK1 is required for Fas receptor induced death of mouse primary motor neurons, and mutSOD1 motor neurons demonstrate increased susceptibility (Raoul et al., Neuron. 2002, 35(6), 1067-83). Mutant SOD1 protein causes motor neuron death through activation of ASK1. Activation of the ASK1 pathway is increased in mutSOD1 motor neurons, and is active early in SOD1 mouse disease progression (Wengenack et al., Brain Res. 2004, 1027(1-2), 73-86; Holsek et al., Brain Res. 2005, 1045(1-2), 185-98). In cells, ASK1 mediates cytotoxic signaling in mutSOD1 expressing cells, and the protective effect of pro-survival pathways in mutSOD1 motor neurons involves inhibition of ASK1 (Pevani et al., Mol Neurobiol. 2014, 49(1):136-48).

In transgenic mouse studies, both genetic deletion (Nishitoh et al., Genes and Dev 2008, 22(11), 1451-64) and pharmacological inhibition of ASK1 (Fujisawa et al., Hum. Mol. Genet. 2016, 25(2), 245-53) has demonstrated reduced motor neuron loss and increased/extended lifespan, as well as reduced neuroinflammation in the SOD1_G93A transgenic mouse model of ALS.

Parkinson's disease is a disorder of the nervous system that results from the loss of cells in various parts of the brain, including a region called the substantia nigra. The substantia nigra cells produce dopamine, a chemical messenger responsible for transmitting signals within the brain that allow for coordination of movement. Loss of dopamine causes neurons to fire without normal control, leaving patients less able to direct or control their movement. Parkinson's disease is one of several diseases categorized by clinicians as movement disorders.

In the mitochondrial complex 1 inhibitor MPTP (1-methyl-4-phenyl-1,2,3,6-tetrahydropyridine) model of dopaminergic cell loss, ASK1 deficient mice are shown to be relatively resistant to MPTP lesions. MPTP-induced dopamine neuron toxicity and motor impairment is also attenuated in ASK1 knock-out mice, as is neuroinflammation, suggesting protective effects of ASK1 inhibition (Lee et al., PlosOne 2012; 7(1), e29935). Abolishing ASK activity in another MPTP model also attenuated dopaminergic cell loss (Karunakaran et al., FASEB J. 2007, 21(9), 2226-36).

Accumulation of pathogenic proteins such as alpha-synuclein, in alpha-synucleopathies including Parkinson's disease, and its overexpression and aggregation in model systems is associated with neuroinflammation and increased oxidative stress. AlphaSynuclein transgenic mice deficient in ASK1 demonstrate improved motor function (Lee et al., NeuroBiolAging 2015, 36(1), 519-26).

Further, in 6-hydroxydopamine (6-OHDA, a toxin that causes dopaminergic cell loss) models, attenuating the ASK1 signaling cascade provides protection against dopaminergic neuron loss (Hu et al., J Neurosci. 2011, 31(1), 247-61)

AD is a type of dementia that causes problems with memory, thinking and behavior. In AD the brain cells degenerate and die, causing a steady decline in memory and mental function. AD is characterized by increased levels of Amyloid-beta peptides and hyper-phosphorylated Tau which lead to the hallmark pathologies ABeta-amyloid plaques and Tau tangles.

ASK1 activation may be associated with AD. Neurons treated with toxic ABeta peptides demonstrate increased toxicity due to oxidative stress (ROS). Exposure to ABeta Peptides leads to ASK1 activation (Wang et al., J Mol Neurosci. 2015, 55(1), 227-32). ABeta-induced neuronal death via ROS-mediated ASK1 activation is a key mechanism for ABeta-induced neurotoxicity (Kadowaki et al., Cell Death Differ. 2005, 12(1), 19-24). ASK1 is also required for ROS-induced JNK activation and apoptosis.

Huntington's disease is an inherited disease that causes the progressive breakdown (degeneration) of nerve cells in the brain. Huntington's disease has a broad impact on a person's functional abilities and usually results in movement, thinking (cognitive) and psychiatric disorders. Mutations in the HTT gene cause Huntington disease. The HTT gene provides instructions for making a protein called huntingtin. Although the function of this protein is unknown, it appears to play an important role in nerve cells (neurons) in the brain.

The HTT mutation that causes Huntington disease involves a DNA segment known as a CAG trinucleotide repeat. This segment is made up of a series of three DNA building blocks (cytosine, adenine, and guanine) that appear multiple times in a row. Normally, the CAG segment is repeated 10 to 35 times within the gene. In people with Huntington disease, the CAG segment is repeated 36 to more than 120 times. People with 36 to 39 CAG repeats may or may not develop the signs and symptoms of Huntington disease, while people with 40 or more repeats almost always develop the disorder. During protein synthesis, the expanded CAG repeats are translated into a series of uninterrupted glutamine residues forming what is known as a polyglutamine tract ("polyQ"). Such polyglutamine tracts may be subject to increased aggregation.

Studies have shown that ASK1 is essential for endoplasmic reticulum stress-induced neuronal cell death triggered by expanded polyglutamine repeats. (Nishitoh et al., Genes Dev. 2002, 16(11), 1345-55).

Another embodiment of the invention includes a method for treating an autoimmune disease in a subject comprising administering to the subject a therapeutically effective amount of a compound disclosed herein, or a pharmaceutically acceptable salt thereof.

In one embodiment, the autoimmune disease is selected from rheumatoid arthritis, systemic lupus erythematosus, multiple sclerosis, diabetes, systemic sclerosis, Grave's disease, Guillain-Barre syndrome, myasthenia gravis, psoriasis, Crohn's disease, ulcerative colitis, optic neuritis, and Sjogren's syndrome.

In one embodiment, the autoimmune disease is multiple sclerosis (MS).

Multiple sclerosis (MS) involves an immune-mediated process in which an abnormal response of the body's immune system is directed against the central nervous system (CNS), which is made up of the brain, spinal cord and optic nerves. The immune system attacks, myelin, which surrounds and insulates nerve fibers. When myelin is damaged, scar tissue is formed (sclerosis) which gives the disease its name. 20% of MS patients initially present with optic neuritis, and 30-70% of MS patients develop optic neuritis during the course of disease (loss of visual acuity, which can lead to neuromyelitis optica severe and irreversible visual loss). Optic neuritis is inflammation of the optic nerve, which is the most common form of optic neuropathy.

In experimental autoimmune encephalomyelitis (EAE) models of inflammation, demyelination, and axonal degeneration, the severity of EAE is reduced in ASK1 deficient mice, as well as mice treated with ASK1 inhibitors. Inhibitors of ASK1 suppressed EAE-induced inflammation in both the spinal cord and optic nerves, suggesting the TLR-ASK1-p38 pathway may serve as a therapeutic target for immune-related demyelinating disorders (Guo et al., EMBOMol. Med. 2 (2010) 504-515; Azuchi et al., Neurosci Lett. 2017, 639, 82-87).

In one embodiment, the invention provides a method of treating a cardiovascular disease in a subject comprising administering to the subject a therapeutically effective amount of a compound disclosed herein, or a pharmaceutically acceptable salt thereof.

Cardiovascular diseases refer to diseases of the cardiovasculature (heart and blood vessels) arising from any one or more than one of, for example, heart failure (including congestive heart failure, diastolic heart failure and systolic heart failure), acute heart failure, ischemia, recurrent ischemia, myocardial infarction, arrhythmias, angina (including exercise-induced angina, variant angina, stable angina, unstable angina), acute coronary syndrome, diabetes, atherosclerosis, and intermittent claudication. Cardiovascular diseases also include diseases associated with malfunction of heart valves which do not allow sufficient amount of blood to flow through (such as valvular stenosis, valvular insufficiency or regurgitation, congenital valve disease, bicuspid aortic valve disease, or acquired valve disease).

"Intermittent claudication" means the pain associated with peripheral artery disease. "Peripheral artery disease" or PAD is a type of occlusive peripheral vascular disease (PVD). PAD affects the arteries outside the heart and brain. The most common symptom of PAD is a painful cramping in the hips, thighs, or calves when walking, climbing stairs, or exercising. The pain is called intermittent claudication. When listing the symptom intermittent claudication, it is intended to include both PAD and PVD.

Arrhythmia refers to any abnormal heart rate. Bradycardia refers to abnormally slow heart rate whereas tachycardia refers to an abnormally rapid heart rate. As used herein, the treatment of arrhythmia is intended to include the treatment of supra ventricular tachycardias such as atrial fibrillation, atrial flutter, AV nodal reentrant tachycardia, atrial tachycardia, and the ventricular tachycardias (VTs), including idiopathic ventricular tachycardia, ventricular fibrillation, pre-excitation syndrome, and Torsade de Pointes (TdP).

In another embodiment, the invention provides a method for treating ischemia in a subject comprising administering to the subject a therapeutically effective amount of a compound disclosed herein, or a pharmaceutically acceptable salt thereof.

Activation of ASK1 by reactive oxygen species (ROS) has been linked to vascular injury and neuronal death following cerebral ischemia. Studies show that induction of ASK1 expression promotes apoptotic cell death following ischemia and silencing ASK1 expression reduces cerebral infarction in the brain (Kim et al BrainRes. 2011, 1412, 73-78). The inhibition of ASK1 has been shown to exert protective effects in ischemia induced brain edema (Song et al., BrainRes. 2015, 1595, 143-155). Preventing ASK1 activation in a cerebral ischemia-reperfusion model is also shown to exert neuroprotection (Liu et al., Neuroscience. 2013, 229, 36-48). In a middle cerebral artery (MCA) occlusion model, ASK1 inhibition showed decreased neuronal death as well as in hypoxia/reperfusion injury models (Cheon et al., Front Cell Neurosci. 2016, 10, 213).

In one embodiment, the invention provides a method for treating liver injury in a subject comprising administering to the subject a therapeutically effective amount of a compound disclosed herein, or a pharmaceutically acceptable salt thereof.

Acetaminophen (APAP) overdose is the most common form of drug-induced liver injury. JNK activation is a consequence of oxidative stress produced during APAP metabolism, resulting in hepatocyte damage with necrotic and apoptotic cell death. (Nakagawa et al., Gastroenterology. 2008, 135(4), 1311-21). It has been shown that ASK1 inhibitors protect against APAP induced liver injury (Xie et al., Toxicol Appl Pharmacol. 2015, 286(1), 1-9; He et al., Asian Pac J Trop Med. 2016, 9(3), 283-7).

As used herein, the term "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or 'treatment" refers to obtaining desired pharmacological and/or physiological effect. The effect can be therapeutic, which includes achieving, partially or substantially, one or more of the following results: partially or totally reducing the extent of the disease, disorder or syndrome; ameliorating or improving a clinical symptom or indicator associated with the disorder; or delaying, inhibiting or decreasing the likelihood of the progression of the disease, disorder or syndrome.

The dose of a compound provided herein, or a pharmaceutically acceptable salt thereof, administered to a subject can be 10 µg-500 mg.

Administering a compound described herein, or a pharmaceutically acceptable salt thereof, to a mammal comprises any suitable delivery method. Administering a compound described herein, or a pharmaceutically acceptable salt thereof, to a mammal includes administering a compound described herein, or a pharmaceutically acceptable salt thereof, topically, enterally, parenterally, transdermally, transmucosally, via inhalation, intracisternally, epidurally, intravaginally, intravenously, intramuscularly, subcutaneously, intradermally or intravitreally to the mammal. Administering a compound described herein, or a pharmaceutically acceptable salt thereof, to a mammal also includes administering topically, enterally, parenterally, transdermally, transmucosally, via inhalation, intracisternally, epidurally, intravaginally, intravenously, intramuscularly, subcutaneously, intradermally or intravitreally to a mammal a compound that metabolizes within or on a surface of the body of the mammal to a compound described herein, or a pharmaceutically acceptable salt thereof.

Thus, a compound or pharmaceutically acceptable salt thereof as described herein, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compound or pharmaceutically acceptable salt thereof as described herein may be combined with one or more excipients and used in the form of ingestible tablets, buccal tablets, troches, capsules, elixirs, suspensions, syrups, or wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions can be such that an effective dosage level will be obtained.

The tablets, troches, pills, capsules, and the like can include the following: binders such as gum tragacanth, acacia, corn starch or gelatin; excipients such as dicalcium phosphate; a disintegrating agent such as corn starch, potato starch, alginic acid and the like; a lubricant such as magnesium stearate; or a sweetening agent such as sucrose, fructose, lactose or aspartame or a flavoring agent.

The active compound may also be administered intravenously or intraperitoneally by infusion or injection. Solutions of the active compound or its salts can be prepared in water, optionally mixed with a nontoxic surfactant.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions. In all cases, the ultimate dosage form should be sterile, fluid and stable under the conditions of manufacture and storage.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation can be vacuum drying and the freeze drying techniques, which can yield a powder of the active ingredient plus any additional desired ingredient present in the previously sterile-filtered solutions.

Exemplary solid carriers can include finely divided solids such as talc, clay, microcrystalline cellulose, silica, alumina and the like. Useful liquid carriers include water, alcohols or glycols or water-alcohol/glycol blends, in which the compounds or pharmaceutically acceptable salts thereof as described herein can be dissolved or dispersed at effective levels, optionally with the aid of non-toxic surfactants.

Useful dosages of a compound or pharmaceutically acceptable salt thereof as described herein can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

The amount of a compound or pharmaceutically acceptable salt thereof as described herein, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.1 to about 10 mg/kg of body weight per day.

The compound or a pharmaceutically acceptable salt thereof as described herein can be conveniently administered in unit dosage form; for example, containing 0.01 to 10 mg, or 0.05 to 1 mg, of active ingredient per unit dosage form. In some embodiments, a dose of 5 mg/kg or less can be suitable.

The desired dose may conveniently be presented in a single dose or as divided doses administered at appropriate intervals.

The disclosed method can include a kit comprising a compound or pharmaceutically acceptable salt thereof as described herein and instructional material which can describe administering a compound or pharmaceutically acceptable salt thereof as described herein or a composition comprising a compound or pharmaceutically acceptable salt thereof as described herein to a cell or a subject. This should be construed to include other embodiments of kits that are known to those skilled in the art, such as a kit comprising a (such as sterile) solvent for dissolving or suspending a compound or pharmaceutically acceptable salt thereof as described herein or composition prior to administering a compound or pharmaceutically acceptable salt thereof as described herein or composition to a cell or a subject. In some embodiments, the subject can be a human.

Example 1: $5^5$-Bromo-$1^4$H-6-oxa-3-aza-2(2,6)-pyridina-1(3,4)-triazola-5(1,2)-benzenacyclodecaphan-4-one

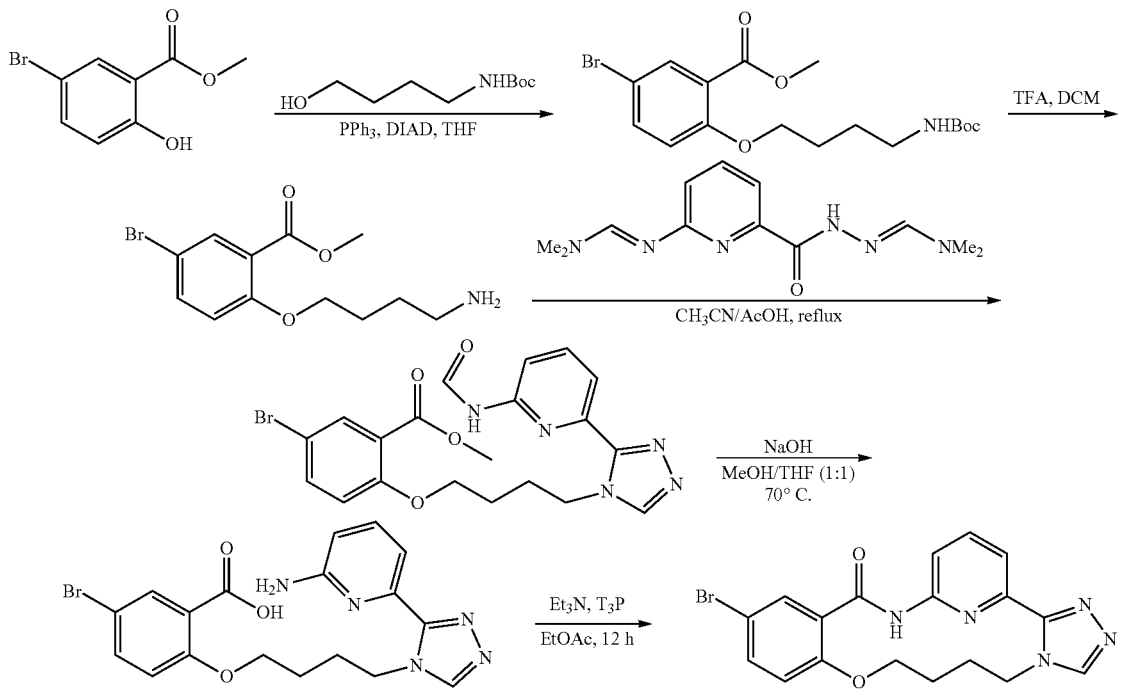

Step A. Methyl 5-bromo-2-(4-((tert-butoxycarbonyl)amino)butoxy)benzoate

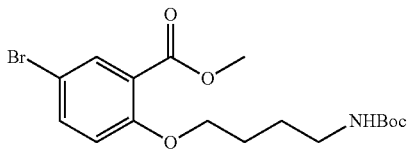 [SMILES: COC(=O)c1cc(Br)ccc1OCCCCNC(=O)OC(C)(C)C]

A stirred solution of methyl 5-bromo-2-hydroxybenzoate (100 g, 432.8 mmol) and tert-butyl (4-hydroxybutyl)carbamate (98.3 g, 519.3 mmol), PPh$_3$ (124.9 g, 476.1 mmol) in THF (1.5 L) was treated with DIAD (89.2 mL, 454.5 mmol) at 0° C. for 30 min. The resulting mixture was stirred at 30° C. for 12 h. After this time the reaction was partitioned between EtOAc and water. The separated organic layer was washed with brine, dried over MgSO₄, filtered and evaporated under vacuum. The product was purified by column chromatography on silica gel, using a gradient of elution: petroleum ether/EtOAc (100/1 to 5/1) to give the title compound (130 g, 75%) as a white solid. ¹H NMR (400 MHz, CDCl₃) δ ppm 7.91 (d, J=2.5 Hz, 1H), 7.53 (dd, J=8.9, 2.6 Hz, 1H), 6.84 (d, J=9.0 Hz, 1H), 4.82 (br s, 1H), 4.04 (t, J=6.0 Hz, 2H), 3.84-3.97 (m, 3H), 3.20 (q, J=6.4 Hz, 2H), 1.83-1.91 (m, 2H), 1.63-1.75 (m, 2H), 1.40-1.49 (m, 9H). MS (ESI): 424.1 [(M+Na) (⁷⁹Br)]⁺.

Step B. Methyl 2-(4-aminobutoxy)-5-bromobenzoate

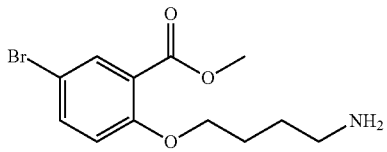 [SMILES: COC(=O)c1cc(Br)ccc1OCCCCN]

A solution of methyl 5-bromo-2-(4-((tert-butoxycarbonyl)amino)butoxy)benzoate (130 g, 323.2 mmol) and TFA (368.5 g, 3.2 mol) in DCM (2 L) was stirred at 40° C. for 5 h. After this time the mixture was concentrated under vacuum. The product was taken up in EtOAc (500 mL) and washed with sat aq. NaHCO₃. The combined organic layers were concentrated under vacuum to give the title compound (90 g, 92%) as yellow solid. ¹H NMR (400 MHz, DMSO-d₆) δ ppm 7.77 (d, J=2.8 Hz, 1H), 7.70 (dd, J=8.9, 2.6 Hz, 1H), 7.14 (d, J=8.8 Hz, 1H), 4.01-4.11 (m, 2H), 3.81 (s, 3H), 3.10-3.71 (m, 2H), 2.77-2.92 (m, 2H), 1.61-1.85 (m, 4H). MS (ESI): 302.0 [(M+H) (⁷⁹Br)]⁺.

Step C. Methyl 5-bromo-2-(4-(3-(6-formamidopyridin-2-yl)-4H-1,2,4-triazol-4-yl)butoxy)benzoate

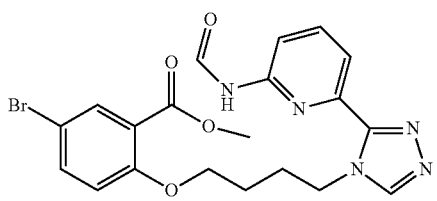 [SMILES: COC(=O)c1cc(Br)ccc1OCCCCn1cnnc1-c1cccc(NC=O)n1]

A solution of methyl 2-(4-aminobutoxy)-5-bromobenzoate (17 g, 64.8 mmol) and (E)-N'-(6-(2-((E)-(dimethylamino)methylene)hydrazine-1-carbonyl)pyridin-2-yl)-N,N-dimethylformimidamide (39.2 g, 129.6 mmol) in CH₃CN/AcOH (500 mL, 1/1) was stirred at 90° C. for 24 h. After this time the mixture was purified by column chromatography on silica gel, using a gradient of elution: DCM/MeOH (100/1 to 1/1) to give the title compound (26 g, 85%) as the major product as a yellow oil which was used without further purification in the next step. MS (ESI): 474.1 [(M+H) (⁷⁹Br)]⁺.

Step D. 2-(4-(3-(6-Aminopyridin-2-yl)-4H-1,2,4-triazol-4-yl)butoxy)-5-bromobenzoic acid

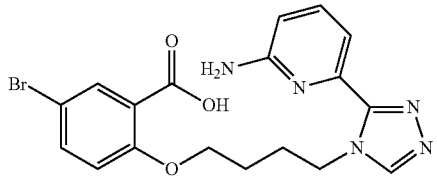 [SMILES: Nc1cccc(-c2nncn2CCCCOc2ccc(Br)cc2C(=O)O)n1]

A solution of methyl 5-bromo-2-(4-(3-(6-formamidopyridin-2-yl)-4H-1,2,4-triazol-4-yl)butoxy)benzoate (26 g, 55 mmol) and NaOH (4.39 g, 109.6 mmol) in THF/MeOH (500 mL, 1/1) was stirred at 70° C. for 10 h. After this time the solvent was evaporated under vacuum to give the title compound (23 g, 97%) as a yellow oil. The crude product was carried forward in Step E without further purification. MS (ESI): 432.1 [(M+H) (⁷⁹Br)]⁺.

Step E. 5⁵-Bromo-1⁴H-6-oxa-3-aza-2(2,6)-pyridina-1(3,4)-triazola-5(1,2)-benzenacyclodecaphan-4-one

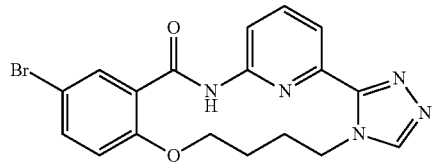 [SMILES: O=C1Nc2cccc(n2)-c2nncn2CCCCOc2ccc(Br)cc21]

A solution of 2-(4-(3-(6-aminopyridin-2-yl)-4H-1,2,4-triazol-4-yl)butoxy)-5-bromobenzoic acid (16.5 g, 95.4 mmol) in Et₃N (250 mL) and T₃P (250 mL, ≥50 wt. % in EtOAc) was stirred at 80° C. for 4 h. After this time the mixture was allowed to cool to room temperature and treated with MeOH (100 mL). The resulting solid was filtered and dried under vacuum. The solid was then triturated with DCM at 30° C. for 1 h and the resulting solid was filtered and dried under vacuum to give the title compound (9 g, 41%) as a white solid. ¹H NMR (400 MHz, CDCl₃) δ ppm 11.32 (s, 1H), 8.37 (s, 1H), 8.20 (s, 1H), 8.01 (d, J=7.8 Hz, 2H), 7.86-7.94 (m, 1H), 7.59 (dd, J=8.8, 2.5 Hz, 1H), 6.91 (d, J=8.6 Hz, 1H), 4.21-4.33 (m, 4H), 2.67 (s, 2H), 2.01-2.12 (m, 2H). MS (ESI): 416.0 [(M+H) (⁸¹Br)]⁺.

Example 2: 1⁴H-6-Oxa-3-aza-2(2,6)-pyridina-1(3,4)-triazola-5(1,2)-benzenacyclodecaphan-4-one

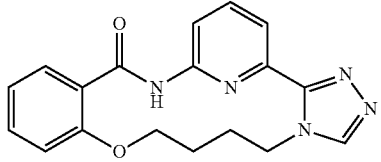 [SMILES: O=C1Nc2cccc(n2)-c2nncn2CCCCOc2ccccc21]

A reaction vial charged with 5⁵-bromo-1⁴H-6-oxa-3-aza-2(2,6)-pyridina-1(3,4)-triazola-5(1,2)-benzenacyclodecaphan-4-one (25 mg, 0.06 mmol) and Pd(dtbpf)Cl₂ (8 mg, 12 μmol) was purged with N₂ for 10 min. After this time, THF (600 μL) was added followed by Et₃N (49 mg, 0.48 mmol) and triethylsilane (28 mg, 0.24 mmol) and the resulting stirred reaction mixture was heated at 100° C. for 3 h. The reaction mixture was then allowed to cool to room temperature. DCM (2 mL) and MeOH (0.1 mL) were added, the solids were filtered off and the filtrate was concentrated under vacuum and purified by column chromatography (4 g silica gel, MeOH in DCM 0-15%) to give the crude product (19 mg, 94%). Further purification by HPLC (using a Sunfire Prep C18 OBD, 5 μm 30×50 mm column and using water/CH$_3$CN (containing 0.1% TFA) from 90/10 to 50/50 as the mobile phase at a flow rate of 50 mL/min) gave the title compound (13 mg, 48%). $^1$H NMR (400 MHz, CDCl$_3$) δ ppm 11.41 (s, 1H), 8.49 (s, 1H), 8.21 (dd, J=7.8, 1.8 Hz, 1H), 8.05 (dd, J=7.9, 0.9 Hz, 1H), 7.92 (d, J=0.7 Hz, 1H), 7.85-7.90 (m, 1H), 7.42-7.51 (m, 1H), 7.11 (t, J=7.6 Hz, 1H), 6.97 (d, J=8.3 Hz, 1H), 4.20-4.34 (m, 4H), 2.60-2.74 (m, 2H), 1.98-2.08 (m, 2H). MS (ESI): 336.1 [M+H]$^+$.

Example 3: 5$^5$-Morpholino-1$^4$H-6-oxa-3-aza-2(2,6)-pyridina-1(3,4)-triazola-5(1,2)-benzenacyclodecaphan-4-one

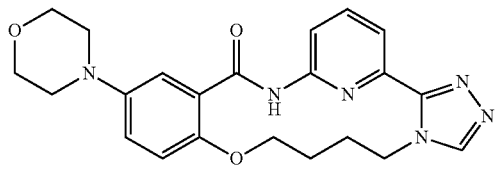

To a solution of 5-bromo-1$^4$H-6-oxa-3-aza-2(2,6)-pyridina-1(3,4)-triazola-5(1,2)-benzenacyclodecaphan-4-one (130 mg, 0.31 mmol), morpholine (82 μL, 0.94 mmol), sodium tert-butoxide (75 mg, 0.78 mmol) and XPhos (30 mg, 0.06 mmol) in a mixture of THF (4 mL) and DMF (0.4 mL) was added Pd$_2$(dba)$_3$ (29 mg, 0.03 mmol) under a stream of N$_2$ and the resulting reaction mixture was heated at reflux for 3 h. After this time the reaction mixture was allowed to cool to room temperature and EtOAc (1 mL) was added. The precipitates were filtered off and the filtrate was concentrated under vacuum and purified by column chromatography (4 g silica gel, 5-40% MeOH in DCM) to give the title compound (46 mg, 35%) as a yellow oil. $^1$H NMR (400 MHz, CDCl$_3$) δ ppm 11.49 (s, 1H), 8.14 (s, 1H), 7.95 (d, J=8.3 Hz, 1H), 7.89-7.93 (m, 1H), 7.78-7.84 (m, 1H), 7.74 (d, J=3.0 Hz, 1H), 6.99 (dd, J=8.9, 3.1 Hz, 1H), 6.90 (d, J=8.8 Hz, 1H), 4.14-4.22 (m, 4H), 3.77-3.83 (m, 4H), 3.05-3.13 (m, 4H), 2.56 (br dd, J=2.8, 1.5 Hz, 2H), 1.93-2.02 (m, 2H). MS (ESI): 421.2 [M+H]$^+$.

Example 4: 5$^5$-(2-Oxa-6-azaspiro[3.3]heptan-6-yl)-1$^4$H-6-oxa-3-aza-2(2,6)-pyridina-1(3,4)-triazola-5(1,2)-benzenacyclodecaphan-4-one

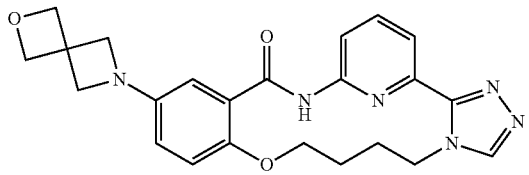 [SMILES: O=C1Nc2cccc(n2)-c2nncn2CCCCOc2ccc(N3CC4(COC4)C3)cc21]

A reaction vial was charged with 2-oxa-6-azaspiro[3.3]heptane (108 mg, 1.1 mmol, purchased from J&W Pharmlab, LLC, CAS#174-78-7), 5$^5$-bromo-1$^4$H-6-oxa-3-aza-2(2,6)-pyridina-1(3,4)-triazola-5(1,2)-benzenacyclodecaphan-4-one (150 mg, 0.36 mmol) and sodium tert-butoxide (104 mg, 1.1 mmol) was purged with N$_2$ for 10 min. THF (1 mL) was then added and the resulting stirred mixture was heated at reflux. Simultaneously, THF (0.50 mL) was added to a N$_2$ purged vial containing Pd$_2$dba$_3$ (33 mg, 0.03 mmol) and XPhos (34 mg, 0.07 mmol). The contents were stirred at reflux for 15 min before been cooled to room temperature. The resulting solution was transferred to the first reaction vial. The resulting dark red solution was stirred at reflux for 8 h. After this time the reaction mixture was cooled to room temperature, filtered and concentrated under vacuum. The resulting crude product was purified by column chromatography (4 g silica gel, MeOH in DCM 1-15%) to give the title compound (33 mg, 21%) as a pale yellow solid. $^1$H NMR (400 MHz, CDCl$_3$) δ ppm 11.60 (s, 1H), 8.27 (s, 1H), 8.05 (d, J=8.5 Hz, 1H), 8.00 (d, J=7.4 Hz, 1H), 7.87-7.96 (m, 1H), 7.36 (d, J=3.0 Hz, 1H), 6.95 (d, J=8.8 Hz, 1H), 6.62 (dd, J=8.8, 3.3 Hz, 1H), 4.85 (s, 4H), 4.25-4.32 (m, 2H), 4.22 (t, J=4.9 Hz, 2H), 4.05 (s, 4H), 2.66 (br s, 2H), 1.99-2.12 (m, 2H). MS (ESI): 433.2 [M+H]$^+$.

Example 5: 5$^5$-(3-Oxa-8-azabicyclo[3.2.1]octan-8-yl)-1$^4$H-6-oxa-3-aza-2(2,6)-pyridina-1(3,4)-triazola-5(1,2)-benzenacyclodecaphan-4-one

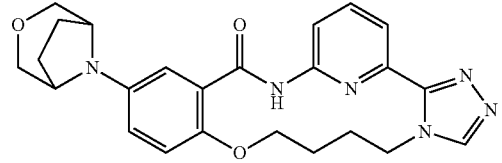 [SMILES: O=C1Nc2cccc(n2)-c2nncn2CCCCOc2ccc(N3C4CCC3COC4)cc21]

The title compound was synthesized according to the general procedure described in Example 4 and using 5$^5$-bromo-1$^4$H-6-oxa-3-aza-2(2,6)-pyridina-1(3,4)-triazola-5(1,2)-benzenacyclodecaphan-4-one (25 mg, 0.06 mmol) and 3-oxa-8-azabicyclo[3.2.1]octane hydrochloride (27 mg, 0.18 mmol, purchased from Advanced ChemBlocks Inc., CAS#904316-92-3) to give the desired product (8 mg, 30%) as a yellow film. $^1$H NMR (400 MHz, CDCl$_3$) δ ppm 11.54 (s, 1H) 8.23 (s, 1H) 7.97 (d, J=8.0 Hz, 1H) 7.93 (d, J=6.8 Hz, 1H) 7.85 (d, J=8.0 Hz, 1H) 7.66 (s, 1H) 6.93 (s, 2H) 4.14-4.29 (m, 4H) 3.97-4.07 (m, 2H) 3.89 (d, J=10.8 Hz, 2H) 3.50 (d, J=10.5 Hz, 2H) 2.52-2.68 (m, 2H) 1.91-2.07 (m, 4H) 1.73-1.90 (m, 2H). MS (ESI): 447.2 [M+H]$^+$.

Example 6: 5$^5$-(6-Oxa-3-azabicyclo[3.1.1]heptan-3-yl)-1$^4$H-6-oxa-3-aza-2(2,6)-pyridina-1(3,4)-triazola-5(1,2)-benzenacyclodecaphan-4-one

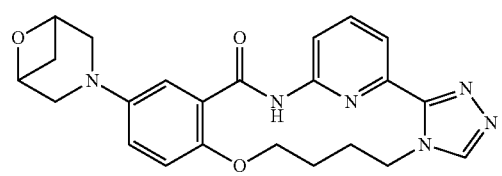 [SMILES: O=C1Nc2cccc(n2)-c2nncn2CCCCOc2ccc(N3CC4CC(C3)O4)cc21]

The title compound was synthesized according to the general procedure described in Example 4 and using 5$^5$-bromo-1$^4$H-6-oxa-3-aza-2(2,6)-pyridina-1(3,4)-triazola-5(1,2)-benzenacyclodecaphan-4-one (25 mg, 0.06 mmol) and 6-oxa-3-azabicyclo[3.1.1]heptane (20 mg, 0.18 mmol, purchased from Combi-Blocks, CAS#112461-31-1) to give the desired product (3 mg, 12%) as a yellow film. $^1$H NMR (400 MHz, CDCl$_3$) δ ppm 11.66 (s, 1H), 9.08 (br s, 1H), 8.07 (d, J=8.0 Hz, 1H), 7.94-7.99 (m, 1H), 7.90 (d, J=8.0 Hz, 1H), 7.60 (d, J=3.0 Hz, 1H), 6.98 (d, J=9.0 Hz, 1H), 6.88 (dd, J=8.8, 3.0 Hz, 1H), 4.72 (d, J=6.5 Hz, 2H), 4.34-4.42 (m, 2H), 4.15-4.21 (m, 2H), 3.16-3.31 (m, 2H), 2.59-2.74 (m, 2H), 1.97-2.14 (m, 4H), 1.74 (br s, 2H). MS (ESI): 433.1 [M+H]$^+$.

Example 7: 5$^5$-(8-Oxa-3-azabicyclo[3.2.1]oct-3-yl)-1$^4$H-6-oxa-3-aza-2(2,6)-pyridina-1(3,4)-triazola-5(1,2)-benzenacyclodecaphan-4-one

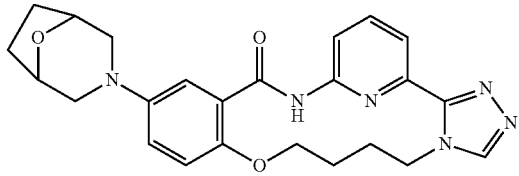 [SMILES: O=C1Nc2cccc(n2)-c2nncn2CCCCOc2ccc(N3CC4CCC(C3)O4)cc21]

The title compound was synthesized according to the general procedure described in Example 4 and using 5$^5$-bromo-1$^4$H-6-oxa-3-aza-2(2,6)-pyridina-1(3,4)-triazola-5(1,2)-benzenacyclodecaphan-4-one (25 mg, 0.06 mmol) and 8-oxa-3-azabicyclo[3.2.1]octane hydrochloride (27 mg, 0.18 mmol, purchased from Ark Pharma, Inc. CAS#54745-74-3) to give the desired product (3 mg, 11%) as a yellow film. $^1$H NMR (400 MHz, CDCl$_3$) δ ppm 11.54 (s, 1H), 8.35 (m, 1H), 8.00 (dd, J=8.2, 0.9 Hz, 1H), 7.94 (d, J=7.0 Hz, 1H), 7.86 (d, J=8.0 Hz, 1H), 7.64-7.68 (m, 1H), 6.89-6.93 (m, 2H), 4.40-4.46 (m, 2H), 4.23 (br d, J=5.8 Hz, 2H), 4.17 (br t, J=5.4 Hz, 2H), 3.28 (br d, J=10.8 Hz, 2H), 2.96 (dd, J=11.4, 2.1 Hz, 2H), 2.62 (br s, 2H), 2.00 (br s, 2H), 1.91 (br s, 4H). MS (ESI): 447.2 [M+H]$^+$.

Example 8: 5$^5$-(3-Oxa-6-azabicyclo[3.1.1]heptan-6-yl)-1$^4$H-6-oxa-3-aza-2(2,6)-pyridina-1(3,4)-triazola-5(1,2)-benzenacyclodecaphan-4-one

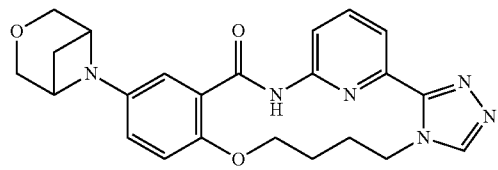 [SMILES: O=C1Nc2cccc(n2)-c2nncn2CCCCOc2ccc(N3C4COCC3C4)cc21]

The title compound was synthesized according to the general procedure described in Example 4 and using 5$^5$-bromo-1$^4$H-6-oxa-3-aza-2(2,6)-pyridina-1(3,4)-triazola-5(1,2)-benzenacyclodecaphan-4-one (25 mg, 0.06 mmol) and 3-oxa-6-azabicyclo[3.1.1]heptane (18 mg, 0.18 mmol, purchased from J&W Pharmlab, LLC., CAS#286390-20-3) to give the desired product (6 mg, 23%) as a yellow film. $^1$H NMR (400 MHz, CDCl$_3$) δ ppm 11.56 (s, 1H), 8.16 (s, 1H), 7.97 (dd, J=8.0, 0.8 Hz, 1H), 7.93 (d, J=7.0 Hz, 1H), 7.81-7.87 (m, 1H), 7.35 (d, J=3.0 Hz, 1H), 6.92 (d, J=8.8 Hz, 1H), 6.61 (dd, J=8.5, 3.0 Hz, 1H), 4.30 (d, J=11.0 Hz, 2H), 4.22 (br d, J=5.8 Hz, 4H), 4.15-4.20 (m, 2H), 3.65 (d, J=10.5 Hz, 2H), 2.70-2.80 (m, 2H), 2.59 (br s, 2H), 1.98-2.05 (m, 2H). MS (ESI): 433.1 [M+H]$^+$.

Example 9: 5$^5$-(3,3-Difluoroazetidin-1-yl)-1$^4$H-6-oxa-3-aza-2(2,6)-pyridina-1(3,4)-triazola-5(1,2)-benzenacyclodecaphan-4-one

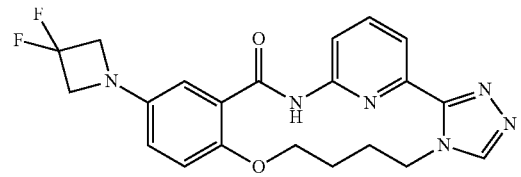 [SMILES: O=C1Nc2cccc(n2)-c2nncn2CCCCOc2ccc(N3CC(F)(F)C3)cc21]

A reaction vial was charged with 3,3-difluoroazetidine hydrochloride (23 mg, 0.18 mmol, purchased from Sigma-Aldrich, CAS#288315-03-7), 5$^5$-bromo-1$^4$H-6-oxa-3-aza-2(2,6)-pyridina-1(3,4)-triazola-5(1,2)-benzenacyclodecaphan-4-one (25 mg, 0.06 mmol), sodium tert-butoxide (35 mg, 0.36 mmol), XPhos (6 mg, 0.012 mmol) and Pd$_2$dba$_3$ (5 mg, 0.006 mmol). Under a N$_2$ atmosphere THF (0.5 mL) was added and the resulting mixture was heated at reflux for 2 h, cooled to room temperature and concentrated under vacuum. The crude product was purified by column chromatography (4 g silica gel, MeOH in DCM 0-15% 10 min) to give the title compound (6 mg, 23%) as a yellow solid. $^1$H NMR (400 MHz, CDCl$_3$) δ ppm 11.52 (s, 1H), 8.21 (s, 1H), 7.97 (dd, J=8.0, 0.8 Hz, 1H), 7.92-7.95 (m, 1H), 7.85 (d, J=7.8 Hz, 1H), 7.33 (d, J=3.0 Hz, 1H), 6.92 (d, J=8.8 Hz, 1H), 6.58 (dd, J=8.8, 3.0 Hz, 1H), 4.18 (s, 8H) 2.59 (br s, 2H), 1.94-2.06 (m, 2H). MS (ESI): 427.2 [M+H]$^+$.

Example 10: 5$^5$-(3,3-Difluoropyrrolidin-1-yl)-1$^4$H-6-oxa-3-aza-2(2,6)-pyridina-1(3,4)-triazola-5(1,2)-benzenacyclodecaphan-4-one

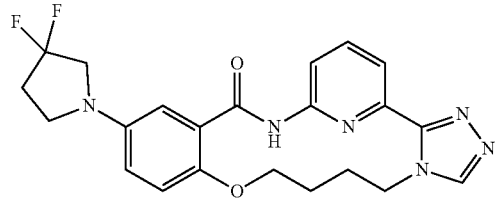 [SMILES: O=C1Nc2cccc(n2)-c2nncn2CCCCOc2ccc(N3CCC(F)(F)C3)cc21]

The title compound was synthesized according to the general procedure described in Example 9 and using 5$^5$-bromo-1$^4$H-6-oxa-3-aza-2(2,6)-pyridina-1(3,4)-triazola-5(1,2)-benzenacyclodecaphan-4-one (25 mg, 0.06 mmol) and 3,3-difluoropyrrolidine hydrochloride (26 mg, 0.18 mmol, purchased from Combi-Blocks Inc., CAS#163457-23-6) to give the desired product (7 mg, 26%) as a yellow film. $^1$H NMR (400 MHz, CDCl$_3$) δ ppm 11.56 (s, 1H), 8.26 (s, 1H), 7.98 (dd, J=8.0, 0.8 Hz, 1H), 7.92 (dd, J=7.8, 0.8 Hz, 1H), 7.80-7.87 (m, 1H), 7.38 (d, J=3.3 Hz, 1H), 6.92 (d, J=8.8 Hz, 1H), 6.62 (dd, J=9.0, 3.3 Hz, 1H), 4.18-4.28 (m, 2H), 4.15 (t, J=5.0 Hz, 2H), 3.63 (t, J=13.3 Hz, 2H), 3.48 (t, J=7.0 Hz, 2H), 2.52-2.68 (m, 2H), 2.44 (tt, J=13.9, 7.15 Hz, 2H), 1.91-2.05 (m, 2H). MS (ESI): 441.2 [M+H]$^+$.

Example 11: 5⁵-(3,3-Difluoropiperidin-1-yl)-1⁴H-6-oxa-3-aza-2(2,6)-pyridina-1(3,4)-triazola-5(1,2)-benzenacyclodecaphan-4-one

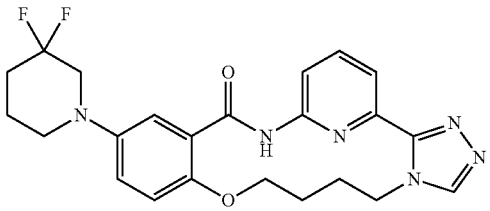 [SMILES: O=C1Nc2cccc(n2)-c2nncn2CCCCOc2ccc(N3CCCC(F)(F)C3)cc21]

The title compound was synthesized according to the general procedure described in Example 9 and using 5⁵-bromo-1⁴H-6-oxa-3-aza-2(2,6)-pyridina-1(3,4)-triazola-5(1,2)-benzenacyclodecaphan-4-one (25 mg, 0.06 mmol) and 3,3-difluoropiperidine hydrochloride (29 mg, 0.18 mmol, purchased from Sigma-Aldrich, CAS#496807-97-7) to give the desired product (7 mg, 25%) as a yellow film. $^1$H NMR (400 MHz, CDCl$_3$) δ ppm 11.49 (s, 1H), 8.19 (s, 1H), 7.97 (dd, J=8.0, 0.8 Hz, 1H), 7.91-7.95 (m, 1H), 7.81-7.87 (m, 1H), 7.77 (d, J=3.3 Hz, 1H), 7.03 (dd, J=9.0, 3.3 Hz, 1H), 6.91 (d, J=8.8 Hz, 1H), 4.12-4.28 (m, 4H), 3.30 (t, J=11.3 Hz, 2H), 3.11-3.17 (m, 2H), 2.53-2.68 (m, 2H), 1.90-2.04 (m, 4H), 1.82-1.90 (m, 2H). MS (ESI): 455.2 [M+H]⁺.

Example 12: 5⁵-(4,4-Difluoropiperidin-1-yl)-1⁴H-6-oxa-3-aza-2(2,6)-pyridina-1(3,4)-triazola-5(1,2)-benzenacyclodecaphan-4-one

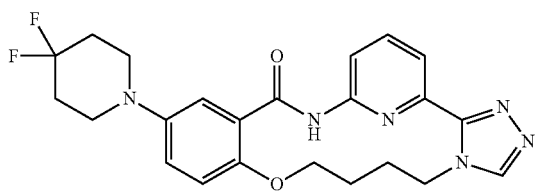 [SMILES: O=C1Nc2cccc(n2)-c2nncn2CCCCOc2ccc(N3CCC(F)(F)CC3)cc21]

The title compound was synthesized according to the general procedure described in Example 9 and using 5⁵-bromo-1⁴H-6-oxa-3-aza-2(2,6)-pyridina-1(3,4)-triazola-5(1,2)-benzenacyclodecaphan-4-one (25 mg, 0.06 mmol) and 4,4-difluoropiperidine hydrochloride (29 mg, 0.18 mmol, purchased from Matrix Scientific, CAS#144230-52-4) to give the desired product (9 mg, 33%) as a yellow film. $^1$H NMR (400 MHz, CDCl$_3$) δ ppm 11.49 (s, 1H), 8.18 (s, 1H), 7.97 (dd, J=8.0, 0.8 Hz, 1H), 7.94 (dd, J=7.8, 0.8 Hz, 1H), 7.85 (d, J=7.8 Hz, 1H), 7.81 (d, J=3.0 Hz, 1H), 7.08 (dd, J=8.8, 3.3 Hz, 1H), 6.92 (d, J=9.0 Hz, 1H), 4.16-4.25 (m, 4H), 3.25-3.32 (m, 4H), 2.60 (br s, 2H), 1.95-2.14 (m, 6H). MS (ESI): 455.2 [M+H]⁺.

Example 13: 5⁵-(4-Ethylpiperazin-1-yl)-1⁴H-6-oxa-3-aza-2(2,6)-pyridina-1(3,4)-triazola-5(1,2)-benzenacyclodecaphan-4-one

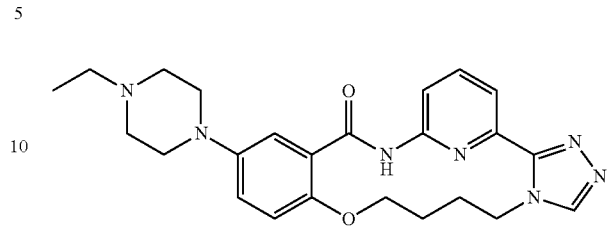

The title compound was synthesized according to the general procedure described in Example 4 and using 5⁵-bromo-1⁴H-6-oxa-3-aza-2(2,6)-pyridina-1(3,4)-triazola-5(1,2)-benzenacyclodecaphan-4-one (25 mg, 0.06 mmol) and 1-ethylpiperazine (21 mg, 0.18 mmol, purchased from TCI, CAS#5308-25-8) to give the title compound (3 mg, 11%) as a yellow residue. $^1$H NMR (400 MHz, CDCl$_3$) δ ppm 11.53 (s, 1H), 8.15 (s, 1H), 7.98 (dd, J=8.0, 0.8 Hz, 1H), 7.93 (d, J=6.8 Hz, 1H), 7.82-7.87 (m, 1H), 7.78 (d, J=3.3 Hz, 1H), 7.02 (dd, J=9.0, 3.3 Hz, 1H), 6.91 (d, J=9.0 Hz, 1H), 4.15-4.26 (m, 4H), 3.14-3.21 (m, 4H), 2.58 (br s, 6H), 2.40-2.47 (m, 2H), 1.94-2.04 (m, 2H), 1.08 (t, J=7.3 Hz, 3H). MS (ESI): 448.2 [M+H]⁺.

Example 14: 5⁵-(2,5-Dihydrofuran-3-yl)-1⁴H-6-oxa-3-aza-2(2,6)-pyridina-1(3,4)-triazola-5(1,2)-benzenacyclodecaphan-4-one

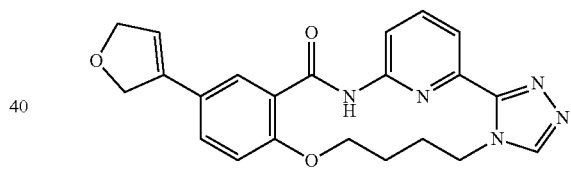

A reaction vial was charged with 2-(2,5-dihydrofuran-3-yl)-4,4,5,5-tetramethyl-1,3,2-dioxaborolane (28 mg, 0.14 mmol, purchased from Combi-Blocks, Inc., CAS#212127-80-5), 5⁵-bromo-1⁴H-6-oxa-3-aza-2(2,6)-pyridina-1(3,4)-triazola-5(1,2)-benzenacyclodecaphan-4-one (50 mg, 0.12 mmol), Pd(dtbpf)Cl$_2$ (9 mg, 0.013 mmol) and potassium phosphate (53 mg, 0.25 mmol). The vial was purged with N$_2$ for 10 min, DMSO (0.8 mL) was added and the resulting mixture was heated at 80° C. for 6 h. After this time the reaction mixture was allowed to reach room temperature upon which it was filtered and subjected to HPLC purification (using a Sunfire Prep C18 OBD, 5 μm 30×50 mm column and using water/CH$_3$CN (containing 0.1% TFA) from 90/10 to 10/90 as the mobile phase at a flow rate of 50 mL/min) to give the title compound (19 mg, 39%) as a beige film. $^1$H NMR (400 MHz, CD$_3$OD) δ ppm 9.09 (s, 1H), 7.99 (s, 2H), 7.91 (d, J=2.5 Hz, 1H), 7.87 (dd, J=4.8, 3.5 Hz, 1H), 7.42 (dd, J=8.8, 2.5 Hz, 1H), 7.05 (d, J=8.5 Hz, 1H), 6.94 (t, J=1.9 Hz, 1H), 4.48 (t, J=9.5 Hz, 2H), 4.35-4.43 (m, 2H), 4.28 (br t, J=5.0 Hz, 2H), 2.93 (td, J=9.6, 1.9 Hz, 2H), 2.53-2.66 (m, 2H), 2.05 (s, 2H). MS (ESI): 404.2 [M+H]⁺.

Example 15: rac-5⁵-(Tetrahydrofuran-3-yl)-1⁴H-6-oxa-3-aza-2(2,6)-pyridina-1(3,4)-triazola-5(1,2)-benzenacyclodecaphan-4-one

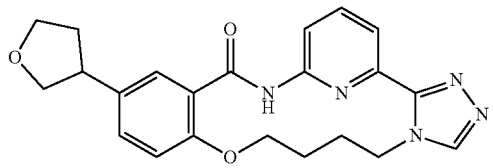 [SMILES: O=C1Nc2cccc(n2)-c2nncn2CCCCOc2ccc(C3CCOC3)cc21]

To a N₂ purged reaction vial charged with 5⁵-(2,5-dihydrofuran-3-yl)-1⁴H-6-oxa-3-aza-2(2,6)-pyridina-1(3,4)-triazola-5(1,2)-benzenacyclodecaphan-4-one (14 mg, 0.034 mmol) in EtOH (5 mL) was added 10% Pd (37 mg, 0.035 mmol, 10% on C). A balloon filled with hydrogen was installed and the resulting solution was purged for 10 min and stirred under a hydrogen atmosphere overnight. After this time the Pd/C was filtered off through a plug of Celite, the cake was washed with MeOH, the volatiles were removed under vacuum and the resulting crude product was subjected to HPLC (using a Sunfire Prep C18 OBD, 5 μm 30×50 mm column and using water/CH₃CN (containing 0.1% TFA) from 90/10 to 10/90 as the mobile phase at a flow rate of 50 mL/min) to give the title compound (3 mg, 17%) as an off white solid. ¹H NMR (400 MHz, CDCl₃) δ ppm 11.42 (s, 1H), 8.49 (br s, 1H), 8.09 (d, J=2.5 Hz, 1H), 8.04 (dd, J=7.9, 0.9 Hz, 1H), 7.91-7.96 (m, 1H), 7.85-7.91 (m, 1H), 7.36 (dd, J=8.5, 2.5 Hz, 1H), 6.94 (d, J=8.5 Hz, 1H), 4.21-4.32 (m, 4H), 4.09 (dd, J=8.4, 7.7 Hz, 1H), 4.03 (td, J=8.5, 4.6 Hz, 1H), 3.82-3.92 (m, 1H), 3.65 (dd, J=8.4, 7.4 Hz, 1H), 3.39 (quin, J=7.8 Hz, 1H), 2.60 (s, 2H), 2.33 (dtd, J=12.4, 7.7, 4.5 Hz, 1H), 1.98-2.07 (m, 2H) 1.92-1.98 (m, 1H). MS (ESI): 406.1 [M+H]⁺.

Example 16: 5⁵-(3,6-Dihydro-2H-pyran-4-yl)-1⁴H-6-oxa-3-aza-2(2,6)-pyridina-1(3,4)-triazola-5(1,2)-benzenacyclodecaphan-4-one

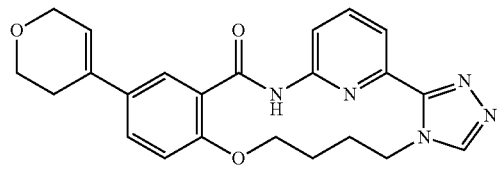 [SMILES: O=C1Nc2cccc(n2)-c2nncn2CCCCOc2ccc(C3=CCOCC3)cc21]

The title compound was synthesized according to the general procedure described in Example 14 and using 5⁵-bromo-1⁴H-6-oxa-3-aza-2(2,6)-pyridina-1(3,4)-triazola-5(1,2)-benzenacyclodecaphan-4-one (47 mg, 0.11 mmol) and 2-(3,6-dihydro-2H-pyran-4-yl)-4,4,5,5-tetramethyl-1,3,2-dioxaborolane (29 mg, 0.14 mmol, purchased from J&W Pharmalab, LLC., CAS#287944-16-5) to give the desired product (9 mg, 22%) as a white solid. ¹H NMR (400 MHz, CD₃OD) δ ppm 8.97 (s, 1H), 8.18 (d, J=2.5 Hz, 1H), 8.05 (d, J=4.3 Hz, 2H), 7.88-7.94 (m, 1H), 7.66 (dd, J=8.7, 2.4 Hz, 1H), 7.20 (d, J=8.8 Hz, 1H), 6.22 (s, 1H), 4.34-4.44 (m, 4H), 4.31 (q, J=2.6 Hz, 2H), 3.94 (t, J=5.5 Hz, 2H), 2.66 (s, 2H), 2.53 (br d, J=1.8 Hz, 2H), 2.09 (br s, 2H). MS (ESI): 418.1 [M+H]⁺.

Example 17: 5⁵-(Tetrahydro-2H-pyran-4-yl)-1⁴H-6-oxa-3-aza-2(2,6)-pyridina-1(3,4)-triazola-5(1,2)-benzenacyclodecaphan-4-one

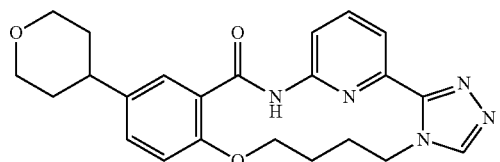

The title compound was synthesized according to the general procedure described in Example 15 and using 5⁵-(3,6-dihydro-2H-pyran-4-yl)-1⁴H-6-oxa-3-aza-2(2,6)-pyridina-1(3,4)-triazola-5(1,2)-benzenacyclodecaphan-4-one (5 mg, 0.01 mmol) to give the desired product (4.8 mg, 95%) as a beige solid. ¹H NMR (400 MHz, CD₃OD) δ ppm 8.63 (s, 1H), 7.98-8.04 (m, 3H), 7.87 (dd, J=5.5, 3.0 Hz, 1H), 7.47 (dd, J=8.5, 2.3 Hz, 1H), 7.17 (d, J=8.5 Hz, 1H), 4.29-4.37 (m, 4H), 4.01-4.08 (m, 2H), 3.53-3.61 (m, 2H), 2.79-2.89 (m, 1H), 2.64 (br d, J=10.0 Hz, 2H), 2.00-2.10 (m, 2H), 1.73-1.82 (m, 4H). MS (ESI): 420.2 [M+H]⁺.

Example 18: 5⁵-Methyl-1⁴H-6-oxa-3-aza-2(2,6)-pyridina-1(3,4)-triazola-5(1,2)-benzenacyclodecaphan-4-one

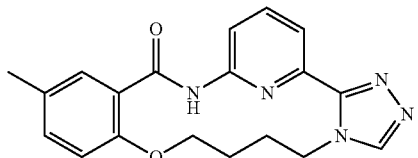

A reaction vial was charged with trimethylboroxine (91 mg, 0.72 mmol), 5⁵-bromo-1⁴H-6-oxa-3-aza-2(2,6)-pyridina-1(3,4)-triazola-5(1,2)-benzenacyclodecaphan-4-one (30 mg, 0.072 mmol), cesium carbonate (71 mg, 0.22 mmol) and Pd(PPh₃)₄ (8 mg, 0.007 mmol) and was purged with N₂. THF (1.00 mL) was added and the stirred resulting yellow mixture was heated at reflux overnight. After this time the reaction was cooled to rt, the volatiles were removed under reduced pressure and DCM (2 mL) was added. The resulting solids were filtered off and the filtrate was purified by column chromatography (4 g silica gel, MeOH in DCM 0-15%) to give the title compound (3 mg, 12%) as an off white solid. ¹H NMR (400 MHz, CDCl₃) δ ppm 11.42 (s, 1H), 8.16 (s, 1H), 8.01 (d, J=2.5 Hz, 1H), 7.99 (d, J=8.3 Hz, 1H), 7.94 (d, J=7.3 Hz, 1H), 7.84 (s, 1H), 7.24 (dd, J=8.4, 2.4 Hz, 1H), 6.86 (d, J=8.3 Hz, 1H), 4.12-4.27 (m, 4H), 2.52-2.72 (m, 2H), 2.30 (s, 3H), 1.92-2.09 (m, 2H). MS (ESI): 350.2 [M+H]⁺.

Example 19: 5⁵-Vinyl-1⁴H-6-oxa-3-aza-2(2,6)-pyridina-1(3,4)-triazola-5(1,2)-benzenacyclodecaphan-4-one

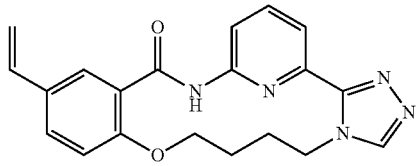 [SMILES: C=Cc1ccc2c(c1)C(=O)Nc1cccc(n1)-c1nncn1CCCCO2]

A reaction vial was charged with 5⁵-bromo-1⁴H-6-oxa-3-aza-2(2,6)-pyridina-1(3,4)-triazola-5(1,2)-benzenacyclodecaphan-4-one (500 mg, 1.2 mmol) and Pd(dtbpf)Cl$_2$ (110 mg, 0.17 mmol), potassium vinyltrifluoroborate (243 mg, 1.8 mmol) and potassium phosphate (282 mg, 1.3 mmol). The reaction vial was purged with N$_2$ for 15 min, THF (8 mL) was added and the resulting mixture was heated at 80° C. for 2 h. After this time the reaction mixture was cooled to room temperature, filtered and evaporated under vacuum. HPLC purification of the resulting crude product (using a Sunfire Prep C18 OBD, 5 μm 30×50 mm column and using water/CH$_3$CN (containing 0.1% TFA) from 90/10 to 10/90 as the mobile phase at a flow rate of 50 mL/min) gave the title compound (320 mg, 73%) as a beige solid. ¹H NMR (400 MHz, CD$_3$OD) δ ppm 8.84 (s, 1H), 8.13 (s, 1H), 7.96-8.04 (m, 2H), 7.88 (dd, J=5.6, 2.4 Hz, 1H), 7.59 (br d, J=8.8 Hz, 1H), 7.14 (d, J=8.5 Hz, 1H), 6.70 (dd, J=17.7, 11.2 Hz, 1H), 5.74 (d, J=17.8 Hz, 1H), 5.22 (d, J=10.8 Hz, 1H), 4.27-4.42 (m, 4H), 2.53-2.68 (m, 2H), 2.05 (br s, 2H). MS (ESI): 362.2 [M+H]⁺.

Example 20: 4-Oxo-1⁴H-6-oxa-3-aza-2(2,6)-pyridina-1(3,4)-triazola-5(1,2)-benzenacyclodecaphane-5⁵-carbonitrile

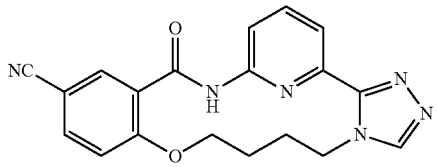 [SMILES: N#Cc1ccc2c(c1)C(=O)Nc1cccc(n1)-c1nncn1CCCCO2]

A mixture of 5⁵-bromo-1⁴H-6-oxa-3-aza-2(2,6)-pyridina-1(3,4)-triazola-5(1,2)-benzenacyclodecaphan-4-one (200 mg, 0.48 mmol), K$_4$Fe(CN)$_6$ (76 mg, 0.2 mmol), Pd(PPh$_3$)$_4$ (56 mg, 0.048 mmol) and DBU (10 mg, 0.072 mmol) in t-BuOH/H$_2$O (1:1, 5 mL) was stirred at 90° C. for 17 h. After this time the solvent was removed under vacuum to give the crude product which was purified by HPLC (using a Phenomenex Synergi C18, 4 μm 150×30 mm column and using CH$_3$CN/water (containing 0.05% HCl), from 31% to 46% as the mobile phase at a flow rate of 25 mL/min) to give the title compound (30 mg, 17%) as a white solid. ¹H NMR (400 MHz, DMSO-d$_6$) δ ppm 10.92 (s, 1H), 8.95 (s, 1H), 8.23 (d, J=2.4 Hz, 1H), 8.02-8.07 (m, 2H), 7.85-7.87 (m, 2H), 7.43 (d, J=8.8 Hz, 1H), 4.35-4.37 (m, 2H), 4.23-4.27 (m, 2H), 2.45-2.50 (m, 2H), 1.86-1.91 (m, 2H). MS (ESI): 361.1 [M+H]⁺.

Example 21: 5⁵-(4-Methyl-1H-imidazol-1-yl)-1⁴H-6-oxa-3-aza-2(2,6)-pyridina-1(3,4)-triazola-5(1,2)-benzenacyclodecaphan-4-one

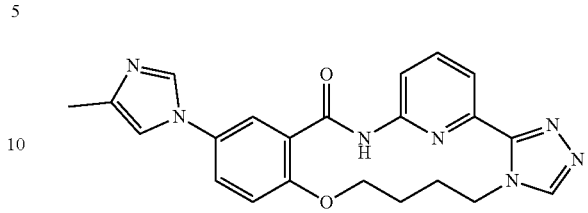

A reaction vial was charged with 5⁵-bromo-1⁴H-6-oxa-3-aza-2(2,6)-pyridina-1(3,4)-triazola-5(1,2)-benzenacyclodecaphan-4-one (300 mg, 0.72 mmol), sodium tert-butoxide (209 mg, 2.2 mmol) and 4-methyl-1H-imidazole (178 mg, 2.2 mmol). The reaction vial was purged with N$_2$, tert-butanol (3 mL) was added and the mixture was heated at 85° C. Simultaneously, a vial containing a solution of dtbpf (70 mg, 0.14 mmol) and Pd$_2$dba$_3$ (66 mg, 0.072 mmol) in toluene (1.5 mL) was heated at reflux for 15 minutes, cooled to room temperature and then added to the first vial. The resulting mixture was heated at reflux for 4 h. After this time the reaction was cooled to room temperature and MeOH (2 mL) was added and the reaction mixture was filtered. The resulting product was washed with MeOH (2×4 mL) and the combined organic extracts were evaporated under vacuum and purified by HPLC (using an XTerra Prep RP18 OBD, 10 μm 50×250 mm column and using water (containing 0.1% TFA)/CH$_3$CN from 90/10 to 10/90 as the mobile phase at a flow rate of 50 mL/min) to give the title compound (48 mg, 16%) as a white solid. ¹H NMR (400 MHz, CD$_3$OD) δ ppm 9.34 (d, J=1.8 Hz, 1H), 8.76 (s, 1H), 8.31 (d, J=3.0 Hz, 1H), 7.96-8.05 (m, 2H), 7.85 (s, 2H), 7.79 (d, J=1.5 Hz, 1H), 7.44 (d, J=9.0 Hz, 1H), 4.43 (t, J=4.9 Hz, 2H), 4.31-4.39 (m, 2H), 2.62 (br d, J=6.3 Hz, 2H), 2.46 (d, J=1.0 Hz, 3H), 2.09 (br s, 2H). MS (ESI): 416.2 [M+H]⁺.

Example 22: 5⁵-(4-Cyclopropyl-1H-imidazol-1-yl)-1⁴H-6-oxa-3-aza-2(2,6)-pyridina-1(3,4)-triazola-5(1,2)-benzenacyclodecaphan-4-one

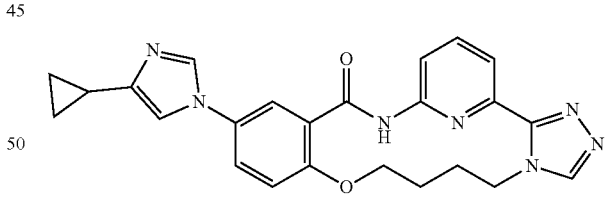

The title compound was synthesized according to the general procedure described in Example 21 and using 5⁵-bromo-1⁴H-6-oxa-3-aza-2(2,6)-pyridina-1(3,4)-triazola-5(1,2)-benzenacyclodecaphan-4-one (25 mg, 0.06 mmol) and 4-cyclopropyl-1H-imidazole (20 mg, 0.18 mmol, purchased from Combi-Blocks Inc., CAS#89830-98-8) to give the desired product (3 mg, 11%) as a white solid. ¹H NMR (400 MHz, CD$_3$OD) δ ppm 9.32 (d, J=1.8 Hz, 1H), 8.77 (s, 1H), 8.35 (d, J=3.0 Hz, 1H), 8.01-8.08 (m, 2H), 7.91 (dd, J=7.0, 1.2 Hz, 1H), 7.88 (dd, J=8.9, 2.9 Hz, 1H), 7.80 (dd, J=1.6, 0.9 Hz, 1H), 7.47 (d, J=9.0 Hz, 1H), 4.46 (t, J=5.1 Hz, 2H), 4.34-4.41 (m, 2H), 2.62-2.73 (m, 2H), 2.07-2.15 (m, 2H), 2.01-2.07 (m, 1H), 1.11-1.18 (m, 2H), 0.89-0.95 (m, 2H). MS (ESI): 442.2 [M+H]⁺.

Example 23: 5⁵-(1-Methyl-1H-pyrazol-5-yl)-1⁴H-6-oxa-3-aza-2(2,6)-pyridina-1(3,4)-triazola-5(1,2)-benzenacyclodecaphan-4-one

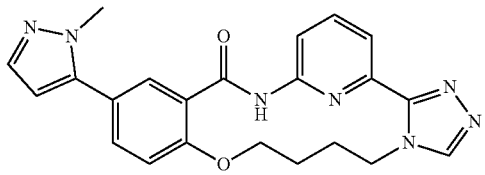 [SMILES: Cn1nccc1-c1ccc2c(c1)C(=O)Nc1cccc(n1)-c1nncn1CCCCO2]

A stirred solution of 5⁵-bromo-1⁴H-6-oxa-3-aza-2(2,6)-pyridina-1(3,4)-triazola-5(1,2)-benzenacyclodecaphan-4-one (300 mg, 0.72 mmol) and 1-methyl-5-(4,4,5,5-tetramethyl-1,3,2-dioxaborolan-2-yl)-1H-pyrazole (151 mg, 0.72 mmol), $K_2CO_3$ (201 mg, 1.45 mmol) and Pd(dppf)Cl$_2$ (53 mg, 0.07 mmol) in DMF (15 mL) and $H_2O$ (3 mL) was degassed with $N_2$ and the mixture was heated to 100° C. for 2 h. After this time the reaction was cooled to rt, filtered and purified by HPLC (using a Phenomenex Synergi C18, 4 μm 150×30 mm column and using $CH_3CN$/water (containing 0.05% HCl), from 30% to 50% as the mobile phase at a flow rate of 25 mL/min) to give the title compound (38 mg, 13%) as a brown solid. $^1$H NMR (400 MHz, DMSO-$d_6$) δ ppm 11.20 (s, 1H), 9.05 (s, 1H), 8.01-8.08 (m, 1H), 8.01 (s, 1H), 7.90-7.92 (m, 2H), 7.86-7.88 (m, 1H), 7.46 (s, 1H), 7.37-7.40 (m, 1H), 6.42 (s, 1H), 4.52-4.55 (m, 2H), 4.30-4.37 (m, 2H), 3.82 (s, 3H), 2.45-2.47 (m, 2H), 1.94-1.96 (m, 2H). MS (ESI): 416.1 [M+H]⁺.

Example 24: 5⁵-(1-Methyl-1H-pyrazol-4-yl)-1⁴H-6-oxa-3-aza-2(2,6)-pyridina-1(3,4)-triazola-5(1,2)-benzenacyclodecaphan-4-one

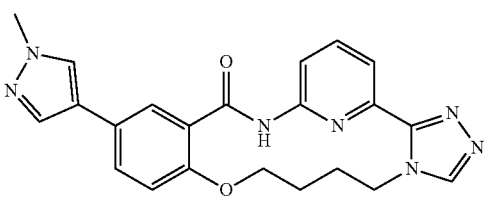 [SMILES: Cn1cc(-c2ccc3c(c2)C(=O)Nc2cccc(n2)-c2nncn2CCCCO3)cn1]

A stirred solution of 5⁵-bromo-1⁴H-6-oxa-3-aza-2(2,6)-pyridina-1(3,4)-triazola-5(1,2)-benzenacyclodecaphan-4-one (300 mg, 0.72 mmol), 1-methyl-4-(4,4,5,5-tetramethyl-1,3,2-dioxaborolan-2-yl)-1H-pyrazole (151 mg, 0.72 mmol), $K_2CO_3$ (201 mg, 1.45 mmol) and Pd(dppf)Cl$_2$ (53 mg, 0.07 mmol) in DMF (15 mL) and $H_2O$ (3 mL) was degassed with $N_2$ and the mixture was heated to 100° C. for 2 h. After this time the reaction was filtered and the residue was purified by HPLC (using a Phenomenex Synergi C18, 4 μm 150×30 mm column and using water (containing 0.05% HCl)/$CH_3CN$ from 22 to 42% as the mobile phase at a flow rate of 25 mL/min) to give the title compound (40 mg, 13%) as a white solid. $^1$H NMR (400 MHz, DMSO-$d_6$) δ ppm 11.27 (s, 1H), 8.85 (s, 1H), 8.15 (s, 1H), 8.06-8.09 (m, 2H), 7.89-7.91 (m, 1H), 7.84-7.85 (m, 2H), 7.74-7.77 (m, 1H), 7.26-7.28 (m, 1H), 4.29-4.32 (m, 4H), 3.82 (s, 3H), 2.46-2.48 (m, 2H), 1.93-1.94 (m, 2H). MS (ESI): 416.2 [M+H]⁺.

Example 25: 5⁵-(Pyridin-2-yl)-1⁴H-6-oxa-3-aza-2(2,6)-pyridina-1(3,4)-triazola-5(1,2)-benzenacyclodecaphan-4-one

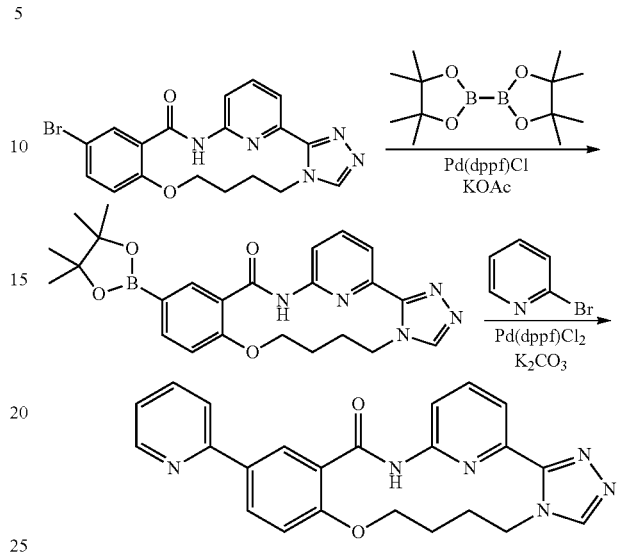

Step A: 5⁵-(4,4,5,5-Tetramethyl-1,3,2-dioxaborolan-2-yl)-1⁴H-6-oxa-3-aza-2(2,6)-pyridina-1(3,4)-triazola-5(1,2)-benzenacyclodecaphan-4-one

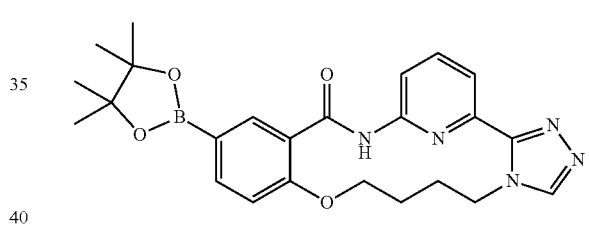

A stirred solution of 5⁵-bromo-1⁴H-6-oxa-3-aza-2(2,6)-pyridina-1(3,4)-triazola-5(1,2)-benzenacyclodecaphan-4-one (500 mg, 1.21 mmol) and 4,4,4',4',5,5,5',5'-octamethyl-2,2'-bi(1,3,2-dioxaborolane) (460 mg, 1.81 mmol) in DMSO (15 mL) was added KOAc (178 mg, 1.81 mmol) and Pd(dppf)Cl$_2$ (88.5 mg, 0.12 mmol). The mixture was stirred at 90° C. under a $N_2$ atmosphere for 2 h. After this time the mixture was cooled to room temperature and water (50 mL) was added. The aqueous layer was extracted with EtOAc (3×50 mL) and the combined organic extracts were evaporated under vacuum to give the title compound (556 mg, 100%) as a brown oil.

Step B: 5⁵-(Pyridin-2-yl)-1⁴H-6-oxa-3-aza-2(2,6)-pyridina-1(3,4)-triazola-5(1,2)-benzenacyclodecaphan-4-one

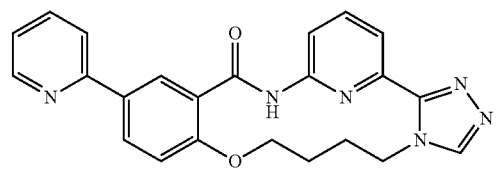 [SMILES: O=C1Nc2cccc(n2)-c2nncn2CCCCOc2ccc(-c3ccccn3)cc21]

A solution of 5⁵-(4,4,5,5-tetramethyl-1,3,2-dioxaborolan-2-yl)-1⁴H-6-oxa-3-aza-2(2,6)-pyridina-1(3,4)-triazola-5(1,2)-benzenacyclodecaphan-4-one (556 mg, 1.21 mmol), 2-bromopyridine (164 mg, 1.45 mmol), K₂CO₃ (333 mg, 2.41 mmol) and Pd(dppf)Cl₂ (88 mg, 0.12 mmol) in dioxane/H₂O (40 mL, 10/1) was stirred at 90° C. under a N₂ atmosphere for 4 h. After this time the mixture was concentrated under vacuum and purified by column chromatography on silica gel eluting with petroleum ether/EtOAc (using a gradient of elution of: 50/1 to 0/1) to give the title compound (143 mg, 29%) as a yellow solid. ¹H NMR (400 MHz, CDCl₃) δ ppm 11.46 (s, 1H), 8.83 (d, J=2.8 Hz, 1H), 8.68 (td, J=0.8, 3.2 Hz, 1H), 8.33 (dd, J=2.4, 6.4 Hz, 1H), 8.22 (s, 1H), 8.08 (d, J=7.6 Hz, 1H), 8.03 (dd, J=0.8, 6.8 Hz, 1H), 7.88-7.98 (m, 1H), 7.80-7.86 (m, 1H), 7.75-7.80 (m, 1H), 7.22-7.25 (m, 1H), 7.15 (d, J=8.8 Hz, 1H), 4.34-4.43 (m, 2H), 4.26-4.34 (m, 2H), 2.73 (br s, 2H), 2.11 (br s, 2H). MS (ESI): 413.2 [M+H]⁺.

Example 26: 5⁵-(Pyridin-3-yl)-1⁴H-6-oxa-3-aza-2(2,6)-pyridina-1(3,4)-triazola-5(1,2)-benzenacyclodecaphan-4-one

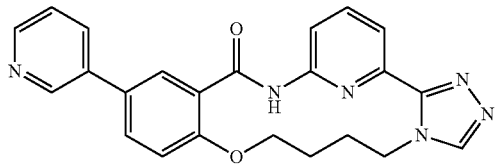 [SMILES: O=C1Nc2cccc(n2)-c2nncn2CCCCOc2ccc(-c3cccnc3)cc21]

To a stirred solution of 5⁵-bromo-1⁴H-6-oxa-3-aza-2(2,6)-pyridina-1(3,4)-triazola-5(1,2)-benzenacyclodecaphan-4-one (200 mg, 0.48 mmol), pyridin-3-ylboronic acid (119 mg, 0.97 mmol) and K₂CO₃ (132 mg, 0.97 mmol) in DMF (3 mL) and H₂O (0.3 mL) under a N₂ atmosphere was added Pd(dppf)Cl₂ (35 mg, 0.048 mmol) and the mixture was stirred at 100° C. for 3 h. After this time the reaction was cooled to room temperature and filtered. The filtrate was purified by HPLC (using a Phenomenex Synergi C18, 4 μm 150×30 mm column and using water (containing 0.05% HCl)/CH₃CN from 14 to 29% as the mobile phase at a flow rate of 25 mL/min) as a brown solid. ¹H NMR (400 MHz, CDCl₃) δ ppm 11.46 (s, 1H), 8.89 (s, 1H), 8.62 (d, J=5.0 Hz, 1H), 8.54 (d, J=2.5 Hz, 1H), 8.24 (s, 1H), 8.06 (dd, J=7.5, 11.0 Hz, 2H), 7.91-7.97 (m, 2H), 7.77 (dd, J=2.5, 8.5 Hz, 1H), 7.40 (dd, J=5.0, 8.0 Hz, 1H), 7.17 (d, J=8.5 Hz, 1H), 4.39 (t, J=4.8 Hz, 2H), 4.28-4.35 (m, 2H), 2.68-2.79 (m, 2H), 2.08-2.17 (m, 2H). MS (ESI): 413.2 [M+H]⁺.

Example 27: 5⁵-(Pyridin-4-yl)-1⁴H-6-oxa-3-aza-2(2,6)-pyridina-1(3,4)-triazola-5(1,2)-benzenacyclodecaphan-4-one

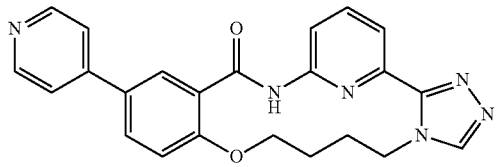 [SMILES: O=C1Nc2cccc(n2)-c2nncn2CCCCOc2ccc(-c3ccncc3)cc21]

To a stirred solution of 5⁵-bromo-1⁴H-6-oxa-3-aza-2(2,6)-pyridina-1(3,4)-triazola-5(1,2)-benzenacyclodecaphan-4-one (200 mg, 0.48 mmol), 4-(4,4,5,5-tetramethyl-1,3,2-dioxaborolan-2-yl)pyridine (119 mg, 0.58 mmol) and K₂CO₃ (132 mg, 0.97 mmol) in DMF (3 mL) and H₂O (0.3 mL) under a N₂ atmosphere was added Pd(dppf)Cl₂ (35 mg, 0.048 mmol) and the mixture was heated at 100° C. for 3 h. After this time the reaction was cooled to room temperature and filtered. The filtrate was purified by HPLC (using a Phenomenex Synergi C18, 4 μm 150×30 mm column and using water (containing 0.05% HCl)/CH₃CN from 11 to 31% as the mobile phase at a flow rate of 25 mL/min) to give the title compound (73 mg, 37%) as a brown solid. ¹H NMR (400 MHz, CDCl₃) δ ppm 11.43 (s, 1H), 8.69 (br s, 2H), 8.62 (d, J=2.5 Hz, 1H), 8.24 (s, 1H), 8.07 (t, J=8.3 Hz, 2H), 7.91-7.98 (m, 1H), 7.83 (dd, J=2.5, 8.5 Hz, 1H), 7.57 (d, J=6.0 Hz, 2H), 7.17 (d, J=9.0 Hz, 1H), 4.40 (t, J=5.0 Hz, 2H), 4.27-4.35 (m, 2H), 2.68-2.81 (m, 2H), 2.07-2.16 (m, 2H). MS (ESI): 413.1 [M+H]⁺.

Example 28: 5⁵-(Methylsulfonyl)-1⁴H-6-oxa-3-aza-2(2,6)-pyridina-1(3,4)-triazola-5(1,2)-benzenacyclodecaphan-4-one

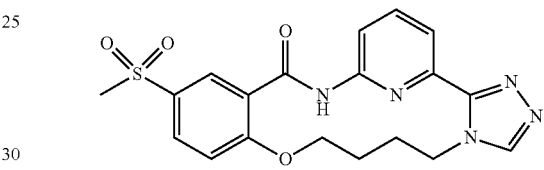

A suspension of 5⁵-bromo-1⁴H-6-oxa-3-aza-2(2,6)-pyridina-1(3,4)-triazola-5(1,2)-benzenacyclodecaphan-4-one (50 mg, 0.12 mmol), sodium methanesulfinate (15 mg, 0.15 mmol), copper iodide (2 mg, 0.01 mmol) and L-proline sodium salt (3 mg, 0.02 mol) in NMP (1 mL) was degassed by purging with N₂ for 15 min. The resulting mixture was heated at 100° C. for 8 h. After this time the reaction mixture was filtered and purified by HPLC (using a Sunfire Prep C18 OBD, 5 μm 30×50 mm column and using water/CH₃CN (containing 0.1% TFA) from 90/10 to 30/70 as the mobile phase at a flow rate of 50 mL/min) to give the title compound (14 mg, 22%). ¹H NMR (400 MHz, CD₃CN) δ ppm 11.26 (br s, 1H), 8.64 (d, J=2.8 Hz, 1H), 8.44-8.50 (m, 1H), 8.07-8.14 (m, 1H), 7.99-8.06 (m, 2H), 7.93-7.99 (m, 1H), 7.36-7.43 (m, 1H), 4.43-4.48 (m, 2H), 4.25-4.35 (m, 2H), 3.12 (s, 3H), 2.58-2.71 (m, 2H), 2.02-2.12 (m, 2H). MS (ESI): 414.1 [M+H]⁺.

Example 29: 5⁵-(1-Methyl-1H-imidazol-5-yl)-1⁴H-6-oxa-3-aza-2(2,6)-pyridina-1(3,4)-triazola-5(1,2)-benzenacyclodecaphan-4-one

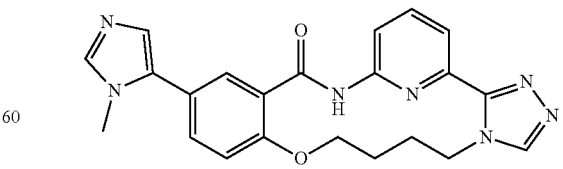

A solution of 5⁵-(4,4,5,5-tetramethyl-1,3,2-dioxaborolan-2-yl)-1⁴H-6-oxa-3-aza-2(2,6)-pyridina-1(3,4)-triazola-5(1,2)-benzenacyclodecaphan-4-one (300 mg, 0.65 mmol; Example 25, Step A), 5-bromo-1-methyl-1H-imidazole (126 mg, 0.78 mmol), K$_2$CO$_3$ (180 mg, 1.30 mmol) and Pd(dppf)Cl$_2$ (48 mg, 0.065 mmol) in dioxane/H$_2$O (15 mL, 10/1) was stirred at 90° C. under a N$_2$ atmosphere for 4 h. After this time the mixture was concentrated under vacuum, MeOH (4 mL) was added and the mixture was purified by HPLC (using a Phenomenex Synergi C18, 4 μm 150×30 mm column and using CH$_3$CN/water (containing 0.05% HCl), from 24% to 39% as the mobile phase at a flow rate of 25 mL/min) to give the title compound (27 mg, 10%) as yellow solid. $^1$H NMR (400 MHz, DMSO-d$_6$) δ ppm 11.19 (s, 1H), 9.22 (s, 1H), 8.84 (s, 1H), 8.07-8.16 (m, 2H), 7.94 (s, 1H), 7.90 (dd, J=3.2, 2.8 Hz, 2H), 7.87 (s, 1H), 7.49 (d, J=8.8 Hz, 1H), 4.42 (t, J=4.8 Hz, 2H), 4.26-4.34 (m, 2H), 3.84 (s, 3H), 2.53 (m, 2H), 1.99 (m, 2H). MS (ESI): 438.2 [M+Na]$^+$.

Example 30: 5$^5$-(1-Methyl-1H-1,2,3-triazol-4-yl)-1$^4$H-6-oxa-3-aza-2(2,6)-pyridina-1(3,4)-triazola-5(1,2)-benzenacyclodecaphan-4-one

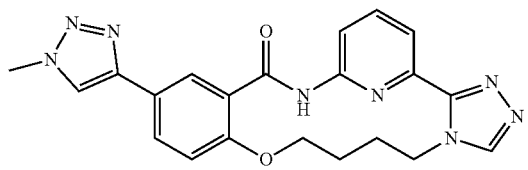 [SMILES: Cn1cc(-c2ccc3c(c2)C(=O)Nc2cccc(n2)-c2nncn2CCCCO3)nn1]

A mixture of 5$^5$-(4,4,5,5-tetramethyl-1,3,2-dioxaborolan-2-yl)-1$^4$H-6-oxa-3-aza-2(2,6)-pyridina-1(3,4)-triazola-5(1,2)-benzenacyclodecaphan-4-one (200 mg, 0.43 mmol; Example 25, Step A), 4-bromo-1-methyl-1H-1,2,3-triazole (84 mg, 0.52 mmol), Pd(dppf)Cl$_2$ (63 mg, 0.09 mmol) and K$_2$CO$_3$ (178 mg, 1.29 mmol) in DMF/H$_2$O (6 mL, 5/1) was stirred at 90° C. for 2 h under a N$_2$ atmosphere. After this time the reaction mixture was cooled to rt, filtered and concentrated under vacuum to give the crude product. Purification by column chromatography on silica (petroleum ether/EtOAc, 1/1 and then DCM/MeOH, 10/1) gave the crude desired product. Further purification by HPLC (using a Phenomenex Synergi C18, 4 μm 150×30 mm column and using CH$_3$CN/water (containing 0.05% HCl), from 27% to 47% as the mobile phase at a flow rate of 25 mL/min) gave the title compound (15 mg, 7%) as a white solid. $^1$H NMR (400 MHz, DMSO-d$_6$) δ ppm 11.27 (s, 1H), 8.81 (s, 1H), 8.55 (s, 1H), 8.42 (d, J=2.4 Hz, 1H), 8.07 (t, J=8.0 Hz, 1H), 8.00-8.02 (m, 1H), 7.91 (d, J=8.0 Hz, 1H), 7.85 (d, J=7.6 Hz, 1H), 7.37 (d, J=8.8 Hz, 1H), 4.34-4.37 (m, 2H), 4.25-4.29 (m, 2H), 4.06 (s, 3H), 2.46-2.47 (m, 2H), 1.94-1.95 (m, 2H). MS (ESI): 439.2 [M+Na]$^+$.

Example 31: 5$^5$-(Pyrrolidine-1-carbonyl)-1$^4$H-6-oxa-3-aza-2(2,6)-pyridina-1(3,4)-triazola-5(1,2)-benzenacyclodecaphan-4-one

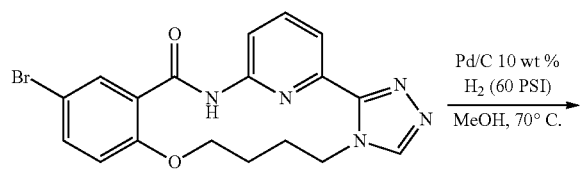

Step A: Methyl 4-oxo-1$^4$H-6-oxa-3-aza-2(2,6)-pyridina-1(3,4)-triazola-5(1,2)-benzenacyclodecaphane-5$^5$-carboxylate

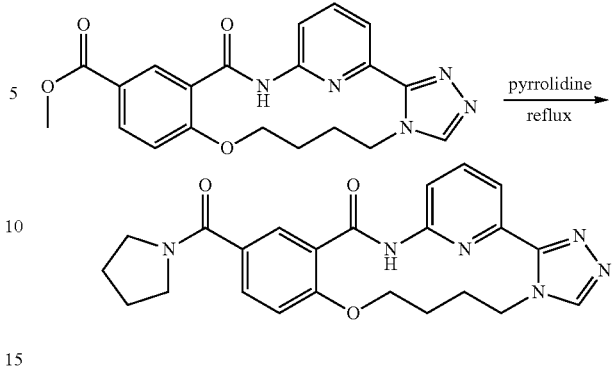

An autoclave was charged with a suspension of 5$^5$-bromo-1$^4$H-6-oxa-3-aza-2(2,6)-pyridina-1(3,4)-triazola-5(1,2)-benzenacyclodecaphan-4-one (250 mg, 0.6 mmol), triethylamine (0.5 mL, 4.0 mmol) and [1,1'-bis(dicyclopentylphosphino)ferrocene]dichloropalladium(II) (39 mg, 0.06 mmol) in MeOH (8 mL) and DMF (6 mL). The autoclave was sealed, purged with carbon monoxide three times and the pressure was set to 60 PSI at room temperature. The reaction mixture was heated to 70° C. and held at that temperature for 30 h. The brown suspension was concentrated under vacuum and DMSO (3.0 mL) was added, the resulting solution was filtered and subjected to HPLC purification (using an XTerra Prep RP18 OBD, 10 μm 50×250 mm column and using water (containing 0.1% TFA)/CH$_3$CN from 90/10 to 10/90 as the mobile phase at a flow rate of 50 mL/min) to give the title compound (150 mg, 63%) as a white solid. $^1$H NMR (400 MHz, CDCl$_3$) δ ppm 11.11-11.29 (m, 1H), 8.84-8.95 (m, 1H), 8.30-8.49 (m, 1H), 8.09-8.21 (m, 1H), 8.03 (br d, J=7.8 Hz, 1H), 7.96 (br d, J=8.3 Hz, 1H), 7.90 (br d, J=7.5 Hz, 1H), 6.93-7.08 (m, 1H), 4.17-4.43 (m, 4H), 3.87 (s, 3H), 2.06 (br s, 2H), 1.31 (br s, 2H). MS (ESI): 394.1 [M+H]$^+$.

Step B: 5$^5$-(Pyrrolidine-1-carbonyl)-1$^4$H-6-oxa-3-aza-2(2,6)-pyridina-1(3,4)-triazola-5(1,2)-benzenacyclodecaphan-4-one

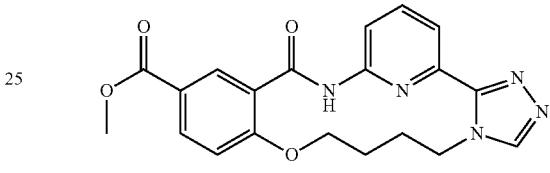

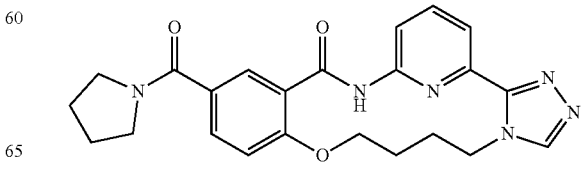

A reaction vial was charged with methyl 4-oxo-1⁴H-6-oxa-3-aza-2(2,6)-pyridina-1(3,4)-triazola-5(1,2)-benzenacyclodecaphane-5⁵-carboxylate (25 mg, 0.06 mmol) and pyrrolidine (0.5 mL, 6.0 mmol) and the resulting mixture was heated at reflux for 12 h. After this time the volatiles were removed under reduced pressure and the resulting residue was subjected to HPLC purification (using a Sunfire Prep C18 OBD, 5 μm 30×50 mm column and using water/CH₃CN (containing 0.1% TFA) from 90/10 to 30/70 as the mobile phase at a flow rate of 50 mL/min) to give the title compound (4 mg, 15%) as a white solid. ¹H NMR (400 MHz, CD₃OD) δ ppm 8.69, (s, 1H), 8.30 (d, J=8.0 Hz, 1H), 8.20 (d, J=2.5 Hz, 1H), 8.01-8.07 (m, 1H), 7.94-8.00 (m, 1H), 7.59 (dd, J=8.8, 2.8 Hz, 1H), 6.98 (d, J=8.8 Hz, 1H), 4.76 (t, J=7.0 Hz, 1H), 4.72-4.80 (m, 1H), 3.55 (br s, 2H), 3.12-3.20 (m, 2H), 2.98 (br s, 2H), 1.88-2.19 (m, 6H), 1.68-1.80 (m, 2H). MS (ESI): 433.1 [M+H]⁺.

Example 32: 5⁵-(1,3-Dimethyl-1H-pyrazol-4-yl)-1⁴H-6-oxa-3-aza-2(2,6)-pyridina-1(3,4)-triazola-5(1,2)-benzenacyclodecaphan-4-one

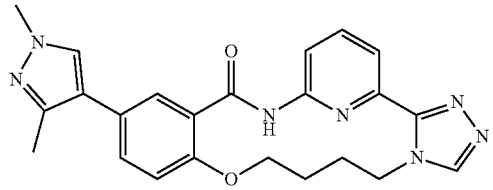 [SMILES: Cc1nn(C)cc1-c1ccc2c(c1)C(=O)Nc1cccc(n1)-c1nncn1CCCCO2]

A reaction vial was charged with 1,3-dimethyl-4-(4,4,5,5-tetramethyl-1,3,2-dioxaborolan-2-yl)pyrazole (96 mg, 0.43 mmol), 5⁵-bromo-1⁴H-6-oxa-3-aza-2(2,6)-pyridina-1(3,4)-triazola-5(1,2)-benzenacyclodecaphan-4-one (150 mg, 0.36 mmol), Pd(dppf)Cl₂ (26 mg, 0.04 mmol) and K₃PO₄ (160 mg, 0.75 mmol). The vial was purged with N₂ for 10 min. DMSO (2.0 mL) was added and the resulting mixture was heated to 80° C. for 2 h. After this time the reaction mixture was allowed to reach room temperature. Filtration resulted in the isolation of the title compound (25 mg, 16%). The filtrate was subjected to HPLC purification (using an XTerra Prep RP18 OBD, 10 μm 50×250 mm column and using water (containing 0.1% TFA)/CH₃CN from 90/10 to 10/90 as the mobile phase at a flow rate of 50 mL/min) to give another batch of the title compound (14 mg, 9%) as a white solid. ¹H NMR (400 MHz, DMSO-d₆) δ ppm 11.33 (s, 1H), 8.74 (s, 1H), 8.04-8.11 (m, 1H), 8.03 (d, J=2.3 Hz, 1H), 7.94 (s, 1H), 7.92 (dd, J=0.8, 8.3 Hz, 1H), 7.87 (dd, J=0.8, 7.5 Hz, 1H), 7.64 (dd, J=2.5, 8.5 Hz, 1H), 7.33 (d, J=8.8 Hz, 1H), 4.36 (br t, J=5.0 Hz, 2H), 4.25-4.33 (m, 2H), 3.79 (s, 3H), 2.42-2.48 (m, 2H), 2.30 (s, 3H), 1.98 (br s, 2H). MS (ESI): 430.2 [M+H]⁺.

Example 33: 5⁵-(1,3,5-Trimethyl-1H-pyrazol-4-yl)-1⁴H-6-oxa-3-aza-2(2,6)-pyridina-1(3,4)-triazola-5(1,2)-benzenacyclodecaphan-4-one

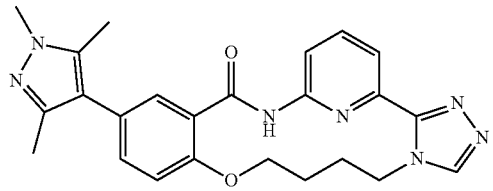 [SMILES: Cc1nn(C)c(C)c1-c1ccc2c(c1)C(=O)Nc1cccc(n1)-c1nncn1CCCCO2]

A reaction vial was charged with 1-methyl-5-(4,4,5,5-tetramethyl-1,3,2-dioxaborolan-2-yl)triazole (45 mg, 0.22 mol), 5⁵-bromo-1⁴H-6-oxa-3-aza-2(2,6)-pyridina-1(3,4)-triazola-5(1,2)-benzenacyclodecaphan-4-one (75 mg, 0.18 mmol), Pd(dppf)Cl₂ (13 mg, 0.02 mmol) and K₃PO₄ (80 mg, 0.38 mmol). The vial was purged with N₂ for 10 min. DMSO (1 mL) was added and the resulting mixture was heated to 80° C. for 2 h. After this time, the reaction mixture was allowed to reach room temperature and the solids were removed by filtration. The filtrate was subjected to HPLC purification (using an XTerra Prep RP18 OBD, 10 μm 50×250 mm column and using water (containing 0.1% TFA)/CH₃CN from 90/10 to 40/60 as the mobile phase at a flow rate of 50 mL/min) to give the title compound (57 mg, 56%) as a white solid. ¹H NMR (400 MHz, CD₃OD) δ ppm 9.15 (s, 1H), 7.99 (td, J=2.5, 5.5 Hz, 3H), 7.86 (dd, J=3.1, 5.4 Hz, 1H), 7.50 (dd, J=2.4, 8.4 Hz, 1H), 7.29 (d, J=8.8 Hz, 1H), 4.29-4.46 (m, 4H), 3.88 (s, 3H), 2.55-2.69 (m, 2H), 2.32 (s, 3H), 2.29 (s, 3H), 2.05 (br d, J=14.1 Hz, 2H). MS (ESI): 444.2 [M+H]⁺.

Example 34: 5⁵-(1,3-Dimethyl-1H-pyrazol-5-yl)-1⁴H-6-oxa-3-aza-2(2,6)-pyridina-1(3,4)-triazola-5(1,2)-benzenacyclodecaphan-4-one

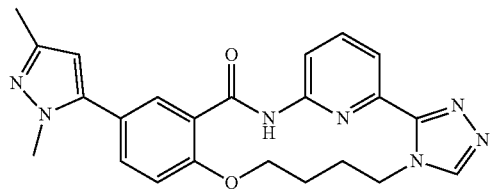 [SMILES: Cc1cc(-c2ccc3c(c2)C(=O)Nc2cccc(n2)-c2nncn2CCCCO3)n(C)n1]

A reaction vial was charged with 1,3-dimethyl-5-(4,4,5,5-tetramethyl-1,3,2-dioxaborolan-2-yl)pyrazole (48 mg, 0.22 mmol), 5⁵-bromo-1⁴H-6-oxa-3-aza-2(2,6)-pyridina-1(3,4)-triazola-5(1,2)-benzenacyclodecaphan-4-one (75 mg, 0.18 mmol), Pd(dppf)Cl₂ (13 mg, 0.02 mmol) and K₃PO₄ (80 mg, 0.38 mmol). The vial was purged with N₂ for 10 min. DMSO (1.0 mL) was added and the resulting mixture was heated to 80° C. for 2 h. After this time, the reaction mixture was allowed to reach room temperature and the solids were removed by filtration. The filtrate was subjected to HPLC purification (using an XTerra Prep RP18 OBD, 10 μm 50×250 mm column and using water (containing 0.1% TFA)/CH₃CN from 90/10 to 40/60 as the mobile phase at a flow rate of 50 mL/min) to give the title compound (5 mg, 5%) as a white solid. ¹H NMR (400 MHz, CD₃OD) δ ppm 8.91 (s, 1H), 8.21 (d, J=2.5 Hz, 1H), 8.01-8.14 (m, 2H), 7.94 (dd, J=2.0, 6.5 Hz, 1H), 7.72 (dd, J=2.5, 8.5 Hz, 1H), 7.39 (d, J=8.8 Hz, 1H), 6.26 (s, 1H), 4.37-4.49 (m, 4H), 3.85 (s, 3H), 2.64-2.77 (m, 3H), 2.30 (s, 3H), 2.13 (br s, 2H). MS (ESI): 430.2 [M+H]⁺.

Example 35: 5⁵-(1-Cyclobutyl-1H-pyrazol-4-yl)-1⁴H-6-oxa-3-aza-2(2,6)-pyridina-1(3,4)-triazola-5(1,2)-benzenacyclodecaphan-4-one

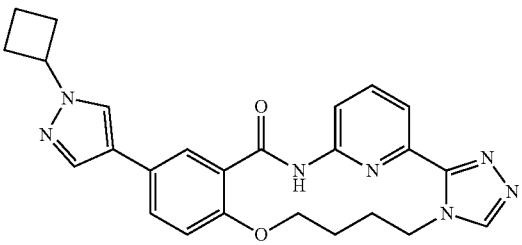 [SMILES: O=C1Nc2cccc(n2)-c2nncn2CCCCOc2ccc(-c3cnn(C4CCC4)c3)cc21]

A reaction vial was charged with 1-cyclobutyl-4-(4,4,5,5-tetramethyl-1,3,2-dioxaborolan-2-yl)-1H-pyrazole (49 mg, 0.20 mmol), 5⁵-bromo-1⁴H-6-oxa-3-aza-2(2,6)-pyridina-1(3,4)-triazola-5(1,2)-benzenacyclodecaphan-4-one (75 mg, 0.18 mmol), Pd(dppf)Cl$_2$ (13 mg, 0.02 mmol) and K$_3$PO$_4$ (80 mg, 0.38 mmol). The vial was purged with N$_2$ for 10 min. DMSO (1 mL) was added and the resulting mixture was heated to 80° C. for 2 h. After this time, the reaction mixture was allowed to reach room temperature and the solids were removed by filtration. The filtrate was subjected to HPLC purification (using an XTerra Prep RP18 OBD, 10 μm 50×250 mm column and using water (containing 0.1% TFA)/CH$_3$CN from 90/10 to 40/60 as the mobile phase at a flow rate of 50 mL/min) to give the title compound (57 mg, 56%) as a white solid. ¹H NMR (400 MHz, DMSO-d$_6$) δ ppm 11.30 (s, 1H), 8.77 (s, 1H), 8.34 (d, J=0.8 Hz, 1H), 8.16 (d, J=2.5 Hz, 1H), 8.05-8.12 (m, 1H), 7.90-7.94 (m, 2H), 7.87 (dd, J=0.8, 7.8 Hz, 1H), 7.81 (dd, J=2.5, 8.5 Hz, 1H), 7.31 (d, J=8.8 Hz, 1H), 4.84 (quin, J=8.5 Hz, 1H), 4.35 (br t, J=5.0 Hz, 2H), 4.25-4.32 (m, 2H), 2.35-2.56 (m, 6H), 1.97 (br d, J=6.0 Hz, 2H), 1.75-1.86 (m, 2H). MS (ESI): 456.2 [M+H]⁺.

Example 36: 5⁵-(1-Isopropyl-1H-pyrazol-4-yl)-1⁴H-6-oxa-3-aza-2(2,6)-pyridina-1(3,4)-triazola-5(1,2)-benzenacyclodecaphan-4-one

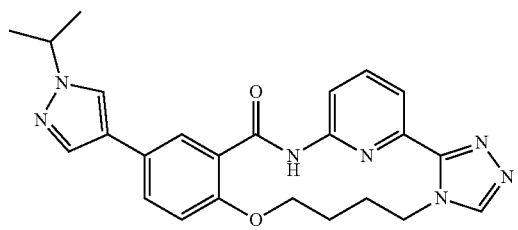 [SMILES: CC(C)n1cc(-c2ccc3c(c2)C(=O)Nc2cccc(n2)-c2nncn2CCCCO3)cn1]

A reaction vial was charged with 1-isopropyl-4-(4,4,5,5-tetramethyl-1,3,2-dioxaborolan-2-yl)-1H-pyrazole (34 mg, 0.14 mmol), 5⁵-bromo-1⁴H-6-oxa-3-aza-2(2,6)-pyridina-1(3,4)-triazola-5(1,2)-benzenacyclodecaphan-4-one (50 mg, 0.12 mmol), Pd(dppf)Cl$_2$ (9 mg, 0.01 mmol) and K$_3$PO$_4$ (53 mg, 0.25 mmol). The vial was purged with N$_2$ for 10 min. NMP (1.0 mL) was added and the resulting mixture was heated to 100° C. for 2 h. After this time, the reaction mixture was allowed to reach room temperature and the solids were removed by filtration. The filtrate was subjected to HPLC purification (using an XTerra Prep RP18 OBD, 10 μm 50×250 mm column and using water (containing 0.1% TFA)/CH$_3$CN from 90/10 to 40/60 as the mobile phase at a flow rate of 50 mL/min) to give the title compound (16 mg, 23%) as a white solid. ¹H NMR (400 MHz, CD$_3$OD) δ ppm 8.91 (s, 1H), 8.17 (d, J=2.5 Hz, 1H), 7.97 (s, 1H), 7.95 (s, 1H), 7.94 (s, 1H), 7.78-7.84 (m, 1H), 7.76 (s, 1H), 7.62 (dd, J=2.3, 8.5 Hz, 1H), 7.08 (d, J=8.8 Hz, 1H), 4.48-4.61 (m, 1H), 4.22-4.36 (m, 4H), 2.53 (br s, 2H), 1.96-2.09 (m, 2H), 1.53 (d, J=6.5 Hz, 6H). MS (ESI): 444.2 [M+H]⁺.

Example 37: 5⁵-(1,5-Dimethyl-1H-pyrazol-4-yl)-1⁴H-6-oxa-3-aza-2(2,6)-pyridina-1(3,4)-triazola-5(1,2)-benzenacyclodecaphan-4-one

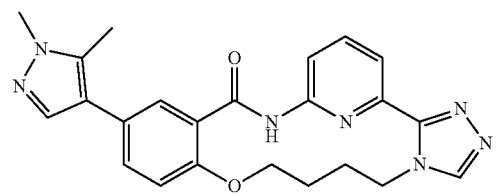 [SMILES: Cc1c(-c2ccc3c(c2)C(=O)Nc2cccc(n2)-c2nncn2CCCCO3)cnn1C]

A reaction vial was charged with 1,5-dimethyl-4-(4,4,5,5-tetramethyl-1,3,2-dioxaborolan-2-yl)-1H-pyrazole (32 mg, 0.14 mmol), 5⁵-bromo-1⁴H-6-oxa-3-aza-2(2,6)-pyridina-1(3,4)-triazola-5(1,2)-benzenacyclodecaphan-4-one (50 mg, 0.12 mmol) and Pd(dppf)Cl$_2$ (9 mg, 0.01 mmol) and K$_3$PO$_4$ (53 mg, 0.25 mmol. The vial was purged with N$_2$ for 10 min. NMP (1.0 mL) was added and the resulting mixture was heated to 100° C. for 2 h. After this time, the reaction mixture was allowed to reach room temperature and the solids were removed by filtration. The filtrate was subjected to HPLC purification (using an XTerra Prep RP18 OBD, 10 μm 50×250 mm column and using water (containing 0.1% TFA)/CH$_3$CN from 90/10 to 40/60 as the mobile phase at a flow rate of 50 mL/min) to give the title compound (12 mg, 18%) as a white solid. ¹H NMR (400 MHz, CD$_3$OD) δ ppm 9.20 (br s, 1H), 8.07 (br s, 3H), 7.91 (br s, 1H), 7.53-7.68 (m, 2H), 7.10-7.33 (m, 1H), 4.30-4.51 (m, 4H), 3.74-3.95 (m, 3H), 2.67 (br s, 2H), 2.35-2.47 (m, 3H), 2.09 (br s, 2H). MS (ESI): 430.1 [M+H]⁺.

Example 38: 5⁵-(1-(Oxetan-3-yl)-1H-pyrazol-4-yl)-1⁴H-6-oxa-3-aza-2(2,6)-pyridina-1(3,4)-triazola-5(1,2)-benzenacyclodecaphan-4-one

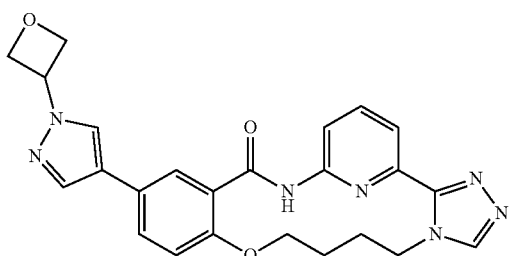

A reaction vial was charged with 1-(oxetan-3-yl)-4-(4,4,5,5-tetramethyl-1,3,2-dioxaborolan-2-yl)-1H-pyrazole (54 mg, 0.22 mmol), 5⁵-bromo-1⁴H-6-oxa-3-aza-2(2,6)-pyridina-1(3,4)-triazola-5(1,2)-benzenacyclodecaphan-4-one (75 mg, 0.18 mmol), Pd(dppf)Cl$_2$ (13 mg, 0.02 mmol) and K$_3$PO$_4$ (80 mg, 0.38 mmol). The vial was purged with N₂ for 10 min. NMP (1 mL) was added and the resulting mixture was heated to 100° C. for 2 h. After this time, the reaction mixture was allowed to reach room temperature and the solids were removed by filtration. The filtrate was subjected to HPLC purification (using an XTerra Prep RP18 OBD, 10 μm 50×250 mm column and using water (containing 0.1% TFA)/CH₃CN from 90/10 to 40/60 as the mobile phase at a flow rate of 50 mL/min) to give the title compound (3 mg, 4%) as a white solid. ¹H NMR (400 MHz, CD₃CN) δ ppm 11.51 (s, 1H), 8.31-8.36 (m, 2H), 8.08 (d, J=0.8 Hz, 1H), 7.97-8.02 (m, 2H), 7.95 (s, 1H), 7.89-7.94 (m, 1H), 7.75 (dd, J=2.5, 8.5 Hz, 1H), 7.22 (d, J=8.5 Hz, 1H), 5.49-5.59 (m, 1H), 5.02 (s, 2H), 5.01 (s, 2H), 4.36 (t, J=5.0 Hz, 2H), 4.24-4.31 (m, 2H), 2.61 (br s, 2H), 2.06 (br s, 2H). MS (ESI): 458.2 [M+H]⁺.

Example 39: 5⁵-(1-(2-(Dimethylamino)ethyl)-1H-pyrazol-4-yl)-1⁴H-6-oxa-3-aza-2(2,6)-pyridina-1(3,4)-triazola-5(1,2)-benzenacyclodecaphan-4-one

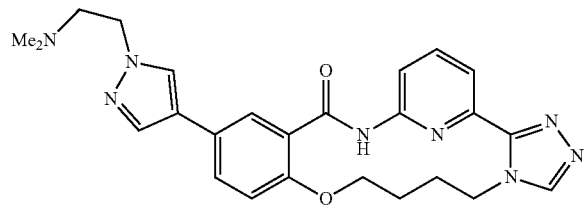 [SMILES: CN(C)CCn1cc(-c2ccc3c(c2)C(=O)Nc2cccc(n2)-c2nncn2CCCCO3)cn1]

A mixture of 5⁵-bromo-1⁴H-6-oxa-3-aza-2(2,6)-pyridina-1(3,4)-triazola-5(1,2)-benzenacyclodecaphan-4-one (700 mg, 1.69 mmol), N,N-dimethyl-2-(4-(4,4,5,5-tetramethyl-1,3,2-dioxaborolan-2-yl)-1H-pyrazol-1-yl)ethan-1-amine (493 mg, 1.86 mmol), Pd(dppf)Cl₂ (123 mg, 0.17 mmol) and K₂CO₃ (467 mg, 3.38 mmol) in dioxane/H₂O (20 mL, 10/1) was stirred at 90° C. under a N₂ atmosphere for 3 h. After this time the mixture was concentrated, MeOH was added (6 mL) and the mixture was purified by column chromatography on silica gel using DCM/MeOH (from 100/1 to 1/1) as eluent to give the title compound (600 mg, 66%) as white solid. ¹H NMR (400 MHz, MeOD) δ ppm 8.61 (s, 1H), 8.21 (d, J=2.4 Hz, 1H), 8.00 (s, 1H), 7.94-7.98 (m, 2H), 7.85 (d, J=6.0 Hz, 1H), 7.81 (s, 1H), 7.64 (dd, J=2.4, 8.8 Hz, 1H), 7.13 (d, J=8.8 Hz, 1H), 4.26-4.38 (m, 6H), 2.95 (t, J=6.8 Hz, 2H), 2.47-2.62 (m, 2H), 2.40 (s, 6H), 2.05-2.08 (m, 2H). MS (ESI): 473.0 [M+H]⁺.

Example 40: 5⁵-(5-Methyl-4,5,6,7-tetrahydropyrazolo[1,5-a]pyrazin-3-yl)-1⁴H-6-oxa-3-aza-2(2,6)-pyridina-1(3,4)-triazola-5(1,2)-benzenacyclodecaphan-4-one

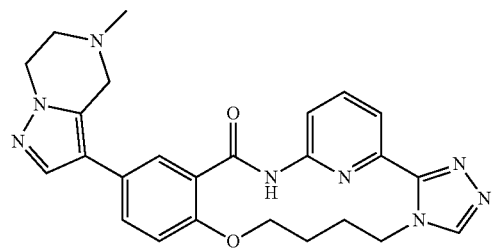 [SMILES: CN1CCn2ncc(-c3ccc4c(c3)C(=O)Nc3cccc(n3)-c3nncn3CCCCO4)c2C1]

A mixture of 5⁵-(4,4,5,5-tetramethyl-1,3,2-dioxaborolan-2-yl)-1⁴H-6-oxa-3-aza-2(2,6)-pyridina-1(3,4)-triazola-5(1,2)-benzenacyclodecaphan-4-one (200 mg, 0.43 mmol), 3-bromo-5-methyl-4,5,6,7-tetrahydropyrazolo[1,5-a]pyrazine (140 mg, 0.65 mmol), K₂CO₃ (180 mg, 1.3 mmol) and Peppsi-IPr (57 mg, 0.09 mmol) in EtOH (10 mL) and H₂O (1 mL) was stirred at 100° C. for 17 h. After this time the volatiles were removed under reduced pressure to give the crude product which was purified by HPLC (using a Phenomenex Synergi C18, 4 μm 150×30 mm column and using CH₃CN/water (containing 0.05% HCl), from 16% to 36% as the mobile phase at a flow rate of 25 mL/min) to give the title compound (10 mg, 5%) as a white solid. ¹H NMR (400 MHz, DMSO-d₆) δ ppm 11.26 (s, 1H), 8.78 (s, 1H), 8.03-8.12 (m, 1H), 7.83-7.98 (m, 4H), 7.63 (dd, J=2.5, 8.7 Hz, 1H), 7.37 (d, J=8.6 Hz, 1H), 4.66-4.90 (m, 2H), 4.40-4.56 (m, 2H), 4.33-4.39 (m, 2H), 4.24-4.32 (m, 2H), 3.69-3.99 (m, 2H), 3.02 (s, 3H), 2.38-2.45 (m, 2H), 1.88-2.03 (m, 2H). MS (ESI): 471.2 [M+H]⁺.

Example 41: 5⁵-(1H-Imidazol-1-yl)-1⁴H-6-oxa-3-aza-2(2,6)-pyridina-1(3,4)-triazola-5(1,2)-benzenacyclodecaphan-4-one

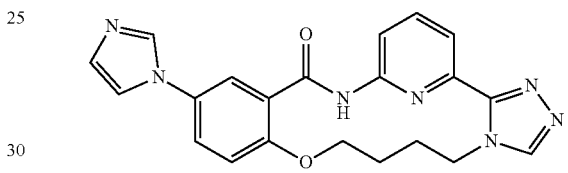

A mixture of 5-bromo-1⁴H-6-oxa-3-aza-2(2,6)-pyridina-1(3,4)-triazola-5(1,2)-benzenacyclodecaphan-4-one (146 mg, 0.35 mmol), 1H-imidazole (48 mg, 0.7 mmol), (1R, 2R)—N¹,N²-dimethylcyclohexane-1,2-diamine (10 mg, 0.07 mmol), Cs₂CO₃ (239 mg, 0.76 mmol) and CuI (7 mg, 0.035 mmol) in dioxane (2 mL) was stirred at 110° C. under a N₂ atmosphere for 17 h. After this time water was added (15 mL) and the mixture was extracted with DCM (2×20 mL). The organic phase was dried over Na₂SO₄, filtered and concentrated to give the crude product which was purified by column chromatography on silica using a gradient of elution DCM/MeOH (100/1 to 20/1). Further purification by HPLC (using a Phenomenex Synergi C18, 4 μm 150×30 mm column and using CH₃CN/water (containing 0.05% HCl), from 13% to 33% as the mobile phase at a flow rate of 25 mL/min) gave the title compound (55 mg, 20%) as a white solid. ¹H NMR (400 MHz, DMSO-d₆) δ ppm 11.15 (s, 1H), 9.77 (s, 1H), 8.98 (s, 1H), 8.29-8.33 (m, 2H), 8.10 (t, J=8.0 Hz, 1H), 8.01 (dd, J=8.8 Hz, J=2.8 Hz, 1H), 7.89-7.92 (m, 3H), 7.55 (d, J=9.2 Hz, 1H), 4.39-4.41 (m, 2H), 4.28-4.33 (m, 2H), 2.52-2.55 (m, 2H), 1.94-1.97 (m, 2H). MS (ESI): 402.1 [M+H]⁺.

Example 42: 5⁵-(4,5-Dimethyl-1H-imidazol-1-yl)-1⁴H-6-oxa-3-aza-2(2,6)-pyridina-1(3,4)-triazola-5(1,2)-benzenacyclodecaphan-4-one

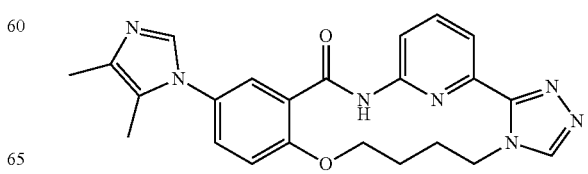

A mixture of 5⁵-bromo-1⁴H-6-oxa-3-aza-2(2,6)-pyridina-1(3,4)-triazola-5(1,2)-benzenacyclodecaphan-4-one (150 mg, 0.36 mmol), 4,5-dimethyl-1H-imidazole (104 mg, 1.04 mmol), quinolin-8-ol (8 mg, 0.05 mmol), CuI (10 mg, 0.05 mmol) and K$_2$CO$_3$ (100 mg, 0.72 mmol) in DMSO (3 mL) was stirred at 110° C. for 24 h. The mixture was filtered and the filtrate was purified by HPLC (using a Phenomenex Synergi C18, 4 μm 150×30 mm column and using CH$_3$CN/water (containing 0.05% HCl), from 12% to 42% as the mobile phase at a flow rate of 25 mL/min) to give the title compound (15 mg, 10%) as a white solid. $^1$H NMR (400 MHz, DMSO-d$_6$) δ ppm 11.16 (s, 1H), 9.30 (s, 1H), 8.82 (s, 1H), 8.03-8.19 (m, 2H), 7.78-7.95 (m, 3H), 7.53 (d, J=9.2 Hz, 1H), 4.38-4.46 (m, 2H), 4.24-4.32 (m, 2H), 2.63-2.68 (m, 1H), 2.53 (s, 1H), 2.31 (s, 3H), 2.10 (s, 3H), 1.93-2.01 (m, 2H). MS (ESI): 430.2 [M+H]⁺.

Example 43: 5⁵-(2-Methyl-1H-imidazol-1-yl)-1⁴H-6-oxa-3-aza-2(2,6)-pyridina-1(3,4)-triazola-5(1,2)-benzenacyclodecaphan-4-one

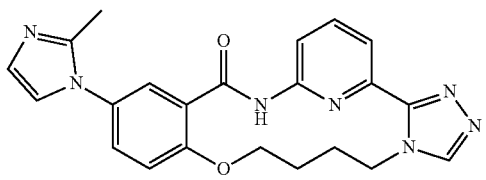 [SMILES: Cc1nccn1-c1ccc2c(c1)C(=O)Nc1cccc(n1)-c1nncn1CCCCO2]

A solution of 5⁵-bromo-1⁴H-6-oxa-3-aza-2(2,6)-pyridina-1(3,4)-triazola-5(1,2)-benzenacyclodecaphan-4-one (200 mg, 0.48 mmol), 2-methyl-1H-imidazole (357 mg, 4.35 mmol), dimethylglycine (199 mg, 1.93 mmol), CuI (184 mg, 0.96 mmol) and K$_2$CO$_3$ (367 mg, 2.66 mmol) in DMSO (15 mL) was stirred at 110° C. under a N$_2$ atmosphere for 12 h. After this time the mixture was filtered and purified by HPLC (using a Phenomenex Synergi C18, 4 μm 150×30 mm column and using CH$_3$CN/water (containing 0.05% HCl), from 10% to 30% as the mobile phase at a flow rate of 25 mL/min) to provide the title compound (50 mg, 25%) as yellow solid. $^1$H NMR (400 MHz, DMSO-d$_6$) δ ppm 11.16 (s, 1H), 8.94 (s, 1H), 8.14 (d, J=3.2 Hz, 1H), 8.06-8.12 (m, 1H), 7.89 (dd, J=2.8, 5.0 Hz, 3H), 7.85 (dd, J=2.8, 6.0 Hz, 1H), 7.76 (d, J=2.0 Hz, 1H), 7.53 (d, J=8.8 Hz, 1H), 4.41 (s, 2H), 4.29 (d, J=9.6 Hz, 2H), 2.52 (s, 3H), 2.50-2.51 (m, 2H), 1.97 (s, 2H). MS (ESI): 438.1 [M+Na]⁺.

Example 44: 5⁵-(1H-Pyrazol-1-yl)-1⁴H-6-oxa-3-aza-2(2,6)-pyridina-1(3,4)-triazola-5(1,2)-benzenacyclodecaphan-4-one

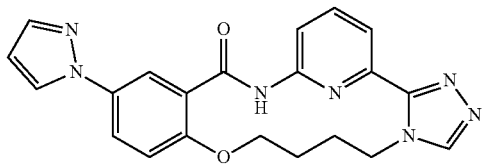 [SMILES: O=C1Nc2cccc(n2)-c2nncn2CCCCOc2ccc(-n3cccn3)cc21]

A mixture of 5⁵-bromo-1⁴H-6-oxa-3-aza-2(2,6)-pyridina-1(3,4)-triazola-5(1,2)-benzenacyclodecaphan-4-one (200 mg, 0.48 mmol), 1H-pyrazole (328 mg, 4.82 mmol), (1R,2R)—N$^1$,N$^2$-dimethylcyclohexane-1,2-diamine (274 mg, 1.93 mmol), CuI (184 mg, 0.96 mmol) and K$_2$CO$_3$ (400 mg, 2.9 mmol) in DMF (15 mL) was stirred at 110° C. for 48 h. After this time the mixture was filtered and the filtrate was purified by HPLC (using a Phenomenex Synergi C18, 4 μm 150×30 mm column and using CH$_3$CN/water (containing 0.05% HCl), from 29% to 49% as the mobile phase at a flow rate of 25 mL/min) to give the title compound (87 mg, 45%) as a white solid. $^1$H NMR (400 MHz, DMSO-d$_6$) δ ppm 11.30 (s, 1H), 8.98 (s, 1H), 8.53 (d, J=2.2 Hz, 1H), 8.39 (d, J=2.6 Hz, 1H), 7.99-8.15 (m, 2H), 7.84-7.97 (m, 2H), 7.74 (s, 1H), 7.42 (d, J=8.8 Hz, 1H), 6.54 (s, 1H), 4.23-4.34 (m, 4H), 2.51-2.54 (m, 2H), 1.97 (br s, 2H). MS (ESI): 402.1 [M+H]⁺.

Example 45: 5⁵-(3-Methyl-1H-pyrazol-1-yl)-1⁴H-6-oxa-3-aza-2(2,6)-pyridina-1(3,4)-triazola-5(1,2)-benzenacyclodecaphan-4-one and Example 45a: 5⁵-(5-Methyl-1H-pyrazol-1-yl)-1⁴H-6-oxa-3-aza-2(2,6)-pyridina-1(3,4)-triazola-5(1,2)-benzenacyclodecaphan-4-one

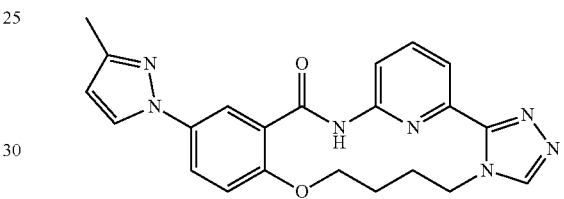

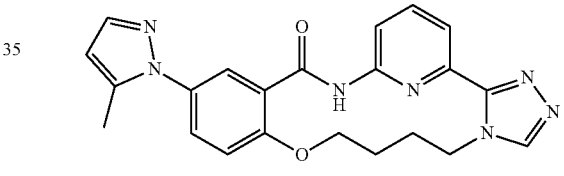

A mixture of 5⁵-bromo-1⁴H-6-oxa-3-aza-2(2,6)-pyridina-1(3,4)-triazola-5(1,2)-benzenacyclodecaphan-4-one (300 mg, 0.73 mmol), 3-methyl-1H-pyrazole (238 mg, 2.9 mmol), CuI (55 mg, 0.29 mmol), K$_2$CO$_3$ (300 mg, 2.2 mmol) and quinolin-5-ol (126 mg, 0.87 mmol) in DMF (10 mL) was stirred at 130° C. under a N$_2$ atmosphere for 17 h. After this time the mixture was filtered and the filtrate was purified by HPLC (using a Phenomenex Synergi C18, 4 μm 150×30 mm column and using CH$_3$CN/water (containing 0.05% HCl), from 33% to 53% as the mobile phase at a flow rate of 25 mL/min) to give in order of elution: 5⁵-(3-methyl-1H-pyrazol-1-yl)-1⁴H-6-oxa-3-aza-2(2,6)-pyridina-1(3,4)-triazola-5(1,2)-benzenacyclodecaphan-4-one (80 mg, 24%). $^1$H NMR (400 MHz, DMSO-d$_6$) δ ppm 11.32 (s, 1H), 9.02 (s, 1H), 8.35-8.40 (m, 2H), 8.09-8.10 (m, 1H), 7.88-7.99 (m, 3H), 7.39 (d, J=9.2 Hz, 1H), 6.33 (s, 1H), 4.30-4.36 (m, 4H), 2.49-2.50 (m, 2H), 2.27 (s, 3H), 1.96-1.97 (m, 2H). MS (ESI): 438.1 [M+Na]⁺; and 5⁵-(5-methyl-1H-pyrazol-1-yl)-1⁴H-6-oxa-3-aza-2(2,6)-pyridina-1(3,4)-triazola-5(1,2)-benzenacyclodecaphan-4-one (15 mg, 4%). $^1$H NMR (400 MHz, DMSO-d$_6$) δ ppm 11.27 (s, 1H), 8.85 (s, 1H), 8.02-8.08 (m, 2H), 7.86-7.92 (m, 2H), 7.75-7.77 (m, 1H), 7.56 (s, 1H), 7.42 (d, J=8.8 Hz, 1H), 6.28 (s, 1H), 4.27-4.39 (m, 4H), 2.49-2.50 (m, 2H), 2.32 (s, 3H), 1.96-1.97 (m, 2H). MS (ESI): 438.1 [M+Na]⁺.

Example 46: 5⁵-(3,5-Dimethyl-1H-pyrazol-1-yl)-1⁴H-6-oxa-3-aza-2(2,6)-pyridina-1(3,4)-triazola-5(1,2)-benzenacyclodecaphan-4-one

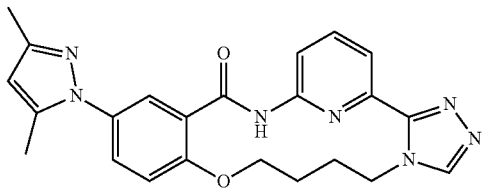 [SMILES: Cc1cc(C)n(-c2ccc3c(c2)C(=O)Nc2cccc(n2)-c2nncn2CCCCO3)n1]

A mixture of 5⁵-(4,4,5,5-tetramethyl-1,3,2-dioxaborolan-2-yl)-1⁴H-6-oxa-3-aza-2(2,6)-pyridina-1(3,4)-triazola-5(1,2)-benzenacyclodecaphan-4-one (100 mg, 0.22 mmol), 3,5-dimethyl-1H-pyrazole (42 mg, 0.43 mmol) and Cu(OAc)₂ (39 mg, 0.22 mmol) in pyridine (2 mL) was stirred at 60° C. for 12 h. After this time the solvent was removed and the residue was purified by HPLC (using an Agela ASB, 5 μm 150×25 mm column and using water (containing 0.225% HCOOH)/CH₃CN, from 29% to 59% as the mobile phase at a flow rate of 25 mL/min) to give the title compound (20 mg) as a white solid. ¹H NMR (400 MHz, DMSO-d₆) δ ppm 11.28 (s, 1H), 8.68 (s, 1H), 8.03-8.09 (m, 1H), 8.01 (d, J=2.8 Hz, 1H), 7.87 (dd, J=8.0, 10.4 Hz, 2H), 7.71 (dd, J=2.8, 8.8 Hz, 1H), 7.39 (d, J=8.8 Hz, 1H), 6.07 (s, 1H), 4.34-4.42 (m, 2H), 4.21-4.32 (m, 2H), 2.51 (s, 2H), 2.28 (s, 3H), 2.17 (s, 3H), 1.97 (s, 2H). MS (ESI): 430.2 [M+H]⁺.

Example 47: 5⁵-(Aminomethyl)-1⁴H-6-oxa-3-aza-2(2,6)-pyridina-1(3,4)-triazola-5(1,2)-benzenacyclodecaphan-4-one

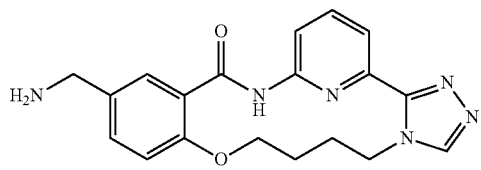 [SMILES: NCc1ccc2c(c1)C(=O)Nc1cccc(n1)-c1nncn1CCCCO2]

A mixture of 4-oxo-1⁴H-6-oxa-3-aza-2(2,6)-pyridina-1(3,4)-triazola-5(1,2)-benzenacyclodecaphane-5⁵-carbonitrile (150 mg, 0.42 mmol) and Raney Ni (150 mg) in NH₃/MeOH (15 mL) was stirred at 20° C. under H₂ (15 Psi) for 17 h. The reaction mixture was filtered and the filter cake was washed with DCM/MeOH (10/1, 5×10 mL). The organic phase was dried over Na₂SO₄, filtered and concentrated to give the crude which was purified by HPLC (using an Xtimate C18, 5 μm 150×25 mm column and using water (containing 10 mM NH₄HCO₃)/CH₃CN, from 31% to 46% as the mobile phase at a flow rate of 25 mL/min) to give the title compound (45 mg, 30%) as a white solid. ¹H NMR (400 MHz, DMSO-d₆) δ ppm 11.33 (s, 1H), 8.67 (s, 1H), 8.05 (t, J=8.0 Hz, 1H), 7.98 (d, J=2.4 Hz, 1H), 7.89 (d, J=7.6 Hz, 1H), 7.84 (d, J=7.6 Hz, 1H), 7.54 (d, J=8.8 Hz, 1H), 7.23 (d, J=8.4 Hz, 1H), 4.23-4.31 (m, 4H), 3.74 (s, 2H), 2.54-2.55 (m, 2H), 1.94-1.95 (m, 2H). MS (ESI): 365.0 [M+H]⁺.

Example 48: 5⁵-((Dimethylamino)methyl)-1⁴H-6-oxa-3-aza-2(2,6)-pyridina-1(3,4)-triazola-5(1,2)-benzenacyclodecaphan-4-one

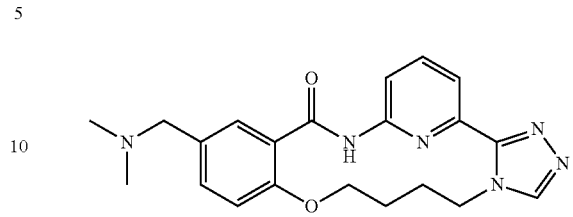

A mixture of 5⁵-(aminomethyl)-1⁴H-6-oxa-3-aza-2(2,6)-pyridina-1(3,4)-triazola-5(1,2)-benzenacyclodecaphan-4-one (100 mg, 0.27 mmol), formaldehyde (100 mg, 3.3 mmol) in MeOH (10 mL) was stirred at 60° C. for 2 h. The volatiles were removed under reduced pressure to give the crude material which was purified by HPLC (using an Xtimate C18, 5 μm 150×25 mm column and using water (containing 10 mM NH₄HCO₃/CH₃CN, from 25% to 65% as the mobile phase at a flow rate of 25 mL/min) to give the title compound (15 mg, 14%) as a white solid. ¹H NMR (400 MHz, MeOD) δ ppm 8.67 (s, 1H), 8.27 (d, J=2.8 Hz, 1H), 8.03-8.08 (m, 2H), 7.94 (d, J=6.0 Hz, 1H), 7.74 (dd, J=8.4 and 2.0 Hz, 1H), 7.39 (d, J=8.8 Hz, 1H), 4.43-4.46 (m, 2H), 4.35-4.40 (m, 2H), 3.01 (s, 2H), 2.84 (s, 6H), 2.68-2.70 (m, 2H), 2.12-2.13 (m, 2H). MS (ESI): 393.1 [M+H]⁺.

Example 49: 5⁵-(2-Hydroxypropan-2-yl)-1⁴H-6-oxa-3-aza-2(2,6)-pyridina-1(3,4)-triazola-5(1,2)-benzenacyclodecaphan-4-one

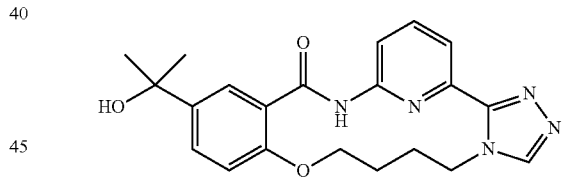

A mixture of methyl 4-oxo-1⁴H-6-oxa-3-aza-2(2,6)-pyridina-1(3,4)-triazola-5(1,2)-benzenacyclodecaphane-5⁵-carboxylate (200 mg, 0.51 mmol) in THF (1 mL) was added dropwise methylmagnesium bromide (1M in diethyl ether, 5 mL, 5 mmol), then stirred at 18° C. for 12 h. After this time the mixture was quenched with sat. aq. NH₄Cl (20 mL) and extracted with EtOAc (3×20 mL). The combined organic layers were concentrated and purified by preparative TLC (DCM/MeOH=20/1) to give the title compound (130 mg, 65%) as a white solid. ¹H NMR (400 MHz, CDCl₃) δ ppm 11.49 (s, 1H), 8.33 (d, J=2.8 Hz, 1H), 8.22 (s, 1H), 8.04 (dd, J=8.0, 16.0 Hz, 2H), 7.90-7.95 (m, 1H), 7.74 (dd, J=2.8, 8.8 Hz, 1H), 7.02 (d, J=8.4 Hz, 1H), 4.25-4.34 (m, 4H), 2.64-2.76 (m, 2H), 2.04-2.11 (m, 2H), 1.62 (s, 6H). MS (ESI): 394.0 [M+H]⁺.

Example 50: 5⁵-(2-Methoxypropan-2-yl)-1⁴H-6-oxa-3-aza-2(2,6)-pyridina-1(3,4)-triazola-5(1,2)-benzenacyclodecaphan-4-one

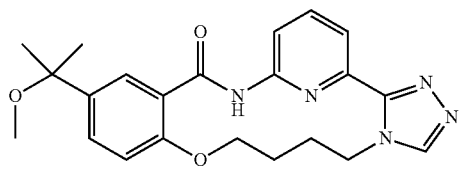 [SMILES: COC(C)(C)c1ccc2c(c1)C(=O)Nc1cccc(n1)-c1nncn1CCCCO2]

A mixture of 5⁵-(2-hydroxypropan-2-yl)-1⁴H-6-oxa-3-aza-2(2,6)-pyridina-1(3,4)-triazola-5(1,2)-benzenacyclodecaphan-4-one (200 mg, 0.51 mmol) and TsOH (87 mg, 0.51 mmol) in MeOH (15 mL) was stirred at 18° C. for 3 h. The mixture was treated with water (5 mL) and EtOAc (15 mL) and the pH was adjusted to 7-8 with sat. aq. NaHCO$_3$. The mixture was extracted with EtOAc (3×20 mL). The combined organic layers were concentrated and purified by HPLC (using an Xtimate C18, 5 μm 150×25 mm column and using water (containing 10 mM NH$_4$HCO$_3$)/CH$_3$CN, from 31% to 61% as the mobile phase at a flow rate of 25 mL/min) to give the title compound (30 mg, 14%) as a white solid. ¹H NMR (400 MHz, CDCl$_3$) δ ppm 11.50 (s, 1H), 8.27 (d, J=2.8 Hz, 1H), 8.22 (s, 1H), 8.06 (d, J=7.6 Hz, 1H), 8.02 (d, J=7.6 Hz, 1H), 7.90-7.94 (m, 1H), 7.63 (dd, J=2.0, 8.4 Hz, 1H), 7.04 (d, J=8.8 Hz, 1H), 4.27-4.34 (m, 4H), 3.07 (s, 3H), 2.62-2.77 (m, 2H), 2.05-2.13 (m, 2H), 1.56 (s, 6H). MS (ESI): 430.1 [M+Na]⁺.

Example 51: 2-Methyl-2-(4-oxo-1⁴H-6-oxa-3-aza-2(2,6)-pyridina-1(3,4)-triazola-5(1,2)-benzenacyclodecaphane-5⁵-yl)propanenitrile

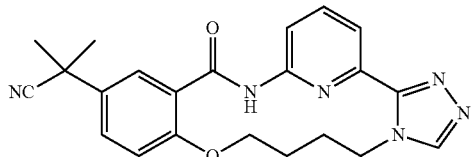

To a solution of TMSCN (228 mg, 2.3 mmol) in DCM (25 mL) was added SnCl$_4$ (299 mg, 1.15 mmol) at 0° C. followed by 5⁵-(2-hydroxypropan-2-yl)-1⁴H-6-oxa-3-aza-2(2,6)-pyridina-1(3,4)-triazola-5(1,2)-benzenacyclodecaphan-4-one (90 mg, 0.23 mmol) in DCM (25 mL). The mixture was stirred at 31° C. for 30 minutes. After this time the volatiles were removed under reduced pressure and the crude product was purified by pre-HPLC (using an Agela ASB, 5 μm 150×25 mm column and using water (containing 0.225% HCOOH)/CH$_3$CN, from 45% to 55% as the mobile phase at a flow rate of 25 mL/min) to give the title compound (15 mg, 16%) as a white solid. ¹H NMR (400 MHz, CDCl$_3$) δ ppm 11.21 (s, 1H), 8.78 (s, 1H), 8.03-8.09 (m, 2H), 7.83-7.89 (m, 2H), 7.70-7.72 (m, 1H), 7.33 (d, J=8.8 Hz, 1H), 4.31-4.34 (m, 2H), 4.23-4.28 (m, 2H), 2.44 (br, 2H), 1.94 (br, 2H), 1.69 (s, 6H). MS (ESI): 403.2 [M+H]⁺.

Example 52: 5⁴-Fluoro-5⁵-(pyridin-4-yl)-1⁴H-6-oxa-3-aza-2(2,6)-pyridina-1(3,4)-triazola-5(1,2)-benzenacyclodecaphan-4-one

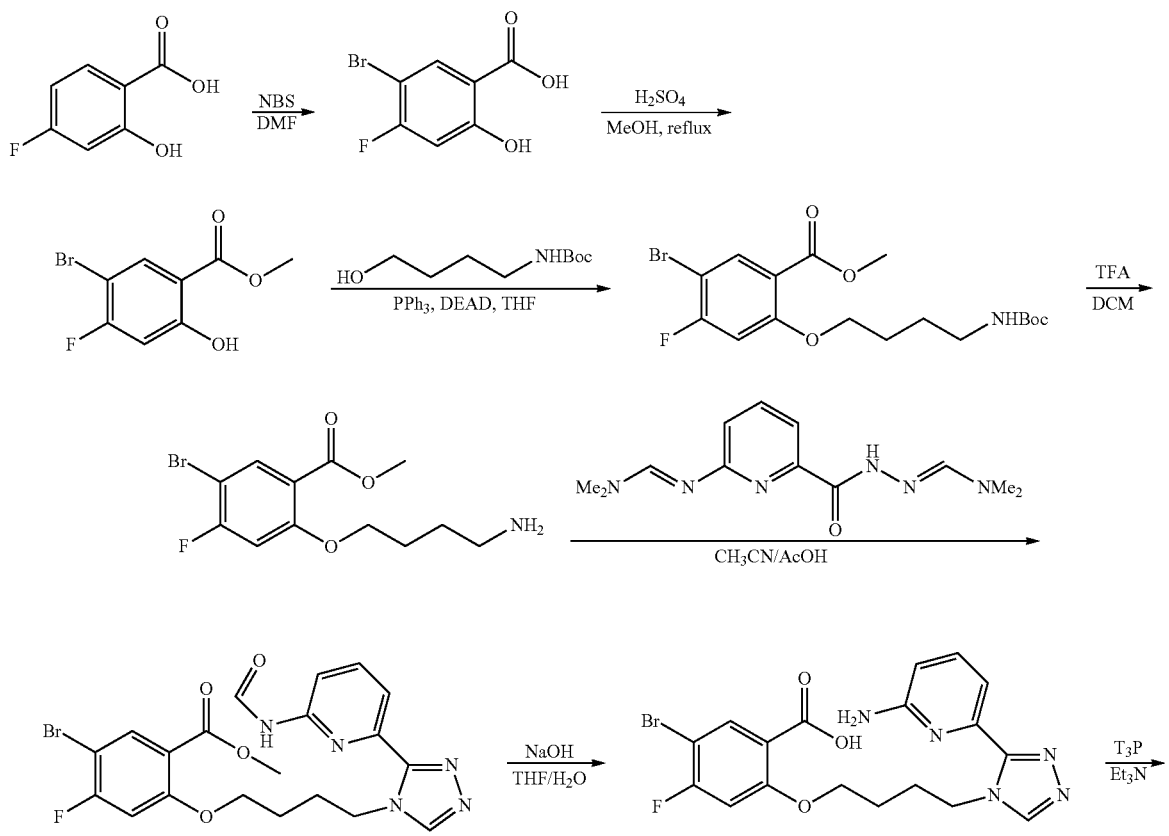

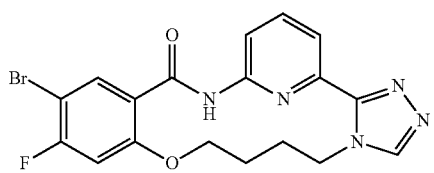 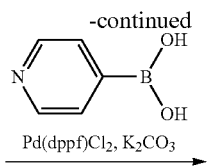 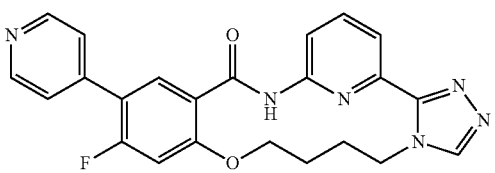

Step A. 5-Bromo-4-fluoro-2-hydroxybenzoic acid

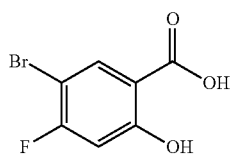 [SMILES: O=C(O)c1cc(Br)c(F)cc1O]

A mixture of 4-fluoro-2-hydroxybenzoic acid (46 g, 0.29 mol) in DMF (500 mL) was treated with NBS (58 g, 0.32 mol). The reaction mixture was stirred at 18° C. for 24 h. After this time the mixture was treated with EtOAc (100 mL), washed with $H_2O$ (3×500 mL) and sat. aq. LiCl (4×300 mL). The organic phase was dried over $Na_2SO_4$, filtered and concentrated to give the title compound (69 g, 100%) as a white solid. $^1$H NMR (400 MHz, DMSO-$d_6$) δ ppm 8.01 (d, J=8.5 Hz, 1H), 7.06 (d, J=10.0 Hz, 1H).

Step B. Methyl 5-bromo-4-fluoro-2-hydroxybenzoate

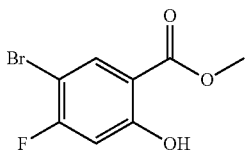

To a stirred mixture of 5-bromo-4-fluoro-2-hydroxybenzoic acid (75 g, 0.32 mol) in MeOH (800 mL) was added $H_2SO_4$ (80 mL). The reaction mixture was stirred at 80° C. for 17 h. After this time the volatiles were removed under reduced pressure and the resulting residue was dissolved in $H_2O$ (200 mL). The pH was adjusted to 10-11 by addition of aqueous NaOH and the aqueous layer was extracted with DCM (3×200 mL). The combined organic extracts were dried over $Na_2SO_4$, filtered and concentrated to give the title compound (70 g, 88%) as a white solid. $^1$H NMR (400 MHz, DMSO-$d_6$) δ ppm 10.84 (br s, 1H), 8.01 (d, J=8.0 Hz, 1H), 7.06 (d, J=10.5 Hz, 1H), 3.88 (s, 3H).

Step C. Methyl 5-bromo-2-(4-((tert-butoxycarbonyl)amino)butoxy)-4-fluorobenzoate

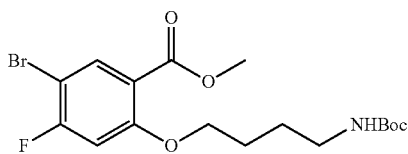 [SMILES: COC(=O)c1cc(Br)c(F)cc1OCCCCNC(=O)OC(C)(C)C]

To a stirred mixture of methyl 5-bromo-4-fluoro-2-hydroxybenzoate (30 g, 0.12 mol), tert-butyl (4-hydroxybutyl)carbamate (32 g, 0.17 mol) and $PPh_3$ (38 g, 0.15 mol) in THF (400 mL) was dropwise added DIAD (30.7 mL, 0.16 mol). The reaction mixture was stirred at 18° C. for 0.5 h. After this time the volatiles were removed under reduced pressure to give a crude product. Petroleum ether/EtOAc (6/1) was added until a solid precipitated. The mixture was filtered and the organic layer was concentrated to give the title compound (30 g, 59%) as a white solid. The product was used without further purification in the next step.

Step D. Methyl 2-(4-aminobutoxy)-5-bromo-4-fluorobenzoate

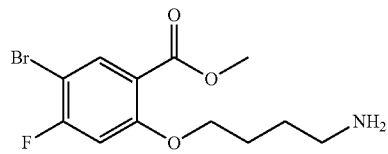 [SMILES: COC(=O)c1cc(Br)c(F)cc1OCCCCN]

A mixture of methyl 5-bromo-2-(4-((tert-butoxycarbonyl)amino)butoxy)-4-fluorobenzoate (30 g, 0.071 mol) in TFA/DCM (100 mL, 1/1) was stirred at 18° C. for 2 h. After this time the volatiles were removed under reduced pressure and the resulting residue was dissolved in $H_2O$ (50 mL). The pH of the aqueous layer was adjusted to 10-11 by addition of aqueous NaOH and it was extracted with EtOAc (3×200 mL). The combined organic extracts were dried over $Na_2SO_4$, filtered and concentrated to give the title compound (23 g, 100%) as a white solid. MS (ESI): 321.9 [(M+H)($^{81}$Br)]$^+$.

Step E. Methyl 5-bromo-4-fluoro-2-(4-(3-(6-formamidopyridin-2-yl)-4H-1,2,4-triazol-4-yl)butoxy)benzoate

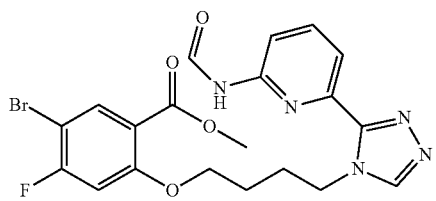 [SMILES: COC(=O)c1cc(Br)c(F)cc1OCCCCn1cnnc1-c1cccc(NC=O)n1]

A mixture of methyl 2-(4-aminobutoxy)-5-bromo-4-fluorobenzoate (22 g, 56 mmol) and (E)-N'-(6-(2-((E)-(dimethylamino)methylene)hydrazine-1-carbonyl)pyridin-2-yl)-N,N-dimethylformimidamide (11.2 g, 43 mmol) in AcOH (200 mL) and $CH_3CN$ (200 mL) was stirred at 90° C. under $N_2$ for 17 h. After this time the volatiles were removed under reduced pressure to give the crude product which was purified by column chromatography on silica using EtOAc as eluent followed by DCM/MeOH (1/0 to 10/1) to give the title compound (13 g, 61%) as a white solid. MS (ESI): 494.0 [(M+H) ($^{81}$Br)]$^+$.

Step F. 2-(4-(3-(6-Aminopyridin-2-yl)-4H-1,2,4-triazol-4-yl)butoxy)-5-bromo-4-fluorobenzoic acid

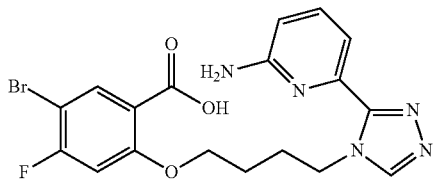 [SMILES: Nc1cccc(-c2nncn2CCCCOc2cc(F)c(Br)cc2C(=O)O)n1]

A mixture of methyl 5-bromo-4-fluoro-2-(4-(3-(6-formamidopyridin-2-yl)-4H-1,2,4-triazol-4-yl)butoxy)benzoate (6 g, 12.2 mmol) and NaOH (1.46 g, 36.6 mmol) in THF/H$_2$O (4/1, 75 mL) was stirred at 70° C. for 17 h. After this time the volatiles were removed under reduced pressure to give the title compound (5.5 g, 100%) as a white solid which was used without further purification in next step without further purification. MS (ESI): 450.0 [(M+H) ($^{79}$Br)]$^+$.

Step G. 5$^5$-Bromo-5$^4$-fluoro-1$^4$H-6-oxa-3-aza-2(2,6)-pyridina-1(3,4)-triazola-5(1,2)-benzenacyclodecaphan-4-one

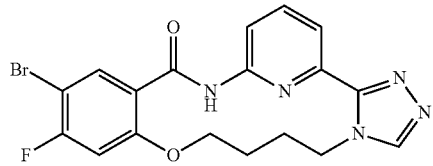 [SMILES: O=C1Nc2cccc(n2)-c2nncn2CCCCOc2cc(F)c(Br)cc21]

To a mixture of 2-(4-(3-(6-aminopyridin-2-yl)-4H-1,2,4-triazol-4-yl)butoxy)-5-bromo-4-fluorobenzoic acid (9.5 g, 21.1 mmol) was added T$_3$P (90 mL, ≥50 wt. % in EtOAc) and Et$_3$N (90 mL) and the reaction was stirred at 80° C. for 17 h. After this time the volatiles were removed under reduced pressure to give the crude product to which was added H$_2$O (20 mL). The solid was collected by filtration, purified by recrystallization from MeOH to give the title compound (3.2 g, 35%) as a white solid. $^1$H NMR (400 MHz, DMSO-d$_6$) δ ppm 10.99 (s, 1H), 8.66 (s, 1H), 8.14 (d, J=8.4 Hz, 1H), 8.01-8.10 (m, 1H), 7.85 (dd, J=3.7, 7.6 Hz, 2H), 7.46 (d, J=10.8 Hz, 1H), 4.33 (br t, J=4.6 Hz, 2H), 4.18-4.28 (m, 2H), 2.38-2.41 (m, 2H), 1.87-1.97 (m, 2H). MS (ESI): 432.0 [(M+H) ($^{79}$Br)]$^+$.

Step H. 5$^4$-Fluoro-5$^5$-(pyridin-4-yl)-1$^4$H-6-oxa-3-aza-2(2,6)-pyridina-1(3,4)-triazola-5(1,2)-benzenacyclodecaphan-4-one

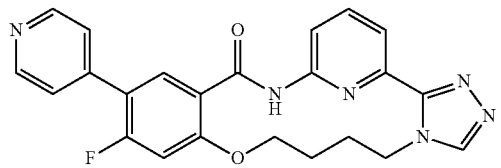 [SMILES: O=C1Nc2cccc(n2)-c2nncn2CCCCOc2cc(F)c(-c3ccncc3)cc21]

A mixture of 5-bromo-5$^4$-fluoro-1$^4$H-6-oxa-3-aza-2(2,6)-pyridina-1(3,4)-triazola-5(1,2)-benzenacyclodecaphan-4-one (150 mg, 0.35 mmol), pyridin-4-ylboronic acid (51 mg, 0.42 mmol), K$_2$CO$_3$ (96 mg, 0.69 mmol) and Pd(dppf)Cl$_2$ (25 mg, 0.035 mmol) in dioxane/H$_2$O (5/1, 5 mL) was stirred at 90° C. under N$_2$ for 2 h. After this time the volatiles were removed under reduced pressure to give the crude product which was purified by column chromatography on silica gel using DCM/MeOH (1/0 to 30/1) as eluent to give the title compound (60 mg, 40%) as a brown solid. $^1$H NMR (400 MHz, DMSO-d$_6$) δ ppm 11.03 (s, 1H), 8.66-8.67 (m, 3H), 8.17 (d, J=9.2 Hz, 1H), 8.07 (t, J=9.0 Hz, 1H), 7.85-7.88 (m, 2H), 7.60-7.61 (m, 2H), 7.43 (d, J=13.2 Hz, 1H), 4.38-4.40 (m, 2H), 4.24-4.28 (m, 2H), 2.45-2.46 (m, 2H), 1.94-1.97 (m, 2H). MS (ESI): 431.1 [M+H]$^+$.

Example 53: 5$^4$-Fluoro-5$^5$-(2-(trifluoromethyl)pyridin-4-yl)-1$^4$H-6-oxa-3-aza-2(2,6)-pyridina-1(3,4)-triazola-5(1,2)-benzenacyclodecaphan-4-one

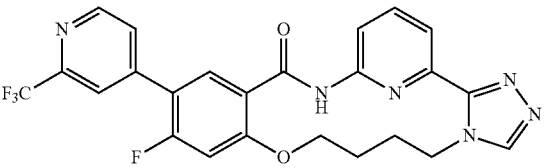 [SMILES: O=C1Nc2cccc(n2)-c2nncn2CCCCOc2cc(F)c(-c3ccnc(C(F)(F)F)c3)cc21]

To a solution of 5$^5$-bromo-5$^4$-fluoro-1$^4$H-6-oxa-3-aza-2(2,6)-pyridina-1(3,4)-triazola-5(1,2)-benzenacyclodecaphan-4-one (80 mg, 0.185 mmol) in dioxane/H$_2$O (5/1, 3 mL) under a N$_2$ atmosphere was added 4-(4,4,5,5-tetramethyl-1,3,2-dioxaborolan-2-yl)-2-(trifluoromethyl)pyridine (56 mg, 0.2 mmol) and K$_2$CO$_3$ (51 mg, 0.37 mmol) followed by Pd(dppf)Cl$_2$ (6.8 mg, 0.009 mmol). The mixture was stirred at 80° C. for 2 h. After this time the mixture was concentrated under vacuum to give the crude product, which was purified by column chromatography using DCM/MeOH (100/1 to 100/3) to give the title compound (75 mg, 65%) as a yellow solid. $^1$H NMR (400 MHz, DMSO-d$_6$) δ ppm 10.97 (s, 1H), 8.85 (d, J=4.8 Hz, 1H), 8.66 (s, 1H), 8.24 (d, J=9.2 Hz, 1H), 8.02-8.08 (m, 2H), 7.94 (d, J=4.8 Hz, 1H), 7.84 (d, J=8.0 Hz, 2H), 7.42 (d, J=13.2 Hz, 1H), 4.35-4.38 (m, 2H), 4.21-4.26 (m, 2H), 2.41-2.42 (m, 2H), 1.94 (br, 2H). MS (ESI): 499.1 [M+H]$^+$.

Example 54: 5⁴-Fluoro-5⁵-(2-methylpyridin-4-yl)-1⁴H-6-oxa-3-aza-2(2,6)-pyridina-1(3,4)-triazola-5(1,2)-benzenacyclodecaphan-4-one

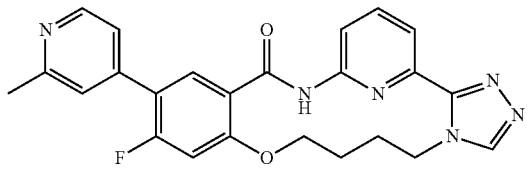 [SMILES: Cc1cc(-c2cc3c(cc2F)OCCCCn2cnnc2-c2cccc(n2)NC3=O)ccn1]

A mixture of 5⁵-bromo-5⁴-fluoro-1⁴H-6-oxa-3-aza-2(2,6)-pyridina-1(3,4)-triazola-5(1,2)-benzenacyclodecaphan-4-one (80 mg, 0.18 mmol), 2-methyl-4-(4,4,5,5-tetramethyl-1,3,2-dioxaborolan-2-yl)pyridine (60 mg, 0.28 mmol), Pd(dppf)Cl$_2$ (27 mg, 0.037 mmol) and K$_2$CO$_3$ (52 mg, 0.37 mmol) in dioxane (5 mL) and H$_2$O (0.5 mL) was stirred at 85° C. for 3 h. After this time the volatiles were removed under reduced pressure to give the crude product which was purified by column chromatography on silica gel eluting with DCM/MeOH (1/0 to 30/1) to give the title compound (65 mg, 63%) as a brown solid. $^1$H NMR (400 MHz, DMSO-d$_6$) δ ppm 11.06 (s, 1H), 8.69 (s, 1H), 8.54 (d, J=4.9 Hz, 1H), 8.18 (d, J=8.8 Hz, 1H), 8.05-8.11 (m, 1H), 7.89 (dd, J=3.7, 8.1 Hz, 2H), 7.49 (s, 1H), 7.38-7.46 (m, 2H), 4.41 (br t, J=4.9 Hz, 2H), 4.23-4.32 (m, 2H), 2.55 (s, 3H), 2.51-2.54 (m, 2H), 1.92-2.05 (m, 2H). MS (ESI): 445.1 [M+H]⁺.

Example 55: 5⁴-Fluoro-5⁵-(2-fluoropyridin-4-yl)-1⁴H-6-oxa-3-aza-2(2,6)-pyridina-1(3,4)-triazola-5(1,2)-benzenacyclodecaphan-4-one

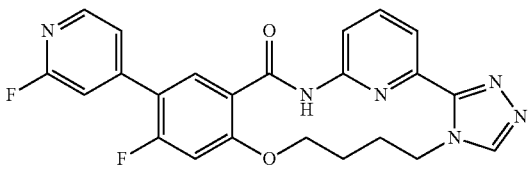 [SMILES: O=C1Nc2cccc(n2)-c2nncn2CCCCOc2cc(F)c(-c3ccnc(F)c3)cc21]

A mixture of 5⁵-bromo-5⁴-fluoro-1⁴H-6-oxa-3-aza-2(2,6)-pyridina-1(3,4)-triazola-5(1,2)-benzenacyclodecaphan-4-one (80 mg, 0.18 mmol), (2-fluoropyridin-4-yl)boronic acid (26 mg, 0.18 mmol), Pd(dppf)Cl$_2$ (13.5 mg, 0.018 mmol), K$_2$CO$_3$ (51 mg, 0.37 mmol) in dioxane/H$_2$O (5/1, 12 mL) was degassed by bubbling N$_2$ through the mixture. The reaction was then stirred at 90° C. for 2 h. After this time the solvent was removed and the residue was purified by column chromatography on silica gel eluting with DCM/MeOH (100/1 to 20/1) to give the title compound (62 mg, 59%) as a yellow solid. $^1$H NMR (400 MHz, DMSO-d$_6$) δ ppm 10.98 (s, 1H), 8.67 (s, 1H), 8.32-8.34 (d, J=5.2 Hz, 1H), 8.19-8.22 (d, J=9.2 Hz, 1H), 8.04-8.08 (m, 1H), 7.85-7.87 (m, 2H), 7.58-7.59 (m, 1H), 7.42-7.45 (m, 2H), 4.37-4.40 (m, 2H), 4.23-4.27 (m, 2H), 2.44-2.47 (m, 2H), 1.93-1.95 (m, 2H). MS (ESI): 449.0 [M+H]⁺.

Example 56: 5⁵-(2-Cyclopropylpyridin-4-yl)-5⁴-fluoro-1⁴H-6-oxa-3-aza-2(2,6)-pyridina-1(3,4)-triazola-5(1,2)-benzenacyclodecaphan-4-one

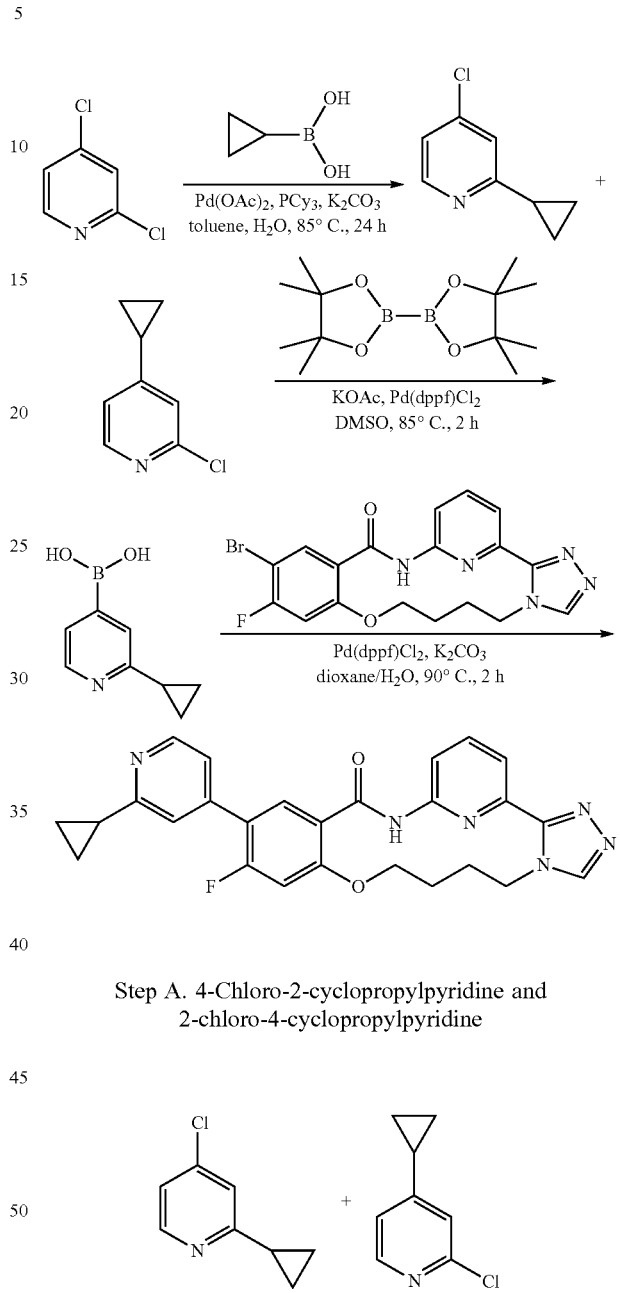

Step A. 4-Chloro-2-cyclopropylpyridine and 2-chloro-4-cyclopropylpyridine

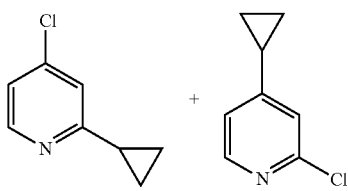 [SMILES: Clc1ccnc(C2CC2)c1 ; Clc1cc(C2CC2)ccn1]

A mixture of 2,4-dichloropyridine (4 g, 27 mmol), cyclopropylboronic acid (5.1 g, 59 mmol), Pd(OAc)$_2$ (606 mg, 2.7 mmol), K$_2$CO$_3$ (8.22 g, 59 mmol) and PCy$_3$ (1.52 g, 5.4 mmol) in toluene (100 mL) and H$_2$O (20 mL) was degassed with N$_2$. The reaction was stirred at 85° C. under a N$_2$ atmosphere for 12 h. After this time the volatiles were removed under reduced pressure and the residue was purified by column chromatography on silica using EtOAc/petroleum ether (1/100 to 1/5) as eluent to give 4-chloro-2-cyclopropylpyridine (290 mg, 7%) and 2-chloro-4-cyclopropylpyridine (400 mg, 9%) as a white solid. MS (ESI): 153.9 [M+H]⁺.

Step B. (2-Cyclopropylpyridin-4-yl)boronic acid

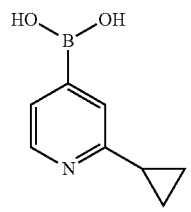

A mixture of 4-chloro-2-cyclopropylpyridine (100 mg, 0.65 mmol), 4,4,4',4',5,5,5',5'-octamethyl-2,2'-bi(1,3,2-dioxaborolane) (198 mg, 0.78 mmol), KOAc (128 mg, 1.31 mmol) and Pd(dppf)Cl$_2$ (47 mg, 0.065 mmol) in dioxane (4 mL) was degassed with N$_2$ and was stirred at 120° C. for 12 h. After this time the volatiles were removed under reduced pressure and the residue was purified by HPLC (using a Phenomenex Synergi C18, 4 μm 150×30 mm column and using CH$_3$CN/water (containing 0.05% HCl), from 0% to 15% as the mobile phase at a flow rate of 25 mL/min) to give the title compound (25 mg, 16%) as a white solid. $^1$H NMR (400 MHz, MeOD) δ ppm 8.49 (d, J=6.0 Hz, 1H), 7.93 (d, J=5.6 Hz, 1H), 7.76 (s, 1H), 2.32-2.36 (m, 1H), 1.44-1.47 (m, 2H), 1.22-1.25 (m, 2H).

Step C. 5$^5$-(2-Cyclopropylpyridin-4-yl)-5$^4$-fluoro-1$^4$H-6-oxa-3-aza-2(2,6)-pyridina-1(3,4)-triazola-5(1,2)-benzenacyclodecaphan-4-one

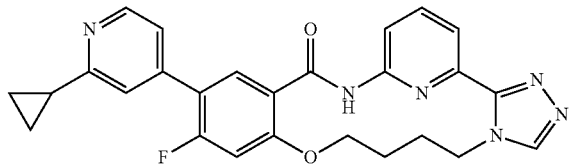 [SMILES: O=C1Nc2cccc(n2)-c2nncn2CCCCOc2cc(F)c(-c3ccnc(C4CC4)c3)cc21]

A mixture of 5$^5$-bromo-5$^4$-fluoro-1$^4$H-6-oxa-3-aza-2(2,6)-pyridina-1(3,4)-triazola-5(1,2)-benzenacyclodecaphan-4-one (20 mg, 0.082 mmol), (2-cyclopropylpyridin-4-yl)boronic acid (16 mg, 0.098 mmol), K$_2$CO$_3$ (23 mg, 0.16 mmol) and Pd(dppf)Cl$_2$ (6 mg, 0.08 mmol) in dioxane/H$_2$O (5/1, 1 mL) was stirred at 90° C. under a N$_2$ atmosphere for 2 h. After this time the volatiles were removed under reduced pressure to give the crude product which was purified by column chromatography on silica using DCM/MeOH (30/1) as eluent to give the title compound (10 mg, 46%) as a white solid. $^1$H NMR (400 MHz, DMSO-d$_6$) δ ppm 11.03 (s, 1H), 8.68 (s, 1H), 8.47 (d, J=5.2 Hz, 1H), 8.16 (d, J=8.8 Hz, 1H), 8.05-8.07 (m, 1H), 7.85-7.89 (m, 2H), 7.52 (s, 1H), 7.41 (d, J=12.8 Hz, 1H), 7.31-7.32 (m, 1H), 4.38-4.40 (m, 2H), 4.26-4.28 (m, 2H), 2.54-2.55 (m, 2H), 2.19-2.20 (m, 1H), 1.97-1.98 (m, 2H), 0.95-0.97 (m, 4H). MS (ESI): 471.1 [M+H]$^+$.

Example 57: 5$^4$-Fluoro-5$^5$-(6-methylpyridin-3-yl)-1$^4$H-6-oxa-3-aza-2(2,6)-pyridina-1(3,4)-triazola-5(1,2)-benzenacyclodecaphan-4-one

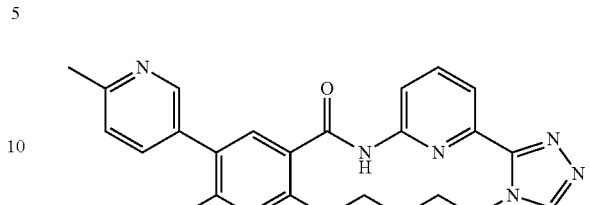

A mixture of 5$^5$-bromo-5$^4$-fluoro-1$^4$H-6-oxa-3-aza-2(2,6)-pyridina-1(3,4)-triazola-5(1,2)-benzenacyclodecaphan-4-one (80 mg, 0.18 mmol), (6-methylpyridin-3-yl)boronic acid (38 mg, 0.28 mmol), Pd(dppf)Cl$_2$ (40 mg, 0.05 mmol) and K$_2$CO$_3$ (51 mg, 0.37 mmol) in dioxane/H$_2$O (3 mL, 10/1) was stirred at 90° C. for 4 h. After this time the mixture was concentrated and purified by column chromatography on silica gel using petroleum ether/EtOAc (100/1) followed by DCM/MeOH (100/1 to 10/1) as eluents to give the title compound (40 mg, 49%) as a white solid. $^1$H NMR (400 MHz, DMSO-d$_6$) δ ppm 11.06 (s, 1H), 8.58-8.71 (m, 2H), 8.01-8.12 (m, 2H), 7.82-7.90 (m, 3H), 7.34-7.43 (m, 2H), 4.37 (m, 2H), 4.20-4.29 (m, 2H), 2.51 (m, 5H), 1.95 (m, 2H). MS (ESI): 445.1 [M+H]$^+$.

Example 58: 5$^4$-Fluoro-5$^5$-(5-(trifluoromethyl)pyridin-3-yl)-1$^4$H-6-oxa-3-aza-2(2,6)-pyridina-1(3,4)-triazola-5(1,2)-benzenacyclodecaphan-4-one

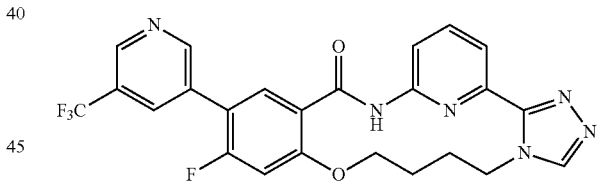

A mixture of 5$^5$-bromo-5$^4$-fluoro-1$^4$H-6-oxa-3-aza-2(2,6)-pyridina-1(3,4)-triazola-5(1,2)-benzenacyclodecaphan-4-one (80 mg, 0.19 mmol), 3-(4,4,5,5-tetramethyl-1,3,2-dioxaborolan-2-yl)-5-(trifluoromethyl)pyridine (61 mg, 0.22 mmol), K$_2$CO$_3$ (51.0 mg, 0.37 mmol) and Pd(dppf)Cl$_2$ (13.5 mg, 0.019 mmol) in dioxane/H$_2$O (5/1, 4 mL) was stirred at 90° C. under N$_2$ for 2 h. After this time the volatiles were removed under reduced pressure to give the crude product which was purified by column chromatography on silica using DCM/MeOH (30/1) as eluent to give the title compound (64 mg, 69%) as a brown solid. $^1$H NMR (400 MHz, DMSO-d$_6$) δ ppm 11.01 (s, 1H), 9.07 (s, 1H), 9.01 (s, 1H), 8.67 (s, 1H), 8.41 (s, 1H), 8.20 (d, J=9.2 Hz, 1H), 8.03-8.05 (m, 1H), 7.84-7.87 (m, 2H), 7.44 (d, J=12.4 Hz, 1H), 4.37-4.39 (m, 2H), 4.23-4.27 (m, 2H), 2.54-2.55 (m, 2H), 1.94-1.95 (m, 2H). MS (ESI): 498.9 [M+H]$^+$.

Example 59: $5^5$-(6-Cyclopropylpyridin-3-yl)-$5^4$-fluoro-$1^4$H-6-oxa-3-aza-2(2,6)-pyridina-1(3,4)-triazola-5(1,2)-benzenacyclodecaphan-4-one

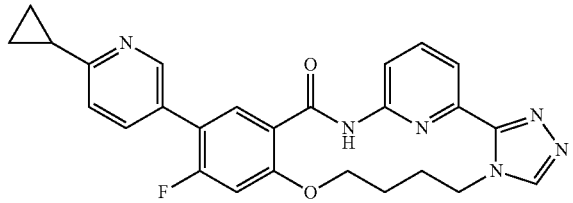 [SMILES: O=C1Nc2cccc(n2)-c2nncn2CCCCOc2cc(F)c(-c3ccc(C4CC4)nc3)cc21]

A mixture of $5^5$-bromo-$5^4$-fluoro-$1^4$H-6-oxa-3-aza-2(2,6)-pyridina-1(3,4)-triazola-5(1,2)-benzenacyclodecaphan-4-one (80, 0.19 mmol), (6-cyclopropylpyridin-3-yl)boronic acid (45 mg, 0.28 mmol), $K_2CO_3$ (51 mg, 0.37 mmol) and Pd(dppf)Cl$_2$ (27 mg, 0.037 mmol) in dioxane/H$_2$O (4/1, 2 mL) was stirred at 85° C. under N$_2$ for 2 h. After this time the volatiles were removed under reduced pressure to give the crude compound which was purified by column chromatography on silica using DCM/MeOH (30/1) as eluent to give the title compound (35 mg, 40%) as a brown solid. $^1$H NMR (400 MHz, DMSO-d$_6$) δ ppm 11.09 (s, 1H), 8.70 (s, 1H), 8.59 (s, 1H), 8.06-8.11 (m, 2H), 7.84-7.91 (m, 3H), 7.39-7.44 (m, 2H), 4.39-4.40 (m, 2H), 4.27-4.28 (m, 2H), 2.54-2.55 (m, 2H), 2.17-2.18 (m, 1H), 1.98-1.99 (m, 2H), 0.99-1.01 (m, 4H). MS (ESI): 471.1 [M+H]$^+$.

Example 60: $5^4$-Fluoro-$5^5$-(pyrimidin-5-yl)-$1^4$H-6-oxa-3-aza-2(2,6)-pyridina-1(3,4)-triazola-5(1,2)-benzenacyclodecaphan-4-one

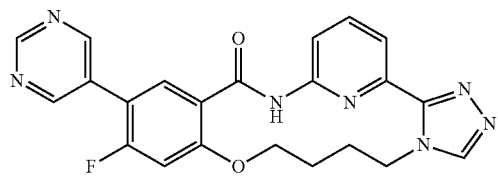 [SMILES: O=C1Nc2cccc(n2)-c2nncn2CCCCOc2cc(F)c(-c3cncnc3)cc21]

A mixture of $5^5$-bromo-$5^4$-fluoro-$1^4$H-6-oxa-3-aza-2(2,6)-pyridina-1(3,4)-triazola-5(1,2)-benzenacyclodecaphan-4-one (80 mg, 0.19 mmol), pyrimidin-5-ylboronic acid (27 mg, 0.22 mmol), $K_2CO_3$ (51 mg, 0.37 mmol) and Pd(dppf)Cl$_2$ (13.9 mg, 0.019 mmol) in DMF/H$_2$O (5/1, 5 mL) was stirred at 90° C. under N$_2$ for 1 h. After this time water (20 mL) was added upon which a solid formed. The solid was filtered off and dried under vacuum to give the crude product which was purified by column chromatography on silica using DCM/MeOH (30/1) as eluent to provide the title compound (45 mg, 56%) as a white solid. $^1$H NMR (400 MHz, DMSO-d$_6$) δ ppm 11.01 (s, 1H), 9.22 (s, 1H), 9.04 (s, 2H), 8.67 (s, 1H), 8.20 (d, J=8.8 Hz, 1H), 8.04-8.08 (m, 1H), 7.85-7.88 (m, 2H), 7.46 (d, J=12.0 Hz, 1H), 4.37-4.39 (m, 2H), 4.24-4.28 (m, 2H), 2.54-2.55 (m, 2H), 1.95-1.96 (m, 2H). MS (ESI): 432.0 [M+H]$^+$.

Example 61: $5^4$-Fluoro-$5^5$-(pyridazin-4-yl)-$1^4$H-6-oxa-3-aza-2(2,6)-pyridina-1(3,4)-triazola-5(1,2)-benzenacyclodecaphan-4-one

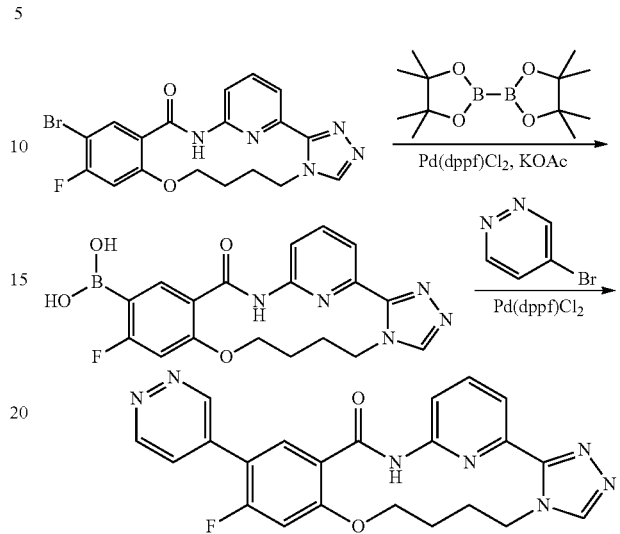

Step A. ($5^4$-Fluoro-4-oxo-$1^4$H-6-oxa-3-aza-2(2,6)-pyridina-1(3,4)-triazola-5(1,2)-benzenacyclodecaphane-$5^5$-yl)boronic acid

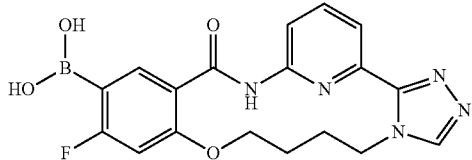 [SMILES: O=C1Nc2cccc(n2)-c2nncn2CCCCOc2cc(F)c(B(O)O)cc21]

A mixture of $5^5$-bromo-$5^4$-fluoro-$1^4$H-6-oxa-3-aza-2(2,6)-pyridina-1(3,4)-triazola-5(1,2)-benzenacyclodecaphan-4-one (200 mg, 0.46 mmol), 4,4,4',4',5,5,5',5'-octamethyl-2,2'-bi(1,3,2-dioxaborolane) (587 mg, 2.31 mmol) and KOAc (136 mg, 1.39 mmol), Pd(dppf)Cl$_2$ (34 mg, 0.05 mmol) in dioxane (5 mL) was stirred at 85° C. under N$_2$ for 12 h. After this time the mixture was concentrated and water was added (5 mL). The mixture was extracted with DCM/MeOH (10/1, 3×15 mL) and the combined organic extracts were concentrated to give the title compound (222 mg, crude), which was used without further purification in the next step. MS (ESI): 398.0 [M+H]$^+$.

Step B. $5^4$-Fluoro-$5^5$-(pyridazin-4-yl)-$1^4$H-6-oxa-3-aza-2(2,6)-pyridina-1(3,4)-triazola-5(1,2)-benzenacyclodecaphan-4-one

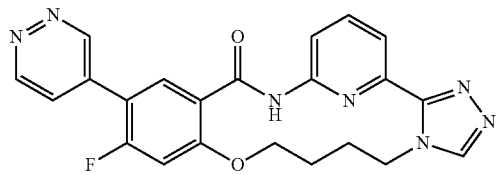 [SMILES: O=C1Nc2cccc(n2)-c2nncn2CCCCOc2cc(F)c(-c3ccnnc3)cc21]

A mixture of (5⁴-fluoro-4-oxo-1⁴H-6-oxa-3-aza-2(2,6)-pyridina-1(3,4)-triazola-5(1,2)-benzenacyclodecaphane-5⁵-yl)boronic acid (250 mg, 0.63 mmol), 4-bromopyridazine (166 mg, 1.04 mmol), Pd(dppf)Cl₂ (74 mg, 0.10 mmol) and K₂CO₃ (144 mg, 1.04 mol) in dioxane (15 mL) and H₂O (2 mL) was stirred at 90° C. for 3 h. After this time the volatiles were removed under reduced pressure to give the crude product which was purified by HPLC (using a Phenomenex Synergi C18, 4 μm 150×30 mm column and using CH₃CN/water (containing 0.05% HCl), from 25% to 40% as the mobile phase at a flow rate of 25 mL/min) to give the title compound (58 mg, 21%) as a white solid. ¹H NMR (400 MHz, DMSO-d₆) δ ppm 10.97 (s, 1H), 9.56 (s, 1H), 9.37 (d, J=5.6 Hz, 1H), 9.06 (s, 1H), 8.29 (d, J=9.2 Hz, 1H), 8.02-8.14 (m, 2H), 7.90 (t, J=8.0 Hz, 2H), 7.46-7.49 (m, 1H), 4.36-4.42 (m, 2H), 4.27-4.35 (m, 2H), 2.41-2.46 (m, 2H), 1.88-2.02 (m, 2H). MS (ESI): 432.1 [M+H]⁺.

Example 62: 5⁵-(1,5-Dimethyl-1H-pyrazol-4-yl)-5⁴-fluoro-1⁴H-6-oxa-3-aza-2(2,6)-pyridina-1(3,4)-triazola-5(1,2)-benzenacyclodecaphan-4-one

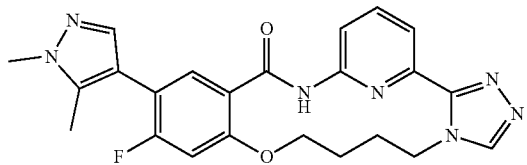 [SMILES: Cc1c(-c2cc3c(cc2F)OCCCCn2cnnc2-c2cccc(n2)NC3=O)cnn1C]

A solution of 5-bromo-5⁴-fluoro-1⁴H-6-oxa-3-aza-2(2,6)-pyridina-1(3,4)-triazola-5(1,2)-benzenacyclodecaphan-4-one (150 mg, 0.35 mmol), (1,5-dimethyl-1H-pyrazol-4-yl)boronic acid (58 mg, 0.42 mmol), K₂CO₃ (96 mg, 0.69 mmol) and Pd(dppf)Cl₂ (25 mg, 0.035 mmol) in dioxane/H₂O (3 mL, 10/1) was stirred at 90° C. under N₂ for 4 h. After this time the mixture was filtered and purified by HPLC (using a Phenomenex Synergi C18, 4 μm 150×30 mm column and using CH₃CN/water (containing 0.05% HCl), from 32% to 52% as the mobile phase at a flow rate of 25 mL/min) to give the title compound (13 mg, 8.64%) as a white solid. ¹H NMR (400 MHz, DMSO-d₆) δ ppm 11.03-11.19 (m, 1H), 8.67 (s, 1H), 8.00-8.10 (m, 1H), 7.82-7.96 (m, 3H), 7.49 (s, 1H), 7.33 (br d, J=11.7 Hz, 1H), 4.31-4.41 (m, 2H), 4.19-4.30 (m, 2H), 3.79 (s, 3H), 3.25-3.30 (m, 2H), 2.25 (s, 2H), 1.96 (br s, 3H). MS (ESI): 448.1 [M+H]⁺.

Example 63: 5⁴-Fluoro-5⁵-(1-methyl-1H-pyrazol-4-yl)-1⁴H-6-oxa-3-aza-2(2,6)-pyridina-1(3,4)-triazola-5(1,2)-benzenacyclodecaphan-4-one

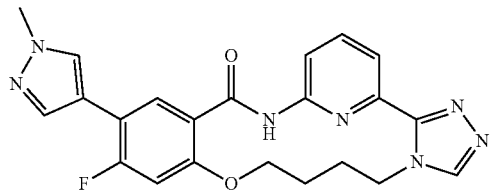 [SMILES: Cn1cc(-c2cc3c(cc2F)OCCCCn2cnnc2-c2cccc(n2)NC3=O)cn1]

A solution of 5⁵-bromo-5⁴-fluoro-1⁴H-6-oxa-3-aza-2(2,6)-pyridina-1(3,4)-triazola-5(1,2)-benzenacyclodecaphan-4-one (150 mg, 0.35), 1-methyl-4-(4,4,5,5-tetramethyl-1,3,2-dioxaborolan-2-yl)-1H-pyrazole (87 mg, 0.42 mmol), K₂CO₃ (96 mg, 0.70 mmol) and Pd(dppf)Cl₂ (25 mg, 0.035 mmol) in dioxane/H₂O (3 mL, 10/1) was stirred at 90° C. under N₂ for 4 h. After this time the mixture was filtered and purified by HPLC (using a Phenomenex Synergi C18, 4 μm 150×30 mm column and using CH₃CN/water (containing 0.05% HCl), from 31% to 51% as the mobile phase at a flow rate of 25 mL/min) to provide the title compound (50 mg, 33%) as a yellow solid. The product was further purified by HPLC (using an Xtimate C18, 5 μm 150×25 mm column and using water (containing 10 mM NH₄HCO₃)/CH₃CN, from 30% to 60% as the mobile phase at a flow rate of 25 mL/min) to provide the title compound (5 mg, 12%) as a white solid. ¹H NMR (400 MHz, DMSO-d₆) δ ppm 11.07 (s, 1H), 8.67 (s, 1H), 8.21 (t, J=8.8 Hz, 1H), 8.16 (s, 1H), 8.06 (t, J=8.0 Hz, 1H), 7.84-7.88 (m, 3H), 7.31 (d, J=13.2 Hz, 1H), 4.32-4.34 (m, 2H), 4.23-4.27 (m, 2H), 3.88 (s, 3H), 2.42-2.43 (m, 2H), 1.93-1.94 (m, 2H). MS (ESI): 434.1 [M+H]⁺.

Example 64: 5⁵-(1-(2-(Dimethylamino)ethyl)-1H-pyrazol-4-yl)-5⁴-fluoro-1⁴H-6-oxa-3-aza-2(2,6)-pyridina-1(3,4)-triazola-5(1,2)-benzenacyclodecaphan-4-one

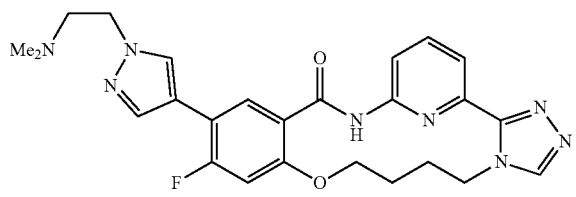 [SMILES: CN(C)CCn1cc(-c2cc3c(cc2F)OCCCCn2cnnc2-c2cccc(n2)NC3=O)cn1]

To a solution of 5⁵-bromo-5⁴-fluoro-1⁴H-6-oxa-3-aza-2(2,6)-pyridina-1(3,4)-triazola-5(1,2)-benzenacyclodecaphan-4-one (100 mg, 0.23 mmol) in DME/H₂O (10/1, 3 mL) under a N₂ atmosphere was added N,N-dimethyl-2-(4-(4,4,5,5-tetramethyl-1,3,2-dioxaborolan-2-yl)-1H-pyrazol-1-yl)ethan-1-amine (74 mg, 0.28 mmol), K₂CO₃ (64 mg, 0.46 mmol) followed by Pd(dtbpf)Cl₂ (15 mg, 0.02 mmol) and the mixture was stirred at 80° C. for 18 h. After this time the reaction was concentrated under vacuum to give the crude, which was purified by HPLC (using a Phenomenex Synergi C18, 4 μm 150×30 mm column and using CH₃CN/water (containing 0.05% HCl), from 17% to 37% as the mobile phase at a flow rate of 25 mL/min) to give the title compound (26 mg, 23%) as an off-white solid. ¹H NMR (400 MHz, MeOD) δ ppm 9.34 (s, 1H), 8.25 (d, J=9.2 Hz, 1H), 8.09 (s, 1H), 7.89-8.05 (m, 2H), 7.86 (d, J=7.6 Hz, 2H), 6.98-6.85 (m, 1H), 4.69 (t, J=6.4 Hz, 2H), 4.45-4.43 (m, 2H), 4.41-4.33 (m, 2H), 3.78 (t, J=6.0 Hz, 2H), 3.04 (s, 6H), 2.58 (br, 2H), 2.09 (br, 2H). MS (ESI): 491 [M+H]⁺.

Example 65: 5⁴-Fluoro-5⁵-(5-methyl-4,5,6,7-tetra-hydropyrazolo[1,5-a]pyrazin-3-yl)-1⁴H-6-oxa-3-aza-2(2,6)-pyridina-1(3,4)-triazola-5(1,2)-benzenacyclo-decaphan-4-one

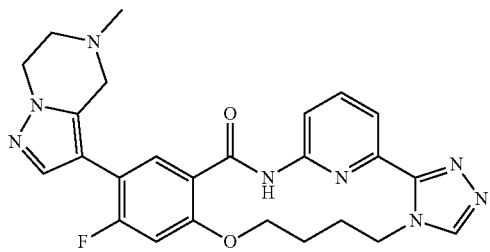 [SMILES: CN1CCn2ncc(-c3cc4c(cc3F)OCCCCn3cnnc3-c3cccc(n3)NC4=O)c2C1]

A mixture of (5⁴-fluoro-4-oxo-1⁴H-6-oxa-3-aza-2(2,6)-pyridina-1(3,4)-triazola-5(1,2)-benzenacyclodecaphane-5⁵-yl)boronic acid (200 mg, 0.5 mmol), 3-bromo-5-methyl-4,5,6,7-tetrahydropyrazolo[1,5-a]pyrazine (90 mg, 0.42 mmol), K₂CO₃ (173 mg, 1.25 mmol), and PEPPSI (56.6 mg, 83.4 umol) in EtOH/H₂O (10/1, 5 mL) was stirred at 100° C. for 2 h. After this time the mixture was concentrated and DMF (5 mL) was added. The product was purified by HPLC (using a Phenomenex Synergi C18, 4 μm 150×30 mm column and using CH₃CN/water (containing 0.05% HCl), from 10% to 30% as the mobile phase at a flow rate of 25 mL/min) to give the title compound (50 mg, 24%) as a yellow solid as the HCl salt. ¹H NMR (400 MHz, DMSO-d₆) δ ppm 11.96 (s, 1H), 11.10 (s, 1H), 9.16 (s, 1H), 8.09-8.13 (m, 1H), 7.90-7.95 (m, 3H), 7.86 (s, 1H), 7.38-7.41 (m, 1H), 4.58-4.63 (m, 2H), 4.48-4.53 (m, 2H), 4.36-4.37 (m, 4H), 3.70-4.00 (m, 2H), 2.98 (s, 3H), 2.48-2.51 (m, 2H), 1.89-1.97 (m, 2H). MS (ESI): 489.2 [M+H]⁺.

Example 66: 5⁴-Fluoro-5⁵-(4-methyl-1H-imidazol-1-yl)-1⁴H-6-oxa-3-aza-2(2,6)-pyridina-1(3,4)-triazola-5(1,2)-benzenacyclodecaphan-4-one

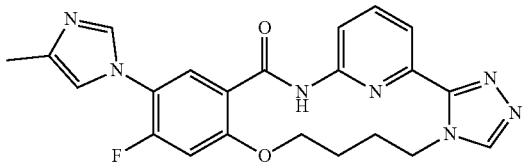 [SMILES: Cc1cn(-c2cc3c(cc2F)OCCCCn2cnnc2-c2cccc(n2)NC3=O)cn1]

A mixture of (5⁴-fluoro-4-oxo-1⁴H-6-oxa-3-aza-2(2,6)-pyridina-1(3,4)-triazola-5(1,2)-benzenacyclodecaphane-5⁵-yl)boronic acid (50 mg, 0.13 mmol), 4-methyl-1H-imidazole (17 mg, 0.21 mmol) and Cu(OAc)₂ (56 mg, 0.31 mmol) in pyridine (1 mL) was stirred at 60° C. for 12 h.

After this time the solvent was removed and the residue was purified by HPLC (using a Phenomenex Synergi C18, 4 μm 150×30 mm column and using CH₃CN/water (containing 0.05% HCl), from 42% to 57% as the mobile phase at a flow rate of 25 mL/min) to give the title compound (26 mg, 48%) as white solid. ¹H NMR (400 MHz, DMSO-d₆) δ ppm 10.99 (s, 1H), 9.51 (s, 1H), 8.92 (s, 1H), 8.29 (d, J=8.4 Hz, 1H), 8.04-8.13 (m, 1H), 7.82-7.92 (m, 3H), 7.65 (d, J=12.8 Hz, 1H), 4.36-4.45 (m, 2H), 4.29 (s, 2H), 2.30-2.44 (m, 5H), 1.96 (s, 2H). MS (ESI): 434.0 [M+H]⁺.

Example 67: 5⁵-(3,6-Dihydro-2H-pyran-4-yl)-5⁴-fluoro-1⁴H-6-oxa-3-aza-2(2,6)-pyridina-1(3,4)-triazola-5(1,2)-benzenacyclodecaphan-4-one

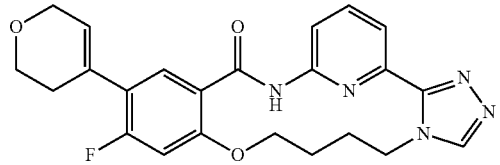 [SMILES: O=C1Nc2cccc(n2)-c2nncn2CCCCOc2cc(F)c(C3=CCOCC3)cc21]

To a mixture of 5⁵-bromo-5⁴-fluoro-1⁴H-6-oxa-3-aza-2(2,6)-pyridina-1(3,4)-triazola-5(1,2)-benzenacyclodecaphan-4-one (250 mg, 0.58 mmol), 2-(3,6-dihydro-2H-pyran-4-yl)-4,4,5,5-tetramethyl-1,3,2-dioxaborolane (243 mg, 1.16 mmol) and K₃PO₄ (182 mg, 1.16 mmol) in dioxane/H₂O (7 mL/1.4 mL) under N₂ was added Pd(dppf)Cl₂ (42 mg, 0.06 mmol). The mixture was stirred at 90° C. for 2 h. After this time the mixture was concentrated and the crude product was purified by HPLC (using a Phenomenex Synergi C18, 4 μm 150×30 mm column and using CH₃CN/water (containing 0.05% HCl), from 35% to 88% as the mobile phase at a flow rate of 25 mL/min) to afford the title compound (30 mg, 12%) as white solid. ¹H NMR (400 MHz, DMSO-d₆) δ ppm 11.07 (s, 1H), 8.73 (s, 1H), 8.04 (t, J=7.6 Hz, 1H), 7.93 (d, J=9.2 Hz, 1H), 7.83-7.87 (m, 2H), 7.23 (d, J=12.8 Hz, 1H), 6.11 (s, 1H), 4.31-4.32 (m, 2H), 4.20-4.27 (m, 4H), 3.78-3.82 (m, 2H), 2.41 (s, 4H), 1.93 (s, 2H). MS (ESI): 436.1 [M+H]⁺.

Example 68: 5⁴-Fluoro-5⁵-(tetrahydro-2H-pyran-4-yl)-1⁴H-6-oxa-3-aza-2(2,6)-pyridina-1(3,4)-triazola-5(1,2)-benzenacyclodecaphan-4-one

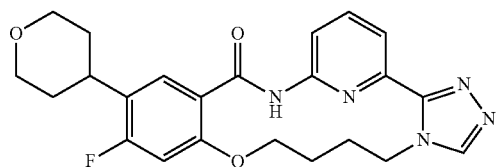 [SMILES: O=C1Nc2cccc(n2)-c2nncn2CCCCOc2cc(F)c(C3CCOCC3)cc21]

To a solution of 5-(3,6-dihydro-2H-pyran-4-yl)-5⁴-fluoro-1⁴H-6-oxa-3-aza-2(2,6)-pyridina-1(3,4)-triazola-5(1,2)-benzenacyclodecaphan-4-one (80 mg, 0.18 mmol) in MeOH/THF (100 mL/10 mL) was added Pd (80 mg, 10% on C). The mixture was stirred at 30° C. under H₂ of 30 psi for 2 h. After this time the mixture was filtered and the filter cake was washed with DCM. The filtrate was concentrated under vacuum to give the crude product, which was purified by column chromatography on silica gel using DCM/MeOH (1/0 to 95/5) to give the title compound (57 mg, 72%) as a white solid. ¹H NMR (400 MHz, DMSO-d₆) δ ppm 11.08 (s, 1H), 8.66 (s, 1H), 8.03 (t, J=8.0 Hz, 1H), 7.80-8.00 (m, 3H), 7.16 (d, J=12.4 Hz, 1H), 4.19-4.28 (m, 4H), 3.93 (d, J=10.0 Hz, 2H), 3.44 (t, J=10.0 Hz, 2H), 2.99-3.01 (m, 1H), 2.39-2.40 (m, 2H), 1.91 (br, 2H), 1.71-1.67 (m, 4H). MS (ESI): 438.1 [M+H]⁺.

Example 69: 5⁴-Fluoro-5⁵-(1-methyl-1,2,3,6-tetrahydropyridin-4-yl)-1⁴H-6-oxa-3-aza-2(2,6)-pyridina-1(3,4)-triazola-5(1,2)-benzenacyclodecaphan-4-one

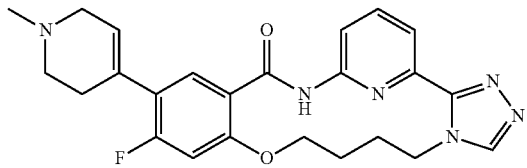 [SMILES: CN1CC=C(c2cc3c(cc2F)OCCCCn2cnnc2-c2cccc(n2)NC3=O)CC1]

To a solution of 5⁵-bromo-5⁴-fluoro-1⁴H-6-oxa-3-aza-2(2,6)-pyridina-1(3,4)-triazola-5(1,2)-benzenacyclodecaphan-4-one (90 mg, 0.21 mmol) in EtOH/water (10/1, 3 mL) under a N₂ atmosphere was added 1-methyl-4-(4,4,5,5-tetramethyl-1,3,2-dioxaborolan-2-yl)-1,2,3,6-tetrahydropyridine (93 mg, 0.42 mmol) and K₂CO₃ (58 mg, 0.42 mmol) followed by PEPPSI-IPr (14 mg, 0.02 mmol). The mixture was stirred at 90° C. for 1.5 h. After this time the solvent was removed under reduced pressure and the crude product was purified by column chromatography on silica gel using DCM/MeOH (100/1 to 20/1) as eluent to give the title compound (37 mg, 40%) as a white solid. ¹H NMR (400 MHz, DMSO-d₆) δ ppm 11.09 (s, 1H), 8.68 (s, 1H), 8.06 (t, J=7.8 Hz, 1H), 7.93 (d, J=9.2 Hz, 1H), 7.87 (dd, J=4.4, 7.6 Hz, 2H), 7.22 (d, J=13.2 Hz, 1H), 6.01 (br s, 1H), 4.33 (t, J=5.0 Hz, 2H), 4.23-4.29 (m, 2H), 3.02 (br d, J=3.2 Hz, 2H), 2.55-2.59 (m, 2H), 2.45 (br s, 4H), 2.28 (s, 3H), 1.90-1.99 (m, 2H). MS (ESI): 449.2 [M+H]⁺.

Example 70: 5⁴-Fluoro-5⁵-(1-methylpiperidin-4-yl)-1⁴H-6-oxa-3-aza-2(2,6)-pyridina-1(3,4)-triazola-5(1,2)-benzenacyclodecaphan-4-one

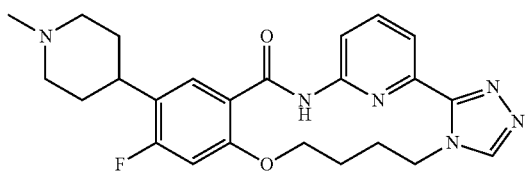 [SMILES: CN1CCC(c2cc3c(cc2F)OCCCCn2cnnc2-c2cccc(n2)NC3=O)CC1]

To a solution of 5-fluoro-5⁵-(1-methyl-1,2,3,6-tetrahydropyridin-4-yl)-1⁴H-6-oxa-3-aza-2(2,6)-pyridina-1(3,4)-triazola-5(1,2)-benzenacyclodecaphan-4-one (117 mg, 0.26 mmol,) in MeOH (40 mL) was added Pd (150 mg, 10% on C) at 30° C. The mixture was stirred at 30° C. under H₂ atmosphere (15 PSI) for 15 h. After this time the mixture was filtered and the filter cake was washed with DCM. The filtrate was concentrated under vacuum to give the crude product, which was purified by HPLC (using an Xtimate C18, 5 μm 150×25 mm column and using water (containing 10 mM NH₄HCO₃)/CH₃CN, from 25% to 55% as the mobile phase at a flow rate of 25 mL/min) to give the title compound (5 mg, 4%) as a white solid. ¹H NMR (400 MHz, DMSO-d₆) δ ppm 11.12 (s, 1H), 8.67 (s, 1H), 8.05 (t, J=7.8 Hz, 1H), 7.82-7.94 (m, 3H), 7.19 (d, J=12.4 Hz, 1H), 4.21-4.35 (m, 4H), 2.88 (d, J=10.6 Hz, 2H), 2.69-2.77 (m, 1H), 2.43-2.46 (m, 2H), 2.20 (s, 3H), 1.89-2.03 (m, 4H), 1.65-1.76 (m, 4H). MS (ESI): 451.3 [M+H]⁺.

Example 71: 5⁴-Fluoro-5⁵-morpholino-1⁴H-6-oxa-3-aza-2(2,6)-pyridina-1(3,4)-triazola-5(1,2)-benzenacyclodecaphan-4-one

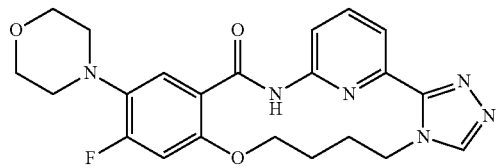 [SMILES: O=C1Nc2cccc(n2)-c2nncn2CCCCOc2cc(F)c(N3CCOCC3)cc21]

A mixture of compound 5⁵-bromo-5⁴-fluoro-1⁴H-6-oxa-3-aza-2(2,6)-pyridina-1(3,4)-triazola-5(1,2)-benzenacyclodecaphan-4-one (100 mg, 0.23 mmol), morpholine (0.1 mL, 1.16 mmol), RuPhos (21 mg, 0.05 mmol), t-BuONa (44 mg, 0.5 mmol) and Pd₂(dba)₃ (21 mg, 0.023 mmol) in dioxane/THF (1/1, 6 mL) was stirred at 120° C. under N₂ for 3 h. After this time the volatiles were removed under reduced pressure to give the crude which was purified by column chromatography on silica gel using DCM/MeOH (30/1). Further purification by SFC (using a Chiralcel OD-3 3 μm, 50×4.6 mm column and using 40% of ethanol (containing 0.05% Et₂NH) in CO₂ as the mobile phase and at a flow rate of 4 mL/min at a column temperature of 40° C.) gave the title compound (47 mg, 47%) as a white solid. ¹H NMR (400 MHz, DMSO-d₆) δ ppm 11.20 (s, 1H), 8.67 (s, 1H), 8.05 (t, J=8.0 Hz, 1H), 7.83-7.87 (m, 2H), 7.63 (d, J=10.0 Hz, 1H), 7.28 (d, J=13.6 Hz, 1H), 4.22-4.29 (m, 4H), 3.73-3.74 (m, 4H), 2.97-2.98 (m, 4H), 2.41-2.42 (m, 2H), 1.92-1.93 (m, 2H). MS (ESI): 439.2 [M+H]⁺.

Example 72: 5⁵-(6-Oxa-3-azabicyclo[3.1.1]heptan-3-yl)-5⁴-fluoro-1⁴H-6-oxa-3-aza-2(2,6)-pyridina-1(3,4)-triazola-5(1,2)-benzenacyclodecaphan-4-one

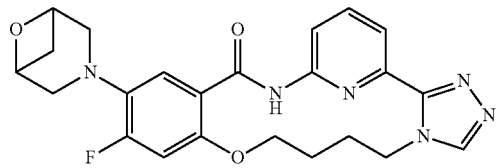 [SMILES: O=C1Nc2cccc(n2)-c2nncn2CCCCOc2cc(F)c(N3CC4CC(C3)O4)cc21]

To a solution of 5⁵-bromo-5⁴-fluoro-1⁴H-6-oxa-3-aza-2(2,6)-pyridina-1(3,4)-triazola-5(1,2)-benzenacyclodecaphan-4-one (107 mg, 0.25 mmol) in THF/dioxane (1/1, 6 mL) under a N₂ atmosphere was added 6-oxa-3-azabicyclo[3.1.1]heptane (100 mg, 0.37 mmol, tosylate salt) and t-BuONa (71 mg, 0.74 mmol) followed by Pd₂(dba)₃ (23 mg, 0.025 mmol) and X-phos (9 mg, 0.025 mmol). The mixture was stirred at 115° C. for 5 h. After this time the mixture was concentrated under vacuum to give the crude product which was purified by pre-HPLC (using a Waters Xbridge Prep OBD C18, 5 μm 150×30 mm column and using water (containing 0.05% NH₃.H₂O)/CH₃CN, from 25% to 55% as the mobile phase at a flow rate of 25 mL/min) to give the desired product. Further purification by SFC (using an AD 3 μm, 250×30 mm column and using 40% of ethanol (containing 0.1% NH₃.H₂O) in CO₂ as the mobile phase, at a flow rate of 4 mL/min, with a column temperature of 40° C.) gave the title compound (10 mg, 9%) as a white solid. ¹H NMR (400 MHz, DMSO-d₆) δ ppm 11.33 (s, 1H), 8.70 (s, 1H), 8.06 (t, J=8.0 Hz, 1H), 7.84-7.91 (m, 2H), 7.61 (d, J=10.4 Hz, 1H), 7.61 (d, J=11.6 Hz, 1H), 4.64 (d, J=6.0 Hz, 2H), 4.30-4.25 (m, 4H), 3.65 (d, J=11.2 Hz, 2H), 3.50 (d, J=11.2 Hz, 2H), 3.05-3.11 (m, 1H), 2.44-2.46 (m, 2H), 2.15 (J=8.4 Hz, 1H), 1.96 (br, 2H). MS (ESI): 450.9 [M+H]+.

Example 73: 5⁴-Fluoro-5⁵-(4-methylpiperazin-1-yl)-1⁴H-6-oxa-3-aza-2(2,6)-pyridina-1(3,4)-triazola-5(1,2)-benzenacyclodecaphan-4-one

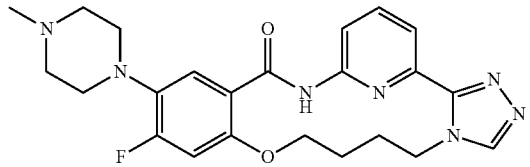 [SMILES: CN1CCN(c2cc3c(cc2F)OCCCCn2cnnc2-c2cccc(n2)NC3=O)CC1]

To a solution of 5⁵-bromo-5⁴-fluoro-1⁴H-6-oxa-3-aza-2(2,6)-pyridina-1(3,4)-triazola-5(1,2)-benzenacyclodecaphan-4-one (90 mg, 0.21 mmol) in DMF (3 mL) under a N₂ atmosphere was added 1-methylpiperazine (0.12 mL, 1.05 mmol) and t-BuONa (61 mg, 0.63 mmol) followed by Pd₂(dba)₃ (18 mg, 0.02 mmol) and Xphos (9 mg, 0.02 mmol). The mixture was stirred at 110° C. for 5 h. After this time the reaction was concentrated under vacuum to give the crude product which was purified by by pre-HPLC (using an Xtimate C18, 5 μm 150×25 mm column and using water (containing 10 mM NH₄HCO₃)/CH₃CN, from 37% to 67% as the mobile phase at a flow rate of 25 mL/min) to give the title compound (10 mg, 13%) as a yellow solid. ¹H NMR (400 MHz, DMSO-d₆) δ ppm 11.23 (s, 1H), 8.69 (s, 1H), 8.07 (t, J=8.0 Hz, 1H), 7.88 (t, J=7.6 Hz, 2H), 7.66 (d, J=9.2 Hz, 1H), 7.30 (d, J=13.6 Hz, 1H), 4.28-4.34 (m, 4H), 2.80-3.03 (m, 4H), 2.51-2.54 (m, 2H), 2.30-2.36 (m, 4H), 2.09-2.23 (m, 3H), 1.93-1.99 (m, 2H). MS (ESI): 452.1 [M+H]+.

Example 74: 5⁴-Fluoro-4-oxo-1⁴H-6-oxa-3-aza-2(2,6)-pyridina-1(3,4)-triazola-5(1,2)-benzenacyclodecaphane-55-carbonitrile

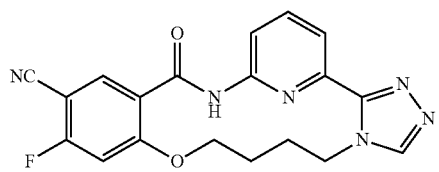 [SMILES: N#Cc1cc2c(cc1F)OCCCCn1cnnc1-c1cccc(n1)NC2=O]

A mixture of 5-bromo-5⁴-fluoro-1⁴H-6-oxa-3-aza-2(2,6)-pyridina-1(3,4)-triazola-5(1,2)-benzenacyclodecaphan-4-one (100 mg, 0.23 mmol), Zn(CN)₂ (27 mg, 0.23 mmol), Zn (9 mg, 0.14 mmol), dppf (25 mg, 0.046 mmol) and Pd₂(dba)₃ (21 mg, 0.023 mmol) in DMA (5 mL) was stirred at 120° C. under N₂ for 17 h. After this time the reaction mixture was filtered and the filtrate was purified by HPLC (using a Phenomenex Synergi C18, 4 μm 150×30 mm column and using CH₃CN/water (containing 0.05% HCl), from 35% to 55% as the mobile phase at a flow rate of 25 mL/min) to provide the title compound (30 mg, 34%) as a white solid. ¹H NMR (400 MHz, DMSO-d₆) δ ppm 10.76 (s, 1H), 8.92 (s, 1H), 8.32 (d, J=8.0 Hz, 1H), 8.08 (t, J=8.0 Hz, 1H), 7.84-7.87 (m, 2H), 7.54 (d, J=11.6 Hz, 1H), 4.35-4.36 (m, 2H), 4.23-4.27 (m, 2H), 2.42-2.43 (m, 2H), 1.87-1.91 (m, 2H). MS (ESI): 379.0 [M+H]+.

Example 75: 5⁴-Fluoro-5⁵-(2-methoxyethoxy)-1⁴H-6-oxa-3-aza-2(2,6)-pyridina-1(3,4)-triazola-5(1,2)-benzenacyclodecaphan-4-one

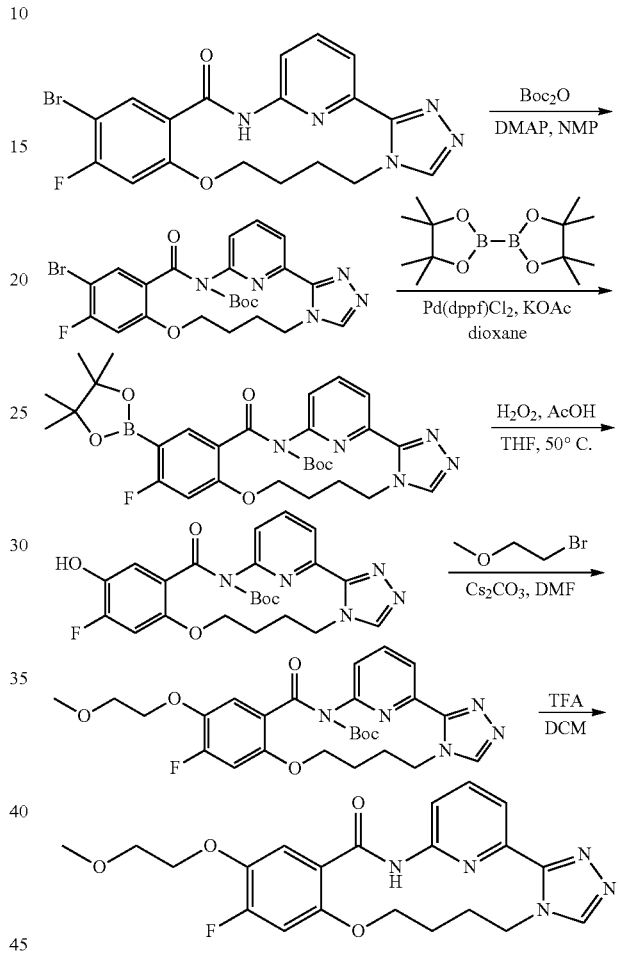

Step A. tert-Butyl 5⁵-bromo-5⁴-fluoro-4-oxo-1⁴H-6-oxa-3-aza-2(2,6)-pyridina-1(3,4)-triazola-5(1,2)-benzenacyclodecaphane-3-carboxylate

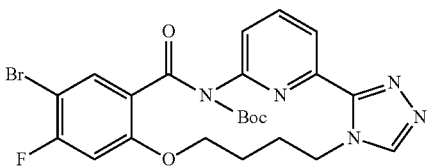 [SMILES: CC(C)(C)OC(=O)N1C(=O)c2cc(Br)c(F)cc2OCCCCn2cnnc2-c2cccc1n2]

To a solution of 5⁵-bromo-5⁴-fluoro-1⁴H-6-oxa-3-aza-2(2,6)-pyridina-1(3,4)-triazola-5(1,2)-benzenacyclodecaphan-4-one (390 mg, 0.9 mmol) in NMP (10 mL) was added Boc₂O (981 mg, 4.5 mmol) and DMAP (221 mg, 1.8 mmol). The mixture was stirred at 50° C. for 4 h. After this time DCM/MeOH (10/1, 50 mL) was added and the mixture was washed with NH₄Cl (aq., 50 mL). The separated organic layer was washed with brine (30 mL), dried over Na₂SO₄, filtered and concentrated under vacuum to give the crude product, which was purified by column chromatography on silica gel using DCM/MeOH (100/1 to 100/3) as eluent to give the title compound (1 g) as a yellow oil. The compound was used without further purification in the next step. MS (ESI): 532.1 [(M+H) ($^{79}$Br)]⁺.

Step B. tert-Butyl 5⁴-fluoro-4-oxo-5⁵-(4,4,5,5-tetramethyl-1,3,2-dioxaborolan-2-yl)-1⁴H-6-oxa-3-aza-2(2,6)-pyridina-1(3,4)-triazola-5(1,2)-benzenacyclodecaphane-3-carboxylate

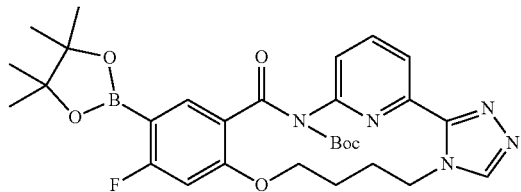 [SMILES: CC(C)(C)OC(=O)N1C(=O)c2cc(B3OC(C)(C)C(C)(C)O3)c(F)cc2OCCCCn2cnnc2-c2cccc1n2]

To a solution of tert-butyl 5⁵-bromo-5⁴-fluoro-4-oxo-1⁴H-6-oxa-3-aza-2(2,6)-pyridina-1(3,4)-triazola-5(1,2)-benzenacyclodecaphane-3-carboxylate (950 mg, 1.78 mmol) in dioxane (10 mL) under a N₂ atmosphere was added 4,4,4',4',5,5,5',5'-octamethyl-2,2'-bi(1,3,2-dioxaborolane) (454 mg, 1.78 mmol) and KOAc (349 mg, 3.56 mmol) followed by Pd(dppf)Cl₂ (131 mg, 0.18 mmol). The mixture was stirred at 95° C. for 18 h. After this time the mixture was concentrated to give the crude product, which was purified by column chromatography on silica gel using DCM/MeOH (100/1 to 100/3) as eluent to give the title compound (280 mg, 27%) as a brown gum. MS (ESI): 580.2 [M+H]⁺.

Step C. tert-Butyl 5⁴-fluoro-5⁵-hydroxy-4-oxo-1⁴H-6-oxa-3-aza-2(2,6)-pyridina-1(3,4)-triazola-5(1,2)-benzenacyclodecaphane-3-carboxylate

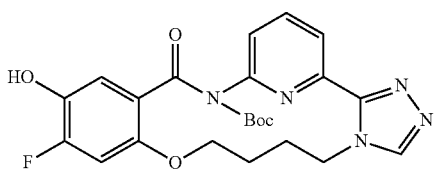 [SMILES: CC(C)(C)OC(=O)N1C(=O)c2cc(O)c(F)cc2OCCCCn2cnnc2-c2cccc1n2]

To a solution of tert-butyl 5⁴-fluoro-4-oxo-5⁵-(4,4,5,5-tetramethyl-1,3,2-dioxaborolan-2-yl)-1⁴H-6-oxa-3-aza-2(2,6)-pyridina-1(3,4)-triazola-5(1,2)-benzenacyclodecaphane-3-carboxylate (270 mg, 0.47 mmol) in THF (50 mL) was added AcOH (1.4 mL) and H₂O₂ (2.8 mL). The mixture was stirred at 50° C. for 2 h. After this time the reaction was quenched with sat. aq. NH₄Cl (100 mL) and H₂O (500 mL) was added. The mixture was concentrated to give the title compound 260 mg, crude) as a yellow solid. MS (ESI): 470.2 [M+H]⁺.

Step D. tert-Butyl 5⁴-fluoro-5⁵-(2-methoxyethoxy)-4-oxo-1⁴H-6-oxa-3-aza-2(2,6)-pyridina-1(3,4)-triazola-5(1,2)-benzenacyclodecaphane-3-carboxylate

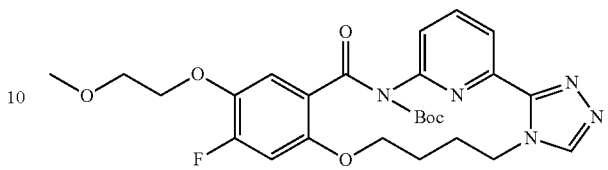

To a solution of tert-butyl 5⁴-fluoro-5⁵-hydroxy-4-oxo-1⁴H-6-oxa-3-aza-2(2,6)-pyridina-1(3,4)-triazola-5(1,2)-benzenacyclodecaphane-3-carboxylate (100 mg, 0.13 mmol) in DMF (8 mL) was added Cs₂CO₃ (85 mg, 0.26 mmol) and 1-bromo-2-methoxyethane (27 mg, 0.19 mmol). The mixture was stirred at 16° C. for 36 h. After this time the mixture was filtered and the filtrate was purified by pre-HPLC (using a Waters XSELECT C18, 5 μm 150×30 mm column and using water (containing 0.1% TFA)/CH₃CN, from 25% to 55% as the mobile phase at a flow rate of 25 mL/min) to give the title compound (10 mg) as a yellow solid. MS (ESI): 528.1 [M+H]⁺. A portion of the deprotected compound: 5⁴-fluoro-5⁵-(2-methoxyethoxy)-1⁴H-6-oxa-3-aza-2(2,6)-pyridina-1(3,4)-triazola-5(1,2)-benzenacyclodecaphan-4-one (15 mg) was also isolated (see step E for analytical data).

Step E. 5⁴-Fluoro-5⁵-(2-methoxyethoxy)-1⁴H-6-oxa-3-aza-2(2,6)-pyridina-1(3,4)-triazola-5(1,2)-benzenacyclodecaphan-4-one

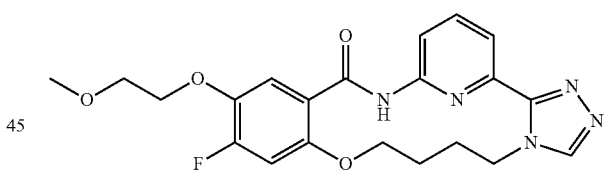

To a solution of tert-butyl 5⁴-fluoro-5⁵-(2-methoxyethoxy)-4-oxo-1⁴H-6-oxa-3-aza-2(2,6)-pyridina-1(3,4)-triazola-5(1,2)-benzenacyclodecaphane-3-carboxylate (10 mg, 0.023 mmol) in DCM (8 mL) was added TFA (2 mL). The mixture was stirred at 25° C. for 2 h. After this time water (100 mL) was added and the mixture was concentrated under vacuum. The crude product was purified by HPLC (using a Waters Xbridge Prep OBD C18, 5 μm 150×30 mm column and using water (containing 0.05% NH₃.H₂O)/CH₃CN, from 26% to 56% as the mobile phase at a flow rate of 25 mL/min) to give the title compound (13 mg, 17% over two steps) as a white solid. ¹H NMR (400 MHz, DMSO-d₆) δ ppm 11.23 (s, 1H), 8.66 (s, 1H), 8.04 (t, J=8.0 Hz 1H), 7.84 (t, J=8.0 Hz, 2H), 7.69 (d, J=9.6 Hz, 1H), 7.34 (d, J=12.8 Hz, 1H), 4.17-4.28 (m, 6H), 3.64-3.67 (m, 2H), 3.30 (s, 3H), 2.40-2.41 (m, 2H), 1.92 (br, 2H). MS (ESI): 428.0 [M+H]⁺.

Example 76: 5⁵-(2-(Dimethylamino)ethoxy)-5⁴-fluoro-1⁴H-6-oxa-3-aza-2(2,6)-pyridina-1(3,4)-triazola-5(1,2)-benzenacyclodecaphan-4-one

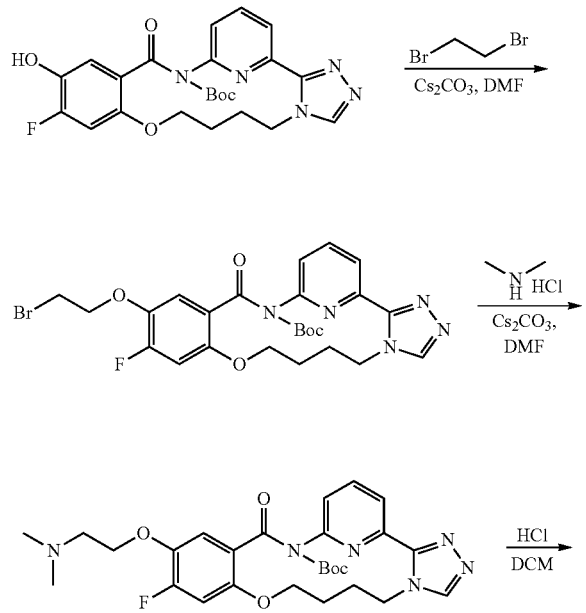

Step A. tert-Butyl 5⁵-(2-bromoethoxy)-5⁴-fluoro-4-oxo-1⁴H-6-oxa-3-aza-2(2,6)-pyridina-1(3,4)-triazola-5(1,2)-benzenacyclodecaphane-3-carboxylate

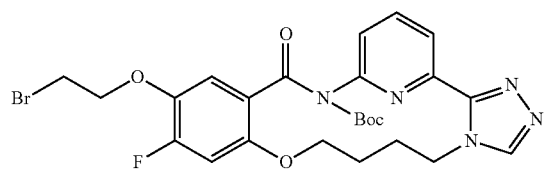 [SMILES: CC(C)(C)OC(=O)N1C(=O)c2cc(OCCBr)c(F)cc2OCCCCn2cnnc2-c2cccc1n2]

To a solution of tert-butyl 5⁴-fluoro-5⁵-hydroxy-4-oxo-1⁴H-6-oxa-3-aza-2(2,6)-pyridina-1(3,4)-triazola-5(1,2)-benzenacyclodecaphane-3-carboxylate (180 mg, crude, 0.38 mmol) in DMF (10 mL) was added Cs₂CO₃ (1.2 g, 3.8 mmol) and 1,2-dibromoethane (710 mg, 3.8 mmol). The mixture was stirred at 50° C. for 2 h. After this time the reaction was concentrated to give the crude product (218 mg), which was used in the next step without further purification. MS (ESI): 578.1 [(M+H) (⁸¹Br)]⁺.

Step B. tert-Butyl 5⁵-(2-(dimethylamino)ethoxy)-5⁴-fluoro-4-oxo-1⁴H-6-oxa-3-aza-2(2,6)-pyridina-1(3,4)-triazola-5(1,2)-benzenacyclodecaphane-3-carboxylate

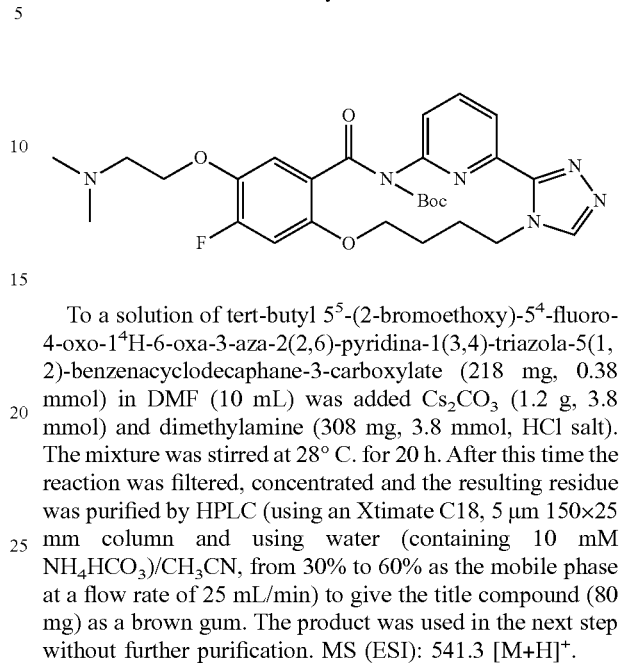

To a solution of tert-butyl 5⁵-(2-bromoethoxy)-5⁴-fluoro-4-oxo-1⁴H-6-oxa-3-aza-2(2,6)-pyridina-1(3,4)-triazola-5(1,2)-benzenacyclodecaphane-3-carboxylate (218 mg, 0.38 mmol) in DMF (10 mL) was added Cs₂CO₃ (1.2 g, 3.8 mmol) and dimethylamine (308 mg, 3.8 mmol, HCl salt). The mixture was stirred at 28° C. for 20 h. After this time the reaction was filtered, concentrated and the resulting residue was purified by HPLC (using an Xtimate C18, 5 μm 150×25 mm column and using water (containing 10 mM NH₄HCO₃)/CH₃CN, from 30% to 60% as the mobile phase at a flow rate of 25 mL/min) to give the title compound (80 mg) as a brown gum. The product was used in the next step without further purification. MS (ESI): 541.3 [M+H]⁺.

Step C. 5⁵-(2-(Dimethylamino)ethoxy)-5⁴-fluoro-1⁴H-6-oxa-3-aza-2(2,6)-pyridina-1(3,4)-triazola-5(1,2)-benzenacyclodecaphan-4-one

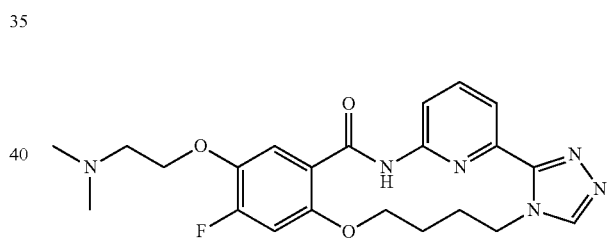

To a solution of tert-butyl 5-(2-(dimethylamino)ethoxy)-5⁴-fluoro-4-oxo-1⁴H-6-oxa-3-aza-2(2,6)-pyridina-1(3,4)-triazola-5(1,2)-benzenacyclodecaphane-3-carboxylate (80 mg, 0.38 mmol) in DCM (8 mL) was added HCl/EA (6 mL, 4M). The mixture was stirred at 29° C. for 1 h. After this time water (100 mL) was added and the reaction was concentrated under vacuum to give the crude product, which was purified by HPLC (using a YMC-Actus Pro C18, 5 μm 150×30 mm and using water (containing 0.1% TFA)/CH₃CN, from 27 to 57% as the mobile phase at a flow rate of 25 mL/min). Further purification by HPLC (using an Xtimate C18, 5 μm 150×25 mm column and using water (containing 10 mM NH₄HCO₃)/CH₃CN, from 37% to 67% as the mobile phase at a flow rate of 25 mL/min) gave the title compound (10 mg, 8%,) as a white solid. ¹H NMR (400 MHz, DMSO-d₆) δ ppm 11.26 (s, 1H), 8.69 (s, 1H), 8.07-8.10 (m, 1H), 7.86-7.91 (m, 2H), 7.73 (d, J=9.2 Hz, 1H), 7.36 (d, J=12.8 Hz, 1H), 4.27-4.33 (m, 4H), 4.17 (t, J=5.6 Hz, 2H), 3.70-3.76 (m, 2H), 2.60-2.68 (m, 2H), 2.23 (s, 6H), 1.96-1.98 (m, 2H). MS (ESI): 441.2 [M+H]⁺.

Example 77: 5⁵-(1-(2-(Dimethylamino)ethyl)-1H-pyrazol-4-yl)-5⁴-(trifluoromethyl)-1⁴H-6-oxa-3-aza-2(2,6)-pyridina-1(3,4)-triazola-5(1,2)-benzenacyclo-decaphan-4-one

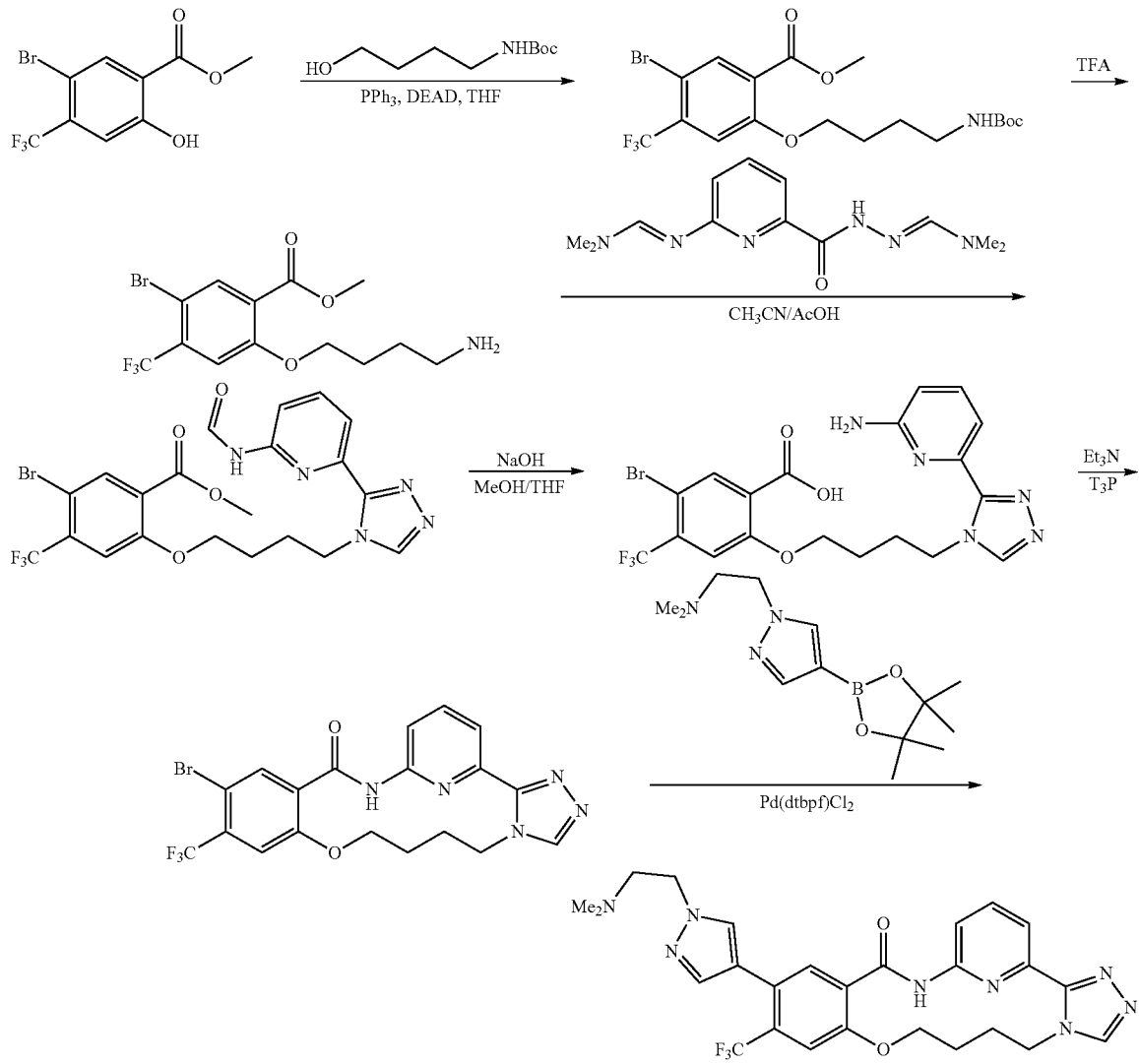

Step A. Methyl 5-bromo-2-(4-((tert-butoxycarbonyl)amino)butoxy)-4-(trifluoromethyl)benzoate

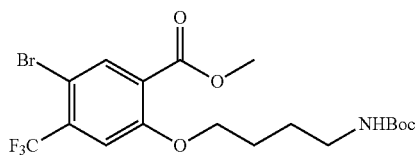 [SMILES: COC(=O)c1cc(Br)c(C(F)(F)F)cc1OCCCCNC(=O)OC(C)(C)C]

A solution of methyl 5-bromo-2-hydroxy-4-(trifluoromethyl)benzoate (6.0 g, 20.1 mmol), tert-butyl (4-hydroxybutyl)carbamate (5.32 g, 28.1 mmol) and PPh₃ (6.32 g, 24.08 mmol) in THF (50 mL) at 0° C. was added DIAD (5.1 mL, 26.1 mmol) dropwise via syringe. The reaction was stirred at 30° C. for 3 h. After this time the mixture was concentrated and purified by HPLC (using a Phenomenex Synergi Max-RP, 10 μm 250×50 mm column and using water (containing 10 mM NH₄HCO₃)/CH₃CN from 20% to 80% as the mobile phase at a flow rate of 115 mL/min) to provide the title compound (2.0 g, 21%) as a white solid. MS (ESI): 470.0 [(M+H) (⁷⁹Br)]⁺.

Step B. Methyl 2-(4-aminobutoxy)-5-bromo-4-(trifluoromethyl)benzoate

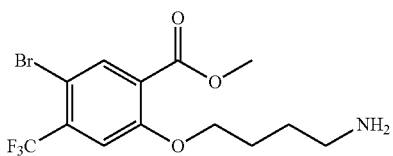 [SMILES: COC(=O)c1cc(Br)c(C(F)(F)F)cc1OCCCCN]

A solution of methyl 5-bromo-2-(4-((tert-butoxycarbonyl)amino)butoxy)-4-(trifluoromethyl)benzoate (1.4 g, 2.98 mmol) in TFA (10 mL) was stirred at 18° C. for 3 h. After this time the mixture was concentrated and water (50 mL) and DCM (50 mL) were added. The mixture was adjusted to pH 7-8 with sat. aq. NaHCO$_3$ and extracted with DCM (3×30 mL). The combined organic layers were concentrated to give the title compound (1.1 g, 100%) as a yellow gum. MS (ESI): 371.9 [(M+H) ($^{81}$Br)]$^+$.

Step C. Methyl 5-bromo-2-(4-(3-(6-formamidopyridin-2-yl)-4H-1,2,4-triazol-4-yl)butoxy)-4-(trifluoromethyl)benzoate

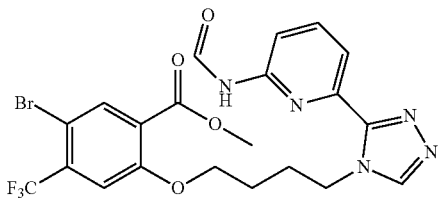 [SMILES: COC(=O)c1cc(Br)c(C(F)(F)F)cc1OCCCCn1cnnc1-c1cccc(NC=O)n1]

A solution of methyl 2-(4-aminobutoxy)-5-bromo-4-(trifluoromethyl)benzoate (1.02 g, 2.74 mmol) and (E)-N'-(6-(2-((E)-(dimethylamino)methylene)hydrazine-1-carbonyl)pyridin-2-yl)-N,N-dimethylformimidamide (0.6 g, 2.29 mmol) in CH$_3$CN/AcOH (1/1, 10 mL) was stirred at 80° C. for 12 h. After this time the reaction mixture was concentrated and purified by column chromatography on silica gel using DCM/MeOH (100/1 to 1/1) as eluent to give the title compound (600 mg, 48%) as yellow solid. MS (ESI): 542.0 [(M+H) ($^{79}$Br)]$^+$.

Step D. 2-(4-(3-(6-Aminopyridin-2-yl)-4H-1,2,4-triazol-4-yl)butoxy)-5-bromo-4-(trifluoromethyl)benzoic acid

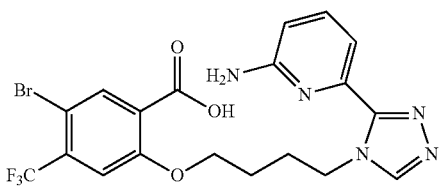 [SMILES: Nc1cccc(-c2nncn2CCCCOc2cc(C(F)(F)F)c(Br)cc2C(=O)O)n1]

A solution of methyl 5-bromo-2-(4-(3-(6-formamidopyridin-2-yl)-4H-1,2,4-triazol-4-yl)butoxy)-4-(trifluoromethyl)benzoate (600 mg, 1.11 mmol) and NaOH (88 mg, 2.21 mmol) in THF/MeOH (1/1, 40 mL) was stirred at 70° C. for 12 h. After this time the volatiles were removed under reduced pressure to give the title compound (600 mg, crude) as a yellow solid. MS (ESI): 500.0 [(M+H) ($^{79}$Br)]$^+$.

Step E. 5$^5$-Bromo-5$^4$-(trifluoromethyl)-1$^4$H-6-oxa-3-aza-2(2,6)-pyridina-1(3,4)-triazola-5(1,2)-benzenacyclodecaphan-4-one

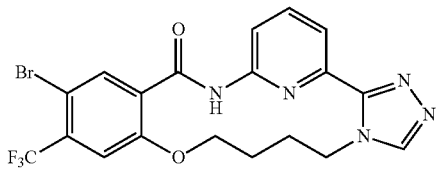 [SMILES: O=C1Nc2cccc(n2)-c2nncn2CCCCOc2cc(C(F)(F)F)c(Br)cc21]

A solution of 2-(4-(3-(6-aminopyridin-2-yl)-4H-1,2,4-triazol-4-yl)butoxy)-5-bromo-4-(trifluoromethyl)benzoic acid (100 mg, 0.18) in triethylamine/T$_3$P (≥50 wt. % in EtOAc) (10 mL, 1/1) was stirred at 50° C. for 4 h. After this time the mixture was treated with sat. aq. NaCl and extracted with EtOAc (3×50 mL). The combined organic extracts were concentrated and purified by HPLC (using a Phenomenex Synergi C18, 4 μm 150×30 mm column and using water (containing 0.05% HCl)/CH$_3$CN, from 47% to 62% as the mobile phase at a flow rate of 25 mL/min). The resulting product was treated with EtOAc (3 mL) and stirred at room temperature for 3 min until a solid form. Subsequent filtration gave the title compound (35 mg, 40%) as a white solid. $^1$H NMR (400 MHz, DMSO-d$_6$) δ ppm 10.99 (s, 1H), 8.76-8.85 (m, 1H), 8.21 (s, 1H), 8.06-8.12 (m, 1H), 7.86 (dd, J=7.2, 13.2 Hz, 2H), 7.64 (s, 1H), 4.36-4.44 (m, 2H), 4.21-4.30 (m, 2H), 2.35-2.43 (m, 2H), 1.86-1.97 (m, 2H). MS (ESI): 484.0 [(M+H) ($^{81}$Br)]$^+$.

Step F. 5$^5$-(1-(2-(Dimethylamino)ethyl)-1H-pyrazol-4-yl)-5$^4$-(trifluoromethyl)-1$^4$H-6-oxa-3-aza-2(2,6)-pyridina-1(3,4)-triazola-5(1,2)-benzenacyclodecaphan-4-one

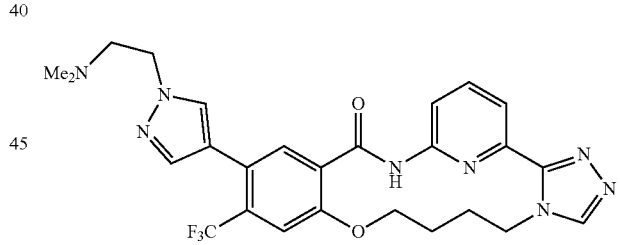

To a solution of 5$^5$-bromo-5$^4$-(trifluoromethyl)-1$^4$H-6-oxa-3-aza-2(2,6)-pyridina-1(3,4)-triazola-5(1,2)-benzenacyclodecaphan-4-one (60 mg, 0.124 mmol) and N,N-dimethyl-2-(4-(4,4,5,5-tetramethyl-1,3,2-dioxaborolan-2-yl)-1H-pyrazol-1-yl)ethan-1-amine (99 mg, 0.373 mmol) in DME/H$_2$O (3 mL/0.3 mL) was added Cs$_2$CO$_3$ (122 mg, 0.37 mmol) and Pd(dtbpf)Cl$_2$ (8.0 mg, 0.012 mmol) and the mixture was stirred at 95° C. for 2 h. After this time the mixture was concentrated to give the crude product, which was purified by preparative TLC (MeOH/DCM=1/15) to give the title compound (15 mg, 22%) as a white solid. $^1$H NMR (400 MHz, DMSO-d$_6$) δ ppm 11.40 (s, 1H), 8.34 (s, 1H), 8.26 (s, 1H), 8.07 (t, J=8.0 Hz, 2H), 7.96 (t, J=8.0 Hz, 2H), 7.69 (d, J=12.0 Hz, 2H), 4.37-4.48 (m, 4H), 4.30-4.36 (m, 2H), 2.89-3.08 (m, 2H), 2.69-2.83 (m, 2H), 2.39 (s, 6H), 2.09-2.19 (m, 2H). MS (ESI): 541.1 [M+H]$^+$.

Example 78: 5⁴-(1-Methyl-1,2,3,6-tetrahydropyridin-4-yl)-1⁴H-6-oxa-3-aza-2(2,6)-pyridina-1(3,4)-triazola-5(1,2)-benzenacyclodecaphan-4-one

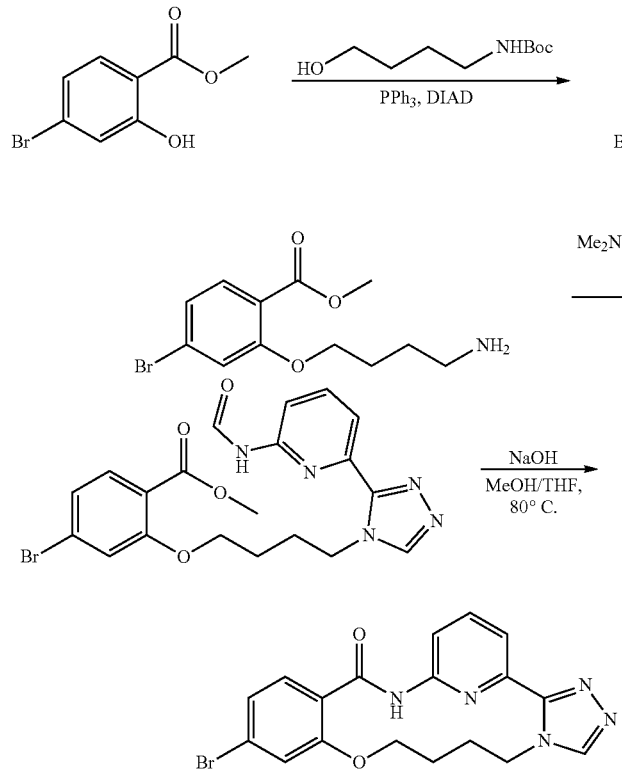

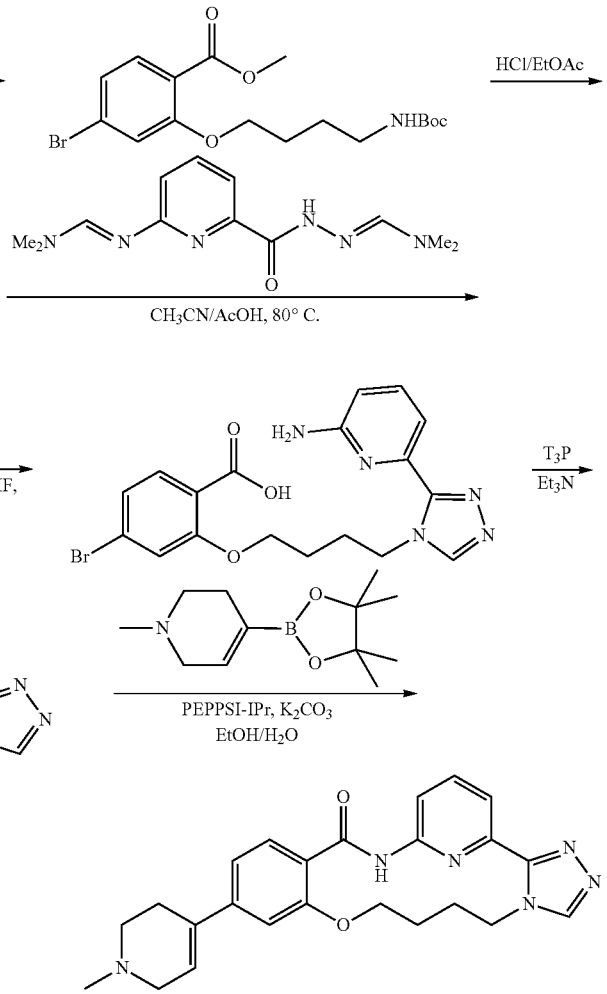

crude product (5 g), which was purified by chromatography on silica gel using DCM/MeOH (100/1 to 10/1) as eluent to give the title compound (4.5 g, 52%) as an oil. MS (ESI): 403.8 [(M+H) ($^{81}$Br)]⁺.

Step A. Methyl 4-bromo-2-(4-((tert-butoxycarbonyl)amino)butoxy)benzoate

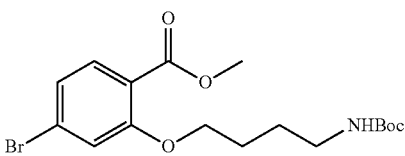 [SMILES: COC(=O)c1ccc(Br)cc1OCCCCNC(=O)OC(C)(C)C]

To a solution of methyl 4-bromo-2-hydroxybenzoate (5 g, 21.6 mmol) in THF (30 mL) was added tert-butyl (4-hydroxybutyl)carbamate (4.91 g, 26 mmol) and PPh₃ (6.81 g, 26 mmol) and the mixture was stirred at 28° C. for 10 min. After this time DIAD (5.5 mL, 28.1 mmol) was added dropwise over 1 min and the mixture was stirred at 28° C. for 2 h. After this time, the mixture was concentrated and petroleum ether/EtOAc (20 mL, 5/1) was added. The mixture was filtered and the filtrate was concentrated to give the crude product (5 g), which was purified by chromatography on silica gel using DCM/MeOH (100/1 to 10/1) as eluent to give the title compound (4.5 g, 52%) as an oil. MS (ESI): 403.8 [(M+H) ($^{81}$Br)]⁺.

Step B. Methyl 2-(4-aminobutoxy)-4-bromobenzoate

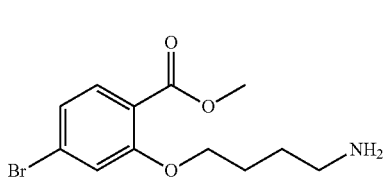 [SMILES: COC(=O)c1ccc(Br)cc1OCCCCN]

A solution of methyl 4-bromo-2-(4-((tert-butoxycarbonyl)amino)butoxy)benzoate (4.5 g, 11.2 mmol) in HCl/EtOAc (50 mL) with stirred at 28° C. for 5 h. After this time the mixture was concentrated to afford the title compound (6.5 g) which was used without further purification in the next step. MS (ESI): 304.0 [(M+H) ($^{81}$Br)]⁺.

Step C. Methyl 4-bromo-2-(4-(3-(6-formamidopyridin-2-yl)-4H-1,2,4-triazol-4-yl)butoxy)benzoate

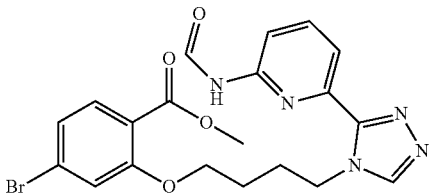 [SMILES: COC(=O)c1ccc(Br)cc1OCCCCn1cnnc1-c1cccc(NC=O)n1]

To a solution of methyl 2-(4-aminobutoxy)-4-bromobenzoate (5.7 g, 18.9 mmol) in CH$_3$CN/AcOH (20 mL, 1/1) was added (E)-N'-(6-(2-((E)-(dimethylamino)methylene)hydrazine-1-carbonyl)pyridin-2-yl)-N,N-dimethylformimidamide (3.8 g, 14.5 mmol) and the mixture was stirred at 80° C. for 17 h. After this time the mixture was concentrated to afford the crude product which was purified by chromatography on silica gel using petroleum ether/EtOAc (100/1 to 0/1) as eluent to give the title compound (4.5 g) as a white solid. MS (ESI): 474.1 [(M+H) ($^{79}$Br)]$^+$.

Step D. 2-(4-(3-(6-Aminopyridin-2-yl)-4H-1,2,4-triazol-4-yl)butoxy)-4-bromobenzoic acid

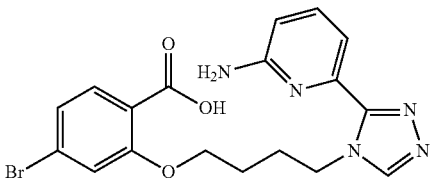 [SMILES: Nc1cccc(-c2nncn2CCCCOc2cc(Br)ccc2C(=O)O)n1]

To a solution of methyl 4-bromo-2-(4-(3-(6-formamidopyridin-2-yl)-4H-1,2,4-triazol-4-yl)butoxy)benzoate (4.5 g, 9.5 mmol) in MeOH/THF (40 mL, 1/1) was added NaOH (1.14 g, 28.5 mmol) and the mixture was stirred at 80° C. for 15 h. After this time the mixture was concentrated to afford the title compound (4.2 g) as a yellow solid, which was used without further purification in the next step. MS (ESI): 434.0 [(M+H) ($^{81}$Br)]$^+$.

Step E. 5$^4$-Bromo-1$^4$H-6-oxa-3-aza-2(2,6)-pyridina-1(3,4)-triazola-5(1,2)-benzenacyclodecaphan-4-one

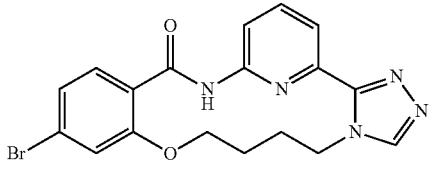 [SMILES: O=C1Nc2cccc(n2)-c2nncn2CCCCOc2cc(Br)ccc21]

A solution of 2-(4-(3-(6-aminopyridin-2-yl)-4H-1,2,4-triazol-4-yl)butoxy)-4-bromobenzoic acid (4.0 g, 9.25 mmol) in triethylamine/T$_3$P (≥50 wt. % in EtOAc) (80 mL, 1:1) was stirred at 50° C. for 3 h. After this time water (50 mL) was added and the mixture was extracted with DCM/MeOH (10/1, 3×100 mL). The combined organic extracts were washed with water, dried over Na$_2$SO$_4$, filtered and concentrated to give the crude product which was purified by column chromatography on silica gel with DCM/MeOH (30/1 to 20/1) as eluent to give the title compound (1.02 g, 27%) as a white solid. $^1$H NMR (400 MHz, DMSO-d$_6$) δ ppm 11.08 (s, 1H), 8.68 (s, 1H), 8.06 (t, J=7.2 Hz, 1H), 7.83-7.95 (m, 3H), 7.52 (s, 1H), 7.37 (d, J=8.6 Hz, 1H), 4.36 (s, 2H), 4.17-4.30 (m, 2H), 2.37-2.46 (m, 2H), 1.88-1.99 (m, 2H). MS (ESI): 414.0 [(M+H) ($^{79}$Br)]$^+$.

Step F. 5$^4$-(1-Methyl-1,2,3,6-tetrahydropyridin-4-yl)-1$^4$H-6-oxa-3-aza-2(2,6)-pyridina-1(3,4)-triazola-5(1,2)-benzenacyclodecaphan-4-one

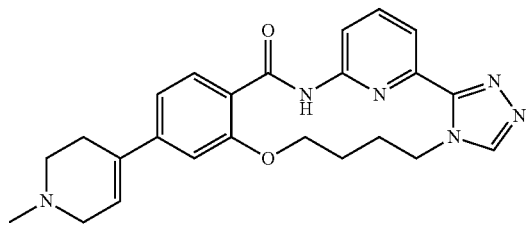 [SMILES: CN1CC=C(c2ccc3c(c2)OCCCCn2cnnc2-c2cccc(n2)NC3=O)CC1]

To a solution of 5$^4$-bromo-1$^4$H-6-oxa-3-aza-2(2,6)-pyridina-1(3,4)-triazola-5(1,2)-benzenacyclodecaphan-4-one (150 mg, 0.36 mmol) in EtOH/H$_2$O (95%, 3 mL) under a N$_2$ atmosphere was added 1-methyl-4-(4,4,5,5-tetramethyl-1,3,2-dioxaborolan-2-yl)-1,2,3,6-tetrahydropyridine (160 mg, 0.7 mmol) and K$_2$CO$_3$ (149 mg, 1.08 mmol) followed by PEPPSI-IPr (24.5 mg, 0.04 mmol). The mixture was stirred at 95° C. for 1 h. After this time the mixture was concentrated to give the crude product, which was purified by pre-HPLC (using a Waters Xbridge Prep OBD C18, 5 μm 150×30 mm column and using water (containing 0.05% NH$_3$.H$_2$O)/CH$_3$CN, from 28% to 58% as the mobile phase at a flow rate of 25 mL/min) to give the the title compound (70 mg, 45%) as a yellow solid. $^1$H NMR (400 MHz, DMSO-d$_6$) δ ppm 11.32 (s, 1H), 8.66 (s, 1H), 7.86-8.06 (m, 2H), 7.82-7.85 (m, 2H), 7.22-7.25 (m, 2H), 6.38 (s, 1H), 4.37-4.38 (m, 2H), 4.22-4.27 (m, 2H), 3.17-3.18 (m, 2H), 2.70-2.71 (m, 2H), 2.55-2.56 (m, 4H), 2.37 (s, 3H), 1.95-1.96 (m, 2H). MS (ESI): 431.2 [M+H]$^+$.

Example 79: 5$^4$-(1-Methylpiperidin-4-yl)-1$^4$H-6-oxa-3-aza-2(2,6)-pyridina-1(3,4)-triazola-5(1,2)-benzenacyclodecaphan-4-one

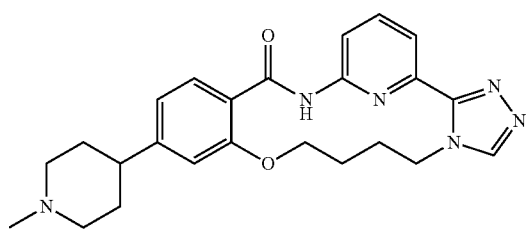 [SMILES: CN1CCC(c2ccc3c(c2)OCCCCn2cnnc2-c2cccc(n2)NC3=O)CC1]

To a solution of 5$^4$-(1-methyl-1,2,3,6-tetrahydropyridin-4-yl)-1$^4$H-6-oxa-3-aza-2(2,6)-pyridina-1(3,4)-triazola-5(1,2)-benzenacyclodecaphan-4-one (55 mg, 0.13 mmol) in MeOH (30 mL) was added Pd (15 mg, 10% on C). The mixture was stirred under a H$_2$ atmosphere (45 psi) at 30° C. for 2 h. After this time the mixture was concentrated to give the crude product, which was purified by HPLC (using an Xtimate C18, 5 μm 150×25 mm column and using water (containing 10 mM NH$_4$HCO$_3$)/CH$_3$CN, from 30% to 50% as the mobile phase at a flow rate of 25 mL/min) to give the title compound (40 mg, 72%) as a yellow solid. $^1$H NMR (400 MHz, DMSO-d$_6$) δ ppm 11.30 (s, 1H), 8.68 (s, 1H), 8.04 (d, J=7.6 Hz, 1H), 7.83-7.95 (m, 3H), 7.14 (s, 1H), 7.05 (d, J=8.0 Hz, 1H), 4.34 (br, 2H), 4.25 (t, J=8.0 Hz, 2H), 2.86 (d, J=11.2 Hz, 2H), 2.51-2.52 (m, 1H), 2.48-2.49 (m, 2H), 2.19 (s, 3H), 1.93-1.98 (m, 4H), 1.68-1.74 (m, 4H). MS (ESI): 433.2 [M+H]$^+$.

Example 80: 5$^4$-Morpholino-1$^4$H-6-oxa-3-aza-2(2,6)-pyridina-1(3,4)-triazola-5(1,2)-benzenacyclodecaphan-4-one

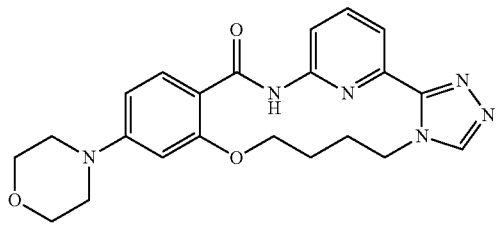 [SMILES: O=C1Nc2cccc(n2)-c2nncn2CCCCOc2cc(N3CCOCC3)ccc21]

A mixture of 5$^4$-bromo-1$^4$H-6-oxa-3-aza-2(2,6)-pyridina-1(3,4)-triazola-5(1,2)-benzenacyclodecaphan-4-one (100 mg, 0.24 mmol), morpholine (42 μL, 0.48 mmol), RuPhos (22 mg, 0.048 mmol), Pd$_2$(dba)$_3$ (22 mg, 0.024 mmol) and NaO$^t$Bu (46 mg, 0.48 mmol) in dioxane (2.5 mL) and THF (2.5 mL) was stirred at 100° C. under N$_2$ for 2 h. After this time the mixture was concentrated and DMSO (5 mL) was added. The mixture was purified by HPLC (using an Xtimate C18, 5 μm 150×25 mm column and using water (containing 10 mM NH$_4$HCO$_3$)/CH$_3$CN, from 36% to 56% as the mobile phase at a flow rate of 25 mL/min) to give the title compound (52 mg, 51%) as white solid. $^1$H NMR (400 MHz, DMSO-d$_6$) δ ppm 11.29 (s, 1H), 8.65 (s, 1H), 7.95-8.03 (m, 1H), 7.84-7.89 (m, 2H), 7.80 (d, J=7.2 Hz, 1H), 6.66-6.73 (m, 1H), 6.63 (s, 1H), 4.32 (s, 2H), 4.18-4.28 (m, 2H), 3.65-3.79 (m, 4H), 3.29 (s, 4H), 2.50 (s, 2H), 1.94 (s, 2H). MS (ESI): 421.2 [M+H]$^+$.

Example 81: 5$^4$-(4-Methylpiperazin-1-yl)-1$^4$H-6-oxa-3-aza-2(2,6)-pyridina-1(3,4)-triazola-5(1,2)-benzenacyclodecaphan-4-one

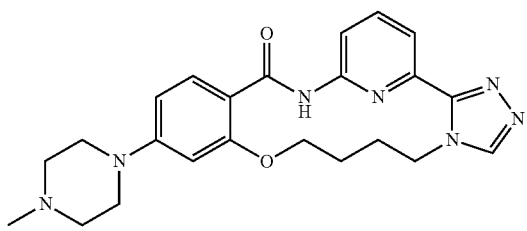 [SMILES: CN1CCN(c2ccc3c(c2)OCCCCn2cnnc2-c2cccc(n2)NC3=O)CC1]

To a solution of 5$^4$-bromo-1$^4$H-6-oxa-3-aza-2(2,6)-pyridina-1(3,4)-triazola-5(1,2)-benzenacyclodecaphan-4-one (80 mg, 0.19 mmol) in dioxane/THF (3 mL, 1:1) under a N$_2$ atmosphere was added 1-methylpiperazine (39 mg, 0.38 mmol) and NaO$^t$Bu (37 mg, 0.38 mmol) followed by Pd$_2$(dba)$_3$ (17.7 mg, 0.02 mmol) and Ruphos (18 mg, 0.02 mmol). The mixture was stirred at 110° C. for 2 h. After this time the reaction was concentrated and purified by HPLC (using a Waters Xbridge Prep OBD C18, 5 μm 150×30 mm column and using water (containing 0.05% NH$_3$.H$_2$O and 10 mM NH$_4$HCO$_3$)/CH$_3$CN, from 20% to 50% as the mobile phase at a flow rate of 25 mL/min) to give the title compound (33 mg, 39%) as a white solid. $^1$H NMR (400 MHz, DMSO-d$_6$) δ ppm 11.30 (s, 1H), 8.67 (s, 1H), 8.00 (t, J=8.4 Hz, 1H), 7.80-7.88 (m, 3H), 6.68-6.70 (m, 1H), 6.62 (d, J=2.0 Hz, 1H), 4.27-4.36 (m, 2H), 4.22-4.26 (m, 2H), 3.31-3.33 (m, 4H), 2.49-2.55 (m, 2H), 2.41-2.47 (m, 4H), 2.23 (s, 3H), 1.90-1.95 (m, 2H). MS (ESI): 434.2 [M+H]$^+$.

Example 82: (S)-5$^4$-(2,4-Dimethylpiperazin-1-yl)-1$^4$H-6-oxa-3-aza-2(2,6)-pyridina-1(3,4)-triazola-5(1,2)-benzenacyclodecaphan-4-one and Example 83: (R)-5$^4$-(2,4-Dimethylpiperazin-1-yl)-1$^4$H-6-oxa-3-aza-2(2,6)-pyridina-1(3,4)-triazola-5(1,2)-benzenacyclodecaphan-4-one

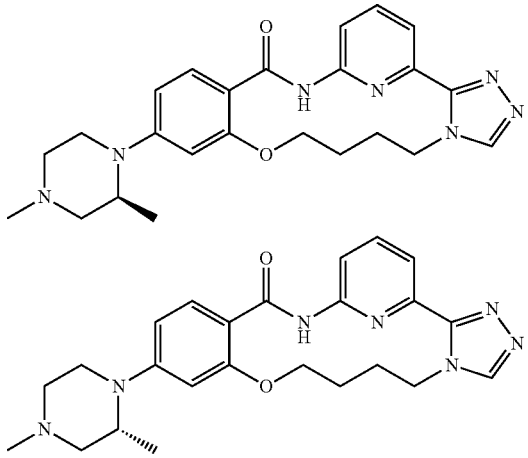

To a solution of 5$^4$-bromo-1$^4$H-6-oxa-3-aza-2(2,6)-pyridina-1(3,4)-triazola-5(1,2)-benzenacyclodecaphan-4-one (200 mg, 0.48 mmol) in THF/dioxane (6 mL, 1:1) under a N$_2$ atmosphere was added NaO$^t$Bu (93 mg, 0.96 mmol) and 1,3-dimethylpiperazine (110 mg, 0.96 mmol) followed by Pd$_2$(dba)$_3$ (44 mg, 0.048 mmol) and Ruphos (45 mg, 0.096 mmol). The mixture was stirred at 110° C. for 2 h. After this time the solvent was removed under reduced pressure and the residue was purified by HPLC (using a Phenomenex Synergi C18, 4 μm 150×30 mm column and using water (containing 0.05% HCl)/CH$_3$CN, from 14% to 34% as the mobile phase at a flow rate of 25 mL/min) to give the title compound (55 mg, 24%) as a mixture of enantiomers. Chiral separation (55 mg, 0.123 mmol) was performed by SFC (using a DAICEL CHIRALPAK AS-H, 5 μm 250×30 mm column and using 45% EtOH (containing 0.1% NH$_4$OH) in CO$_2$ as the mobile phase at a flow rate of 40 mL/min) to give in order of elution:

Peak 1: (22 mg, 40%, absolute stereochemistry was arbitrarily assigned)$^1$H NMR (400 MHz, DMSO-d$_6$) δ ppm 11.30 (s, 1H), 8.67 (s, 1H), 8.0 (t, J=8.0 Hz, 1H), 7.80-7.89 (m, 3H), 6.65 (d, J=8.8 Hz, 1H), 6.56 (s, 1H), 4.32-4.37 (m, 2H), 4.23-4.27 (m, 3H), 3.59-3.62 (m, 1H), 3.04-3.07 (m, 1H), 2.84-2.87 (m, 1H), 2.70-2.73 (m, 1H), 2.50-2.56 (m, 3H), 2.18-2.25 (m, 3H), 1.94-2.01 (m, 3H), 1.12 (d, J=6.4 Hz, 3H). MS (ESI): 448.3 [M+H]$^+$.

Peak 2: (24 mg, 44%, absolute stereochemistry was arbitrarily assigned) $^1$H NMR (400 MHz, DMSO-d$_6$) δ ppm 11.30 (s, 1H), 8.67 (s, 1H), 8.0 (t, J=8.0 Hz, 1H), 7.80-7.89 (m, 3H), 6.65 (d, J=8.8 Hz, 1H), 6.56 (s, 1H), 4.32-4.37 (m, 2H), 4.23-4.27 (m, 3H), 3.59-3.62 (m, 1H), 3.04-3.07 (m, 1H), 2.84-2.87 (m, 1H), 2.70-2.73 (m, 1H), 2.50-2.56 (m, 3H), 2.18-2.25 (m, 3H), 1.94-2.01 (m, 3H), 1.12 (d, J=6.4 Hz, 3H). MS (ESI): 448.3 [M+H]$^+$.

Example 84: 5$^4$-(1-Methyl-1H-pyrazol-4-yl)-1$^4$H-6-oxa-3-aza-2(2,6)-pyridina-1(3,4)-triazola-5(1,2)-benzenacyclodecaphan-4-one To a solution of 5$^4$-bromo-1$^4$H-6-oxa-3-aza-2(2,6)-pyridina-1(3,4)-triazola-5(1,2)-benzenacyclodecaphan-4-one (100 mg, 0.24 mmol) in dioxane (5 mL) and H$_2$O (1 mL) was added 1-methyl-4-(4,4,5,5-tetramethyl-1,3,2-dioxaborolan-2-yl)-1H-pyrazole (75 mg, 0.36 mmol), Pd(dppf)Cl$_2$ (18 mg, 0.024 mmol) and K$_2$CO$_3$ (67 mg, 0.48 mmol). The mixture was degassed by purging with N$_2$ and stirred at 95° C. for 16 h. After this time, the mixture was concentrated to give the crude product, which was purified by HPLC (using an Xtimate C18, 5 μm 150×25 mm column and using water (containing 10 mM NH$_4$HCO$_3$)/CH$_3$CN, from 25% to 55% as the mobile phase at a flow rate of 25 mL/min) to give the title compound (40 mg, 40%) as a red solid. $^1$H NMR (400 MHz, DMSO-d$_6$) δ ppm 11.35 (s, 1H), 8.69 (s, 1H), 8.35 (s, 1H), 8.03-8.10 (m, 2H), 8.00 (d, J=8.0 Hz, 1H), 7.92 (d, J=8.2 Hz, 1H), 7.86 (d, J=7.2 Hz, 1H), 7.47 (s, 1H), 7.38 (d, J=8.2 Hz, 1H), 4.40-4.47 (m, 2H), 4.24-4.33 (m, 2H), 3.89 (s, 3H), 2.53-2.54 (m, 2H), 1.96-2.05 (m, 2H). MS (ESI): 416.2 [M+H]$^+$.

Example 85: 5$^5$-Fluoro-5$^4$-(1-methyl-1,2,3,6-tetrahydropyridin-4-yl)-1$^4$H-6-oxa-3-aza-2(2,6)-pyridina-1(3,4)-triazola-5(1,2)-benzenacyclodecaphan-4-one

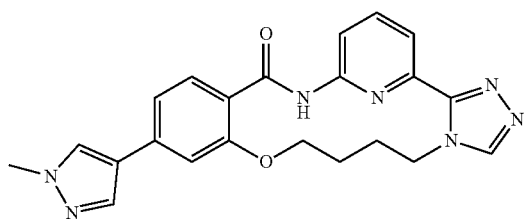 [SMILES: Cn1cc(-c2ccc3c(c2)OCCCCn2cnnc2-c2cccc(n2)NC3=O)cn1]

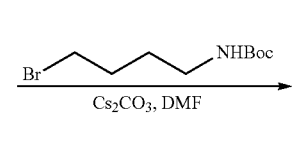

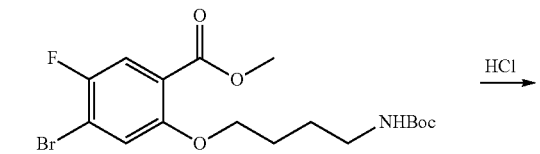

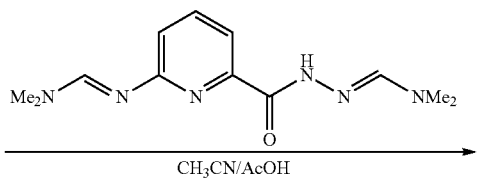

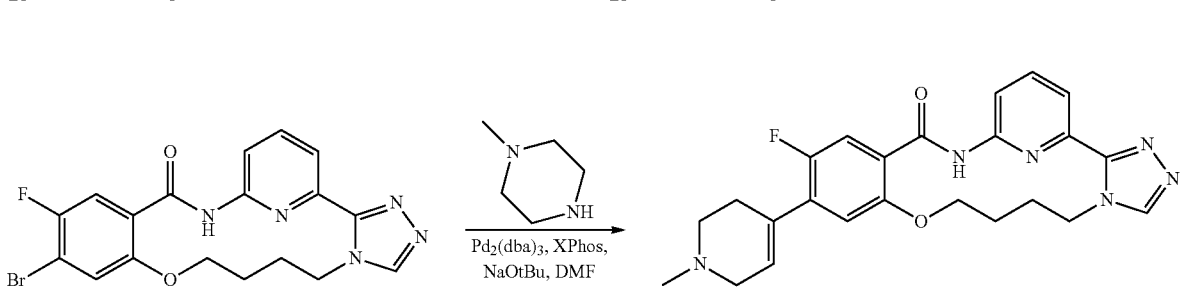

Step A. Methyl 4-bromo-2-(4-((tert-butoxycarbonyl)amino)butoxy)-5-fluorobenzoate

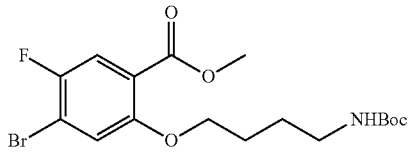 [SMILES: COC(=O)c1cc(F)c(Br)cc1OCCCCNC(=O)OC(C)(C)C]

To a solution of methyl 4-bromo-5-fluoro-2-hydroxybenzoate (360 mg, 1.44 mmol) in DMF (8 mL) was added tert-butyl (4-bromobutyl)carbamate (438 mg, 1.73 mmol) and Cs$_2$CO$_3$ (939 mg, 2.88 mmol) and the reaction was stirred at 25° C. for 18 h. After this time, the mixture was poured into water (20 mL) and extracted with EtOAc (3×20 mL). The combined organic extracts were washed with brine (20 mL), dried over Na$_2$SO$_4$, filtered and concentrated under vacuum to give the crude product, which was purified by column chromatography on silica using petroleum ether/EtOAc (10/1 to 5/1) as eluent to give the title compound (500 mg, 83%) as a yellow solid. $^1$H NMR (400 MHz, DMSO-d$_6$) δ ppm 7.59 (d, J=8.8 Hz, 1H), 7.47 (d, J=5.2 Hz, 1H), 6.85-6.81 (m, 1H), 4.01-4.04 (m, 2H), 3.77 (s, 3H), 2.91-2.96 (m, 2H), 1.61-1.67 (m, 2H), 1.37-1.54 (m, 2H), 1.35 (s, 9H).

Step B. Methyl 2-(4-aminobutoxy)-4-bromo-5-fluorobenzoate

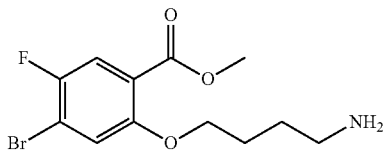 [SMILES: COC(=O)c1cc(F)c(Br)cc1OCCCCN]

To a solution of methyl 4-bromo-2-(4-((tert-butoxycarbonyl)amino)butoxy)-5-fluorobenzoate (500 mg, 1.2 mmol) in DCM (5 mL) was added HCl/EtOAc (5 mL, 4M) and the mixture was stirred at 23° C. for 1 h. After this time the mixture was concentrated under vacuum to give the title compound (450 mg, 96%) as a white solid.

Step C. Methyl 4-bromo-5-fluoro-2-(4-(3-(6-formamidopyridin-2-yl)-4H-1,2,4-triazol-4-yl)butoxy)benzoate

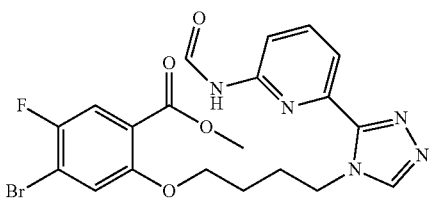 [SMILES: COC(=O)c1cc(F)c(Br)cc1OCCCCn1cnnc1-c1cccc(NC=O)n1]

To a solution of methyl 2-(4-aminobutoxy)-4-bromo-5-fluorobenzoate (450 mg, 1.15 mmol) in AcOH/CH$_3$CN (1/1, 10 mL) was added (E)-N'-(6-(2-((E)-(dimethylamino)methylene)hydrazine-1-carbonyl)pyridin-2-yl)-N,N-dimethylformimidamide (452 mg, 1.72 mmol) and the mixture was stirred at 28° C. for 18 h. After this time the mixture was adjusted to pH 7-8 by addition of sat. aq. NaHCO$_3$ followed by extraction with DCM/MeOH (10/1, 3×20 mL). The combined organic layers were washed with brine (20 mL), dried over Na$_2$SO$_4$, filtered and concentrated under vacuum to give the crude product, which was purified by preparative TLC (100% EtOAc) and column chromatography on silica gel using DCM/MeOH (30/1) as eluent to give the title compound (200 mg, 36%) as a yellow oil. MS (ESI): 516.1 [(M+Na) ($^{81}$Br)]$^+$.

Step D. 2-(4-(3-(6-Aminopyridin-2-yl)-4H-1,2,4-triazol-4-yl)butoxy)-4-bromo-5-fluorobenzoic acid

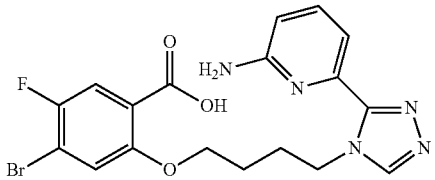 [SMILES: Nc1cccc(-c2nncn2CCCCOc2cc(Br)c(F)cc2C(=O)O)n1]

To a solution of methyl 4-bromo-5-fluoro-2-(4-(3-(6-formamidopyridin-2-yl)-4H-1,2,4-triazol-4-yl)butoxy)benzoate (200 mg, 0.4 mmol) in MeOH (8 mL) was added NaOH (52 mg, 1.2 mmol) and the mixture was stirred at 70° C. for 3 h. After this time the reaction was concentrated under vacuum to give the crude product, which was lyophilized to give the title product (300 mg, crude) as a yellow solid. MS (ESI): 451.9 [(M+H) ($^{81}$Br)]$^+$.

Step E. 5$^4$-Bromo-5$^5$-fluoro-1$^4$H-6-oxa-3-aza-2(2,6)-pyridina-1(3,4)-triazola-5(1,2)-benzenacyclodecaphan-4-one

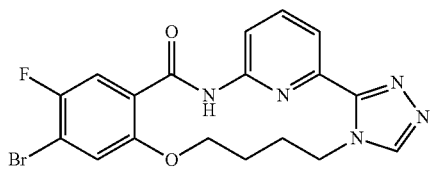

A solution of 2-(4-(3-(6-aminopyridin-2-yl)-4H-1,2,4-triazol-4-yl)butoxy)-4-bromo-5-fluorobenzoic acid (290 mg, crude) in triethylamine/T$_3$P (≥50 wt. % in EtOAc) (1/1, 8 mL) was heated at 110° C. in a microwave reactor for 3 minutes. After this time the mixture was poured into water (15 mL) and extracted with DCM/MeOH (10/1, 3×15 mL). The combined organic extracts were washed with brine (20 mL), dried over Na$_2$SO$_4$, filtered and concentrated under vacuum to give the crude product, which was purified by column chromatography on silica using DCM/MeOH (1/0 to 30/1) to give the title compound (110 mg, 55% over two steps) as a yellow solid. MS (ESI): 432.1 [(M+H) ($^{79}$Br)]$^+$.

Step F. 5⁵-Fluoro-5⁴-(1-methyl-1,2,3,6-tetrahydro-pyridin-4-yl)-1⁴H-6-oxa-3-aza-2(2,6)-pyridina-1(3,4)-triazola-5(1,2)-benzenacyclodecaphan-4-one

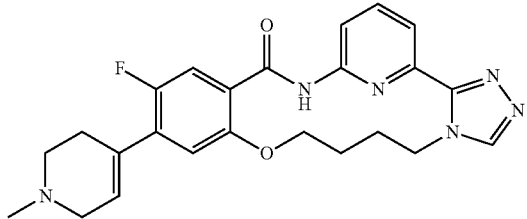 [SMILES: CN1CC=C(c2cc3c(cc2F)C(=O)Nc2cccc(n2)-c2nncn2CCCCO3)CC1]

To a solution of 5⁴-bromo-5⁵-fluoro-1⁴H-6-oxa-3-aza-2(2,6)-pyridina-1(3,4)-triazola-5(1,2)-benzenacyclodecaphan-4-one (150 mg, 0.35 mmol) in EtOH (5 mL) and water (1 mL) was added 1-methyl-4-(4,4,5,5-tetramethyl-1,3,2-dioxaborolan-2-yl)-1,2,3,6-tetrahydropyridine (116 mg, 0.52 mmol), PEPPSI-IPr catalyst (24 mg, 0.035 mmol) and K₂CO₃ (96 mg, 0.65 mmol). The mixture was degassed by purging with N₂ followed by stirring at 95° C. for 2 h. After this time, the mixture was filtered and the filtrate was concentrated to give the crude product, which was dissolved in DCM (25 mL) and MeOH (2.5 mL) and stirred at 30° C. for 0.5 h. The mixture was filtered and the filtrate was concentrated to give the title compound (120 mg, 77%) as a white solid. ¹H NMR (400 MHz, DMSO-d₆) δ ppm 11.33 (s, 1H), 8.68 (s, 1H), 8.02-8.09 (m, 1H), 7.83-7.90 (m, 2H), 7.68 (d, J=11.6 Hz, 1H), 7.19 (d, J=6.2 Hz, 1H), 6.17 (s, 1H), 4.36 (t, J=4.6 Hz, 2H), 4.22-4.29 (m, 2H), 3.16 (s, 1H), 3.04 (d, J=2.8 Hz, 2H), 2.53-2.58 (m, 3H), 2.45 (d, J=7.4 Hz, 2H), 2.28 (s, 3H), 1.90-2.00 (m, 2H). MS (ESI): 449.3 [M+H]⁺.

Example 86: 5⁵-Fluoro-5⁴-(1-methylpiperidin-4-yl)-1⁴H-6-oxa-3-aza-2(2,6)-pyridina-1(3,4)-triazola-5(1,2)-benzenacyclodecaphan-4-one

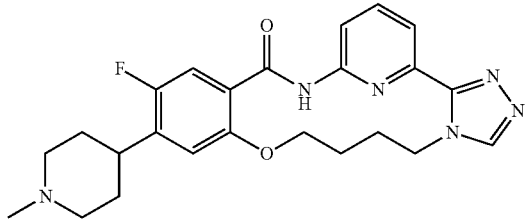

To the mixture of 5⁵-fluoro-5⁴-(1-methyl-1,2,3,6-tetrahydropyridin-4-yl)-1⁴H-6-oxa-3-aza-2(2,6)-pyridina-1(3,4)-triazola-5(1,2)-benzenacyclodecaphan-4-one (95 mg, 0.21 mmol) in MeOH (25 mL) was added Pd (20 mg, 0.019 mmol, 10% on C). The mixture was stirred at 35° C. under a hydrogen atmosphere (40 psi) for 4 h. After this time the mixture was filtered to remove the Pd/C and the filtrate was concentrated to give the title compound (60 mg, 63%) as a white solid. ¹H NMR (400 MHz, DMSO-d₆) δ ppm 11.30 (s, 1H), 8.62 (s, 1H), 8.03-8.08 (m, 1H), 7.85-7.94 (m, 2H), 7.69 (d, J=11.0 Hz, 1H), 7.22 (d, J=5.8 Hz, 1H), 4.39 (t, J=5.0 Hz, 2H), 4.25-4.33 (m, 2H), 2.90 (d, J=11.8 Hz, 2H), 2.78-2.86 (m, 1H), 2.53-2.55 (m, 2H), 2.23 (s, 3H), 1.99-2.06 (m, 3H), 1.78-1.89 (m, 3H), 1.70-1.78 (m, 2H). MS (ESI): 451.1 [M+H]⁺.

Example 87: 5⁵-Fluoro-5⁴-morpholino-1⁴H-6-oxa-3-aza-2(2,6)-pyridina-1(3,4)-triazola-5(1,2)-benzenacyclodecaphan-4-one

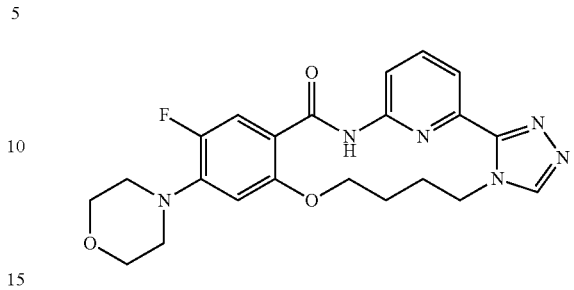

A solution of 5⁴-bromo-5⁵-fluoro-1⁴H-6-oxa-3-aza-2(2,6)-pyridina-1(3,4)-triazola-5(1,2)-benzenacyclodecaphan-4-one (80 mg, 0.18 mmol), morpholine (81 µL, 0.92 mmol), RuPhos (17 mg, 0.037 mmol), Pd₂(dba)₃ (17 mg, 0.018 mmol) and NaOⁱBu (35 mg, 0.37 mmol) in dioxane (2 mL) and THF (2 mL) was stirred under N₂ at 100° C. for 2 h. After this time the mixture was concentrated and DMF (5 mL) was added. The crude product was purified by HPLC (using an Xtimate C18, 5 µm 150×25 mm column and using water (containing 10 mM NH₄HCO₃)/CH₃CN, from 26% to 46% as the mobile phase at a flow rate of 25 mL/min) to give the title compound (31 mg, 37%) as white solid. ¹H NMR (400 MHz, DMSO-d₆) δ ppm 11.34 (s, 1H), 8.68 (s, 1H), 8.02-8.08 (m, 1H), 7.88 (d, J=8.4 Hz, 1H), 7.85 (d, J=6.8 Hz, 1H), 7.67 (d, J=14.4 Hz, 1H), 6.78 (d, J=7.6 Hz, 1H), 4.37 (t, J=4.8 Hz, 2H), 4.22-4.31 (m, 2H), 3.70-3.81 (m, 4H), 3.16-3.27 (m, 4H), 2.52-2.53 (s, 2H), 1.92-2.04 (s, 2H). MS (ESI): 439.3 [M+H]⁺.

Example 88: 5⁵-Fluoro-5⁴-((2-methoxyethyl)amino)-1⁴H-6-oxa-3-aza-2(2,6)-pyridina-1(3,4)-triazola-5(1,2)-benzenacyclodecaphan-4-one

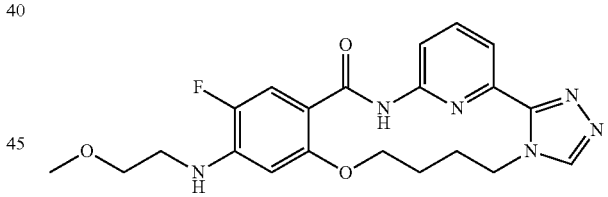

To a solution of 5⁴-bromo-5⁵-fluoro-1⁴H-6-oxa-3-aza-2(2,6)-pyridina-1(3,4)-triazola-5(1,2)-benzenacyclodecaphan-4-one (200 mg, 0.46 mmol) in DMF (5 mL) under a N₂ atmosphere was added 2-methoxyethan-1-amine (0.4 mL, 4.63 mmol), Pd₂(dba)₃ (42 mg, 0.05 mmol), XPhos (44 mg, 0.09 mmol) and NaOⁱBu (133 mg, 1.4 mmol) at 30° C. The mixture was degassed by purging with N₂ and it was heated at 110° C. for 16 h. After this time the mixture was filtered and the filtrate was purified by HPLC (using a Waters Xbridge Prep OBD C18, 5 µm 150×30 mm column and using water (containing 0.04% NH₃.H₂O and 10 mM NH₄HCO₃)/CH₃CN, from 22% to 52% as the mobile phase at a flow rate of 25 mL/min) to give the title compound (47 mg, 24%) as a white solid. ¹H NMR (400 MHz, DMSO-d₆) δ ppm 11.32 (s, 1H), 8.68 (s, 1H), 7.97-8.05 (m, 1H), 7.79-7.90 (m, 2H), 7.56 (d, J=12.8 Hz, 1H), 6.52 (d, J=7.2 Hz, 1H), 6.36-6.45 (m, 1H), 4.20-4.37 (m, 4H), 3.48-3.59 (m, 2H), 3.37-3.43 (m, 2H), 3.29 (s, 3H), 2.40-2.46 (m, 2H), 1.92-2.03 (m, 2H). MS (ESI): 427.2 [M+H]⁺.

Example 89: (R)-8-Methyl-1⁴H-6-oxa-3-aza-2(2,6)-pyridina-1(3,4)-triazola-5(1,2)-benzenacyclodecaphan-4-one and Example 90: (S)-8-Methyl-1⁴H-6-oxa-3-aza-2(2,6)-pyridina-1(3,4)-triazola-5(1,2)-benzenacyclodecaphan-4-one
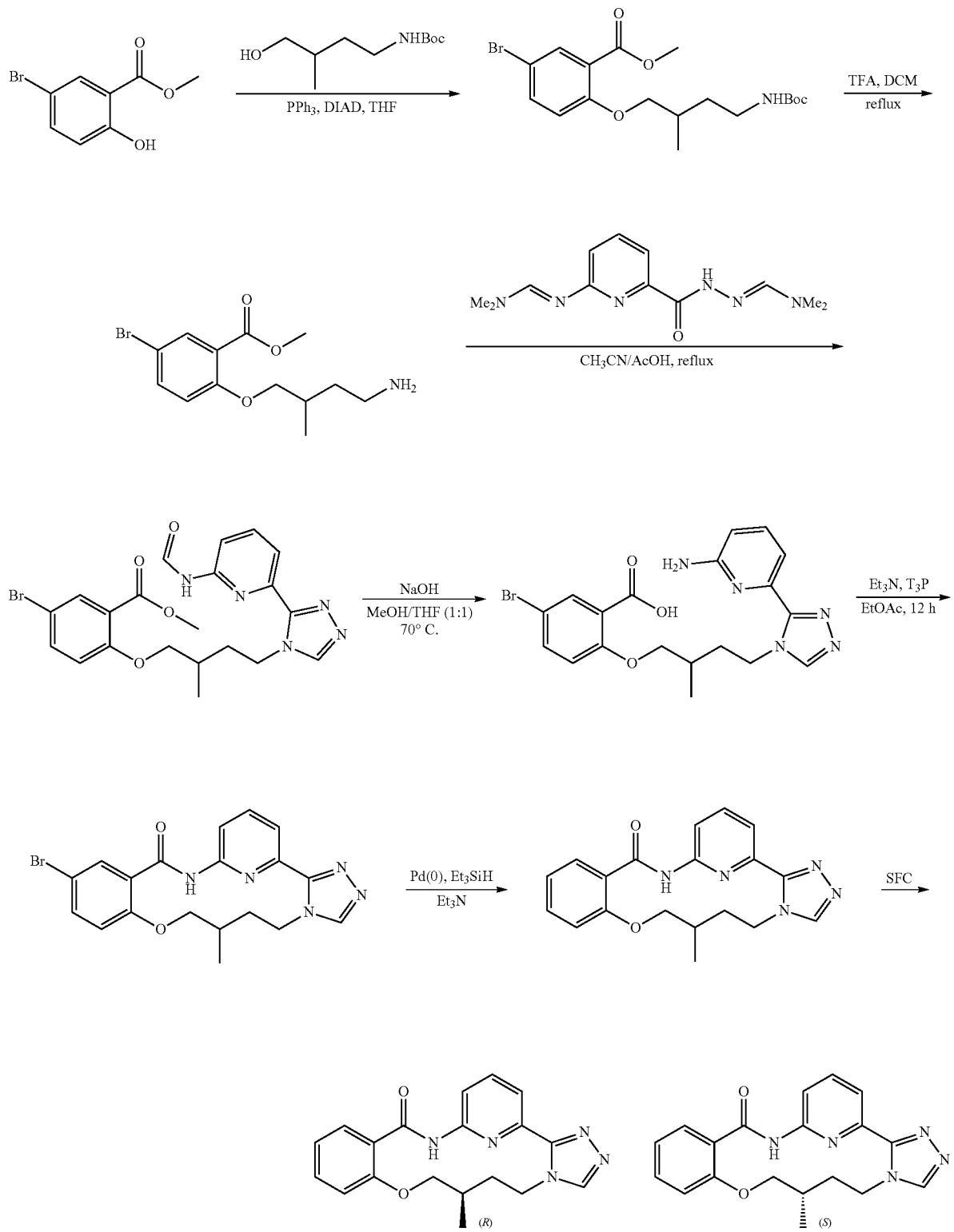

Step A. rac-Methyl 5-bromo-2-(4-((tert-butoxycarbonyl)amino)-2-methylbutoxy)benzoate

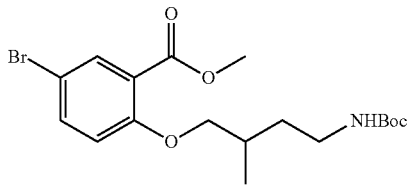 [SMILES: COC(=O)c1cc(Br)ccc1OCC(C)CCNC(=O)OC(C)(C)C]

The title compound was synthesized according to the general procedure described in Example 1, Step A and using methyl 5-bromo-2-hydroxy-benzoate (10 g, 43.3 mmol) to give the desired product (8.8 g, 49%) as a white solid. $^1$H NMR (400 MHz, CDCl$_3$) δ ppm 7.80-8.08 (m, 1H), 7.41-7.64 (m, 1H), 6.71-6.96 (m, 1H), 4.79-4.93 (m, 1H), 3.89 (s, 3H), 3.79-3.88 (m, 2H), 3.13-3.30 (m, 2H), 2.00-2.17 (m, 1H), 1.65-1.80 (m, 1H), 1.50-1.59 (m, 1H), 1.43 (s, 9H), 1.08 (d, J=6.8 Hz, 3H). MS (ESI): 438.0 [(M+Na) ($^{79}$Br)]$^+$.

Step B. rac-Methyl 2-(4-amino-2-methylbutoxy)-5-bromobenzoate

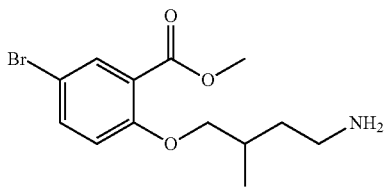 [SMILES: COC(=O)c1cc(Br)ccc1OCC(C)CCN]

The title compound was synthesized according to the general procedure described in Example 1, Step B and using rac-methyl 5-bromo-2-(4-((tert-butoxycarbonyl)amino)-2-methylbutoxy)benzoate (12.7 g, 30.5 mmol) to give the desired product (9.1 g, 94%) as a colorless oil. $^1$H NMR (400 MHz, CDCl$_3$) δ ppm 7.96 (d, J=2.5 Hz, 1H), 7.56 (dd, J=8.9, 2.6 Hz, 1H), 6.85 (d, J=9.0 Hz, 1H), 6.14-7.08 (m, 2H), 3.86-3.93 (m, 2H), 3.85 (s, 3H), 3.02-3.21 (m, 2H), 2.13-2.30 (m, 1H), 1.84-1.98 (m, 1H), 1.70-1.84 (m, 1H), 1.05 (d, J=6.8 Hz, 3H). MS (ESI): 316.1 [(M+H) ($^{79}$Br)]$^+$.

Step C. rac-Methyl 5-bromo-2-(4-(3-(6-formamidopyridin-2-yl)-4H-1,2,4-triazol-4-yl)-2-methylbutoxy)benzoate

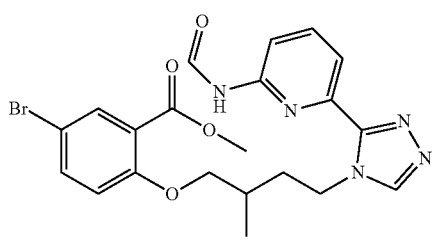 [SMILES: COC(=O)c1cc(Br)ccc1OCC(C)CCn1cnnc1-c1cccc(NC=O)n1]

The title compound was synthesized according to the general procedure described in Example 1, Step C and using rac-methyl 2-(4-amino-2-methylbutoxy)-5-bromobenzoate (9.1 g, 28.8 mmol) and N,6-bis[(Z)-dimethylaminomethyleneamino]pyridine-2-carboxamide (3.8 g, 14.4 mmol) to give the title compound (4.9 g, 69%) as the major product as a yellow oil which was used without further purification in the next step. MS (ESI): 488.0 [(M+H) ($^{79}$Br)]$^+$.

Step D. rac-2-(4-(3-(6-Aminopyridin-2-yl)-4H-1,2,4-triazol-4-yl)-2-methylbutoxy)-5-bromobenzoic acid

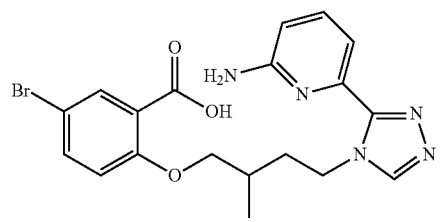 [SMILES: CC(CCn1cnnc1-c1cccc(N)n1)COc1ccc(Br)cc1C(=O)O]

The title compound was synthesized according to the general procedure described in Example 1, Step D and using rac-methyl-5-bromo-2-(4-(3-(6-formamidopyridin-2-yl)-4H-1,2,4-triazol-4-yl)-2-methylbutoxy)benzoate (4.9 g, 10.0 mmol) to give the desired product as a yellow solid. The crude product was carried forward in Step E without further purification. MS (ESI): 446.1 [(M+H) ($^{79}$Br)]$^+$.

Step E. rac-5$^5$-Bromo-8-methyl-1$^4$H-6-oxa-3-aza-2(2,6)-pyridina-1(3,4)-triazola-5(1,2)-benzenacyclodecaphan-4-one

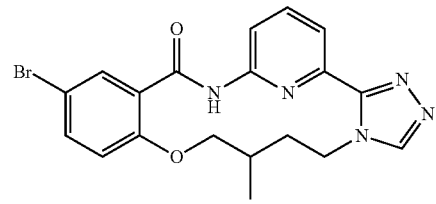 [SMILES: CC1CCn2cnnc2-c2cccc(n2)NC(=O)c2cc(Br)ccc2OC1]

The title compound was synthesized according to the general procedure described in Example 1, Step E and using rac-2-(4-(3-(6-aminopyridin-2-yl)-4H-1,2,4-triazol-4-yl)-2-methylbutoxy)-5-bromobenzoic acid (0.5 g, 1.1 mmol) to give the desired product (220 mg, 36%) as a beige solid. $^1$H NMR (400 MHz, CD$_3$OD) δ ppm 9.20 (s, 1H) 8.21 (d, J=2.8 Hz, 1H) 8.01-8.13 (m, 2H) 7.95 (d, J=7.3 Hz, 1H) 7.72 (dd, J=8.8, 2.8 Hz, 1H) 7.23 (d, J=9.0 Hz, 1H) 4.52 (s, 2H) 4.34-4.41 (m, 1H) 3.96-4.06 (m, 1H) 2.10-2.24 (m, 1H) 1.70-1.86 (m, 2H) 1.30-1.38 (m, 1H) 1.27 (d, J=7.0 Hz, 3H). MS (ESI): 428.1 [(M+H) ($^{79}$Br)]$^+$.

Step F: rac-8-Methyl-1⁴H-6-oxa-3-aza-2(2,6)-pyridina-1(3,4)-triazola-5(1,2)-benzenacyclodecaphan-4-one

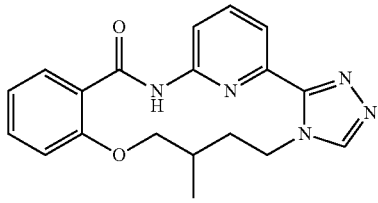 [SMILES: CC1CCn2cnnc2-c2cccc(n2)NC(=O)c2ccccc2OC1]

The title compound was synthesized according to the general procedure described in Example 2 and using rac-5⁵-bromo-8-methyl-1⁴H-6-oxa-3-aza-2(2,6)-pyridina-1(3,4)-triazola-5(1,2)-benzenacyclodecaphan-4-one (63 mg, 0.15 mmol) to give the title compound (30 mg, 0.07 mmol, 44%). MS (ESI): 350.1 [M+H]⁺.

Step G: (R)-8-Methyl-1⁴H-6-oxa-3-aza-2(2,6)-pyridina-1(3,4)-triazola-5(1,2)-benzenacyclodecaphan-4-one and (S)-8-Methyl-1⁴H-6-oxa-3-aza-2(2,6)-pyridina-1(3,4)-triazola-5(1,2)-benzenacyclodecaphan-4-one

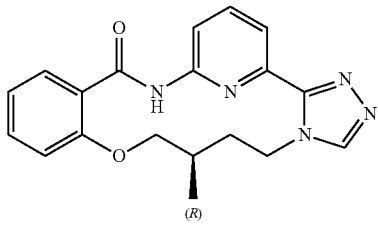

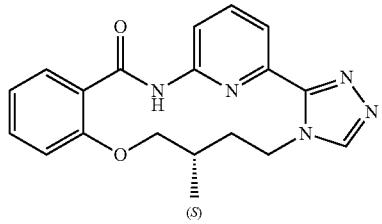

rac-8-Methyl-1⁴H-6-oxa-3-aza-2(2,6)-pyridina-1(3,4)-triazola-5(1,2)-benzenacyclodecaphan-4-one (24 mg) was purified by SFC (using a Chiralpak OD-H, 5 μm 250×30 mm column and using 45% MeOH (containing 0.1% Et₂NH) in CO₂ as the mobile phase at a flow rate of 100 mL/min (ABPR 120 bar, MBPR 40 psi)) to give in order of elution: (R)-8-methyl-1⁴H-6-oxa-3-aza-2(2,6)-pyridina-1(3,4)-triazola-5(1,2)-benzenacyclodecaphan-4-one (8 mg, 33%, absolute stereochemistry arbitrarily assigned) and (S)-8-methyl-1⁴H-6-oxa-3-aza-2(2,6)-pyridina-1(3,4)-triazola-5(1,2)-benzenacyclodecaphan-4-one (8 mg, 33%, absolute stereochemistry arbitrarily assigned). ¹H NMR (400 MHz, CDCl₃) δ ppm 11.41 (s, 1H), 8.25 (br d, J=1.8 Hz, 1H), 8.24 (s, 1H), 8.02 (d, J=8.0 Hz, 1H), 7.99 (d, J=7.5 Hz, 1H), 7.90 (d, J=8.0 Hz, 1H), 7.47-7.55 (m, 1H), 7.16 (t, J=7.4 Hz, 1H), 7.02 (d, J=8.3 Hz, 1H), 4.40 (dt, J=4.0, 12.9 Hz, 1H), 4.30-4.15 (m, 2H), 3.92 (t, J=9.7 Hz, 1H), 3.41-3.55 (m, 1H), 2.11 (br d, J=7.0 Hz, 1H), 1.58-1.73 (m, 1H), 1.24 (d, J=7.0 Hz, 3H). MS (ESI): 350.1 [M+H]⁺.

Example 91: (S)-10-Methyl-1⁴H-6-oxa-3-aza-2(2,6)-pyridina-1(3,4)-triazola-5(1,2)-benzenacyclodecaphan-4-one and Example 92: (R)-10-Methyl-1⁴H-6-oxa-3-aza-2(2,6)-pyridina-1(3,4)-triazola-5(1,2)-benzenacyclodecaphan-4-one

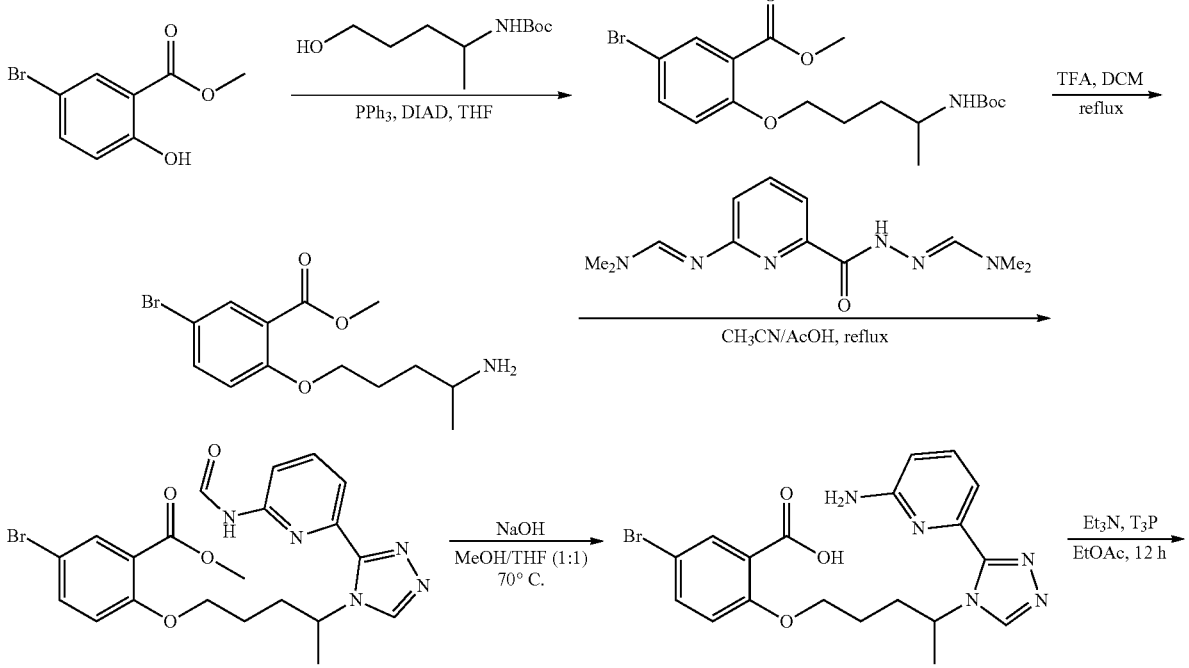

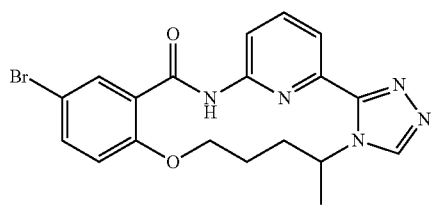
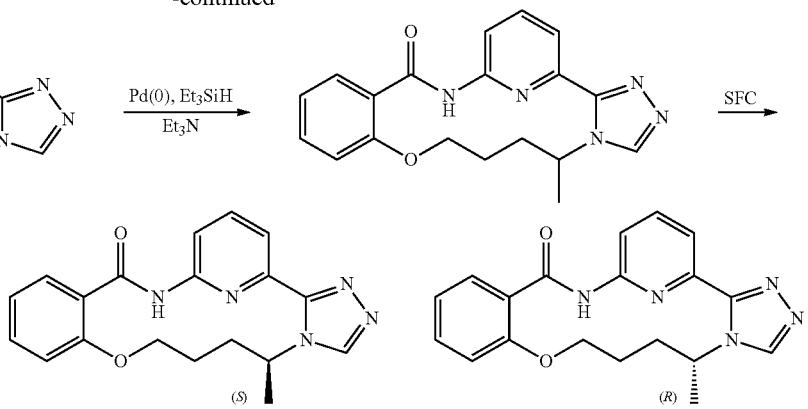

Step A. rac-Methyl 5-bromo-2-((4-((tert-butoxycarbonyl)amino)pentyl)oxy)benzoate

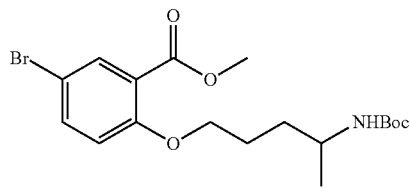 [SMILES: COC(=O)c1cc(Br)ccc1OCCCC(C)NC(=O)OC(C)(C)C]

The title compound was synthesized according to the general procedure described in Example 1, Step A and using methyl 5-bromo-2-hydroxy-benzoate (5.0 g, 21.6 mmol) to give the desired product (5.8 g, 64%) as a colorless oil. $^1$H NMR (400 MHz, CDCl$_3$) δ ppm 7.90 (d, J=2.5 Hz, 1H), 7.53 (dd, J=8.8, 2.5 Hz, 1H), 6.85 (d, J=8.8 Hz, 1H), 4.43-4.62 (m, 1H), 4.03 (t, J=6.0 Hz, 2H), 3.89 (s, 3H), 3.70 (br s, 1H), 1.80-1.94 (m, 2H), 1.61-1.71 (m, 1H), 1.43 (s, 9H), 1.25-1.33 (m, 1H), 1.17 (d, J=6.5 Hz, 3H). MS (ESI): 438.0 [(M+Na) ($^{79}$Br)]$^+$.

Step B. rac-methyl 2-((4-aminopentyl)oxy)-5-bromobenzoate

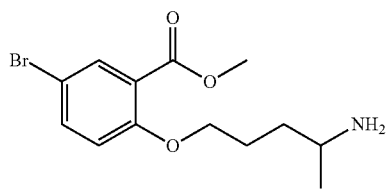 [SMILES: COC(=O)c1cc(Br)ccc1OCCCC(C)N]

The title compound was synthesized according to the general procedure described in Example 1, Step B and using rac-methyl 5-bromo-2-((4-((tert-butoxycarbonyl)amino)pentyl)oxy)benzoate (5.7 g, 13.7 mmol) to give the desired product (4.5 g) as a colorless oil which was used without further purification. $^1$H NMR (400 MHz, CDCl$_3$) δ ppm 7.94 (d, J=2.8 Hz, 1H), 7.55 (dd, J=8.9, 2.6 Hz, 1H), 6.83 (d, J=8.8 Hz, 1H), 5.81-7.05 (m, 2H), 3.99-4.08 (m, 2H), 3.84 (s, 3H), 3.33-3.45 (m, 1H), 1.77-2.03 (m, 4H), 1.33 (d, J=6.5 Hz, 3H). MS (ESI): 316.1 [(M+H) ($^{79}$Br)]$^+$.

Step C. rac-Methyl 5-bromo-2-((4-(3-(6-formamidopyridin-2-yl)-4H-1,2,4-triazol-4-yl)pentyl)oxy)benzoate

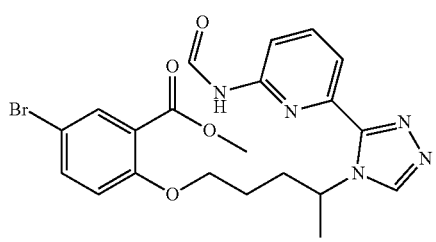 [SMILES: COC(=O)c1cc(Br)ccc1OCCCC(C)n1cnnc1-c1cccc(NC=O)n1]

The title compound was synthesized according to the general procedure described in Example 1, Step C and using rac-methyl 2-((4-aminopentyl)oxy)-5-bromobenzoate (4.5 g, 14.3 mmol) and N,6-bis[(E)-dimethylaminomethyleneamino]pyridine-2-carboxamide (1.5 g, 5.7 mmol) to give the title compound (1.6 g, 60%) as the major product as a yellow oil which was used without further purification in the next step. MS (ESI): 488.0 [(M+H) ($^{79}$Br)]$^+$.

Step D. rac-2-((4-(3-(6-Aminopyridin-2-yl)-4H-1,2,4-triazol-4-yl)pentyl)oxy)-5-bromobenzoic acid The title compound was synthesized according to the general procedure described in Example 1, Step D and using rac-methyl 5-bromo-2-(4-(3-(6-formamidopyridin-2-yl)-4H-1,2,4-triazol-4-yl)-2-methylbutoxy)benzoate (1.6 g, 3.41 mmol) to give the desired product as a yellow solid.

Step E: rac-5⁵-Bromo-10-methyl-1⁴H-6-oxa-3-aza-2 (2,6)-pyridina-1(3,4)-triazola-5(1,2)-benzenacyclo-decaphan-4-one

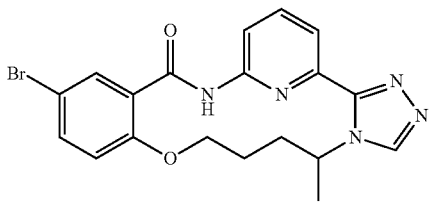

The title compound was synthesized according to the general procedure described in Example 1, Step E and using rac-2-((4-(3-(6-aminopyridin-2-yl)-4H-1,2,4-triazol-4-yl)pentyl)oxy)-5-bromobenzoic acid (0.5 g, 1.1 mmol) to give the desired product (178 mg, 39%) as a beige solid. $^1$H NMR (400 MHz, CD$_3$OD) δ ppm 9.14 (s, 1H), 8.13 (s, 1H), 8.01-8.06 (m, 1H), 7.93-7.97 (m, 1H), 7.86 (d, J=7.3 Hz, 1H), 7.65 (br d, J=8.8 Hz, 1H), 7.12 (d, J=9.0 Hz, 1H), 4.71-4.82 (m, 1H), 4.42-4.52 (m, 1H), 4.13-4.24 (m, 1H), 3.23-3.31 (m, 1H), 2.17-2.33 (m, 1H), 1.82-1.95 (m, 2H), 1.68 (d, J=6.8 Hz, 3H). MS (ESI): 428.1 [(M+H) ($^{79}$Br)]$^+$.

Step F: rac-10-Methyl-1⁴H-6-oxa-3-aza-2(2,6)-pyridina-1(3,4)-triazola-5(1,2)-benzenacyclode-caphan-4-one

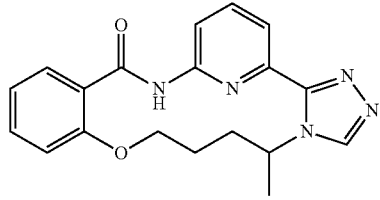 [SMILES: CC1CCCOc2ccccc2C(=O)Nc2cccc(n2)-c2nncn21]

The title compound was synthesized according to the general procedure described in Example 2 and using rac-5⁵-bromo-10-methyl-1⁴H-6-oxa-3-aza-2(2,6)-pyridina-1(3,4)-triazola-5(1,2)-benzenacyclodecaphan-4-one (61 mg, 0.14 mmol) to give the title compound (20 mg, 40%) as a white solid. MS (ESI): 350.1 [M+H]$^+$.

Step G: (S)-10-Methyl-1⁴H-6-oxa-3-aza-2(2,6)-pyridina-1(3,4)-triazola-5(1,2)-benzenacyclode-caphan-4-one and (R)-10-Methyl-1⁴H-6-oxa-3-aza-2 (2,6)-pyridina-1(3,4)-triazola-5(1,2)-benzenacyclodecaphan-4-one

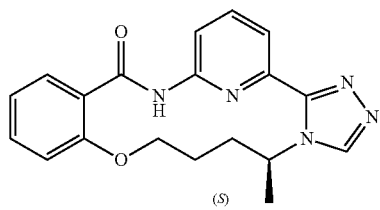

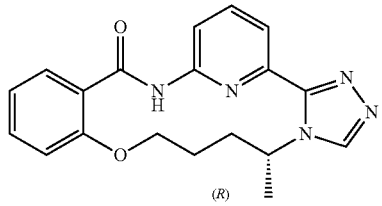

rac-10-Methyl-1⁴H-6-oxa-3-aza-2(2,6)-pyridina-1(3,4)-triazola-5(1,2)-benzenacyclodecaphan-4-one (11 mg) was purified by SFC (using a Chiralpak OD-H, 5 μm 250×300 mm column and using 45% MeOH (containing 0.1% Et$_2$NH) in CO$_2$ as the mobile phase at a flow rate of 100 mL/min (ABPR 120 BAR, MBPR 40 PSI)) to give in order of elution (S)-10-methyl-1⁴H-6-oxa-3-aza-2(2,6)-pyridina-1 (3,4)-triazola-5(1,2)-benzenacyclodecaphan-4-one (4 mg, 36%, absolute stereochemistry was arbitrarily assigned) and (R)-10-methyl-1⁴H-6-oxa-3-aza-2(2,6)-pyridina-1(3,4)-triazola-5(1,2)-benzenacyclodecaphan-4-one (4 mg, 36%, absolute stereochemistry was arbitrarily assigned). $^1$H NMR (400 MHz, CDCl$_3$) δ ppm 11.44 (s, 1H), 8.30 (s, 1H), 8.19 (dd, J=7.8, 1.8 Hz, 1H), 7.92-7.96 (m, 1H), 7.87-7.91 (m, 1H), 7.84 (d, J=7.8 Hz, 1H), 7.45 (ddd, J=8.3, 7.4, 1.9 Hz, 1H), 7.06-7.12 (m, 1H), 6.94 (d, J=7.8 Hz, 1H), 4.63-4.74 (m, 1H), 4.39 (dt, J=9.2, 3.2 Hz, 1H), 4.07-4.14 (m, 1H), 3.34-3.40 (m, 1H), 2.10-2.24 (m, 1H), 1.68-1.88 (m, 2H), 1.57 (d, J=7.0 Hz, 3H). MS (ESI): 350.1 [M+H]$^+$.

Example 93: (R)-10-Methyl-5⁵-(4-methyl-1H-imidazol-1-yl)-1⁴H-6-oxa-3-aza-2(2,6)-pyridina-1(3,4)-triazola-5(1,2)-benzenacyclodecaphan-4-one and Example 94: (S)-10-Methyl-5⁵-(4-methyl-1H-imidazol-1-yl)-1⁴H-6-oxa-3-aza-2(2,6)-pyridina-1(3,4)-triazola-5(1,2)-benzenacyclodecaphan-4-one

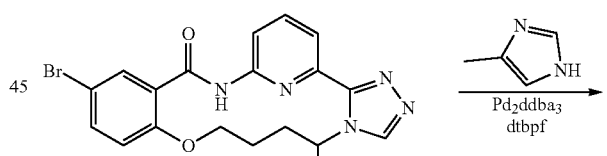

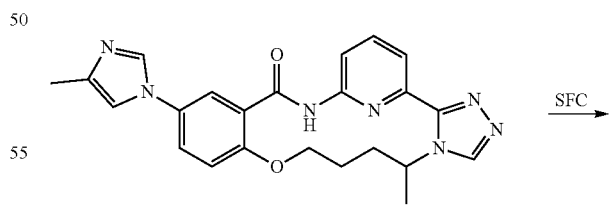

107

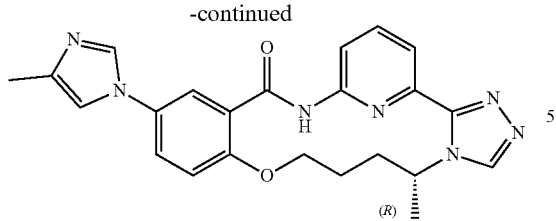

Step A. rac-10-Methyl-5⁵-(4-methyl-1H-imidazol-1-yl)-1⁴H-6-oxa-3-aza-2(2,6)-pyridina-1(3,4)-triazola-5(1,2)-benzenacyclodecaphan-4-one The title compound was synthesized according to the general procedure described in Example 21 and using rac-5⁵-bromo-10-methyl-1⁴H-6-oxa-3-aza-2(2,6)-pyridina-1(3,4)-triazola-5(1,2)-benzenacyclodecaphan-4-one (120 mg, 0.28 mmol) to give the desired product (11 mg, 0.03 mmol, 9%).

Step B. (S)-10-Methyl-5⁵-(4-methyl-1H-imidazol-1-yl)-1⁴H-6-oxa-3-aza-2(2,6)-pyridina-1(3,4)-triazola-5(1,2)-benzenacyclodecaphan-4-one and (R)-10-Methyl-5⁵-(4-methyl-1H-imidazol-1-yl)-1⁴H-6-oxa-3-aza-2(2,6)-pyridina-1(3,4)-triazola-5(1,2)-benzenacyclodecaphan-4-one

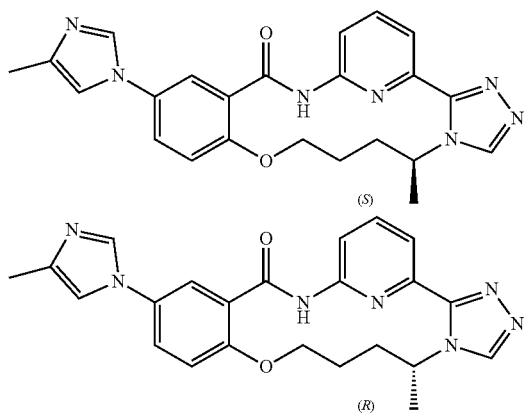

rac-10-Methyl-5⁵-(4-methyl-1H-imidazol-1-yl)-1⁴H-6-oxa-3-aza-2(2,6)-pyridina-1(3,4)-triazola-5(1,2)-benzenacyclodecaphan-4-one (11 mg) was purified by SFC (Chiralpak OD-H, 5 μm 30×250 mm column and using 45% MeOH (containing 0.1% Et₂NH) in CO₂ as the mobile phase at a flow rate of 100 mL/min (ABPR 120 bar, MBPR 40 psi)) to give in order of elution: (S)-10-methyl-5⁵-(4-methyl-1H-imidazol-1-yl)-1⁴H-6-oxa-3-aza-2(2,6)-pyridina-1(3,4)-triazola-5(1,2)-benzenacyclodecaphan-4-one (5 mg, 45%, absolute stereochemistry was arbitrarily assigned) and (R)-10-methyl-5⁵-(4-methyl-1H-imidazol-1-yl)-1⁴H-6-oxa-3-aza-2(2,6)-pyridina-1(3,4)-triazola-5(1,2)-benzenacyclodecaphan-4-one (5 mg, 45%, absolute stereochemistry was arbitrarily assigned). ¹H NMR (400 MHz, CD₃OD) δ ppm 8.80 (s, 1H) 8.12 (d, J=2.8 Hz, 1H) 7.97-8.04 (m, 2H) 7.90-7.94 (m, 1H) 7.83 (dd, J=7.5, 0.8 Hz, 1H) 7.69 (dd, J=8.8, 3.0 Hz, 1H) 7.28 (d, J=9.0 Hz, 1H) 7.25 (s, 1H) 4.68 (dt, J=7.0, 3.5 Hz, 1H) 4.46-4.53 (m, 1H) 4.19 (t, J=9.8 Hz, 1H) 2.72 (q, J=7.2 Hz, 1H) 2.68-2.76 (m, 1H) 2.26 (d, J=0.8 Hz, 2H) 1.76-1.94 (m, 3H) 1.63 (d, J=6.8 Hz, 3H). MS (ESI): 430.2 [M+H]⁺.

108

Example 95: (R)-10-Methyl-5⁵-(1-methyl-1H-pyrazol-4-yl)-1⁴H-6-oxa-3-aza-2(2,6)-pyridina-1(3,4)-triazola-5(1,2)-benzenacyclodecaphan-4-one and
Example 96: (S)-10-Methyl-5⁵-(1-methyl-1H-pyrazol-4-yl)-1⁴H-6-oxa-3-aza-2(2,6)-pyridina-1(3,4)-triazola-5(1,2)-benzenacyclodecaphan-4-one

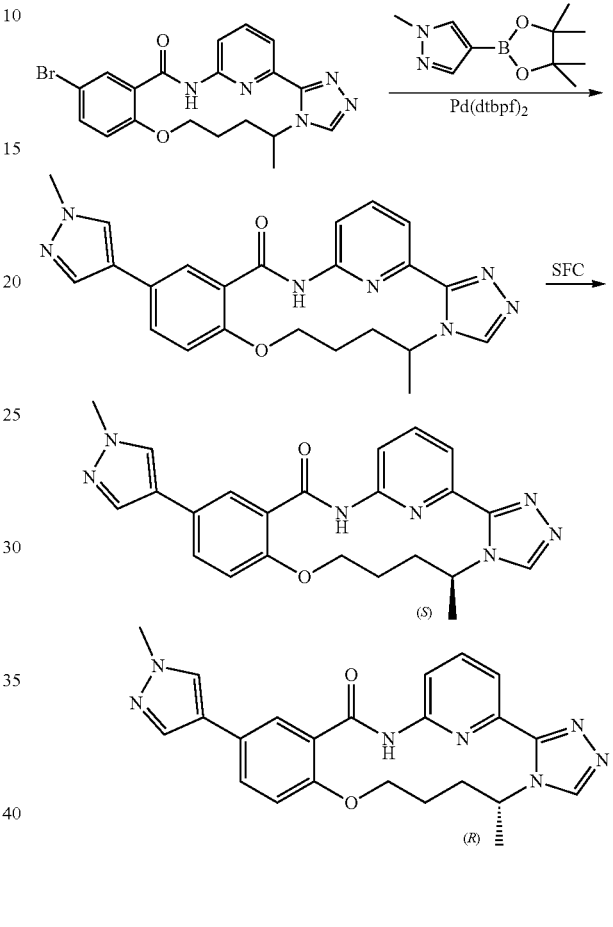

Step A. rac-10-Methyl-5⁵-(1-methyl-1H-pyrazol-4-yl)-1⁴H-6-oxa-3-aza-2(2,6)-pyridina-1(3,4)-triazola-5(1,2)-benzenacyclodecaphan-4-one

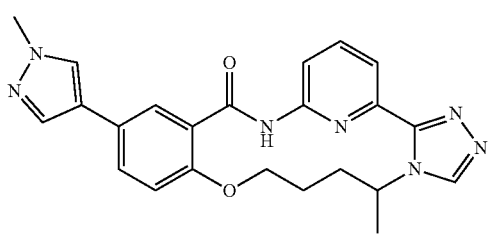 [SMILES: CC1CCCOc2ccc(-c3cnn(C)c3)cc2C(=O)Nc2cccc(n2)-c2nncn21]

The title compound was synthesized according to the general procedure described in Example 24 and using rac-5⁵-bromo-10-methyl-1⁴H-6-oxa-3-aza-2(2,6)-pyridina-1(3,4)-triazola-5(1,2)-benzenacyclodecaphan-4-one (60 mg, 0.14 mmol) and 1-methyl-4-(4,4,5,5-tetramethyl-1,3,2-dioxaborolan-2-yl)pyrazole (36 mg, 0.18 mmol) to give the title compound (15 mg, 20%).

Step B. (R)-10-Methyl-5⁵-(1-methyl-1H-pyrazol-4-yl)-1⁴H-6-oxa-3-aza-2(2,6)-pyridina-1(3,4)-triazola-5(1,2)-benzenacyclodecaphan-4-one and (S)-10-Methyl-5⁵-(1-methyl-1H-pyrazol-4-yl)-1⁴H-6-oxa-3-aza-2(2,6)-pyridina-1(3,4)-triazola-5(1,2)-benzenacyclodecaphan-4-one

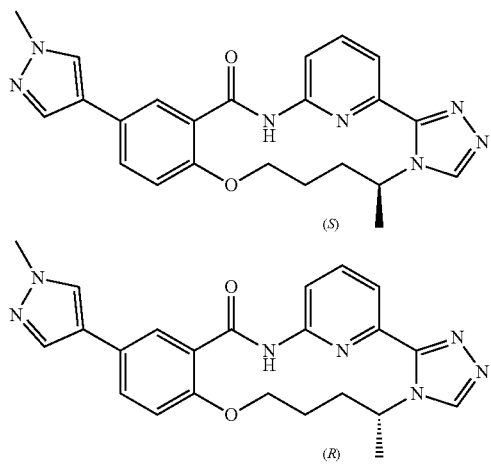

rac-10-Methyl-5⁵-(1-methyl-1H-pyrazol-4-yl)-1⁴H-6-oxa-3-aza-2(2,6)-pyridina-1(3,4)-triazola-5(1,2)-benzenacyclodecaphan-4-one (15 mg, 0.034 mmol) was purified by SFC (Chiralpak OD-H, 5 μm 30×250 mm and using 45% MeOH (containing 0.1% Et₂NH) in CO₂ as the mobile phase at a flow rate of 100 mL/min (ABPR 120 bar, MBPR 40 psi)) to give in order of elution: (S)-10-methyl-5⁵-(4-methyl-1H-imidazol-1-yl)-1⁴H-6-oxa-3-aza-2(2,6)-pyridina-1(3,4)-triazola-5(1,2)-benzenacyclodecaphan-4-one (5 mg, 33%, absolute stereochemistry was arbitrarily assigned) and (R)-10-methyl-5⁵-(4-methyl-1H-imidazol-1-yl)-1⁴H-6-oxa-3-aza-2(2,6)-pyridina-1(3,4)-triazola-5(1,2)-benzenacyclodecaphan-4-one (5 mg, 33%, absolute stereochemistry was arbitrarily assigned). $^1$H NMR (400 MHz, CD₃OD) δ ppm 8.82 (s, 1H), 8.23 (d, J=2.5 Hz, 1H), 8.02-8.07 (m, 1H), 7.97-8.00 (m, 1H), 7.95 (s, 1H), 7.84 (dd, J=7.4, 0.9 Hz, 1H), 7.80 (d, J=0.8 Hz, 1H), 7.72 (dd, J=8.5, 2.5 Hz, 1H), 7.19 (d, J=8.5 Hz, 1H), 4.72 (br s, 1H), 4.46-4.54 (m, 1H), 4.22 (br t, J=10.0 Hz, 1H), 3.93 (s, 3H), 2.26 (br s, 1H), 1.80-1.98 (m, 3H), 1.65 (d, J=6.8 Hz, 3H). MS (ESI): 430.1 [M+H]⁺.

Example 97: (S)-5⁴-Fluoro-10-methyl-1⁴H-6-oxa-3-aza-2(2,6)-pyridina-1(3,4)-triazola-5(1,2)-benzenacyclodecaphan-4-one and Example 98: (R)-5⁴-Fluoro-10-methyl-1⁴H-6-oxa-3-aza-2(2,6)-pyridina-1(3,4)-triazola-5(1,2)-benzenacyclodecaphan-4-one

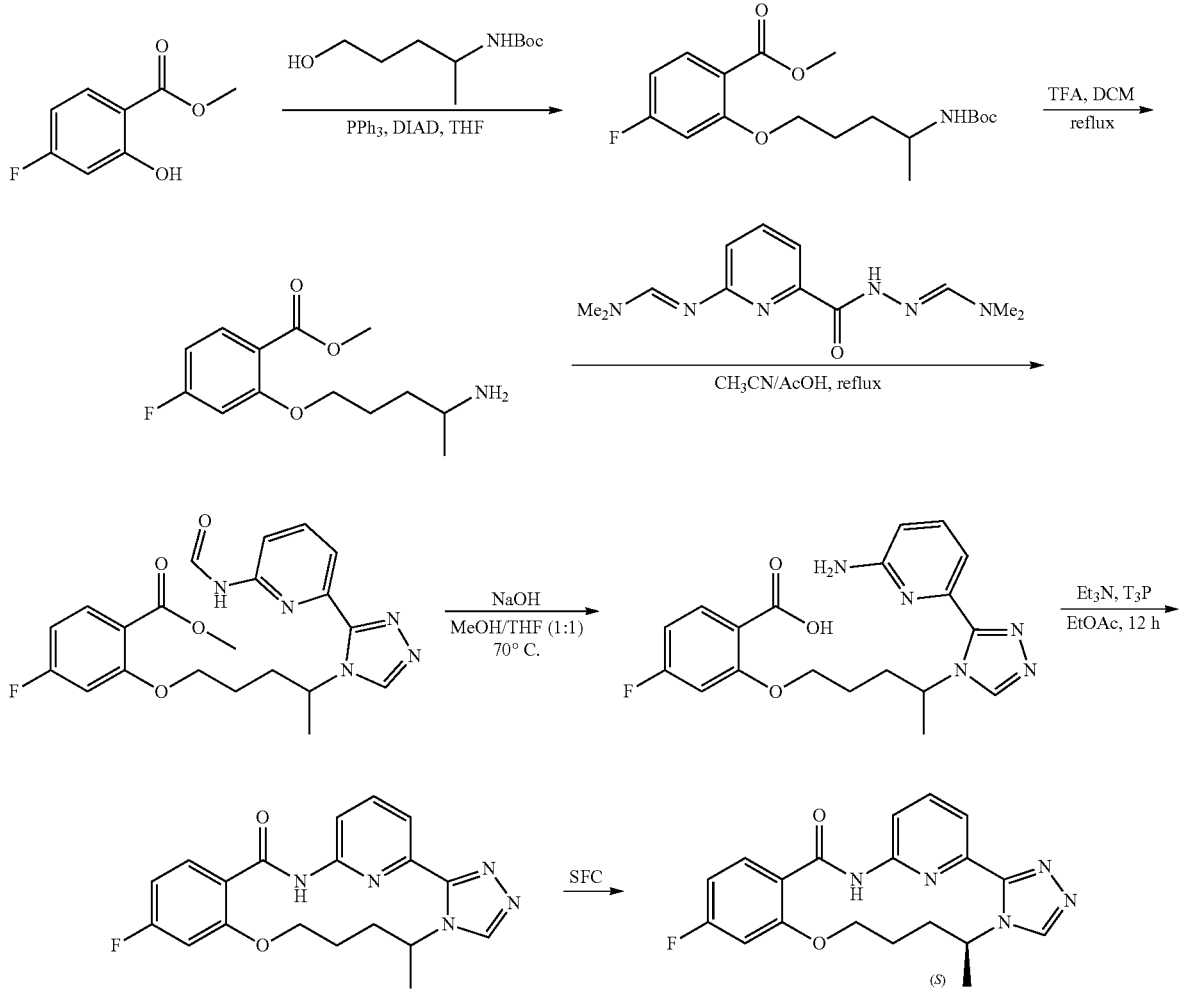

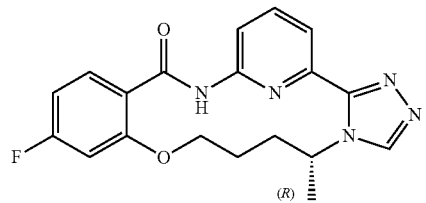

Step A. rac-Methyl 2-((4-((tert-butoxycarbonyl)amino)pentyl)oxy)-4-fluorobenzoate

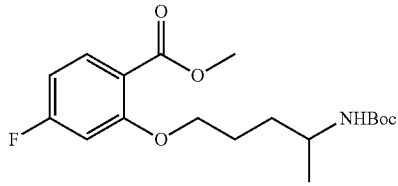 [SMILES: COC(=O)c1ccc(F)cc1OCCCC(C)NC(=O)OC(C)(C)C]

The title compound was synthesized according to the general procedure described in Example 1, Step A and using methyl 4-fluoro-2-hydroxybenzoate (5.0 g, 29.4 mmol) and tert-butyl N-(4-hydroxy-1-methyl-butyl)carbamate (5.97 g, 29.4 mmol). The product was purified by column chromatography on silica gel using Heptanes/(EtOAc/EtOH, 3/1) from 1/0 to 1/1 to give the desired product (6.8 g, 65%) as a colorless oil. $^1$H NMR (400 MHz, CDCl$_3$) δ ppm 7.84 (dd, J=6.9, 9.2 Hz, 1H), 6.62-6.69 (m, 2H), 4.52 (br s, 1H), 3.95-4.11 (m, 2H), 3.87 (s, 3H), 3.70 (br s, 1H), 1.89 (quin, J=7.1 Hz, 2H), 1.57-1.72 (m, 2H), 1.42 (s, 9H), 1.17 (d, J=6.5 Hz, 3H).

Step B. rac-Methyl 2-((4-aminopentyl)oxy)-4-fluorobenzoate

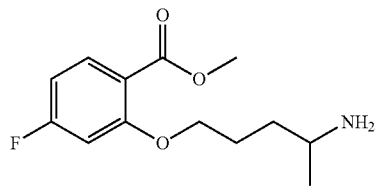 [SMILES: COC(=O)c1ccc(F)cc1OCCCC(C)N]

The title compound was synthesized according to the general procedure described in Example 1, Step B and using rac-methyl 2-((4-((tert-butoxycarbonyl)amino)pentyl)oxy)-4-fluorobenzoate (6.8 g, 19.1 mmol) to give the desired product (4.88 g, 100%) as a colorless oil which was used without further purification in the next step. $^1$H NMR (400 MHz, CDCl$_3$) δ ppm 7.86-7.93 (m, 1H), 6.62-6.72 (m, 2H), 3.99-4.14 (m, 2H), 3.83 (s, 3H), 3.37-3.49 (m, 1H), 1.78-2.10 (m, 4H), 1.31-1.40 (m, 3H).

Step C. rac-Methyl 4-fluoro-2-((4-(3-(6-formamidopyridin-2-yl)-4H-1,2,4-triazol-4-yl)pentyl)oxy)benzoate

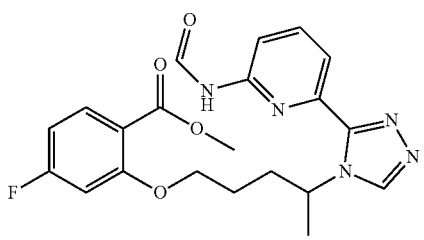 [SMILES: COC(=O)c1ccc(F)cc1OCCCC(C)n1cnnc1-c1cccc(NC=O)n1]

The title compound was synthesized according to the general procedure described in Example 1, Step C and using rac-methyl 2-((4-aminopentyl)oxy)-4-fluorobenzoate (4.8 g, 19 mmol) and N,6-bis[(E)-dimethylaminomethyleneamino]pyridine-2-carboxamide (2.5 g, 9.5 mmol) to give the title compound (2.8 g, 69%) as the major product as a yellow oil which was used without further purification in the next step.

Step D. rac-2-((4-(3-(6-Aminopyridin-2-yl)-4H-1,2,4-triazol-4-yl)pentyl)oxy)-4-fluorobenzoic acid

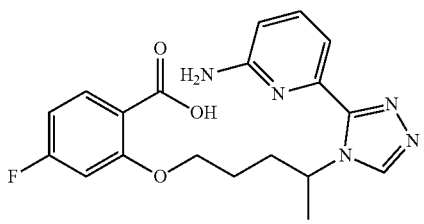 [SMILES: CC(CCCOc1cc(F)ccc1C(=O)O)n1cnnc1-c1cccc(N)n1]

The title compound was synthesized according to the general procedure described in Example 1, Step D and using rac-methyl 4-fluoro-2-((4-(3-(6-formamidopyridin-2-yl)-4H-1,2,4-triazol-4-yl)pentyl)oxy)benzoate (2.8 g, 6.5 mmol) to give the desired product (2.52 g, crude) which was used without further purification in the next step.

Step E: rac-5⁴-Fluoro-10-methyl-1⁴H-6-oxa-3-aza-2
(2,6)-pyridina-1(3,4)-triazola-5(1,2)-benzenacyclo-
decaphan-4-one

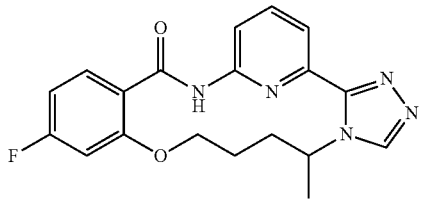 [SMILES: CC1CCCOc2cc(F)ccc2C(=O)Nc2cccc(n2)-c2nncn21]

The title compound was synthesized according to the general procedure described in Example 1, Step E and using rac-2-((4-(3-(6-aminopyridin-2-yl)-4H-1,2,4-triazol-4-yl)pentyl)oxy)-4-fluorobenzoic acid (500 mg, 1.3 mmol) to give the desired product (133 mg, 28%) as a beige solid. MS (ESI): 368.1 [M+H]⁺.

Step F: (S)-5⁴-Fluoro-10-methyl-1⁴H-6-oxa-3-aza-2
(2,6)-pyridina-1(3,4)-triazola-5(1,2)-benzenacyclo-
decaphan-4-one and (R)-5⁴-Fluoro-10-methyl-1⁴H-
6-oxa-3-aza-2(2,6)-pyridina-1(3,4)-triazola-5(1,2)-
benzenacyclodecaphan-4-one

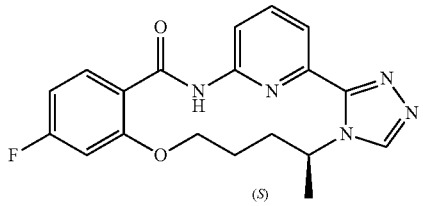

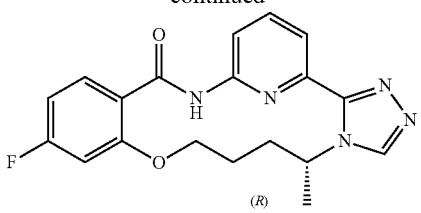

rac-5⁴-Fluoro-10-methyl-1⁴H-6-oxa-3-aza-2(2,6)-pyridina-1(3,4)-triazola-5(1,2)-benzenacyclodecaphan-4-one (85 mg, 0.23 mol) was purified by SFC (Chiralcel AD-H 5 μm, 30×250 mm and using 50% ethanol (containing 0.1% Et₂NH) in CO₂ as the mobile phase at a flow rate of 100 mL/min (ABPR 120 bar, MBPR 40 psi)) to give in order of elution: (S)-5⁴-fluoro-10-methyl-1⁴H-6-oxa-3-aza-2(2,6)-pyridina-1(3,4)-triazola-5(1,2)-benzenacyclodecaphan-4-one (30 mg, 35%, absolute stereochemistry was arbitrarily assigned) and (R)-5⁴-fluoro-10-methyl-1⁴H-6-oxa-3-aza-2(2,6)-pyridina-1(3,4)-triazola-5(1,2)-benzenacyclodecaphan-4-one (32 mg, 38%, absolute stereochemistry was arbitrarily assigned). ¹H NMR (400 MHz, DMSO-d₆) δ ppm 11.13 (s, 1H), 8.86 (s, 1H), 8.07 (t, J=7.8 Hz, 1H), 8.02 (t, J=7.4 Hz, 1H), 7.80-7.88 (m, 2H), 7.19 (dd, J=2.4, 11.17 Hz, 1H), 7.00 (dt, J=2.3, 8.4 Hz, 1H), 4.59 (dt, J=2.4, 6.5 Hz, 1H), 4.45-4.50 (m, 1H), 4.16 (t, J=10.0 Hz, 1H), 2.04-2.18 (m, 2H), 1.65-1.85 (m, 2H), 1.54 (d, J=6.78 Hz, 3H). MS (ESI): 368.1 [M+H]⁺.

Example 99: (S)-5⁵-Fluoro-10-methyl-1⁴H-6-oxa-3-
aza-2(2,6)-pyridina-1(3,4)-triazola-5(1,2)-benzena-
cyclodecaphan-4-one and Example 100: (R)-5⁵-
Fluoro-10-methyl-1⁴H-6-oxa-3-aza-2(2,6)-pyridina-
1(3,4)-triazola-5(1,2)-benzenacyclodecaphan-4-one

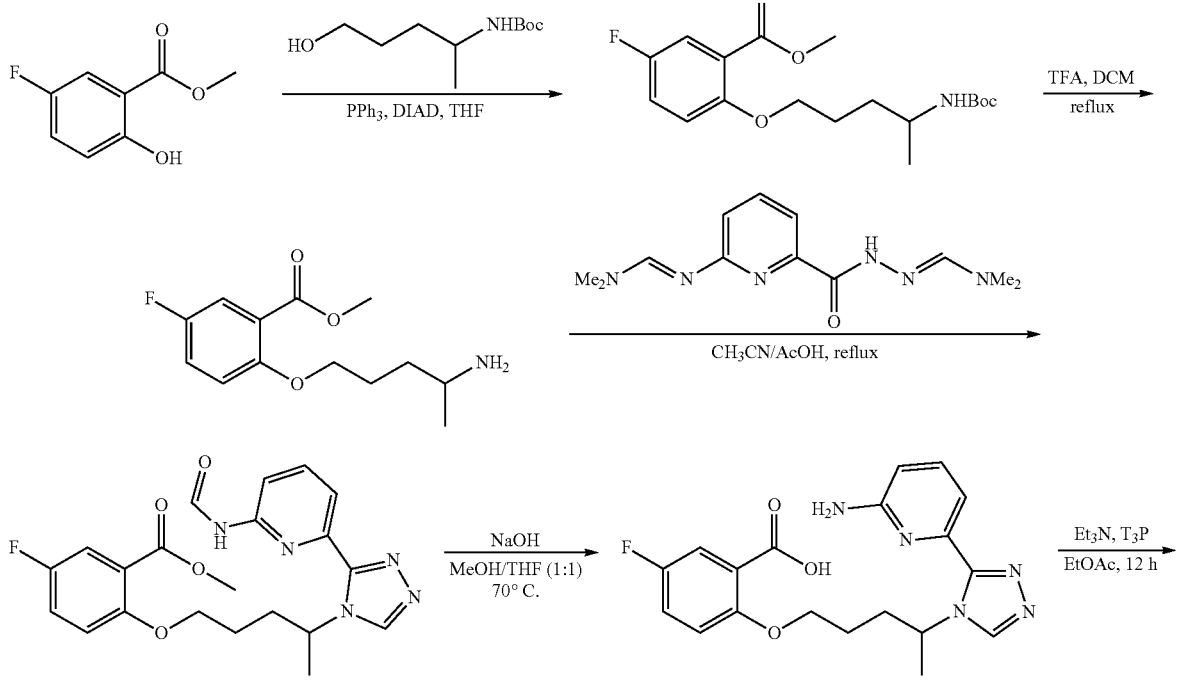

-continued

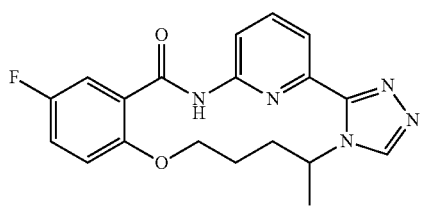

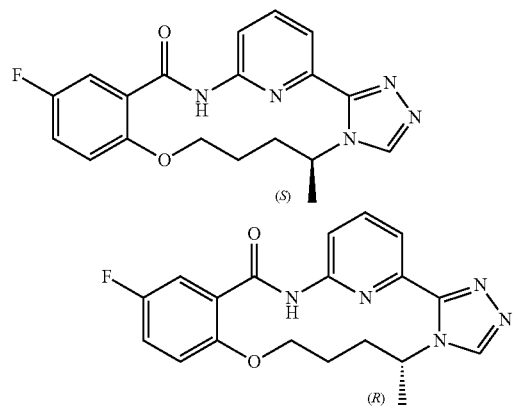

Step A. rac-Methyl 2-((4-((tert-butoxycarbonyl)amino)pentyl)oxy)-5-fluorobenzoate

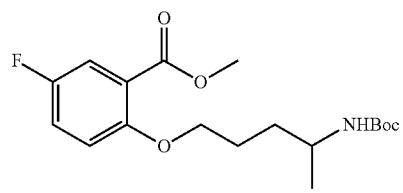 [SMILES: COC(=O)c1cc(F)ccc1OCCCC(C)NC(=O)OC(C)(C)C]

The title compound was synthesized according to the general procedure described in Example 1, Step A and using methyl 5-fluoro-2-hydroxybenzoate (5.0 g, 29.4 mmol) and tert-butyl N-(4-hydroxy-1-methyl-butyl)carbamate (5.97 g, 29.4 mmol). The product was purified by column chromatography on silica gel using Heptanes/(EtOAc:EtOH, 3:1) from 1/0 to 1/1 to give the desired product (7.7 g, 74%).

Step B. rac-Methyl 2-((4-aminopentyl)oxy)-5-fluorobenzoate

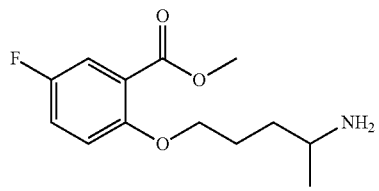 [SMILES: COC(=O)c1cc(F)ccc1OCCCC(C)N]

The title compound was synthesized according to the general procedure described in Example 1, Step B and using rac-methyl 2-((4-(((tert-butoxycarbonyl)amino)pentyl)oxy)-5-fluorobenzoate (7.7 g, 21.7 mmol) to give the desired product (5.8 g, crude) which was used without further purification in the next step. MS (ESI): 256.1 [M+H]$^+$.

Step C. rac-Methyl 5-fluoro-2-((4-(3-(6-formamidopyridin-2-yl)-4H-1,2,4-triazol-4-yl)pentyl)oxy)benzoate

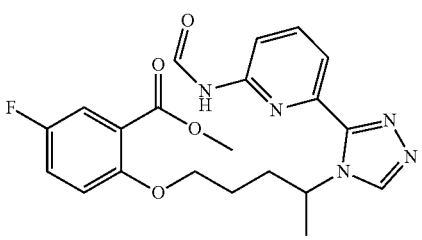 [SMILES: COC(=O)c1cc(F)ccc1OCCCC(C)n1cnnc1-c1cccc(NC=O)n1]

The title compound was synthesized according to the general procedure described in Example 1, Step C and using rac-methyl 2-((4-aminopentyl)oxy)-5-fluorobenzoate (5.8 g, 22.9 mmol) and N,6-bis[(E)-dimethylaminomethyleneamino]pyridine-2-carboxamide (3.0 g, 11.4 mmol) to give the title compound (1.8 g, 36%) as the major product as a yellow oil which was used without further purification in the next step. MS (ESI): 428.2 [M+H]$^+$.

Step D. rac-2-((4-(3-(6-Aminopyridin-2-yl)-4H-1,2,4-triazol-4-yl)pentyl)oxy)-5-fluorobenzoic acid

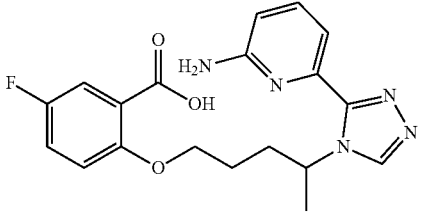 [SMILES: CC(CCCOc1ccc(F)cc1C(=O)O)n1cnnc1-c1cccc(N)n1]

The title compound was synthesized according to the general procedure described in Example 1, Step D and using rac-methyl 5-fluoro-2-((4-(3-(6-formamidopyridin-2-yl)-4H-1,2,4-triazol-4-yl)pentyl)oxy)benzoate (1.95 g, 4.6 mmol) to give the title compound (2.0 g, crude) which was used without further purification in the next step. MS (ESI): 386.1 [M+H]$^+$.

117

Step E: rac-5⁵-Fluoro-10-methyl-1⁴H-6-oxa-3-aza-2(2,6)-pyridina-1(3,4)-triazola-5(1,2)-benzenacyclodecaphan-4-one

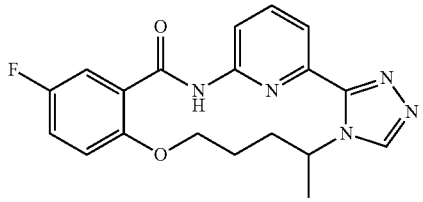 [SMILES: CC1CCCOc2ccc(F)cc2C(=O)Nc2cccc(n2)-c2nncn21]

The title compound was synthesized according to the general procedure described in Example 1, Step E and using rac-2-((4-(3-(6-aminopyridin-2-yl)-4H-1,2,4-triazol-4-yl)pentyl)oxy)-5-fluorobenzoic acid (2.0 g, 5.2 mmol) to give the desired product (190 mg, 10%). MS (ESI): 368.1 [M+H]⁺.

Step F: (S)-5⁵-Fluoro-10-methyl-1⁴H-6-oxa-3-aza-2(2,6)-pyridina-1(3,4)-triazola-5(1,2)-benzenacyclodecaphan-4-one and (R)-5⁵-Fluoro-10-methyl-1⁴H-6-oxa-3-aza-2(2,6)-pyridina-1(3,4)-triazola-5(1,2)-benzenacyclodecaphan-4-one

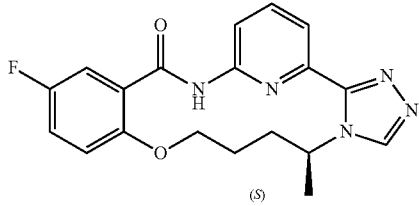

(S)

118

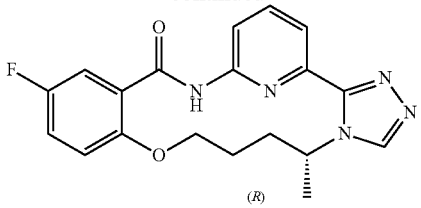

(R)

rac-5⁵-Fluoro-10-methyl-1⁴H-6-oxa-3-aza-2(2,6)-pyridina-1(3,4)-triazola-5(1,2)-benzenacyclodecaphan-4-one (190 mg, 0.52 mmol) was purified by SFC (using a Chiralcel OD-H, 5 μm 30×250 mm column and using 40% MeOH (containing 0.1% Et₂NH) in CO₂ as the mobile phase at a flow rate of 100 mL/min (ABPR 120 bar, MBPR 40 psi)) to give in order of elution (S)-5⁵-fluoro-10-methyl-1⁴H-6-oxa-3-aza-2(2,6)-pyridina-1(3,4)-triazola-5(1,2)-benzenacyclodecaphan-4-one (39 mg, 20%, absolute stereochemistry was arbitrarily assigned) and (R)-5⁵-Fluoro-10-methyl-1⁴H-6-oxa-3-aza-2(2,6)-pyridina-1(3,4)-triazola-5(1,2)-benzenacyclodecaphan-4-one (37 mg, 19%, absolute stereochemistry was arbitrarily assigned). ¹H NMR (500 MHz, DMSO-d₆) δ ppm 11.36 (s, 1H), 8.87 (s, 1H), 8.08 (t, J=7.94 Hz, 1H), 7.85 (d, J=7.94 Hz, 1H), 7.82 (d, J=7.94 Hz, 1H), 7.71 (dd, J=3.05, 9.16 Hz, 1H), 7.47 (t, J=8.14 Hz, 1H), 7.31 (dd, J=4.27, 9.16 Hz, 1H), 4.62 (ddd, J=3.36, 6.87, 10.53 Hz, 1H), 4.43-4.47 (m, 1H), 4.15-4.20 (m, 1H), 2.08-2.16 (m, 2H), 1.71-1.84 (m, 2H), 1.53 (d, J=6.71 Hz, 3H). MS (ESI): 368.1 [M+H]⁺.

Example 101: (S)-5⁵-Bromo-5⁴-fluoro-10-methyl-1⁴H-6-oxa-3-aza-2(2,6)-pyridina-1(3,4)-triazola-5(1,2)-benzenacyclodecaphan-4-one and Example 102: (R)-5⁵-Bromo-5⁴-fluoro-10-methyl-1⁴H-6-oxa-3-aza-2(2,6)-pyridina-1(3,4)-triazola-5(1,2)-benzenacyclodecaphan-4-one

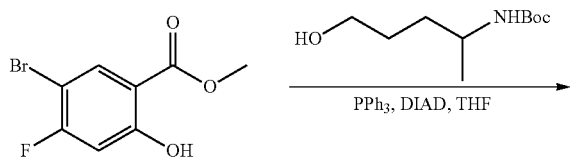

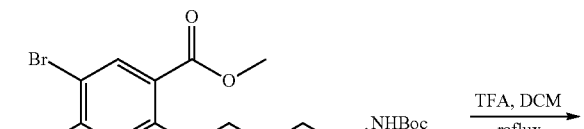

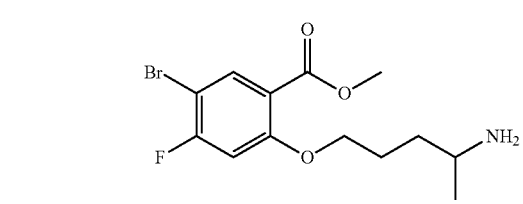

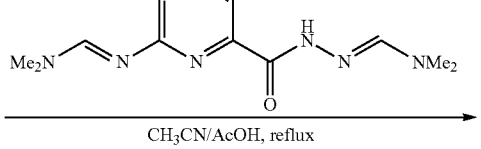

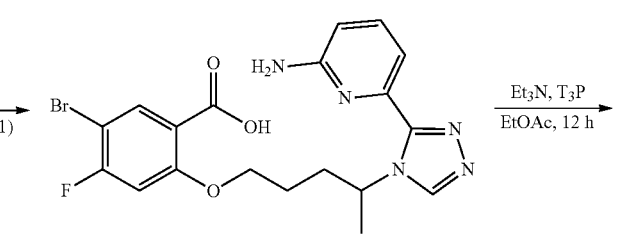

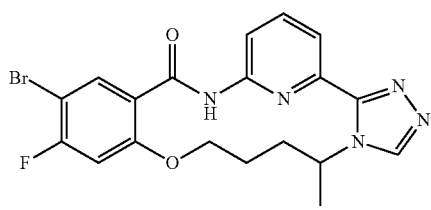 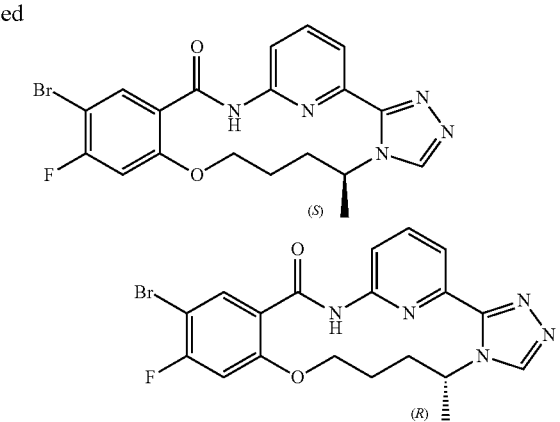

Step A. rac-Methyl 5-bromo-2-((4-((tert-butoxycarbonyl)amino)pentyl)oxy)-4-fluorobenzoate Step C. rac-Methyl 5-bromo-4-fluoro-2-((4-(3-(6-formamidopyridin-2-yl)-4H-1,2,4-triazol-4-yl)pentyl)oxy)benzoate

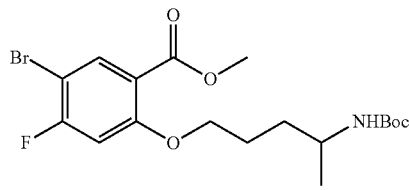 [SMILES: COC(=O)c1cc(Br)c(F)cc1OCCCC(C)NC(=O)OC(C)(C)C] 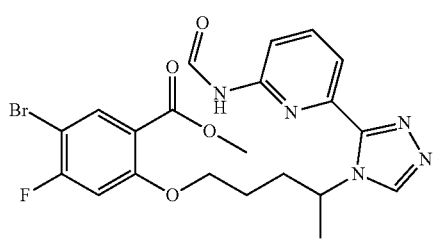 [SMILES: COC(=O)c1cc(Br)c(F)cc1OCCCC(C)n1cnnc1-c1cccc(NC=O)n1]

The title compound was synthesized according to the general procedure described in Example 1, Step A and using methyl 5-bromo-4-fluoro-2-hydroxybenzoate (30 g, 0.12 mol) to give the desired product (52 g, 100% crude) as a brown gum. MS (ESI): 456.1 [(M+Na) ($^{79}$Br)]$^+$.

Step B. rac-Methyl 2-((4-aminopentyl)oxy)-5-bromo-4-fluorobenzoate

The title compound was synthesized according to the general procedure described in Example 1, Step C and using rac-methyl 2-((4-aminopentyl)oxy)-5-bromo-4-fluorobenzoate (15 g, 45 mmol) and N,6-bis[(E)-dimethylaminomethyleneamino]pyridine-2-carboxamide (9.8 g, 37 mmol) to give the title compound (16 g, crude) as the major product as a yellow oil which was used without further purification in the next step. MS (ESI): 508.0 [(M+H) ($^{81}$Br)]$^+$.

Step D. rac-2-((4-(3-(6-Aminopyridin-2-yl)-4H-1,2,4-triazol-4-yl)pentyl)oxy)-5-bromo-4-fluorobenzoic acid

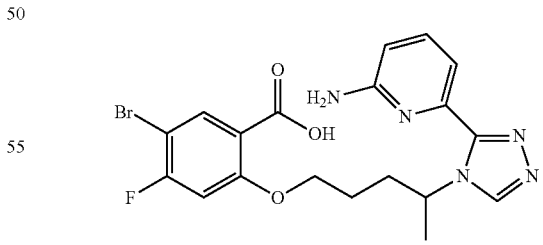

The title compound was synthesized according to the general procedure described in Example 1, Step B and using rac-methyl 5-bromo-2-((4-((tert-butoxycarbonyl)amino)pentyl)oxy)-4-fluorobenzoate (51 g, 0.12 mol) to give the desired product (44 g, 89%) as a white solid. MS (ESI): 333.9 [(M+H) ($^{79}$Br)]$^+$.

The title compound was synthesized according to the general procedure described in Example 1, Step D and using rac-methyl 5-bromo-4-fluoro-2-((4-(3-(6-formamidopyridin-2-yl)-4H-1,2,4-triazol-4-yl)pentyl)oxy)benzoate (9 g, 18 mmol) to give the desired product as a yellow solid (9 g, 100% crude) which was used without further purification in the next step. MS (ESI): 466.1 [(M+H) ($^{81}$Br)]$^+$.

Step E: rac-5⁵-Bromo-5⁴-fluoro-10-methyl-1⁴H-6-oxa-3-aza-2(2,6)-pyridina-1(3,4)-triazola-5(1,2)-benzenacyclodecaphan-4-one

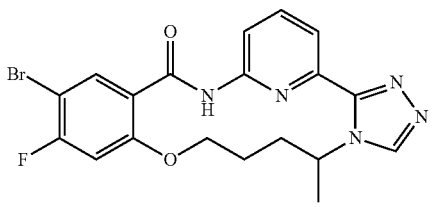

The title compound was synthesized according to the general procedure described in Example 1, Step E and using rac-2-((4-(3-(6-aminopyridin-2-yl)-4H-1,2,4-triazol-4-yl)pentyl)oxy)-5-bromo-4-fluorobenzoic acid (4.2 g, 9 mmol) to give the desired product (1 g, 25%) as a white solid. MS (ESI): 446.0 [(M+H) (⁷⁹Br)]⁺.

Step F: (S)-5⁵-Bromo-5⁴-fluoro-10-methyl-1⁴H-6-oxa-3-aza-2(2,6)-pyridina-1(3,4)-triazola-5(1,2)-benzenacyclodecaphan-4-one and (R)-5⁵-Bromo-5⁴-fluoro-10-methyl-1⁴H-6-oxa-3-aza-2(2,6)-pyridina-1(3,4)-triazola-5(1,2)-benzenacyclodecaphan-4-one

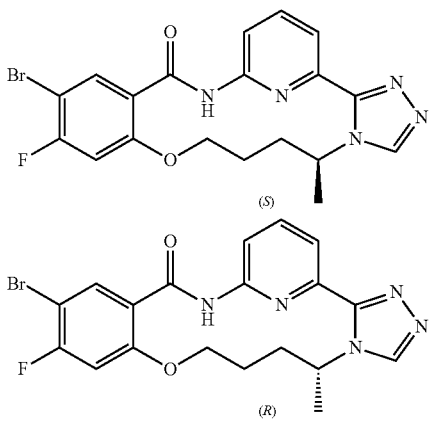

rac-5⁵-Bromo-5⁴-fluoro-10-methyl-1⁴H-6-oxa-3-aza-2(2,6)-pyridina-1(3,4)-triazola-5(1,2)-benzenacyclodecaphan-4-one (500 mg) was purified by SFC (using a Chiralpak AD-3, 3 μm 50×4.6 mm column and using 40% of ethanol (containing 0.05% Et₂NH) in CO₂ as the mobile phase at a flow rate of 4 mL/min with a column temperature of 40° C.) to give in order of elution:

Peak 1 (absolute stereochemistry was arbitrarily assigned), (S)-5⁵-Bromo-5⁴-fluoro-10-methyl-1⁴H-6-oxa-3-aza-2(2,6)-pyridina-1(3,4)-triazola-5(1,2)-benzenacyclodecaphan-4-one (180 mg, 36%) ¹H NMR (400 MHz, DMSO-d₆) δ ppm 11.01 (s, 1H), 8.85 (s, 1H), 8.04-8.11 (m, 2H), 7.78-7.82 (m, 2H), 7.41 (d, J=11.2 Hz, 1H), 4.43-4.53 (m, 2H), 4.10-4.15 (m, 1H), 3.09-3.11 (m, 1H), 2.04-2.06 (m, 1H), 1.69-1.78 (m, 2H), 1.50 (d, J=6.8 Hz, 3H). MS (ESI): 446.0 [(M+H) (⁷⁹Br)]⁺.

Peak 2 (absolute stereochemistry was arbitrarily assigned), (R)-5⁵-Bromo-5⁴-fluoro-10-methyl-1⁴H-6-oxa-3-aza-2(2,6)-pyridina-1(3,4)-triazola-5(1,2)-benzenacyclodecaphan-4-one (180 mg, 36%). ¹H NMR (400 MHz, DMSO-d₆) δ ppm 11.02 (s, 1H), 8.85 (s, 1H), 8.04-8.12 (m, 2H), 7.79-7.82 (m, 2H), 7.41 (d, J=10.4 Hz, 1H), 4.43-4.54 (m, 2H), 4.11-4.16 (m, 1H), 3.09-3.12 (m, 1H), 2.04-2.07 (m, 1H), 1.69-1.75 (m, 2H), 1.51 (d, J=6.8 Hz, 3H). MS (ESI): 448.1 [(M+H) (⁸¹Br)]⁺.

Example 103: (S)-5⁴-Fluoro-10-methyl-5⁵-morpholino-1⁴H-6-oxa-3-aza-2(2,6)-pyridina-1(3,4)-triazola-5(1,2)-benzenacyclodecaphan-4-one

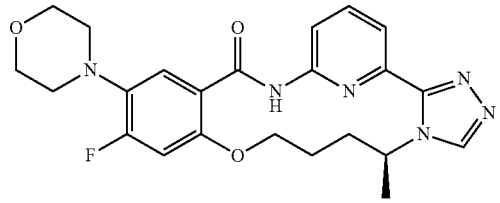 [SMILES: C[C@H]1CCCOc2cc(F)c(N3CCOCC3)cc2C(=O)Nc2cccc(n2)-c2nncn21]

A mixture of (S)-5⁵-bromo-5⁴-fluoro-10-methyl-1⁴H-6-oxa-3-aza-2(2,6)-pyridina-1(3,4)-triazola-5(1,2)-benzenacyclodecaphan-4-one (40 mg, 0.089 mmol), morpholine (39 μL, 0.45 mmol), RuPhos (8 mg, 0.02 mmol), t-BuONa (17 mg, 0.18 mmol) and Pd₂(dba)₃ (8 mg, 0.009 mmol) in dioxane/THF (1/1, 2 mL) was stirred at 120° C. under N₂ for 4 h. After this time, the volatiles were removed under reduced pressure to give the crude product which was purified by column chromatography on silica gel using DCM/MeOH (30/1) as eluent. Further purification by SFC (using a Chiralpak AD-3 50 mm×4.6 mm×3 μm column and 40% ethanol (with 0.05% Et₂NH) in CO₂ as the mobile phase at a flow rate of 4 mL/min with a column temperature of 40° C.) gave the title compound (40 mg, 33%) as a white solid. ¹H NMR (400 MHz, DMSO-d₆) δ ppm 11.25 (s, 1H), 8.85 (s, 1H), 8.03-8.07 (m, 1H), 7.78-7.84 (m, 2H), 7.61 (d, J=10.0 Hz, 1H), 7.23 (d, J=13.6 Hz, 1H), 4.60-4.61 (m, 1H), 4.40-4.41 (m, 1H), 4.09-4.14 (m, 1H), 3.72-3.75 (m, 4H), 3.07-3.09 (m, 1H), 2.96-2.97 (m, 4H), 2.08-2.09 (m, 1H), 1.70-1.79 (m, 2H), 1.52 (d, J=6.8 Hz, 3H). MS (ESI): 453.1 [M+H]⁺.

Example 104: (10S)-5⁵-(6-Oxa-3-azabicyclo[3.1.1]heptan-3-yl)-5⁴-fluoro-10-methyl-1⁴H-6-oxa-3-aza-2(2,6)-pyridina-1(3,4)-triazola-5(1,2)-benzenacyclodecaphan-4-one

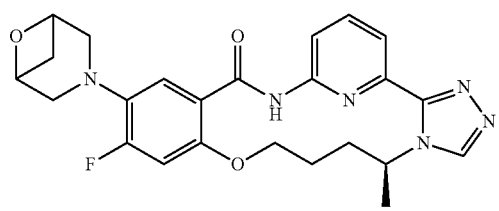 [SMILES: C[C@H]1CCCOc2cc(F)c(N3CC4CC(C3)O4)cc2C(=O)Nc2cccc(n2)-c2nncn21]

To a solution of (S)-5⁵-bromo-5⁴-fluoro-10-methyl-1⁴H-6-oxa-3-aza-2(2,6)-pyridina-1(3,4)-triazola-5(1,2)-benzenacyclodecaphan-4-one (158 mg, 0.35 mmol) in THF/dioxane (1/1, 5 mL) under a N₂ atmosphere was added 6-oxa-3-azabicyclo[3.1.1]heptane (80 mg, 0.29 mmol, tosylate salt) and t-BuONa (85 mg, 0.88 mmol) followed by Pd₂(dba)₃ (27 mg, 0.03 mmol) and Ruphos (14 mg, 0.03 mmol). The mixture was stirred at 110° C. for 10 h. After this time the mixture was concentrated to give the crude product, which was purified by HPLC (using an Agela ASB, 5 μm 150×25 mm column and using water (containing 0.225% HCOOH)/CH$_3$CN, from 32% to 47% as the mobile phase at a flow rate of 25 mL/min). Further purification by HPLC (using a Waters Xbridge Prep OBD C18, 5 μm 150×30 mm column and using water (containing 0.05% NH$_3$.H$_2$O)/CH$_3$CN, from 28% to 58% as the mobile phase at a flow rate of 25 mL/min) gave the title compound (25 mg, 19%) as an off-white solid. $^1$H NMR (400 MHz, CDCl$_3$) δ ppm 11.49 (s, 1H), 8.37 (s, 1H), 7.91-8.01 (m, 3H), 7.84-7.85 (m, 1H), 6.77 (d, J=14.4 Hz, 1H), 4.79-4.80 (m, 1H), 4.66-4.69 (m, 2H), 4.33-4.35 (m, 1H), 4.13 (t, J=9.6 Hz, 1H), 3.69-3.77 (m, 4H), 3.40-3.46 (m, 1H), 3.21-3.23 (m, 1H), 2.28-2.31 (m, 2H), 1.81-1.91 (m, 2H), 1.64 (d, J=6.8 Hz, 3H). MS (ESI): 465.0 [M+H]$^+$.

Example 105: (S)-5$^4$-Fluoro-10-methyl-5$^5$-(4-methylpiperazin-1-yl)-1$^4$H-6-oxa-3-aza-2(2,6)-pyridina-1(3,4)-triazola-5(1,2)-benzenacyclodecaphan-4-one

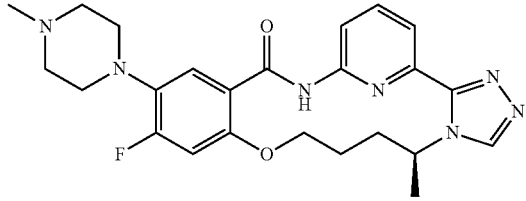 [SMILES: C[C@H]1CCCOc2cc(F)c(N3CCN(C)CC3)cc2C(=O)Nc2cccc(n2)-c2nncn21]

The title compound was synthesized according to the general procedure described in Example 4 and using (S)-5$^5$-bromo-5$^4$-fluoro-10-methyl-1$^4$H-6-oxa-3-aza-2(2,6)-pyridina-1(3,4)-triazola-5(1,2)-benzenacyclodecaphan-4-one and 1-methylpiperazine (80 mg, 0.18 mmol) in toluene (5 mL). Purification by HPLC (using a Phenomenex Synergi C18, 4 μm 150×30 mm column and using water (containing 0.225% HCOOH)/CH$_3$CN, from 15% to 35% as the mobile phase at a flow rate of 25 mL/min) gave the title compound (10 mg, 12%) as a gray solid. $^1$H NMR (400 MHz, MeOD) δ ppm 8.80 (s, 1H), 7.90 (t, J=7.6 Hz, 1H), 7.80 (d, J=8.0 Hz, 1H), 7.63-7.70 (m, 2H), 6.95 (d, J=13.6 Hz, 1H), 4.66 (br, 1H), 4.33 (d, J=9.2 Hz, 1H), 4.05 (t, J=9.6 Hz, 1H), 3.11-3.22 (m, 9H), 2.77 (s, 3H), 2.16 (br, 1H), 1.71-1.82 (m, 2H), 1.62 (d, J=6.8 Hz, 3H). MS (ESI): 466.2 [M+H]$^+$.

Example 106: (S)-5$^4$-Fluoro-10-methyl-5$^5$-(1-methyl-1,2,3,6-tetrahydropyridin-4-yl)-1$^4$H-6-oxa-3-aza-2(2,6)-pyridina-1(3,4)-triazola-5(1,2)-benzenacyclodecaphan-4-one

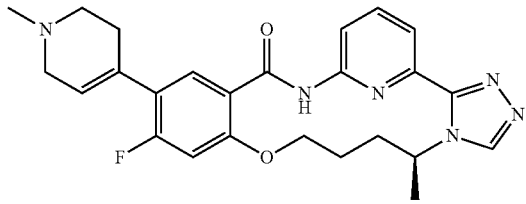 [SMILES: C[C@H]1CCCOc2cc(F)c(C3=CCN(C)CC3)cc2C(=O)Nc2cccc(n2)-c2nncn21]

The title compound was synthesized according to the general procedure described in Example 69 and using (S)-5$^5$-bromo-5$^4$-fluoro-10-methyl-1$^4$H-6-oxa-3-aza-2(2,6)-pyridina-1(3,4)-triazola-5(1,2)-benzenacyclodecaphan-4-one and 1-methylpiperazine (140 mg, 0.31 mmol) and 1-methyl-4-(4,4,5,5-tetramethyl-1,3,2-dioxaborolan-2-yl)-1,2,3,6-tetrahydropyridine (1.14 g, 0.63 mmol,) in ethanol/H$_2$O (5.5 mL, 10/1). Purification by by column chromatography on silica gel eluting with DCM/MeOH (100/1 to 10/1) gave the title compound (130 mg, 78%) as a white solid. $^1$H NMR (400 MHz, CDCl$_3$) δ ppm 11.29 (s, 1H), 8.37 (s, 1H), 8.20 (d, J=9.2 Hz, 1H), 7.94-8.01 (m, 2H), 7.88-7.94 (m, 1H), 6.70 (d, J=12.0 Hz, 1H), 6.03 (br s, 1H), 4.70-4.84 (m, 1H), 4.41 (d, J=9.2 Hz, 1H), 4.15 (t, J=10.0 Hz, 1H), 3.36-3.47 (m, 1H), 3.18 (d, J=3.2 Hz, 2H), 2.68-2.77 (m, 2H), 2.62 (s, 2H), 2.45 (s, 3H), 2.24 (s, 1H), 1.82-1.93 (m, 2H), 1.64 (d, J=6.8 Hz, 3H). MS (ESI): 463.3 [M+H]$^+$.

Example 107: (S)-5$^4$-Fluoro-10-methyl-5$^5$-(1-methylpiperidin-4-yl)-1$^4$H-6-oxa-3-aza-2(2,6)-pyridina-1(3,4)-triazola-5(1,2)-benzenacyclodecaphan-4-one

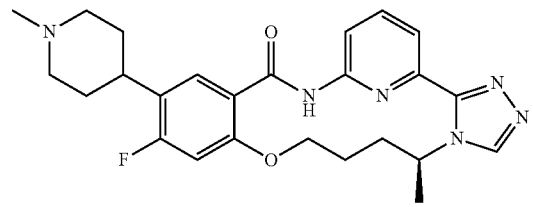 [SMILES: C[C@H]1CCCOc2cc(F)c(C3CCN(C)CC3)cc2C(=O)Nc2cccc(n2)-c2nncn21]

The title compound was synthesized according to the general procedure described in Example 70 and using (S)-5$^4$-Fluoro-10-methyl-5$^5$-(1-methyl-1,2,3,6-tetrahydropyridin-4-yl)-1$^4$H-6-oxa-3-aza-2(2,6)-pyridina-1(3,4)-triazola-5(1,2)-benzenacyclodecaphan-4-one (80 mg, 0.17 mmol). Purification by HPLC (using a Waters Xbridge Prep OBD C18, 5 μm 150×30 mm column and using water (containing 0.05% NH$_3$.H$_2$O and 10 mM NH$_4$HCO$_3$)/CH$_3$CN, from 30% to 60% as the mobile phase at a flow rate of 25 mL/min) gave the title compound (20 mg, 25%) as white solid. $^1$H NMR (400 MHz, CDCl$_3$) δ ppm 11.30 (s, 1H), 8.37 (s, 1H), 8.17 (d, J=8.8 Hz, 1H), 7.94-8.01 (m, 2H), 7.86-7.94 (m, 1H), 6.70 (d, J=11.2 Hz, 1H), 4.75 (d, J=6.8 Hz, 1H), 4.39 (d, J=9.2 Hz, 1H), 4.14 (t, J=9.2 Hz, 1H), 3.42 (t, J=10.0 Hz, 1H), 3.08 (d, J=10.4 Hz, 2H), 2.81 (t, J=11.2 Hz, 1H), 2.40 (s, 3H), 2.16-2.28 (m, 3H), 1.95-2.02 (m, 2H), 1.85 (d, J=11.6 Hz, 4H), 1.64 (d, J=7.2 Hz, 3H). MS (ESI): 465.2 [M+H]$^+$.

Example 108: (S)-5$^5$-(3,6-Dihydro-2H-pyran-4-yl)-5$^4$-fluoro-10-methyl-1$^4$H-6-oxa-3-aza-2(2,6)-pyridina-1(3,4)-triazola-5(1,2)-benzenacyclodecaphan-4-one

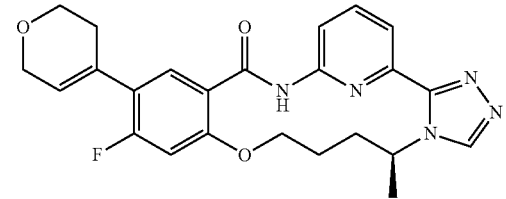 [SMILES: C[C@H]1CCCOc2cc(F)c(C3=CCOCC3)cc2C(=O)Nc2cccc(n2)-c2nncn21]

The title compound was synthesized according to the general procedure described in Example 67 and using (S)-

5⁴-Fluoro-10-methyl-5⁵-(1-methyl-1,2,3,6-tetrahydropyridin-4-yl)-1⁴H-6-oxa-3-aza-2(2,6)-pyridina-1(3,4)-triazola-5(1,2)-benzenacyclodecaphan-4-one (150 mg, 0.34 mmol). Purification by HPLC (using an Agela ASB, 5 μm 150×25 mm column and using water (containing 0.225% HCOOH)/CH₃CN, from 35% to 64% as the mobile phase at a flow rate of 25 mL/min) gave the title compound (97 mg, 57%) as a white solid. ¹H NMR (400 MHz, DMSO-d₆) δ ppm 11.11 (s, 1H), 8.86 (s, 1H), 8.06 (t, J=6.8 Hz, 1H), 7.92 (d, J=9.2 Hz, 1H), 7.81-7.85 (m, 2H), 7.18-7.21 (m, 1H), 6.11 (m, 1H), 4.45-4.57 (m, 2H), 4.21-4.22 (m, 2H), 4.12-4.17 (m, 1H), 3.81 (t, J=5.6 Hz, 2H), 3.13-3.14 (m, 1H), 2.40-2.45 (m, 2H), 2.06-2.12 (m, 1H), 1.74-1.80 (m, 2H), 1.56 (d, J=7.2 Hz, 3H). MS (ESI): 450.1 [M+H]⁺.

Example 109: (S)-5⁴-Fluoro-5⁵-(3-fluoropyridin-4-yl)-10-methyl-1⁴H-6-oxa-3-aza-2(2,6)-pyridina-1(3,4)-triazola-5(1,2)-benzenacyclodecaphan-4-one

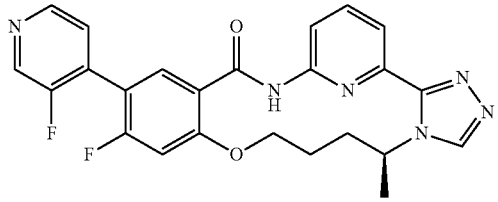 [SMILES: C[C@H]1CCCOc2cc(F)c(-c3ccncc3F)cc2C(=O)Nc2cccc(n2)-c2nncn21]

The title compound was synthesized according to the general procedure described in Example 55 and using (S)-5⁵-bromo-5⁴-fluoro-10-methyl-1⁴H-6-oxa-3-aza-2(2,6)-pyridina-1(3,4)-triazola-5(1,2)-benzenacyclodecaphan-4-one (40 mg, 0.09 mmol) and (3-fluoropyridin-4-yl)boronic acid (30 mg, 0.13 mmol) in dioxane/H₂O (5 mL/1 mL). Purification by HPLC (using a Phenomenex Synergi C18, 4 μm 150×30 mm column and using water (containing 0.225% HCOOH)/CH₃CN, from 40% to 60% as the mobile phase at a flow rate of 25 mL/min) gave the title compound (24 mg, 59%) as a gray solid. ¹H NMR (400 MHz, MeOD) δ ppm 8.82 (s, 1H), 8.58 (s, 1H), 8.50 (d, J=4.8 Hz, 1H), 8.21 (d, J=8.4 Hz, 1H), 8.02 (t, J=7.6 Hz, 1H), 7.93 (d, J=12.0 Hz, 1H), 7.84 (d, J=7.2 Hz, 1H), 7.59 (t, J=5.6 Hz, 1H), 7.21 (d, J=11.6 Hz, 1H), 4.63-4.74 (m, 2H), 4.52-4.57 (m, 1H), 4.24 (t, J=10.4 Hz, 1H), 2.19-2.31 (m, 1H), 1.83-1.93 (m, 2H), 1.65 (d, J=6.8 Hz, 3H). MS (ESI): 463.3 [M+H]⁺.

Example 110: (S)-5⁴-Fluoro-10-methyl-5⁵-(pyrimidin-5-yl)-1⁴H-6-oxa-3-aza-2(2,6)-pyridina-1(3,4)-triazola-5(1,2)-benzenacyclodecaphan-4-one

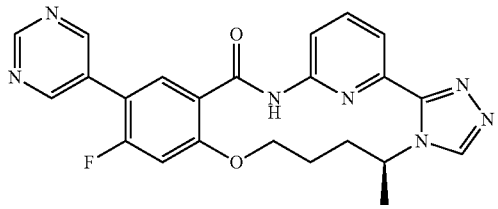 [SMILES: C[C@H]1CCCOc2cc(F)c(-c3cncnc3)cc2C(=O)Nc2cccc(n2)-c2nncn21]

The title compound was synthesized according to the general procedure described in Example 60 and using (S)-5⁵-bromo-5⁴-fluoro-10-methyl-1⁴H-6-oxa-3-aza-2(2,6)-pyridina-1(3,4)-triazola-5(1,2)-benzenacyclodecaphan-4-one (50 mg, 0.11 mmol) and pyrimidin-5-ylboronic acid (35 mg, 0.17 mmol) in dioxane/H₂O (4 mL/0.8 mL). Purification by HPLC (using an Xtimate C18, 5 μm 150×25 mm column and using water (containing 10 mM NH₄HCO₃)/CH₃CN, from 20% to 60% as the mobile phase at a flow rate of 25 mL/min) gave the title compound (23 mg, 44%) as a gray solid. ¹H NMR (400 MHz, CDCl₃) δ ppm 11.04 (s, 1H), 9.23 (s, 1H), 9.04 (s, 2H), 8.87 (s, 1H), 8.19 (d, J=8.8 Hz, 1H), 8.08 (d, J=8.0 Hz, 1H), 7.84 (q, J=8.0 Hz, 2H), 7.42 (d, J=12.4 Hz, 1H), 4.49-4.63 (m, 2H), 4.21 (t, J=10.0 Hz, 1H), 3.13-3.22 (m, 1H), 2.08-2.19 (m, 1H), 1.73-1.88 (m, 2H), 1.54 (d, J=7.2 Hz, 3H). MS (ESI): 446.3 [M+H]⁺.

Example 111: (S)-5⁴-Fluoro-10-methyl-5⁵-(5-(trifluoromethyl)pyridin-3-yl)-1⁴H-6-oxa-3-aza-2(2,6)-pyridina-1(3,4)-triazola-5(1,2)-benzenacyclodecaphan-4-one

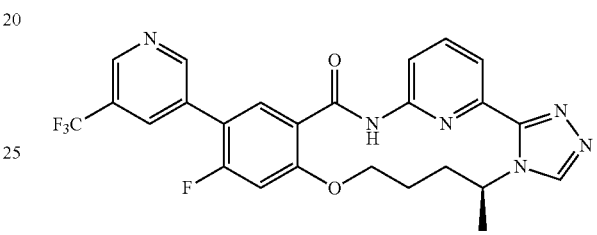

The title compound was synthesized according to the general procedure described in Example 58 and using (S)-5⁵-bromo-5⁴-fluoro-10-methyl-1⁴H-6-oxa-3-aza-2(2,6)-pyridina-1(3,4)-triazola-5(1,2)-benzenacyclodecaphan-4-one (60 mg, 0.13 mmol) and 3-(4,4,5,5-tetramethyl-1,3,2-dioxaborolan-2-yl)-5-(trifluoromethyl)pyridine (73 mg, 0.27 mmol). Purification by column chromatography on silica gel using DCM/MeOH (1/0 to 50/1 to 30/1) gave the title compound (60 mg, 58%) as a brown solid. ¹H NMR (400 MHz, CDCl₃) δ ppm 11.06 (s, 1H), 9.00-9.14 (m, 2H), 8.89 (s, 1H), 8.44 (s, 1H), 8.22 (d, J=9.0 Hz, 1H), 8.06-8.15 (m, 1H), 7.85 (dd, J=8.0, 16.1 Hz, 2H), 7.44 (d, J=12.0 Hz, 1H), 4.50-4.66 (m, 2H), 4.17-4.29 (m, 1H), 3.14-3.26 (m, 1H), 2.08-2.21 (m, 1H), 1.72-1.92 (m, 2H), 1.55 (d, J=7.0 Hz, 3H). MS (ESI): 513.1 [M+H]⁺.

Example 112: (S)-5⁴-Fluoro-10-methyl-5⁵-(pyridin-4-yl)-1⁴H-6-oxa-3-aza-2(2,6)-pyridina-1(3,4)-triazola-5(1,2)-benzenacyclodecaphan-4-one

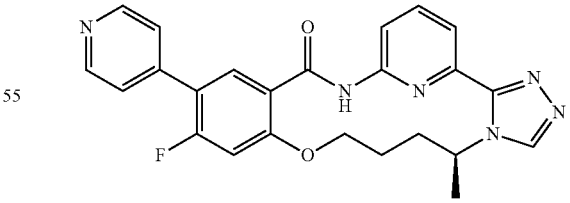

The title compound was synthesized according to the general procedure described in Example 52, Step H and using (S)-5⁵-bromo-5⁴-fluoro-10-methyl-1⁴H-6-oxa-3-aza-2(2,6)-pyridina-1(3,4)-triazola-5(1,2)-benzenacyclodecaphan-4-one (80 mg, 0.18 mmol). Purification by column chromatography on silica gel using DCM/MeOH (1/0 to 20/1) gave the title compound (75 mg, 42%) as a white solid.

$^1$H NMR (400 MHz, DMSO-d$_6$) δ ppm 11.06 (s, 1H), 8.86 (s, 1H), 8.66 (d, J=6.4 Hz, 2H), 8.14 (d, J=8.8 Hz, 1H), 8.03-8.10 (m, 1H), 7.79-7.85 (m, 2H), 7.60 (d, J=4.4 Hz, 2H), 7.36-7.40 (m, 1H), 4.47-4.62 (m, 2H), 4.16-4.21 (m, 1H), 3.10-3.21 (m, 1H), 2.03-2.17 (m, 1H), 1.68-1.86 (m, 2H), 1.52 (d, J=7.2 Hz, 3H). MS (ESI): 445.1 [M+H]$^+$.

Example 113: (S)-5$^4$-Fluoro-10-methyl-5$^5$-(4-methyl-1H-imidazol-1-yl)-1$^4$H-6-oxa-3-aza-2(2,6)-pyridina-1(3,4)-triazola-5(1,2)-benzenacyclodecaphan-4-one

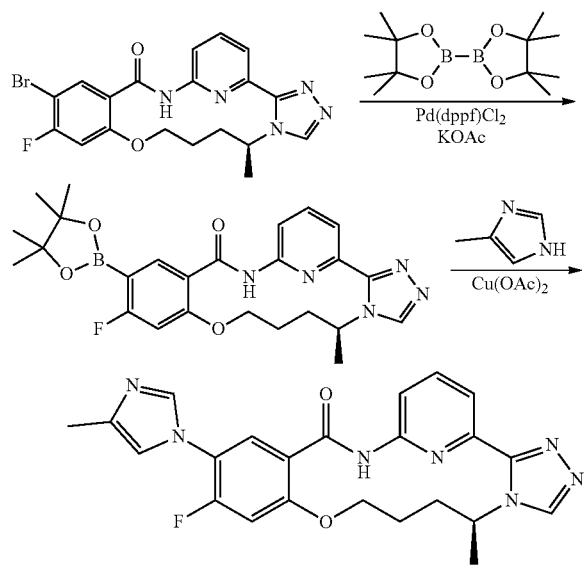

Step A. (S)-5$^4$-Fluoro-10-methyl-5$^5$-(4,4,5,5-tetramethyl-1,3,2-dioxaborolan-2-yl)-1$^4$H-6-oxa-3-aza-2(2,6)-pyridina-1(3,4)-triazola-5(1,2)-benzenacyclodecaphan-4-one

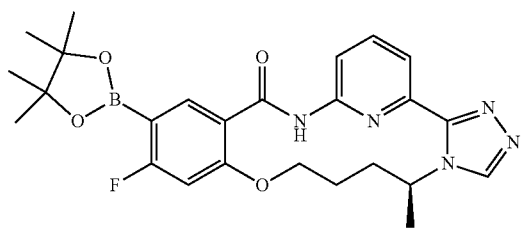 [SMILES: C[C@H]1CCCOc2cc(F)c(B3OC(C)(C)C(C)(C)O3)cc2C(=O)Nc2cccc(n2)-c2nncn21]

To a solution of (S)-5$^5$-bromo-5$^4$-fluoro-10-methyl-1$^4$H-6-oxa-3-aza-2(2,6)-pyridina-1(3,4)-triazola-5(1,2)-benzenacyclodecaphan-4-one (50 mg, 0.11 mmol) and 4,4,4',4',5,5,5',5'-octamethyl-2,2'-bi(1,3,2-dioxaborolane) (17 mg, 0.2 mmol) in 1,4-dioxane (2 mL) under a N$_2$ atmosphere was added KOAc (22 mg, 0.22 mmol) and Pd(dppf)Cl$_2$ (8 mg, 0.01 mmol) and the reaction was heated at 110° C. for 20 h. After this time, the mixture was concentrated to give the crude product, which was purified by column chromatography on silica gel eluting with DCM/MeOH (from 0 to 6% of MeOH in DCM) to give the title compound (50 mg, 90%) as a red oil. MS (ESI): 494.2 [M+H]$^+$.

Step B. (S)-5$^4$-Fluoro-10-methyl-5$^5$-(4-methyl-1H-imidazol-1-yl)-1$^4$H-6-oxa-3-aza-2(2,6)-pyridina-1(3,4)-triazola-5(1,2)-benzenacyclodecaphan-4-one

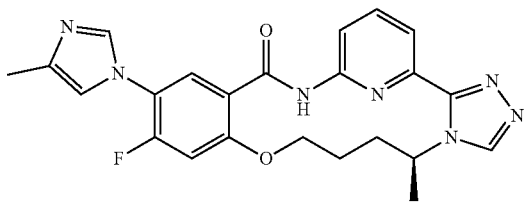 [SMILES: Cc1cn(-c2cc3c(cc2F)OCCC[C@H](C)n2cnnc2-c2cccc(n2)NC3=O)cn1]

The title compound was synthesized according to the general procedure described in Example 66 and using (S)-5$^4$-fluoro-10-methyl-5$^5$-(4,4,5,5-tetramethyl-1,3,2-dioxaborolan-2-yl)-1$^4$H-6-oxa-3-aza-2(2,6)-pyridina-1(3,4)-triazola-5(1,2)-benzenacyclodecaphan-4-one (50 mg, 0.11 mmol) and 4-methyl-1H-imidazole (17 mg, 0.2 mmol) in pyridine (5 mL). Purification by HPLC (using an Xtimate C18, 5 μm 150×25 mm column and using water (containing 10 mM NH$_4$HCO$_3$)/CH$_3$CN, from 28% to 58% as the mobile phase at a flow rate of 25 mL/min) to give the title compound (15 mg, 33%) as a yellow oil. $^1$H NMR (400 MHz, CDCl$_3$) δ ppm 11.29 (s, 1H), 8.39 (s, 1H), 8.32 (d, J=8.8 Hz, 1H), 7.91-8.05 (m, 3H), 7.73 (s, 1H), 6.91-7.02 (m, 2H), 4.79 (s, 1H), 4.49 (d, J=9.2 Hz, 1H), 4.19-4.29 (m, 1H), 3.45 (d, J=12.0 Hz, 1H), 2.32 (s, 4H), 1.81-2.00 (m, 2H), 1.68 (d, J=7.2 Hz, 3H). MS (ESI): 448.0 [M+H]$^+$.

Example 114: (S)-5$^4$-Fluoro-10-methyl-5$^5$-(1-methyl-1H-pyrazol-4-yl)-1$^4$H-6-oxa-3-aza-2(2,6)-pyridina-1(3,4)-triazola-5(1,2)-benzenacyclodecaphan-4-one

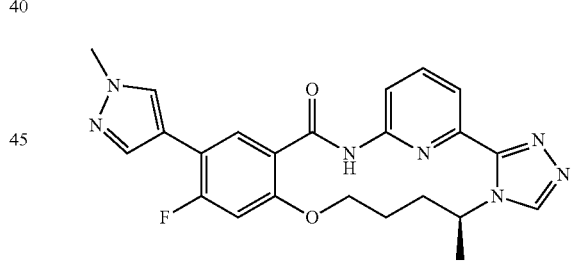

A mixture of (S)-5$^5$-bromo-5$^4$-fluoro-10-methyl-1$^4$H-6-oxa-3-aza-2(2,6)-pyridina-1(3,4)-triazola-5(1,2)-benzenacyclodecaphan-4-one (100 mg, 0.22 mmol), 1-methyl-4-(4,4,5,5-tetramethyl-1,3,2-dioxaborolan-2-yl)-1H-pyrazole (56 mg, 0.27 mmol), K$_2$CO$_3$ (61 mg, 0.44 mmol) and Pd(dppf)Cl$_2$ (16 mg, 0.022 mmol) in dioxane/H$_2$O (5/1, 12 mL) was stirred at 90° C. under a N$_2$ atmosphere for 2 h. After this time the mixture was filtered and the filtrate was concentrated to give the crude product which was purified by HPLC (using a Phenomenex Synergi C18, 4 μm 150×30 mm column and using water (containing 0.05% HCl)/CH$_3$CN, from 30% to 60% as the mobile phase at a flow rate of 25 mL/min) to give the title compound (67 mg, 61%) as a white solid. $^1$H NMR (400 MHz, DMSO-d$_6$) δ ppm 11.12 (s, 1H), 9.23 (s, 1H), 8.08-8.19 (m, 3H), 7.81-7.90 (m, 3H), 7.25-7.28 (m, 1H), 4.61-4.67 (m, 1H), 4.41-4.47 (m, 1H), 4.12-

4.17 (m, 1H), 3.87 (s, 3H), 3.12-3.15 (m, 1H), 2.05-2.11 (m, 1H), 1.76-1.78 (m, 2H), 1.54 (d, J=6.8 Hz, 3H). MS (ESI): 448.2 [M+H]$^+$.

Example 115: (S)-5$^5$-(1-(2-(Dimethylamino)ethyl)-1H-pyrazol-4-yl)-5$^4$-fluoro-10-methyl-1$^4$H-6-oxa-3-aza-2(2,6)-pyridina-1(3,4)-triazola-5(1,2)-benzenacyclodecaphan-4-one

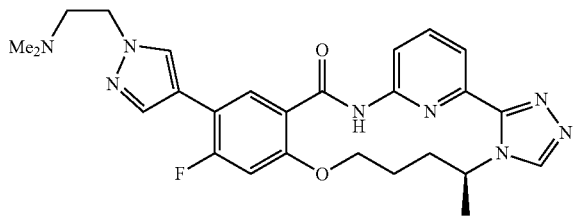 [SMILES: C[C@H]1CCCOc2cc(F)c(-c3cnn(CCN(C)C)c3)cc2C(=O)Nc2cccc(n2)-c2nncn21]

The title compound was synthesized according to the general procedure described in Example 64 and using (S)-5$^5$-bromo-5$^4$-fluoro-10-methyl-1$^4$H-6-oxa-3-aza-2(2,6)-pyridina-1(3,4)-triazola-5(1,2)-benzenacyclodecaphan-4-one (65 mg, 0.15 mmol), and N,N-dimethyl-2-(4-(4,4,5,5-tetramethyl-1,3,2-dioxaborolan-2-yl)-1H-pyrazol-1-yl)ethan-1-amine (65 mg, 0.25 mmol). The product was purified by column chromatography on silica gel using DCM/MeOH (from 0 to 5% of MeOH in DCM) as eluent to give the title compound (30 mg, 40%) as a colorless oil. $^1$H NMR (400 MHz, DMSO-d$_6$) δ ppm 11.13 (s, 1H), 8.87 (s, 1H), 8.18-8.25 (m, 2H), 8.04-8.11 (m, 2H), 7.84-7.89 (m, 2H), 7.81 (d, J=7.6 Hz, 1H), 7.27 (d, J=12.8 Hz, 1H), 4.53-4.63 (m, 1H), 4.47 (d, J=9.2 Hz, 1H), 4.24 (t, J=6.4 Hz, 2H), 4.16 (t, J=9.6 Hz, 1H), 3.10-3.20 (m, 1H), 2.67-2.71 (m, 2H), 2.08-2.18 (m, 7H), 1.69-1.86 (m, 2H), 1.53 (d, J=6.8 Hz, 3H). MS (ESI): 505.3 [M+H]$^+$.

Example 116: (S)-5$^5$-(2-(Dimethylamino)ethoxy)-5$^4$-fluoro-10-methyl-1$^4$H-6-oxa-3-aza-2(2,6)-pyridina-1(3,4)-triazola-5(1,2)-benzenacyclodecaphan-4-one

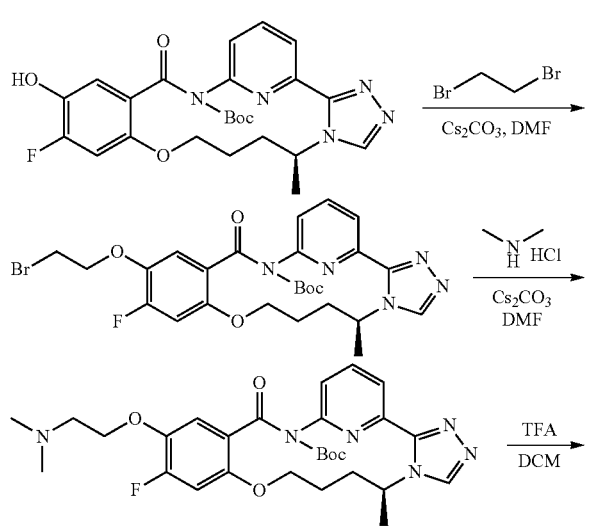

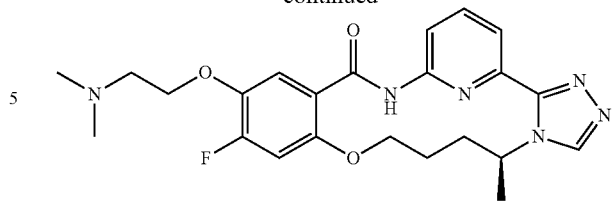

Step A. tert-Butyl (S)-5$^5$-(2-bromoethoxy)-5$^4$-fluoro-10-methyl-4-oxo-1$^4$H-6-oxa-3-aza-2(2,6)-pyridina-1(3,4)-triazola-5(1,2)-benzenacyclodecaphane-3-carboxylate

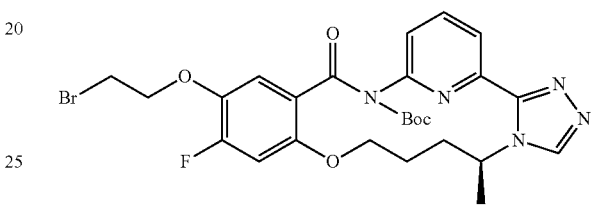

A mixture of tert-butyl (S)-5$^4$-fluoro-5$^5$-hydroxy-10-methyl-4-oxo-1$^4$H-6-oxa-3-aza-2(2,6)-pyridina-1(3,4)-triazola-5(1,2)-benzenacyclodecaphane-3-carboxylate (90 mg, 0.19 mmol), 1,2-dibromoethane (175 mg, 0.93 mmol) and Cs$_2$CO$_3$ (185 mg, 0.6 mmol) in DMF (4 mL) was stirred at 50° C. for 17 h. The reaction mixture was filtered and the volatiles were removed under reduced pressure to give the crude product (112 mg, 100%) which was used without further purification in the next step.

Step B. tert-Butyl (S)-5$^5$-(2-(dimethylamino)ethoxy)-5$^4$-fluoro-10-methyl-4-oxo-1$^4$H-6-oxa-3-aza-2(2,6)-pyridina-1(3,4)-triazola-5(1,2)-benzenacyclodecaphane-3-carboxylate

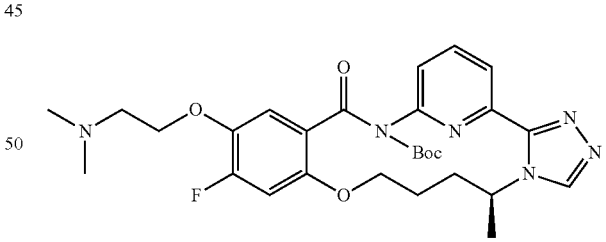

A mixture of tert-butyl (S)-5$^5$-(2-bromoethoxy)-5$^4$-fluoro-10-methyl-4-oxo-1$^4$H-6-oxa-3-aza-2(2,6)-pyridina-1(3,4)-triazola-5(1,2)-benzenacyclodecaphane-3-carboxylate (112 mg, 0.19 mmol), dimethylamine (77 mg, 0.95 mmol, HCl salt) and Cs$_2$CO$_3$ (309 mg, 0.95 mmol) in DMF (3 mL) was stirred at 25° C. for 17 h. After this time H$_2$O (20 mL) was added and the mixture was extracted with DCM (3×10 mL). The separated organic phase was dried over Na$_2$SO$_4$, filtered and concentrated to give the crude product which was purified by preparative TLC using DCM/MeOH (10/1) as eluent to give the title compound (40 mg, 38%) as a brown gum. MS (ESI): 555.1 [M+H]$^+$.

131

Step C. (S)-5⁵-(2-(Dimethylamino)ethoxy)-5⁴-fluoro-10-methyl-1⁴H-6-oxa-3-aza-2(2,6)-pyridina-1(3,4)-triazola-5(1,2)-benzenacyclodecaphan-4-one

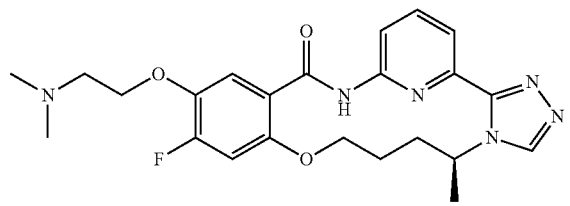 [SMILES: C[C@H]1CCCOc2cc(F)c(OCCN(C)C)cc2C(=O)Nc2cccc(n2)-c2nncn21]

A mixture of tert-butyl (S)-5⁵-(2-(dimethylamino)ethoxy)-5⁴-fluoro-10-methyl-4-oxo-1⁴H-6-oxa-3-aza-2(2,6)-pyridina-1(3,4)-triazola-5(1,2)-benzenacyclodecaphane-3-carboxylate (35 mg, 0.063 mmol) in DCM (3 mL) and TFA (3 mL) was stirred at 25° C. for 1 h. After this time the volatiles were removed under reduced pressure to give the crude product which was purified by HPLC (using a Phenomenex Synergi C18, 4 μm 150×30 mm column and using water (containing 0.05% HCl)/CH₃CN, from 15% to 35% as the mobile phase at a flow rate of 25 mL/min) to give the title compound as the HCl salt (6 mg, 21%) as a white solid. ¹H NMR (400 MHz, DMSO-d₆) δ ppm 11.26 (s, 1H), 10.53-10.60 (m, 1H), 9.17 (s, 1H), 8.09-8.11 (m, 1H), 7.82-7.87 (m, 2H), 7.75-7.77 (m, 1H), 7.34-7.37 (m, 1H), 4.64-4.70 (m, 1H), 4.41-4.48 (m, 3H), 4.10-4.16 (m, 1H), 3.53-3.54 (m, 2H), 3.08-3.15 (m, 1H), 2.85 (s, 3H), 2.84 (s, 3H), 2.06-2.12 (m, 1H), 1.74-1.81 (m, 2H), 1.54 (d, J=6.8 Hz, 3H). MS (ESI): 455.0 [M+H]⁺.

Example 117: (S)-5⁴-Fluoro-5⁵-(2-methoxyethoxy)-10-methyl-1⁴H-6-oxa-3-aza-2(2,6)-pyridina-1(3,4)-triazola-5(1,2)-benzenacyclodecaphan-4-one

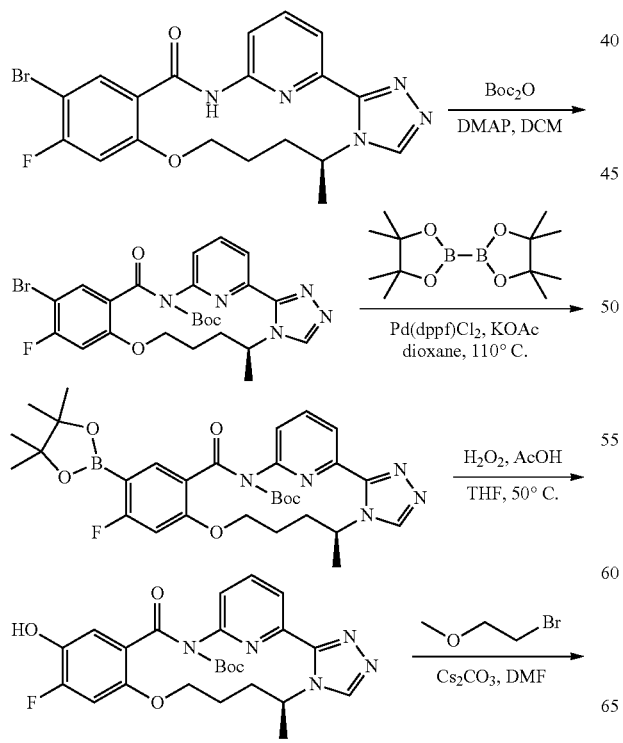

Step A. tert-Butyl (S)-5⁵-bromo-5⁴-fluoro-10-methyl-4-oxo-1⁴H-6-oxa-3-aza-2(2,6)-pyridina-1(3,4)-triazola-5(1,2)-benzenacyclodecaphane-3-carboxylate

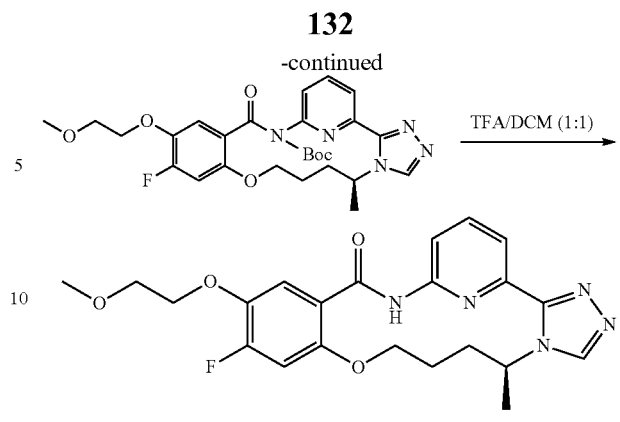

A mixture of (S)-5⁵-bromo-5⁴-fluoro-10-methyl-1⁴H-6-oxa-3-aza-2(2,6)-pyridina-1(3,4)-triazola-5(1,2)-benzenacyclodecaphan-4-one (500 mg, 1.12 mmol), DMAP (273.3 mg, 2.24 mmol) and Boc₂O (484 mg, 2.24 mmol) in DCM (20 mL) was stirred at 20° C. for 1 h. After this time the reaction was quenched with sat. aq. NH₄Cl (50 mL) and extracted with DCM (2×50 mL). The separated organic layer was dried over Na₂SO₄, filtered and concentrated to give the title compound (600 mg, 98%) as a yellow solid which was used in next step without further purification.

Step B. tert-Butyl (S)-5⁴-fluoro-10-methyl-4-oxo-5⁵-(4,4,5,5-tetramethyl-1,3,2-dioxaborolan-2-yl)-1⁴H-6-oxa-3-aza-2(2,6)-pyridina-1(3,4)-triazola-5(1,2)-benzenacyclodecaphane-3-carboxylate

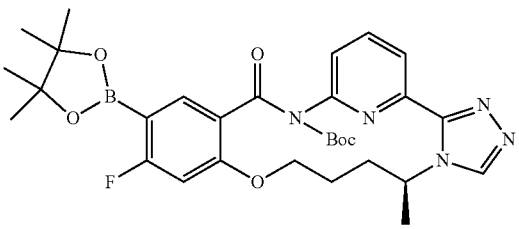 [SMILES: C[C@H]1CCCOc2cc(F)c(B3OC(C)(C)C(C)(C)O3)cc2C(=O)N(C(=O)OC(C)(C)C)c2cccc(n2)-c2nncn21]

A mixture of tert-butyl (S)-5⁵-bromo-5⁴-fluoro-10-methyl-4-oxo-1⁴H-6-oxa-3-aza-2(2,6)-pyridina-1(3,4)-triazola-5(1,2)-benzenacyclodecaphane-3-carboxylate (500 mg, 0.92 mmol), 4,4,4',4',5,5,5',5'-octamethyl-2,2'-bi(1,3,2-dioxaborolane) (580 mg, 2.3 mmol), KOAc (320 mg, 3.22 mmol) dioxane (20 mL) was stirred under N₂ at 110° C. for 3 h. After this time the volatiles were removed under reduced pressure to give the crude product which was purified by column chromatography on silica gel using DCM/MeOH (30/1) as eluent to give the title compound (560 mg, 93%) as a brown gum. MS (ESI): 594.2 [M+H]$^+$.

Step C. tert-Butyl (S)-5$^4$-fluoro-5$^5$-hydroxy-10-methyl-4-oxo-1$^4$H-6-oxa-3-aza-2(2,6)-pyridina-1(3,4)-triazola-5(1,2)-benzenacyclodecaphane-3-carboxylate

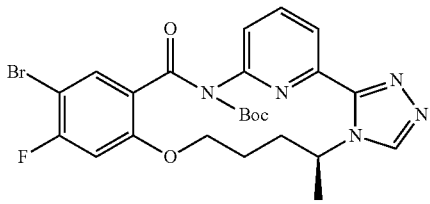 [SMILES: C[C@H]1CCCOc2cc(F)c(Br)cc2C(=O)N(C(=O)OC(C)(C)C)c2cccc(n2)-c2nncn21]

A mixture of tert-butyl (S)-5$^4$-fluoro-10-methyl-4-oxo-5$^5$-(4,4,5,5-tetramethyl-1,3,2-dioxaborolan-2-yl)-1$^4$H-6-oxa-3-aza-2(2,6)-pyridina-1(3,4)-triazola-5(1,2)-benzenacyclodecaphane-3-carboxylate (150 mg, 0.25 mmol), H$_2$O$_2$ (0.5 mL) and AcOH (0.5 mL) in THF (6 mL) was stirred at 50° C. for 3 h. After this time H$_2$O (50 mL) was added and the mixture was extracted with DCM (3×30 mL). The combined organic extracts were dried over MgSO$_4$, filtered and concentrated to give the title compound (120 mg, 100% crude) as a brown gum. MS (ESI): 484.2 [M+H]$^+$.

Step D. tert-Butyl (S)-5$^4$-fluoro-5$^5$-(2-methoxyethoxy)-10-methyl-4-oxo-1$^4$H-6-oxa-3-aza-2(2,6)-pyridina-1(3,4)-triazola-5(1,2)-benzenacyclodecaphane-3-carboxylate

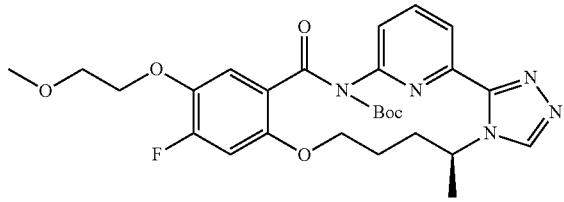 [SMILES: COCCOc1cc2c(cc1F)OCCC[C@H](C)n1cnnc1-c1cccc(n1)N(C(=O)OC(C)(C)C)C2=O]

A mixture of tert-butyl (S)-5$^4$-fluoro-5$^5$-hydroxy-10-methyl-4-oxo-1$^4$H-6-oxa-3-aza-2(2,6)-pyridina-1(3,4)-triazola-5(1,2)-benzenacyclodecaphane-3-carboxylate (100 mg, 0.21 mmol), 1-bromo-2-methoxyethane (57 mg, 0.42 mmol) and Cs$_2$CO$_3$ (202 mg, 0.62 mmol) in DMF (5 mL) was stirred at 20° C. for 17 h. After this time, H$_2$O (50 mL) was added and the mixture was extracted with DCM (3×20 mL). The combined organic extracts were dried over Na$_2$SO$_4$, filtered and concentrated to give the crude product which was purified by column chromatography on silica gel using DCM/MeOH (20/1) as eluent to give the title compound (80 mg, 71%) as a brown solid. MS (ESI): 542.1 [M+H]$^+$.

Step E. (S)-5$^4$-Fluoro-5$^5$-(2-methoxyethoxy)-10-methyl-1$^4$H-6-oxa-3-aza-2(2,6)-pyridina-1(3,4)-triazola-5(1,2)-benzenacyclodecaphan-4-one

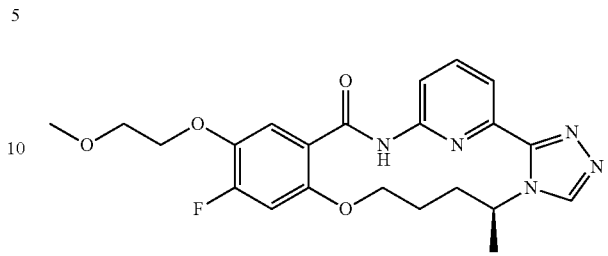

A mixture of tert-butyl (S)-5$^4$-fluoro-5$^5$-(2-methoxyethoxy)-10-methyl-4-oxo-1$^4$H-6-oxa-3-aza-2(2,6)-pyridina-1(3,4)-triazola-5(1,2)-benzenacyclodecaphane-3-carboxylate (70 mg, 0.13 mmol) in TFA (2 mL) and DCM (2 mL) was stirred at 20° C. for 1 h. After this time the volatiles were removed under reduced pressure to give the crude product which was purified by HPLC (using a Phenomenex Synergi C18, 4 μm 150×30 mm column and using water (containing 0.05% HCl)/CH$_3$CN, from 35% to 50% as the mobile phase at a flow rate of 25 mL/min) to give the title compound (27 mg, 47%) as a white solid. $^1$H NMR (400 MHz, DMSO-d$_6$) δ ppm 11.29 (s, 1H), 9.14 (s, 1H), 8.09 (t, J=8.0 Hz, 1H), 7.87 (d, J=8.4 Hz, 1H), 7.82 (d, J=7.6 Hz, 1H), 7.68 (d, J=9.6 Hz, 1H), 7.30-7.33 (m, 1H), 4.63-4.69 (m, 1H), 4.37-4.43 (m, 1H), 4.18 (t, J=4.4 Hz, 2H), 4.10-4.14 (m, 1H), 3.66 (t, J=4.4 Hz, 2H), 3.30 (s, 3H), 3.10-3.12 (m, 1H), 2.06-2.12 (m, 1H), 1.72-1.80 (m, 2H), 1.53 (d, J=7.2 Hz, 3H). MS (ESI): 442.1 [M+H]$^+$.

Example 118: (S)-5$^4$-Fluoro-10-methyl-4-oxo-1$^4$H-6-oxa-3-aza-2(2,6)-pyridina-1(3,4)-triazola-5(1,2)-benzenacyclodecaphane-5$^5$-carbonitrile

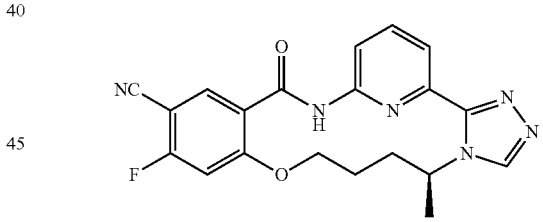

A stirred solution of (S)-5$^5$-bromo-5$^4$-fluoro-10-methyl-1$^4$H-6-oxa-3-aza-2(2,6)-pyridina-1(3,4)-triazola-5(1,2)-benzenacyclodecaphan-4-one (100 mg, 0.23 mmol), Zn(CN)$_2$ (32 mg, 0.27 mmol), Zn (9 mg, 0.14 mmol), dppf (25.0 mg, 0.05 mmol) and Pd$_2$(dba)$_3$ (21 mg, 0.023 mmol) in DMA (4.5 mL) was stirred at 120° C. under a N$_2$ for 17 h. After this time, the reaction mixture was filtered and the filtrate was purified by HPLC (using an Xtimate C18, 5 μm 150×25 mm column and using water (containing 10 mM NH$_4$HCO$_3$)/CH$_3$CN, from 36% to 76% as the mobile phase at a flow rate of 25 mL/min). Further purification by HPLC (using a Phenomenex Synergi C18, 4 μm 150×30 mm column and using water (containing 0.05% HCl)/CH$_3$CN, from 29% to 49% as the mobile phase at a flow rate of 25 mL/min) gave the title compound (11 mg, 12%) as a white solid. $^1$H NMR (400 MHz, DMSO-d$_6$) δ ppm 10.77 (s, 1H), 9.07 (s, 1H), 8.29 (d, J=7.6 Hz, 1H), 8.09 (t, J=8.0 Hz, 1H), 7.78-7.83 (m, 2H), 7.49 (d, J=12 Hz, 1H), 4.47-4.49 (m, 2H), 4.13-4.18 (m, 1H), 3.13-3.18 (m, 1H), 2.05-2.06 (m, 1H), 1.68-1.79 (m, 2H), 1.50 (d, J=7.2 Hz, 3H). MS (ESI): 393.1 [M+H]+.

Example 119: (S)-5⁵-Bromo-10-methyl-5⁴-(methylsulfonyl)-1⁴H-6-oxa-3-aza-2(2,6)-pyridina-1(3,4)-triazola-5(1,2)-benzenacyclodecaphan-4-one

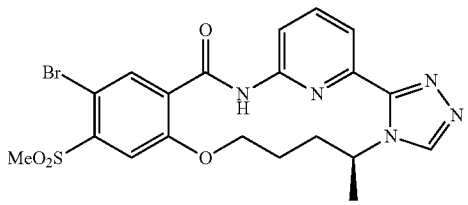 [SMILES: C[C@H]1CCCOc2cc(S(C)(=O)=O)c(Br)cc2C(=O)Nc2cccc(n2)-c2nncn21]

To a solution of (S)-5⁵-bromo-5⁴-fluoro-10-methyl-1⁴H-6-oxa-3-aza-2(2,6)-pyridina-1(3,4)-triazola-5(1,2)-benzenacyclodecaphan-4-one (50 mg, 0.112 mmol) in DMSO (3 mL) under a N₂ atmosphere was added methanesulfinate (17 mg, 0.17 mmol, sodium salt), CuI (13 mg, 0.067 mmol) followed by L-proline (15 mg, 0.13 mmol). The mixture was stirred at 110° C. for 8 h. After this time the mixture was cooled to room temperature and the mixture was treated with an additional portion of methanesulfinate (17 mg, 0.17 mmol, sodium salt), CuI (13 mg, 0.067 mmol) and L-proline (15 mg, 0.13 mmol) and the mixture was heated at 110° C. for 5 h. After this time the mixture was cooled to room temperature and an additional portion of methanesulfinate (17 mg, 0.17 mmol, sodium salt), CuI (13 mg, 0.067 mmol) and L-proline (15 mg, 0.13 mmol) and the mixture was heated at 110° C. for 2 days. After this time, the mixture was filtered and the filtrate was purified by HPLC (using a Waters Xbridge Prep OBD C18, 5 μm 150×30 mm column and using water (containing 0.05% NH₃.H₂O and 10 mM NH₄HCO₃)/CH₃CN, from 30% to 60% as the mobile phase at a flow rate of 25 mL/min) to give the title compound (6 mg, 11%) as a white solid. ¹H NMR (400 MHz, DMSO-d₆) δ ppm 11.01 (s, 1H), 8.78-9.03 (m, 1H), 8.20 (s, 1H), 8.07-8.09 (m, 1H), 7.80 (br d, J=7.0 Hz, 2H), 7.74 (s, 1H), 4.50 (br s, 2H), 4.22 (br s, 1H), 3.43 (s, 3H), 3.16 (br s, 1H), 2.07 (br s, 1H), 1.75 (br s, 2H), 1.49-1.51 (br d, J=8 Hz, 3H). MS (ESI): 508.1 [(M+H) (⁸¹Br)]+.

Example 120: (S)-5⁴-Bromo-10-methyl-1⁴H-6-oxa-3-aza-2(2,6)-pyridina-1(3,4)-triazola-5(1,2)-benzenacyclodecaphan-4-one and Example 121: (R)-5⁴-Bromo-10-methyl-1⁴H-6-oxa-3-aza-2(2,6)-pyridina-1(3,4)-triazola-5(1,2)-benzenacyclodecaphan-4-one

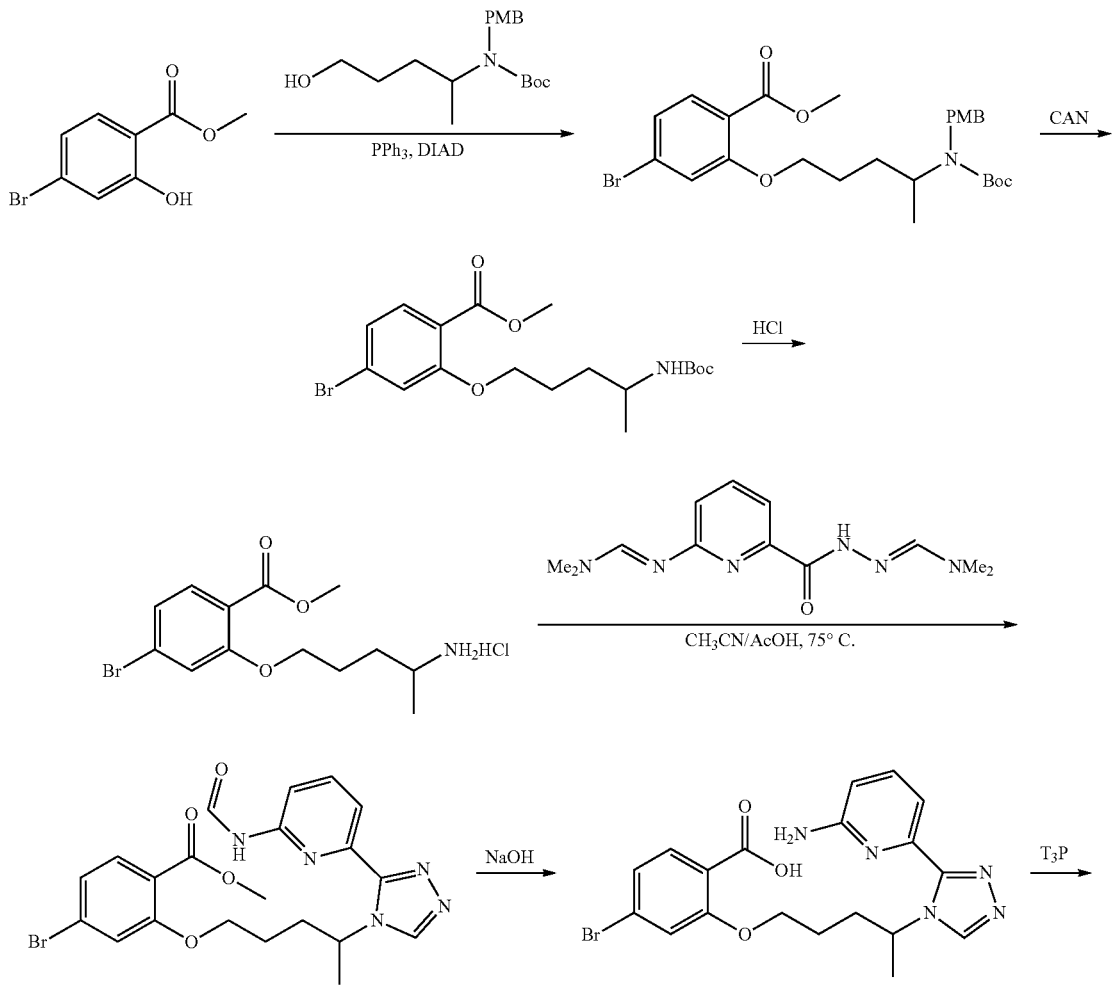

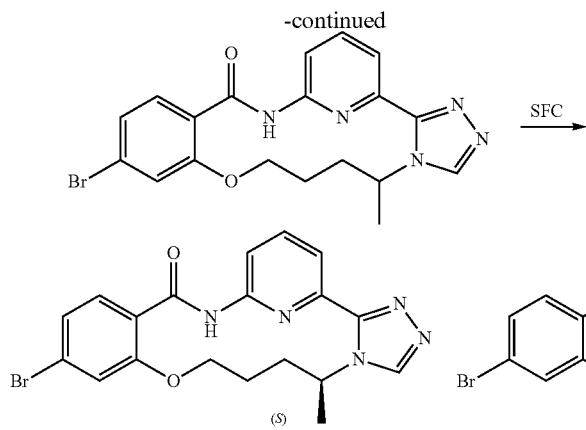

Step A. rac-Methyl 4-bromo-2-((4-((tert-butoxycarbonyl)(4-methoxybenzyl)amino)pentyl)oxy)benzoate

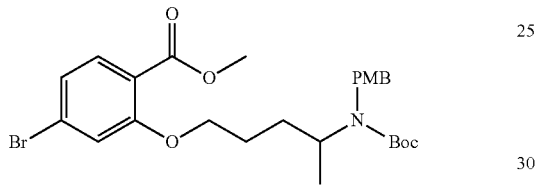

To a solution of methyl 4-bromo-2-hydroxybenzoate (10 g, 43.3 mmol) in tetrahydrofuran (150 mL) was added rac-tert-butyl (5-hydroxypentan-2-yl)(4-methoxybenzyl) carbamate (21 g, 64.9 mmol) and PPh$_3$ (17.0 g, 64.9 mmol) and the mixture was cooled to 0° C. and treated with DIAD (13.6 mL, 69.2 mmol) dropwise via syringe. The mixture was stirred at 28° C. for 3 h and after this time the reaction was concentrated and petroleum ether/EtOAc (50 mL, 5/1) was added. The mixture was stirred at 28° C. for 15 min, filtered and concentrated to give the crude. The crude was purified by column chromatography on silica gel using petroleum ether/EtOAc (100/1 to 10/1) as an eluent to give the title compound (17 g, 69%) as a yellow gum. MS (ESI): 558.1 [(M+Na) ($^{79}$Br)]$^+$.

Step B. rac-Methyl 4-bromo-2-((4-((tert-butoxycarbonyl)amino)pentyl)oxy)benzoate

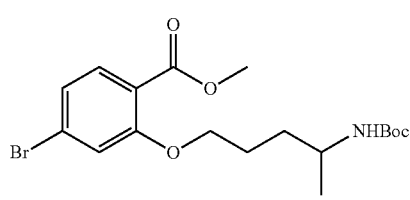 [SMILES: COC(=O)c1ccc(Br)cc1OCCCC(C)NC(=O)OC(C)(C)C]

To a solution of rac-methyl 4-bromo-2-((4-((tert-butoxycarbonyl)(4-methoxybenzyl)amino)pentyl)oxy)benzoate (16 g, 29.8 mmol) in CH$_3$CN/water (150 mL, 1/1) was added ceric ammonium nitrate (32.7 g, 59.6 mmol) at 0° C. The mixture was stirred at 28° C. for 30 min followed by the addition of water (500 mL). The mixture was extracted with EtOAc (3×500 mL) and the combined organic layer was washed with brine (1 L), dried over anhydrous sodium sulfate, filtered and concentrated to give the title compound (12.4 g) as a yellow solid. MS (ESI): 416.2 [(M+H) ($^{79}$Br)]$^+$.

Step C. rac-Methyl 2-((4-aminopentyl)oxy)-4-bromobenzoate hydrochloride

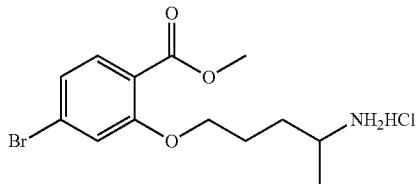

A solution of rac-methyl 4-bromo-2-((4-((tert-butoxycarbonyl)amino)pentyl)oxy)benzoate (11 g, 26.4 mmol) in hydrochloric acid (100 mL, 4.0 M) was stirred at 28° C. for 30 min. After this time the mixture was filtered and EtOAc (50 mL) was added. The mixture was stirred at 28° C. for 15 min and filtered to give the title compound (7.5 g, 80%) as a white solid. MS (ESI): 318.0 [(M+H) ($^{81}$Br)]$^+$.

Step D. rac-Methyl 4-bromo-2-((4-(3-(6-formamidopyridin-2-yl)-4H-1,2,4-triazol-4-yl)pentyl)oxy)benzoate

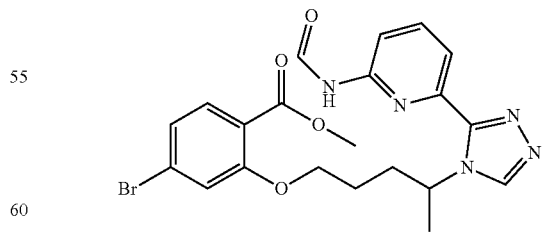

A solution of rac-methyl 2-((4-aminopentyl)oxy)-4-bromobenzoate hydrochloride (3.5 g, 9.9 mmol) and (E)-N'-(6-(2-((E)-(dimethylamino)methylene)hydrazine-1-carbonyl)pyridin-2-yl)-N,N-dimethylformimidamide (6.1 g, 17.3 mmol) in CH$_3$CN/AcOH (40 mL, 1/1) was stirred at 80° C.

for 24 h. After this time the reaction was concentrated and purified by column chromatography on silica gel using petroleum ether/EtOAc (100/1 to 0/1) as an eluent to give the title compound (3.8 g, 79%) as a yellow solid.

Step E. rac-2-((4-(3-(6-Aminopyridin-2-yl)-4H-1,2,4-triazol-4-yl)pentyl)oxy)-4-bromobenzoic acid

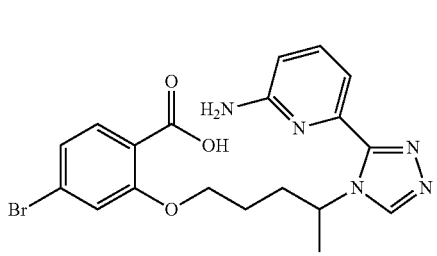 [SMILES: CC(CCCOc1cc(Br)ccc1C(=O)O)n1cnnc1-c1cccc(N)n1]

To a solution of rac-methyl 4-bromo-2-((4-(3-(6-formamidopyridin-2-yl)-4H-1,2,4-triazol-4-yl)pentyl)oxy)benzoate (3.8 g, 7.8 mmol) in tetrahydrofuran (20 mL) and MeOH (20 mL) was added sodium hydroxide (934 mg, 23.3 mmol) and the mixture was stirred at 80° C. for 12 h. After this time the mixture was concentrated to give the title compound (3.4 g, 95% yield) which was used in next step without further purification. MS (ESI): 447.9 [(M+H) ($^{81}$Br)]$^+$.

Step F. rac-5$^4$-Bromo-10-methyl-1$^4$H-6-oxa-3-aza-2(2,6)-pyridina-1(3,4)-triazola-5(1,2)-benzenacyclodecaphan-4-one

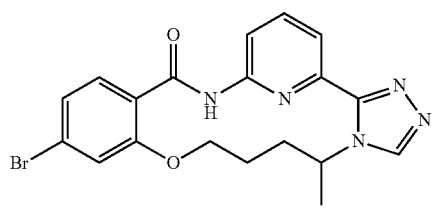 [SMILES: CC1CCCOc2cc(Br)ccc2C(=O)Nc2cccc(n2)-c2nncn21]

A solution of rac-2-((4-(3-(6-aminopyridin-2-yl)-4H-1,2,4-triazol-4-yl)pentyl)oxy)-4-bromobenzoic acid (3.2 g, 7.2 mmol), T$_3$P (68.4 g, 107.5 mmol, ≥50 wt. % in EtOAc) and Et$_3$N (19.9 mL, 143.4 mmol) in EtOAc (20 mL) was stirred at 50° C. for 12 h. After this time the mixture was filtered and the filter cake was suspended in water (20 mL) for 30 min. The suspension was filtered and the solid was dried under reduced pressure to give the title compound (1.1 g, 37% yield) as a white solid. MS (ESI): 430.1 [(M+H) ($^{81}$Br)]$^+$.

Step G. (S)-5$^4$-Bromo-10-methyl-1$^4$H-6-oxa-3-aza-2(2,6)-pyridina-1(3,4)-triazola-5(1,2)-benzenacyclodecaphan-4-one and (R)-5$^4$-Bromo-10-methyl-1$^4$H-6-oxa-3-aza-2(2,6)-pyridina-1(3,4)-triazola-5(1,2)-benzenacyclodecaphan-4-one

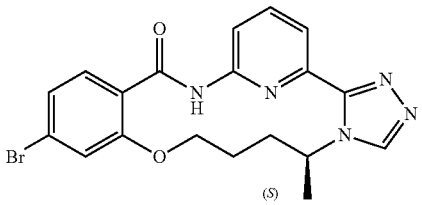

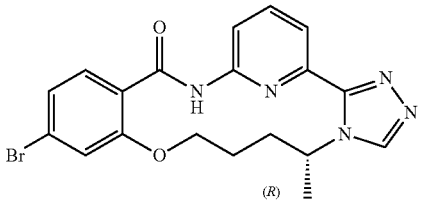

rac-5$^4$-Bromo-10-methyl-1$^4$H-6-oxa-3-aza-2(2,6)-pyridina-1(3,4)-triazola-5(1,2)-benzenacyclodecaphan-4-one (600 mg, 1.4 mmol) was separated by SFC (using an AD column (250×30 mm×5 μm) and 50% EtOH (containing 0.1% ammonium hydroxide) in CO$_2$ as the mobile phase at a flow rate of 60 mL/min) to provide in order of elution:

Peak 1 (absolute stereochemistry arbitrarily assigned): (S)-5$^4$-bromo-10-methyl-1$^4$H-6-oxa-3-aza-2(2,6)-pyridina-1(3,4)-triazola-5(1,2)-benzenacyclodecaphan-4-one (180 mg, 30% yield) as white solid. $^1$H NMR (400 MHz, DMSO-d$_6$) δ ppm 11.12 (s, 1H), 8.87 (s, 1H), 8.08 (t, J=7.6 Hz, 1H), 7.78-7.91 (m, 3H), 7.49 (s, 1H), 7.36 (d, J=8.8 Hz, 1H), 4.58 (s, 1H), 4.50 (d, J=9.2 Hz, 1H), 4.18 (t, J=9.6 Hz, 1H), 3.14 (d, J=11.6 Hz, 1H), 2.11 (s, 1H), 1.70-1.83 (m, 1H), 1.69-1.82 (m, 1H), 1.54 (d, J=7.2 Hz, 3H). MS (ESI): 430.1 [(M+H) ($^{81}$Br)]$^+$.

Peak 2 (absolute stereochemistry arbitrarily assigned): (R)-5$^4$-bromo-10-methyl-1$^4$H-6-oxa-3-aza-2(2,6)-pyridina-1(3,4)-triazola-5(1,2)-benzenacyclodecaphan-4-one (240 mg, 40% yield) as a white solid. $^1$H NMR (400 MHz, DMSO-d$_6$) δ ppm 11.09 (s, 1H), 8.85 (s, 1H), 8.08 (t, J=8.0 Hz, 1H), 7.83 (t, J=8.4 Hz, 2H), 7.79 (d, J=7.6 Hz, 1H), 7.46 (s, 1H), 7.34 (dd, J=1.2, 8.4 Hz, 1H), 4.41-4.60 (m, 2H), 4.09-4.20 (m, 1H), 3.06-3.17 (m, 1H), 2.07 (s, 1H), 1.67-1.82 (m, 2H), 1.51 (d, J=7.2 Hz, 3H). MS (ESI): 428.0 [(M+H) ($^{79}$Br)]$^+$.

Example 122: (S)-10-Methyl-5⁴-(4-methylpiperazin-1-yl)-1⁴H-6-oxa-3-aza-2(2,6)-pyridina-1(3,4)-triazola-5(1,2)-benzenacyclodecaphan-4-one and
Example 123: (R)-10-Methyl-5⁴-(4-methylpiperazin-1-yl)-1⁴H-6-oxa-3-aza-2(2,6)-pyridina-1(3,4)-triazola-5(1,2)-benzenacyclodecaphan-4-one

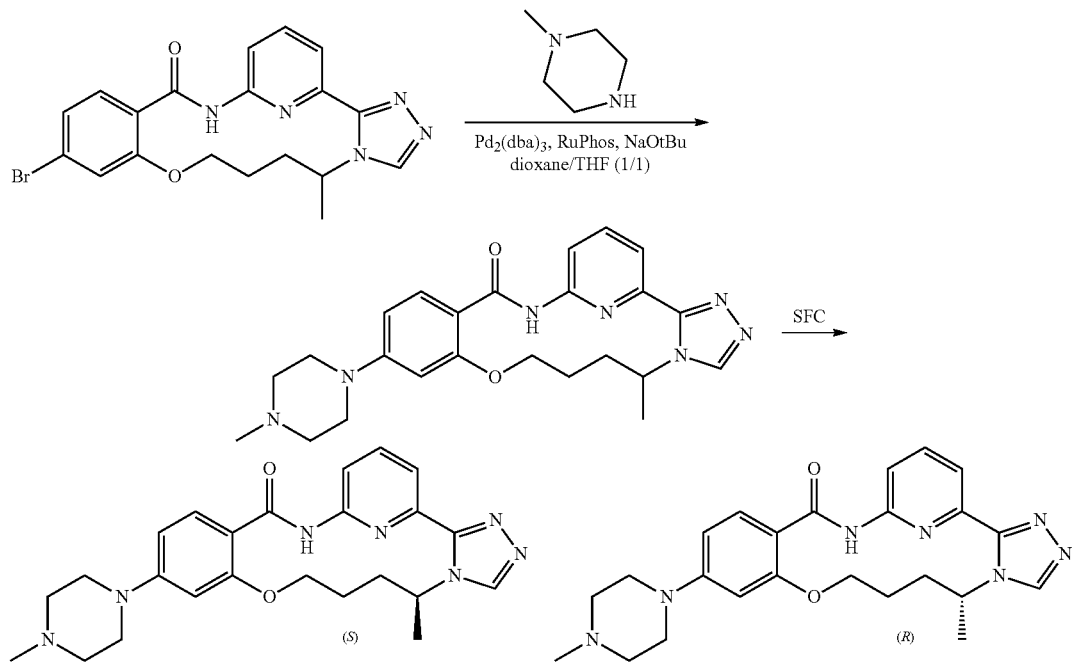

Step A. rac-10-Methyl-5⁴-(4-methylpiperazin-1-yl)-1⁴H-6-oxa-3-aza-2(2,6)-pyridina-1(3,4)-triazola-5(1,2)-benzenacyclodecaphan-4-one To a solution of rac-5⁴-bromo-10-methyl-1⁴H-6-oxa-3-aza-2(2,6)-pyridina-1(3,4)-triazola-5(1,2)-benzenacyclodecaphan-4-one (220 mg, 0.51 mmol) in dioxane/THF (1/1, 8 mL) under a N₂ atmosphere was added sodium tert-butoxide (148 mg, 1.5 mmol) and 1-methylpiperazine (257 mg, 2.6 mmol) followed by Pd₂(dba)₃ (47 mg, 0.05 mmol) and RuPhos (24 mg, 0.05 mmol). The mixture was stirred at 110° C. for 3.5 h, concentrated under vacuum and purified by HPLC (using a Phenomenex Synergi C18, 4 µm 150×30 mm column and using water (containing 0.05% HCl)/CH₃CN, from 11% to 31% as the mobile phase at a flow rate of 25 mL/min) to give the title compound (150 mg, 65% yield) as a yellow solid. MS (ESI): 448.3 [M+H]⁺.

Step B. (S)-10-Methyl-5⁴-(4-methylpiperazin-1-yl)-1⁴H-6-oxa-3-aza-2(2,6)-pyridina-1(3,4)-triazola-5(1,2)-benzenacyclodecaphan-4-one and (R)-10-Methyl-5⁴-(4-methylpiperazin-1-yl)-1⁴H-6-oxa-3-aza-2(2,6)-pyridina-1(3,4)-triazola-5(1,2)-benzenacyclodecaphan-4-one

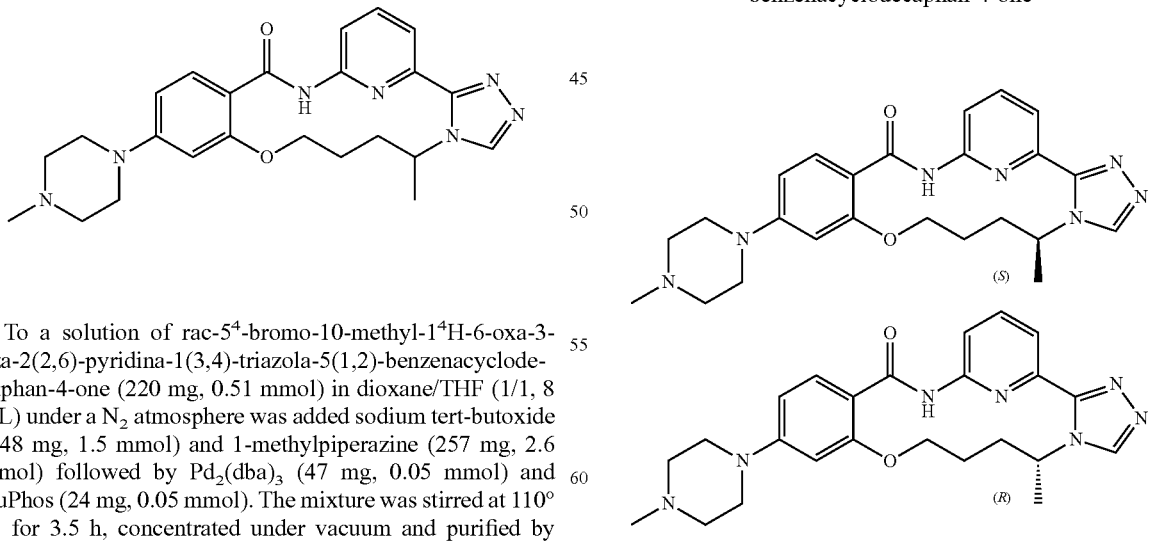

rac-10-Methyl-5⁴-(4-methylpiperazin-1-yl)-1⁴H-6-oxa-3-aza-2(2,6)-pyridina-1(3,4)-triazola-5(1,2)-benzenacyclodecaphan-4-one (150 mg) was purified by SFC (using a Chiralpak AS-H 5 µm 250×30 mm column and using 45%

EtOH (containing 0.1% NH$_3$.H$_2$O) in CO$_2$ as the mobile phase) to provide in order of elution:

Peak 1 (absolute stereochemistry arbitrarily assigned): (S)-10-methyl-5$^4$-(4-methylpiperazin-1-yl)-1$^4$H-6-oxa-3-aza-2(2,6)-pyridina-1(3,4)-triazola-5(1,2)-benzenacyclodecaphan-4-one (Rt=5.35 min, 56 mg) as a white solid. $^1$H NMR (400 MHz, MeOD) δ ppm 8.83 (s, 1H), 7.99 (t, J=8.0 Hz, 1H), 7.90-7.93 (m, 2H), 7.82 (d, J=7.6 Hz, 1H), 6.65 (d, J=8.8 Hz, 1H), 6.53 (s, 1H), 4.74 (br, 1H), 4.42-4.49 (m, 1H), 4.17 (t, J=9.6 Hz, 1H), 3.42 (br s, 4H), 3.30 (br, 1H), 2.65 (br s, 4H), 2.40 (s, 3H), 2.24 (br, 1H), 1.86 (br s, 2H), 1.66 (d, J=6.8 Hz, 3H). MS (ESI): 448.3 [M+H]$^+$.

Peak 2 (absolute stereochemistry arbitrarily assigned): (R)-10-methyl-5$^4$-(4-methylpiperazin-1-yl)-1$^4$H-6-oxa-3-aza-2(2,6)-pyridina-1(3,4)-triazola-5(1,2)-benzenacyclodecaphan-4-one (Rt=6.22 min, 54 mg) as a white solid. $^1$H NMR (400 MHz, MeOD) δ ppm 8.83 (s, 1H), 7.90-8.02 (m, 3H), 7.82 (d, J=7.2 Hz, 1H), 6.68 (d, J=8.8 Hz, 1H), 6.60 (s, 1H), 4.72 (br, 1H), 4.46 (d, J=10.0 Hz, 1H), 4.17 (t, J=9.6 Hz, 1H), 3.66 (br s, 4H), 3.40 (br s, 4H), 3.27-3.26 (m, 1H), 2.95 (s, 3H), 2.24 (br, 1H), 1.89-1.81 (m, 2H), 1.66 (d, J=6.8 Hz, 3H). MS (ESI): 448.2 [M+H]$^+$.

Example 124: (S)-5$^5$-Bromo-5$^4$-fluoro-9-methyl-1$^4$H-6-oxa-3-aza-2(2,6)-pyridina-1(3,4)-triazola-5(1,2)-benzenacyclodecaphan-4-one and Example 125: (R)-5$^5$-Bromo-5$^4$-fluoro-9-methyl-1$^4$H-6-oxa-3-aza-2(2,6)-pyridina-1(3,4)-triazola-5(1,2)-benzenacyclodecaphan-4-one

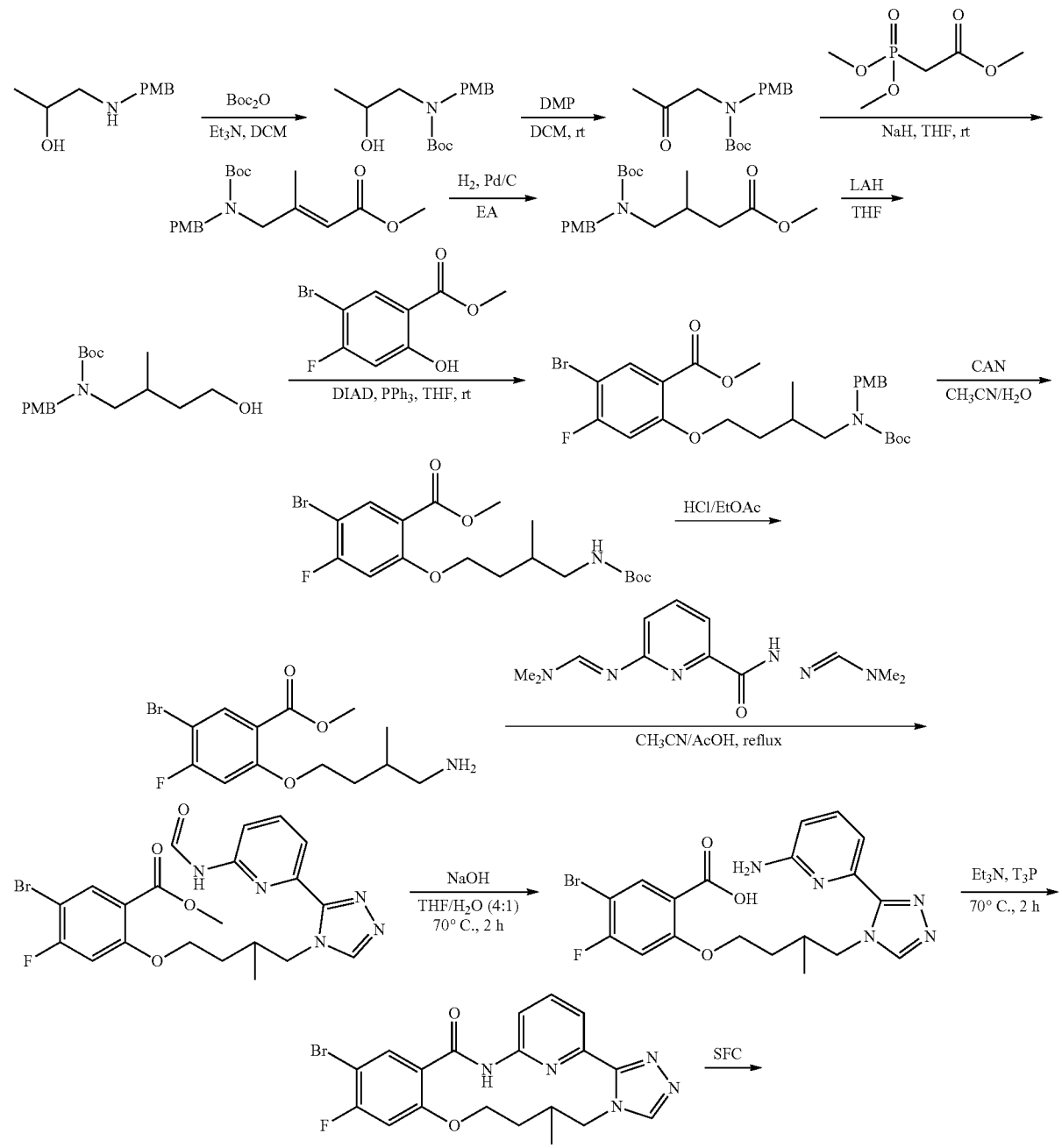

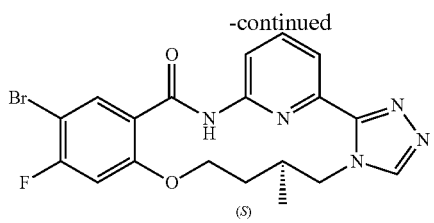
(S)

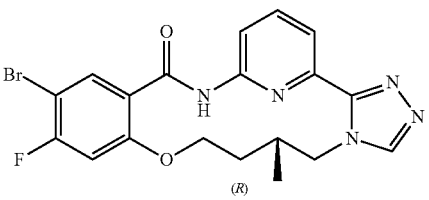
(R)

Step A. rac-tert-Butyl (2-hydroxypropyl)(4-methoxybenzyl)carbamate

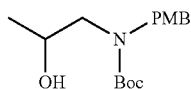

To a stirred mixture of rac-1-((4-methoxybenzyl)amino)propan-2-ol (145 g, 0.74 mol) in DCM (50 mL) was added Boc$_2$O (193 g, 0.89 mol) followed by Et$_3$N (97.2 g, 0.96 mol) and the mixture was stirred at 10° C. for 17 h. After this time the solvent was removed under vacuum to give the title compound (220 g, 100% crude) as colorless oil which was used without further purification in the next step. $^1$H NMR (400 MHz, CDCl$_3$) δ ppm 7.18 (d, J=7.6 Hz, 2H), 6.88 (d, J=7.2 Hz, 2H), 4.45 (s, 2H), 3.95-4.00 (m, 1H), 3.83 (s, 3H), 3.32-3.40 (m, 1H), 3.11-3.15 (m, 1H), 1.50 (s, 9H), 1.13 (d, J=6.4 Hz, 3H).

Step B. rac-tert-Butyl (4-methoxybenzyl)(2-oxopropyl)carbamate

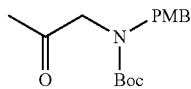

To a stirred mixture of rac-tert-butyl (2-hydroxypropyl)(4-methoxybenzyl)carbamate (20 g, 68 mmol) in DCM (200 mL) at 0° C. was added DMP (43 g, 0.1 mol) portionwise and after the addition was completed the mixture was stirred at 10° C. for 17 h. After this time the mixture was filtered and the organic phase was washed with water (200 mL), dried over Na$_2$SO$_4$, filtered and concentrated to give the crude product which was purified by column chromatography on silica using petroleum ether/EtOAc (20/1 to 5/1) as eluent to give the title compound (13.5 g, 68%) as a colorless oil. $^1$H NMR (400 MHz, CDCl$_3$) δ ppm 7.14-7.17 (m, 2H), 6.86-6.89 (m, 2H), 4.26-4.27 (m, 2H), 3.89-3.93 (m, 2H), 3.71 (s, 3H), 1.97-1.98 (m, 3H), 1.33-1.37 (m, 9H).

Step C. rac-Methyl (E)-4-((tert-butoxycarbonyl)(4-methoxybenzyl)amino)-3-methylbut-2-enoate

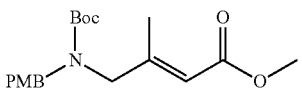

To a stirred mixture of NaH (3.7 g, 92 mmol, 60% dispersion in oil) in THF (500 mL) at 0° C. under a N$_2$ atmosphere was dropwise added methyl 2-(dimethoxyphosphoryl)acetate (16.8 g, 92 mmol) in THF (100 mL). After 30 min stirring at 10° C., the mixture was cooled to 0° C. and rac-tert-butyl (4-methoxybenzyl)(2-oxopropyl)carbamate (13.5 g, 46 mmol) in THF (100 mL) was added dropwise and the mixture was stirred at 10° C. for 17 h. After this time the reaction was quenched with water (500 mL) and extracted with EtOAc (3×500 mL). The organic phase was dried over Na$_2$SO$_4$, filtered and concentrated to give the crude product which was purified by column chromatography on silica using petroleum ether/EtOAc (50/1 to 10/1) as eluent to give the title compound (18.5 g, 58%) as colorless gum. $^1$H NMR (400 MHz, CDCl$_3$) δ (400 MHz, CDCl$_3$) δ ppm 7.15-7.20 (m, 2H), 6.88 (d, J=8.4 Hz, 2H), 5.69 (s, 1H), 4.32-4.37 (m, 2H), 3.86-3.87 (m, 1H), 3.82 (s, 3H), 3.74-3.75 (m, 1H), 3.73 (s, 3H), 2.07 (s, 3H), 1.49-1.50 (m, 9H).

Step D. rac-Methyl 4-((tert-butoxycarbonyl)(4-methoxybenzyl)amino)-3-methylbutanoate

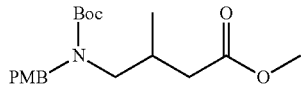

A mixture of rac-methyl (E)-4-((tert-butoxycarbonyl)(4-methoxybenzyl)amino)-3-methylbut-2-enoate (8.5 g, 24 mmol) and Pd (4 g, 10% on C) in EtOAc (100 mL) was stirred at 10° C. under H$_2$ (15 psi) for 17 h. The mixture was filtered and concentrated to give the title compound (8.5 g, 100% crude) as a colorless gum. $^1$H NMR (400 MHz, CDCl$_3$) δ ppm 7.15-7.19 (m, 2H), 6.81-6.86 (m, 2H), 4.32-4.45 (m, 2H), 3.79 (s, 3H), 3.66 (s, 3H), 2.98-3.14 (m, 2H), 2.32-2.33 (m, 2H), 2.10-2.12 (m, 1H), 1.45-1.48 (m, 9H), 0.91 (d, J=6.0 Hz, 3H).

Step E. rac-tert-Butyl (4-hydroxy-2-methylbutyl)(4-methoxybenzyl)carbamate

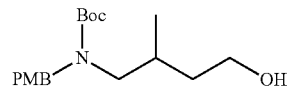

To a stirred mixture of LAH (1.84 g, 48 mmol) in THF (70 mL) at 0° C. under a N$_2$ atmosphere was dropwise added rac-methyl 4-((tert-butoxycarbonyl)(4-methoxybenzyl)amino)-3-methylbutanoate (8.5 g, 24 mmol) in THF (30 mL) and the mixture was stirred at 10° C. for 30 minutes. After this time water (1.8 mL) was added slowly at 0° C. followed by 15% aq. NaOH solution (1.8 mL) and water (5.5 mL).

After 10 min stirring, Na₂SO₄ was added and the mixture was stirred for 30 min. After this time the mixture was filtered and the solid was washed with DCM/MeOH (10/1, 3×10 mL). The organic phase was dried over Na₂SO₄, filtered and concentrated to give the crude product which was purified by column chromatography on silica gel using petroleum ether/EtOAc (10/1 to 3/1) as eluent to give the title compound (7 g, 90%) as a colorless oil. $^1$H NMR (400 MHz, CDCl₃) δ ppm 7.15 (d, J=6.8 Hz, 2H), 6.85 (d, J=8.8 Hz, 2H), 4.38-4.39 (m, 2H), 3.80 (s, 3H), 3.61-3.70 (m, 2H), 3.08-3.26 (m, 1H), 2.90-2.96 (m, 1H), 1.95-1.96 (m, 1H), 1.42-1.59 (m, 11H), 0.90 (d, J=6.0 Hz, 3H).

Step F. rac-Methyl 5-bromo-2-(4-((tert-butoxycarbonyl)(4-methoxybenzyl)amino)-3-methylbutoxy)-4-fluorobenzoate

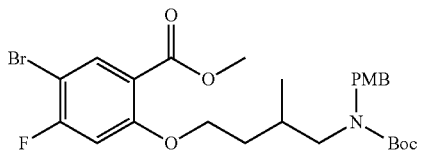

To a stirred mixture of methyl 5-bromo-4-fluoro-2-hydroxybenzoate (4 g, 0.016 mol), rac-tert-butyl (4-hydroxy-2-methylbutyl)(4-methoxybenzyl)carbamate (5.2 g, 16 mmol), PPh₃ (5 g, 0.019 mol) in THF (100 mL) was dropwise added DIAD (4.1 mL, 0.02 mol) under a N₂ atmosphere at 0° C. and the reaction mixture was stirred at 10° C. for 2 h. After this time the volatiles were removed under reduced pressure to give the crude product which was purified by column chromatography on silica gel using petroleum ether/EtOAc (10/1 to 3/1) as eluent to give the title compound (5 g, 46%) as a colorless gum. $^1$H NMR (400 MHz, CDCl₃) δ ppm 8.04 (d, J=8.4 Hz, 1H), 7.13-7.14 (m, 2H), 6.80-6.85 (m, 2H), 6.70-6.71 (m, 1H), 4.37-4.45 (m, 2H), 3.98-3.99 (m, 2H), 3.85 (s, 3H), 3.78 (s, 3H), 3.08-3.16 (m, 2H), 2.11-2.12 (m, 1H), 1.87-1.88 (m, 1H), 1.61-1.62 (m, 1H), 1.46 (s, 9H), 0.94 (d, J=6.8 Hz, 3H).

Step G. rac-Methyl 5-bromo-2-(4-((tert-butoxycarbonyl)amino)-3-methylbutoxy)-4-fluorobenzoate

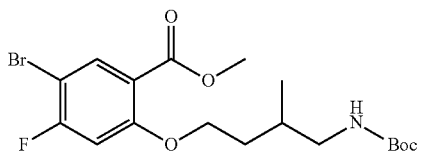 [SMILES: COC(=O)c1cc(Br)c(F)cc1OCCC(C)CNC(=O)OC(C)(C)C]

A mixture of rac-methyl 5-bromo-2-(4-((tert-butoxycarbonyl)(4-methoxybenzyl)amino)-3-methylbutoxy)-4-fluorobenzoate (4.5 g, 8.1 mmol) and CAN (13.2 g, 25 mmol) in CH₃CN/water (1/1, 100 mL) was stirred at 10° C. for 30 min. After this time water (500 mL) was added and the mixture was extracted with EtOAc (3×200 mL). The combined organic extracts were dried over Na₂SO₄, filtered and concentrated to give the title compound (5 g, 100% crude) as a colorless gum. MS (ESI): 434.0 [(M+H) ($^{79}$Br)]⁺.

Step H. rac-Methyl 2-(4-amino-3-methylbutoxy)-5-bromo-4-fluorobenzoate

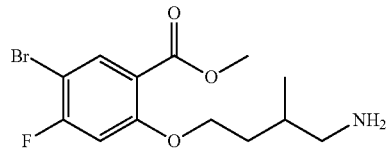 [SMILES: COC(=O)c1cc(Br)c(F)cc1OCCC(C)CN]

To a mixture of rac-methyl 5-bromo-2-(4-((tert-butoxycarbonyl)amino)-3-methylbutoxy)-4-fluorobenzoate (3.5 g, 8.1 mmol) in EtOAc (10 mL) was added HCl/EtOAc (20 mL) and the mixture was stirred at 10° C. for 1 h. After this time, the volatiles were removed under reduced pressure to give the crude product which was dissolved in water (20 mL) and extracted with EtOAc (20 mL). The pH of the aqueous phase was adjusted to 10 and extracted with DCM (3×20 mL). The organic phase was dried over Na₂SO₄, filtered and concentrated to give the title compound (1.8 g, 67%) as an orange gum.

Step I. rac-Methyl 5-bromo-4-fluoro-2-(4-(3-(6-formamidopyridin-2-yl)-4H-1,2,4-triazol-4-yl)-3-methylbutoxy)benzoate

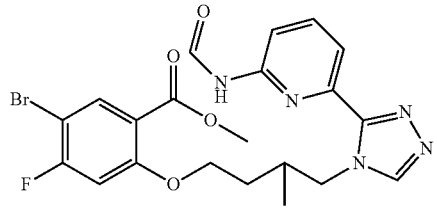 [SMILES: COC(=O)c1cc(Br)c(F)cc1OCCC(C)Cn1cnnc1-c1cccc(NC=O)n1]

A mixture of rac-methyl 2-(4-amino-3-methylbutoxy)-5-bromo-4-fluorobenzoate (1.8 g, 5.4 mmol) and (E)-N'-(6-(2-((E)-(dimethylamino)methylene)hydrazine-1-carbonyl)pyridin-2-yl)-N,N-dimethylformimidamide (1.2 g, 4.5 mmol) in AcOH (20 mL) and CH₃CN (20 mL) was stirred at 80° C. for 17 h. After this time the volatiles were removed under reduced pressure to give the crude product which was purified by column chromatography on silica gel using petroleum ether/EtOAc (10/1) and then DCM/MeOH (40/1) as eluent to give the title compound (800 mg, 35%) as a colorless gum. MS (ESI): 508.0 [(M+H) ($^{81}$Br)]⁺.

Step J. rac-2-(4-(3-(6-Aminopyridin-2-yl)-4H-1,2,4-triazol-4-yl)-3-methylbutoxy)-5-bromo-4-fluorobenzoic acid

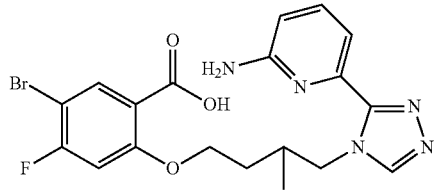 [SMILES: CC(CCOc1cc(F)c(Br)cc1C(=O)O)Cn1cnnc1-c1cccc(N)n1]

A mixture of rac-methyl 5-bromo-4-fluoro-2-(4-(3-(6-formamidopyridin-2-yl)-4H-1,2,4-triazol-4-yl)-3-methylbutoxy)benzoate (800 mg, 1.58 mmol) and NaOH (158 mg, 3.95 mmol) in THF/H$_2$O (5/1, 12 mL) was stirred at 70° C. for 2 h. After this time, the volatiles were removed under reduced pressure to give the title compound (900 mg, 100% crude) as a yellow solid which was used without further purification in the next step.

Step K. rac-5$^5$-Bromo-5$^4$-fluoro-9-methyl-1$^4$H-6-oxa-3-aza-2(2,6)-pyridina-1(3,4)-triazola-5(1,2)-benzenacyclodecaphan-4-one

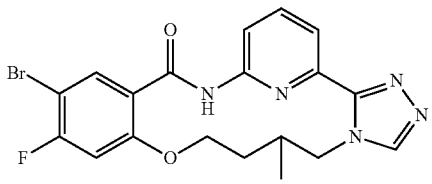 [SMILES: CC1CCOc2cc(F)c(Br)cc2C(=O)Nc2cccc(n2)-c2nncn2C1]

A mixture of rac-2-(4-(3-(6-aminopyridin-2-yl)-4H-1,2,4-triazol-4-yl)-3-methylbutoxy)-5-bromo-4-fluorobenzoic acid (800 mg, 1.7 mmol) in T$_3$P (20 mL, ≥50 wt. % in EtOAc) and Et$_3$N (20 mL) was stirred at 70° C. for 2 h. After this time, water (100 mL) was added and the mixture was stirred until a solid was formed (30 min). The solid was filtered and dried under vacuum to give the crude product which was purified by column chromatography on silica gel using DCM/MeOH (1:0 to 40/1) as eluent to give the title compound (180 mg, 23%) as a white solid. 1H NMR (400 MHz, DMSO-d$_6$) δ ppm 10.99 (s, 1H), 8.66 (s, 1H), 8.14 (d, J=8.4 Hz, 1H), 8.02-8.06 (m, 1H), 7.84-7.88 (m, 2H), 7.44 (d, J=10.8 Hz, 1H), 4.48-4.51 (m, 1H), 4.39-4.41 (m, 1H), 4.21-4.26 (m, 1H), 3.82-3.89 (m, 1H), 3.17-3.19 (m, 1H), 1.99-2.06 (m, 1H), 1.63-1.66 (m, 1H), 0.92 (d, J=6.0 Hz, 3H). MS (ESI): 447.8 [(M+H) ($^{81}$Br)]$^+$.

Step L. (S)-5$^5$-Bromo-5$^4$-fluoro-9-methyl-1$^4$H-6-oxa-3-aza-2(2,6)-pyridina-1(3,4)-triazola-5(1,2)-benzenacyclodecaphan-4-one and (R)-5$^5$-Bromo-5$^4$-fluoro-9-methyl-1$^4$H-6-oxa-3-aza-2(2,6)-pyridina-1(3,4)-triazola-5(1,2)-benzenacyclodecaphan-4-one

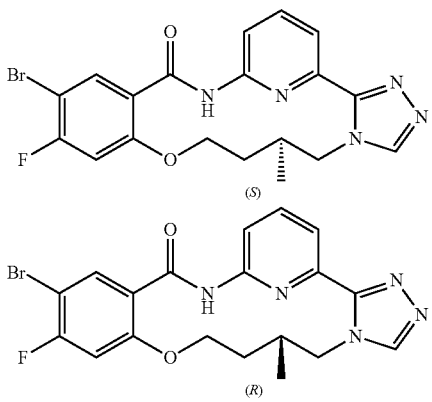

rac-5$^5$-Bromo-5$^4$-fluoro-9-methyl-1$^4$H-6-oxa-3-aza-2(2,6)-pyridina-1(3,4)-triazola-5(1,2)-benzenacyclodecaphan-4-one (140 mg) was purified by SFC (using a Chiralpak AD-3 3 μm 50×4.6 mm column and using 40% ethanol (containing 0.05% Et$_2$NH) in CO$_2$ as the mobile phase at a flow rate of 4 mL/min with a column temperature of 40° C.) to give in order of elution:

Peak 1 (absolute stereochemistry arbitrarily assigned): (S)-5$^5$-Bromo-5$^4$-fluoro-9-methyl-1$^4$H-6-oxa-3-aza-2(2,6)-pyridina-1(3,4)-triazola-5(1,2)-benzenacyclodecaphan-4-one (50 mg, 36%) as a white solid. $^1$H NMR (400 MHz, DMSO-d$_6$) δ ppm 10.98 (s, 1H), 8.67 (s, 1H), 8.13 (d, J=8.4 Hz, 1H), 8.01-8.05 (m, 1H), 7.82-7.87 (m, 2H), 7.42 (d, J=10.8 Hz, 1H), 4.48-4.50 (m, 1H), 4.38-4.41 (m, 1H), 4.20-4.25 (m, 1H), 3.82-3.87 (m, 1H), 3.15-3.17 (m, 1H), 1.99-2.05 (m, 1H), 1.60-1.66 (m, 1H), 0.92 (d, J=6.4 Hz, 3H). MS (ESI): 447.8 [(M+H) ($^{81}$Br)]$^+$.

Peak 2 (absolute stereochemistry arbitrarily assigned): (R)-5$^5$-Bromo-5$^4$-fluoro-9-methyl-1$^4$H-6-oxa-3-aza-2(2,6)-pyridina-1(3,4)-triazola-5(1,2)-benzenacyclodecaphan-4-one (50 mg, 36%) as a white solid. $^1$H NMR (400 MHz, DMSO-d$_6$) δ ppm 10.98 (s, 1H), 8.67 (s, 1H), 8.13 (d, J=8.4 Hz, 1H), 8.01-8.05 (m, 1H), 7.82-7.87 (m, 2H), 7.42 (d, J=10.8 Hz, 1H), 4.48-4.50 (m, 1H), 4.38-4.41 (m, 1H), 4.20-4.25 (m, 1H), 3.82-3.87 (m, 1H), 3.15-3.17 (m, 1H), 1.99-2.05 (m, 1H), 1.60-1.66 (m, 1H), 0.92 (d, J=6.4 Hz, 3H). MS (ESI): 447.8 [(M+H) ($^{81}$Br)]$^+$.

Example 126: (S)-5$^4$-Fluoro-9-methyl-5$^5$-morpholino-1$^4$H-6-oxa-3-aza-2(2,6)-pyridina-1(3,4)-triazola-5(1,2)-benzenacyclodecaphan-4-one

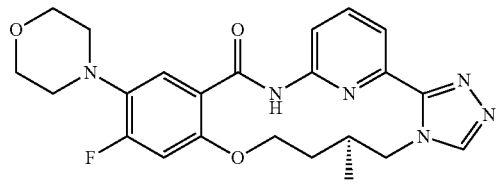 [SMILES: C[C@H]1CCOc2cc(F)c(N3CCOCC3)cc2C(=O)Nc2cccc(n2)-c2nncn2C1]

To a solution of (S)-5$^5$-bromo-5$^4$-fluoro-9-methyl-1$^4$H-6-oxa-3-aza-2(2,6)-pyridina-1(3,4)-triazola-5(1,2)-benzenacyclodecaphan-4-one (200 mg, 0.45 mmol) in THF/dioxane (1/1, 8 mL) was sequentially added morpholine (0.2 mL, 2.24 mmol), t-BuONa (130 mg, 1.35 mmol), Pd$_2$(dba)$_3$ (43 mg, 0.04 mmol) and RuPhos (21 mg, 0.04 mmol) under a N$_2$ atmosphere and the mixture was stirred at 110° C. for 18 h. After this time water (10 mL) was added and the mixture was extracted with DCM/MeOH (10/1, 3×10 mL). The combined organic extracts were washed with brine (20 mL), dried over Na$_2$SO$_4$, filtered and concentrated under vacuum to give the crude product, which was purified by pre-HPLC (using an Xtimate C18, 5 μm 150×25 mm column and using water (containing 10 mM NH$_4$HCO$_3$)/CH$_3$CN, from 27% to 67% as the mobile phase at a flow rate of 25 mL/min) to give the title compound (26 mg, 13%) as a yellow solid. $^1$H NMR (400 MHz, DMSO-d$_6$) δ ppm 11.20 (s, 1H), 8.65 (s, 1H), 8.01-8.06 (m, 1H), 7.85-7.88 (m, 2H), 7.62-7.66 (m, 1H), 7.23-7.28 (m, 1H), 4.42-4.51 (m, 2H), 4.20 (t, J=10.0 Hz, 1H), 3.80-3.85 (m, 1H), 3.72-3.75 (m, 4H), 3.18-3.22 (m, 1H), 2.95-2.98 (m, 4H), 2.00 (t, J=13.6 Hz, 1H), 1.65 (t, J=13.6 Hz, 1H), 0.93 (d, J=6.4 Hz, 3H). MS (ESI): 453.1 [M+H]$^+$.

Example 127: (S)-5⁴-Fluoro-9-methyl-5⁵-(1-methylpiperidin-4-yl)-1⁴H-6-oxa-3-aza-2(2,6)-pyridina-1(3,4)-triazola-5(1,2)-benzenacyclodecaphan-4-one

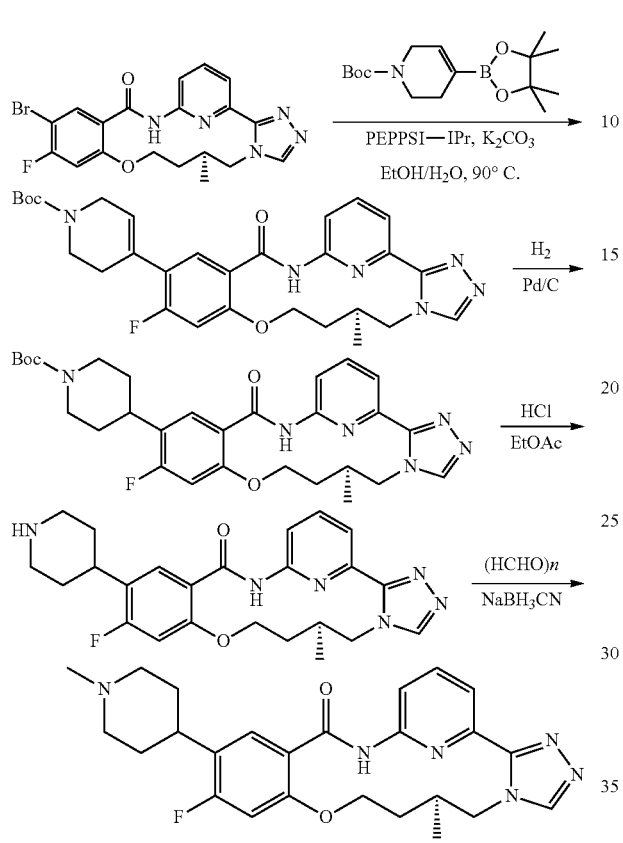

Step A. tert-Butyl (S)-4-(5⁴-fluoro-9-methyl-4-oxo-1⁴H-6-oxa-3-aza-2(2,6)-pyridina-1(3,4)-triazola-5(1,2)-benzenacyclodecaphane-5⁵-yl)-3,6-dihydropyridine-1(2H)-carboxylate

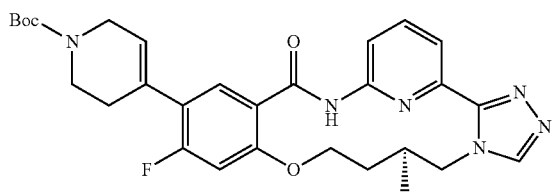 [SMILES: C[C@H]1CCOc2cc(F)c(C3=CCN(C(=O)OC(C)(C)C)CC3)cc2C(=O)Nc2cccc(n2)-c2nncn2C1]

A solution of (S)-5⁵-bromo-5⁴-fluoro-9-methyl-1⁴H-6-oxa-3-aza-2(2,6)-pyridina-1(3,4)-triazola-5(1,2)-benzenacyclodecaphan-4-one (300 mg, 0.67 mmol), tert-butyl 4-(4,4,5,5-tetramethyl-1,3,2-dioxaborolan-2-yl)-3,6-dihydropyridine-1(2H)-carboxylate (416 mg, 1.34 mmol), K₂CO₃ (186 mg, 1.34 mmol) and PEPPSI-IPr (51 mg, 0.067 mmol) in ethanol/H₂O (11 mL, 10/1) was stirred under a N₂ atmosphere at 90° C. for 1 h. After this time the reaction was concentrated and purified by column chromatography on silica gel using DCM/MeOH (100/1 to 10/1) as eluent to give the title compound (320 mg, 87%) as a white solid. MS (ESI): 549.3 [M+H]⁺.

Step B. tert-Butyl (S)-4-(5⁴-fluoro-9-methyl-4-oxo-1⁴H-6-oxa-3-aza-2(2,6)-pyridina-1(3,4)-triazola-5(1,2)-benzenacyclodecaphane-5⁵-yl)piperidine-1-carboxylate

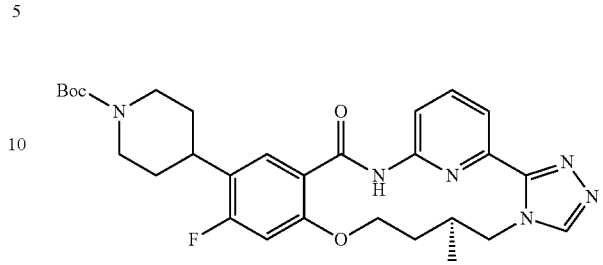

A solution of tert-butyl (S)-4-(5⁴-fluoro-9-methyl-4-oxo-1⁴H-6-oxa-3-aza-2(2,6)-pyridina-1(3,4)-triazola-5(1,2)-benzenacyclodecaphane-5⁵-yl)-3,6-dihydropyridine-1(2H)-carboxylate (320 mg, 0.58 mmol) and Pd (400 mg, 10% on C) in MeOH (40 mL) was stirred under a H₂ atmosphere (15 psi) at 28° C. for 12 h. After this time the mixture was filtered and concentrated to give the title compound (200 mg, 62%) as a white solid. MS (ESI): 551.3 [M+H]⁺.

Step C. (S)-5⁴-Fluoro-9-methyl-5⁵-(piperidin-4-yl)-1⁴H-6-oxa-3-aza-2(2,6)-pyridina-1(3,4)-triazola-5(1,2)-benzenacyclodecaphan-4-one

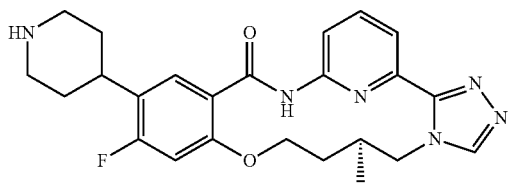 [SMILES: C[C@H]1CCOc2cc(F)c(C3CCNCC3)cc2C(=O)Nc2cccc(n2)-c2nncn2C1]

A solution of tert-butyl (S)-4-(5⁴-fluoro-9-methyl-4-oxo-1⁴H-6-oxa-3-aza-2(2,6)-pyridina-1(3,4)-triazola-5(1,2)-benzenacyclodecaphane-5⁵-yl)piperidine-1-carboxylate (200 mg, 0.36 mmol) in HCl/EtOAc (5 mL, 4M) was stirred at 28° C. for 1 h. After this time the mixture was concentrated to give the title compound (164 mg, crude HCl salt) as a white gum. MS (ESI): 451.1 [M+H]⁺.

Step D. (S)-5⁴-Fluoro-9-methyl-5⁵-(1-methylpiperidin-4-yl)-1⁴H-6-oxa-3-aza-2(2,6)-pyridina-1(3,4)-triazola-5(1,2)-benzenacyclodecaphan-4-one

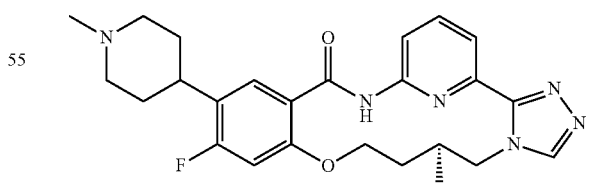

A solution of (S)-5⁴-fluoro-9-methyl-5⁵-(piperidin-4-yl)-1⁴H-6-oxa-3-aza-2(2,6)-pyridina-1(3,4)-triazola-5(1,2)-benzenacyclodecaphan-4-one (163 mg, 0.36 mmol), and formaldehyde (272 mg, 9.05 mmol) in MeOH (15 mL) was added NaBH₃CN (341 mg, 5.43 mmol) and the mixture was stirred at 28° C. for 4 h. After this time the mixture was treated with water (50 mL) and extracted with DCM (3×50 mL). The combined organic extracts were washed with brine (150 mL), dried over Na₂SO₄, filtered and concentrated. The product was washed with EtOAc (5 mL) and filtered to give the title compound (51 mg, 30%) as a white solid. $^1$H NMR (400 MHz, CDCl₃) δ ppm 11.23 (s, 1H), 8.21 (d, J=9.2 Hz, 1H), 8.16 (s, 1H), 8.02-8.05 (m, 2H), 7.90-7.92 (m, 1H), 6.71-6.74 (m, 1H), 4.60-4.63 (m, 1H), 4.39-4.42 (m, 1H), 4.18-4.21 (m, 1H), 3.70-3.76 (m, 1H), 3.45-3.51 (m, 1H), 3.05-3.08 (m, 2H), 2.75-2.88 (m, 1H), 2.39 (s, 3H), 2.13-2.17 (m, 3H), 1.97-2.00 (m, 2H), 1.74-1.79 (m, 3H), 1.10 (d, J=6.8 Hz, 3H). MS (ESI): 465.2 [M+H]⁺.

Example 128: (S)-5⁴-Fluoro-5⁵-(2-fluoropyridin-3-yl)-9-methyl-1⁴H-6-oxa-3-aza-2(2,6)-pyridina-1(3,4)-triazola-5(1,2)-benzenacyclodecaphan-4-one

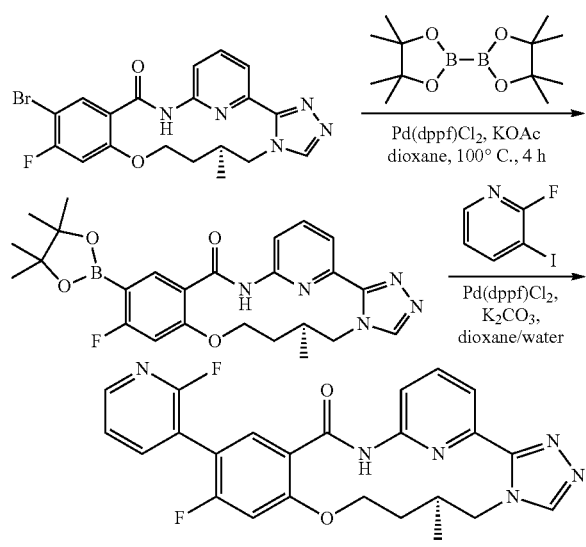

Step A. (S)-5⁴-Fluoro-9-methyl-5⁵-(4,4,5,5-tetramethyl-1,3,2-dioxaborolan-2-yl)-1⁴H-6-oxa-3-aza-2(2,6)-pyridina-1(3,4)-triazola-5(1,2)-benzenacyclodecaphan-4-one

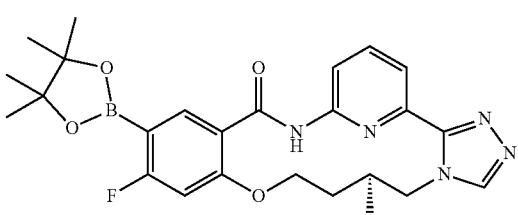

A mixture of (S)-5⁵-bromo-5⁴-fluoro-9-methyl-1⁴H-6-oxa-3-aza-2(2,6)-pyridina-1(3,4)-triazola-5(1,2)-benzenacyclodecaphan-4-one (300 mg, 0.67 mmol), 4,4,4',4',5,5,5',5'-octamethyl-2,2'-bi(1,3,2-dioxaborolane) (512 mg, 2.02 mmol), KOAc (132 mg, 1.34 mmol) and Pd(dppf)Cl₂ (49 mg, 0.07 mmol) in dioxane (6 mL) was degassed with N₂ and the mixture was stirred at 100° C. for 4 h. After this time, the volatiles were removed under reduced pressure. The crude product was dissolved in DCM (20 mL) and the organic layer was washed with water (2×20 mL). The organic layer was dried over Na₂SO₄, filtered and concentrated to give the title compound (100 mg, crude) which was used in the next step without further purification. MS (ESI): 494.2 [M+H]⁺.

Step B. (S)-5⁴-Fluoro-5⁵-(2-fluoropyridin-3-yl)-9-methyl-1⁴H-6-oxa-3-aza-2(2,6)-pyridina-1(3,4)-triazola-5(1,2)-benzenacyclodecaphan-4-one

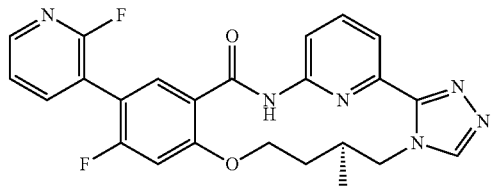 [SMILES: C[C@H]1CCOc2cc(F)c(-c3cccnc3F)cc2C(=O)Nc2cccc(n2)-c2nncn2C1]

To a solution of (S)-5⁴-Fluoro-9-methyl-5⁵-(4,4,5,5-tetramethyl-1,3,2-dioxaborolan-2-yl)-1⁴H-6-oxa-3-aza-2(2,6)-pyridina-1(3,4)-triazola-5(1,2)-benzenacyclodecaphan-4-one (100 mg, 0.2 mmol) in dioxane/water (2 mL, 10/1) was added 2-fluoro-3-iodopyridine (90 mg, 0.4 mmol), K₂CO₃ (56 mg, 0.4 mmol) and Pd(dppf)Cl₂ (15 mg, 0.02 mmol) and the resulting mixture was stirred at 90° C. for 2 h. After this time the mixture was filtered and the filtrate was purified by HPLC (using a Waters Xbridge Prep OBD C18, 5 μm 150×30 mm column and using water (containing 0.05% NH₃.H₂O and 10 mM NH₄HCO₃)/CH₃CN, from 39% to 69% as the mobile phase at a flow rate of 25 mL/min) to give the title compound (19 mg, 21%) as a white solid. $^1$H NMR (400 MHz, DMSO-d₆) δ ppm 11.04 (s, 1H), 8.67 (s, 1H), 8.31 (d, J=4.4 Hz, 1H), 8.04-8.11 (m, 3H), 7.85-7.88 (m, 2H), 7.47-7.53 (m, 1H), 7.39-7.42 (m, 1H), 4.55-4.57 (m, 1H), 4.41-4.44 (m, 1H), 4.30 (t, J=10.4 Hz, 1H), 3.87 (t, J=12.7 Hz, 1H), 3.21-2.37 (m, 1H), 2.02-2.08 (m, 1H), 1.63-1.68 (m, 1H), 0.95 (d, J=6.0 Hz, 3H). MS (ESI): 463.1 [M+H]⁺.

Example 129: (S)-5⁴-Fluoro-5⁵-(6-fluoropyridin-3-yl)-9-methyl-1⁴H-6-oxa-3-aza-2(2,6)-pyridina-1(3,4)-triazola-5(1,2)-benzenacyclodecaphan-4-one

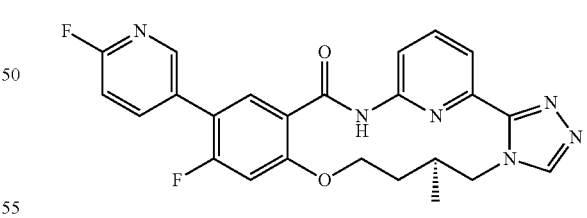

To a solution of (S)-5⁵-bromo-5⁴-fluoro-9-methyl-1⁴H-6-oxa-3-aza-2(2,6)-pyridina-1(3,4)-triazola-5(1,2)-benzenacyclodecaphan-4-one (100 mg, 0.22 mmol) and (6-fluoropyridin-3-yl)boronic acid (47 mg, 0.33 mmol) in dioxane/H₂O (6 mL, 1/1) was added Pd(dppf)Cl₂ (16 mg, 0.022 mmol) and K₂CO₃ (372 mg, 0.66 mmol) under a N₂ atmosphere and the mixture was stirred at 95° C. for 3 h. After this time the mixture was concentrated to give the crude product, which was purified by HPLC (using an Xtimate C18, 5 μm 150×25 mm column and using water (containing 10 mM NH₄HCO₃)/CH₃CN, from 34% to 65% as the mobile phase at a flow rate of 25 mL/min) to give the title compound (29 mg, 28%) as a white solid. ¹H NMR (400 MHz, DMSO-d₆) δ ppm 11.07 (s, 1H), 8.69 (s, 1H), 8.45 (s, 1H), 8.22 (t, J=6.8 Hz, 1H), 8.14 (d, J=9.2 Hz, 1H), 8.07 (t, J=8.0 Hz, 1H), 7.89 (d, J=7.8 Hz, 2H), 7.42 (d, J=12.4 Hz, 1H), 7.34 (dd, J=2.4, 8.6 Hz, 1H), 4.53-4.61 (m, 1H), 4.45 (d, J=12.0 Hz, 1H), 4.31 (t, J=10.0 Hz, 1H), 3.90 (t, J=12.4 Hz, 1H), 3.24-3.30 (m, 1H), 2.08 (t, J=12.4 Hz, 1H), 1.68 (t, J=11.2 Hz, 1H), 0.97 (d, J=6.4 Hz, 3H). MS (ESI): 463.2 [M+H]⁺.

Example 130: (S)-5⁵-(1-(2-(Dimethylamino)ethyl)-1H-pyrazol-4-yl)-5⁴-fluoro-9-methyl-1⁴H-6-oxa-3-aza-2(2,6)-pyridina-1(3,4)-triazola-5(1,2)-benzenacyclodecaphan-4-one

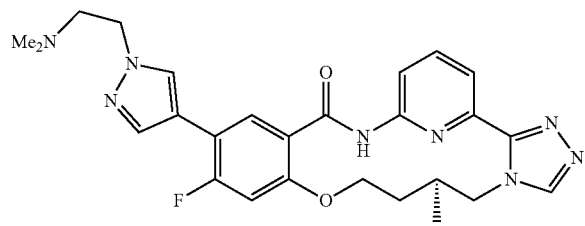 [SMILES: C[C@H]1CCOc2cc(F)c(-c3cnn(CCN(C)C)c3)cc2C(=O)Nc2cccc(n2)-c2nncn2C1]

To a solution of (S)-5⁵-bromo-5⁴-fluoro-9-methyl-1⁴H-6-oxa-3-aza-2(2,6)-pyridina-1(3,4)-triazola-5(1,2)-benzenacyclodecaphan-4-one (150 mg, 0.34 mmol) in EtOH (5 mL) and H₂O (0.5 mL) was added N,N-dimethyl-2-(4-(4,4,5,5-tetramethyl-1,3,2-dioxaborolan-2-yl)-1H-pyrazol-1-yl)ethan-1-amine (91 mg, 0.34 mmol), PEPPSI (46 mg, 67 umol) and K₂CO₃ (116 mg, 0.84 mmol) and the reaction mixture was stirred at 90° C. for 2 h. After this time the reaction suspension was poured into water (20 mL) and extracted with EtOAc (3×25 mL). The combined organic extracts were dried over Na₂SO₄, filtered and concentrated. The crude product was purified by HPLC (using an Xtimate C18, 5 μm 150×25 mm column and using water (containing 10 mM NH₄HCO₃)/CH₃CN, from 30% to 60% as the mobile phase at a flow rate of 25 mL/min) to give the title compound (31 mg, 18%) as a white solid. ¹H NMR (400 MHz, DMSO-d₆) δ ppm 11.11 (s, 1H), 8.67 (s, 1H), 8.21-8.26 (m, 2H), 8.05-8.07 (m, 1H), 7.87-7.91 (m, 3H), 7.28-7.32 (m, 1H), 4.42-4.54 (m, 2H), 4.22-4.29 (m, 3H), 3.85-3.92 (m, 1H), 3.22-3.26 (m, 1H), 2.66-2.70 (m, 2H), 2.18 (s, 6H), 2.01-2.08 (m, 1H), 1.64-1.70 (m, 1H), 0.95 (d, J=6.4 Hz, 3H). MS (ESI): 505.2 [M+H]⁺.

Example 131 (S)-5⁴-Fluoro-9-methyl-5⁵-(5-methyl-4,5,6,7-tetrahydropyrazolo[1,5-a]pyrazin-3-yl)-1⁴H-6-oxa-3-aza-2(2,6)-pyridina-1(3,4)-triazola-5(1,2)-benzenacyclodecaphan-4-one

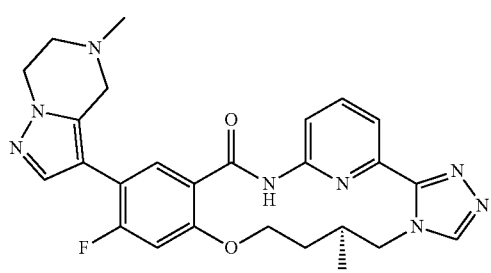 [SMILES: C[C@H]1CCOc2cc(F)c(-c3cnn4c3CN(C)CC4)cc2C(=O)Nc2cccc(n2)-c2nncn2C1]

To a solution of (S)-5⁴-fluoro-9-methyl-5⁵-(4,4,5,5-tetramethyl-1,3,2-dioxaborolan-2-yl)-1⁴H-6-oxa-3-aza-2(2,6)-pyridina-1(3,4)-triazola-5(1,2)-benzenacyclodecaphan-4-one (100 mg, 0.202 mmol) and 3-bromo-5-methyl-4,5,6,7-tetrahydropyrazolo[1,5-a]pyrazine (53 mg, 0.243 mmol) in dioxane/H₂O (5/1, 6 mL) was added Pd(dppf)Cl₂ (15 mg, 0.02 mmol) and K₂CO₃ (85 mg, 0.61 mmol) and the reaction was stirred under a N₂ atmosphere at 95° C. for 16 h. After this time the mixture was concentrated to give the crude product, which was dissolved in DCM/MeOH (10/1, 60 mL) and filtered. The filtrate was concentrated and the resulting residue was purified by HPLC (using an Xtimate C18, 5 μm 150×25 mm column and using water (containing 10 mM NH₄HCO₃)/CH₃CN, from 30% to 60% as the mobile phase at a flow rate of 25 mL/min) to give the title compound as a white solid. ¹H NMR (400 MHz, CD₃OD) δ ppm 8.64 (s, 1H), 8.07 (d, J=8.8 Hz, 1H), 7.97-8.05 (m, 2H), 7.92 (dd, J=1.2, 7.2 Hz, 1H), 7.71 (s, 1H), 7.16 (d, J=12.4 Hz, 1H), 4.51-4.59 (m, 2H), 4.32 (t, J=9.6 Hz, 1H), 4.25 (t, J=5.6 Hz, 2H), 3.94 (t, J=13.2 Hz, 1H), 3.77 (s, 2H), 3.36-3.47 (m, 1H), 3.03 (t, J=5.6 Hz, 2H), 2.54 (s, 3H), 2.10-2.21 (m, 1H), 1.76-1.86 (m, 1H), 1.10 (d, J=6.8 Hz, 3H). MS (ESI): 503.1 [M+H]⁺.

Example 132: (R)-5⁴-Fluoro-9-methyl-5⁵-(5-methyl-4,5,6,7-tetrahydropyrazolo[1,5-a]pyrazin-3-yl)-1⁴H-6-oxa-3-aza-2(2,6)-pyridina-1(3,4)-triazola-5(1,2)-benzenacyclodecaphan-4-one

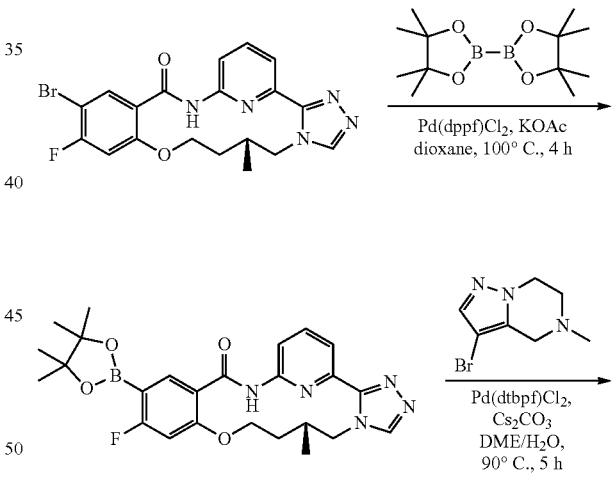

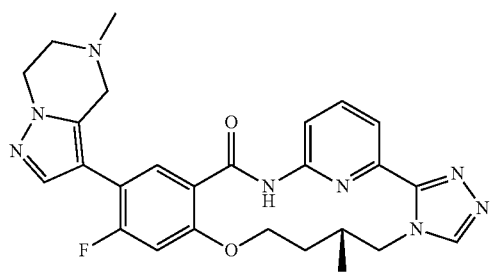

Step A. (R)-5⁴-Fluoro-9-methyl-5⁵-(4,4,5,5-tetramethyl-1,3,2-dioxaborolan-2-yl)-1⁴H-6-oxa-3-aza-2(2,6)-pyridina-1(3,4)-triazola-5(1,2)-benzenacyclodecaphan-4-one

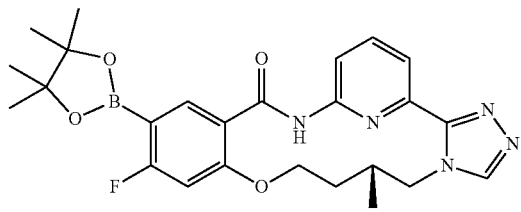 [SMILES: C[C@@H]1CCOc2cc(F)c(B3OC(C)(C)C(C)(C)O3)cc2C(=O)Nc2cccc(n2)-c2nncn2C1]

The title compound was synthesized according to the general procedure described in Example 128, Step A and using (R)-5⁵-bromo-5⁴-fluoro-9-methyl-1⁴H-6-oxa-3-aza-2(2,6)-pyridina-1(3,4)-triazola-5(1,2)-benzenacyclodecaphan-4-one (200 mg, 0.45 mmol) to give the desired product (220 mg, crude) which was used in next step without further purification. MS (ESI): 494.3 [M+H]⁺.

Step B. (R)-5⁴-Fluoro-9-methyl-5⁵-(5-methyl-4,5,6,7-tetrahydropyrazolo[1,5-a]pyrazin-3-yl)-1⁴H-6-oxa-3-aza-2(2,6)-pyridina-1(3,4)-triazola-5(1,2)-benzenacyclodecaphan-4-one

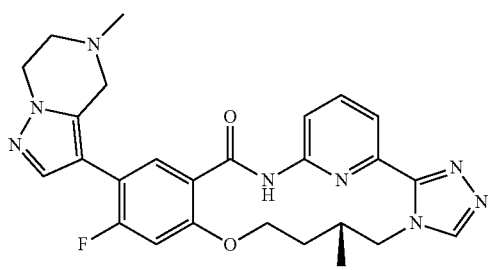 [SMILES: C[C@@H]1CCOc2cc(F)c(-c3cnn4c3CN(C)CC4)cc2C(=O)Nc2cccc(n2)-c2nncn2C1]

The title compound was synthesized according to the general procedure described in Example 128, Step B and using (R)-5⁴-Fluoro-9-methyl-5⁵-(4,4,5,5-tetramethyl-1,3,2-dioxaborolan-2-yl)-1⁴H-6-oxa-3-aza-2(2,6)-pyridina-1(3,4)-triazola-5(1,2)-benzenacyclodecaphan-4-one (200 mg, 0.40 mmol). Purification by HPLC (using a Waters Xbridge Prep OBD C18, 5 μm 150×30 mm column and using water (containing 0.05% NH₃·H₂O and 10 mM NH₄HCO₃)/CH₃CN, from 24% to 54% as the mobile phase at a flow rate of 25 mL/min) gave the desired product (54 mg, 26%) as a white solid. ¹H NMR (400 MHz, DMSO-d₆) δ ppm 11.11 (s, 1H), 8.66 (s, 1H), 7.97-8.09 (m, 1H), 7.83-7.95 (m, 3H), 7.66 (s, 1H), 7.30 (br d, J=12.1 Hz, 1H), 4.48-4.57 (m, 1H), 4.38-4.47 (m, 1H), 4.25 (br t, J=10.1 Hz, 1H), 4.08-4.18 (m, 2H), 3.87 (br t, J=12.6 Hz, 1H), 3.56-3.64 (m, 2H), 3.20-3.27 (m, 1H), 2.82-2.92 (m, 2H), 2.40 (s, 3H), 1.96-2.10 (m, 1H), 1.65 (br t, J=10.8 Hz, 1H), 0.94 (d, J=6.4 Hz, 3H). MS (ESI): 503.2 [M+H]⁺.

Example 133: (S)-5⁴-Fluoro-9-methyl-5⁵-(4-methyl-1H-imidazol-1-yl)-1⁴H-6-oxa-3-aza-2(2,6)-pyridina-1(3,4)-triazola-5(1,2)-benzenacyclodecaphan-4-one

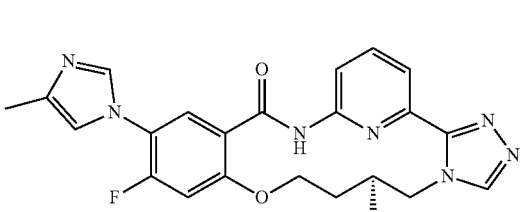

To a solution of (S)-5⁵-bromo-5⁴-fluoro-9-methyl-1⁴H-6-oxa-3-aza-2(2,6)-pyridina-1(3,4)-triazola-5(1,2)-benzenacyclodecaphan-4-one (60 mg, 0.13 mmol) in Pyridine/DCM (1/1, 8 mL) was added 4-methyl-1H-imidazole (165 mg, 2.02 mmol) and Cu(OAc)₂ (15 mg, 0.082 mmol) and the mixture was stirred at 60° C. for 3 h. After this time the mixture was concentrated and the crude product was purified by HPLC (using an Xtimate C18, 5 μm 150×25 mm column and using water (containing 10 mM NH₄HCO₃)/CH₃CN, from 23% to 53% as the mobile phase at a flow rate of 25 mL/min) to give the title compound (8 mg, 15%) as a white solid. ¹H NMR (400 MHz, DMSO-d₆) δ ppm 11.06 (s, 1H), 8.69 (s, 1H), 8.03-8.13 (m, 2H), 7.84-7.95 (m, 3H), 7.54 (d, J=12.6 Hz, 1H), 7.27 (s, 1H), 4.52-4.62 (m, 1H), 4.46 (dd, J=2.8, 13.0 Hz, 1H), 4.31 (t, J=10.4 Hz, 1H), 3.89 (t, J=12.4 Hz, 1H), 3.21-3.26 (m, 1H), 2.18 (s, 3H), 2.02-2.12 (m, 1H), 1.63-1.74 (m, 1H), 0.96 (d, J=6.6 Hz, 3H). MS (ESI): 448.1 [M+H]⁺.

Example 134: (S)-5⁴-Fluoro-9-methyl-5⁵-((3-methyloxetan-3-yl)ethynyl)-1⁴H-6-oxa-3-aza-2(2,6)-pyridina-1(3,4)-triazola-5(1,2)-benzenacyclodecaphan-4-one

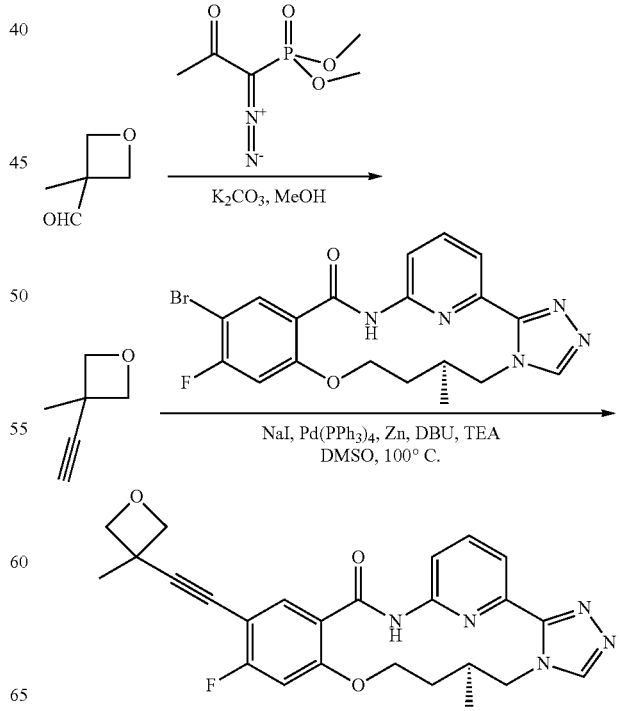

Step A. 3-Ethynyl-3-methyloxetane

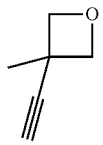

To a solution of 3-methyloxetane-3-carbaldehyde (100 mg, 1.0 mmol) in MeOH (20 mL) was added $K_2CO_3$ (278 mg, 2.0 mmol) and dimethyl (1-diazo-2-oxopropyl)phosphonate (230 mg, 1.2 mmol) at 0° C. and the mixture was stirred at 30° C. for 18 h. After this time $H_2O$ (20 mL) was added to the reaction and the mixture was extracted with DCM (3×20 mL). The combined organic extracts were washed with brine (20 mL), dried over $Na_2SO_4$, filtered and concentrated to give the crude product (90 mg, crude) as yellow oil which was used in the next step without further purification. $^1$H NMR (400 MHz, DMSO-$d_6$) δ ppm 4.60 (d, J=5.2 Hz, 2H), 4.32 (d, J=5.6 Hz, 2H), 3.34 (s, 1H), 1.50 (s, 3H).

Step B. (S)-$5^4$-Fluoro-9-methyl-$5^5$-((3-methyloxetan-3-yl)ethynyl)-$1^4$H-6-oxa-3-aza-2(2,6)-pyridina-1(3,4)-triazola-5(1,2)-benzenacyclodecaphan-4-one

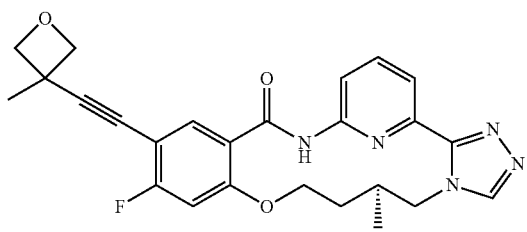 [SMILES: C[C@H]1CCOc2cc(F)c(C#CC3(C)COC3)cc2C(=O)Nc2cccc(n2)-c2nncn2C1]

To a solution of (S)-$5^5$-bromo-$5^4$-fluoro-9-methyl-$1^4$H-6-oxa-3-aza-2(2,6)-pyridina-1(3,4)-triazola-5(1,2)-benzenacyclodecaphan-4-one (80 mg, 0.18 mmol) in DMSO (3 mL) was added 3-ethynyl-3-methyloxetane (35 mg, 0.36 mmol), NaI (8.1 mg, 0.054 mmol), Et$_3$N (55 mg, 0.54 mmol), DBU (55 mg, 0.36 mmol) and Zn (3.5 mg, 0.054 mmol) followed by Pd(PPh$_3$)$_4$(47 mg, 0.04 mmol) under a $N_2$ atmosphere. The mixture was stirred at 100° C. for 20 h. After this time, the mixture was filtered and the filtrate was purified by HPLC (using an Xtimate C18, 5 μm 150×25 mm column and using water (containing 10 mM $NH_4HCO_3$)/$CH_3CN$, from 35% to 65% as the mobile phase at a flow rate of 25 mL/min) to give the title compound (30 mg, 36%) as a yellow solid. $^1$H NMR (400 MHz, DMSO-$d_6$) δ ppm 10.96 (s, 1H), 8.65 (s, 1H), 7.98-8.05 (m, 2H), 7.82-7.87 (m, 2H), 7.30 (d, J=12.4 Hz, 1H), 4.73 (d, J=5.2 Hz, 2H), 4.48-4.49 (m, 1H), 4.41-4.44 (m, 2H), 4.40-4.41 (m, 1H), 4.36-4.38 (m, 1H), 3.85-3.89 (m, 1H), 3.16-3.23 (m, 1H), 2.03 (d, J=12.0 Hz, 1H), 1.62-1.66 (m, 4H), 0.92 (d, J=6.4 Hz, 3H). MS (ESI): 462.2 [M+H]$^+$.

Example 135: (S)-$5^4$-Fluoro-$5^5$-(2-methoxyethoxy)-9-methyl-$1^4$H-6-oxa-3-aza-2(2,6)-pyridina-1(3,4)-triazola-5(1,2)-benzenacyclodecaphan-4-one

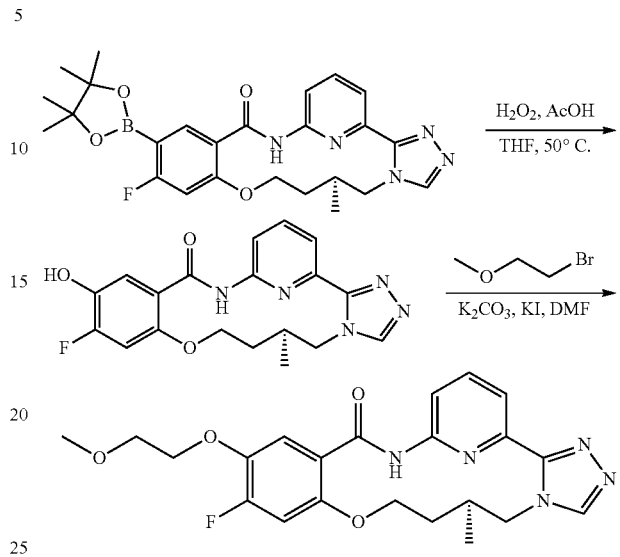

Step A. (S)-$5^4$-Fluoro-$5^5$-hydroxy-9-methyl-$1^4$H-6-oxa-3-aza-2(2,6)-pyridina-1(3,4)-triazola-5(1,2)-benzenacyclodecaphan-4-one

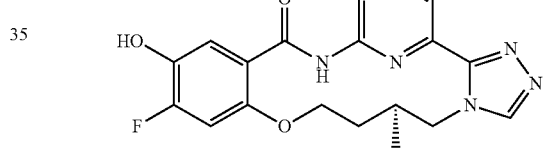

To a mixture of (S)-$5^4$-fluoro-9-methyl-$5^5$-(4,4,5,5-tetramethyl-1,3,2-dioxaborolan-2-yl)-$1^4$H-6-oxa-3-aza-2(2,6)-pyridina-1(3,4)-triazola-5(1,2)-benzenacyclodecaphan-4-one (100 mg, 0.20 mmol) in THF (6 mL) was added $H_2O_2$(0.5 mL) and AcOH (0.5 mL) and stirring was continued at 50° C. for 12 h. After this time, water (10 mL) was added and the resulting mixture was extracted with EtOAc (3×20 mL) and the combined organic extracts were concentrated. The crude product was purified by column chromatography on silica gel using EtOAc/petroleum ether (1/10 to 1/1) as eluent to give the title compound (70 mg, 91%) as a white solid. MS (ESI): 384.1 [M+H]$^+$.

Step B. (S)-$5^4$-Fluoro-$5^5$-(2-methoxyethoxy)-9-methyl-$1^4$H-6-oxa-3-aza-2(2,6)-pyridina-1(3,4)-triazola-5(1,2)-benzenacyclodecaphan-4-one

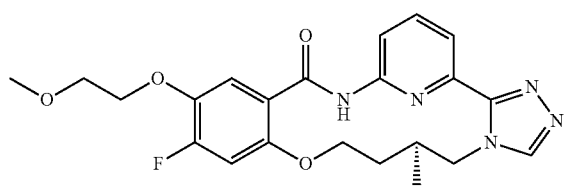 [SMILES: COCCOc1cc2c(cc1F)OCC[C@H](C)Cn1cnnc1-c1cccc(n1)NC2=O]

A solution of (S)-5⁴-fluoro-5⁵-hydroxy-9-methyl-1⁴H-6-oxa-3-aza-2(2,6)-pyridina-1(3,4)-triazola-5(1,2)-benzenacyclodecaphan-4-one (10 mg, 0.026 mmol), 1-bromo-2-methoxyethane (4.3 mg, 0.031 mmol), KI (4.3 mg, 0.026 mmol) and K$_2$CO$_3$ (7.2 mg, 0.052 mmol) in DMF (1 mL) was stirred at 100° C. for 12 h. After this time the reaction was filtered and purified by HPLC (using a Phenomenex Synergi C18, 4 μm 150×30 mm column and using water (containing 0.225% HCOOH)/CH$_3$CN, from 28% to 58% as the mobile phase at a flow rate of 25 mL/min) to give the title compound (8 mg, 69%) as a white solid. $^1$H NMR (400 MHz, DMSO-d$_6$) δ ppm 11.25 (s, 1H), 8.68 (s, 1H), 8.02-8.12 (m, 1H), 7.89 (d, J=8.0 Hz, 2H), 7.74 (d, J=10.0 Hz, 1H), 7.35 (d, J=13.2 Hz, 1H), 4.42-4.53 (m, 2H), 4.18-4.27 (m, 3H), 3.82-3.95 (m, 1H), 3.65-3.73 (m, 2H), 3.33 (s, 3H), 3.13-3.27 (m, 1H), 1.96-2.10 (m, 1H), 1.69 (br t, J=10.8 Hz, 1H), 0.96 (d, J=6.4 Hz, 3H). MS (ESI): 442.0 [M+H]$^+$.

Example 136: (S)-5⁵-Bromo-7-methyl-1⁴H-6-oxa-3-aza-2(2,6)-pyridina-1(3,4)-triazola-5(1,2)-benzenacyclodecaphan-4-one and Example 137: (R)-5⁵-Bromo-7-methyl-1⁴H-6-oxa-3-aza-2(2,6)-pyridina-1(3,4)-triazola-5(1,2)-benzenacyclodecaphan-4-one

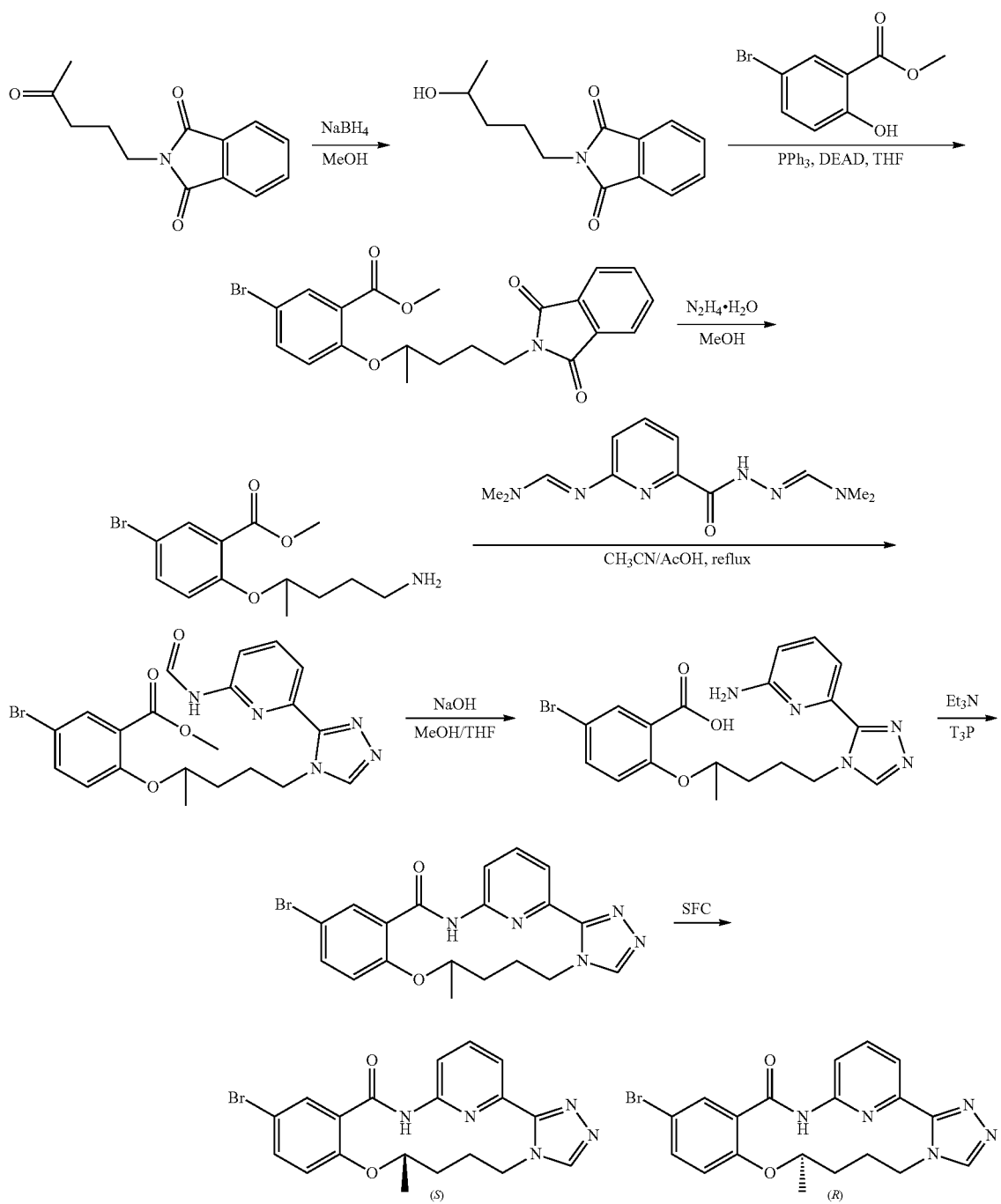

Step A.
rac-2-(4-Hydroxypentyl)isoindoline-1,3-dione

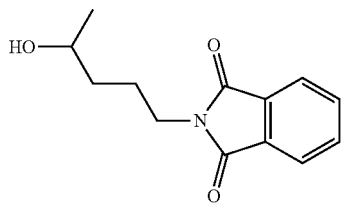 [SMILES: CC(O)CCCN1C(=O)c2ccccc2C1=O]

To a stirred mixture of 2-(4-oxopentyl)isoindoline-1,3-dione (38 g, 164 mmol) in MeOH (400 mL) was added NaBH₄ (1.87 g, 49.3 mmol) and the reaction stirring was continued at 16° C. for 5 h. After this time the volatiles were removed under reduced pressure to give the crude product which was poured into saturated aqueous NH₄Cl (50 mL). Water (200 mL) was then added and the mixture was extracted with EtOAc (3×200 mL). The combined organic extracts were concentrated to give the crude product which was purified by column chromatography on silica gel using petroleum ether/EtOAc (20/1 to 3/1) to give the title compound (20 g, 50%) as a white solid.

Step B. rac-Methyl 5-bromo-2-((5-(1,3-dioxoisoindolin-2-yl)pentan-2-yl)oxy)benzoate

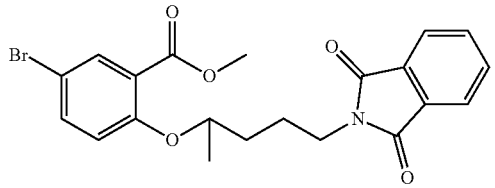 [SMILES: COC(=O)c1cc(Br)ccc1OC(C)CCCN1C(=O)c2ccccc2C1=O]

To a stirred mixture of rac-2-(4-hydroxypentyl)isoindoline-1,3-dione (26.25 g, 113 mmol), methyl 5-bromo-2-hydroxybenzoate (26 g, 113 mmol) and PPh₃ (35.4 g, 135 mmol) in THF (400 mL) was added DIAD (26.5 mL, 135 mmol) at 0° C. and the reaction mixture was stirred at 16° C. for 17 h. After this time the volatiles were removed under reduced pressure to give the crude product which was purified by column chromatography on silica gel using petroleum ether/EtOAc (from 10/1 to 3/1) as eluent to give the title compound (30 g, 60%) as colourless oil. MS (ESI): 467.8 [(M+Na) (⁷⁹Br)]⁺.

Step C. rac-Methyl 2-((5-aminopentan-2-yl)oxy)-5-bromobenzoate

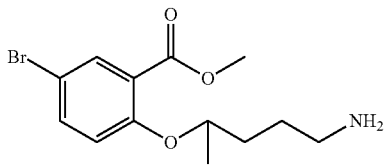 [SMILES: COC(=O)c1cc(Br)ccc1OC(C)CCCN]

A mixture of rac-methyl 5-bromo-2-((5-(1,3-dioxoisoindolin-2-yl)pentan-2-yl)oxy)benzoate (5.5 g, 12.4 mmol) and N₂H₄.H₂O (944 mg, 18.5 mmol) in MeOH (50 mL) was stirred at 50° C. for 17 h. After this time the volatiles were removed under reduced pressure and the resulting residue was dissolved in H₂O (20 mL). The pH was adjusted to 11-12 by addition of aq. NaOH and the mixture was extracted with EtOAc (3×50 mL). The combined organic extracts were dried over Na₂SO₄, filtered and concentrated to give the title compound (3.5 g, 90%) as a brown solid. MS (ESI): 315.9 [(M+H) (⁷⁹Br)]⁺.

Step D. rac-Methyl 5-bromo-2-((5-(3-(6-formamidopyridin-2-yl)-4H-1,2,4-triazol-4-yl)pentan-2-yl)oxy)benzoate

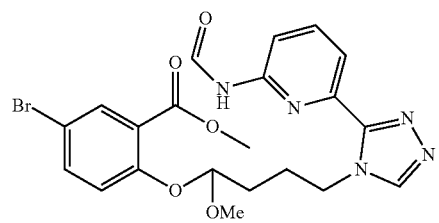 [SMILES: COC(=O)c1cc(Br)ccc1OC(CCCn1cnnc1-c1cccc(NC=O)n1)OC]

A mixture of rac-methyl 2-((5-aminopentan-2-yl)oxy)-5-bromobenzoate (3.5 g, 11.1 mmol) and (E)-N'-(6-(2-((E)-(dimethylamino)methylene)hydrazine-1-carbonyl)pyridin-2-yl)-N,N-dimethylformimidamide (2.23 g, 8.51 mmol) in AcOH (30 mL) and CH₃CN (30 mL) was stirred under a N₂ atmosphere at 80° C. for 17 h. After this time the volatiles were removed under reduced pressure to give the crude product which was purified by column chromatography on silica using EtOAc followed by DCM/MeOH (1/0 to 30/1) as eluent to give the title compound (2 g, 48%) as a white solid. MS (ESI): 490.0 [(M+H) (⁸¹Br)]⁺.

Step E. rac-2-((5-(3-(6-Aminopyridin-2-yl)-4H-1,2,4-triazol-4-yl)pentan-2-yl)oxy)-5-bromobenzoic acid

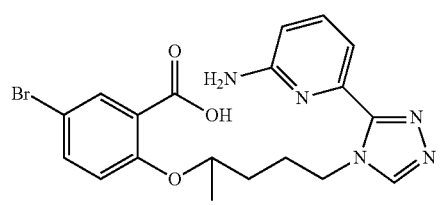 [SMILES: CC(CCCn1cnnc1-c1cccc(N)n1)Oc1ccc(Br)cc1C(=O)O]

A mixture of rac-methyl 5-bromo-2-((5-(3-(6-formamidopyridin-2-yl)-4H-1,2,4-triazol-4-yl)pentan-2-yl)oxy)benzoate (2 g, 4.1 mmol) and NaOH (0.41 g, 10.2 mmol) in THF/MeOH (1/1, 40 mL) was stirred at 70° C. for 17 h. After this time the volatiles were removed under reduced pressure to give the title compound (1.83 g, 100% crude) as a white solid which was used without further purification in the next step. MS (ESI): 446.0 [(M+H) (⁷⁹Br)]⁺.

Step F. rac-5⁵-Bromo-7-methyl-1⁴H-6-oxa-3-aza-2 (2,6)-pyridina-1(3,4)-triazola-5(1,2)-benzenacyclo-decaphan-4-one

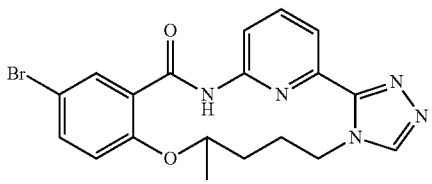 [SMILES: CC1CCCn2cnnc2-c2cccc(n2)NC(=O)c2cc(Br)ccc2O1]

A mixture of rac-2-((5-(3-(6-aminopyridin-2-yl)-4H-1,2,4-triazol-4-yl)pentan-2-yl)oxy)-5-bromobenzoic acid (1.83 g, 4.1 mmol) in T$_3$P (15 mL, ≥50 wt. % in EtOAc) and Et$_3$N (15 mL) was stirred at 70° C. for 3 h. After this time the volatiles were removed under reduced pressure to give the crude product. H$_2$O (50 mL) was then added and the resulting solid was collected by filtration, and dried under vacuum to give the title compound (1 g, 57%) as a brown solid. MS (ESI): 429.9 [(M+H) ($^{81}$Br)]⁺.

Step G. (S)-5⁵-Bromo-7-methyl-1⁴H-6-oxa-3-aza-2(2,6)-pyridina-1(3,4)-triazola-5(1,2)-benzenacyclo-decaphan-4-one and (R)-5⁵-Bromo-7-methyl-1⁴H-6-oxa-3-aza-2(2,6)-pyridina-1(3,4)-triazola-5(1,2)-benzenacyclodecaphan-4-one

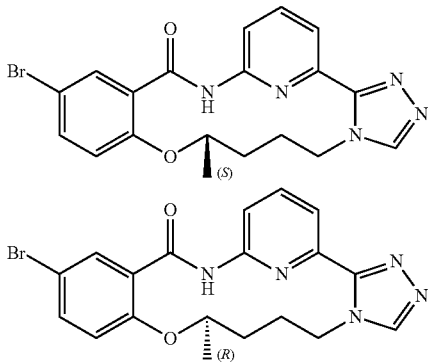

rac-5⁵-Bromo-7-methyl-1⁴H-6-oxa-3-aza-2(2,6)-pyridina-1(3,4)-triazola-5(1,2)-benzenacyclodecaphan-4-one (100 mg) was purified by SFC (using a Chiralpak AD-3 3 μm, 50×4.6 mm column and using 40% ethanol (containing 0.05% Et$_2$NH) in CO$_2$ as the mobile phase at a flow rate of 4 mL/min (at a column temperature of 40° C.)) to give in order of elution:

Peak 1 (absolute stereochemistry arbitrarily assigned): (S)-5⁵-bromo-7-methyl-1⁴H-6-oxa-3-aza-2(2,6)-pyridina-1(3,4)-triazola-5(1,2)-benzenacyclodecaphan-4-one (30 mg, 30%) as a white solid. ¹H NMR (400 MHz, DMSO-d$_6$) δ ppm 11.19 (s, 1H), 8.69 (s, 1H), 8.04-8.12 (m, 2H), 7.90-7.94 (m, 2H), 7.77 (dd, J=2.8, 8.8 Hz, 1H), 7.29 (d, J=8.8 Hz, 1H), 5.03-5.11 (m, 1H), 4.19-4.34 (m, 2H), 2.88-3.02 (m, 1H), 1.88-2.09 (m, 3H), 1.34 (d, J=6.4 Hz, 3H). MS (ESI): 429.9 [(M+H) ($^{81}$Br)]⁺.

Peak 2 (absolute stereochemistry arbitrarily assigned): (R)-5⁵-bromo-7-methyl-1⁴H-6-oxa-3-aza-2(2,6)-pyridina-1(3,4)-triazola-5(1,2)-benzenacyclodecaphan-4-one (40 mg, 40%) as a white solid. ¹H NMR (400 MHz, DMSO-d$_6$) δ ppm 11.19 (s, 1H), 8.69 (s, 1H), 8.02-8.15 (m, 2H), 7.92 (d, J=7.8 Hz, 2H), 7.77 (dd, J=2.7, 9.0 Hz, 1H), 7.29 (d, J=8.8 Hz, 1H), 5.01-5.12 (m, 1H), 4.19-4.35 (m, 2H), 2.88-3.03 (m, 1H), 1.88-2.09 (m, 3H), 1.33 (d, J=5.9 Hz, 3H). MS (ESI): 427.9 [(M+H) ($^{79}$Br)]⁺.

Example 138: (S)-7-Methyl-1⁴H-6-oxa-3-aza-2(2,6)-pyridina-1(3,4)-triazola-5(1,2)-benzenacyclodecaphan-4-one

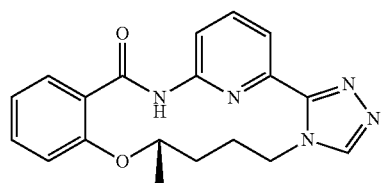 [SMILES: C[C@H]1CCCn2cnnc2-c2cccc(n2)NC(=O)c2ccccc2O1]

A mixture of (S)-5⁵-bromo-7-methyl-1⁴H-6-oxa-3-aza-2(2,6)-pyridina-1(3,4)-triazola-5(1,2)-benzenacyclodecaphan-4-one (100 mg, 0.23 mmol) and Pd (100 g, 10% on C) in MeOH (20 mL) was stirred under H$_2$ (15 psi) at 18° C. for 4 h. After this time, the mixture was filtered and concentrated to give the crude product which was purified by SFC (using an OD 250 mm×30 mm×5 μm column and 40% EtOH (with 0.1% ammonium hydroxide) in CO$_2$ as the mobile phase at a flow rate of 50 mL/min) to give the title compound (50 mg, 61%) as a yellow solid. ¹H NMR (400 MHz, DMSO-d$_6$) δ ppm 11.31 (s, 1H), 8.70 (s, 1H), 8.06 (d, J=6.8 Hz, 2H), 7.84-7.97 (m, 2H), 7.62 (s, 1H), 7.30 (d, J=8.0 Hz, 1H), 7.15 (s, 1H), 5.08 (s, 1H), 4.27 (s, 2H), 3.01 (s, 1H), 1.95 (s, 3H), 1.35 (d, J=6.0 Hz, 3H). MS (ESI): 350.1 [M+H]⁺.

Example 139: (R)-7-Methyl-1⁴H-6-oxa-3-aza-2(2,6)-pyridina-1(3,4)-triazola-5(1,2)-benzenacyclodecaphan-4-one

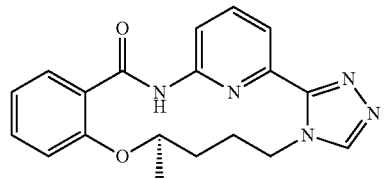 [SMILES: C[C@@H]1CCCn2cnnc2-c2cccc(n2)NC(=O)c2ccccc2O1]

A mixture of (R)-5⁵-bromo-7-methyl-1⁴H-6-oxa-3-aza-2(2,6)-pyridina-1(3,4)-triazola-5(1,2)-benzenacyclodecaphan-4-one (100 mg, 0.23 mmol) and Pd (100 mg, 10% on C) in MeOH (10 mL) was stirred at under H$_2$ at 18° C. for 4 h. After this time the mixture was filtered and the filtrate was concentrated to provide the title compound (30 mg, 37%) as a white solid. ¹H NMR (400 MHz, DMSO-d$_6$) δ ppm 11.29 (s, 1H), 8.68 (s, 1H), 8.00-8.09 (m, 2H), 7.90 (dd, J=7.7, 20.0 Hz, 2H), 7.55-7.64 (m, 1H), 7.28 (d, J=8.3 Hz, 1H), 7.08-7.18 (m, 1H), 5.07 (br s, 1H), 4.26 (br d, J=12.7 Hz, 2H), 2.91-3.05 (m, 1H), 1.85-2.07 (m, 3H), 1.33 (d, J=6.1 Hz, 3H). MS (ESI): 350.0 [M+H]⁺.

Example 140: (S)-7-Methyl-5⁵-(4-methylpiperazin-1-yl)-1⁴H-6-oxa-3-aza-2(2,6)-pyridina-1(3,4)-triazola-5(1,2)-benzenacyclodecaphan-4-one

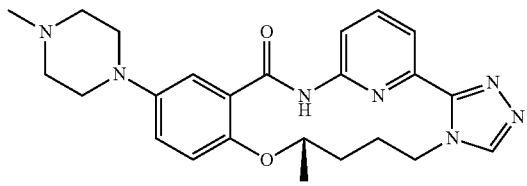 [SMILES: C[C@H]1CCCn2cnnc2-c2cccc(n2)NC(=O)c2cc(N3CCN(C)CC3)ccc2O1]

To a solution of (S)-5⁵-bromo-7-methyl-1⁴H-6-oxa-3-aza-2(2,6)-pyridina-1(3,4)-triazola-5(1,2)-benzenacyclodecaphan-4-one (100 mg, 0.23 mmol) in dioxane/THF (1/1, 4 mL) was added 1-methylpiperazine (47 mg, 0.46 mmol) and NaOtBu (45 mg, 0.46 mmol) followed by Pd$_2$(dba)$_3$ (21 mg, 0.02 mmol) and Ruphos (22 mg, 0.04 mmol) under a N$_2$ atmosphere and the mixture was stirred at 110° C. for 2 h. After this time the mixture was poured into water (10 mL) and extracted with DCM/MeOH (3×20 mL). The organic layer was washed with brine (50 mL), dried over Na$_2$SO$_4$, filtered and concentrated to give the crude product which was purified by HPLC (using a Waters Xbridge Prep OBD C18, 5 μm 150×30 mm column and using water (containing 0.05% NH$_3$.H$_2$O and 10 mM NH$_4$HCO$_3$)/CH$_3$CN, from 20% to 50% as the mobile phase at a flow rate of 25 mL/min) to give the title compound (37 mg, 35%) as a green solid. $^1$H NMR (400 MHz, DMSO-d$_6$) δ ppm 11.46 (s, 1H), 8.68 (s, 1H), 8.04-8.06 (m, 1H), 7.93 (d, J=7.6 Hz, 1H), 7.87 (dd, J=0.8, 7.8 Hz, 1H), 7.58 (d, J=2.8 Hz, 1H), 7.17-7.21 (m, 2H), 4.96-4.97 (m, 1H), 4.18-4.28 (m, 2H), 3.07-3.10 (m, 4H), 2.94-2.96 (m, 1H), 2.44-2.50 (m, 4H), 2.22 (s, 3H), 1.81-2.03 (m, 3H), 1.31 (d, J=6.4 Hz, 3H). MS (ESI): 448.1 [M+H]$^+$.

Example 141: (R)-7-Methyl-5⁵-(4-methylpiperazin-1-yl)-1⁴H-6-oxa-3-aza-2(2,6)-pyridina-1(3,4)-triazola-5(1,2)-benzenacyclodecaphan-4-one

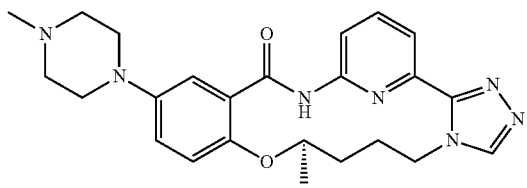 [SMILES: C[C@@H]1CCCn2cnnc2-c2cccc(n2)NC(=O)c2cc(N3CCN(C)CC3)ccc2O1]

The title compound was synthesized according to the general procedure described in Example 140 and using (R)-5⁵-bromo-7-methyl-1⁴H-6-oxa-3-aza-2(2,6)-pyridina-1(3,4)-triazola-5(1,2)-benzenacyclodecaphan-4-one (100 mg, 0.23 mmol). The product was purified by HPLC (using a Waters Xbridge Prep OBD C18, 5 μm 150×30 mm column and using water (containing 0.05% NH$_3$.H$_2$O)/CH$_3$CN, from 19% to 49% as the mobile phase at a flow rate of 25 mL/min) to give the desired product (76 mg, 73%) as a yellow solid. $^1$H NMR (400 MHz, DMSO-d$_6$) δ ppm 11.43 (s, 1H), 8.66 (s, 1H), 8.03 (t, J=8.0 Hz, 1H), 7.90 (d, J=7.6 Hz, 1H), 7.84 (d, J=7.2 Hz, 1H), 7.55 (d, J=2.8 Hz, 1H), 7.11-7.18 (m, 2H), 4.91-4.94 (m, 1H), 4.17-4.28 (m, 2H), 3.04-3.08 (m, 4H), 2.91-2.94 (m, 1H), 2.43-2.46 (m, 4H), 2.20 (s, 3H), 1.83-1.99 (m, 3H), 1.28 (d, J=6.4 Hz, 3H). MS (ESI): 448.2 [M+H]$^+$.

Example 142: (S)-7-Methyl-5⁵-morpholino-1⁴H-6-oxa-3-aza-2(2,6)-pyridina-1(3,4)-triazola-5(1,2)-benzenacyclodecaphan-4-one

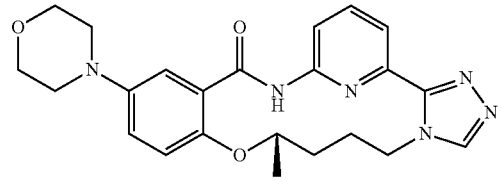 [SMILES: C[C@H]1CCCn2cnnc2-c2cccc(n2)NC(=O)c2cc(N3CCOCC3)ccc2O1]

A mixture of (S)-5⁵-bromo-7-methyl-1⁴H-6-oxa-3-aza-2(2,6)-pyridina-1(3,4)-triazola-5(1,2)-benzenacyclodecaphan-4-one (100 mg, 0.23 mmol), morpholine (0.1 mL, 1.2 mmol), t-BuONa (56 mg, 0.47 mmol), Pd$_2$(dba)$_3$ (22 mg, 0.023 mmol) and RuPhos (23 mg, 0.05 mmol) in dioxane/THF (5 mL, 1/1) was stirred under a N$_2$ atmosphere at 120° C. for 4 h. After this time the mixture was purified by column chromatography on silica gel using DCM/MeOH (100/1 to 10/1) as eluent to give the title compound (75 mg, 74%) as a white solid. $^1$H NMR (400 MHz, DMSO-d$_6$) δ ppm 11.45 (s, 1H), 8.67 (s, 1H), 8.02-8.07 (m, 1H), 7.92 (d, J=8.0 Hz, 1H), 7.86 (d, J=7.6 Hz, 1H), 7.57 (d, J=2.4 Hz, 1H), 7.13-7.25 (m, 2H), 4.96 (d, J=4.4 Hz, 1H), 4.14-4.35 (m, 2H), 3.67-3.77 (m, 4H), 3.01-3.10 (m, 4H), 2.94 (d, J=7.2 Hz, 1H), 1.80-2.08 (m, 3H), 1.30 (d, J=6.4 Hz, 3H). MS (ESI): 435.1 [M+H]$^+$.

Example 143: (R)-7-Methyl-5⁵-morpholino-1⁴H-6-oxa-3-aza-2(2,6)-pyridina-1(3,4)-triazola-5(1,2)-benzenacyclodecaphan-4-one

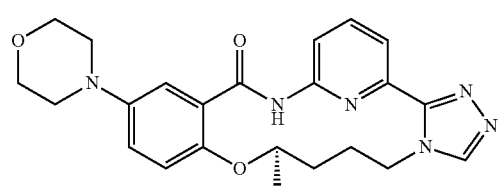

The title compound was synthesized according to the general procedure described in Example 142 and using (R)-5⁵-bromo-7-methyl-1⁴H-6-oxa-3-aza-2(2,6)-pyridina-1(3,4)-triazola-5(1,2)-benzenacyclodecaphan-4-one (100 mg, 0.23 mmol). The product was purified by column chromatography on silica gel using DCM/MeOH (100/0 to 30/1) as eluent to give the title compound (56 mg, 55%) as a white solid. $^1$H NMR (400 MHz, DMSO-d$_6$) δ ppm 11.45 (s, 1H), 8.67 (s, 1H), 8.01-8.08 (m, 1H), 7.92 (d, J=7.9 Hz, 1H), 7.86 (d, J=7.5 Hz, 1H), 7.57 (d, J=2.6 Hz, 1H), 7.14-7.25 (m, 2H), 4.92-5.01 (m, 1H), 4.15-4.32 (m, 2H), 3.70-3.79 (m, 4H), 3.02-3.10 (m, 4H), 2.88-2.99 (m, 1H), 1.82-2.08 (m, 3H), 1.30 (d, J=6.1 Hz, 3H). MS (ESI): 435.1 [M+H]$^+$.

Example 144: (S)-7-Methyl-5⁵-(pyridin-4-yl)-1⁴H-6-oxa-3-aza-2(2,6)-pyridina-1(3,4)-triazola-5(1,2)-benzenacyclodecaphan-4-one

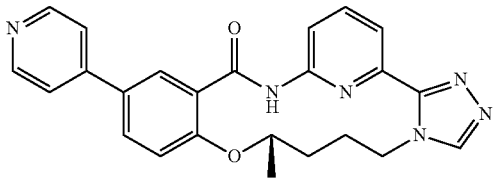 [SMILES: C[C@H]1CCCn2cnnc2-c2cccc(n2)NC(=O)c2cc(-c3ccncc3)ccc2O1]

A mixture of (S)-5⁵-bromo-7-methyl-1⁴H-6-oxa-3-aza-2(2,6)-pyridina-1(3,4)-triazola-5(1,2)-benzenacyclodecaphan-4-one (90 mg, 0.21 mmol), pyridin-4-ylboronic acid (39 mg, 0.31 mmol), Pd(dppf)Cl₂ (17 mg, 0.021 mmol) and K₂CO₃ (58 mg, 0.420 mmol) in dioxane/H₂O (3 mL, 10/1) was stirred under a N₂ atmosphere at 90° C. for 3 h. After this time the mixture was purified by column chromatography on silica gel using DCM/MeOH (100/1 to 10/1) as eluent to give the title compound (70 mg, 78%) as a white solid. ¹H NMR (400 MHz, DMSO-d₆) δ ppm 11.22 (s, 1H), 8.68 (s, 1H), 8.60-8.66 (m, 2H), 8.41 (d, J=2.4 Hz, 1H), 8.02-8.12 (m, 2H), 7.92 (dd, J=7.6, 14.4 Hz, 2H), 7.73 (d, J=6.4 Hz, 2H), 7.44 (d, J=8.8 Hz, 1H), 5.16 (s, 1H), 4.27 (d, J=7.2 Hz, 2H), 2.99 (s, 1H), 1.91-2.00 (m, 3H), 1.36 (d, J=6.4 Hz, 3H). MS (ESI): 427.1 [M+H]⁺.

Example 145: (R)-7-Methyl-5⁵-(pyridin-4-yl)-1⁴H-6-oxa-3-aza-2(2,6)-pyridina-1(3,4)-triazola-5(1,2)-benzenacyclodecaphan-4-one

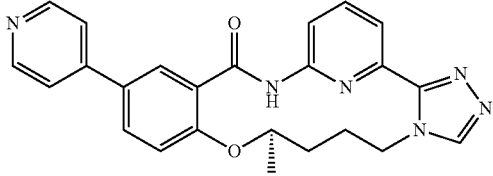 [SMILES: C[C@@H]1CCCn2cnnc2-c2cccc(n2)NC(=O)c2cc(-c3ccncc3)ccc2O1]

The title compound was synthesized according to the general procedure described in Example 144 and using (R)-5⁵-bromo-7-methyl-1⁴H-6-oxa-3-aza-2(2,6)-pyridina-1(3,4)-triazola-5(1,2)-benzenacyclodecaphan-4-one (100 mg, 0.23 mmol). The product was purified by column chromatography on silica gel using DCM/MeOH (100/1 to 100/4) as eluent to give the title compound (68 mg, 69%) as a yellow solid. ¹H NMR (400 MHz, DMSO-d₆) δ ppm 11.22 (s, 1H), 8.68 (s, 1H), 8.62 (d, J=6.0 Hz, 2H), 8.40 (d, J=2.0 Hz, 1H), 8.04-8.07 (m, 2H), 7.89-7.95 (m, 2H), 7.72 (d, J=6.4 Hz, 2H), 7.43-7.44 (m, 1H), 5.15 (d, J=6.0 Hz, 1H), 4.21-4.31 (m, 2H), 2.93-2.99 (m, 1H), 1.93-2.04 (m, 3H), 1.35 (t, J=6.0 Hz, 3H). MS (ESI): 427.0 [M+H]⁺.

Example 146: (S)-5⁵-(1-(2-(Dimethylamino)ethyl)-1H-pyrazol-4-yl)-7-methyl-1⁴H-6-oxa-3-aza-2(2,6)-pyridina-1(3,4)-triazola-5(1,2)-benzenacyclodecaphan-4-one

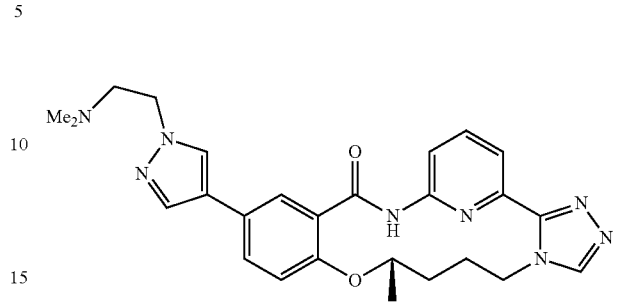

A mixture of (S)-5⁵-bromo-7-methyl-1⁴H-6-oxa-3-aza-2(2,6)-pyridina-1(3,4)-triazola-5(1,2)-benzenacyclodecaphan-4-one (90 mg, 0.21 mmol) and N,N-dimethyl-2-(4-(4,4,5,5-tetramethyl-1,3,2-dioxaborolan-2-yl)-1H-pyrazol-1-yl)ethan-1-amine (84 mg, 0.31 mmol) in dioxane/H₂O (3 mL, 10/1) was treated with Pd(dppf)Cl₂ (17 mg, 0.021 mmol) and K₂CO₃ (58 mg, 0.42 mmol) and the mixture was stirred at 90° C. for 3 h. After this time the mixture was concentrated and the resulting residue was purified by column chromatography on silica gel using DCM/MeOH (100/1 to 10/1) as eluent to give the title compound (75 mg, 73%) as a white solid. ¹H NMR (400 MHz, DMSO-d₆) δ ppm 11.31 (s, 1H), 8.68 (s, 1H), 8.23 (s, 1H), 8.17 (d, J=2.8 Hz, 1H), 8.04-8.09 (m, 1H), 7.93 (d, J=8.0 Hz, 1H), 7.87-7.90 (m, 2H), 7.77 (dd, J=2.8, 11.2 Hz, 1H), 7.28 (d, J=9.2 Hz, 1H), 5.06 (br s, 1H), 4.24 (br s, 4H), 2.96 (br s, 1H), 2.78 (br s, 2H), 2.25 (br s, 6H), 1.85-2.10 (m, 3H), 1.33 (d, J=6.0 Hz, 3H). MS (ESI): 487.2 [M+H]⁺.

Example 147: (R)-5⁵-(1-(2-(Dimethylamino)ethyl)-1H-pyrazol-4-yl)-7-methyl-1⁴H-6-oxa-3-aza-2(2,6)-pyridina-1(3,4)-triazola-5(1,2)-benzenacyclodecaphan-4-one

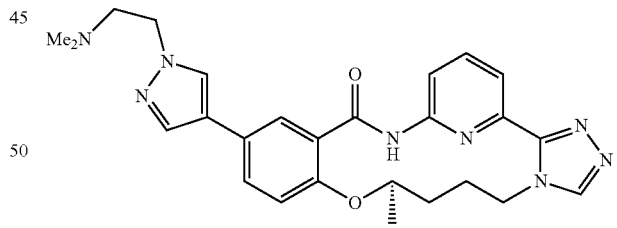

The title compound was synthesized according to the general procedure described in Example 146 and using (R)-5⁵-bromo-7-methyl-1⁴H-6-oxa-3-aza-2(2,6)-pyridina-1(3,4)-triazola-5(1,2)-benzenacyclodecaphan-4-one (100 mg, 0.23 mmol). The product was purified by HPLC (using an Xtimate C18, 5 μm 150×25 mm column and using water (containing 10 mM NH₄HCO₃)/CH₃CN, from 37% to 67% as the mobile phase at a flow rate of 25 mL/min) to give the desired product (47 mg, 48%) as a brown solid. ¹H NMR (400 MHz, DMSO-d₆) δ ppm 11.32 (s, 1H), 8.68 (s, 1H), 8.24 (s, 1H), 8.17-8.18 (m, 1H), 8.05-8.08 (m, 1H), 7.90-7.96 (m, 3H), 7.77 (dd, J=8.0 Hz, 2.4 Hz, 1H), 7.28 (d, J=8.8 Hz, 1H), 5.07 (br, 1H), 4.21-4.30 (m, 4H), 2.97-3.00 (m, 1H), 2.85 (br, 2H), 2.30 (s, 6H), 1.92-2.05 (m, 3H), 1.35 (d, J=6.0 Hz, 3H). MS (ESI): 487.2 [M+H]⁺.

Example 148: (S)-7-Methyl-5⁵-(4-methyl-1H-imidazol-1-yl)-1⁴H-6-oxa-3-aza-2(2,6)-pyridina-1(3,4)-triazola-5(1,2)-benzenacyclodecaphan-4-one

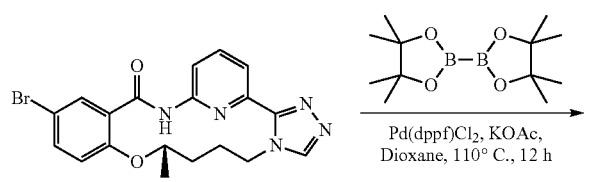

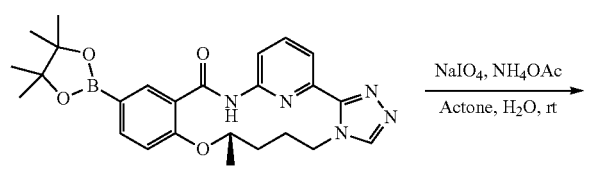

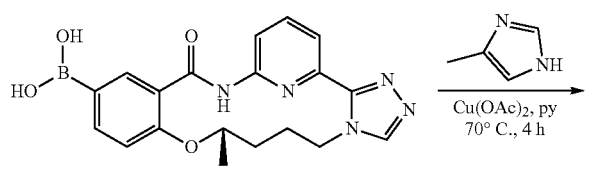

Step A. (S)-7-Methyl-5⁵-(4,4,5,5-tetramethyl-1,3,2-dioxaborolan-2-yl)-1⁴H-6-oxa-3-aza-2(2,6)-pyridina-1(3,4)-triazola-5(1,2)-benzenacyclodecaphan-4-one

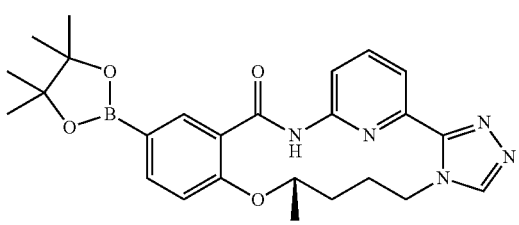 [SMILES: C[C@H]1CCCn2cnnc2-c2cccc(n2)NC(=O)c2cc(B3OC(C)(C)C(C)(C)O3)ccc2O1]

A mixture of (S)-5⁵-bromo-7-methyl-1⁴H-6-oxa-3-aza-2(2,6)-pyridina-1(3,4)-triazola-5(1,2)-benzenacyclodecaphan-4-one (200 mg, 0.47 mmol), 4,4,4',4',5,5,5',5'-octamethyl-2,2'-bi(1,3,2-dioxaborolane) (237 mg, 0.93 mmol), KOAc (92 mg, 0.93 mmol) and Pd(dppf)Cl₂ (34 mg, 0.05 mmol) in dioxane (5 mL) was degassed with N₂ and stirred at 110° C. for 12 hr. After this time the solvent was removed and the residue was extracted with EtOAc (20 mL) and washed with water (15 mL). The separated organic layer was dried with Na₂SO₄ (?) and concentrated to give crude product (200 mg), which was used in the next step without further purification. MS (ESI): 476.0 [M+H]⁺.

Step B. (S)-(7-Methyl-4-oxo-1⁴H-6-oxa-3-aza-2(2,6)-pyridina-1(3,4)-triazola-5(1,2)-benzenacyclodecaphane-5⁵-yl)boronic acid

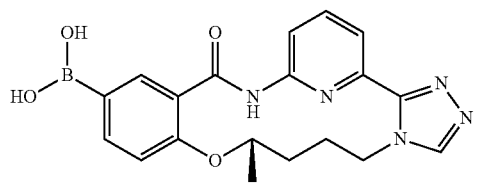 [SMILES: C[C@H]1CCCn2cnnc2-c2cccc(n2)NC(=O)c2cc(B(O)O)ccc2O1]

To a mixture of (S)-7-methyl-5⁵-(4,4,5,5-tetramethyl-1,3,2-dioxaborolan-2-yl)-1⁴H-6-oxa-3-aza-2(2,6)-pyridina-1(3,4)-triazola-5(1,2)-benzenacyclodecaphan-4-one (200 mg, 0.42 mmol) in acetone (3 mL) and water (3 mL) was added NH₄OAc (81 mg, 1.05 mmol) and NaIO4 (270 mg, 1.26 mmol) and the mixture was stirred at 18° C. for 12 h. After this time water (10 mL) was added and the suspension was filtered. The solid was dried under vacuum to give the desired product (130 mg, 91%) as a brown solid. MS (ESI): 394.1 [M+H]⁺.

Step C. (S)-7-Methyl-5⁵-(4-methyl-1H-imidazol-1-yl)-1⁴H-6-oxa-3-aza-2(2,6)-pyridina-1(3,4)-triazola-5(1,2)-benzenacyclodecaphan-4-one

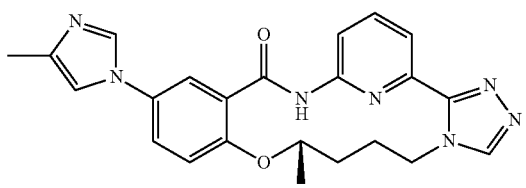 [SMILES: Cc1cn(-c2ccc3c(c2)C(=O)Nc2cccc(n2)-c2nncn2CCC[C@H](C)O3)cn1]

A mixture of (S)-(7-methyl-4-oxo-1⁴H-6-oxa-3-aza-2(2,6)-pyridina-1(3,4)-triazola-5(1,2)-benzenacyclodecaphane-5⁵-yl)boronic acid (160 mg, 0.41 mmol), 4-methyl-1H-imidazole (67 mg, 0.81 mmol), and Cu(OAc)₂ (148 mg, 0.814 mmol) in pyridine (3 mL) was stirred at 70° C. for 5 h. After this time the volatiles were removed under reduced pressure to give the crude product which was purified by HPLC (using a Phenomenex Synergi C18, 4 μm 150×30 mm column and using water (containing 0.05% HCl)/CH₃CN, from 14% to 29% as the mobile phase at a flow rate of 25 mL/min) to give the title compound (20 mg, 11%) as a white solid. ¹H NMR (400 MHz, DMSO-d₆) δ ppm 11.19 (s, 1H), 9.68 (d, J=1.0 Hz, 1H), 9.17 (s, 1H), 8.29 (d, J=3.0 Hz, 1H), 8.08-8.15 (m, 1H), 8.05 (s, 1H), 7.93-8.01 (m, 3H), 7.56 (d, J=9.0 Hz, 1H), 5.11-5.23 (m, 1H), 4.26-4.45 (m, 2H), 2.88-3.05 (m, 1H), 2.37 (s, 3H), 1.92-2.14 (m, 3H), 1.36 (d, J=6.5 Hz, 3H). MS (ESI): 430.1 [M+H]⁺.

Example 149: (R)-7-Methyl-5⁵-(4-methyl-1H-imidazol-1-yl)-1⁴H-6-oxa-3-aza-2(2,6)-pyridina-1(3,4)-triazola-5(1,2)-benzenacyclodecaphan-4-one

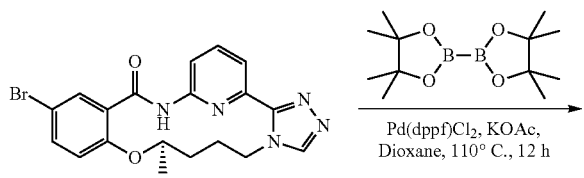

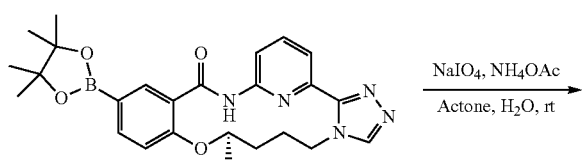

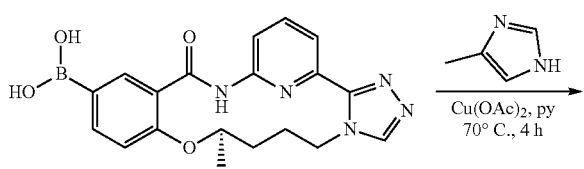

Step A. (R)-7-Methyl-5⁵-(4,4,5,5-tetramethyl-1,3,2-dioxaborolan-2-yl)-1⁴H-6-oxa-3-aza-2(2,6)-pyridina-1(3,4)-triazola-5(1,2)-benzenacyclodecaphan-4-one

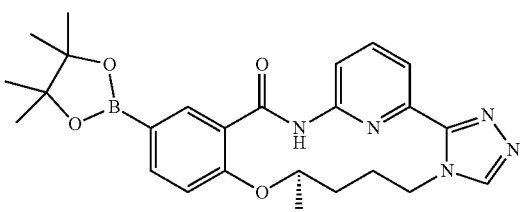

The title compound was synthesized according to the general procedure described in Example 148, Step A and using (R)-5⁵-bromo-7-methyl-1⁴H-6-oxa-3-aza-2(2,6)-pyridina-1(3,4)-triazola-5(1,2)-benzenacyclodecaphan-4-one (200 mg, 0.47 mmol) to give the desired product (332 mg, crude) as a black solid. MS (ESI): 476.2 [M+H]⁺.

Step B. (R)-(7-Methyl-4-oxo-1⁴H-6-oxa-3-aza-2(2,6)-pyridina-1(3,4)-triazola-5(1,2)-benzenacyclodecaphane-5⁵-yl)boronic acid

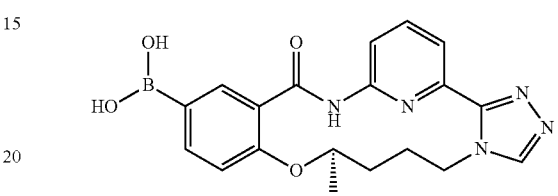

The title compound was synthesized according to the general procedure described in Example 148, Step B and using (R)-7-methyl-5⁵-(4,4,5,5-tetramethyl-1,3,2-dioxaborolan-2-yl)-1⁴H-6-oxa-3-aza-2(2,6)-pyridina-1(3,4)-triazola-5(1,2)-benzenacyclodecaphan-4-one (322 mg, 0.7 mmol) to give the desired product (340 mg, crude) as a gray solid. MS (ESI): 394.0 [M+H]⁺.

Step C. (R)-7-Methyl-5⁵-(4-methyl-1H-imidazol-1-yl)-1⁴H-6-oxa-3-aza-2(2,6)-pyridina-1(3,4)-triazola-5(1,2)-benzenacyclodecaphan-4-one

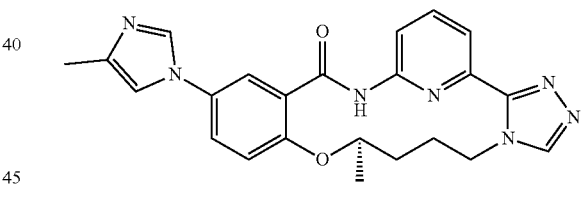

The title compound was synthesized according to the general procedure described in Example 148, Step C and using (R)-(7-methyl-4-oxo-1⁴H-6-oxa-3-aza-2(2,6)-pyridina-1(3,4)-triazola-5(1,2)-benzenacyclodecaphane-5⁵-yl)boronic acid (340 mg, 0.86 mmol). Purification by SFC (using an AD 250 mm×30 mm×10 μm column and 55% EtOH (with 0.1% ammonium hydroxide) in COQ as the mobile phase at a flow rate of 80 mL/min) gave the product which was further purified by HPLC (using an Xtimate C18, 5 μm 150×25 mm column and using water (containing 10 mM NH$_4$HCO$_3$)/CH$_3$CN, from 28% to 58% as the mobile phase at a flow rate of 25 mL/min) to give the title compound (4 mg, 1%) as a white solid. 1H NMR (400 MHz, CD$_3$OD) δ ppm 8.63 (s, 1H), 8.20 (d, J=2.8 Hz, 1H), 8.03 (s, 1H), 8.00-8.02 (m, 2H), 7.89-7.94 (m, 1H), 7.70 (dd, J=3.2, 8.8 Hz, 1H), 7.36 (d, J=8.8 Hz, 1H), 7.25 (s, 1H), 5.08-5.17 (m, 1H), 4.29-4.39 (m, 2H), 3.10-3.22 (m, 1H), 2.26 (s, 3H), 2.08-2.23 (m, 2H), 1.95-2.07 (m, 1H), 1.48 (d, J=6.4 Hz, 3H). MS (ESI): 430.2 [M+H]⁺.

Example 150: (S)-7-Methyl-4-oxo-1⁴H-6-oxa-3-aza-2(2,6)-pyridina-1(3,4)-triazola-5(1,2)-benzenacyclodecaphane-5⁵-carbonitrile

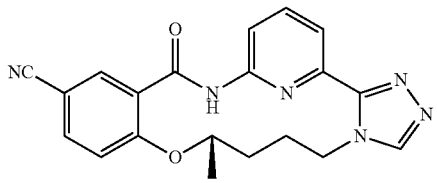 [SMILES: C[C@H]1CCCn2cnnc2-c2cccc(n2)NC(=O)c2cc(C#N)ccc2O1]

A mixture of (S)-5⁵-bromo-7-methyl-1⁴H-6-oxa-3-aza-2(2,6)-pyridina-1(3,4)-triazola-5(1,2)-benzenacyclodecaphan-4-one (100 mg, 0.23 mmol), zinc cyanide (26 mg, 0.28 mmol), Zinc (9 mg, 0.14 mmol), Pd₂(dba)₃ (21 mg, 0.023 mmol) and dppf (26 mg, 0.05 mmol) in DMA (5 mL) was stirred under a N₂ atmosphere at 90° C. for 12 h. After this time the mixture was concentrated and purified by HPLC (using a Waters Xbridge Prep OBD C18, 5 μm 150×30 mm column and using water (containing 0.05% NH₃.H₂O)/CH₃CN, from 24% to 54% as the mobile phase at a flow rate of 25 mL/min) to give the title compound (30 mg, 34%) as white solid. ¹H NMR (400 MHz, DMSO-d₆) δ ppm 11.00 (s, 1H), 8.69 (s, 1H), 8.34 (d, J=2.0 Hz, 1H), 8.03-8.14 (m, 2H), 7.86-7.99 (m, 2H), 7.50 (d, J=9.2 Hz, 1H), 5.19 (br s, 1H), 4.22-4.34 (m, 2H), 2.95 (s, 1H), 1.85-2.09 (m, 3H), 1.35 (d, J=6.0 Hz, 3H). MS (ESI): 375.0 [M+H]⁺.

Example 151: (R)-7-Methyl-4-oxo-1⁴H-6-oxa-3-aza-2(2,6)-pyridina-1(3,4)-triazola-5(1,2)-benzenacyclodecaphane-5⁵-carbonitrile

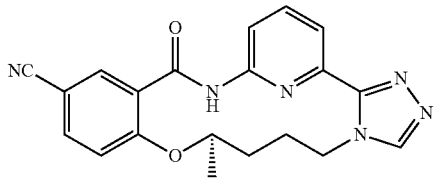 [SMILES: C[C@@H]1CCCn2cnnc2-c2cccc(n2)NC(=O)c2cc(C#N)ccc2O1]

The title compound was synthesized according to the general procedure described in Example 150 and using (R)-5⁵-bromo-7-methyl-1⁴H-6-oxa-3-aza-2(2,6)-pyridina-1(3,4)-triazola-5(1,2)-benzenacyclodecaphan-4-one (100 mg, 0.23 mmol). The product was purified by column chromatography on silica gel using DCM/MeOH (1/0 to 20/1) to give the desired product (45 mg, 51%) as a white solid. ¹H NMR (400 MHz, DMSO-d₆) δ ppm 10.94 (s, 1H), 8.67 (s, 1H), 8.31 (d, J=2.2 Hz, 1H), 7.99-8.13 (m, 2H), 7.85-7.96 (m, 2H), 7.47 (d, J=9.2 Hz, 1H), 5.12-5.20 (m, 1H), 4.18-4.31 (m, 2H), 2.84-3.00 (br s, 1H), 1.85-2.03 (m, 3H), 1.32 (d, J=6.1 Hz, 3H). MS (ESI): 397.0 [M+Na]⁺.

Example 152: 5⁵-Bromo-3-methyl-1⁴H-6-oxa-3-aza-2(2,6)-pyridina-1(3,4)-triazola-5(1,2)-benzenacyclodecaphan-4-one

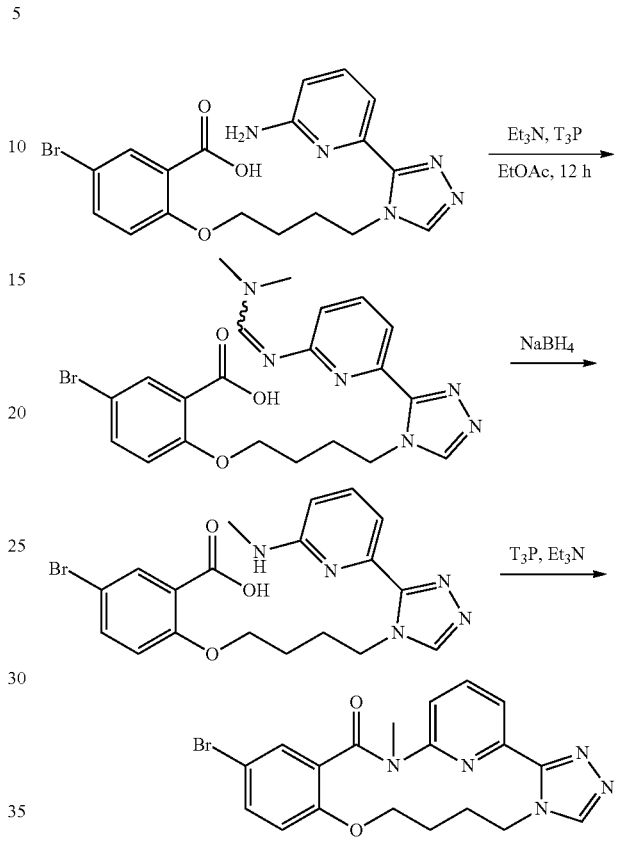

Step A. 5-Bromo-2-(4-(3-(6-(((dimethylamino)methylene)amino)pyridin-2-yl)-4H-1,2,4-triazol-4-yl)butoxy)benzoic acid

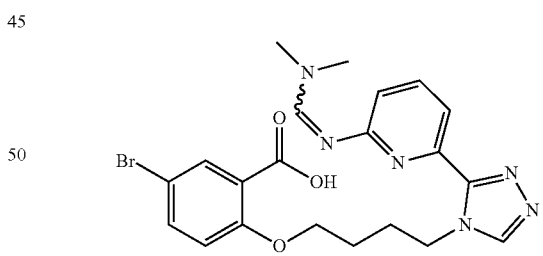

To a solution of 2-(4-(3-(6-aminopyridin-2-yl)-4H-1,2,4-triazol-4-yl)butoxy)-5-bromobenzoic acid (100 mg, 0.23 mmol) in DMF (0.5 mL) was added dimethylformamide dimethyl acetal (165 mg, 1.39 mmol) and the resulting mixture was stirred 100° C. for 2 h. The reaction was cooled to room temperature and the solids were filtered off and dried on the filter frit and under a stream of air. The crude mixture of regioisomers (85 mg, 0.17 mmol) was used without further purification in the next step.

Step B. 5-Bromo-2-(4-(3-(6-(methylamino)pyridin-2-yl)-4H-1,2,4-triazol-4-yl)butoxy)benzoic acid

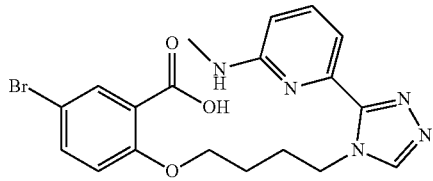 [SMILES: CNc1cccc(-c2nncn2CCCCOc2ccc(Br)cc2C(=O)O)n1]

To a suspension of 5-bromo-2-(4-(3-(6-(((dimethylamino)methylene)amino)pyridin-2-yl)-4H-1,2,4-triazol-4-yl)butoxy)benzoic acid (85 mg, 0.17 mmol) in THF (0.25 mL) and DMF (0.25 mL) was added sodium borohydride (20 mg, 0.52 mmol) and the resulting mixture was stirred for 2 days at room temperature. The volatiles were removed reduced pressure and the resulting residue was purified by column chromatography (4 g SiO$_2$, MeOH in DCM 1-15%) to give the title compound (22 mg, 29%). $^1$H NMR (400 MHz, CDCl$_3$) δ ppm 8.40-8.62 (m, 1H), 8.07 (d, J=2.8 Hz, 1H), 7.52 (br d, J=2.8 Hz, 3H), 6.83 (d, J=8.8 Hz, 1H), 6.37-6.51 (m, 1H), 5.49-6.21 (m, 2H), 4.73 (br t, J=7.2 Hz, 2H), 4.10 (t, J=5.8 Hz, 2H), 2.09 (s, 3H), 1.81-1.92 (m, 2H), 1.19-1.34 (m, 2H). MS (ESI): 446.1 [(M+H) ($^{79}$Br)]$^+$.

Step C. 5$^5$-Bromo-3-methyl-1$^4$H-6-oxa-3-aza-2(2,6)-pyridina-1(3,4)-triazola-5(1,2)-benzenacyclodecaphan-4-one

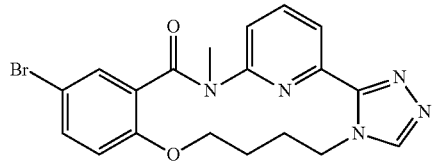 [SMILES: CN1C(=O)c2cc(Br)ccc2OCCCCn2cnnc2-c2cccc1n2]

The title compound was synthesized according to the general procedure described in Example 1, Step E and using 5-bromo-2-((4-(3-(6-aminopyridin-2-yl)-4H-1,2,4-triazol-4-yl)pentyl)oxy)-5-bromobenzoic acid (22 mg, 0.05 mmol) to give the title compound (2 mg, 10%) as a colorless film. $^1$H NMR (400 MHz, CDCl$_3$) δ ppm 8.62 (s, 1H), 7.86 (br s, 1H), 7.76 (br d, J=6.5 Hz, 1H), 7.62 (d, J=2.3 Hz, 1H), 7.39 (dd, J=8.8, 2.3 Hz, 1H), 7.01-7.16 (m, 1H), 6.60 (br d, J=8.3 Hz, 1H), 4.56-5.03 (m, 2H), 3.97-4.51 (m, 2H), 3.53 (s, 3H), 2.09-2.47 (m, 1H), 1.80-2.02 (m, 2H), 1.43-1.76 (m, 1H). MS (ESI): 428.1 [(M+H) ($^{79}$Br)]$^+$.

Example 153: 5$^4$-(Trifluoromethyl)-1$^4$H-6-oxa-3-aza-2(2,6)-pyridina-1(3,4)-triazola-5(1,2)-benzenacyclodecaphan-4-one

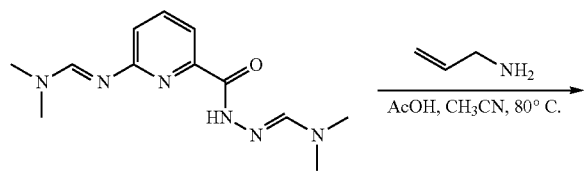

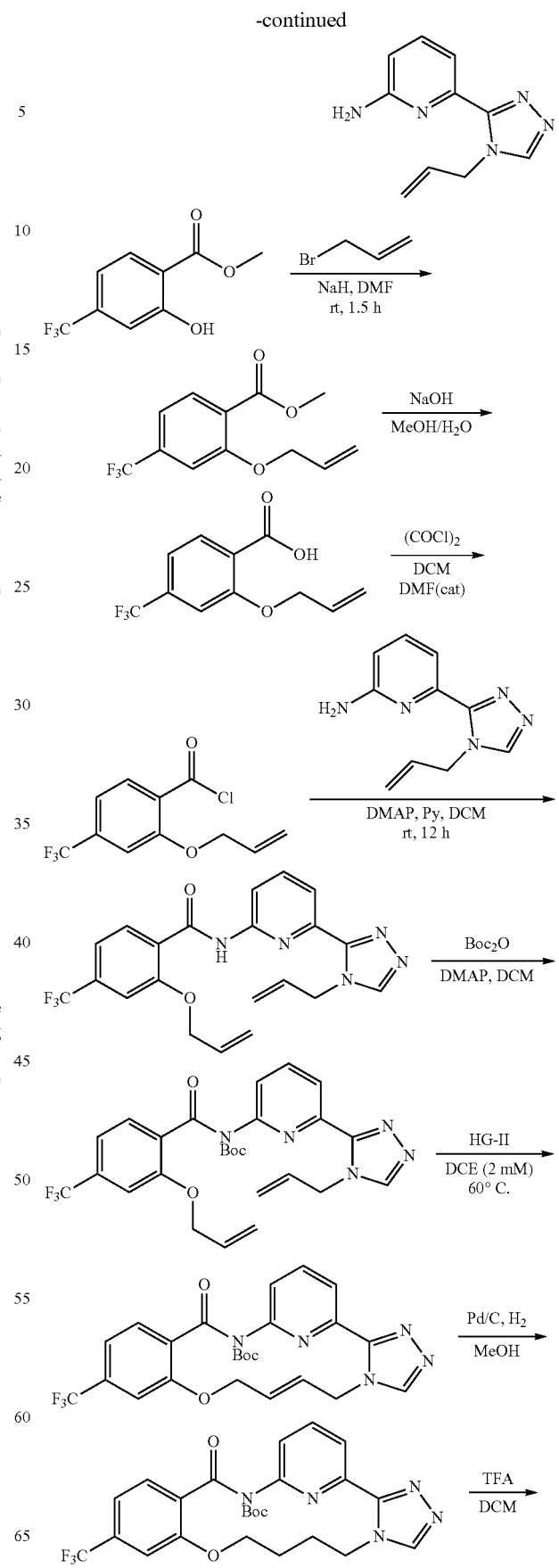

-continued

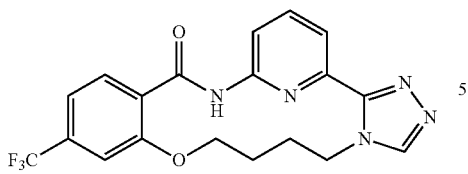

Step A. 6-(4-Allyl-4H-1,2,4-triazol-3-yl)pyridin-2-amine

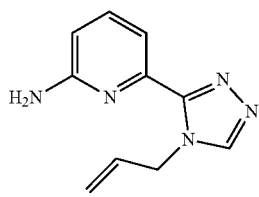

A mixture of (E)-N'-(6-(2-((E)-(dimethylamino)methylene)hydrazine-1-carbonyl)pyridin-2-yl)-N,N-dimethylformimidamide (40 g, 0.15 mmol) and allyl amine (44.2 g) in AcOH (250 mL) and CH$_3$CN (250 mL) was stirred at 80° C. for 17 h. After this time the volatiles were evaporated to give the crude product, which was suspended in EtOAc (50 mL). Addition of a 1:1 mixture of HCl/EtOAc (4M, 50 mL) afforded a solid which was filtered off and dried under vacuum to give the desired product (20 g, 67%) as a yellow solid.

Step B. Methyl 2-(allyloxy)-4-(trifluoromethyl)benzoate

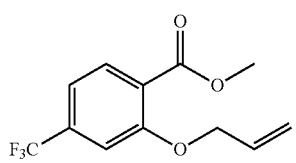 [SMILES: C=CCOc1cc(C(F)(F)F)ccc1C(=O)OC]

To a stirred mixture of methyl 2-hydroxy-4-(trifluoromethyl)benzoate (3.5 g, 15.9 mmol) in DMF (50 mL) was added NaH (1.5 g, 36.2 mmol, 60% dispersion in oil). The mixture was stirred at 30° C. for 30 minutes after which allyl bromide (3.5 g, 28.9 mmol) was added and the reaction was stirred at 30° C. for another 2 h. After this time the reaction was quenched with H$_2$O (150 mL) and extracted with EtOAc (2×100 mL). The combined organic phase was dried over Na$_2$SO$_4$, filtered and concentrated under reduced pressure to give the title compound (4 g, 100%) as a colorless oil which was used in the next step without further purification.

Step C. 2-(Allyloxy)-4-(trifluoromethyl)benzoic acid

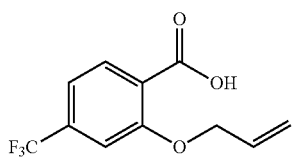

A mixture of methyl 2-(allyloxy)-4-(trifluoromethyl)benzoate (4.0 g, 15.4 mmol) and NaOH (3.1 g, 77 mmol) in MeOH/H$_2$O (30 mL/5 mL) was stirred at 30° C. for 17 h. After this time the volatiles were removed under reduced pressure and the crude product was dissolved in H$_2$O (30 mL) and extracted with EtOAc (2×30 mL). The pH of the aqueous phase was adjusted to 2 with conc. aq. HCl solution upon which a precipitate formed. The solid was collected by filtration and dried under vacuum to give the title compound (3.3 g, 85%) as a white solid. MS (ESI): 246.9 [M+H]$^+$.

Step D. 2-(Allyloxy)-4-(trifluoromethyl)benzoyl chloride

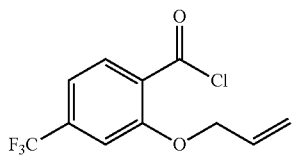 [SMILES: C=CCOc1cc(C(F)(F)F)ccc1C(=O)Cl]

2-(Allyloxy)-4-(trifluoromethyl)benzoic acid (2.0 g, 8 mmol) was dissolved in DMF (0.5 mL) and DCM (50 mL). To the solution was dropwise added oxalyl chloride (4.9 g, 32 mmol). The reaction mixture was stirred at 30° C. for 1 h and evaporated to dryness to give the title compound (2.1 g, 100%) as a brown gum which was used in the next step without further purification.

Step E. N-(6-(4-Allyl-4H-1,2,4-triazol-3-yl)pyridin-2-yl)-2-(allyloxy)-4-(trifluoromethyl)benzamide

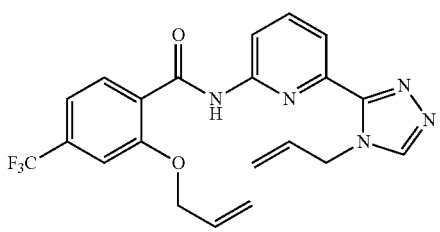 [SMILES: C=CCOc1cc(C(F)(F)F)ccc1C(=O)Nc1cccc(-c2nncn2CC=C)n1]

A mixture of 2-(allyloxy)-4-(trifluoromethyl)benzoyl chloride (2.1 g, 8.0 mmol), 6-(4-allyl-4H-1,2,4-triazol-3-yl)pyridin-2-amine (1.6 g, 8.0 mmol, Example 153, Step A), DMAP (126 mg, 1.6 mmol) and pyridine (2.6 mL, 31.8 mmol) in DCM (25 mL) was stirred at 32° C. for 1 h. After this time the reaction mixture was quenched with water (50 mL) and extracted with DCM (2×50 mL). The organic phase was dried over Na$_2$SO$_4$, filtered and concentrated under reduced pressure. The product was purified by column chromatography on silica gel, eluting with petroleum ether/EtOAc (50/1) to EtOAc, to give the tittle compound (0.7 g, 21%) as a brown gum which was used in the next step without further purification.

Step F. tert-Butyl (6-(4-allyl-4H-1,2,4-triazol-3-yl)pyridin-2-yl)(2-(allyloxy)-4-(trifluoromethyl)benzoyl)carbamate

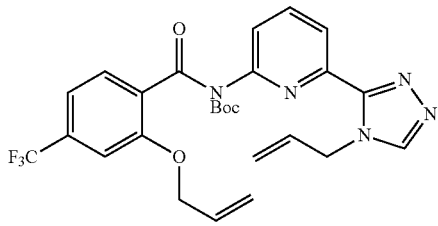 [SMILES: C=CCOc1cc(C(F)(F)F)ccc1C(=O)N(C(=O)OC(C)(C)C)c1cccc(-c2nncn2CC=C)n1]

A mixture of N-(6-(4-allyl-4H-1,2,4-triazol-3-yl)pyridin-2-yl)-2-(allyloxy)-4-(trifluoromethyl)benzamide (1 g, 2.33 mmol), DMAP (0.28 g, 2.33 mmol) and Boc$_2$O (2.5 g, 11.7 mmol) in DCM (25 mL) was stirred at 32° C. for 1 h. After this time the reaction was quenched with sat. aq. NH$_4$Cl (50 mL) and extracted with DCM (2×50 mL). The organic phase was dried over Na$_2$SO$_4$, filtered and concentrated under reduced pressure. The product was purified by column chromatography on silica gel, eluting with petroleum ether/EtOAc (50/1) to EtOAc to give the title compound (0.8 g, 67%) as colorless gum.

Step G: tert-Butyl (E)-4-oxo-5$^4$-(trifluoromethyl)-1$^4$H-6-oxa-3-aza-2(2,6)-pyridina-1(3,4)-triazola-5(1,2)-benzenacyclodecaphan-8-ene-3-carboxylate

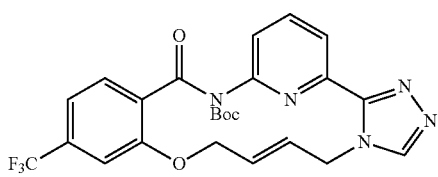

A mixture of N-(6-(4-allyl-4H-1,2,4-triazol-3-yl)pyridin-2-yl)-2-(allyloxy)-4-(trifluoromethyl)benzamide (700 mg, 1.32 mmol) and Hoveyda-Grubb's 2$^{nd}$ generation catalyst (83 mg, 0.13 mmol) in DCE (500 mL) was stirred under a N$_2$ atmosphere at 80° C. for 3 h. After this time the solvent was removed under reduced pressure and the crude residue was purified by column chromatography on silica gel eluting with EtOAc to give the title compound (330 mg, 41%) as a white solid which was used in the next step without further purification.

Step H: tert-Butyl 4-oxo-5$^4$-(trifluoromethyl)-1$^4$H-6-oxa-3-aza-2(2,6)-pyridina-1(3,4)-triazola-5(1,2)-benzenacyclodecaphane-3-carboxylate

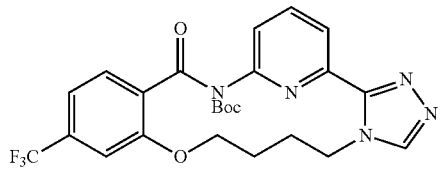 [SMILES: CC(C)(C)OC(=O)N1C(=O)c2ccc(C(F)(F)F)cc2OCCCCn2cnnc2-c2cccc1n2]

To a mixture of tert-butyl (E)-4-oxo-5$^4$-(trifluoromethyl)-1$^4$H-6-oxa-3-aza-2(2,6)-pyridina-1(3,4)-triazola-5(1,2)-benzenacyclodecaphan-8-ene-3-carboxylate (320 mg, 0.64 mmol) in MeOH (15 mL) was added Pd (300 mg, 10% on C) and the mixture was stirred under a H$_2$ atmosphere at 30° C. for 1.5 h. The mixture was filtered and the filtrate was concentrated under reduced pressure to give the title compound (300 mg) as a colorless gum which was used in the next step without further purification.

Step I: 5$^4$-(Trifluoromethyl)-1$^4$H-6-oxa-3-aza-2(2,6)-pyridina-1(3,4)-triazola-5(1,2)-benzenacyclodecaphan-4-one

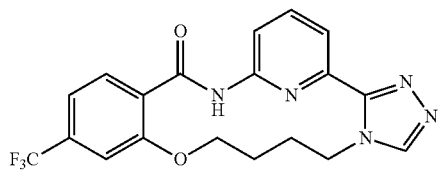 [SMILES: O=C1Nc2cccc(n2)-c2nncn2CCCCOc2cc(C(F)(F)F)ccc21]

To a mixture of tert-butyl 4-oxo-5$^4$-(trifluoromethyl)-1$^4$H-6-oxa-3-aza-2(2,6)-pyridina-1(3,4)-triazola-5(1,2)-benzenacyclodecaphane-3-carboxylate (300 mg, 0.6 mmol) in DCM (2 mL) was added TFA (2 mL) and stirring was continued at 30° C. for 1 h. After this time the solvent was removed under reduced pressure and the product was purified by HPLC (using a Phenomenex Gemini C18 21.2×250 mm×5 μm column and water (containing 0.05% HCl) and CH$_3$CN, from 45% to 65%, as the mobile phase at a flow rate of 25 mL/min) to give the title compound (92 mg, 56%) as a white solid. 1H NMR (400 MHz, DMSO-d$_6$) δ ppm 11.08 (s, 1H), 8.98 (s, 1H), 8.13-8.09 (m, 2H), 7.92-7.89 (m, 2H), 7.60 (s, 1H), 7.52-7.50 (d, J=8.0 Hz, 1H), 4.42-4.45 (m, 2H), 4.30-4.34 (m, 2H), 2.45-2.47 (m, 2H), 1.95-1.97 (m, 2H). MS (ESI): 404.1 [M+H]$^+$.

Example 154: (E)-5$^4$-(Trifluoromethyl)-1$^4$H-6-oxa-3-aza-2(2,6)-pyridina-1(3,4)-triazola-5(1,2)-benzenacyclodecaphan-8-en-4-one

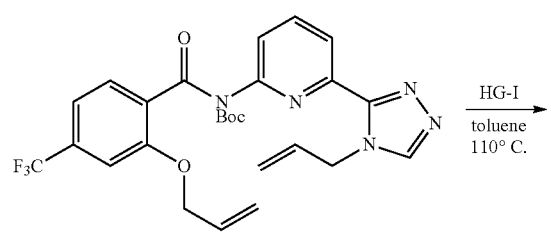

183

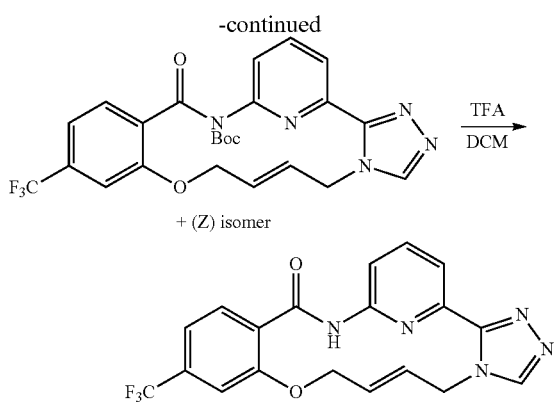

+ (Z) isomer

Step A: tert-Butyl (E)-4-oxo-5⁴-(trifluoromethyl)-1⁴H-6-oxa-3-aza-2(2,6)-pyridina-1(3,4)-triazola-5(1,2)-benzenacyclodecaphan-8-ene-3-carboxylate and tert-Butyl (Z)-4-oxo-5⁴-(trifluoromethyl)-1⁴H-6-oxa-3-aza-2(2,6)-pyridina-1(3,4)-triazola-5(1,2)-benzenacyclodecaphan-8-ene-3-carboxylate

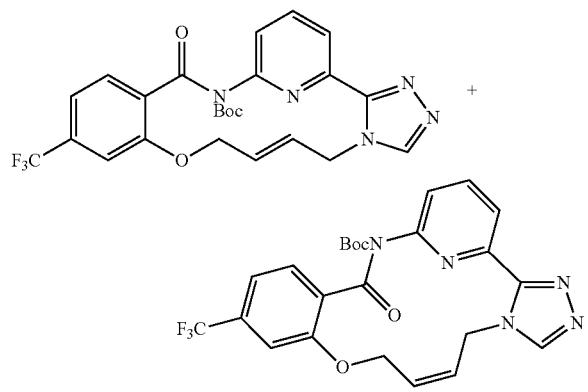

A mixture of tert-butyl (6-(4-allyl-4H-1,2,4-triazol-3-yl)pyridin-2-yl)(2-(allyloxy)-4-(trifluoromethyl)benzoyl)carbamate (2 g, 3.8 mmol, Example 153, Step F) and Hoveyda-Grubb's 1$^{st}$ generation catalyst (0.45 g, 0.76 mmol) in toluene (2.0 L) was stirred under a N$_2$ atmosphere at 110° C. for 17 h. After this time the solvent was evaporated and the crude product was purified by column chromatography on silica, using petroleum ether/EtOAc=1/1 to 0/1 as eluent, to give in order of elution: tert-butyl (E)-4-oxo-5⁴-(trifluoromethyl)-1⁴H-6-oxa-3-aza-2(2,6)-pyridina-1(3,4)-triazola-5(1,2)-benzenacyclodecaphan-8-ene-3-carboxylate (700 mg) and tert-butyl (Z)-4-oxo-5⁴-(trifluoromethyl)-1⁴H-6-oxa-3-aza-2(2,6)-pyridina-1(3,4)-triazola-5(1,2)-benzenacyclodecaphan-8-ene-3-carboxylate (500 mg). Each product was further purified by HPLC (using a Phenomenex Synergi C18, 4 μm 250×21.2 mm column and using water (containing 0.225% HCOOH)/CH$_3$CN, from 38% to 58% as the mobile phase at a flow rate of 25 mL/min) to provide tert-butyl (E)-4-oxo-5⁴-(trifluoromethyl)-1⁴H-6-oxa-3-aza-2(2,6)-pyridina-1(3,4)-triazola-5(1,2)-benzenacyclodecaphan-8-ene-3-carboxylate (145 mg, 9%) and tert-butyl (Z)-4-oxo-5⁴-(trifluoromethyl)-1⁴H-6-oxa-3-aza-2(2,6)-pyridina-1(3,4)-triazola-5(1,2)-benzenacyclodecaphan-8-ene-3-carboxylate (250 mg, 13%) as white solids. MS (ESI): 502.3 [M+H]$^+$

184

Step B: (E)-5⁴-(Trifluoromethyl)-1⁴H-6-oxa-3-aza-2(2,6)-pyridina-1(3,4)-triazola-5(1,2)-benzenacyclodecaphan-8-en-4-one

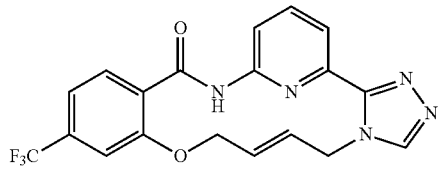

The title compound was prepared according to the procedure described in Example 153, Step I and using tert-butyl (E)-4-oxo-5⁴-(trifluoromethyl)-1⁴H-6-oxa-3-aza-2(2,6)-pyridina-1(3,4)-triazola-5(1,2)-benzenacyclodecaphan-8-ene-3-carboxylate (145 mg, 0.29 mmol) to give the desired product (98 mg, 85%) as a white solid. $^1$H NMR (400 MHz, DMSO-d$_6$) δ ppm 10.87 (s, 1H), 8.69 (s, 1H), 7.99-8.03 (m, 2H), 7.91-7.92 (m, 1H), 7.77-7.79 (m, 2H), 7.51 (d, J=8.4 Hz, 1H), 6.22-6.28 (m, 1H), 6.06-6.09 (m, 1H), 4.92-4.95 (m, 4H). MS (ESI): 402.1 [M+H]$^+$.

Example 155: (Z)-5⁴-(Trifluoromethyl)-1⁴H-6-oxa-3-aza-2(2,6)-pyridina-1(3,4)-triazola-5(1,2)-benzenacyclodecaphan-8-en-4-one

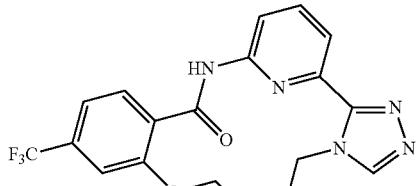

The title compound was prepared according to the procedure described in Example 153, Step I and using tert-butyl (Z)-4-oxo-5⁴-(trifluoromethyl)-1⁴H-6-oxa-3-aza-2(2,6)-pyridina-1(3,4)-triazola-5(1,2)-benzenacyclodecaphan-8-ene-3-carboxylate (150 mg, 0.3 mmol). The product was purified by HPLC (using a Phenomenex Synergi C18, 4 μm 150×30 mm column and using water (containing 0.225% HCOOH)/CH$_3$CN, from 39% to 59% as the mobile phase at a flow rate of 25 mL/min) to give the title compound (80 mg, 67%) as a white solid. $^1$H NMR (400 MHz, DMSO-d$_6$) δ ppm 10.54 (s, 1H), 8.86 (s, 1H), 8.04 (t, J=8.0 Hz, 1H), 7.83-7.92 (m, 4H), 7.56 (d, J=8.0 Hz, 1H), 5.74-5.80 (m, 1H), 5.49-5.52 (m, 3H), 5.05 (d, J=7.6 Hz, 2H). MS (ESI): 402.1 [M+H]$^+$.

Example 156: 5⁴-Fluoro-1⁴H-6-oxa-3-aza-2(2,6)-pyridina-1(3,4)-triazola-5(1,2)-benzenacyclodecaphan-4-one

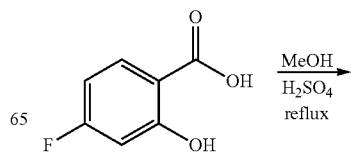

-continued

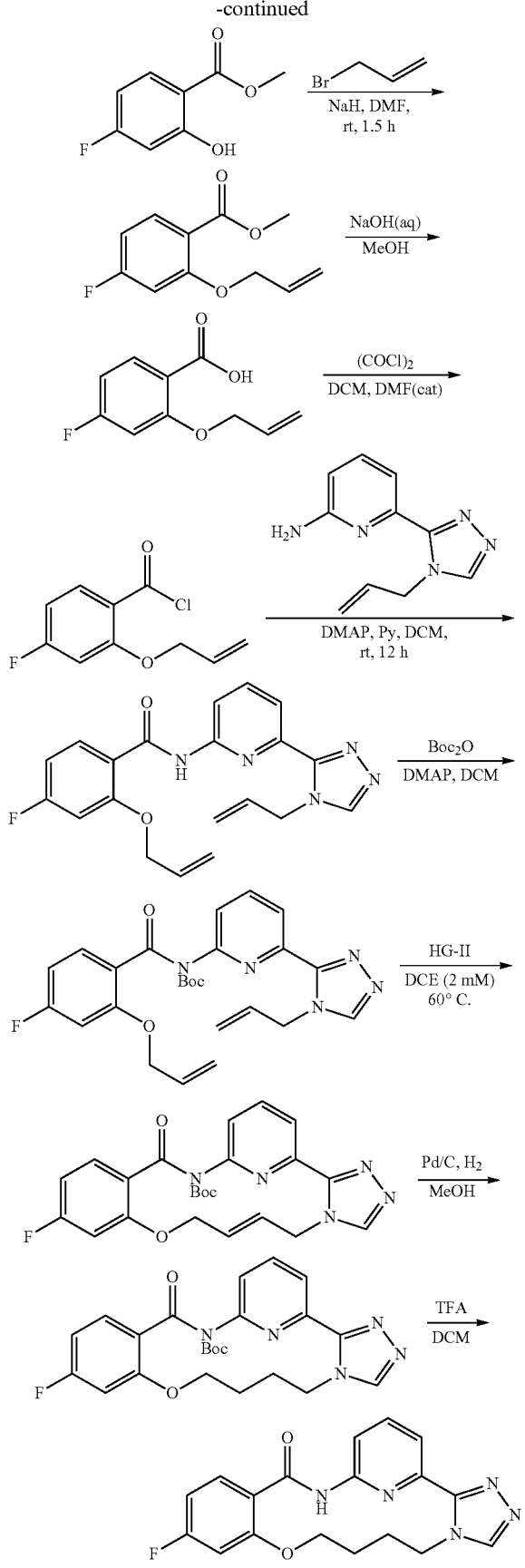

Step A: Methyl 4-fluoro-2-hydroxybenzoate

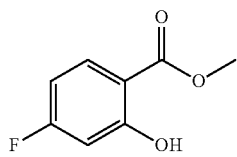

A solution of 4-fluoro-2-hydroxybenzoic acid (5.0 g, 32 mmol) and $H_2SO_4$ (4 mL) in MeOH (26 mL) was stirred at 80° C. for 12 h. After this time the mixture was concentrated under reduced pressure and water (10 mL) was added. The pH was adjusted to 8 by addition of an aqueous solution of NaOH (6 N) and the mixture was extracted with EtOAc (3×50 mL). The combined organic extracts were washed with brine (150 mL), dried over $Na_2SO_4$, filtered and concentrated under vacuum to give the title compound (4.6 g, 87%) as a yellow oil.

Step B: Methyl 2-(allyloxy)-4-fluorobenzoate

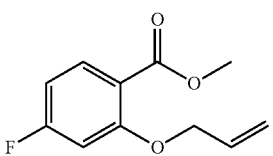

The title compound was prepared according to the procedure described in Example 153, Step B and using methyl 4-fluoro-2-hydroxybenzoate (4.6 g, 27.0 mmol) to give the product (5.0 g, 88%) as a white solid.

Step C: 2-(Allyloxy)-4-fluorobenzoic acid

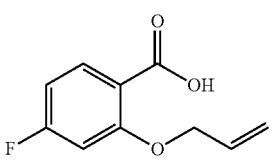

The title compound was prepared according to the procedure described in Example 153, Step C and using methyl 2-(allyloxy)-4-fluorobenzoate (5.0 g, 23.8 mmol) to give the product (4.6 g, 99%) as a yellow solid.

Step D: 2-(Allyloxy)-4-fluorobenzoyl chloride

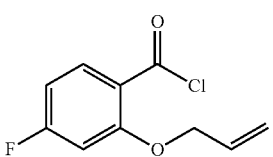

The title compound was prepared according to the procedure described in Example 153, Step D and using 2-(allyloxy)-4-fluorobenzoic acid (4.6 g, 23.45 mmol) to give the product (5.03 g, 100%) as a yellow oil.

Step E: N-(6-(4-Allyl-4H-1,2,4-triazol-3-yl)pyridin-2-yl)-2-(allyloxy)-4-fluorobenzamide

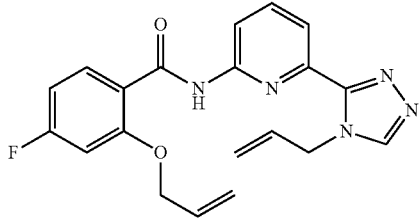 [SMILES: C=CCOc1cc(F)ccc1C(=O)Nc1cccc(-c2nncn2CC=C)n1]

The title compound was prepared according to the procedure described in Example 153, Step E and using 2-(allyloxy)-4-fluorobenzoyl chloride (4.16 g, 19.4 mmol) and 6-(4-allyl-4H-1,2,4-triazol-3-yl)pyridin-2-amine (3.0 g, 14.9 mmol, Example 155, Step A) to give the title compound (1.8 g, 32%) as a yellow solid.

Step F: tert-Butyl (6-(4-allyl-4H-1,2,4-triazol-3-yl)pyridin-2-yl)(2-(allyloxy)-4-fluorobenzoyl)carbamate

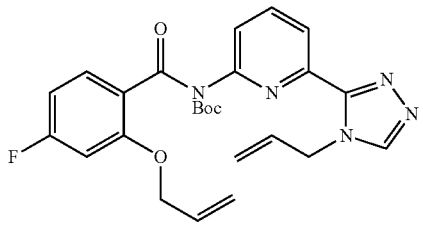 [SMILES: C=CCOc1cc(F)ccc1C(=O)N(C(=O)OC(C)(C)C)c1cccc(-c2nncn2CC=C)n1]

The title compound was prepared according to the procedure described in Example 153, Step F and using (1.8 g, 4.74 mmol) to give the title compound (1.8 g, 79%) as a brown solid. MS (ESI): 480.2 [M+H]$^+$.

Step G: tert-Butyl (E)-5$^4$-fluoro-4-oxo-1$^4$H-6-oxa-3-aza-2(2,6)-pyridina-1(3,4)-triazola-5(1,2)-benzenacyclodecaphan-8-ene-3-carboxylate

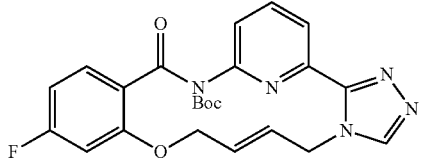 [SMILES: CC(C)(C)OC(=O)N1C(=O)c2ccc(F)cc2OC/C=C/Cn2cnnc2-c2cccc1n2]

The title compound was prepared according to the procedure described in Example 153, Step G and using tert-butyl (6-(4-allyl-4H-1,2,4-triazol-3-yl)pyridin-2-yl)(2-(allyloxy)-4-fluorobenzoyl)carbamate (1.8 g, 3.75 mmol) to give the title compound (600 mg, 35%) as a brown solid. MS (ESI): 452.2 [M+H]$^+$.

Step H: tert-Butyl 5$^4$-fluoro-4-oxo-1$^4$H-6-oxa-3-aza-2(2,6)-pyridina-1(3,4)-triazola-5(1,2)-benzenacyclodecaphane-3-carboxylate

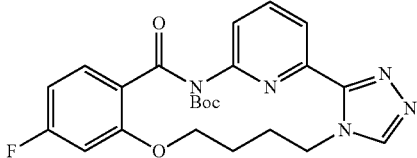 [SMILES: CC(C)(C)OC(=O)N1C(=O)c2ccc(F)cc2OCCCCn2cnnc2-c2cccc1n2]

The title compound was prepared according to the procedure described in Example 153, Step H and using tert-Butyl (E)-5$^4$-fluoro-4-oxo-1$^4$H-6-oxa-3-aza-2(2,6)-pyridina-1(3,4)-triazola-5(1,2)-benzenacyclodecaphan-8-ene-3-carboxylate (400 mg, 0.89 mmol) to give the title compound (400 mg, 75%) as a brown oil. MS (ESI): 454.2 [M+H]$^+$.

Step I: 5$^4$-Fluoro-1$^4$H-6-oxa-3-aza-2(2,6)-pyridina-1(3,4)-triazola-5(1,2)-benzenacyclodecaphan-4-one

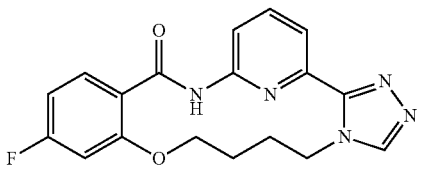 [SMILES: O=C1Nc2cccc(n2)-c2nncn2CCCCOc2cc(F)ccc21]

The title compound was prepared according to the procedure described in Example 153, Step I and using tert-butyl 5$^4$-fluoro-4-oxo-1$^4$H-6-oxa-3-aza-2(2,6)-pyridina-1(3,4)-triazola-5(1,2)-benzenacyclodecaphane-3-carboxylate (400 mg, 0.89 mmol) to give the title compound (100 mg, 32%) as a white solid. $^1$H NMR (400 MHz, DMSO-d$_6$) δ ppm 11.06 (s, 1H), 8.91 (s, 1H), 8.00-8.05 (m, 2H), 7.84-7.89 (m, 2H), 7.20 (dd, J=10.8, 1H), 6.98 (dt, J=9.2 Hz, 1H), 4.24-4.32 (m, 4H), 2.41-2.43 (m, 2H), 1.92-1.93 (m, 2H). MS (ESI): 354.3 [M+H]$^+$.

Example 157: (E)-5$^4$-Fluoro-1$^4$H-6-oxa-3-aza-2(2,6)-pyridina-1(3,4)-triazola-5(1,2)-benzenacyclodecaphan-8-en-4-one

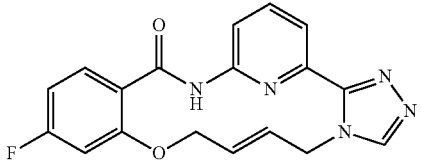 [SMILES: O=C1Nc2cccc(n2)-c2nncn2C/C=C/COc2cc(F)ccc21]

The title compound was prepared according to the procedure described in Example 153, Step I and using tert-butyl (E)-5$^4$-fluoro-4-oxo-1$^4$H-6-oxa-3-aza-2(2,6)-pyridina-1(3,4)-triazola-5(1,2)-benzenacyclodecaphan-8-ene-3-carboxylate to give the title compound after purification by HPLC (using a Phenomenex Synergi C18, 4 μm 150×30 mm column and using water (containing 0.05% HCl)/CH$_3$CN, from 29% to 49% as the mobile phase at a flow rate of 25 mL/min). The product (70 mg, 56%) was isolated as a white solid. $^1$H NMR (400 MHz, DMSO-$d_6$) δ ppm 11.05 (s, 1H), 8.81 (s, 1H), 7.94-8.03 (m, 3H), 7.79 (d, J=8.0 Hz, 1H), 7.38 (dd, J=2.3, 10.8 Hz, 1H), 7.00-7.12 (m, 1H), 6.35-6.39 (m, 1H), 6.06-6.09 (m, 1H), 4.96-5.00 (m, 2H), 4.91-4.93 (m, 2H). MS (ESI): 352.3 [M+H]$^+$.

Example 158: (E)-5$^5$-Fluoro-1$^4$H-6-oxa-3-aza-2(2,6)-pyridina-1(3,4)-triazola-5(1,2)-benzenacyclodecaphan-8-en-4-one

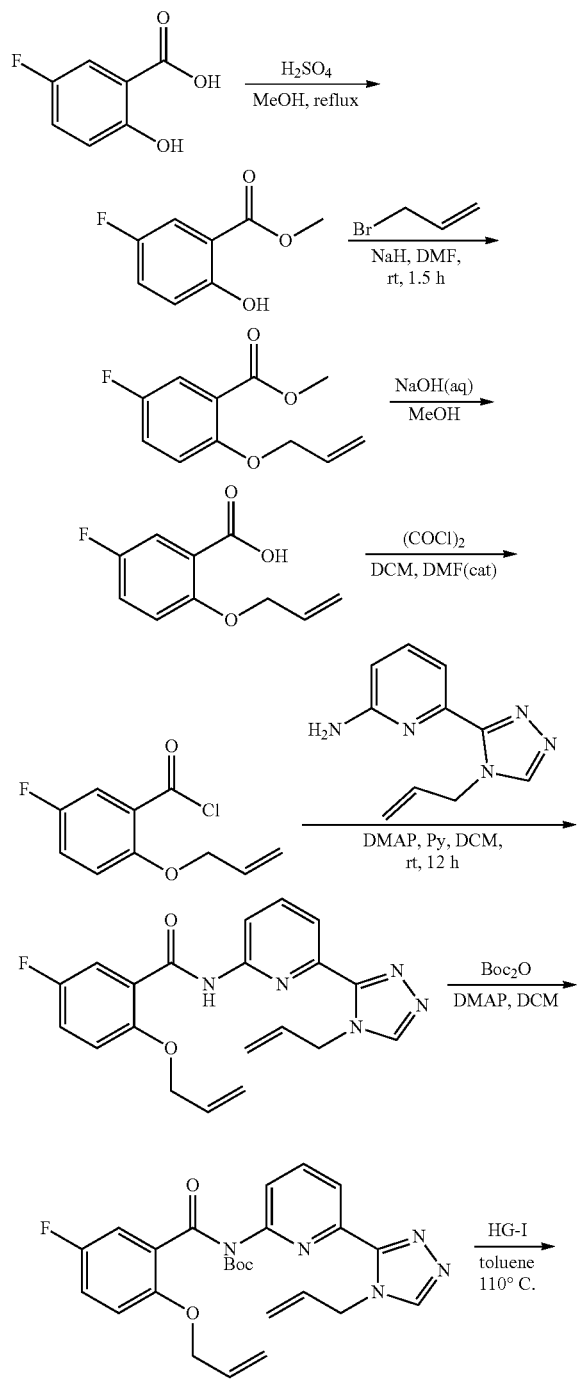

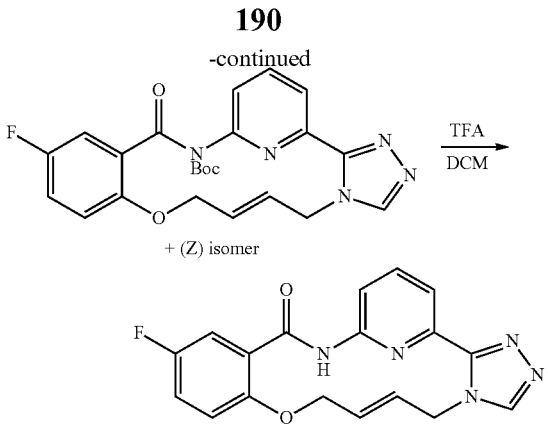

Step A: Methyl 5-fluoro-2-hydroxybenzoate

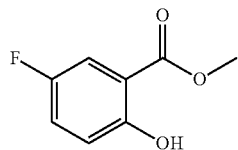

The title compound was prepared according to the procedure described in Example 156, Step A and using 5-fluoro-2-hydroxybenzoic acid (7 g, 44.8 mmol) to give the title compound (5.5 g, 72%) as a brown oil.

Step B: Methyl 2-(allyloxy)-5-fluorobenzoate

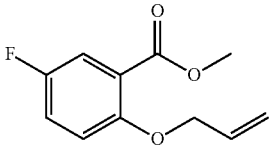

The title compound was prepared according to the procedure described in Example 153, Step B and using methyl 5-fluoro-2-hydroxybenzoate (5.5 g, 32.3 mmol) to give the title compound 4 (3.1 g, 46%) as brown gum. MS (ESI): 211.0 [M+H]$^+$.

Step C: 2-(Allyloxy)-5-fluorobenzoic acid

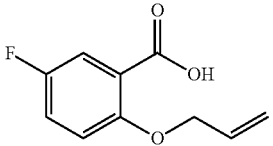

The title compound was prepared according to the procedure described in Example 153, Step C and using methyl 2-(allyloxy)-5-fluorobenzoate (5.5 g, 26.2 mmol) to give the title compound (4.5 g, 88%) as a white solid.

Step D: 2-(Allyloxy)-5-fluorobenzoyl chloride

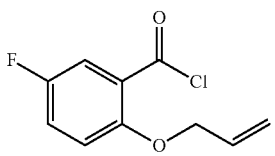

The title compound was prepared according to the procedure described in Example 153, Step D and using 2-(allyloxy)-5-fluorobenzoic acid (2.5 g, 12.74 mmol) to give the title compound (2.74 g, 100%) as a brown gum.

Step E: N-(6-(4-Allyl-4H-1,2,4-triazol-3-yl)pyridin-2-yl)-2-(allyloxy)-5-fluorobenzamide

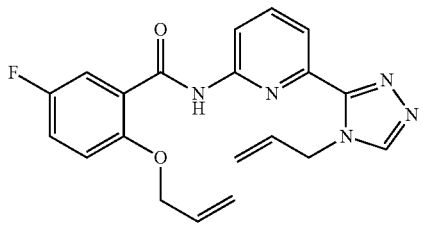 [SMILES: C=CCOc1ccc(F)cc1C(=O)Nc1cccc(-c2nncn2CC=C)n1]

The title compound was prepared according to the procedure described in Example 153, Step E and using 2-(allyloxy)-5-fluorobenzoyl chloride (2.74 g, 12.77 mmol) and 6-(4-allyl-4H-1,2,4-triazol-3-yl)pyridin-2-amine (2.83 g, 14.04 mmol, Example 153, Step A) to give the title compound (2.3 g, 47%) as a brown solid. MS (ESI): 379.9 [M+H]$^+$.

Step F: tert-Butyl (6-(4-allyl-4H-1,2,4-triazol-3-yl)pyridin-2-yl)(2-(allyloxy)-5-fluorobenzoyl)carbamate

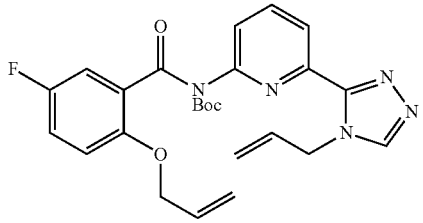 [SMILES: C=CCOc1ccc(F)cc1C(=O)N(C(=O)OC(C)(C)C)c1cccc(-c2nncn2CC=C)n1]

The title compound was prepared according to the procedure described in Example 153, Step F and using N-(6-(4-allyl-4H-1,2,4-triazol-3-yl)pyridin-2-yl)-2-(allyloxy)-5-fluorobenzamide (2.3 g, 6.1 mmol) to give the title compound (2.1 g, 72%) as a white solid. MS (ESI): 480.6 [M+H]$^+$.

Step G: tert-Butyl (E)-5$^5$-fluoro-4-oxo-1$^4$H-6-oxa-3-aza-2(2,6)-pyridina-1(3,4)-triazola-5(1,2)-benzenacyclodecaphan-8-ene-3-carboxylate and tert-butyl (Z)-5$^5$-fluoro-4-oxo-1$^4$H-6-oxa-3-aza-2(2,6)-pyridina-1(3,4)-triazola-5(1,2)-benzenacyclodecaphan-8-ene-3-carboxylate

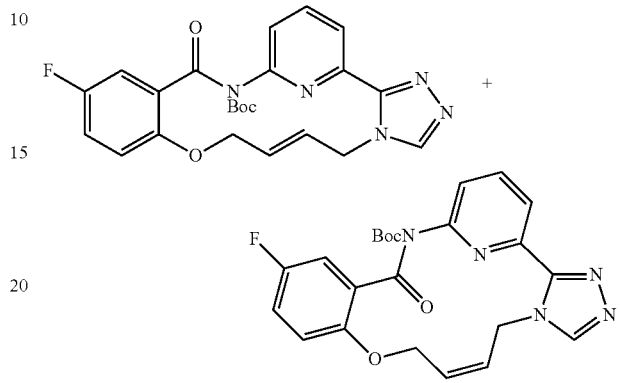

The title compound was prepared according to the procedure described in Example 154, Step A and using tert-butyl (6-(4-allyl-4H-1,2,4-triazol-3-yl)pyridin-2-yl)(2-(allyloxy)-5-fluorobenzoyl)carbamate (2 g, 4.17 mmol). The product was purified by column chromatography on silica (petroleum ether/EtOAc=10/1 to 0/1) to give the title compounds as a mixture of isomers which was further purified by HPLC (using a Phenomenex Synergi C18, 4 μm 250× 21.2 mm column and using water (containing 0.225% HCOOH)/CH$_3$CN, from 34% to 54% as the mobile phase at a flow rate of 25 mL/min) to give in order of elution: tert-butyl (Z)-5$^5$-fluoro-4-oxo-1$^4$H-6-oxa-3-aza-2(2,6)-pyridina-1(3,4)-triazola-5(1,2)-benzenacyclodecaphan-8-ene-3-carboxylate (150 mg, 8%) and tert-butyl (E)-5$^5$-fluoro-4-oxo-1$^4$H-6-oxa-3-aza-2(2,6)-pyridina-1(3,4)-triazola-5(1,2)-benzenacyclodecaphan-8-ene-3-carboxylate (180 mg, 9%). MS (ESI): 474.3 [M+Na]$^+$.

Step H: (E)-5$^5$-Fluoro-1$^4$H-6-oxa-3-aza-2(2,6)-pyridina-1(3,4)-triazola-5(1,2)-benzenacyclodecaphan-8-en-4-one

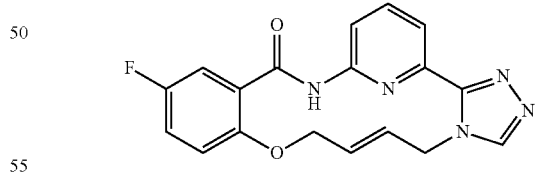

The title compound was prepared according to the procedure described in Example 153, Step I and using tert-butyl (E)-5$^5$-fluoro-4-oxo-1$^4$H-6-oxa-3-aza-2(2,6)-pyridina-1(3,4)-triazola-5(1,2)-benzenacyclodecaphan-8-ene-3-carboxylate (180 mg, 0.4 mmol) to give the title compound (135 mg, 96%) as a white solid. $^1$H NMR (400 MHz, DMSO-d$_6$) δ ppm 11.17 (s, 1H), 8.75 (s, 1H), 7.97-8.04 (m, 1H), 7.93 (d, J=8.4 Hz, 1H), 7.77 (d, J=7.2 Hz, 1H), 7.66 (d, J=8.0 Hz, 1H), 7.40-7.49 (m, 2H), 6.29 (td, J=5.2, 15.7 Hz, 1H), 5.98-6.12 (m, 1H), 4.86-4.95 (m, 4H). MS (ESI): 352.2 [M+H]$^+$.

Example 159: (Z)-5⁵-Fluoro-1⁴H-6-oxa-3-aza-2(2,6)-pyridina-1(3,4)-triazola-5(1,2)-benzenacyclodecaphan-8-en-4-one

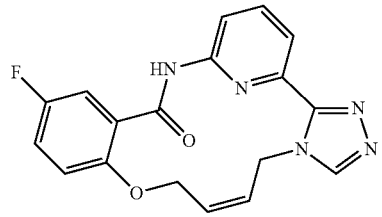 [SMILES: O=C1Nc2cccc(n2)-c2nncn2C/C=C\COc2ccc(F)cc21]

The title compound was prepared according to the procedure described in Example 153, Step I and using tert-butyl (Z)-5⁵-fluoro-4-oxo-1⁴H-6-oxa-3-aza-2(2,6)-pyridina-1(3,4)-triazola-5(1,2)-benzenacyclodecaphan-8-ene-3-carboxylate (300 mg, 0.66 mmol). The product was purified by HPLC (using a Phenomenex Synergi C18, 4 μm 150×30 mm column and using water (containing 0.05% HCl)/CH₃CN, from 36% to 46% as the mobile phase at a flow rate of 25 mL/min) to give the title compound (90 mg, 38%) as a white solid. ¹H NMR (400 MHz, DMSO-d₆) δ ppm 10.73 (s, 1H), 8.93 (s, 1H), 7.99-8.07 (m, 1H), 7.85 (dd, J=7.9, 15.3 Hz, 2H), 7.52-7.59 (m, 2H), 7.44 (dt, J=3.5, 8.6 Hz, 1H), 5.76-5.84 (m, 1H), 5.52-5.60 (m, 1H), 5.37 (br d, J=4.8 Hz, 2H), 4.93 (d, J=7.5 Hz, 2H). MS (ESI): 352.3 [M+H]⁺.

Example 160: 5⁵-Fluoro-1⁴H-6-oxa-3-aza-2(2,6)-pyridina-1(3,4)-triazola-5(1,2)-benzenacyclodecaphan-4-one

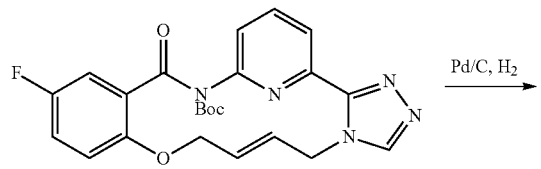

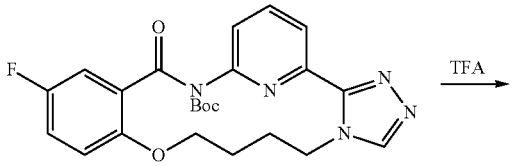

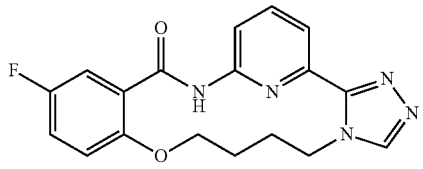

Step A: tert-Butyl 5⁵-fluoro-4-oxo-1⁴H-6-oxa-3-aza-2(2,6)-pyridina-1(3,4)-triazola-5(1,2)-benzenacyclodecaphane-3-carboxylate

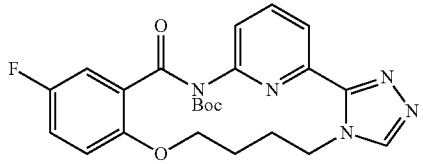 [SMILES: CC(C)(C)OC(=O)N1C(=O)c2cc(F)ccc2OCCCCn2cnnc2-c2cccc1n2]

The title compound was prepared according to the procedure described in Example 153, Step H and using tert-butyl (E)-5⁵-fluoro-4-oxo-1⁴H-6-oxa-3-aza-2(2,6)-pyridina-1(3,4)-triazola-5(1,2)-benzenacyclodecaphan-8-ene-3-carboxylate (300 mg, 0.66 mmol) give the title compound (301 mg, 90% crude) as a brown solid. MS (ESI): 454.2 [M+H]⁺.

Step B: 5⁵-Fluoro-1⁴H-6-oxa-3-aza-2(2,6)-pyridina-1(3,4)-triazola-5(1,2)-benzenacyclodecaphan-4-one

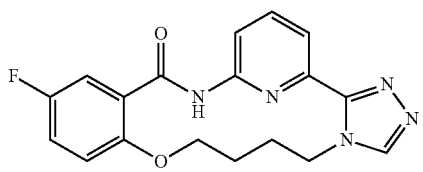 [SMILES: O=C1Nc2cccc(n2)-c2nncn2CCCCOc2ccc(F)cc21]

The title compound was prepared according to the procedure described in Example 153, Step I and using tert-butyl 5⁵-fluoro-4-oxo-1⁴H-6-oxa-3-aza-2(2,6)-pyridina-1(3,4)-triazola-5(1,2)-benzenacyclodecaphane-3-carboxylate (300 mg, 0.66 mmol). The product was purified by HPLC (using a Phenomenex Synergi C18, 4 μm 150×30 mm column and using water (containing 0.05% HCl)/CH₃CN, from 36% to 46% as the mobile phase at a flow rate of 25 mL/min) to give the title compound (60 mg, 28.5%) as a white solid. ¹H NMR (400 MHz, DMSO-d₆) δ ppm 11.33 (s, 1H), 8.84 (s, 1H), 8.03-8.16 (m, 1H), 7.86-7.94 (m, 2H), 7.73 (dd, J=3.5, 9.2 Hz, 1H), 7.46-7.54 (m, 1H), 7.37 (dd, J=4.4, 9.2 Hz, 1H), 4.25-4.39 (m, 4H), 2.41-2.46 (m, 2H), 1.93-2.03 (m, 2H). MS (ESI): 354.3 [M+H]⁺.

Example 161: (Z)-5⁵-Bromo-1⁴H-6-oxa-3-aza-2(2,6)-pyridina-1(3,4)-triazola-5(1,2)-benzenacyclodecaphan-8-en-4-one

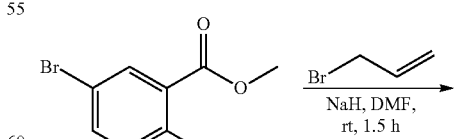

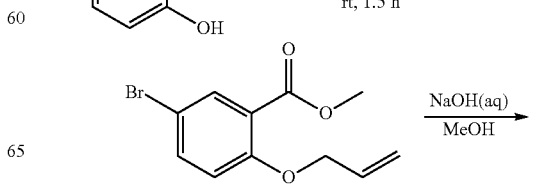

-continued

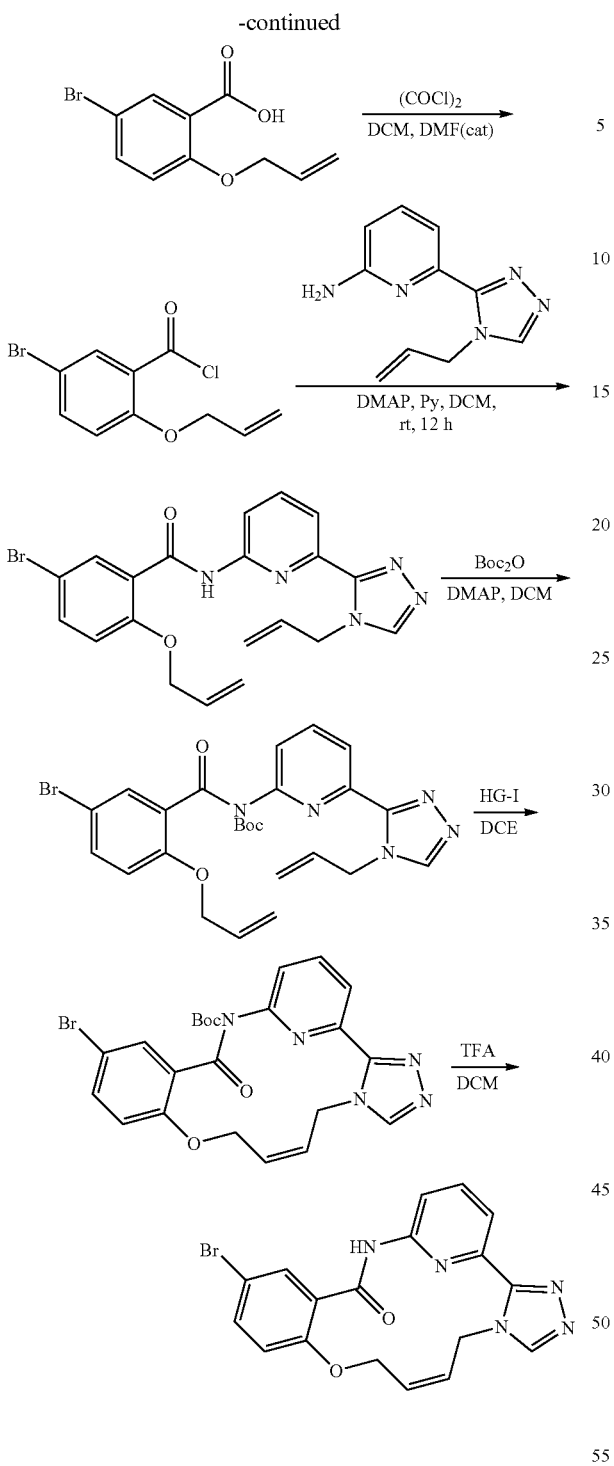

Step A: Methyl 2-(allyloxy)-5-bromobenzoate

The title compound was prepared according to the procedure described in Example 153, Step B and using methyl 5-bromo-2-hydroxybenzoate (500 mg, 2.2 mmol) in DMF (16 mL) to give the desired product (480 mg) as a colorless gum.

Step B: 2-(Allyloxy)-5-bromobenzoic acid

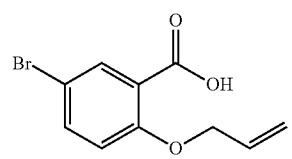

The title compound was prepared according to the procedure described in Example 153, Step C and using methyl 2-(allyloxy)-5-bromobenzoate (480 mg, 1.77 mmol) to give the desired product (400 mg, 88%) as a white solid.

Step C: 2-(Allyloxy)-5-bromobenzoyl chloride

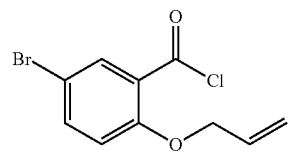

lp;1p

The title compound was prepared according to the procedure described in Example 153, Step D and using 2-(allyloxy)-5-bromobenzoic acid (0.2 g, 0.78 mmol) to give the desired product (0.34 mg, 100% crude) as a brown oil.

Step D: N-(6-(4-Allyl-4H-1,2,4-triazol-3-yl)pyridin-2-yl)-2-(allyloxy)-5-bromobenzamide

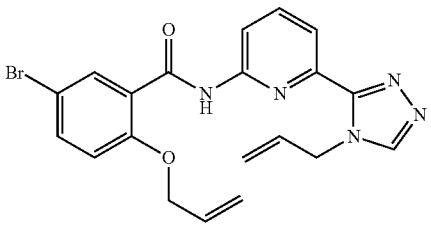 [SMILES: C=CCOc1ccc(Br)cc1C(=O)Nc1cccc(-c2nncn2CC=C)n1]

The title compound was prepared according to the procedure described in Example 153, Step E and using and using 2-(allyloxy)-5-bromobenzoyl chloride (0.34 g, 1.2 mmol) and 6-(4-allyl-4H-1,2,4-triazol-3-yl)pyridin-2-amine (157 mg, 0.78 mmol, Example 153, Step A) to give the desired product (120 mg, 35%) as a colorless gum. MS (ESI): 442.1 [(M+H) ($^{81}$Br)]$^+$.

Step E: tert-Butyl (6-(4-allyl-4H-1,2,4-triazol-3-yl)pyridin-2-yl)(2-(allyloxy)-5-bromobenzoyl)carbamate

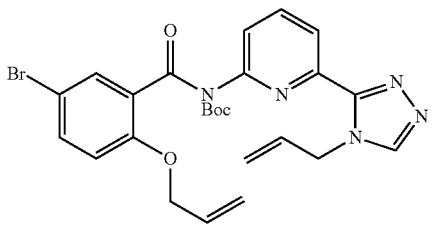 [SMILES: C=CCOc1ccc(Br)cc1C(=O)N(C(=O)OC(C)(C)C)c1cccc(-c2nncn2CC=C)n1]

The title compound was prepared according to the procedure described in Example 153, Step F and using N-(6-(4-allyl-4H-1,2,4-triazol-3-yl)pyridin-2-yl)-2-(allyloxy)-5-bromobenzamide (120 mg, 0.27 mmol) to give the desired product (100 mg, 68%) as colorless gum. MS (ESI): 562.1 [(M+Na) ($^{79}$Br)]$^+$.

Step F: tert-Butyl (Z)-5$^5$-bromo-4-oxo-1$^4$H-6-oxa-3-aza-2(2,6)-pyridina-1(3,4)-triazola-5(1,2)-benzenacyclodecaphan-8-ene-3-carboxylate

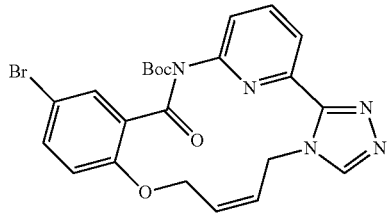 [SMILES: CC(C)(C)OC(=O)N1C(=O)c2cc(Br)ccc2OC/C=C\Cn2cnnc2-c2cccc1n2]

The title compound was prepared according to the procedure described in Example 154, Step A and using tert-butyl (6-(4-allyl-4H-1,2,4-triazol-3-yl)pyridin-2-yl)(2-(allyloxy)-5-bromobenzoyl)carbamate (60 mg, 0.11 mmol) to give the desired product (30 mg, 54%) as a white solid. MS (ESI): 536.1 [(M+Na) ($^{81}$Br)]$^+$.

Step G: (Z)-5$^5$-Bromo-1$^4$H-6-oxa-3-aza-2(2,6)-pyridina-1(3,4)-triazola-5(1,2)-benzenacyclodecaphan-8-en-4-one

The title compound was prepared according to the procedure described in Example 153, Step I and using tert-butyl (Z)-5$^5$-bromo-4-oxo-1$^4$H-6-oxa-3-aza-2(2,6)-pyridina-1(3,4)-triazola-5(1,2)-benzenacyclodecaphan-8-ene-3-carboxylate (30 mg, 0.059 mmol). The product was purified by preparative TLC (EtOAc) to give the desired product (10 mg, 41%) as a white solid. $^1$H NMR (400 MHz, DMSO-d$_6$) δ ppm 10.61 (s, 1H), 8.74 (s, 1H), 8.02 (t, J=8.0 Hz, 1H), 7.45-7.88 (m, 4H), 7.50 (d, J=8.8 Hz, 1H), 5.75-5.80 (m, 1H), 5.51-5.56 (m, 1H), 5.40 (d, J=5.6 Hz, 2H), 4.94 (d, J=7.6 Hz, 2H). MS (ESI): 414.0 [(M+H) ($^{81}$Br)]$^+$.

Example 162: (E)-5$^5$-Bromo-1$^4$H-6-oxa-3-aza-2(2,6)-pyridina-1(3,4)-triazola-5(1,2)-benzenacyclodecaphan-8-en-4-one

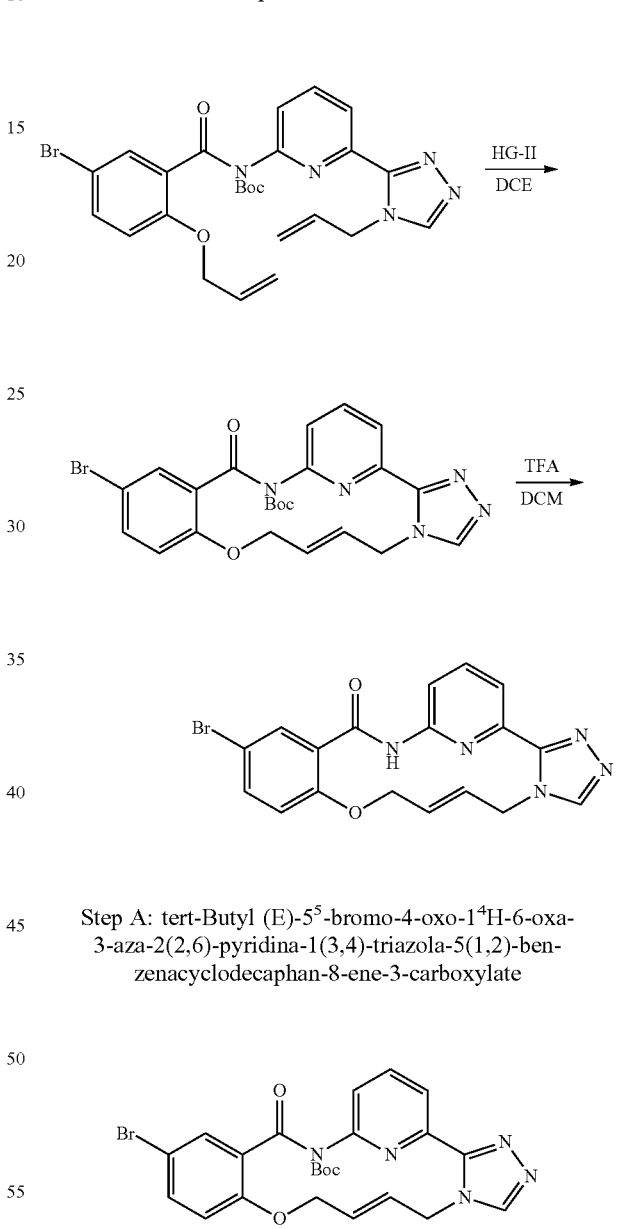

Step A: tert-Butyl (E)-5$^5$-bromo-4-oxo-1$^4$H-6-oxa-3-aza-2(2,6)-pyridina-1(3,4)-triazola-5(1,2)-benzenacyclodecaphan-8-ene-3-carboxylate The title compound was prepared according to the procedure described in Example 153, Step G and using tert-butyl (6-(4-allyl-4H-1,2,4-triazol-3-yl)pyridin-2-yl)(2-(allyloxy)-5-bromobenzoyl)carbamate (1 g, 1.85 mmol) to give tert-butyl (Z)-5$^5$-bromo-4-oxo-1$^4$H-6-oxa-3-aza-2(2,6)-pyridina-1(3,4)-triazola-5(1,2)-benzenacyclodecaphan-8-ene-3-carboxylate (569 mg, 59%) as the major product and the desired trans-isomer (200 mg, 21%) as a brown solid. MS (ESI): 512.1 [(M+H) ($^{79}$Br)]$^+$.

Step B: (E)-5⁵-Bromo-1⁴H-6-oxa-3-aza-2(2,6)-pyridina-1(3,4)-triazola-5(1,2)-benzenacyclodecaphan-8-en-4-one

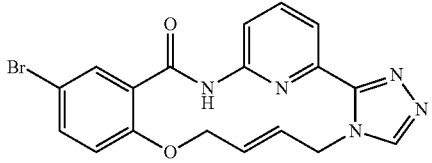 [SMILES: O=C1Nc2cccc(n2)-c2nncn2C/C=C/COc2ccc(Br)cc21]

The title compound was prepared according to the procedure described in Example 153, Step I and using tert-butyl (E)-5⁵-bromo-4-oxo-1⁴H-6-oxa-3-aza-2(2,6)-pyridina-1(3,4)-triazola-5(1,2)-benzenacyclodecaphan-8-ene-3-carboxylate (20 mg, 0.039 mmol). The product was purified by SFC (using a Chiralpak AD 3 μm, 4.6×50 mm Column and using $CO_2$ and MeOH (containing 0.05% $Et_2NH$) as the mobile phase (hold 5% of MeOH for 0.2 min, then from 5% to 40% of MeOH in 1.4 min and hold 40% MeOH for 1.05 min and then then 5% of MeOH for 0.35 min) at a flow rate of 4 mL/min and at a column temperature of 40° C.) to give the desired product (5 mg, 37%) as a white solid. ¹H NMR (400 MHz, DMSO-d₆) δ ppm 11.03 (s, 1H), 8.70 (s, 1H), 7.99-8.01 (m, 2H), 7.92-7.98 (m, 1H), 7.74-7.78 (m, 2H), 7.38 (d, J=8.4 Hz, 1H), 6.25-6.30 (m, 1H), 6.03-6.07 (m, 1H), 4.95 (d, J=4.8 Hz, 2H), 4.86 (d, J=7.6 Hz, 2H). MS (ESI): 412.0 [(M+H) (⁷⁹Br)]⁺.

Example 163: (E)-5³-Bromo-1⁴H-6-oxa-3-aza-2(2,6)-pyridina-1(3,4)-triazola-5(1,2)-benzenacyclodecaphan-8-en-4-one

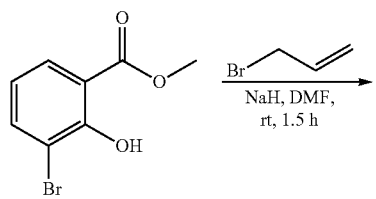

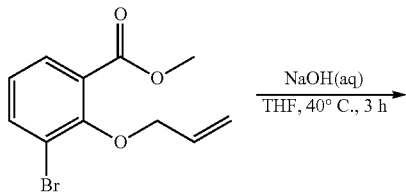

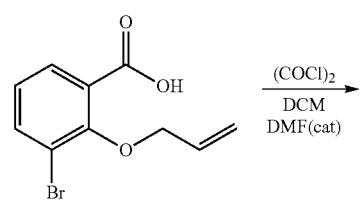

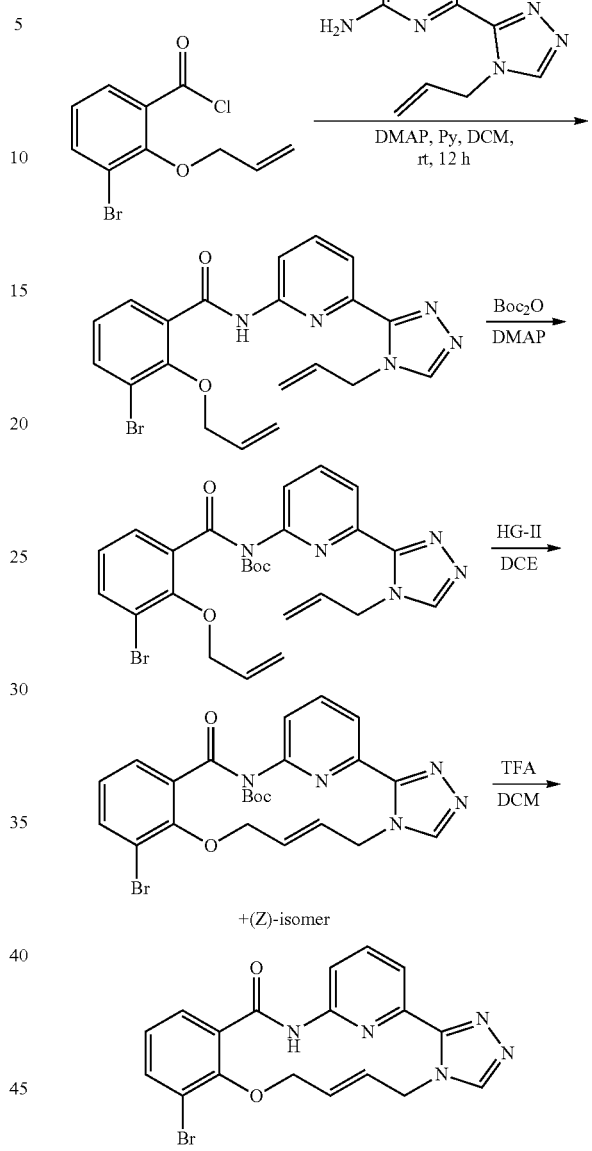

Step A: Methyl 2-(allyloxy)-3-bromobenzoate

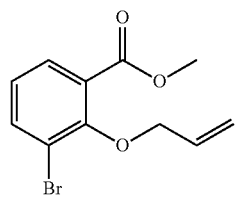

The title compound was prepared according to the procedure described in Example 153, Step B and using methyl 3-bromo-2-hydroxybenzoate (17 g, 73.6 mmol) to give the desired product (19 g, 95%) as a brown oil.

Step B: 2-(Allyloxy)-3-bromobenzoic acid

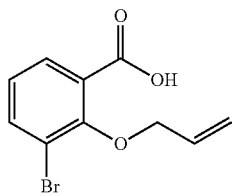

The title compound was prepared according to the procedure described in Example 153, Step C and using methyl 2-(allyloxy)-3-bromobenzoate (19 g, 70.1 mmol) to give the desired product (17 g, 94%) as a brown solid.

Step C: 2-(Allyloxy)-3-bromobenzoyl chloride

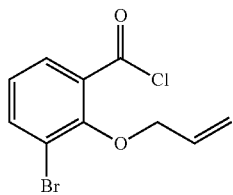

The title compound was prepared according to the procedure described in Example 153, Step D and using 2-(allyloxy)-3-bromobenzoic acid (5 g, 19.4 mmol) to give the title compound (5.36 g, 100%) as brown gum.

Step D: N-(6-(4-Allyl-4H-1,2,4-triazol-3-yl)pyridin-2-yl)-2-(allyloxy)-3-bromobenzamide

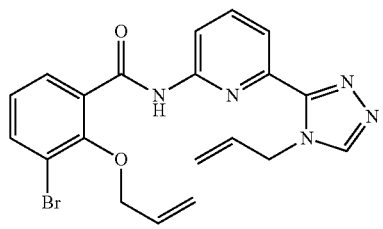 [SMILES: C=CCOc1c(Br)cccc1C(=O)Nc1cccc(-c2nncn2CC=C)n1]

The title compound was prepared according to the procedure described in Example 153, Step E and using 2-(allyloxy)-3-bromobenzoyl chloride (5.36 g, 19.4 mmol) and 6-(4-allyl-4H-1,2,4-triazol-3-yl)pyridin-2-amine (3.91 g, 19.4 mmol, Example 155, Step A) to give the desired product (7 g, 50%) as a brown gum. MS (ESI): 440.0 [(M+H) ($^{79}$Br)]$^{+}$.

Step E: tert-Butyl (6-(4-allyl-4H-1,2,4-triazol-3-yl)pyridin-2-yl)(2-(allyloxy)-3-bromobenzoyl)carbamate

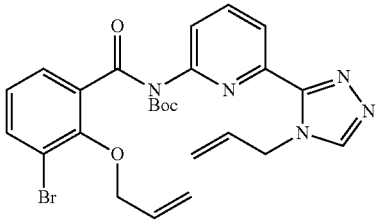 [SMILES: C=CCOc1c(Br)cccc1C(=O)N(C(=O)OC(C)(C)C)c1cccc(-c2nncn2CC=C)n1]

The title compound was prepared according to the procedure described in Example 153, Step F and using N-(6-(4-allyl-4H-1,2,4-triazol-3-yl)pyridin-2-yl)-2-(allyloxy)-3-bromobenzamide (6.0 g, 13.6 mmol) to give the title compound (8.0 g) as a brown oil.

Step F: tert-Butyl (E)-5$^3$-bromo-4-oxo-1$^4$H-6-oxa-3-aza-2(2,6)-pyridina-1(3,4)-triazola-5(1,2)-benzenacyclodecaphan-8-ene-3-carboxylate and tert-Butyl (Z)-5$^3$-bromo-4-oxo-1$^4$H-6-oxa-3-aza-2(2,6)-pyridina-1(3,4)-triazola-5(1,2)-benzenacyclodecaphan-8-ene-3-carboxylate

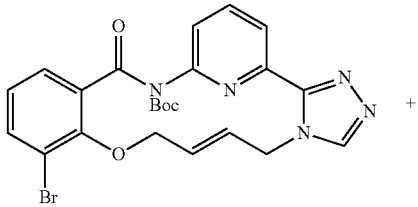

+

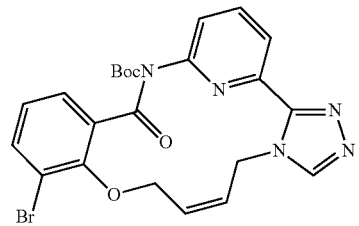

The title compound was prepared according to the procedure described in Example 153, Step G and using tert-butyl (6-(4-allyl-4H-1,2,4-triazol-3-yl)pyridin-2-yl)(2-(allyloxy)-3-bromobenzoyl)carbamate (2.0 g, 3.70 mmol). Purification by HPLC (using a Waters Xbridge Prep OBD C18, 5 μm 150×30 mm column and using water (containing 0.225% HCOOH)/CH$_3$CN, from 20% to 30% as the mobile phase at a flow rate of 25 mL/min) gave in order of elution: tert-butyl (E)-5$^3$-bromo-4-oxo-1$^4$H-6-oxa-3-aza-2(2,6)-pyridina-1(3,4)-triazola-5(1,2)-benzenacyclodecaphan-8-ene-3-carboxylate (500 mg, 13%) and tert-butyl (Z)-5$^3$-bromo-4-oxo-1$^4$H-6-oxa-3-aza-2(2,6)-pyridina-1(3,4)-triazola-5(1,2)-benzenacyclodecaphan-8-ene-3-carboxylate (2.1 g, 55%) as yellow solid. MS (ESI): 514.0 [(M+H) ($^{81}$Br)]$^{+}$.

Step G: (E)-5³-Bromo-1⁴H-6-oxa-3-aza-2(2,6)-pyridina-1(3,4)-triazola-5(1,2)-benzenacyclodecaphan-8-en-4-one

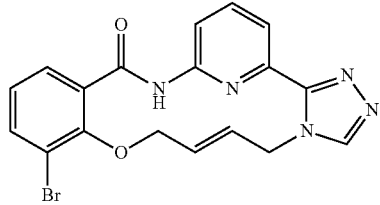 [SMILES: O=C1Nc2cccc(n2)-c2nncn2C/C=C/COc2c(Br)cccc21]

The title compound was prepared according to the procedure described in Example 153, Step I and using tert-butyl (E)-5³-bromo-4-oxo-1⁴H-6-oxa-3-aza-2(2,6)-pyridina-1(3,4)-triazola-5(1,2)-benzenacyclodecaphan-8-ene-3-carboxylate (500 mg, 0.97 mmol) to give the product (370 mg, 92%) as yellow solid. $^1$H NMR (400 MHz, DMSO-$d_6$) δ ppm 11.15 (s, 1H), 8.31 (m, 2H), 8.06-8.09 (m, 1H), 7.93-7.95 (m, 1H), 7.84-7.88 (m, 1H), 7.80 (d, J=9.6 Hz, 1H), 7.18-7.22 (m, 1H), 6.33-6.37 (m, 1H), 5.99-6.07 (m, 1H), 4.97 (d, J=7.4 Hz, 2H), 4.77 (d, J=5.4 Hz, 2H). MS (ESI): 412.1 [(M+H) ($^{79}$Br)]$^+$.

Example 164: (Z)-5³-Bromo-1⁴H-6-oxa-3-aza-2(2,6)-pyridina-1(3,4)-triazola-5(1,2)-benzenacyclodecaphan-8-en-4-one

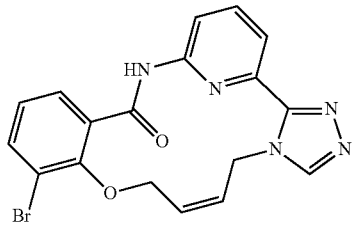 [SMILES: O=C1Nc2cccc(n2)-c2nncn2C/C=C\COc2c(Br)cccc21]

The title compound was prepared according to the procedure described in Example 153, Step I and using tert-butyl (Z)-5³-bromo-4-oxo-1⁴H-6-oxa-3-aza-2(2,6)-pyridina-1(3,4)-triazola-5(1,2)-benzenacyclodecaphan-8-ene-3-carboxylate (150 mg, 0.29 mmol) to give the title compound (100 mg, 83%) as a white solid. $^1$H NMR (400 MHz, CDCl$_3$) δ ppm 11.00 (s, 1H), 8.36 (s, 1H), 8.26 (dd, J=6.4, 1.6 Hz, 1H), 7.93-8.05 (m, 3H), 7.82 (dd, J=7.6 Hz, 1.6 Hz, 1H), 7.24-7.28 (m, 1H), 6.16-6.24 (d, J=11.2 Hz, 1H), 5.89-5.97 (d, J=13.2 Hz, 1H), 4.91-5.08 (m, 2H), 4.84-4.86 (m, 2H). MS (ESI): 414.2 [(M+H) ($^{81}$Br)]$^+$.

Example 165: 5³-Bromo-1⁴H-6-oxa-3-aza-2(2,6)-pyridina-1(3,4)-triazola-5(1,2)-benzenacyclodecaphan-4-one

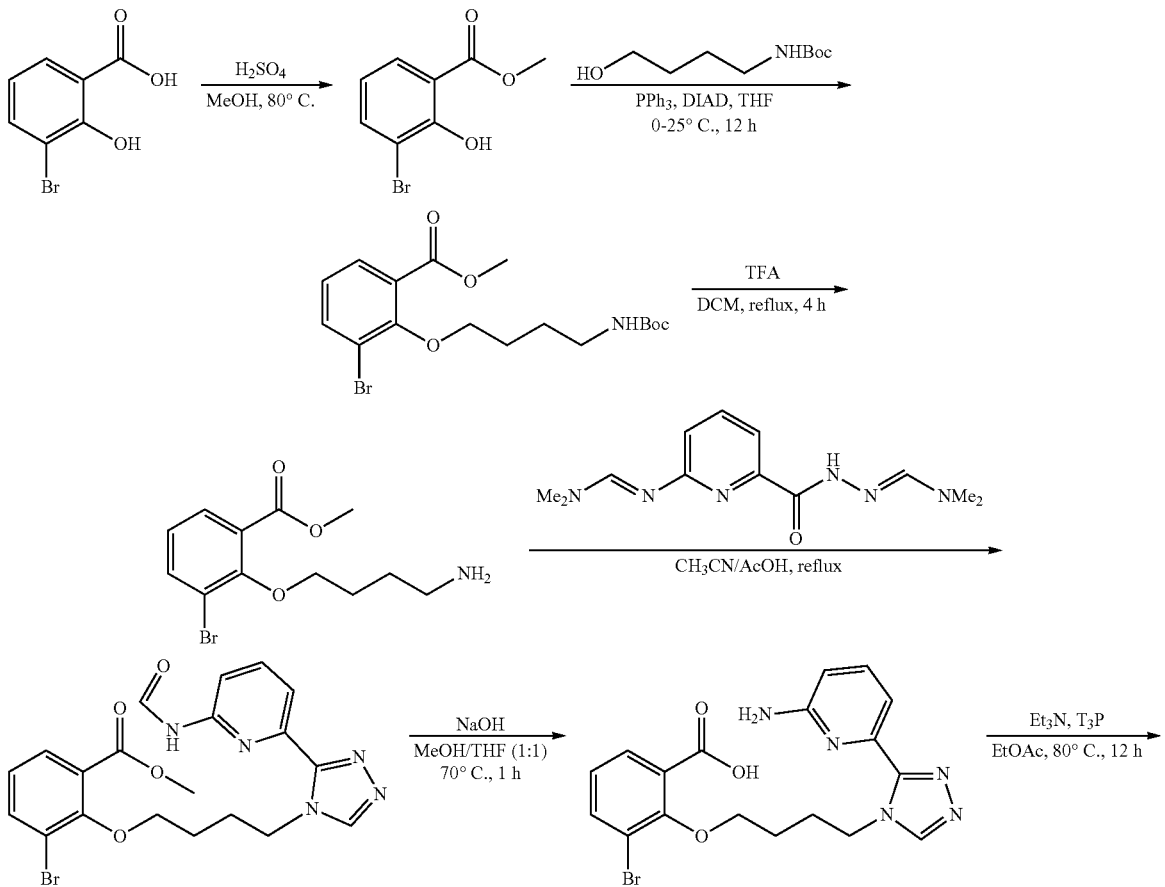

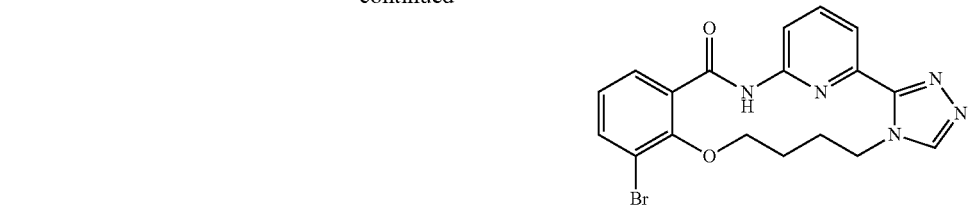

Step A: Methyl 3-bromo-2-hydroxybenzoate

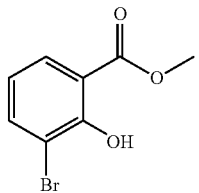

The title compound was prepared according to the procedure described in Example 156, Step A and using 3-bromo-2-hydroxybenzoic acid (35 g, 161.3 mmol) to give the desired product (39 g, crude) as a yellow solid.

Step B: Methyl 3-bromo-2-(4-((tert-butoxycarbonyl)amino)butoxy)benzoate

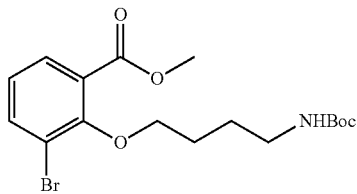 [SMILES: COC(=O)c1cccc(Br)c1OCCCCNC(=O)OC(C)(C)C]

The title compound was prepared according to the procedure described in Example 1, Step A and using methyl 3-bromo-2-hydroxybenzoate (8.0 g, 34.63 mmol). The product was purified by column chromatography on silica gel eluted with (Petrol Ether/EtOAc, from 100/1 to 3/1) to give the title compound (10 g, 72%) as a yellow gum.

Step C: Methyl 2-(4-aminobutoxy)-3-bromobenzoate

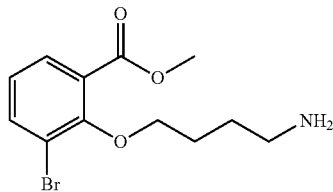 [SMILES: COC(=O)c1cccc(Br)c1OCCCCN]

The title compound was prepared according to the procedure described in Example 1, Step B and using methyl 3-bromo-2-(4-((tert-butoxycarbonyl)amino)butoxy)benzoate (10 g, 24.9 mmol) to give the desired product (7 g, 93%) as a yellow gum. MS (ESI): 302.0 [(M+H) ($^{79}$Br)]$^+$.

Step D: Methyl 3-bromo-2-(4-(3-(6-formamidopyridin-2-yl)-4H-1,2,4-triazol-4-yl)butoxy)benzoate

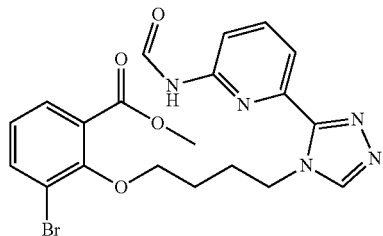 [SMILES: COC(=O)c1cccc(Br)c1OCCCCn1cnnc1-c1cccc(NC=O)n1]

The title compound was prepared according to the procedure described in Example 1, Step C and using methyl 2-(4-aminobutoxy)-3-bromobenzoate (6.9 g, 22.9 mmol) and (E)-N'-(6-(2-((E)-(dimethylamino)methylene)hydrazine-1-carbonyl)pyridin-2-yl)-N,N-dimethylformimidamide (3.0 g, 11.4 mmol). The product was purified by column chromatography on silica gel eluting with DCM/MeOH (from 100/1 to 10/1) to give the title compound (3.7 g, 68%) as a yellow gum. MS (ESI): 474.1 [(M+H) ($^{79}$Br)]$^+$.

Step E: 2-(4-(3-(6-Aminopyridin-2-yl)-4H-1,2,4-triazol-4-yl)butoxy)-3-bromobenzoic acid

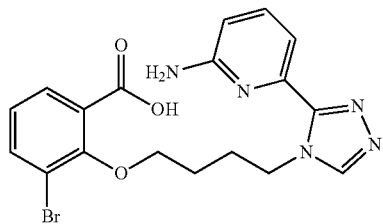 [SMILES: Nc1cccc(-c2nncn2CCCCOc2c(Br)cccc2C(=O)O)n1]

The title compound was prepared according to the procedure described in Example 1, Step D and using methyl 3-bromo-2-(4-(3-(6-formamidopyridin-2-yl)-4H-1,2,4-triazol-4-yl)butoxy)benzoate (3.7 g, 7.8 mmol) to give the desired product (4.9 g) as a yellow solid. MS (ESI): 433.9 [(M+H) ($^{81}$Br)]$^+$.

Step F: 5³-Bromo-1⁴H-6-oxa-3-aza-2(2,6)-pyridina-1(3,4)-triazola-5(1,2)-benzenacyclodecaphan-4-one

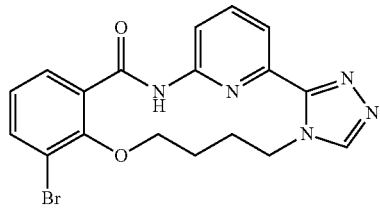

The title compound was prepared according to the procedure described in Example 1, Step E and using 2-(4-(3-(6-aminopyridin-2-yl)-4H-1,2,4-triazol-4-yl)butoxy)-3-bromobenzoic acid (4.3 g, 9.95 mmol) to give the desired product (1.5 g, 36%) as a white solid. ¹H NMR (400 MHz, CDCl₃) δ ppm 11.28 (s, 1H), 8.30 (s, 1H), 8.20-8.22 (dd, J=2.0, 6.0 Hz, 1H), 8.00-8.05 (m, 1H), 7.93-7.99 (m, 2H), 7.80-7.83 (dd, J=1.6, 6.4 Hz, 1H), 7.21-7.26 (m, 1H), 4.20-4.25 (m, 4H), 2.64 (s, 2H), 2.24 (s, 2H). MS (ESI): 414.2 [(M+H) (⁷⁹Br)]⁺.

Example 166: (E)-5³-(Trifluoromethyl)-1⁴H-6-oxa-3-aza-2(2,6)-pyridina-1(3,4)-triazola-5(1,2)-benzenacyclodecaphan-8-en-4-one

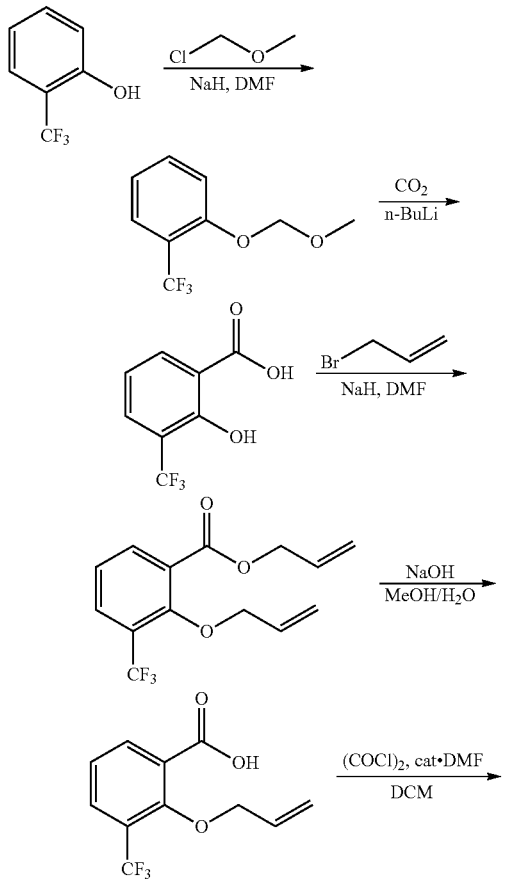

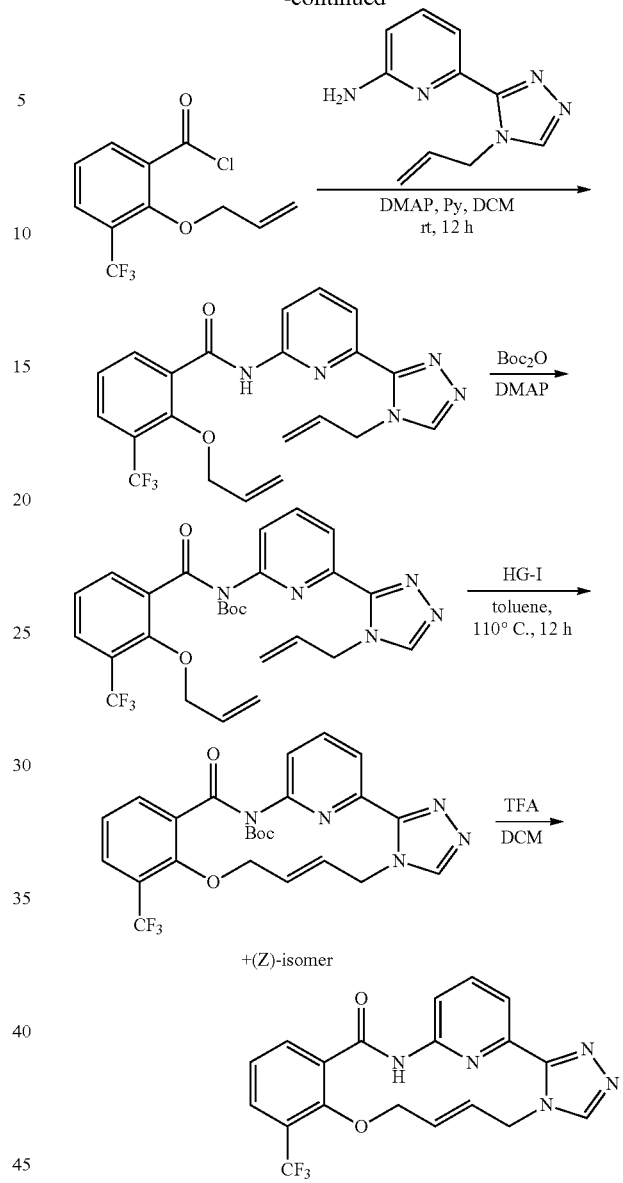

Step A:
1-(Methoxymethoxy)-2-(trifluoromethyl)benzene

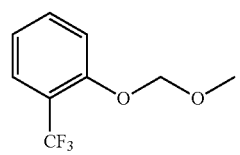

To a stirred mixture of NaH (7.2 g, 0.18 mol, 60% dispersion in oil) in DMF (50 mL) was dropwise added 2-(trifluoromethyl)phenol (25 g, 0.15 mol) in DMF (50 mL) via syringe. After 1 h, chloro(methoxy)methane (15.3 g, 0.19 mol) was added and the mixture was stirred at 25° C. for 17 h. After this time the reaction was quenched with H₂O (200 mL) and extracted with MTBE (200 mL). The organic phase was washed with 2N aq. NaOH solution (100 mL) and 2N aq. HCl solution (100 mL), dried over Na₂SO₄, filtered and concentrated under reduced pressure to give the crude product. Purification by column chromatography on silica (using petroleum ether as eluent) gave the title compound (24 g, 78%) as a colorless oil. ¹H NMR (400 MHz, CDCl₃) δ ppm 7.57 (d, J=7.6 Hz, 1H), 7.44-7.47 (m, 1H), 7.21 (d, J=7.6 Hz, 1H), 7.04-7.06 (m, 1H), 5.26 (s, 2H), 3.49 (s, 3H).

Step B: 2-Hydroxy-3-(trifluoromethyl)benzoic acid

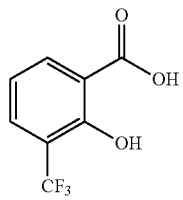 [SMILES: O=C(O)c1cccc(C(F)(F)F)c1O]

A solution of 1-(methoxymethoxy)-2-(trifluoromethyl)benzene (22 g, 0.11 mol) in THF (150 mL) was cooled to −20° C. and n-BuLi (51 mL, 0.13 mol) was added slowly, keeping the temperature at 0° C. After 70 min at −5 to 5° C., the reaction mixture was cooled to −20° C. and CO₂ gas was bubbled through the brown slurry, keeping the temperature below −10° C. (the reaction went from a brown slurry to a dark purple solution). After 10 min, the reaction mixture was cooled to −20° C. and treated with 2N HCl (120 mL). Additional conc. aq. HCl (30 mL) was added. After 30 min, MTBE (140 mL) was added and the organic phase was extracted with 2N NaOH (140 mL) and water (140 mL). The aqueous phase was acidified with 2N HCl (200 mL) and extracted with DCM (3×200 mL). The organic phase was dried over Na₂SO₄, filtered and concentrated under reduced pressure to give the crude product which was purified by column chromatography on silica (using petroleum ether/EtOAc, from 100/1 to 5/1 as eluent) to give the title compound (11 g, 49%) as a yellow solid. ¹H NMR (400 MHz, CDCl₃) δ ppm 11.28 (s, 1H), 8.11 (d, J=8.0 Hz, 1H), 7.82 (d, J=7.6 Hz, 1H), 6.99 (t, J=7.2 Hz, 1H).

Step C: Allyl 2-(allyloxy)-3-(trifluoromethyl)benzoate

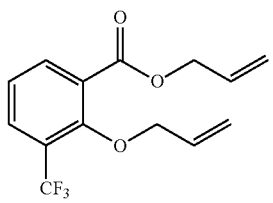 [SMILES: C=CCOC(=O)c1cccc(C(F)(F)F)c1OCC=C]

To a stirred mixture of NaH (2.6 g, 66 mmol, 60% dispersion in oil) in DMF (20 mL) was added 2-hydroxy-3-(trifluoromethyl)benzoic acid (4.5 g, 22 mmol). After 30 min allyl bromide (7.9 g, 66 mmol) was added and the mixture was stirred at 20° C. for 17 h. After this time the reaction was quenched with water (200 mL) and EtOAc (200 mL) was added. The pH of the separated aqueous phase was adjusted to 2 with conc. aq. HCl and extracted with EtOAc (2×200 mL). The organic phase was dried over Na₂SO₄, filtered and concentrated under vacuum to give the title compound (5 g, 93%) as a brown oil. MS (ESI): 286.9 [M+H]⁺.

Step D: 2-(Allyloxy)-3-(trifluoromethyl)benzoic acid

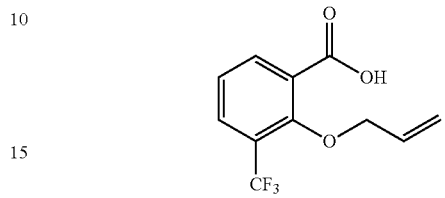

The title compound was prepared according to the procedure described in Example 153, Step C and using allyl 2-(allyloxy)-3-(trifluoromethyl)benzoate (5.0 g, 17.5 mmol) to give the desired product (3.5 g, 81%) as a white solid. ¹H NMR (400 MHz, CDCl₃) δ ppm 8.20 (dd, J=8.0 Hz, J=1.2 Hz, 1H), 7.85 (dd, J=7.6, 1.2 Hz, 1H), 7.32 (t, J=7.6 Hz, 1H), 6.08-6.15 (m, 1H), 5.44 (d, J=16.0 Hz, 1H), 5.33 (d, J=11.6 Hz, 1H), 4.60 (d, J=6.4 Hz, 2H).

Step E: 2-(Allyloxy)-3-(trifluoromethyl)benzoyl chloride

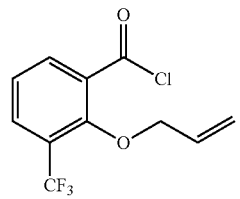 [SMILES: C=CCOc1c(C(=O)Cl)cccc1C(F)(F)F]

The title compound was prepared according to the procedure described in Example 153, Step D and using 2-(allyloxy)-3-(trifluoromethyl)benzoic acid (1.8 g, 7.3 mmol) to give the desired product (1.93 g, 100%) as colorless gum.

Step F: N-(6-(4-Allyl-4H-1,2,4-triazol-3-yl)pyridin-2-yl)-2-(allyloxy)-3-(trifluoromethyl)benzamide

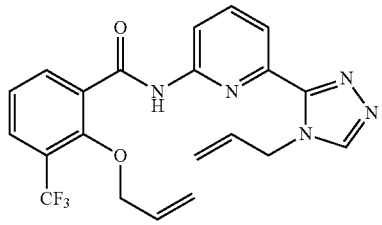

The title compound was prepared according to the procedure described in Example 153, Step E and using 2-(allyloxy)-3-(trifluoromethyl)benzoyl chloride (1.93 g, 7.3 mmol) and 6-(4-allyl-4H-1,2,4-triazol-3-yl)pyridin-2-amine (2.3 g, 9.5 mmol, Example 153, Step A). The crude product was purified by column chromatography on silica (using petroleum ether/EtOAc, from 10/1 to 0/1 as eluent) to give the title compound (2.7 g, 86%) as a white solid. $^1$H NMR (400 MHz, CDCl$_3$) δ ppm 9.79 (s, 1H), 8.49 (d, J=8.4 Hz, 1H), 8.31 (d, J=8.4 Hz, 1H), 8.25 (s, 1H), 8.16 (d, J=7.2 Hz, 1H), 7.95 (t, J=8.0 Hz, 1H), 7.86 (d, J=8.0 Hz, 1H), 7.45 (t, J=8.0 Hz, 1H), 6.04-6.12 (m, 2H), 5.24-5.41 (m, 2H), 5.16-5.22 (m, 4H), 4.57 (d, J=5.6 Hz, 2H).

Step G: tert-Butyl (6-(4-allyl-4H-1,2,4-triazol-3-yl)pyridin-2-yl)(2-(allyloxy)-3-(trifluoromethyl)benzoyl)carbamate

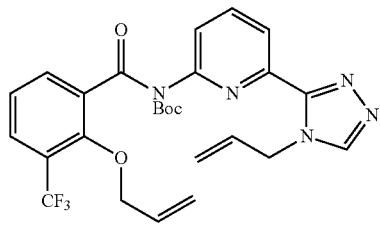

The title compound was prepared according to the procedure described in Example 153, Step F and using N-(6-(4-allyl-4H-1,2,4-triazol-3-yl)pyridin-2-yl)-2-(allyloxy)-3-(trifluoromethyl)benzamide (3.6 g, 8.4 mmol). The product purified by column chromatography on silica (using petroleum ether/EtOAc, from 10/1 to 0/1 as eluent) to give the title compound (4 g, 90%) as colorless gum. $^1$H NMR (400 MHz, CDCl$_3$) δ ppm 8.32 (d, J=8.0 Hz, 1H), 8.21 (s, 1H), 7.98 (t, J=8.0 Hz, 1H), 7.77 (d, J=8.0 Hz, 2H), 7.32-7.35 (m, 2H), 5.93-6.06 (m, 2H), 5.40 (d, J=17.2 Hz, 1H), 5.13-5.27 (m, 3H), 5.06 (d, J=5.6 Hz, 2H), 4.64 (d, J=5.6 Hz, 2H), 1.25 (m, 9H).

Step H: tert-Butyl (E)-4-oxo-5$^3$-(trifluoromethyl)-1$^4$H-6-oxa-3-aza-2(2,6)-pyridina-1(3,4)-triazola-5(1,2)-benzenacyclodecaphan-8-ene-3-carboxylate and tert-Butyl (Z)-4-oxo-5$^3$-(trifluoromethyl)-1$^4$H-6-oxa-3-aza-2(2,6)-pyridina-1(3,4)-triazola-5(1,2)-benzenacyclodecaphan-8-ene-3-carboxylate

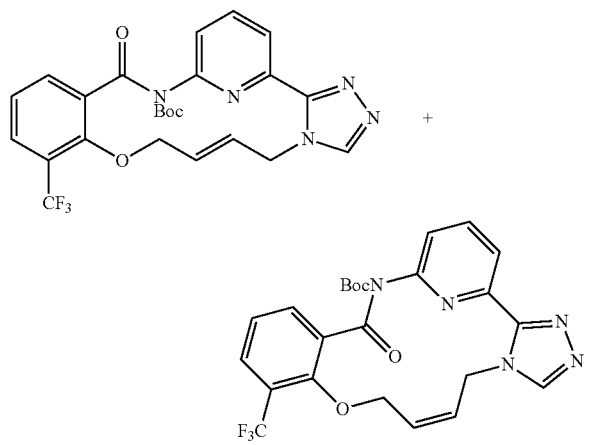

The title compound was prepared according to the procedure described in Example 154, Step A and using tert-butyl (6-(4-allyl-4H-1,2,4-triazol-3-yl)pyridin-2-yl)(2-(allyloxy)-3-(trifluoromethyl)benzoyl)carbamate (2.5 g, 4.7 mmol). The product was sequentially purified by column chromatography on silica (using petroleum ether/EtOAc, from 10/1 to 0/1 as eluent) and HPLC (using a Phenomenex Synergi C18, 4 μm 250×21.2 mm column and using water (containing 0.225% HCOOH)/CH$_3$CN, from 38% to 58% as the mobile phase at a flow rate of 25 mL/min) to give in order of elution tert-butyl (E)-4-oxo-5$^3$-(trifluoromethyl)-1$^4$H-6-oxa-3-aza-2(2,6)-pyridina-1(3,4)-triazola-5(1,2)-benzenacyclodecaphan-8-ene-3-carboxylate (170 mg, 7%) and tert-butyl (Z)-4-oxo-5$^3$-(trifluoromethyl)-1$^4$H-6-oxa-3-aza-2(2,6)-pyridina-1(3,4)-triazola-5(1,2)-benzenacyclodecaphan-8-ene-3-carboxylate (450 mg, 19%) as white solids. MS (ESI): 502.4 [M+H]$^+$.

Step I: (E)-5$^3$-(Trifluoromethyl)-1$^4$H-6-oxa-3-aza-2(2,6)-pyridina-1(3,4)-triazola-5(1,2)-benzenacyclodecaphan-8-en-4-one

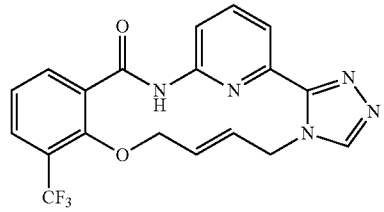 [SMILES: O=C1Nc2cccc(n2)-c2nncn2C/C=C/COc2c1cccc2C(F)(F)F]

The title compound was prepared according to the procedure described in Example 153, Step I and using tert-butyl (E)-4-oxo-5$^3$-(trifluoromethyl)-1$^4$H-6-oxa-3-aza-2(2,6)-pyridina-1(3,4)-triazola-5(1,2)-benzenacyclodecaphan-8-ene-3-carboxylate. $^1$H NMR (400 MHz, DMSO-d$_6$) δ ppm 10.78 (s, 1H), 8.85 (s, 1H), 8.03-8.07 (m, 2H), 7.90 (d, J=8.4 Hz, 1H), 7.77 (d, J=6.8 Hz, 1H), 7.67 (d, J=8.0 Hz, 1H), 7.45 (t, J=7.6 Hz, 1H), 6.12-6.16 (m, 1H), 5.86-5.93 (m, 1H), 4.84 (d, J=5.2 Hz, 2H), 4.74 (d, J=7.2 Hz, 2H). MS (ESI): 402.0 [M+H]$^+$.

Example 167: (Z)-5$^3$-(Trifluoromethyl)-1$^4$H-6-oxa-3-aza-2(2,6)-pyridina-1(3,4)-triazola-5(1,2)-benzenacyclodecaphan-8-en-4-one

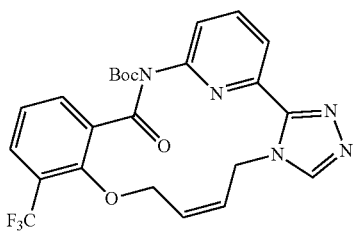 [SMILES: CC(C)(C)OC(=O)N1C(=O)c2cccc(C(F)(F)F)c2OC/C=C\Cn2cnnc2-c2cccc1n2]

The title compound was prepared according to the procedure described in Example 153, Step I and using tert-butyl (Z)-4-oxo-5$^3$-(trifluoromethyl)-1$^4$H-6-oxa-3-aza-2(2,6)-pyridina-1(3,4)-triazola-5(1,2)-benzenacyclodecaphan-8-ene-3-carboxylate (100 mg, 0.2 mmol) to give the product (80 mg, 100%) as a white solid. $^1$H NMR (400 MHz, DMSO-d$_6$) δ ppm 10.74 (s, 1H), 8.80 (s, 1H), 7.89-8.07 (m, 4H), 7.47-7.50 (m, 2H), 5.76-5.82 (m, 1H), 5.60-5.63 (m, 1H), 5.07 (d, J=6.0 Hz, 2H), 4.87 (d, J=6.4 Hz, 2H). MS (ESI): 402.1 [M+H]$^+$.

213

Example 168: (E)-5⁵-Morpholino-1⁴H-6-oxa-3-aza-2(2,6)-pyridina-1(3,4)-triazola-5(1,2)-benzenacyclodecaphan-8-en-4-one

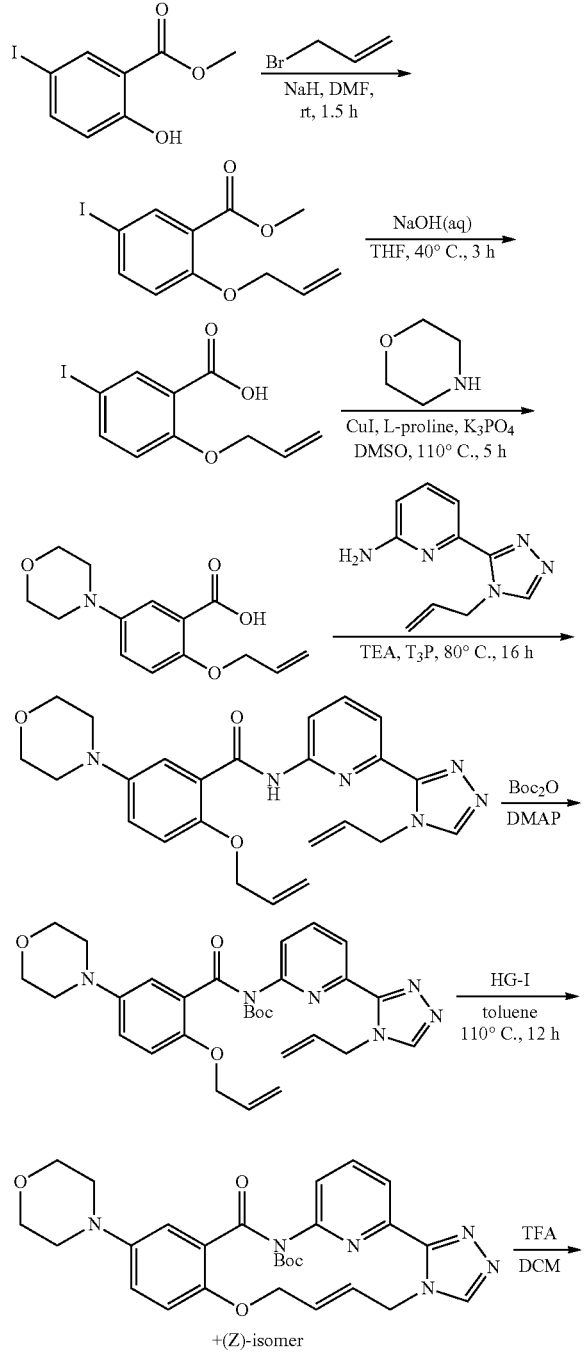

214

Step A: Methyl 2-(allyloxy)-5-iodobenzoate

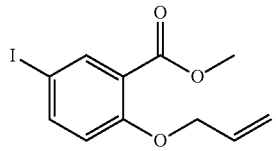

The title compound was prepared according to the procedure described in Example 153, Step B and using methyl 2-hydroxy-5-iodobenzoate (14 g, 0.05 mol) to give the desired product (15.9 g, 100%).

Step B: 2-(Allyloxy)-5-iodobenzoic acid

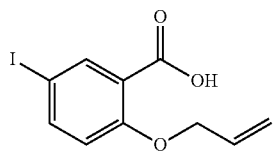

The title compound was prepared according to the procedure described in Example 153, Step C and using methyl 2-(allyloxy)-5-iodobenzoate (15.9 g, 50 mmol) to give the desired product (1.3 g, 86%) as an orange oil.

Step C: 2-(Allyloxy)-5-morpholinobenzoic acid

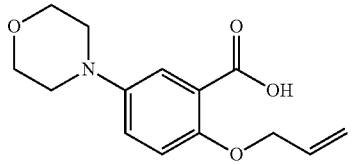 [SMILES: C=CCOc1ccc(N2CCOCC2)cc1C(=O)O]

A mixture of 2-(allyloxy)-5-iodobenzoic acid (4.2 g, 13.8 mmol), morpholine (3.4 mL, 38.6 mmol), CuI (263 mg, 2.8 mmol), L-proline (318 mg, 1.4 mmol) and K₃PO₄ (7.04 g, 33.2 mmol) in DMSO (80 mL) was degassed with N₂ for 15 min at 90° C. and then it was heated at 110° C. for 4 h. After this time the reaction was cooled to rt and water (100 mL) was added. The pH of the mixture was adjusted to 4-5 by addition of a sat. aqueous solution of citric acid in water. The mixture was then extracted with EtOAc (3×150 mL), and the combined organic extracts were washed with water (2×150 mL), brine (150 mL) dried over Na₂SO₄, and concentrated the give the title compound (4.0 g, crude) as a brown oil, which was used in next step without further purification. MS (ESI): 263.9 [M+H]⁺.

Step D: N-(6-(4-Allyl-4H-1,2,4-triazol-3-yl)pyridin-2-yl)-2-(allyloxy)-5-morpholinobenzamide

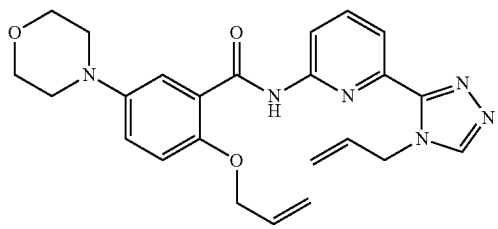 [SMILES: C=CCOc1ccc(N2CCOCC2)cc1C(=O)Nc1cccc(-c2nncn2CC=C)n1]

To a mixture of 2-(allyloxy)-5-morpholinobenzoic acid (1.0 g, 3.8 mmol) and 6-(4-allyl-4H-1,2,4-triazol-3-yl)pyridin-2-amine (746 mg, 3.81 mmol, Example 153, Step A) was added $T_3P$ (6.8 mL, ≥50 wt. % in EtOAc) and $Et_3N$ (7.9 mL, 57 mmol) and the reaction was heated at 80° C. for 16 hours. After this time the reaction was partitioned between EtOAc and $NaHCO_3$. The separated organic layer was dried over $Na_2SO_4$, filtered and evaporated in vacuo. The product was purified by column chromatography (EtOAc/petroleum ether from 1/1 to 1/0 as eluent) to give the title compound (1 g, 59%) as a colorless oil. MS (ESI): 447.1 $[M+H]^+$.

Step E: tert-Butyl (6-(4-allyl-4H-1,2,4-triazol-3-yl)pyridin-2-yl)(2-(allyloxy)-5-morpholinobenzoyl)carbamate

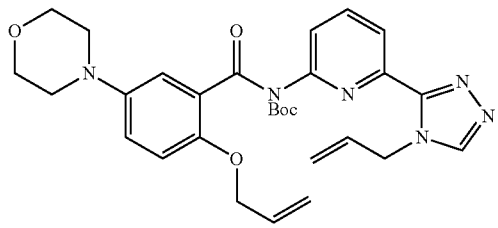 [SMILES: C=CCOc1ccc(N2CCOCC2)cc1C(=O)N(C(=O)OC(C)(C)C)c1cccc(-c2nncn2CC=C)n1]

The title compound was prepared according to the procedure described in Example 153, Step F and using N-(6-(4-allyl-4H-1,2,4-triazol-3-yl)pyridin-2-yl)-2-(allyloxy)-5-morpholinobenzamide (1.0 g, 2.24 mmol). The product was purified by column chromatography on silica gel (using DCM/MeOH, from 100/1 to 20/1 as eluent) to give the title compound (500 mg, 41%) as a yellow gum. MS (ESI): 569.1 $[M+Na]^+$.

Step F: tert-Butyl (E)-$5^5$-morpholino-4-oxo-$1^4$H-6-oxa-3-aza-2(2,6)-pyridina-1(3,4)-triazola-5(1,2)-benzenacyclodecaphan-8-ene-3-carboxylate and tert-Butyl (Z)-$5^5$-morpholino-4-oxo-$1^4$H-6-oxa-3-aza-2(2,6)-pyridina-1(3,4)-triazola-5(1,2)-benzenacyclodecaphan-8-ene-3-carboxylate

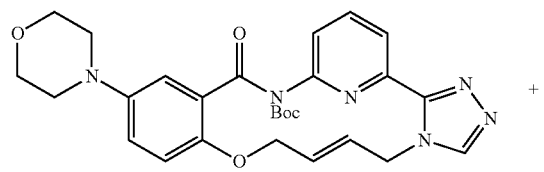

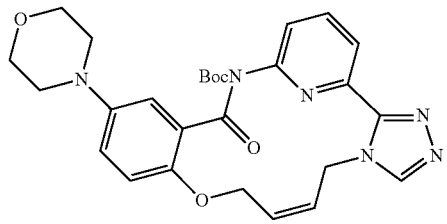 [SMILES: O=C1Nc2cccc(n2)-c2nncn2C/C=C\COc2ccc(N3CCOCC3)cc21]

The title compound was prepared according to the procedure described in Example 154, Step A and using tert-butyl (6-(4-allyl-4H-1,2,4-triazol-3-yl)pyridin-2-yl)(2-(allyloxy)-5-morpholinobenzoyl)carbamate (1.0 g, 1.83 mmol). The product was purified by HPLC (using a Phenomenex Synergi C18, 4 μm 150×30 mm column and using water (containing 0.05% HCl)/$CH_3CN$, from 33% to 48% as the mobile phase at a flow rate of 25 mL/min) to give in order of elution tert-butyl (E)-$5^5$-morpholino-4-oxo-$1^4$H-6-oxa-3-aza-2(2,6)-pyridina-1(3,4)-triazola-5(1,2)-benzenacyclodecaphan-8-ene-3-carboxylate (80 mg, 8%) and tert-butyl (Z)-$5^5$-morpholino-4-oxo-$1^4$H-6-oxa-3-aza-2(2,6)-pyridina-1(3,4)-triazola-5(1,2)-benzenacyclodecaphan-8-ene-3-carboxylate 150 mg, 16%) as a brown solid. MS (ESI): 519.4 $[M+H]^+$.

Step G: (E)-$5^5$-Morpholino-$1^4$H-6-oxa-3-aza-2(2,6)-pyridina-1(3,4)-triazola-5(1,2)-benzenacyclodecaphan-8-en-4-one

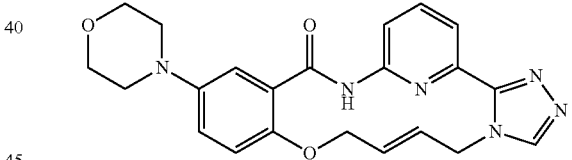

The title compound was prepared according to the procedure described in Example 153, Step I and using tert-butyl (E)-$5^5$-morpholino-4-oxo-$1^4$H-6-oxa-3-aza-2(2,6)-pyridina-1(3,4)-triazola-5(1,2)-benzenacyclodecaphan-8-ene-3-carboxylate (70 mg, 0.135 mmol). The product was purified by HPLC (using a Phenomenex Synergi C18, 150×30 mm×4 μm column and using water (containing 0.05% HCl) and $CH_3CN$, from 33% to 48%, as the mobile phase at a flow rate of 25 mL/min) to give the title compound (40 mg, 71%) as a white solid. $^1$H NMR (400 MHz, DMSO-$d_6$) δ ppm 11.27 (s, 1H), 8.93 (s, 1H), 7.97-8.07 (m, 2H), 7.78 (d, J=7.2 Hz, 1H), 7.56 (s, 1H), 7.33 (s, 2H), 6.28-6.33 (td, J=5.6, 15.2 Hz, 1H), 6.07 (td, J=7.2, 15.6 Hz, 1H), 4.97 (br d, J=4.8 Hz, 2H), 4.84 (br d, J=7.2 Hz, 2H), 3.77-3.79 (m, 4H), 3.13-3.15 (m, 4H). MS (ESI): 441.3 $[M+Na]^+$.

217

Example 169: (Z)-5⁵-Morpholino-1⁴H-6-oxa-3-aza-2(2,6)-pyridina-1(3,4)-triazola-5(1,2)-benzenacyclodecaphan-8-en-4-one

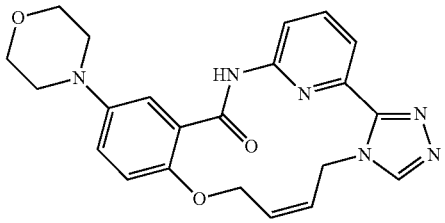

The title compound was prepared according to the procedure described in Example 153, Step I and using tert-butyl (Z)-5⁵-morpholino-4-oxo-1⁴H-6-oxa-3-aza-2(2,6)-pyridina-1(3,4)-triazola-5(1,2)-benzenacyclodecaphan-8-ene-3-carboxylate (100 mg, 0.19 mmol). The product was purified by HPLC (using a Phenomenex Synergi C18, 150×30 mm×4 μm column and using water (containing 0.05% HCl) and $CH_3CN$, from 28% to 68%, as the mobile phase at a flow rate of 25 mL/min) to provide the title compound (75 mg, 93%) as a white solid. $^1H$ NMR (400 MHz, DMSO-$d_6$) δ ppm 10.81 (s, 1H), 9.04 (s, 1H), 8.02 (t, J=7.6 Hz, 1H), 7.84 (d, J=8.4 Hz, 2H), 7.41 (d, J=8.8 Hz, 2H), 7.30 (d, J=7.6 Hz, 1H), 5.78-5.82 (m, 1H), 5.58-5.62 (m, 1H), 5.31 (d, J=5.6 Hz, 2H), 4.85 (d, J=7.6 Hz, 2H), 3.70-3.84 (m, 4H), 3.14-3.15 (m, 4H). MS (ESI): 419.3 [M+H]⁺.

Example 170: 5⁵-Bromo-1⁴H-6-oxa-3-aza-2(2,6)-pyridina-1(3,4)-triazola-5(1,2)-benzenacycloundecaphan-4-one

218

Step A. Methyl 5-bromo-2-((5-((tert-butoxycarbonyl)amino)pentyl)oxy)benzoate

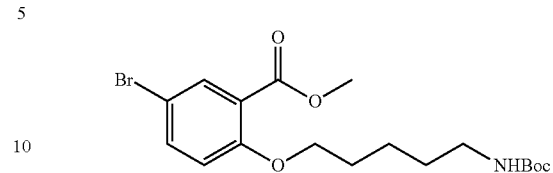

The title compound was synthesized according to the general procedure described in Example 1, Step A and using methyl 5-bromo-2-hydroxy-benzoate (2.5 g, 10.8 mmol) to give the desired product (3.2 g, 70%) as a colorless oil.

Step B. Methyl 2-((5-aminopentyl)oxy)-5-bromobenzoate

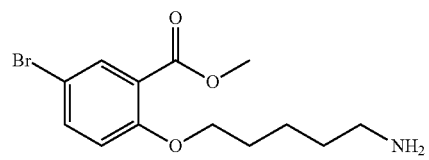 [SMILES: COC(=O)c1cc(Br)ccc1OCCCCCN]

The title compound was synthesized according to the general procedure described in Example 1, Step B and using methyl 5-bromo-2-((5-((tert-butoxycarbonyl)amino)pentyl)oxy)benzoate (16.6 g, 39.9 mmol) to give the desired product (11.9 g, 94%) as a colorless oil. $^1H$ NMR (400 MHz, $CDCl_3$) δ ppm 7.93-8.18 (m, 2H), 7.89 (d, J=2.5 Hz, 1H),

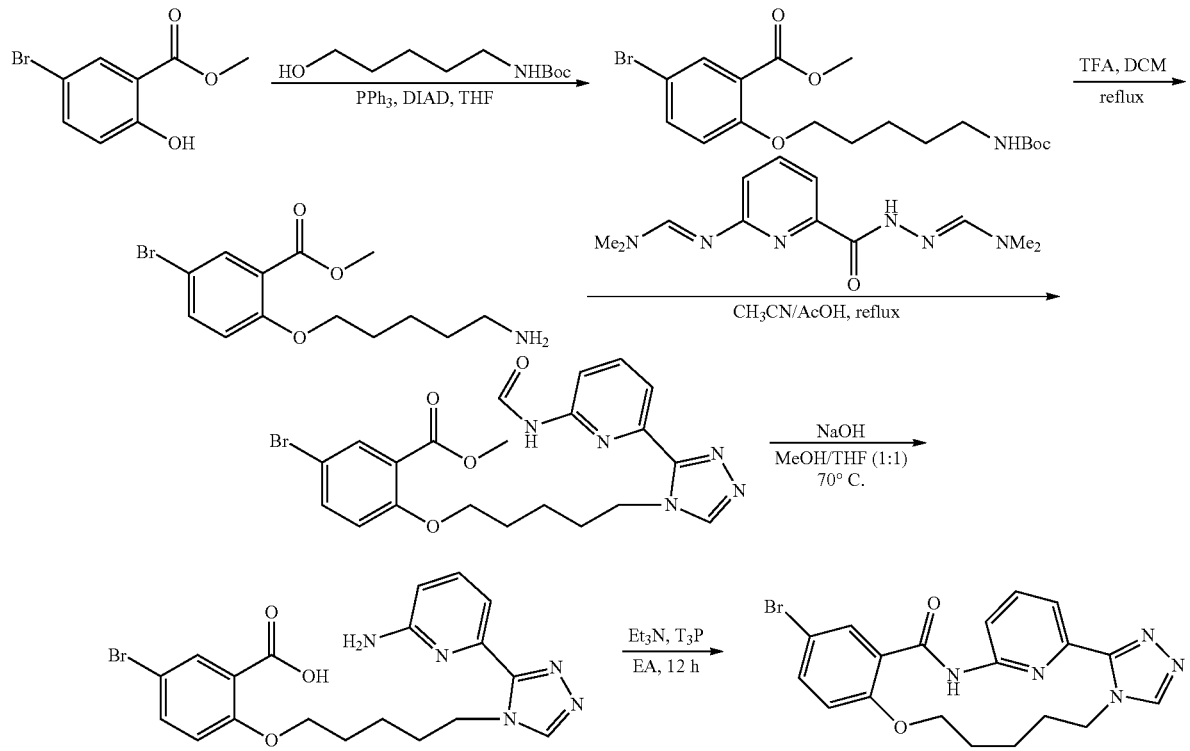

7.55 (dd, J=8.8, 2.5 Hz, 1H), 6.84 (d, J=9.0 Hz, 1H), 4.03 (t, J=5.9 Hz, 2H), 3.86 (s, 3H), 2.99-3.14 (m, 2H), 1.79-1.90 (m, 4H), 1.57-1.71 (m, 2H). MS (ESI): 316.1 [M+H ($^{79}$Br)]$^+$.

Step C. Methyl 5-bromo-2-((5-(3-(6-formamidopyridin-2-yl)-4H-1,2,4-triazol-4-yl)pentyl)oxy)benzoate

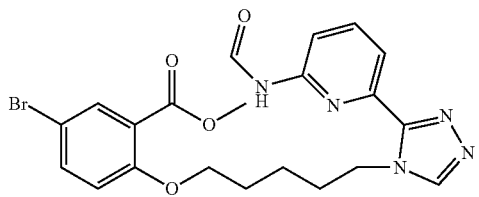 [SMILES: COC(=O)c1cc(Br)ccc1OCCCCCn1cnnc1-c1cccc(NC=O)n1]

The title compound was synthesized according to the general procedure described in Example 1, Step C using methyl 2-((5-aminopentyl)oxy)-5-bromobenzoate (4.8 g, 15.24 mmol) and (E)-N'-(6-(2-((E)-(dimethylamino)methylene)hydrazine-1-carbonyl)pyridin-2-yl)-N,N-dimethylformimidamide (2.0 g, 7.62 mmol) to give the title compound (3.0 g, 79%) as the major product as a yellow solid which was used without further purification in the next step. MS (ESI): 488.1 [(M+H) ($^{79}$Br)]$^+$.

Step D. 2-((5-(3-(6-Aminopyridin-2-yl)-4H-1,2,4-triazol-4-yl)pentyl)oxy)-5-bromobenzoic acid

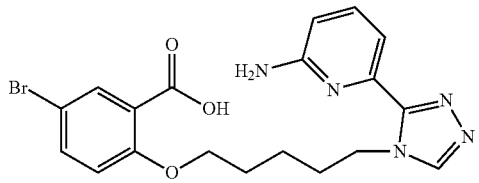 [SMILES: Nc1cccc(-c2nncn2CCCCCOc2ccc(Br)cc2C(=O)O)n1]

The title compound was synthesized according to the general procedure of Example 1 Step D using methyl 5-bromo-2-((5-(3-(6-formamidopyridin-2-yl)-4H-1,2,4-triazol-4-yl)pentyl)oxy)benzoate (3.0 g, 6.2 mmol) to give the desired product which was used without further purification in the next step. MS (ESI): 446.1 [(M+H) ($^{79}$Br)]$^+$.

Step E. 5$^5$-Bromo-1$^4$H-6-oxa-3-aza-2(2,6)-pyridina-1(3,4)-triazola-5(1,2)-benzenacycloundecaphan-4-one

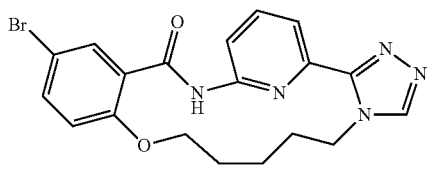 [SMILES: O=C1Nc2cccc(n2)-c2nncn2CCCCCOc2ccc(Br)cc21]

The title compound was synthesized according to the general procedure described in Example 1, Step E and using 2-((5-(3-(6-aminopyridin-2-yl)-4H-1,2,4-triazol-4-yl)pentyl)oxy)-5-bromobenzoic acid (231 mg, 0.52 mmol) to give the desired product (100 mg, 45%). $^1$H NMR (400 MHz, CDCl$_3$) δ ppm 10.62 (s, 1H), 8.53 (dd, J=8.4, 0.9 Hz, 1H), 8.49 (d, J=2.8 Hz, 1H), 8.21 (s, 1H), 8.17 (dd, J=7.7, 0.9 Hz, 1H), 7.93 (t, J=8.0 Hz, 1H), 7.62 (dd, J=8.7, 2.6 Hz, 1H), 6.92 (d, J=8.8 Hz, 1H), 4.26-4.33 (m, 2H), 4.19-4.25 (m, 2H), 2.17-2.29 (m, 2H), 2.02-2.11 (m, 2H), 1.89-1.99 (m, 2H). MS (ESI): 428.1 [(M+H) ($^{79}$Br)]$^+$.

Example 171: 1$^4$H-6-Oxa-3-aza-2(2,6)-pyridina-1(3,4)-triazola-5(1,2)-benzenacycloundecaphan-4-one

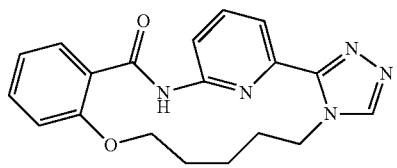 [SMILES: O=C1Nc2cccc(n2)-c2nncn2CCCCCOc2ccccc21]

To a suspension of 5-bromo-1$^4$H-6-oxa-3-aza-2(2,6)-pyridina-1(3,4)-triazola-5(1,2)-benzenacycloundecaphan-4-one (40 mg, 0.09 mmol) in THF (2.00 mL) was added n-BuLi in hexanes (0.37 mL of a 2.5 M solution, 0.93 mmol) at −78° C. After 2 h at this temperature MeOH (1 mL) was added. The reaction mixture was then allowed to warm to room temperature and concentrated under vacuum. The resulting residue was purified by column chromatography (4 g SiO$_2$, using a gradient of elution of MeOH and DCM, from 0 to 15%) to give the title compound (8 mg, 25%) as an off white solid. $^1$H NMR (400 MHz, CDCl$_3$) δ ppm 10.76 (s, 1H), 8.60 (dd, J=8.4, 0.9 Hz, 1H), 8.39 (d, J=6.0 Hz, 1H), 8.32 (s, 1H), 8.16 (dd, J=7.7, 0.9 Hz, 1H), 7.94 (s, 1H), 7.51-7.60 (m, 1H), 7.19 (td, J=7.6, 0.9 Hz, 1H), 7.01-7.07 (m, 1H), 4.30-4.38 (m, 2H), 4.22-4.29 (m, 2H), 2.17-2.34 (m, 2H), 2.03-2.15 (m, 2H), 1.91-2.03 (m, 2H). MS (ESI): 350.2 [M+H]$^+$.

Example 172: 5$^5$-Morpholino-1$^4$H-6-oxa-3-aza-2(2,6)-pyridina-1(3,4)-triazola-5(1,2)-benzenacycloundecaphan-4-one

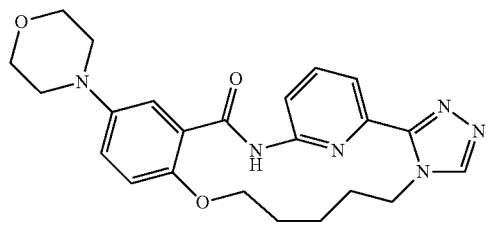 [SMILES: O=C1Nc2cccc(n2)-c2nncn2CCCCCOc2ccc(N3CCOCC3)cc21]

The title compound was synthesized according to the general procedure described in Example 3 and using 5$^5$-bromo-1$^4$H-6-oxa-3-aza-2(2,6)-pyridina-1(3,4)-triazola-5(1,2)-benzenacycloundecaphan-4-one (50 mg, 0.12 mmol) to give the desired product (8 mg, 16%) as a white solid. $^1$H NMR (400 MHz, CDCl$_3$) δ ppm 10.81 (s, 1H), 8.70 (br s, 1H), 8.61 (d, J=8.5 Hz, 1H), 8.06-8.14 (m, 2H), 7.92-8.01 (m, 1H), 7.38 (dd, J=9.0, 3.0 Hz, 1H), 7.03 (d, J=9.0 Hz, 1H), 4.34-4.44 (m, 2H), 4.23 (br t, J=5.0 Hz, 2H), 3.93-4.03 (m, 4H), 3.25-3.38 (m, 4H), 2.26 (br d, J=5.3 Hz, 2H), 2.06 (br s, 2H), 1.95 (br d, J=8.5 Hz, 2H). MS (ESI): 435.1 [M+H]$^+$.

Example 173: 5⁵-(2-Oxa-6-azaspiro[3.3]heptan-6-yl)-1⁴H-6-oxa-3-aza-2(2,6)-pyridina-1(3,4)-triazola-5(1,2)-benzenacycloundecaphan-4-one

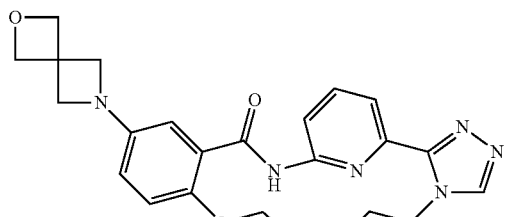

The title compound was synthesized according to the general procedure described in Example 4 and using 5⁵-bromo-1⁴H-6-oxa-3-aza-2(2,6)-pyridina-1(3,4)-triazola-5(1,2)-benzenacycloundecaphan-4-one (33 mg, 0.08 mmol) to give the desired product (24 mg, 70%). ¹H NMR (400 MHz, CDCl₃) δ ppm 10.74 (s, 1H), 8.44 (dd, J=8.3, 1.0 Hz, 1H), 8.11 (s, 1H), 8.04 (dd, J=7.7, 0.9 Hz, 1H), 7.81 (t, J=8.0 Hz, 1H), 7.36 (d, J=3.0 Hz, 1H), 6.81 (d, J=8.8 Hz, 1H), 6.53 (dd, J=8.7, 3.1 Hz, 1H), 4.77 (s, 4H), 4.16-4.23 (m, 2H), 4.05 (t, J=5.0 Hz, 2H), 3.95 (s, 4H), 2.02-2.22 (m, 2H), 1.86-2.02 (m, 2H), 1.71-1.86 (m, 2H). MS (ESI): 447.1 [M+H]⁺.

Example 174: (E)-1⁴H-6-Oxa-3-aza-2(2,6)-pyridina-1(3,4)-triazola-5(1,2)-benzenacycloundecaphan-9-en-4-one and Example 175: (Z)-1⁴H-6-oxa-3-aza-2(2,6)-pyridina-1(3,4)-triazola-5(1,2)-benzenacycloundecaphan-9-en-4-one

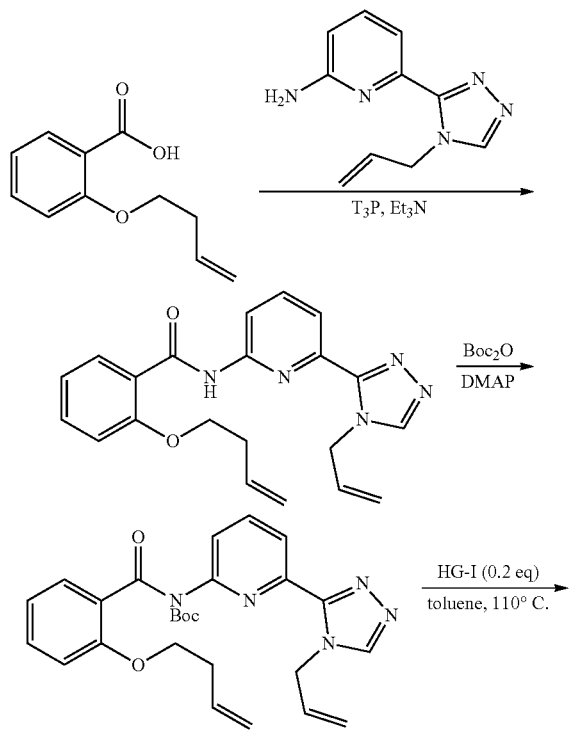

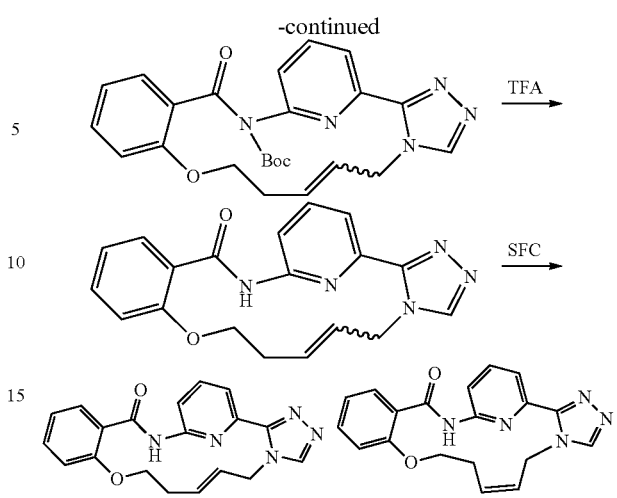

Step A. N-(6-(4-Allyl-4H-1,2,4-triazol-3-yl)pyridin-2-yl)-2-(but-3-en-1-yloxy)benzamide

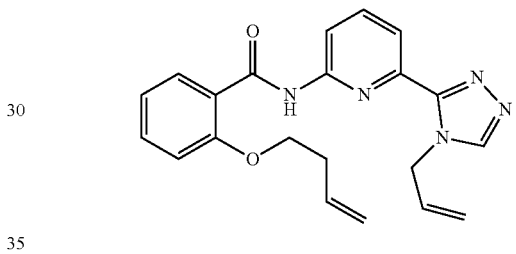

To a stirred of 2-but-3-enoxybenzoic acid (1.25 g, 6.5 mmol) and 6-(4-allyl-1,2,4-triazol-3-yl)pyridin-2-amine (1.31 g, 6.5 mmol) was added T₃P (11.7 mL, ≥50 wt. % in EtOAc) followed by triethylamine (13.5 mL, 97.5 mmol). The reaction was stirred at reflux for 3 h and at room temperature overnight. After this time the reaction was partitioned between EtOAc and sat. aq. NaHCO₃, the organic layer was washed with brine, dried over MgSO4, filtered and concentrated. Column chromatography of the resulting residue on silica gel using heptanes: (EtOH/EtOAc, 1/3), from 1/0 to 1/1 as eluent gave the desired product (850 mg, 35%) as a yellow gum. MS (ESI): 376.2 [M+H]⁺.

Step B. tert-Butyl (6-(4-allyl-4H-1,2,4-triazol-3-yl)pyridin-2-yl)(2-(but-3-en-1-yloxy)benzoyl)carbamate

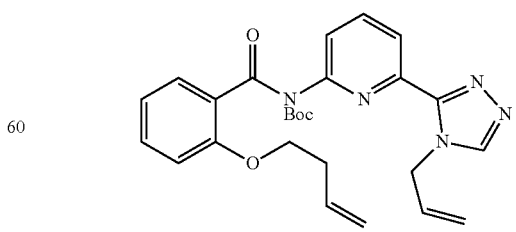

The title compound was prepared according to the procedure described in Example 153, Step F and using N-(6-

(4-allyl-4H-1,2,4-triazol-3-yl)pyridin-2-yl)-2-(but-3-en-1-yloxy)benzamide (850 mg, 2.26 mmol). The product was purified by column chromatography on silica gel using heptanes:(EtOH/EtOAc, 1/3), from 1/0 to 1/1 as eluent to give the desired product (1.07 g, 93%). MS (ESI): 476.2 [M+H]$^+$.

Step C. tert-Butyl 4-oxo-1$^4$H-6-oxa-3-aza-2(2,6)-pyridina-1(3,4)-triazola-5(1,2)-benzenacycloundecaphan-9-ene-3-carboxylate

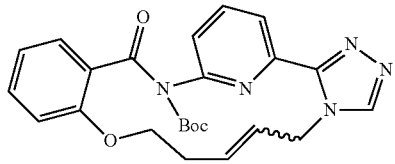 [SMILES: CC(C)(C)OC(=O)N1C(=O)c2ccccc2OCCC=CCn2cnnc2-c2cccc1n2]

The title compound was prepared according to the procedure described in Example 156, Step A and using tert-butyl (6-(4-allyl-4H-1,2,4-triazol-3-yl)pyridin-2-yl)(2-(but-3-en-1-yloxy)benzoyl)carbamate (1.0 g, 2.1 mmol). The product was purified by column chromatography on silica gel using DCM/MeOH (from 1/0 to 9/1) as eluent to give the desired product (257 mg, 27%). MS (ESI): 448.1 [M+H]$^+$.

Step D. 1$^4$H-6-Oxa-3-aza-2(2,6)-pyridina-1(3,4)-triazola-5(1,2)-benzenacycloundecaphan-9-en-4-one

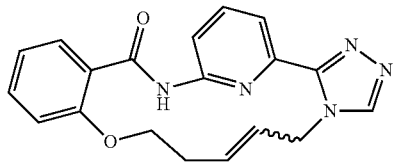 [SMILES: O=C1Nc2cccc(n2)-c2nncn2CC=CCCOc2ccccc21]

The title compound was prepared according to the procedure described in Example 154, Step B and using tert-butyl 4-oxo-1$^4$H-6-oxa-3-aza-2(2,6)-pyridina-1(3,4)-triazola-5(1,2)-benzenacycloundecaphan-9-ene-3-carboxylate (200 mg, 0.45 mmol). The product was purified by column chromatography on silica gel using DCM/MeOH (from 1/0 to 9/1) as eluent to give the desired product (63 mg, 40%) as a 2.7:1 mixture of stereoisomers. MS (ESI): 348.1 [M+H]$^+$.

Step E. (E)-1$^4$H-6-Oxa-3-aza-2(2,6)-pyridina-1(3,4)-triazola-5(1,2)-benzenacycloundecaphan-9-en-4-one and (Z)-1$^4$H-6-oxa-3-aza-2(2,6)-pyridina-1(3,4)-triazola-5(1,2)-benzenacycloundecaphan-9-en-4-one

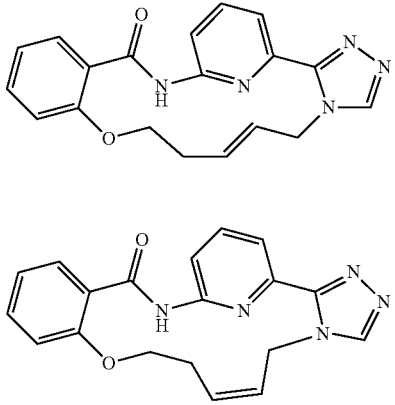

1$^4$H-6-oxa-3-aza-2(2,6)-pyridina-1(3,4)-triazola-5(1,2)-benzenacycloundecaphan-9-en-4-one (63 mg, 0.18 mmol) was purified by SFC (using a Chiralpack IB, 30×250 mm column and 40% MeOH (containing 0.1% Et$_2$NH) in CO$_2$ as the mobile phase at a flow rate of 100 mL/min (ABPR 120 bar and MBPR 40 psi)) to give in order of elution: (E)-1$^4$H-6-Oxa-3-aza-2(2,6)-pyridina-1(3,4)-triazola-5(1,2)-benzenacycloundecaphan-9-en-4-one (31 mg, 49%) $^1$H NMR (400 MHz, DMSO-d$_6$) δ ppm 10.54 (s, 1H), 8.72 (s, 1H), 8.38 (d, J=8.5 Hz, 1H), 8.15 (dd, J=1.8, 7.9 Hz, 1H), 8.03 (t, J=7.9 Hz, 1H), 7.84-7.98 (m, 1H), 7.62-7.73 (m, 1H), 7.31 (d, J=7.9 Hz, 1H), 7.18 (t, J=7.5 Hz, 1H), 5.76-5.92 (m, 2H), 5.04 (s, 2H), 4.35 (br t, J=5.5 Hz, 2H), 2.69 (br d, J=4.3 Hz, 2H); MS (ESI): 348.1 [M+H]$^+$ and (Z)-1$^4$H-6-oxa-3-aza-2(2,6)-pyridina-1(3,4)-triazola-5(1,2)-benzenacycloundecaphan-9-en-4-one (10 mg, 16%). $^1$H NMR (400 MHz, DMSO-d$_6$) δ ppm 10.91 (s, 1H), 8.74 (s, 1H), 8.29-8.35 (m, 1H), 8.18 (dd, J=1.9, 7.9 Hz, 1H), 7.97-8.04 (m, 2H), 7.61-7.70 (m, 1H), 7.30 (d, J=7.8 Hz, 1H), 7.14-7.22 (m, 1H), 5.56-5.67 (m, 1H), 5.44-5.53 (m, 1H), 5.27 (br d, J=2.5 Hz, 2H), 4.33-4.47 (m, 2H), 2.69-2.84 (m, 2H). MS (ESI): 348.1 [M+H]$^+$.

Example 176: (E)-5$^5$-Bromo-5$^4$-fluoro-1$^4$H-6-oxa-3-aza-2(2,6)-pyridina-1(3,4)-triazola-5(1,2)-benzenacycloundecaphan-9-en-4-one and Example 177: (Z)-5$^5$-Bromo-5$^4$-fluoro-1$^4$H-6-oxa-3-aza-2(2,6)-pyridina-1(3,4)-triazola-5(1,2)-benzenacycloundecaphan-9-en-4-one

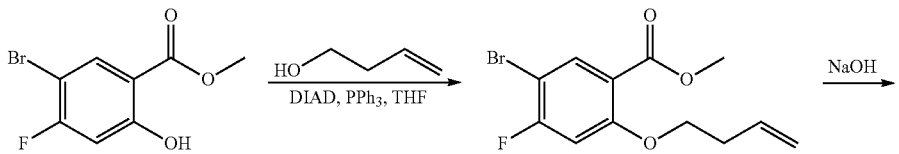

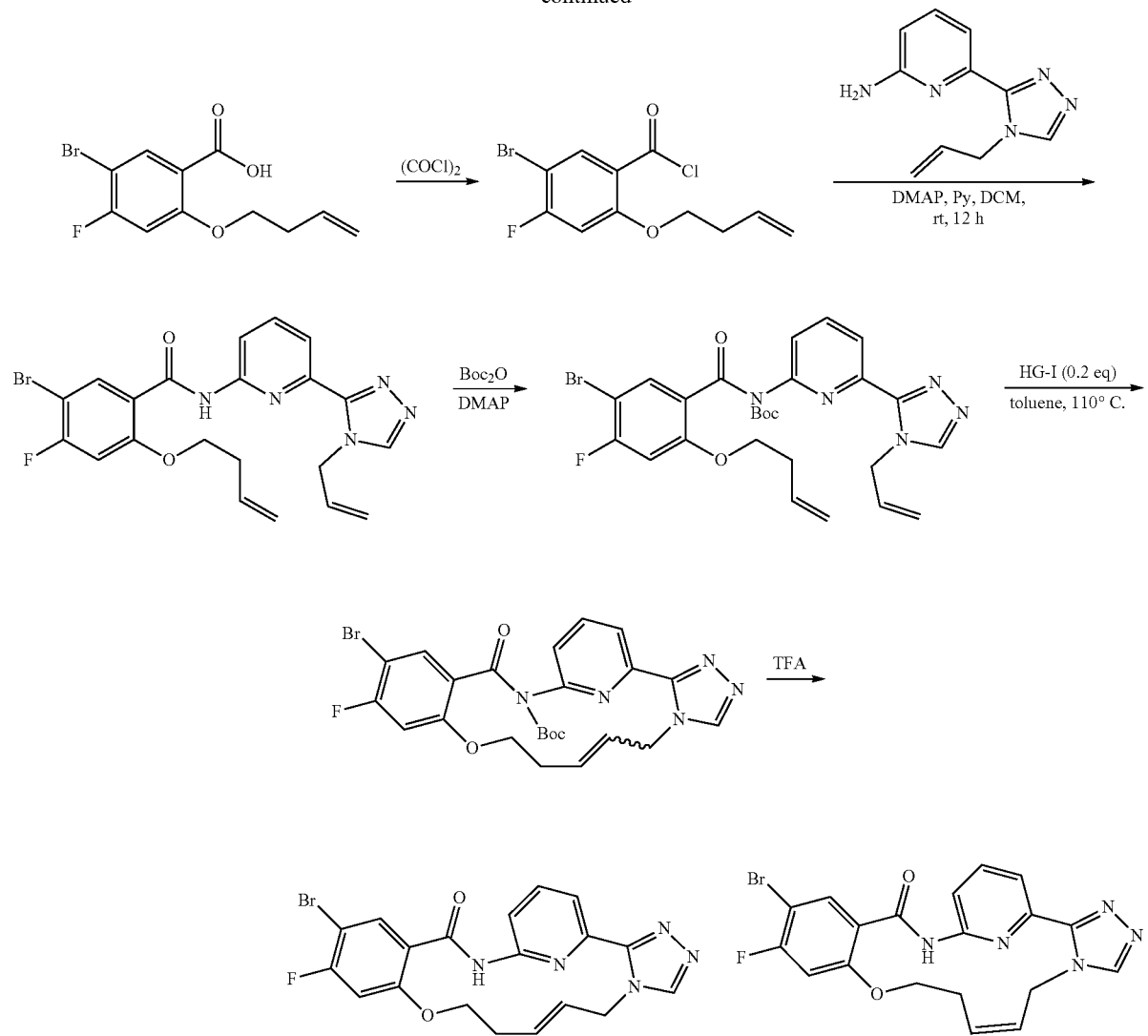

Step A. Methyl 5-bromo-2-(but-3-en-1-yloxy)-4-fluorobenzoate

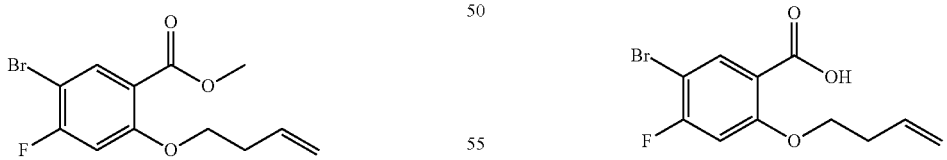

To a solution of methyl 5-bromo-4-fluoro-2-hydroxybenzoate (5 g, 20 mmol), but-3-en-1-ol (1.59 g, 22 mmol) and PPh₃ (6.32 g, 24 mmol) in THF (60 mL) at 0° C. was added DIAD (5.1 mL, 26 mmol) and the mixture was stirred at 16° C. for 3 h. After this time the reaction was concentrated to give the crude product which was was purified by column chromatography on silica gel using petroleum ether/DCM (1/0 to 10/1) as eluent to give the title compound (5 g, 82%) as a white solid. MS (ESI): 302.9 [(M+H) ($^{79}$Br)]$^+$.

Step B. 5-Bromo-2-(but-3-en-1-yloxy)-4-fluorobenzoic acid

A solution of methyl 5-bromo-2-(but-3-en-1-yloxy)-4-fluorobenzoate (4.5 g, 14.8 mmol) and NaOH (1.19 g, 26.7 mmol) in THF/H₂O (4/1, 50 mL) was stirred at 50° C. for 3 h. After this time the mixture was concentrated and water (30 mL) was added. The pH of the mixtures was adjusted to 6 by addition of HCl (3 M aqueous solution). The mixture was then extracted with EtOAc (3×50 mL) and the combined organic extracts were dried over Na₂SO₄, filtered and concentrated to give the title compound (4.2 g, 88%) as a white solid. MS (ESI): 288.9 [(M+H) ($^{81}$Br)]$^+$.

Step C. 5-Bromo-2-(but-3-en-1-yloxy)-4-fluorobenzoyl chloride

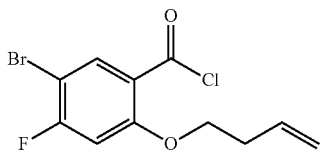 [SMILES: C=CCCOc1cc(F)c(Br)cc1C(=O)Cl]

A solution of 5-bromo-2-(but-3-en-1-yloxy)-4-fluorobenzoic acid (4 g, 13.8 mmol), (COCl)$_2$ (5.27 g, 41.5 mmol) and DMF (0.2 mL) in DCM (40 mL) was stirred at 16° C. for 2 h. After this time the volatiles were removed under reduced pressure to give the title compound (4.26 g, 100% crude) as a yellow oil.

Step D. N-(6-(4-Allyl-4H-1,2,4-triazol-3-yl)pyridin-2-yl)-5-bromo-2-(but-3-en-1-yloxy)-4-fluorobenzamide

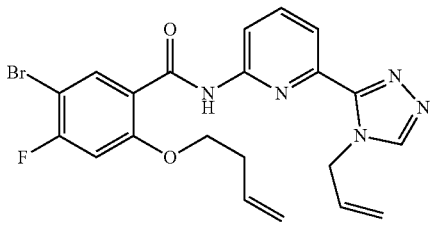 [SMILES: C=CCCOc1cc(F)c(Br)cc1C(=O)Nc1cccc(-c2nncn2CC=C)n1]

A solution of 5-bromo-2-(but-3-en-1-yloxy)-4-fluorobenzoyl chloride (4.26 g, 13.8 mmol), 6-(4-allyl-4H-1,2,4-triazol-3-yl)pyridin-2-amine (3.34 g, 16.6 mmol), and DMAP (0.85 g, 6.9 mmol) in DCM (40 mL) and Py (3 mL) was stirred at 16° C. for 17 h. After this time the mixture was concentrated to give the crude product which was purified by column chromatography on silica gel using petroleum ether/EtOAc (1/0 to 0/1) to give the title compound (3 g, 46%) as a white solid. MS (ESI): 473.8 [(M+H) ($^{81}$Br)]$^+$.

Step E. tert-Butyl (6-(4-allyl-4H-1,2,4-triazol-3-yl)pyridin-2-yl)(5-bromo-2-(but-3-en-1-yloxy)-4-fluorobenzoyl)carbamate

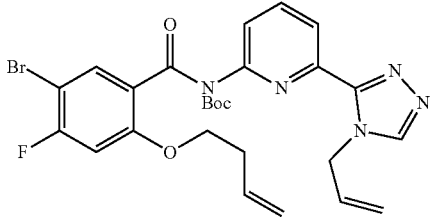 [SMILES: C=CCCOc1cc(F)c(Br)cc1C(=O)N(C(=O)OC(C)(C)C)c1cccc(-c2nncn2CC=C)n1]

A mixture of N-(6-(4-allyl-4H-1,2,4-triazol-3-yl)pyridin-2-yl)-5-bromo-2-(but-3-en-1-yloxy)-4-fluorobenzamide (3 g, 6.3 mmol), DMAP (0.39 g, 3.18 mmol) and Boc$_2$O (4.16 g, 19 mmol) in DCM (30 mL) was stirred at 16° C. for 5 h. After this time the volatiles were removed under reduced pressure to give the crude product which was purified by column chromatography on silica gel using petroleum ether/EtOAc (10/1 to 0/1) as eluent to give the title compound (2 g, 55%) as a brown solid. MS (ESI): 574.1 [(M+H) ($^{81}$Br)]$^+$.

Step F. tert-Butyl 5$^5$-bromo-5$^4$-fluoro-4-oxo-1$^4$H-6-oxa-3-aza-2(2,6)-pyridina-1(3,4)-triazola-5(1,2)-benzenacycloundecaphan-9-ene-3-carboxylate

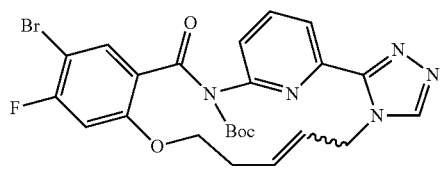 [SMILES: CC(C)(C)OC(=O)N1C(=O)c2cc(Br)c(F)cc2OCCC=CCn2cnnc2-c2cccc1n2]

A mixture of tert-butyl (6-(4-allyl-4H-1,2,4-triazol-3-yl)pyridin-2-yl)(5-bromo-2-(but-3-en-1-yloxy)-4-fluorobenzoyl)carbamate (1.9 g, 3.32 mmol) and Hoveyda-Grubb's 1st generation catalyst (415 mg, 0.66 mmol) in toluene (2 L) was stirred under a N$_2$ atmosphere at 110° C. for 17 h. After this time the volatiles were removed under reduced pressure to give the crude product which was purified by column chromatography on silica gel using DCM/MeOH (1/0 to 30/1) as eluent to give the title compound (600 mg, 31%, mixture of Z/E isomers) as a brown solid. MS (ESI): 545.9 [(M+H) ($^{81}$Br)]$^+$.

Step G. (E)-5$^5$-Bromo-5$^4$-fluoro-1$^4$H-6-oxa-3-aza-2(2,6)-pyridina-1(3,4)-triazola-5(1,2)-benzenacycloundecaphan-9-en-4-one and (Z)-5$^5$-Bromo-5$^4$-fluoro-1$^4$H-6-oxa-3-aza-2(2,6)-pyridina-1(3,4)-triazola-5(1,2)-benzenacycloundecaphan-9-en-4-one

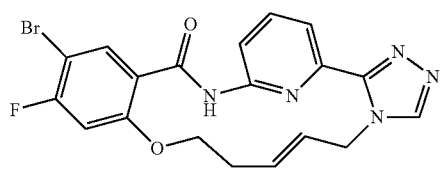

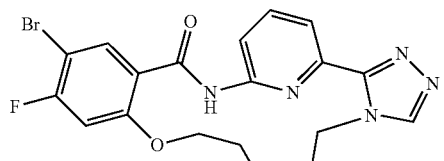

A solution of tert-butyl (E)-5$^5$-bromo-5$^4$-fluoro-4-oxo-1$^4$H-6-oxa-3-aza-2(2,6)-pyridina-1(3,4)-triazola-5(1,2)-benzenacycloundecaphan-9-ene-3-carboxylate and tert-butyl (Z)-5$^5$-bromo-5$^4$-fluoro-4-oxo-1$^4$H-6-oxa-3-aza-2(2,6)-pyridina-1(3,4)-triazola-5(1,2)-benzenacycloundecaphan-9-ene-3-carboxylate (600 mg, 1.1 mmol) in TFA (10 mL) and DCM (10 mL) was stirred at 16° C. for 2 h. After this time the volatiles were removed under reduced pressure to give the crude product which was purified by SFC (using a N OD, 250×30 mm×10 μm column and 40% MeOH (containing 0.1% NH4OH) in CO2 at a flow rate of 60 mL/min) to give in order of elution:

Peak 1: (E)-5$^5$-Bromo-5$^4$-fluoro-1$^4$H-6-oxa-3-aza-2(2,6)-pyridina-1(3,4)-triazola-5(1,2)-benzenacycloundecaphan-9-en-4-one (240 mg, 49%) as a white solid. $^1$H NMR (400 MHz, DMSO-d$_6$) δ ppm 10.31 (s, 1H), 8.70 (s, 1H), 8.23-8.33 (m, 2H), 7.97-8.04 (m, 1H), 7.91 (d, J=7.0 Hz, 1H), 7.44 (d, J=11.0 Hz, 1H), 5.77-5.81 (m, 2H), 4.95-5.04 (m, 2H), 4.27-4.38 (m, 2H), 2.61-2.69 (m, 2H). MS (ESI): 444.1 [(M+H) ($^{79}$Br)]$^+$.

Peak 2: (Z)-5$^5$-Bromo-5$^4$-fluoro-1$^4$H-6-oxa-3-aza-2(2,6)-pyridina-1(3,4)-triazola-5(1,2)-benzenacycloundecaphan-9-en-4-one (40 mg, 8%) as a brown solid. $^1$H NMR (400 MHz, DMSO-d$_6$) δ ppm 10.68 (s, 1H), 8.75 (s, 1H), 8.34 (d, J=7.8 Hz, 1H), 8.23-8.29 (m, 1H), 8.03 (d, J=3.9 Hz, 2H), 7.47 (d, J=10.8 Hz, 1H), 5.45-5.64 (m, 2H), 5.22-5.29 (m, 2H), 4.40-4.47 (m, 2H), 2.73-2.78 (m, 2H). 446.1 [(M+H) ($^{81}$Br)]$^+$.

Example 178: (E)-5$^5$-(1-(2-(Dimethylamino)ethyl)-1H-pyrazol-4-yl)-5$^4$-fluoro-1$^4$H-6-oxa-3-aza-2(2,6)-pyridina-1(3,4)-triazola-5(1,2)-benzenacycloundecaphan-9-en-4-one

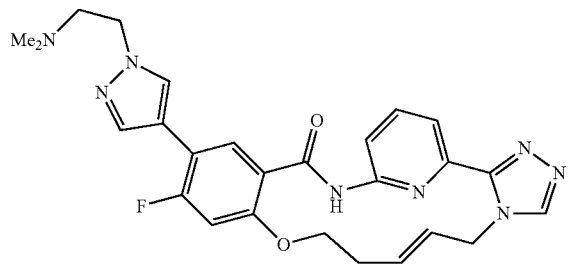 [SMILES: CN(C)CCn1cc(-c2cc3c(cc2F)OCC/C=C/Cn2cnnc2-c2cccc(n2)NC3=O)cn1]

To a solution of (E)-5$^5$-bromo-5$^4$-fluoro-1$^4$H-6-oxa-3-aza-2(2,6)-pyridina-1(3,4)-triazola-5(1,2)-benzenacycloundecaphan-9-en-4-one (60 mg, 0.135 mmol) in DME/H$_2$O (10/1, 5 mL) under a N$_2$ atmosphere was added N,N-dimethyl-2-(4-(4,4,5,5-tetramethyl-1,3,2-dioxaborolan-2-yl)-1H-pyrazol-1-yl)ethan-1-amine (49 mg, 0.27 mmol), Cs$_2$CO$_3$ (132 mg, 0.4 mmol) and Pd(dtbpf)Cl$_2$ (9.1 mg, 0.014 mmol) and the mixture was stirred at 85° C. for 18 h. After this time the mixture was concentrated under reduced pressure to give the crude product which was purified by HPLC (using an Xtimate C18, 5 μm 150×25 mm column and using water (containing 10 mM NH$_4$HCO$_3$)/CH$_3$CN, from 23% to 43% as the mobile phase at a flow rate of 25 mL/min) to give the title compound (3 mg, 4%) as a brown solid. $^1$H NMR (400 MHz, DMSO-d$_6$) δ ppm 10.43 (s, 1H), 8.72 (s, 1H), 8.36-8.40 (m, 2H), 8.23 (s, 1H), 8.05 (t, J=8.0 Hz, 1H), 7.94 (d, J=6.8 Hz, 1H), 7.87 (s, 1H), 7.32 (d, J=13.2 Hz, 1H), 5.84 (s, 2H), 5.04 (s, 2H), 4.37 (s, 2H), 4.25 (s, 2H), 3.33-3.35 (m, 2H), 2.69 (s, 2H), 2.19 (s, 6H). MS (ESI): 503.2 [M+H]$^+$.

Example 179: (Z)-5$^5$-(1-(2-(Dimethylamino)ethyl)-1H-pyrazol-4-yl)-5$^4$-fluoro-1$^4$H-6-oxa-3-aza-2(2,6)-pyridina-1(3,4)-triazola-5(1,2)-benzenacycloundecaphan-9-en-4-one

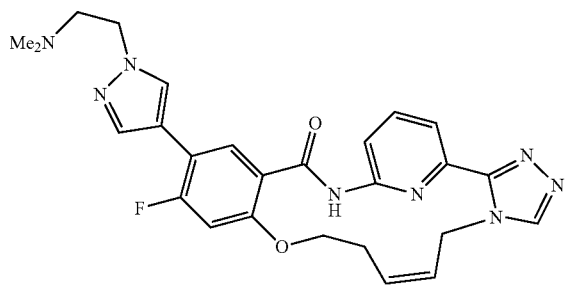 [SMILES: CN(C)CCn1cc(-c2cc3c(cc2F)OCC/C=C\Cn2cnnc2-c2cccc(n2)NC3=O)cn1]

The title compound was synthesized according to the general procedure described in Example 178 and using (Z)-5$^5$-bromo-5$^4$-fluoro-1$^4$H-6-oxa-3-aza-2(2,6)-pyridina-1(3,4)-triazola-5(1,2)-benzenacycloundecaphan-9-en-4-one (30 mg, 0.067 mmol). Purification by HPLC (using a Phenomenex Synergi C18, 150×30 mm×4 μm column and using water (containing 0.05% HCl) and CH$_3$CN, from 20% to 40%, as the mobile phase at a flow rate of 25 mL/min) gave the title compound as the HCl salt (28 mg, 62%) as a white solid. $^1$H NMR (400 MHz, DMSO-d$_6$) δ ppm 10.71 (s, 1H), 10.51 (s, 1H), 9.09 (s, 1H), 8.38 (d, J=9.2 Hz, 1H), 8.28-8.33 (m, 2H), 7.96-8.04 (m, 3H), 7.23-7.27 (m, 1H), 5.48-5.56 (m, 2H), 5.24-5.30 (m, 2H), 4.61-4.64 (m, 2H), 4.35-4.41 (m, 2H), 3.58-3.60 (m, 2H), 2.77 (s, 6H), 2.71-2.73 (m, 2H). MS (ESI): 503.2 [M+H]$^+$.

Example 180: (Z)-5$^4$-Fluoro-5$^5$-(pyridin-4-yl)-1$^4$H-6-oxa-3-aza-2(2,6)-pyridina-1(3,4)-triazola-5(1,2)-benzenacycloundecaphan-9-en-4-one

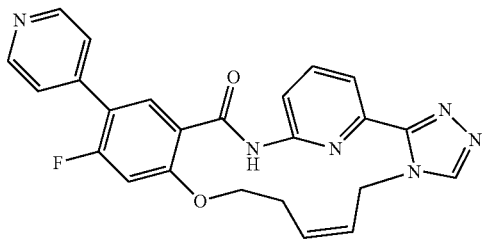 [SMILES: O=C1Nc2cccc(n2)-c2nncn2C/C=C\CCOc2cc(F)c(-c3ccncc3)cc21]

To a solution of (Z)-5$^5$-bromo-5$^4$-fluoro-1$^4$H-6-oxa-3-aza-2(2,6)-pyridina-1(3,4)-triazola-5(1,2)-benzenacycloundecaphan-9-en-4-one (50 mg, 0.112 mmol) in EtOH/H$_2$O (10/1, 2 mL) was added pyridin-4-ylboronic acid (28 mg, 0.22 mmol), K$_2$CO$_3$ (31 mg, 0.22 mmol) and PEPPSI-Ipr (8 mg, 0.011 mmol) under a N$_2$ atmosphere and the reaction was stirred at 90° C. for 1 h. After this time the mixture was concentrated to give the crude product which was purified by column chromatography on silica gel using DCM/MeOH (100/1 to 10/1) as eluent to give the title compound (13 mg, 26%) as a white solid. 1H NMR (400 MHz, DMSO-d$_6$) δ ppm 10.74 (s, 1H), 8.75 (s, 1H), 8.69 (d, J=4.4 Hz, 2H), 8.37 (d, J=9.2 Hz, 1H), 8.28 (m, 1H), 8.03 (s, 2H), 7.62 (d, J=3.6 Hz, 2H), 7.44 (d, J=12.4 Hz, 1H), 5.42-5.68 (m, 2H), 5.27 (s, 2H), 4.49 (s, 2H), 2.78 (s, 2H). MS (ESI): 443.1 [M+H]$^+$.

Example 181: (Z)-5⁴-Fluoro-5⁵-morpholino-1⁴H-6-oxa-3-aza-2(2,6)-pyridina-1(3,4)-triazola-5(1,2)-benzenacycloundecaphan-9-en-4-one

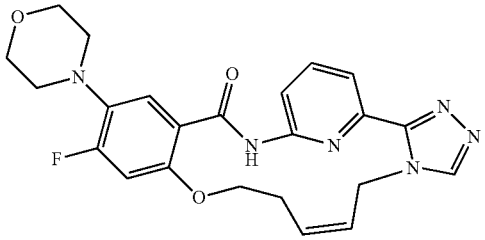 [SMILES: O=C1Nc2cccc(n2)-c2nncn2C/C=C\CCOc2cc(F)c(N3CCOCC3)cc21]

A mixture of (Z)-5⁵-bromo-5⁴-fluoro-1⁴H-6-oxa-3-aza-2 (2,6)-pyridina-1(3,4)-triazola-5(1,2)-benzenacycloundecaphan-9-en-4-one (30 mg, 0.067 mmol), morpholine (29 μL, 0.34 mmol), t-BuONa (13 mg, 0.13 mmol), Pd$_2$(dba)$_3$ (6 mg, 0.007 mmol) and RuPhos (6 mg, 0.014 mmol) in dioxane/THF (2 mL, 1/1) was stirred under a N$_2$ atmosphere at 110° C. for 4 h. After this time the mixture was purified by HPLC (using a Waters Xbridge Prep OBD C18, 5 μm 150×30 mm column and using water (containing 0.05% NH$_3$.H$_2$O)/CH$_3$CN, from 30% to 60% as the mobile phase at a flow rate of 25 mL/min) to give the title compound (5 mg, 16%) as a white solid. 1H NMR (400 MHz, DMSO-d$_6$) δ ppm 10.79 (s, 1H), 8.72 (s, 1H), 8.26 (J=2.8, 6.8 Hz, 1H), 7.98-8.02 (m, 2H), 7.80 (d, J=10.0 Hz, 1H), 7.24 (d, J=14.0 Hz, 1H), 5.54 (br s, 1H), 5.40-5.49 (m, 1H), 5.23 (s, 2H), 4.35 (t, J=4.0 Hz, 2H), 3.72-3.76 (m, 4H), 2.95-2.98 (m, 4H), 2.71 (s, 2H). MS (ESI): 451.0 [M+H]⁺.

Example 182: (Z)-5⁴-Fluoro-5⁵-(5-methyl-4,5,6,7-tetrahydropyrazolo[1,5-a]pyrazin-3-yl)-1⁴H-6-oxa-3-aza-2(2,6)-pyridina-1(3,4)-triazola-5(1,2)-benzenacycloundecaphan-9-en-4-one

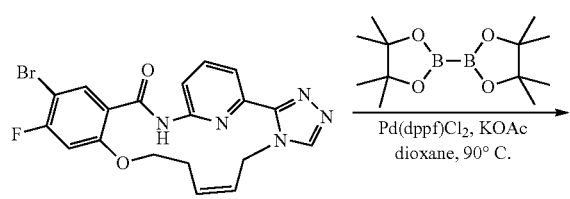

Step A. (Z)-(5⁴-Fluoro-4-oxo-1⁴H-6-oxa-3-aza-2(2,6)-pyridina-1(3,4)-triazola-5(1,2)-benzenacycloundecaphan-9-en-5⁵-yl)boronic acid

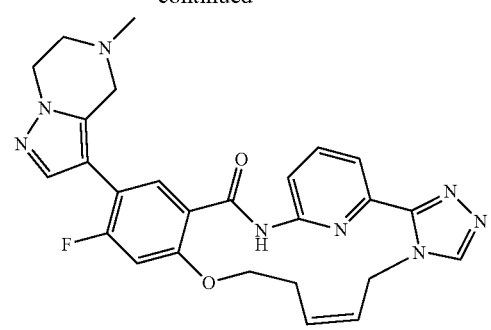

To a solution of compound (Z)-5⁵-bromo-5⁴-fluoro-1⁴H-6-oxa-3-aza-2(2,6)-pyridina-1(3,4)-triazola-5(1,2)-benzenacycloundecaphan-9-en-4-one (50 mg, 0.11 mmol) in dioxane (3 mL) was added 4,4,4',4',5,5,5',5'-octamethyl-2,2'-bi(1,3,2-dioxaborolane) (143 mg, 0.55 mmol) and KOAc (54 mg, 0.55 mmol) followed by Pd(dppf)Cl$_2$ (6 mg, 0.01 mmol) under a N$_2$ atmosphere and the mixture was stirred at 90° C. for 18 h. After this time the mixture was concentrated to give the crude product (180 mg) as a dark gum, which was used without further purification in the next step. MS (ESI): 409.9 [M+H]⁺.

Step B. (Z)-5⁴-Fluoro-5⁵-(5-methyl-4,5,6,7-tetrahydropyrazolo[1,5-a]pyrazin-3-yl)-1⁴H-6-oxa-3-aza-2(2,6)-pyridina-1(3,4)-triazola-5(1,2)-benzenacycloundecaphan-9-en-4-one

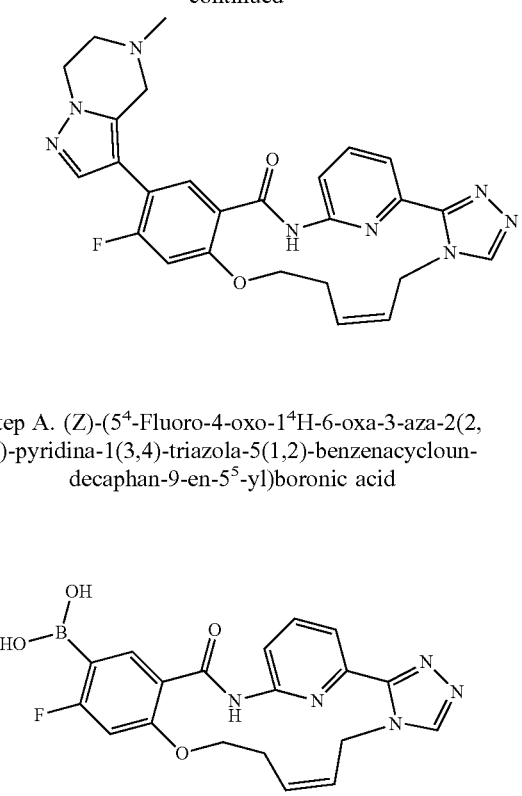

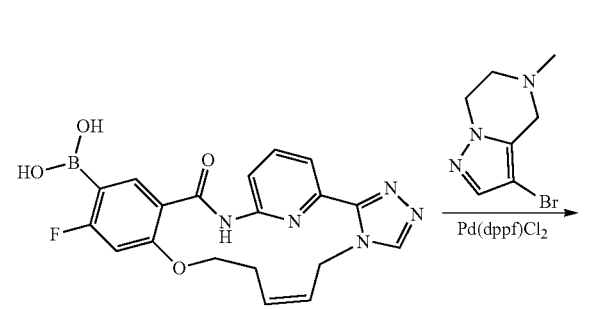

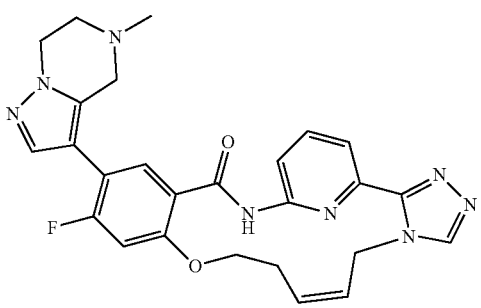 [SMILES: CN1CCn2ncc(-c3cc4c(cc3F)OCC/C=C\Cn3cnnc3-c3cccc(n3)NC4=O)c2C1]

To a solution of (Z)-(5⁴-fluoro-4-oxo-1⁴H-6-oxa-3-aza-2(2,6)-pyridina-1(3,4)-triazola-5(1,2)-benzenacycloundecaphan-9-en-5⁵-yl)boronic acid (180 mg, crude, 0.11 mmol) in DME/H$_2$O (10/1, 6 mL) was added 3-bromo-5-methyl-4,5,6,7-tetrahydropyrazolo[1,5-a]pyrazine (48 mg, 0.22 mmol), K$_2$CO$_3$ (46 mg, 0.33 mmol) and Pd(dtbpf)Cl$_2$ (6 mg, 0.01 mmol) under a N$_2$ atmosphere and the mixture was stirred at 90° C. for 18 h. After this time the mixture was concentrated to give the crude product which was purified by HPLC (using a Phenomenex Synergi C18, 4 μm 150×30 mm column and using water (containing 0.225% HCOOH)/CH$_3$CN, from 15% to 45% as the mobile phase at a flow rate of 25 mL/min) to give the title compound (4.2 mg, 11%, two steps) as a brown solid. ¹H NMR (400 MHz, DMSO-d$_6$) δ ppm 10.75 (s, 1H), 8.73 (s, 1H), 8.28 (t, J=4.4 Hz, 1H), 8.09 (d, J=9.2 Hz, 1H), 8.01 (d, J=4.4 Hz, 2H), 7.73 (s, 1H), 7.32 (d, J=12.0 Hz, 1H), 5.49-5.57 (m, 2H), 5.24 (s, 2H), 4.43 (s, 2H), 4.24 (s, 2H), 3.33 (s, 3H), 2.74 (s, 2H), 2.59-2.60 (m, 4H). MS (ESI): 501.2 [M+H]⁺.

Example 183: 5⁵-Bromo-1⁴H-6-oxa-3-aza-2(2,6)-pyridina-1(3,4)-triazola-5(1,2)-benzenacyclononaphan-4-one

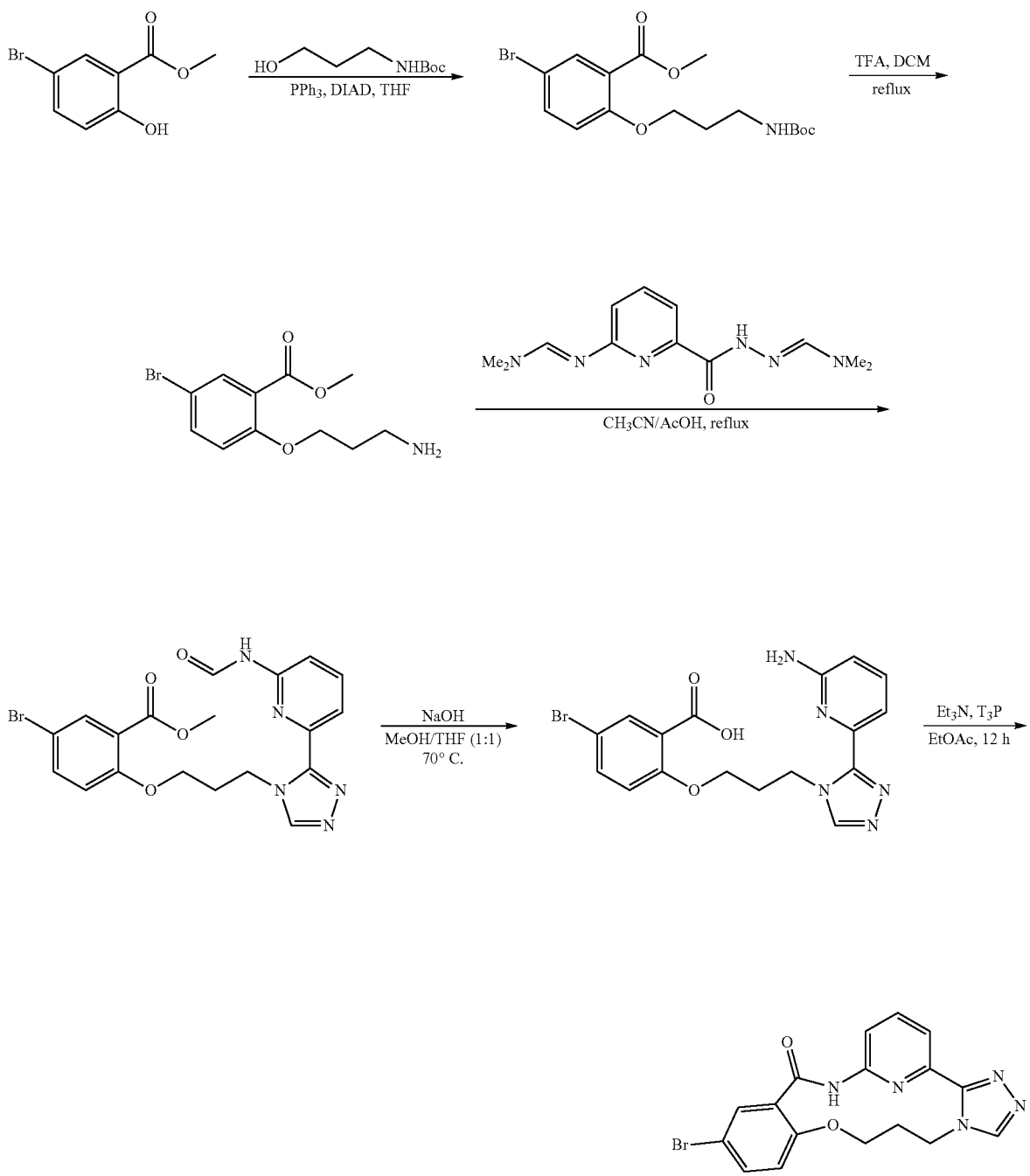

Step A. Methyl 5-bromo-2-(3-((tert-butoxycarbonyl)amino)propoxy)benzoate

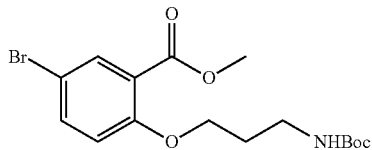 [SMILES: COC(=O)c1cc(Br)ccc1OCCCNC(=O)OC(C)(C)C]

The title compound was synthesized according to the general procedure described in Example 1, Step A and using methyl 5-bromo-2-hydroxy-benzoate (2.5 g, 10.9 mmol) to give the desired product (3.7 g, 89%) as a colorless oil.

Step B. Methyl 2-(3-aminopropoxy)-5-bromobenzoate

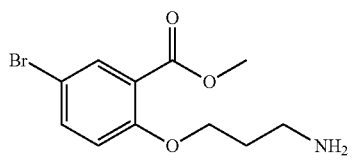

The title compound was synthesized according to the general procedure described in Example 1, Step B and using methyl 5-bromo-2-(3-(tert-butoxycarbonylamino)propoxy)benzoate (1.6 g, 4.0 mmol) to give the desired product (1.1 g, 93%) as a colorless oil.

Step C. Methyl 5-bromo-2-(3-(3-(6-formamidopyridin-2-yl)-4H-1,2,4-triazol-4-yl)propoxy)benzoate

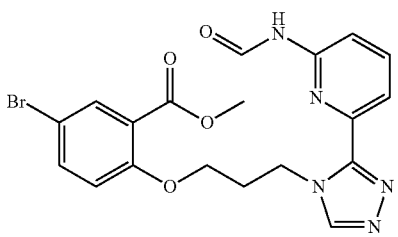 [SMILES: COC(=O)c1cc(Br)ccc1OCCCn1cnnc1-c1cccc(NC=O)n1]

The title compound was synthesized according to the general procedure described in Example 1, Step C and using methyl 2-(3-aminopropoxy)-5-bromobenzoate (1.18 g, 4.10 mmol) and (E)-N'-(6-(2-((E)-(dimethylamino)methylene)hydrazine-1-carbonyl)pyridin-2-yl)-N,N-dimethylformimidamide (538 mg, 2.05 mmol) to give the title compound (670 mg, 71%) as a yellow solid which was used without further purification in the next step. MS (ESI): 460.0 [(M+H) ($^{79}$Br)]$^+$.

Step D. 2-(3-(3-(6-Aminopyridin-2-yl)-4H-1,2,4-triazol-4-yl)propoxy)-5-bromobenzoic acid

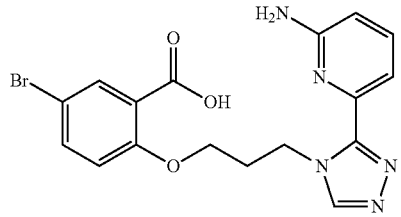 [SMILES: Nc1cccc(-c2nncn2CCCOc2ccc(Br)cc2C(=O)O)n1]

The title compound was synthesized according to the general procedure described in Example 1, Step D and using methyl 5-bromo-2-(3-(3-(6-formamidopyridin-2-yl)-4H-1,2,4-triazol-4-yl)propoxy)benzoate (275 mg, 0.6 mmol) to give the desired product (471 mg) as a yellow solid which was used without further purification in the next step. MS (ESI): 418.1 [(M+H) ($^{79}$Br)]$^+$.

Step E. 5$^5$-Bromo-1$^4$H-6-oxa-3-aza-2(2,6)-pyridina-1(3,4)-triazola-5(1,2)-benzenacyclononaphan-4-one

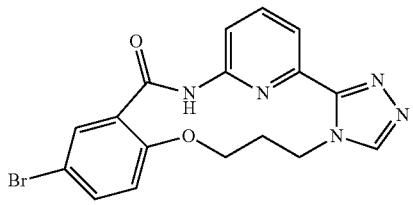 [SMILES: O=C1Nc2cccc(n2)-c2nncn2CCCOc2ccc(Br)cc21]

The title compound was synthesized according to the general procedure described in Example 1, Step E and using 2-(3-(3-(6-aminopyridin-2-yl)-4H-1,2,4-triazol-4-yl)propoxy)-5-bromobenzoic acid (471 mg, 1.1 mmol) to give the title compound (140 mg, 31%) as a white solid. $^1$H NMR (400 MHz, DMSO-d$_6$) δ ppm 10.42 (s, 1H), 8.73 (s, 1H), 7.95 (d, J=7.8 Hz, 1H), 7.85 (dd, J=7.5, 0.8 Hz, 1H), 7.46 (s, 1H), 7.44 (d, J=2.5 Hz, 1H), 7.32 (d, J=7.8 Hz, 1H), 7.01 (d, J=9.0 Hz, 1H), 4.78 (br s, 2H), 4.07 (br s, 2H), 2.19 (br s, 2H). MS (ESI): 400.0 [(M+H) ($^{79}$Br)]$^+$.

Example 184: 5$^5$-Morpholino-1$^4$H-6-oxa-3-aza-2(2,6)-pyridina-1(3,4)-triazola-5(1,2)-benzenacyclononaphan-4-one

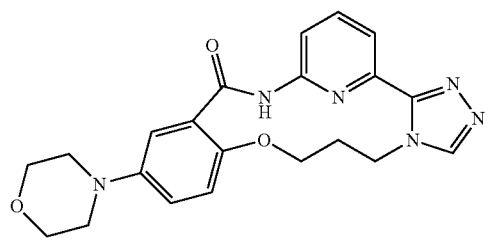 [SMILES: O=C1Nc2cccc(n2)-c2nncn2CCCOc2ccc(N3CCOCC3)cc21]

The title compound was synthesized according to the general procedure of Example 3 and using 5$^5$-bromo-1$^4$H-6-oxa-3-aza-2(2,6)-pyridina-1(3,4)-triazola-5(1,2)-benzenacyclononaphan-4-one (70 mg, 0.17 mmol) to give the desired product (50 mg, 70%) as a white solid. $^1$H NMR (400 MHz, CDCl$_3$) δ ppm 9.50 (s, 1H), 8.27 (s, 1H), 7.90-7.99 (m, 2H), 7.68 (dd, J=7.5, 1.3 Hz, 1H), 7.44 (d, J=3.0 Hz, 1H), 7.06 (dd, J=9.0, 3.0 Hz, 1H), 6.89 (d, J=9.0 Hz, 1H), 4.15-4.26 (m, 2H), 3.84-3.90 (m, 4H), 3.10-3.17 (m, 4H), 2.49 (br s, 2H), 1.86 (br s, 2H). MS (ESI): 407.1 [M+H]$^+$.

Example 185: Brief Description of ASK1 TR-FRET Assay

The protein kinase activity of 5 nM GST-hASK1(Life Technologies PV4011) was assayed with 100 μM ATP and 2 μM of HTRF biotinylated STK Substrate 3 (CisBio Kit 62ST3PEJ), at ambient temperature in 25 mM Hepes, pH 7.5, 50 mM NaCl, 10 mM MgCl$_2$, 0.02% Brij-35, 1 mM DTT, and 1% DMSO.

Briefly, 20 μL aliquots of a 1.5× stock of ASK1, STK Substrate 3 and Assay Buffer were distributed in the wells of a white 384 well Optiplate, prior to addition of 0.3 μL of a 100× compound stock in DMSO, or DMSO alone in Blank and 100% Activity Controls. After a 10 minute pre-incubation, ASK1 protein kinase activity was initiated by addition of 10 μL of 300 μM ATP. After 5 hours, the kinase activity was quenched by addition of 30 μL of CisBio Kit 62ST3PEJ components: 0.5 μM of Streptavidin XL665; and 100×STK Antibody-Eu Cryptate; in Detection Buffer containing sufficient EDTA to chelate Mg$^{2+}$ in the assay buffer. The plates were read after 65 minutes in an Envision Plate reader, with the following components and settings: Top Mirror, Lance Delfia Dual (662); UV Ex Filter, 320 nm (111); Emission Filter for donor, 615 nm (203); Emission Filter for Acceptor; 665 nM (205); and 100 usec delay, with 665/615 ratio output.

After subtracting the blank from the control and test well values, the ASK1 dependent 665/615 ratio output was plotted versus log of compound concentration, and the IC$_{50}$ values obtained from a 4 parameter fit in Graphpad Prism.

The compounds described herein were tested for in the above biochemical assay. The results are provided below, wherein the compound number corresponds to the numbers set forth in the examples above, "+" represents an IC$_{50}$ of less than 10 μM, but greater than 1 μM, "++" represents an IC$_{50}$ of less than or equal to 1 μM but greater than 0.1 μM, and "+++" represents an IC$_{50}$ of less than or equal to 0.1 μM.

TABLE 1

| IC50 | Compounds |
| --- | --- |
| +++ | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 33, 34, 42, 44, 89, 91, 93, 94, 96, 97, 153, 156, 159, 160, 161, 162, 169, 170, 171, 172, 173, |
| ++ | 31, 90, 92, 95, 98, 154, 155, 157, 158, 163, 184 |
| + | 166, 183 |
| Greater than or equal to 10 μM | 152, 164, 167 |

Alternatively, the protein kinase activity of the compounds described herein were tested using the ASK1/MAP3K5 assay by Reaction Biology Corp. The assay procedure can be found on Reaction Biology Corp.website at http://www.reactionbiology.com/webapps/site/KinasePDFs/ASK1_MAP3K5.pdf. ASK1/MAP3K5 was used as the protein kinase and 20 μM of myelin basic protein (MBP) and 10 μM ATP were used as the substrate.

The results are provided below, wherein the compound number corresponds to the numbers set forth in the examples above, "+" represents an IC$_{50}$ of less than 10 μM, but greater than 1 μM, "++" represents an IC$_{50}$ of less than or equal to 1 μM but greater than 0.1 μM, and "+++" represents an IC$_{50}$ of less than or equal to 0.1 μM.

TABLE 2

| IC50 | Compounds |
| --- | --- |
| +++ | 2, 3, 4, 5, 6, 8, 9, 10, 11, 12, 15, 17, 18, 20, 21, 22, 23, 26, 27, 29, 32, 33, 34, 35, 36, 37, 38, 39, 40, 41, 42, 43, 44, 45, 46, 47, 48, 49, 50, 52, 53, 54, 55, 56, 57, 58, 59, 60, 61, 62, 63, 64, 65, 66, 67, 68, 69, 70, 71, 72, 73, 74, 75, 76, 78, 79, 80, 81, 82, 83, 84, 85, 86, 87, 88, 89, 91, 93, 94, 96, 97, 99, 101, 103, 104, 106, 107, 108, 110, 111, 112, 113, 114, 115, 116, 117, 118, 119, 120, 122, 124, 127, 130 134, 135, 136, 137, 140, 141, 142, 143, 144, 145, 146, 147, 148, 149, 151, 156, 168, 171, 172, 173, 174, 175, 176, 177, 178, 179, 180, 181 |
| ++ | 45a, 100, 125, 138, 139, 150, 165, |
| + | 102, 121, 123, |
| Greater than or equal to 10 μM | |

Example 186: Brief Description of ASK1(AUTO PHOS T838) Assay

ASK1 T838 auto phosphorylation was measured in HEK-293T cells using MSD assay format. HEK 293T cells were seeded in 15 cm plates at a density of 18 million cells and 20 mL DMEM with 10% FBS, Pen/Strep media. The plates were incubated at 37° C. overnight. Media on plates was changed to OPTI-MEM, serum free media and cells were transfected with 9 μg of ASK1-V5 tagged full length plasmid using Lipofectamine 2000 (Invitrogen) and the plates were incubated at 37° C. overnight. Cells were trypsinized, counted on Nexcellometer and plated into 96 well tissue culture plates with 100,000 cells/well and 200 μL media. Cells were incubated for 4 hr at 37° C. then ASK1 compounds were added using a HP 300e. Compounds were tested at 20 μM with 3 fold, 10 point dilution points then incubated for 1 hr at 37° C. A lysis buffer (Cell Signaling) was prepared with protease and phosphatase inhibitor and maintained at 4° C. until use. Media from cells was discarded and 120 μL of cold lysis buffer was added to the cells, the plate was shaken 4° C. for 1 hr. Lysate was mixed using Apricot liquid handler; aspirating up and down 16 times at high speed using 50 μL volume. 50 μL of cell lysates were transferred to a pre-coated MSD plates containing mouse anti-V5 antibody (1:500 dilution) and washed 3× with MSD wash buffer (TBST) and blocked with a 3% BSA solution. Plates were then incubated on a plate shaker overnight at 4° C. Plates were washed 3× with MSD wash buffer and 50 μL of rabbit anti-pASK1 T838 antibody was added to the wells and incubated for 2 hr at room temperature on a plate shaker. Plates were then washed and 50 μL of goat anti-rabbit sulfa-tag (1:500 dilution) was added to wells, and incubated for 1 hr at room temperature on a plate shaker. Plates were washed 3× and 150 μL of 2×MSD Read buffer was added to wells. Plates were immediately read on a MSD Instrument Reader where chemoluminecense signal was measured. Data was analyzed using Graph Pad or Genedata, the data was normalized and plotted, % activity versus log of compound concentration. The IC$_{50}$ values were obtained from a 4 parameter fit.

The compounds described herein were tested for in the above cell-based assay. The results are provided below, wherein the compound number corresponds to the numbers set forth in the examples above, "†" represents an IC$_{50}$ of greater than 10 μM, "††" represents an IC$_{50}$ of equal to or less than 10 μM but greater than 1 uM, and "†††" represents an IC$_{50}$ of equal to or less than 1 μM.

| IC$_{50}$ | Compounds |
|---|---|
| ††† | 3, 4, 5, 6, 7, 9, 10, 11, 12, 13, 14, 15, 16, 17, 18, 19, 20, 21, 22, 23, 24, 26, 27, 29, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 91, 93, 94, 96, 97, 99, 101, 103, 104, 105, 106, 107, 108, 109, 110, 111, 112, 113, 114, 115, 116, 117, 118, 119, 120, 122, 124, 126, 127, 128, 129, 130, 131, 132, 133, 134, 135, 136, 139, 140, 141, 142, 143, 144, 145, 146, 147, 148, 149, 150, 151, 153, 156, 159, 160, 168, 169, 172, 173, 174, 175, 178, 179, 180, 181, 182, |
| †† | 2, 8, 25, 28, 30, 45a, 90, 92, 95, 100, 123, 125, 137, 138, 154, 155, 157, 158, 161, 162, 165, 171, 176, 177 |
| † | 98, 102, 121, 152, 163, 164, 166, 167, |

What is claimed is:
1. A compound of Formula (I):

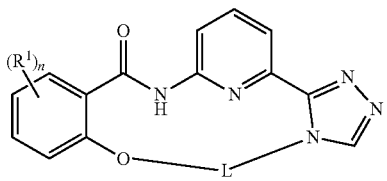

Formula (I)

or a pharmaceutically acceptable salt thereof, wherein:
n is selected from 0, 1 and 2;
L is selected from C$_{3-5}$alkylene and C$_{3-5}$alkenylene, wherein said C$_{3-5}$alkylene and C$_{3-5}$alkenylene are optionally substituted with one or two R$^2$;
R$^1$ in each occurrence is independently selected from C$_{1-6}$alkyl, C$_{2-6}$alkenyl, C$_{2-6}$alkynyl, carbocyclyl, heterocyclyl, halo, —CN, —C(O)R$^{1a}$, —C(O)$_2$R$^{1a}$, —C(O)N(R$^{1a}$)$_2$, —N(R$^{1a}$)$_2$, —N(R$^{1a}$)C(O)R$^{1a}$, —N(R$^{1a}$)C(O)$_2$R$^{1a}$, —N(R$^{1a}$)C(O)N(R$^{1a}$)$_2$, —N(R$^{1a}$)S(O)$_2$R$^{1a}$, —OR$^{1a}$, —OC(O)R$^{1a}$, —OC(O)N(R$^{1a}$)$_2$, —SR$^{1a}$, —S(O)R$^{1a}$, —S(O)$_2$R$^{1a}$, —S(O)N(R$^{1a}$)$_2$, and —S(O)$_2$N(R$^{1a}$)$_2$, wherein said C$_{1-6}$alkyl, C$_{2-6}$alkenyl, C$_{2-6}$alkynyl, carbocyclyl, and heterocyclyl, are optionally substituted with one or more R$^{10}$;
R$^{1a}$ in each occurrence is independently selected from H, C$_{1-6}$alkyl, C$_{2-6}$alkenyl, C$_{2-6}$alkynyl, carbocyclyl, and heterocyclyl, wherein said C$_{1-6}$alkyl, C$_{2-6}$alkenyl, C$_{2-6}$alkynyl, carbocyclyl, and heterocyclyl in each occurrence are optionally and independently substituted with one or more R$^{10}$;
R$^{10}$ in each occurrence is independently selected from C$_{1-6}$alkyl, C$_{2-6}$alkenyl, C$_{2-6}$alkynyl, carbocyclyl, heterocyclyl, halo, —CN, —C(O)R$^{10a}$, —C(O)$_2$R$^{10a}$, —C(O)N(R$^{10a}$)$_2$, —N(R$^{10a}$)$_2$, —N(R$^{10a}$)C(O)R$^{10a}$, —N(R$^{10a}$)C(O)$_2$R$^{10a}$, —N(R$^{10a}$)C(O)N(R$^{10a}$)$_2$, —N(R$^{10a}$)S(O)$_2$R$^{10a}$, —OR$^{10a}$, —OC(O)R$^{10a}$, —OC(O)N(R$^{10a}$)$_2$, —SR$^{10a}$, —S(O)R$^{10a}$, —S(O)$_2$R$^{10a}$, —S(O)N(R$^{10a}$)$_2$, and —S(O)$_2$N(R$^{10a}$)$_2$;
R$^{10a}$ in each occurrence is independently selected from H, C$_{1-6}$alkyl, C$_{2-6}$alkenyl, C$_{2-6}$alkynyl, carbocyclyl, and heterocyclyl;
R$^2$ in each occurrence is independently selected from C$_{1-6}$alkyl, —CN, —C(O)R$^{2a}$, —C(O)$_2$R$^{2a}$, —C(O)N(R$^{2a}$)$_2$, —NO$_2$, —N(R$^{2a}$)$_2$, —N(R$^{2a}$)C(O)R$^{2a}$, —N(R$^{2a}$)C(O)$_2$R$^{2a}$, —N(R$^{2a}$)C(O)N(R$^{2a}$)$_2$, —N(R$^{2a}$)S(O)$_2$R$^{2a}$, —OR$^{2a}$, —OC(O)R$^{2a}$, —OC(O)N(R$^{2a}$)$_2$, —SR$^{2a}$, —S(O)R$^{2a}$, —S(O)$_2$R$^{2a}$, —S(O)N(R$^{2a}$)$_2$, and —S(O)$_2$N(R$^{1a}$)$_2$, wherein said C$_{1-6}$alkyl is optionally substituted with one or more R$^{20}$;
R$^{2a}$ in each occurrence is independently selected from H, C$_{1-6}$alkyl, C$_{2-6}$alkenyl, C$_{2-6}$alkynyl, carbocyclyl, and heterocyclyl wherein said C$_{1-6}$alkyl, C$_{2-6}$alkenyl, C$_{2-6}$alkynyl, carbocyclyl, and heterocyclyl in each occurrence are optionally and independently substituted with one or more R$^{20}$; and
R$^{20}$ is independently selected from C$_{1-6}$alkyl, halo and —OR$^{20a}$; and
R$^{20a}$ in each occurrence is independently selected from H, C$_{1-6}$alkyl, C$_{2-6}$alkenyl, C$_{2-6}$alkynyl, carbocyclyl, and heterocyclyl.

2. The compound of claim 1, or a pharmaceutically acceptable salt thereof, wherein L is C$_{3-5}$alkylene optionally substituted with one or two R$^2$.

3. The compound of claim 1, or a pharmaceutically acceptable salt thereof, wherein L is C$_4$alkylene optionally substituted with one or two R$^2$.

4. The compound of claim 1, or a pharmaceutically acceptable salt thereof, wherein L is C$_4$alkenylene optionally substituted with one or two R$^2$.

5. The compound of claim 1, or a pharmaceutically acceptable salt thereof, wherein:
R$^2$ in each occurrence is independently selected from C$_{1-6}$alkyl, —CN, —C(O)R$^{2a}$, —C(O)$_2$R$^{2a}$, —C(O)N(R$^{2a}$)$_2$, —NO$_2$, —N(R$^{2a}$)$_2$, —N(R$^{2a}$)C(O)R$^{2a}$, —N(R$^{2a}$)C(O)$_2$R$^{2a}$, —OR$^{2a}$, —OC(O)R$^{2a}$, and —OC(O)N(R$^{2a}$)$_2$, wherein said C$_{1-6}$alkyl is optionally substituted with one to four R$^{20}$;
R$^{2a}$ in each occurrence is independently selected from H or C$_{1-6}$alkyl, wherein said C$_{1-6}$alkyl in each occurrence is optionally and independently substituted with one to three R$^{20}$; and
R$^{20}$ is independently halo or —OR$^{20a}$; and
R$^{20a}$ in each occurrence is independently H or C$_{1-6}$alkyl.

6. The compound of claim 5, or a pharmaceutically acceptable salt thereof, wherein R$^2$ is C$_{1-4}$alkyl.

7. The compound of claim 1, or a pharmaceutically acceptable salt thereof, wherein L is —(CH$_2$)$_3$—, —(CH$_2$)$_4$—, —CH$_2$—CH(CH$_3$)—CH$_2$—CH$_2$—, —CH$_2$—CH$_2$—CH$_2$—CH(CH$_3$)—, —(CH$_2$)$_5$—, or —CH$_2$—CH=CH—CH$_2$.

8. The compound of claim 1, or a pharmaceutically acceptable salt thereof, wherein n is 0.

9. The compound of claim 1, or a pharmaceutically acceptable salt thereof, wherein:
R$^1$ in each occurrence is independently selected from C$_{1-6}$alkyl, C$_{2-6}$alkenyl, 4- to 7-membered monocyclic non-aromatic heterocyclyl, 5- to 6-membered N-containing heteroaryl, 6- to 8-membered spiro or bridged bicyclic heterocyclyl, halo, —CN, —C(O)R$^{1a}$, —C(O)$_2$R$^{1a}$, —C(O)N(R$^{1a}$)$_2$, —S(O)$_2$R$^{1a}$, and —S(O)$_2$N(R$^{1a}$)$_2$, wherein said C$_{1-6}$alkyl, C$_{2-6}$alkenyl, 4- to 7-membered monocyclic non-aromatic heterocyclyl, 5- to 6-membered N-containing heteroaryl, and 6- to 8-membered spiro or bridged bicyclic heterocyclyl are optionally substituted with one to four R$^{10}$;

R$^{1a}$ in each occurrence is independently selected from H, C$_{1-6}$alkyl, and 4- to 7-membered monocyclic N-containing non-aromatic heterocyclyl, wherein said C$_{1-6}$alkyl, and 4- to 7-membered monocyclic N-containing non-aromatic heterocyclyl in each occurrence are optionally and independently substituted with one or three R$^{10}$; and R$^{10}$ in each occurrence is independently selected from C$_{1-6}$alkyl, halo, and C$_{3-6}$cycloalkyl.

10. The compound of claim 1, or a pharmaceutically acceptable salt thereof, wherein:

R$^1$ in each occurrence is independently selected from C$_{1-6}$alkyl, C$_{2-6}$alkenyl, C$_{2-6}$alkynyl, C$_{3-6}$cycloalkyl selected from cyclopropyl, cyclobutyl, cyclopentyl, and cyclohexyl, 4- to 7-membered monocyclic heterocyclyl selected from azetidinyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, dihydrofuranyl, imidazolinyl, dihydropyranyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, tetrahydropyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, azepinyl, oxepinyl, thiepinyl, diazepinyl, and thiazepinyl, 6- to 8-membered spiro or bridged bicyclic heterocyclyl selected from 3-azabicyclo[3.1.0]hexanyl, 3-azabicyclo[3.1.1]heptanyl, 2-azaspiro[3.3]heptanyl, 2-oxa-6-azaspiro[3.3]heptanyl, 3-oxa-8-azabicyclo[3.2.1]octanyl, 6-oxa-3-azabicyclo[3.1.1]heptanyl, 8-oxa-3-azabicyclo[3.2.1]octanyl, 3-oxa-6-azabicyclo[3.1.1]heptanyl, and 5-azaspiro[2.3]hexanyl, halo, —CN, —C(O)R$^{1a}$, and —S(O)$_2$R$^{1a}$, wherein said C$_{1-6}$alkyl, C$_{2-6}$alkenyl, C$_{3-6}$cycloalkyl, 4- to 7-membered monocyclic heterocyclyl, and 6- to 8-membered spiro or bridged bicyclic heterocyclyl are optionally substituted with one to four R$^{10}$;

R$^{1a}$ in each occurrence is H, C$_{1-6}$alkyl or 4- to 7-membered monocyclic heterocyclyl selected from azetidinyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, and azepinyl; and R$^{10}$ in each occurrence is independently selected from C$_{1-6}$alkyl, C$_{3-6}$cycloalkyl selected from cyclopropyl, cyclobutyl, cyclopentyl, and cyclohexyl, and halo.

11. The compound of claim 1, or a pharmaceutically acceptable salt thereof, wherein:

n is 1;

R$^1$ in each occurrence is independently selected from —CH$_3$, —CF$_3$, —CH=CH$_2$, heterocyclyl selected from azetidinyl, pyrrolidinyl, tetrahydrofuranyl, piperidinyl, tetrahydropyranyl, piperazinyl, morpholinyl, dihydrofuranyl, dihydropyranyl, imidazolyl, pyrazolyl, triazolyl, pyridinyl, 2-oxa-6-azaspiro[3.3]heptanyl, 3-oxa-8-azabicyclo[3.2.1]octanyl, 6-oxa-3-azabicyclo[3.1.1]heptanyl, 8-oxa-3-azabicyclo[3.2.1]octanyl, and 3-oxa-6-azabicyclo[3.1.1]heptanyl, —Br, —F, —CN, —C(O)R$^{1a}$, and —S(O)$_2$R$^{1a}$, wherein said heterocyclyl is optionally substituted with one to two R$^{10}$;

R$^{1a}$ in each occurrence is H, —CH$_3$, or pyrrolidinyl; and

R$^{10}$ in each occurrence is independently selected from —CH$_3$, —CH$_2$CH$_3$, cyclopropyl, and —F.

12. The compound of claim 1, wherein the compound is represented by the Formula (II):

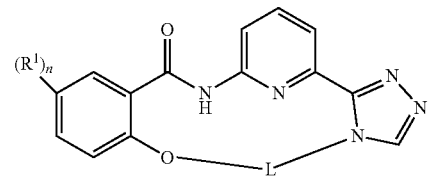

or a pharmaceutically acceptable salt thereof, wherein:

L is —(CH$_2$)$_4$— or —CH$_2$—CH$_2$—CH$_2$—CH(CH$_3$)—;

n is 0 or 1;

R$^1$ is heterocyclyl selected from imidazolyl, pyrazolyl, and 6-oxa-3-azabicyclo[3.1.1]heptanyl, wherein said heterocyclyl is optionally substituted with one R$^{10}$; and R$^{10}$ is C$_{1-4}$alkyl or C$_{3-6}$cycloalkyl.

13. The compound of claim 12, or a pharmaceutically acceptable salt thereof, wherein R$^1$ is heterocyclyl selected from the following:

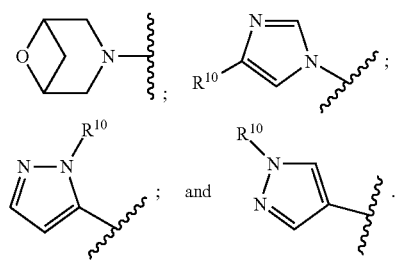

14. The compound of claim 12, or a pharmaceutically acceptable salt thereof, wherein R$^{10}$ is —CH$_3$ or cyclopropyl.

15. A pharmaceutical composition comprising a compound of claim 1, or a pharmaceutically acceptable salt thereof, and a pharmaceutically acceptable excipient.

16. A method of inhibiting apoptosis signal-regulating kinase 1 (ASK1) comprising administering in vitro or in vivo an effective amount of a compound of claim 1 or a pharmaceutically acceptable salt thereof.

* * * * *